US011179397B2

(12) United States Patent
Chin et al.

(10) Patent No.: US 11,179,397 B2
(45) Date of Patent: Nov. 23, 2021

(54) IMIDAZOPYRIMIDINE DERIVATIVES

(71) Applicant: Gilead Sciences, Inc., Foster City, CA (US)

(72) Inventors: Gregory Chin, San Francisco, CA (US); Michael O' Neil Hanrahan Clarke, Redwood City, CA (US); Xiaochun Han, Santa Clara, CA (US); Tim Hansen, San Francisco, CA (US); Yunfeng Eric Hu, San Mateo, CA (US); Dmitry Koltun, Foster City, CA (US); Ryan McFadden, Foster City, CA (US); Michael R. Mish, Foster City, CA (US); Eric Q. Parkhill, Union City, CA (US); David Sperandio, Palo Alto, CA (US); Lianhong Xu, Palo Alto, CA (US); Hai Yang, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/591,092

(22) Filed: Oct. 2, 2019

(65) Prior Publication Data

US 2020/0108071 A1 Apr. 9, 2020

Related U.S. Application Data

(60) Provisional application No. 62/857,386, filed on Jun. 5, 2019, provisional application No. 62/740,800, filed on Oct. 3, 2018.

(51) Int. Cl.

| | |
|---|---|
| ***C07D 487/04*** | (2006.01) |
| ***A61K 31/519*** | (2006.01) |
| ***A61K 45/06*** | (2006.01) |
| ***C07D 471/04*** | (2006.01) |
| ***C07D 471/10*** | (2006.01) |
| ***C07D 519/00*** | (2006.01) |

(52) U.S. Cl.

CPC ............ *A61K 31/519* (2013.01); *A61K 45/06* (2013.01); *C07D 471/04* (2013.01); *C07D 471/10* (2013.01); *C07D 487/04* (2013.01); *C07D 519/00* (2013.01)

(58) Field of Classification Search

CPC ............................ A61K 31/519; C07D 487/04
USPC ....................... 514/250, 259.1; 544/281, 277
See application file for complete search history.

(56) References Cited

U.S. PATENT DOCUMENTS

| | | | |
|---|---|---|---|
| 9,522,881 | B2 | 12/2016 | Zhang et al. |
| 9,815,813 | B2 | 11/2017 | Chen et al. |
| 2017/0204080 | A1 | 7/2017 | Chen et al. |
| 2017/0342078 | A1 | 11/2017 | Jones et al. |
| 2019/0231805 | A1 | 8/2019 | Yu et al. |
| 2020/0317622 | A1 | 10/2020 | Jorand-Lebrun et al. |

FOREIGN PATENT DOCUMENTS

| | | | |
|---|---|---|---|
| CN | 106074571 | A | 11/2016 |
| CN | 106177999 | A | 12/2016 |
| CN | 107266478 | A | 10/2017 |
| CN | 107286150 | A | 10/2017 |
| CN | 108578395 | A | 9/2018 |
| CN | 201811314910.1 | | 11/2018 |
| CN | 109646441 | A | 4/2019 |
| CN | 110143949 | A | 8/2019 |
| CN | 111484491 | | 8/2020 |
| EP | 3712151 | | 9/2020 |
| KR | 20170010302 | A | 1/2017 |
| WO | WO-2011/120902 | A1 | 10/2011 |
| WO | WO-2012/168259 | A1 | 12/2012 |
| WO | WO-2015/107493 | A1 | 7/2015 |
| WO | WO-2015/107494 | A1 | 7/2015 |
| WO | WO-2015/107495 | A1 | 7/2015 |
| WO | WO-2016/151501 | A1 | 9/2016 |
| WO | WO-2016/161282 | A1 | 10/2016 |
| WO | WO-2016/191328 | A1 | 12/2016 |
| WO | WO-2016/196569 | A1 | 12/2016 |
| WO | WO-2016/203404 | A1 | 12/2016 |

(Continued)

OTHER PUBLICATIONS

Chen C et al. (2017), "Identification of demethylincisterol $A_3$ as a selective inhibitor of protein tyrosine phosphatase Shp2", European Journal of Pharmacology 795: 124-133.

(Continued)

*Primary Examiner* — Jeffrey H Murray

(74) *Attorney, Agent, or Firm* — Fish & Richardson P.C.

(57) ABSTRACT

The present disclosure provides a compound of Formula (I):

(I)

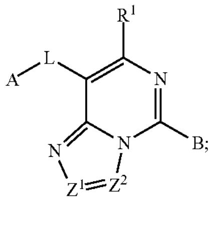

or a pharmaceutically acceptable salt thereof as described herein. The present disclosure also provides pharmaceutical compositions comprising a compound of Formula I, processes for preparing compounds of Formula I, therapeutic methods for treating cancers.

13 Claims, No Drawings

(56) References Cited

FOREIGN PATENT DOCUMENTS

| | | | | |
|---|---|---|---|---|
| WO | WO-2016/203405 A1 | | 12/2016 | |
| WO | WO-2016/203406 A1 | | 12/2016 | |
| WO | WO-2017/079723 A1 | | 5/2017 | |
| WO | WO-2017/100279 A1 | | 6/2017 | |
| WO | WO-2017/156397 A1 | | 9/2017 | |
| WO | WO-2017/210134 A1 | | 12/2017 | |
| WO | WO-2017/211303 A1 | | 12/2017 | |
| WO | WO-2017/216706 A1 | | 12/2017 | |
| WO | WO-2018/013597 A1 | | 1/2018 | |
| WO | WO-2018/130928 A1 | | 7/2018 | |
| WO | WO-2018/136264 A1 | | 7/2018 | |
| WO | WO-2018/136265 A1 | | 7/2018 | |
| WO | WO-2018/172984 A1 | | 9/2018 | |
| WO | WO-2018/218133 A1 | | 11/2018 | |
| WO | WO-2019/051084 A1 | | 3/2019 | |
| WO | WO-2019/051469 A1 | | 3/2019 | |
| WO | WO-2019/067843 A1 | | 4/2019 | |
| WO | WO-2019/075265 A1 | | 4/2019 | |
| WO | WO2019/118909 | * | 6/2019 | ........... C07D 471/04 |
| WO | WO-2019/118909 A1 | | 6/2019 | |
| WO | WO-2019/158019 A1 | | 8/2019 | |
| WO | WO-2019/165073 A1 | | 8/2019 | |
| WO | WO-2019/167000 A1 | | 9/2019 | |
| WO | WO-2019/182960 A1 | | 9/2019 | |
| WO | WO-2019/183364 A1 | | 9/2019 | |
| WO | WO-2019/183367 A1 | | 9/2019 | |
| WO | WO-2019/199792 A1 | | 10/2019 | |
| WO | WO-2019/213318 A1 | | 11/2019 | |
| WO | WO-2020/022323 A1 | | 1/2020 | |
| WO | WO-2020/061101 A1 | | 3/2020 | |
| WO | WO-2020/061103 A1 | | 3/2020 | |
| WO | WO-2020/063760 A1 | | 4/2020 | |
| WO | WO-2020/065452 A1 | | 4/2020 | |
| WO | WO-2020/065453 A1 | | 4/2020 | |
| WO | WO 2020/072656 | | 4/2020 | |
| WO | WO-2020/073945 A1 | | 4/2020 | |
| WO | WO-2020/073949 A1 | | 4/2020 | |
| WO | WO-2020/076723 A1 | | 4/2020 | |
| WO | WO-2020/081848 A1 | | 4/2020 | |
| WO | WO-2020/094018 A1 | | 5/2020 | |
| WO | WO-2020/094104 A1 | | 5/2020 | |
| WO | WO 2020156242 | | 8/2020 | |
| WO | WO 2020156243 | | 8/2020 | |
| WO | WO 2020157750 | | 8/2020 | |
| WO | WO 2020165732 | | 8/2020 | |
| WO | WO 2020165733 | | 8/2020 | |
| WO | WO 2020165734 | | 8/2020 | |
| WO | WO 2020201991 | | 10/2020 | |
| WO | WO 2020210384 | | 10/2020 | |
| WO | WO 2020249079 | | 12/2020 | |
| WO | WO 2021018287 | | 2/2021 | |

OTHER PUBLICATIONS

Eaton E S (2018), "A Cancer Target Revolution", BioCentury Company Profile.

Garcia Fortanet J et al. (2016), "Allosteric Inhibition of SHP2: Identification of a Potent, Selective, and Orally Efficacious Phosphatase Inhibitor", Journal of Medicinal Chemistry, vol. 59, No. 17, pp. 7773-7782.

Gill A (2019), "Discovery of Small Molecule Inhibitors of Oncogenic Mutants of RAS", Revolution Medicines, ACS, Orlando Presentation.

Intl. Search Report—Written Opinion dated Dec. 10, 2019 for Intl. Appl. No. PCT/US2019/054308.

Lamarche M J et al. (2019), "Allosteric SHP2 phosphatase inhibition: Multiple Mechanisms and Chemotypes", AACR Annual Meeting 2019, Atlanta, GA, Poster LB-005.

Lee G J et al. (2019), "Maximizing the therapeutic potential of SHP2 inhibition with rational combination strategies in tumors driven by aberrant RAS-MAPK signaling", Proceedings of the AACR Annual Meeting, Atlanta, GA, Abstract 1322.

Quintana E et al. (2018), "Allosteric inhibition of SHP2 induces anti-tumor immunity in PD-1-sensitive tumors through modulation of both innate and adaptive mechanisms", Fourth CRI-CIMT-EATI-AACR International Cancer Immunotherapy Conference: Translating Science into Survival, New York, NY, Poster A103.

Quintana E et al. (2019), "Allosteric inhibition of SHP2 suppresses CSF-1R signaling and selectively reduces viability of M2 tumor associated macrophages contributing to anti-tumor immunity", Proceedings of the AACR Annual Meeting, Atlanta, GA, Poster A5019.

Singh M (2018), "Combination Strategies to Enhance the Efficacy of SHP2 Inhibition: Mechanisms & Models of Cancer", Revolution Medicines, Presentation.

Xie J et al. (2017), "Allosteric inhibitors of SHP2 with therapeutic potential for cancer treatment", J. Med. Chem., 60(24).

Insogna, Letter to Gilead re U.S. Appl. No. 16/591,092, dated Oct. 2, 2020, 2 pages.

PCT International Preliminary Report on Patentability in International Application No. PCT/US2019/054308, dated Mar. 23, 2021, 7 pages.

* cited by examiner

IMIDAZOPYRIMIDINE DERIVATIVES

CROSS REFERENCE TO RELATED APPLICATIONS

This application claims the benefit of U.S. provisional application Ser. No. 62/740,800 filed on Oct. 3, 2018 and U.S. provisional application Ser. No. 62/857,386 filed on Jun. 5, 2019. The entire contents of these applications are incorporated herein by reference in their entirety.

FIELD

The present disclosure relates generally to compounds that have SHP2 inhibitory action, pharmaceutical compositions comprising said compounds, and methods of making and using said compounds and pharmaceutical compositions.

BACKGROUND

SHP2 (SH2 domain-containing protein tyrosine phosphatase-2) also known as PTPN11 (protein tyrosine phosphatase, non-receptor type 11) is a cytoplasmic tyrosine kinase encoded by the PTPN11 gene. SHP2 can be activated by a wide range of cytokines and growth factors and plays essential roles in development and homeostasis by regulating key intracellular signaling pathways such as the RAS-mitogen activated kinase (MAPK) pathway.

The SHP2 protein contains two N-terminal SH2 domains and a C-terminal phosphatase domain. The SH2 domains act as a conformational switch controlling the activation and sub-cellular localization of SHP2. In its auto-inhibited form, the SH2 domains of SHP2 bind and physically occlude the catalytic site. Binding of the SH2 domains to phosphoproteins switches SHP2 to an open conformation allowing substrates access to the catalytic site. Phosphorylation of two tyrosine residues on the C-terminal tail of SHP2 can recruit proteins important for downstream signaling, thus SHP2 has catalytic and scaffolding functions.

Somatic mutations in SHP2 which disrupt auto-inhibition have been found in juvenile myelomonocytic leukemia (JMML), acute leukemias, and are found rarely in neuroblastomas, AML/MDS, CMML, melanoma, and cancers of the lung, breast, colon and thyroid. Germline mutations in SHP2 have been identified in about half of patients with Noonan's syndrome and in most patients with LEOPARD syndrome. SHP2, therefore, represents a target for development of novel therapies for the treatment of various diseases.

SUMMARY

The present disclosure provides compounds that are SHP2 inhibitors. The disclosure also provides compositions, including pharmaceutical compositions, kits that include the compounds, and methods of using (or administering) and making the compounds. The compounds provided herein are useful in treating diseases, disorders, or conditions that are associated with SHP2 modulation. The disclosure also provides compounds for use in therapy. The disclosure further provides compounds for use in a method of treating a disease, disorder, or condition that is associated with SHP2 modulation. Moreover, the disclosure provides uses of the compounds in the manufacture of a medicament for the treatment of a disease, disorder or condition that is associated with SHP2 modulation.

In one aspect, provided is a compound having the structure of formula I:

(I)

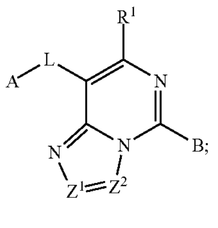

or a pharmaceutically acceptable salt thereof, wherein:

A is selected from $C_{6-10}$aryl, 5-10 membered heteroaryl, $C_{3-12}$cycloalkyl, and 4-12 membered heterocyclyl; each A is optionally substituted with one to six $R^A$ independently selected from halo, cyano, hydroxyl, azido, nitro, $C_{1-6}$alkyl, $C_{1-6}$haloalkyl, $C_{1-6}$alkoxyl, $C_{1-4}$alkylene-OH, oxo, $=NR^{a1}$, $-SR^{a1}$, $-OR^{a1}$, $-NR^{a1}R^{a2}$, $-COR^{a2}$, $-CONR^{a1}R^{a2}$, $-COOR^{a2}$, $-N(R^{a2})-C(O)R^{a2}$, $-N(R^{a2})-C(O)OR^{a2}$, $-N(R^{a2})-C(O)-NR^{a2}R^{a2}$, $-N(R^{a2})-SO_2R^{a2}$, $-SO_2R^{a2}$, $-SO_2OR^{a2}$, $-SO_2NR^{a1}R^{a2}$, $-O-SO_2-NR^{a1}R^{a2}$, $-O(CO)-N-R^{a1}R^{a2}$, $C_{3-8}$cycloalkyl, 3-8 membered heterocyclyl, $C_{6-10}$aryl, 5-10 membered heteroaryl, $-C_{1-4}$alkylene-$C_{3-8}$cycloalkyl, $-C_{1-4}$alkylene-(3-8 membered heterocyclyl), $-C_{1-4}$alkylene-$C_{6-10}$aryl, and $-C_{1-4}$alkylene-(5-10 membered heteroaryl);

wherein the $C_{3-8}$cycloalkyl, 3-8 membered heterocyclyl, $C_{6-10}$aryl, 5-10 membered heteroaryl, $-C_{1-4}$alkylene-$C_{3-8}$ cycloalkyl, $-C_{1-4}$alkylene-(3-8 membered heterocyclyl), $-C_{1-4}$alkylene-$C_{6-10}$aryl, and $-C_{1-4}$alkylene-(5-10 membered heteroaryl) of $R^A$ are independently optionally substituted with one to three groups selected from halo, cyano, hydroxyl, $C_{1-4}$alkyl, $C_{1-4}$haloalkyl, $C_{1-4}$alkoxyl, and $C_{1-4}$alkylene-OH; and wherein the 5-10 membered heteroaryl of A, and $R^A$ contains one to five heteroatoms independently selected from S, N, and O, and optionally comprises one to three C(O) or one $S(O)_2$;

L is selected from a bond, $-S(O_v)-$, $-O-$, $-N(R^{L1})-$, $-C(R^{L2}R^{L3})-$, $-C(R^{L2}R^{L3})-C(R^{L2}R^{L3})$, $-C(R^{L2})=C(R^{L2})-$, and $-C(O)-$;

$R^{L1}$ is selected from H, $C_{1-6}$alkyl, $C_{3-6}$cycloalkyl, 3-6 membered heterocyclyl, $-C(O)-C_{1-6}$alkyl, $-(SO_2)-C_{1-6}$alkyl, and 5-6 membered heteroaryl; wherein each $C_{3-6}$cycloalkyl, 3-6 membered heterocyclyl, and 5-6 membered heteroaryl of $R^{L1}$ is optionally substituted with one to three groups selected from halo, $C_{1-4}$alkyl, and $C_{1-4}$haloalkyl; and $R^{L2}$ and $R^{L3}$ are independently selected from H, halo, hydroxyl, $C_{1-4}$alkyl, $C_{1-4}$haloalkyl, $C_{1-4}$alkylene-OH, and $C_{3-6}$cycloalkyl; wherein each $C_{1-4}$alkylene-OH, and $C_{3-6}$cycloalkyl of $R^{L2}$ and $R^{L3}$ is optionally substituted with one to three halo; or $R^{L2}$ and $R^{L3}$ together with the atom to which they are attached form a 3-6 membered cycloalkyl or heterocyclyl; wherein the 3-6 membered cycloalkyl or heterocyclyl is optionally substituted with one to three groups selected from halo, hydroxyl, $C_{1-4}$alkoxyl, $-(SO_2)-C_{1-6}$alkyl, oxo, and nitro;

$Z^1$ and $Z^2$ are independently selected from N and $CR^3$; wherein $R^3$ is selected from H, halo, hydroxyl, cyano, $C_{1-4}$alkyl, $C_{1-4}$haloalkyl, $C_{1-4}$alkoxyl, $C_{1-4}$alkylene-OH, $-NR^{c1}R^{c2}$, $-C(O)OR^{c1}$, $C_{6-10}$aryl, and 5-10 membered heteroaryl; wherein each $C_{6-10}$aryl, and 5-10 membered heteroaryl of $R^3$ is independently optionally substituted with one to three groups independently selected from halo, hydroxyl, cyano, $C_{1-4}$alkyl, $C_{1-4}$haloalkyl, $C_{1-4}$alkoxyl, —N($R^{c1}$)—$SO_2R^{c1}$, and —$SO_2R^{c1}$;

$R^1$ is selected from H, halo, —$NR^{c1}R^{c2}$, $C_{1-4}$alkyl, and $C_{1-4}$ haloalkyl;

B is selected from

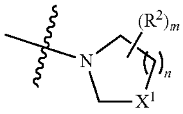
,
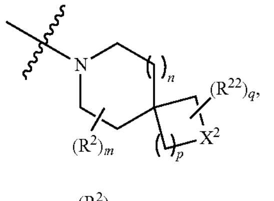
and
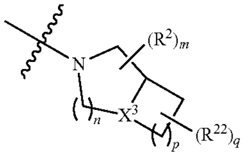

$X^1$ is selected from —$CR^2_2$—, —$CHR^2$—, —$CH_2$—, —O—, —$NR^2$—, and —S($O_v$)—;

$X^2$ is selected from —$CR^{22}_2$—, —$CHR^{22}$—, —$CH_2$—, —O—, —NH—, —$NR^{22}$—, —CO—, and —S($O_v$)—;

$X^3$ is selected from CH and N;

each $R^2$ is independently selected from halo, cyano, nitro, —O—$C_{1-6}$alkyl, oxo, —$NR^{c1}R^{c2}$, ($SO_v$)—$R^{c1}$, —$NR^{c1}$($SO_v$)—$R^{c1}$, —C(O)$OR^{c1}$, —C(O)—$NR^{c1}R^{c2}$, —S($O_2$)—$NR^{c1}R^{c2}$, $C_{1-6}$alkyl, $C_{2-6}$alkenyl, $C_{2-6}$alkynyl, $C_{1-4}$alklene-OH, —$C_{1-4}$alkylene-$NR^{c1}R^{c2}$, $C_{3-8}$cycloalkyl, 3-6 membered heterocyclyl, —O—$C_{3-8}$cycloalkyl, —O-(3-6 membered heterocyclyl), $C_{6-10}$aryl, and 5-10 membered heteroaryl;

wherein the $C_{1-6}$alkyl, $C_{2-6}$alkenyl, $C_{2-6}$alkynyl, $C_{3-8}$cycloalkyl, 3-6 membered heterocyclyl, —O—$C_{1-6}$alkyl, —O—$C_{3-8}$cycloalkyl, —O-(3-6 membered heterocyclyl), $C_{6-10}$aryl, and 5-10 membered heteroaryl of $R^2$ is optionally substituted with one to three groups independently selected from halo, —$NR^{a1}R^{a2}$, hydroxyl, azido, cyano, —SH, $C_{1-4}$alkyl, $C_{1-4}$haloalkyl, $C_{1-4}$alkoxyl, $C_{1-4}$alkylene-OH, —C(O)$OR^{a1}$, $C_{3-8}$cycloalkyl, 3-6 membered heterocyclyl, $C_{6-10}$aryl, and 5-10 membered heteroaryl; or two $R^2$, together with the atoms to which they are attached form a spiro, fused or bridged 3-12 membered cycloalkyl or heterocyclyl; wherein the spiro, fused or bridged 3-12 membered cycloalkyl or heterocyclyl is optionally substituted with one to three groups selected from halo, —$NR^{a1}R^{a2}$, hydroxyl, azido, cyano, —SH, $C_{1-4}$alkyl, $C_{1-4}$haloalkyl, $C_{1-4}$alkoxyl, and $C_{1-4}$alkylene-OH;

each $R^{22}$ is independently selected from halo, —$NR^{c1}R^{c2}$, hydroxyl, azido, cyano, oxo, —C(O)$OR^{c1}$, $C_{1-4}$alkyl, $C_{1-4}$haloalkyl, $C_{1-4}$alkoxyl, $C_{1-4}$alkylene-$NR^{c1}R^{c2}$, —$C_{1-4}$ alkylene-O—$C_{1-4}$alkyl, —$C_{1-4}$alkylene-OH, —$COR^{c1}$, —CO—$NR^{c1}R^{c2}$, —C(O)$OR^{c1}$, —N($R^{c1}$)—C(O)$R^{c1}$, —N($R^{c1}$)—C(O)$OR^{c1}$, —N($R^{c1}$)—C(O)—$NR^{c1}R^{c2}$, —N($R^{c1}$)—($SO_v$)$R^{c1}$, —$SO_2R^{c1}$, —$SO_2OR^{c1}$, —$SO_2R^{c1}R^{c2}$, $C_{3-8}$cycloalkyl, 3-6 membered heterocyclyl, $C_{6-10}$aryl, and 5-10 membered heteroaryl; or two $R^{22}$, together with the atoms to which they are attached, form a 3-12 membered spiro, bridged or fused ring E; wherein the ring E is selected from cycloalkyl, hetercyclyl, aryl, and heteroaryl; and wherein the ring E is optionally substituted with one to three groups selected from halo, cyano, hydroxyl, azido, nitro, $C_{1-6}$alkyl, $C_{1-6}$haloalkyl, $C_{1-6}$alkoxyl, $C_{1-4}$alkylene-OH, oxo, =$NR^{a1}$, —$SR^{a1}$, —$OR^{a1}$, —$NR^{a1}R^{a2}$, —$COR^{a2}$, —$CONR^{a1}R^{a2}$, —$COOR^{a2}$, —N($R^{a2}$)—C(O)$R^{a2}$, —N($R^{a2}$)—C(O)$OR^{a2}$, —N($R^{a2}$)—C(O)—$NR^{a2}R^{a2}R^{a2}$, —N($R^{a2}$)—$SO_2R^{a2}$, —$SO_2R^{a2}$, —$SO_2OR^{a2}$, —$SO_2NR^{a1}R^{a2}$, —O—$SO_2$—$NR^{a1}R^{a2}$, —O(CO)—$NR^{a1}R^{a2}$, $C_{3-8}$cycloalkyl, 3-8 membered heterocyclyl, $C_{6-10}$aryl, 5-10 membered heteroaryl, —$C_{1-4}$alkylene-$C_{3-8}$cycloalkyl, —$C_{1-4}$alkylene-(3-8 membered heterocyclyl), —$C_{1-4}$alkylene-$C_{6-10}$aryl, and —$C_{1-4}$ alkylene-(5-10 membered heteroaryl);

$R^{a1}$ is selected from H, $C_{1-4}$alkyl, $C_{1-4}$haloalkyl, $C_{1-4}$alkylene-OH, $C_{1-4}$alkylene-$COOR^{a2}$, —$C_{1-4}$alkylene-$C_{1-4}$ alkoxyl, and —C(O)—$NH_2$;

$R^{a2}$ is selected from H, $C_{1-4}$alkyl, $C_{1-4}$haloalkyl, $C_{1-4}$alkylene-OH, $C_{3-8}$cycloalkyl, 3-8 membered heterocyclyl, $C_{6-10}$aryl, and 5-10 membered heteroaryl; wherein the $C_{1-4}$alkyl, $C_{1-4}$haloalkyl, $C_{1-4}$alkylene-OH, $C_{3-8}$cycloalkyl, 3-8 membered heterocyclyl, $C_{6-10}$aryl, and 5-6 membered heteroaryl of $R^{a2}$ are independently optionally substituted with one to three groups selected from halo, cyano, hydroxyl, —$COOR^{a3}$, $C_{1-4}$alkyl, $C_{1-4}$haloalkyl, $C_{1-4}$alkylene-OH, and $C_{1-4}$alkoxyl; wherein $R^{a3}$ is selected from H, $C_{1-4}$alkyl, and $C_{1-4}$haloalkyl;

$R^{c1}$ and $R^{c2}$ are independently selected from H, $C_{1-6}$alkyl, and $C_{1-6}$haloalkyl; wherein each of the $C_{1-6}$alkyl and $C_{1-6}$haloalkyl of $R^{c1}$ and $R^{c2}$ is optionally substituted with one or two groups selected from $C_{1-4}$alkoxyl, and $C_{1-4}$alklene-OH;

v is selected from 0, 1, and 2;

n is selected from 0, 1, 2, 3, and 4;

m is selected from 0, 1, 2, 3, 4, 5, 6, 7, and 8;

q is selected from 0, 1, 2, 3, and 4; and p is selected from 0, 1, 2, 3, and 4.

DETAILED DESCRIPTION

Definitions and General Parameters

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —$CONH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

A squiggly line on a chemical group as shown below, for example,

indicates a point of attachment, i.e., it shows the broken bond by which the group is connected to another described group.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. $—(CH_2)_3CH_3$), sec-butyl (i.e. $—CH(CH_3)CH_2CH_3$), isobutyl (i.e. $—CH_2CH(CH_3)_2$) and tert-butyl (i.e. $—C(CH_3)_3$); and "propyl" includes n-propyl (i.e. $—(CH_2)_2CH_3$) and isopropyl (i.e. $—CH(CH_3)_2$).

"$C_{1-6}$alkylene" (including those which are part of other groups) refers to branched and unbranched divalent "alkyl" groups with 1 to 6 carbon atoms. Examples include: methylene, ethylene, propylene, 1-methylethylene, butylene, 1-methylpropylene, 1,1-dimethylethylene or 1,2-dimethylethylene. Unless stated otherwise, the definitions propylene and butylene include all the possible isomeric forms of the groups in question with the same number of carbons. Thus, for example, propylene also includes 1-methylethylene and butylene includes 1-methylpropylene, 1,1-dimethylethylene, and 1,2-dimethylethylene.

"Alkenyl" refers to an unbranched or branched hydrocarbon chain containing at least one carbon-carbon double bond (i.e., unsaturated) and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an unbranched or branched hydrocarbon chain containing at least one carbon-carbon triple bond (i.e., unsaturated) and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy. "Haloalkoxy" refers to an alkoxy group as defined above, wherein one or more hydrogen atoms are replaced by a halogen.

"Acyl" refers to a group —C(═O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amino" refers to the group $—NR^yR^z$ wherein $R^y$ and $R^z$ are independently selected from the group consisting of hydrogen, alkyl, haloalkyl, aryl, or heteroaryl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl. Cycloalkyl groups also include partially unsaturated ring systems containing one or more double bonds, including fused ring systems with one aromatic ring and one non-aromatic ring, but not fully aromatic ring systems.

"Bridged" refers to a ring fusion wherein non-adjacent atoms on a ring are joined by a divalent substituent, such as an alkylenyl or heteroalkylenyl group or a single heteroatom. Quinuclidinyl and admantanyl are examples of bridged ring systems.

The term "fused" refers to a ring which is bound to an adjacent ring.

"Spiro" refers to a ring substituent which is joined by two bonds at the same atom.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl ($—CHF_2$) and trifluoromethyl ($—CF_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, $—S(O)_2—$, and the like, where R is H, alkyl, aryl, cycloalkyl, heteroalkyl, heteroaryl or heterocyclyl, each of which may be optionally substituted. Examples of heteroalkyl groups include —$OCH_3$, —$CH_2OCH_3$, —$SCH_3$, —$CH_2SCH_3$, —$NRCH_3$, and —$CH_2NRCH_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. A heteroaryl also includes oxidized forms of a heteroaryl as defined herein. For example, a heteroaryl includes a pyridyl and any oxidized form of pyridyl such as 2-pyridone, 4-pyridone, or pyridine N-oxide. Similar oxidations would also be included for sulfur-containing ring systems including thiophenes (with either one or two oxidations on sulfur (in oxo or imino form) and higher-nitrogen heterocycles including pyrimidines. As used herein, heteroaryl includes 1 to 20 carbon ring atoms (i.e., $C_{1-20}$ heteroaryl), 3 to 12 carbon ring atoms (i.e., $C_{3-12}$ heteroaryl), or 3 to 8 carbon ring atoms (i.e., $C_{3-8}$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

The term "heterocyclyl" or "heterocycle" as used herein refers to a single saturated or partially unsaturated non-aromatic ring or a non-aromatic multiple ring system that has at least one heteroatom in the ring (i.e., at least one annular heteroatom selected from oxygen, nitrogen, and sulfur). Unless otherwise specified, a heterocyclyl group has from 3 to about 20 annular atoms, for example from 3 to 12 annular atoms, for example from 3 to 10 annular atoms, for example from 5 to 10 annular atoms or for example from 5 to 6 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring (e.g. bicyclic heterocyclyl) system can be connected to each other via fused, spiro and bridged bonds when allowed by valency requirements. The term "heterocyclyl" or "heterocyclic ring" or "heterocycle" includes heterocycloalkenyl groups (i.e., the heterocyclyl group having at least one double bond). A heterocyclyl may be a single ring or multiple rings wherein the multiple rings may be fused, bridged, or spiro. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, "bridged-heterocyclyl" includes bicyclic and tricyclic ring systems. Also as used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Heterocyclyl groups also include partially unsaturated ring systems containing one or more double bonds, including fused ring systems with one aromatic ring and one non-aromatic ring, but not fully aromatic ring systems. Examples include dihydroquinolines (e.g. 3,4-dihydroquinoline), dihydroisoquinolines (e.g. 1,2-dihydroisoquinoline), dihydroimidazole, tetrahydroimidazole, indoline, isoindoline, isoindolones (e.g. isoindolin-1-one), isatin, dihydrophthalazine, quinolinone, spiro[cyclopropane-1,1'-isoindolin]-3'-one, tetrahydroisoquinoline, tetraline, and the like. Additional examples of heterocycles include 3,8-diazabicyclo[3.2.1]octanyl, 2,5-diazabicyclo[2.2.1]heptanyl, 3,6-diazabicyclo[3.1.1]heptanyl, 3-oxa-7,9-diazabicyclo[3.3.1]nonanyl, and hexahydropyrazino[2,1-c][1,4]oxazinyl, for example. As used herein, the terms "heterocycle", "heterocyclyl", and "heterocyclic ring" are used interchangeably.

"Hydroxyl" and "hydroxy" are used interchangeably and refer to —OH.

"Oxo" refers to the group (═O) or (O).

"Sulfonyl" refers to the group —$S(O)_2R$, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

"SHP2" means "Src Homolgy-2 phosphatase" and is also known as SH-PTP2SH-PTP3, Syp, PTPID, PTP2C, SAP-2, or PTPN11.

Whenever the graphical representation of a group terminates in a singly bonded nitrogen atom, that group represents an —NH group unless otherwise indicated. Similarly, unless otherwise expressed, hydrogen atom(s) are implied and deemed present where necessary in view of the knowledge of one of skill in the art to complete valency or provide stability.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, alkoxy, halo, oxo, and hydroxyl; "substituted heterocyclyl" refers to a heterocyclyl group having one or more substituents including alkyl, haloalkyl, heterocyclyl, cycloalkyl, aryl, heteroaryl, alkoxy, halo, oxo, and hydroxyl; "substituted aryl" refers to an aryl group having one or more substituents including halo, alkyl, haloalkyl, cycloalkyl, heterocyclyl, heteroaryl, alkoxy, and cyano; "substituted heteroaryl" refers to an heteroaryl group having one or more substituents including halo, alkyl, haloalkyl, heterocyclyl, heteroaryl, alkoxy, and cyano and "substituted sulfonyl" refers to a group —$S(O)_2R$, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

The compounds of the embodiments disclosed herein, or their pharmaceutically acceptable salts may contain one or more asymmetric centers or chirality axes, and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms or a chirality axe, but which are not mirror-images of each other.

A "tautomer" refers to a proton shift from one atom of a molecule to another atom of the same molecule. The present disclosure includes tautomers of any compounds provided herein.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

A "solvate" is formed by the interaction of a solvent and a compound. Solvates of salts of the compounds provided herein are also provided. Hydrates of the compounds provided herein are also provided.

A "prodrug" is a biologically inactive derivative of a drug that upon administration to the human body is converted to the biologically active parent drug according to some chemical or enzymatic pathway.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^{3}H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or pharmaceutically acceptable salts, isomer, or a mixture thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of SHP2 activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of SHP2" or variants thereof refers to a decrease in activity of SHP2 as a direct or indirect response to the presence of a compound of the present application relative to the activity of SHP2 in the absence of the compound of the present application. "Inhibition of SHP2" refers to a decrease in SHP2 activity as a direct or indirect response to the presence of a compound described herein relative to the activity of SHP2 integrin in the absence of the compound described herein. In some embodiments, the inhibition of SHP2 activity may be compared in the same subject prior to treatment, or other subjects not receiving the treatment.

Compounds

Provided herein are compounds that function as inhibitors of SHP2. In one aspect, provided is a compound having structure of formula (I), or a pharmaceutically acceptable salt thereof:

(I)

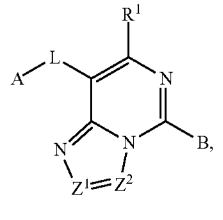

or a pharmaceutically acceptable salt thereof; wherein:

A is selected from $C_{6-10}$aryl, 5-10 membered heteroaryl, $C_{3-12}$cycloalkyl, and 4-12 membered heterocyclyl; each A is optionally substituted with one to six $R^{A}$ independently selected from halo, cyano, hydroxyl, azido, nitro, $C_{1-6}$alkyl, $C_{1-6}$haloalkyl, $C_{1-6}$alkoxyl, $C_{1-4}$alkylene-OH, oxo, $=NR^{a1}$, —$SR^{a1}$, —$OR^{a1}$, —$NR^{a1}R^{a2}$, —$COR^{a2}$, —$CONR^{a1}R^{a2}$, —$COOR^{a2}$, —$N(R^{a2})$—$C(O)R^{a2}$, —$N(R^{a2})$—$C(O)OR^{a2}$, —$N(R^{a2})$—C(O)—$NR^{a2}R^{a2}$, —$N(R^{a2})$—$SO_2R^{a2}$, —$SO_2R^{a2}$, —$SO_2OR^{a2}$, —$SO_2NR^{a1}R^{a2}$, —O—$SO_2$—$NR^{a1}R^{a2}$, —O(CO)—N—$R^{a1}R^{a2}$, $C_{3-8}$Cycloalkyl, 3-8 membered heterocyclyl, $C_{6-10}$aryl, 5-10 membered heteroaryl, —$C_{1-4}$alkylene-$C_{3-8}$cycloalkyl, —$C_{1-4}$alkylene-(3-8 membered heterocyclyl), —$C_{1-4}$alkylene-$C_{6-10}$aryl, and —$C_{1-4}$alkylene-(5-10 membered heteroaryl);

wherein the $C_{3-8}$cycloalkyl, 3-8 membered heterocyclyl, $C_{6-10}$aryl, 5-10 membered heteroaryl, —$C_{1-4}$alkylene-$C_{3-8}$ cycloalkyl, —$C_{1-4}$alkylene-(3-8 membered heterocyclyl), —$C_{1-4}$alkylene-$C_{6-10}$aryl, and —$C_{1-4}$alkylene-(5-10 membered heteroaryl) of $R^A$ are independently optionally substituted with one to three groups selected from halo, cyano, hydroxyl, $C_{1-4}$alkyl, $C_{1-4}$haloalkyl, $C_{1-4}$alkoxyl, and $C_{1-4}$alkylene-OH; and wherein the 5-10 membered heteroaryl of A, and $R^A$ contains one to five heteroatoms independently selected from S, N, and O, and optionally comprises one to three C(O) or one $S(O)_2$;

L is selected from a bond, —$S(O_v)$—, —O—, —$N(R^{L1})$—, —$C(R^{L2}R^{L3})$—, —$C(R^{L2}R^{L3})$—$C(R^{L2}R^{L3})$, —$C(R^{L2})$═C$(R^{L2})$—, and —C(O)—;

$R^{L1}$ is selected from H, $C_{1-6}$alkyl, $C_{3-6}$cycloalkyl, 3-6 membered heterocyclyl, —C(O)—$C_{1-6}$alkyl, —$(SO_2)$—$C_{1-6}$alkyl, and 5-6 membered heteroaryl; wherein each $C_{3-6}$cycloalkyl, 3-6 membered heterocyclyl, and 5-6 membered heteroaryl of $R^{L1}$ is optionally substituted with one to three groups selected from halo, $C_{1-4}$alkyl, and $C_{1-4}$haloalkyl; and $R^{L2}$ and $R^{L3}$ are independently selected from H, halo, hydroxyl, $C_{1-4}$alkyl, $C_{1-4}$haloalkyl, $C_{1-4}$alkylene-OH, and $C_{3-6}$cycloalkyl; wherein each $C_{1-4}$alkylene-OH, and $C_{3-6}$cycloalkyl of $R^{L2}$ and $R^{L3}$ is optionally substituted with one to three halo; or $R^{L2}$ and $R^{L3}$ together with the atom to which they are attached form a 3-6 membered cycloalkyl or heterocyclyl; wherein the 3-6 membered cycloalkyl or heterocyclyl is optionally substituted with one to three groups selected from halo, hydroxyl, $C_{1-4}$alkoxyl, —$(SO_2)$—$C_{1-6}$alkyl, oxo, and nitro;

$Z^1$ and $Z^2$ are independently selected from N and $CR^3$; wherein $R^3$ is selected from H, halo, hydroxyl, cyano, $C_{1-4}$alkyl, $C_{1-4}$haloalkyl, $C_{1-4}$alkoxyl, $C_{1-4}$alkylene-OH, —$NR^{c1}R^{c2}$, —$C(O)OR^{c1}$, $C_{6-10}$aryl, and 5-10 membered heteroaryl; wherein each $C_{6-10}$aryl, and 5-10 membered heteroaryl of $R^3$ is independently optionally substituted with one to three groups independently selected from halo, hydroxyl, cyano, $C_{1-4}$alkyl, $C_{1-4}$haloalkyl, $C_{1-4}$alkoxyl, —$N(R^{c1})$—$SO_2R^{c1}$, and —$SO_2R^{c1}$;

$R^1$ is selected from H, halo, —$NR^{c1}R^{c2}$, $C_{1-4}$alkyl, and $C_{1-4}$ haloalkyl;

B is selected from

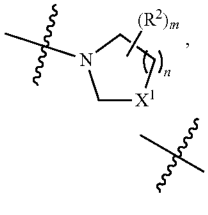
,
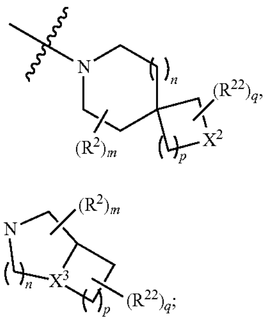
and
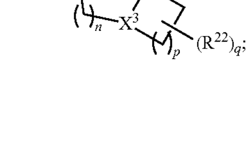
;

$X^1$ is selected from —$CR^2{}_2$—, —$CHR^2$, —$CH_2$—, —O—, —$NR^2$—, and —$S(O_v)$—;

$X^2$ is selected from —$CR^{22}{}_2$—, —$CHR^{22}$—, —$CH_2$—, —O—, —NH—, —$NR^{22}$—, —CO—, and —$S(O_v)$—;

$X^3$ is selected from CH and N;

each $R^2$ is independently selected from halo, cyano, nitro, —O—$C_{1-6}$alkyl, oxo, —$NR^{c1}R^{c2}$, —$(SO_v)$—$R^{c1}$, —$NR^{c1}$ $(SO_v)$—$R^{c1}$, —$C(O)OR^{c1}$, —C(O)—$NR^{c1}R^{c2}$, —$S(O_2)$—$NR^{c1}R^{c2}$, $C_{1-6}$alkyl, $C_{2-6}$alkenyl, $C_{2-6}$alkynyl, $C_{1-4}$alklene-OH, —$C_{1-4}$alkylene-$NR^{c1}R^{c2}$, $C_{3-8}$cycloalkyl, 3-6 membered heterocyclyl, —O—$C_{3-8}$cycloalkyl, —O-(3-6 membered heterocyclyl), $C_{6-10}$aryl, and 5-10 membered heteroaryl;

wherein the $C_{1-6}$alkyl, $C_{2-6}$alkenyl, $C_{2-6}$alkynyl, $C_{3-8}$cycloalkyl, 3-6 membered heterocyclyl, —O—$C_{1-6}$alkyl, —O—$C_{3-8}$cycloalkyl, —O-(3-6 membered heterocyclyl), $C_{6-10}$aryl, and 5-10 membered heteroaryl of $R^2$ is optionally substituted with one to three groups independently selected from halo, —$NR^{a1}R^{a2}$, hydroxyl, azido, cyano, —SH, $C_{1-4}$alkyl, $C_{1-4}$haloalkyl, $C_{1-4}$alkoxyl, $C_{1-4}$alkylene-OH, —$C(O)OR^{a1}$, $C_{3-8}$cycloalkyl, 3-6 membered heterocyclyl, $C_{6-10}$aryl, and 5-10 membered heteroaryl; or two $R^2$, together with the atoms to which they are attached form a spiro, fused or bridged 3-12 membered cycloalkyl or heterocyclyl; wherein the spiro, fused or bridged 3-12 membered cycloalkyl or heterocyclyl is optionally substituted with one to three groups selected from halo, —$NR^{a1}R^{a2}$, hydroxyl, azido, cyano, —SH, $C_{1-4}$alkyl, $C_{1-4}$haloalkyl, $C_{1-4}$alkoxyl, and $C_{1-4}$alkylene-OH;

each $R^{22}$ is independently selected from halo, —$NR^{c1}R^{c2}$, hydroxyl, azido, cyano, oxo, —$C(O)OR^{c1}$, $C_{1-4}$alkyl, $C_{1-4}$haloalkyl, $C_{1-4}$alkoxyl, $C_{1-4}$alkylene-$NR^{c1}R^{c2}$, —$C_{1-4}$ alkylene-O—$C_{1-4}$alkyl, —$C_{1-4}$alkylene-OH, —$COR^{c1}$, —CO—$NR^{c1}R^{c2}$, —$C(O)OR^{c1}$, —$N(R^{c1})$—$C(O)R^{c1}$, —$N(R^{c1})$—$C(O)OR^{c1}$, —$N(R^{c1})$—C(O)—$NR^{c1}R^{c2}$, —$N(R^{c1})$—$(SO_v)R^{c1}$, —$SO_2R^{c1}$, —$SO_2OR^{c1}$, —$SO_2R^{c1}R^{c2}$, $C_{3-8}$cycloalkyl, 3-6 membered heterocyclyl, $C_{6-10}$aryl, and 5-10 membered heteroaryl; or two $R^{22}$, together with the atoms to which they are attached, form a 3-12 membered spiro, bridged or fused ring E; wherein the ring E is selected from cycloalkyl, hetercyclyl, aryl, and heteroaryl; and wherein the ring E is optionally substituted with one to three groups selected from halo, cyano, hydroxyl, azido, nitro, $C_{1-6}$alkyl, $C_{1-6}$haloalkyl, $C_{1-6}$alkoxyl, $C_{1-4}$alkylene-OH, oxo, ═$NR^{a1}$, —$SR^{a1}$, —$OR^{a1}$, —$NR^{a1}R^{a2}$, —$COR^{a2}$, —$CONR^{a1}R^{a2}$, —$COOR^{a2}$, —$N(R^{a2})$—$C(O)R^{a2}$, —$N(R^{a2})$—$C(O)OR^{a2}$, —$N(R^{a2})$—C(O)—$NR^{a2}R^{a2}R^{a2}$, —$N(R^{a2})$—$SO_2R^{a2}$, —$SO_2R^{a2}$, —$SO_2OR^{a2}$, —$SO_2NR^{a1}R^{a2}$, —O—$SO_2$—$NR^{a1}R^{a2}$, —O(CO)—$NR^{a1}R^{a2}C_{3-8}$cycloalkyl, 3-8 membered heterocyclyl, $C_{6-10}$aryl, 5-10 membered heteroaryl, —$C_{1-4}$alkylene-$C_{3-8}$cycloalkyl, —$C_{1-4}$alkylene-(3-8 membered heterocyclyl), —$C_{1-4}$alkylene-$C_{6-10}$aryl, and —$C_{1-4}$ alkylene-(5-10 membered heteroaryl);

$R^{a1}$ is selected from H, $C_{1-4}$alkyl, $C_{1-4}$haloalkyl, $C_{1-4}$alkylene-OH, $C_{1-4}$alkylene-$COOR^{a2}$, —$C_{1-4}$alkylene-$C_{1-4}$ alkoxyl, and —C(O)—$NH_2$;

$R^{a2}$ is selected from H, $C_{1-4}$alkyl, $C_{1-4}$haloalkyl, $C_{1-4}$alkylene-OH, $C_{3-8}$cycloalkyl, 3-8 membered heterocyclyl, $C_{6-10}$aryl, and 5-10 membered heteroaryl; wherein the $C_{1-4}$alkyl, $C_{1-4}$haloalkyl, $C_{1-4}$alkylene-OH, $C_{3-8}$cycloalkyl, 3-8 membered heterocyclyl, $C_{6-10}$aryl, and 5-6 membered heteroaryl of $R^{a2}$ are independently optionally substituted with one to three groups selected from halo, cyano, hydroxyl, —$COOR^{a3}$, $C_{1-4}$alkyl, $C_{1-4}$haloalkyl, $C_{1-4}$alkylene-OH, and $C_{1-4}$alkoxyl; wherein $R^{a3}$ is selected from H, $C_{1-4}$alkyl, and $C_{1-4}$haloalkyl;

$R^{c1}$ and $R^{c2}$ are independently selected from H, $C_{1-6}$alkyl, and $C_{1-6}$haloalkyl; wherein each of the $C_{1-6}$alkyl and $C_{1-6}$haloalkyl of $R^{c1}$ and $R^{c2}$ is optionally substituted with one or two groups selected from $C_{1-4}$alkoxyl, and $C_{1-4}$alklene-OH;

v is selected from 0, 1, and 2;

n is selected from 0, 1, 2, 3, and 4;

m is selected from 0, 1, 2, 3, 4, 5, 6, 7, and 8;

q is selected from 0, 1, 2, 3, and 4; and p is selected from 0, 1, 2, 3, and 4.

In another aspect, provided are compounds of Formula (II), or pharmaceutically acceptable salts thereof:

(II)

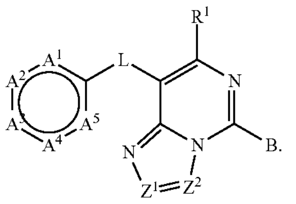

L, $Z^1$, $Z^2$, $R^1$, and B are as defined above in formula (I), or elsewhere in this disclosure. Each $A^1$, $A^2$, $A^3$, $A^4$, and $A^5$ is independently selected from N, $NR^{AA}$, C(O), and $CR^{AA}$; wherein $R^{AA}$ is selected from H and $R^A$.

indicates that the ring containing $A^1$, $A^2$, $A^3$, $A^4$, and $A^5$ is an aryl or heteroaryl.

In another aspect, provided are compounds of Formula (IIa), or pharmaceutically acceptable salts thereof:

(IIa)

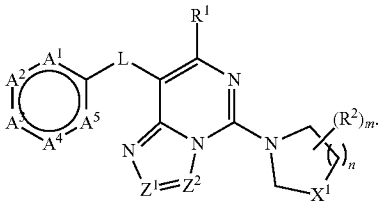

L, $Z^1$, $Z^2$, $R^1$, $R^2$, $X^1$, m, and n are as defined above in formula (I), (II), or elsewhere in this disclosure. $A^1$, $A^2$, $A^3$, $A^4$, and $A^5$ are as defined above in formula (II), or elsewhere in this disclosure.

In another aspect, provided are compounds of Formula (IIb), or pharmaceutically acceptable salts thereof:

(IIb)

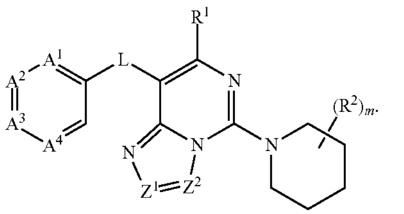

L, $Z^1$, $Z^2$, $R^1$, $R^2$, and m are as defined above in formula (I), (II), (IIa), or elsewhere in this disclosure. $A^1$, $A^2$, $A^3$, and $A^4$ are as defined above in formula (II), (IIa), or elsewhere in this disclosure.

In another aspect, provided are compounds of Formula (IIc), or pharmaceutically acceptable salts thereof:

(IIc)

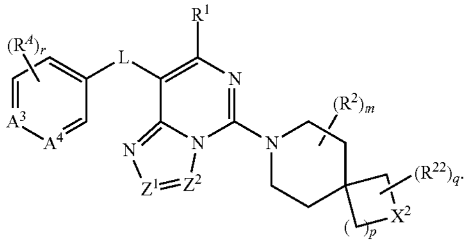

L, $Z^1$, $Z^2$, $R^A$, $R^1$, $R^2$, $R^{22}$, $X^2$, m, p, and q are as defined above in formula (I), (II), or elsewhere in this disclosure. $A^3$ and $A^4$ are as defined above in formula (II), (IIa), (IIb), or elsewhere in this disclosure. r is selected from 0, 1, 2, and 3.

In another aspect, provided are compounds of Formula (IId), or pharmaceutically acceptable salts thereof:

(IId)

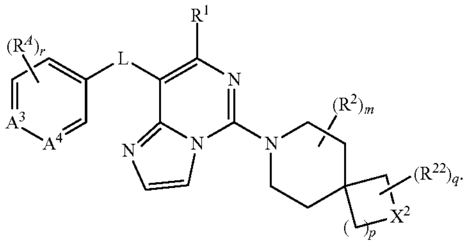

L, $R^A$, $R^1$, $R^2$, $R^{22}$, $X^2$, m, p, and q are as defined above in formula (I), (II), (IIc), or elsewhere in this disclosure. $A^3$ and $A^4$ are as defined above in formula (II), (IIa), (IIb), (IIc), or elsewhere in this disclosure. r is as defined above in formula (IIc).

In another aspect, provided are compounds of Formula (IIe), or pharmaceutically acceptable salts thereof:

(IIe)

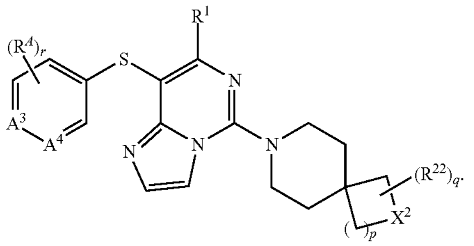

$R^A$, $R^1$, $R^{22}$, $X^2$, p, and q are as defined above in formula (I), (II), (IId), or elsewhere in this disclosure. $A^3$ and $A^4$ are as defined above in formula (II), (IIa), (IIb), (IIc), or elsewhere in this disclosure. r is as defined above in formula (IIc), (IId), or elsewhere in this disclosure.

In another aspect, provided are compounds of Formula (IIf), or pharmaceutically acceptable salts thereof:

(IIf)

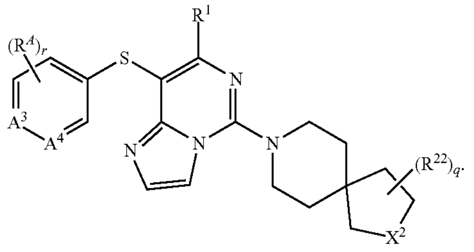

$R^A$, $R^1$, $R^{22}$, $X^2$, and q are as defined above in formula (I), (II), (IIc), (IIf), or elsewhere in this disclosure. $A^3$ and $A^4$ are as defined above in formula (II), (IIa), (IIb), (IIc), (IId), (IIe), or elsewhere in this disclosure. r is as defined above in formula (IIc), (IId), (IIe), or elsewhere in this disclosure.

In another aspect, provided are compounds of Formula (IIg), or pharmaceutically acceptable salts thereof:

(IIg)

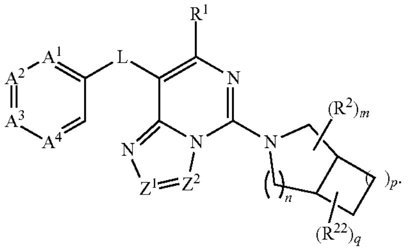

L, $Z^1$, $Z^2$, $R^1$, $R^2$, $R^{22}$, m, n, p, and q are as defined above in formula (I), or elsewhere in this disclosure. $A^1$, $A^2$, $A^3$, $A^4$, and $A^5$ are as defined above in formula (II), or elsewhere in this disclosure.

In another aspect, provided are compounds of Formula (III), or pharmaceutically acceptable salts thereof:

(III)

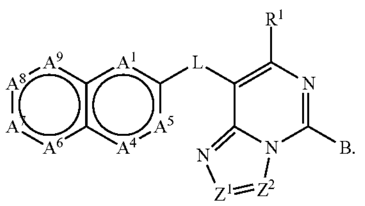

L, $Z^1$, $Z^2$, $R^1$, and B are as defined above in formula (I), or elsewhere in this disclosure. Each $A^1$, $A^4$, $A^5$, $A^6$, $A^7$, $A^8$, and $A^9$ is independently selected from N, $NR^{AA}$, C(O), and $CR^{AA}$; and $R^{AA}$ is selected from H and $R^A$.

In another aspect, provided are compounds of Formula (IIIa), or pharmaceutically acceptable salts thereof:

(IIIa)

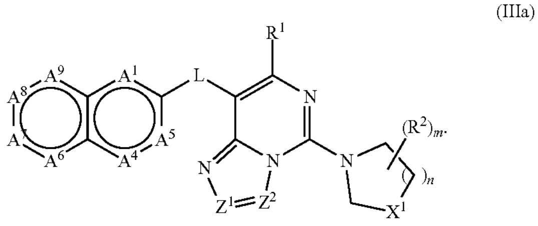

L, $Z^1$, $Z^2$, $R^1$, $R^2$, $X^1$, m, and n are as defined above in formula (I), (III), or elsewhere in this disclosure. $A^1$, $A^4$, $A^5$, $A^6$, $A^7$, $A^8$, and $A^9$ are as defined above in formula (III), or elsewhere in this disclosure.

In another aspect, provided are compounds of Formula (IIIb), or pharmaceutically acceptable salts thereof:

(IIIb)

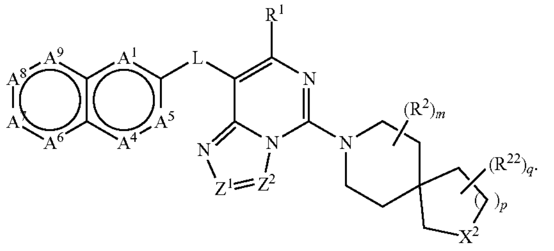

L, $Z^1$, $Z^2$, $R^1$, $R^2$, $R^{22}$, $X^2$, m, p, and q are as defined above in formula (I), or elsewhere in this disclosure. $A^1$, $A^4$, $A^5$, $A^6$, $A^7$, $A^8$, and $A^9$ are as defined above in formula (III), (IIIa), or elsewhere in this disclosure.

In another aspect, provided are compounds of Formula (IIIc), or pharmaceutically acceptable salts thereof:

(IIIc)

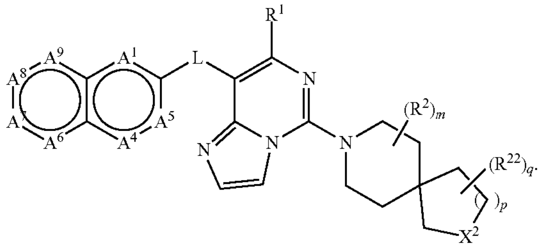

L, $R^1$, $R^2$, $R^{22}$, $X^2$, m, p, and q are as defined above in formula (I), (IIIb), or elsewhere in this disclosure. $A^1$, $A^4$, $A^5$, $A^6$, $A^7$, $A^8$, and $A^9$ are as defined above in formula (III), (IIIa), (IIIb), or elsewhere in this disclosure.

In another aspect, provided are compounds of Formula (IV), or pharmaceutically acceptable salts thereof:

(IV)

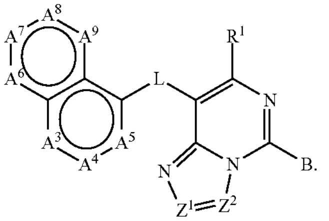

L, $Z^1$, $Z^2$, $R^1$, and B are as defined above in formula (I), or elsewhere in this disclosure. Each $A^3$, $A^4$, $A^5$, $A^6$, $A^7$, $A^8$, and $A^9$ is independently selected from N, $NR^{AA}$, C(O), and $CR^{AA}$; wherein $R^{AA}$ is selected from H and $R^A$.

In another aspect, provided are compounds of Formula (IVa), or pharmaceutically acceptable salts thereof:

(IVa)

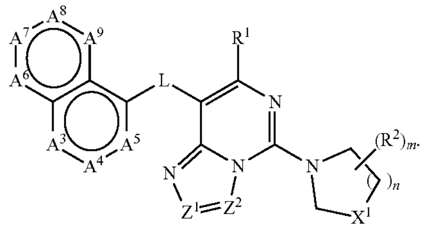

L, $Z^1$, $Z^2$, $R^1$, $R^2$, $X^1$, m, and n are as defined above in formula (I), or elsewhere in this disclosure. $A^3$, $A^4$, $A^5$, $A^6$, $A^7$, $A^8$, and $A^9$ are as defined above in formula (IV), or elsewhere in this disclosure.

In another aspect, provided are compounds of Formula (IVb), or pharmaceutically acceptable salts thereof:

(IVb)

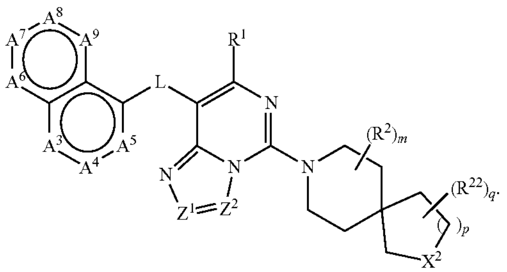

L, $Z^1$, $Z^2$, $R^1$, $R^2$, $X^1$, m, p, and q are as defined above in formula (I), or elsewhere in this disclosure. $A^3$, $A^4$, $A^5$, $A^6$, $A^7$, $A^8$, and $A^9$ are as defined above in formula (IV), (IVa), or elsewhere in this disclosure.

In another aspect, provided are compounds of Formula (IVc), or pharmaceutically acceptable salts thereof:

(IVc)

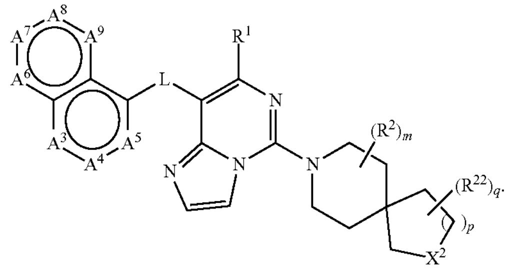

L, $R^1$, $R^2$, $X^2$, m, p, and q are as defined above in formula (I), or elsewhere in this disclosure. $A^3$, $A^4$, $A^5$, $A^6$, $A^7$, $A^8$, and $A^9$ are as defined above in formula (IV), (IVb), or elsewhere in this disclosure.

In another aspect, provided are compounds of Formula (V), or pharmaceutically acceptable salts thereof:

(V)

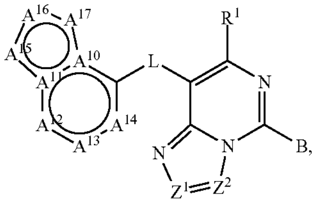

L, $Z^1$, $Z^2$, $R^1$, and B are as defined above in formula (I), or elsewhere in this disclosure. Each $A^{10}$, and $A^{11}$ is independently selected from N and C. Each $A^{12}$, $A^{13}$, and $A^{14}$ is independently selected from N, and $CR^{AA}$; and each $A^{15}$, $A^{16}$, and $A^{17}$ is independently selected from $CR^{AA}$, CO, $NR^{AA}$, O, S, SO, and $SO_2$. $R^{AA}$ is selected from H and $R^A$.

In another aspect, provided are compounds of Formula (Va), or pharmaceutically acceptable salts thereof:

(Va)

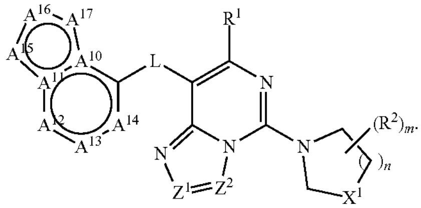

L, $Z^1$, $Z^2$, $R^1$, $R^2$, $X^1$, m, and n are as defined above in formula (I), or elsewhere in this disclosure. $A^{10}$, $A^{11}$, $A^{12}$, $A^{13}$, $A^{14}$, $A^{15}$, $A^{16}$, and $A^{17}$ are as defined above in formula (V), or elsewhere in this disclosure.

In another aspect, provided are compounds of Formula (Vb), or pharmaceutically acceptable salts thereof:

(Vb)

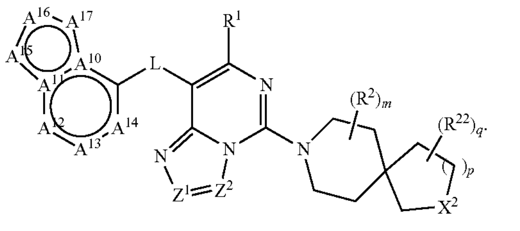

L, $Z^1$, $Z^2$, $R^1$, $R^2$, $R^{22}$, $X^2$, m, p, and q are as defined above in formula (I), or elsewhere in this disclosure. $A^{10}$, $A^{11}$, $A^{12}$, $A^{13}$, $A^{14}$, $A^{15}$, $A^{16}$, and $A^{17}$ are as defined above in formula (V), or elsewhere in this disclosure.

In another aspect, provided are compounds of Formula (Vc), or pharmaceutically acceptable salts thereof:

(Vc)

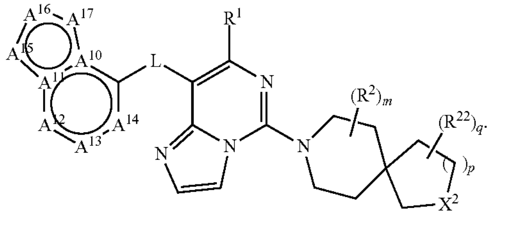

L, $R^1$, $R^2$, $R^{22}$, $X^2$, m, p, and q are as defined above in formula (I), or elsewhere in this disclosure. $A^{10}$, $A^{11}$, $A^{12}$, $A^{13}$, $A^{14}$, $A^{15}$, $A^{16}$, and $A^{17}$ are as defined above in formula (V), or elsewhere in this disclosure.

In another aspect, provided are compounds of Formula (Vc), or pharmaceutically acceptable salts thereof:

(VI)

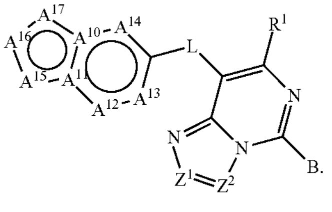

L, $Z^1$, $Z^2$, $R^1$, and B are as defined above in formula (I), or elsewhere in this disclosure. Each $A^{10}$ and $A^{11}$ is independently selected from N and C. Each $A^{12}$, $A^{13}$, and $A^{14}$ is independently selected from N, and $CR^{AA}$. Each $A^{15}$, $A^{16}$, and $A^{17}$ is independently selected from $CR^{AA}$, CO, $NR^{AA}$, O, S, SO, and $SO_2$. $R^{AA}$ is selected from H and $R^A$.

In another aspect, provided are compounds of Formula (VIa), or pharmaceutically acceptable salts thereof:

(VIa)

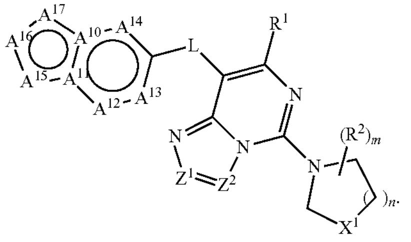

L, $Z^1$, $Z^2$, $R^1$, $R^2$, $X^1$, m, and n are as defined above in formula (I), or elsewhere in this disclosure. $A^{10}$, $A^{11}$, $A^{12}$, $A^{13}$, $A^{14}$, $A^{15}$, $A^{16}$, and $A^{17}$ are as defined above in formula (VI), or elsewhere in this disclosure.

In another aspect, provided are compounds of Formula (VIb), or pharmaceutically acceptable salts thereof:

(VIb)

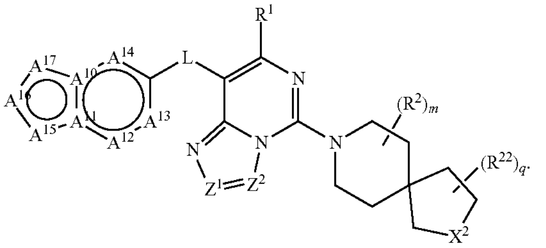

L, $Z^1$, $Z^2$, $R^1$, $R^2$, $R^{22}$, $X^2$, m, and q are as defined above in formula (I), or elsewhere in this disclosure. $A^{10}$, $A^{11}$, $A^{12}$, $A^{13}$, $A^{14}$, $A^{15}$, $A^{16}$, and $A^{17}$ are as defined above in formula (VI), or elsewhere in this disclosure.

In another aspect, provided are compounds of Formula (VIc), or pharmaceutically acceptable salts thereof:

(VIc)

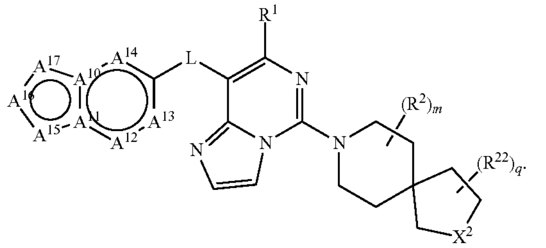

L, $R^1$, $R^2$, $R^{22}$, $X^2$, m, and q are as defined above in formula (I), or elsewhere in this disclosure. $A^{10}$, $A^{11}$, $A^{12}$, $A^{13}$, $A^{14}$, $A^{15}$, $A^{16}$, and $A^{17}$ are as defined above in formula (VI), or elsewhere in this disclosure.

In another aspect, provided are compounds of Formula (VII), or pharmaceutically acceptable salts thereof:

(VII)

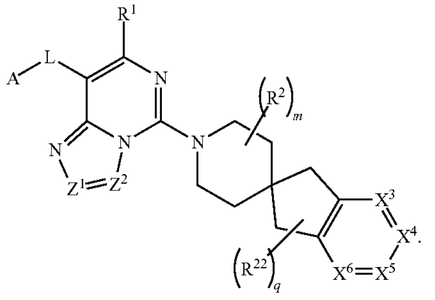

A, L, $Z^1$, $Z^2$, $R^1$, $R^2$, $R^{22}$, m, p, and q are as defined above in formula (I), or elsewhere in this disclosure. Each $X^3$, $X^4$, $X^5$, and $X^6$ is independently selected from $CR^{xx}$, and N. $R^{xx}$ is selected from H, halo, cyano, hydroxyl, azido, nitro, $C_{1-6}$alkyl, $C_{1-6}$haloalkyl, $C_{1-6}$alkoxyl, $C_{1-4}$alkylene-OH, —$SR^{a1}$, —$OR^{a1}$, —$NR^{a1}R^{a2}$, —$COR^{a2}$, —$CONR^{a1}R^{a2}$, —$COOR^{a2}$, —$N(R^{a2})$—$C(O)R^{a2}$, —$N(R^{a2})$—$C(O)OR^{a2}$, —$N(R^{a2})$—C(O)—$NR^{a2}R^{a2}$, —$N(R^{a2})$—$SO_2R^{a2}$, —$SO_2R^{a2}$, —$SO_2OR^{a2}$, —$SO_2NR^{a1}R^{a2}$, —O—$SO_2$—$NR^{a1}R^{a2}$, —O(CO)—$NR^{a1}R^{a2}$, $C_{3-8}$Cycloalkyl, 3-8 membered heterocyclyl, $C_{6-10}$aryl, 5-10 membered heteroaryl, —$C_{1-4}$alkylene-$C_{3-8}$cycloalkyl, —$C_{1-4}$alkylene-(3-8 membered heterocyclyl), —$C_{1-4}$alkylene-$C_{6-10}$aryl, and —$C_{1-4}$alkylene-(5-10 membered heteroaryl).

In some embodiments of formula (I), (II), (IIa), (IIb), (IIc), (IId), (IIg), (IIIa), (IIIa), (IIIb), (IIIc), (IV), (IVa), (IVb), (IVc), (V), (Va), (Vb), (Vc), (VI), (VIa), (VIb), (VIc), or (VII), L is a bond or —S—. In some embodiments, L is a bond. In some embodiments, L is —S—.

In some embodiments of formula (I), or (VII), A is selected from phenyl, naphthyl, pyridinyl, pyridazinyl, pyrazinyl, pyrimidinyl, quinolinyl, indazolyl, indolyl, isoquinolinyl, isoxazolyl, thiophenyl, triazolyl, pyrazolyl, benzothiazolyl, pyridinonyl, quinolinonyl, isoquinolinonyl, quinazolindionyl, pyrazinonyl, pyrimidinonyl, pyrimidinedionyl, pyridazinonyl, quinazolinonyl, benzofuranyl, benzodioxolyl, naphthyridinonyl, chromanyl, isochromanyl, and chromenonyl; and wherein each A is independently optionally substituted with one to six $R^A$.

In some embodiments of formula (I), or (VII), A is selected from:

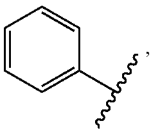 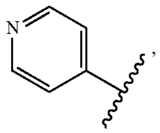 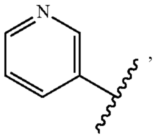

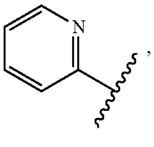 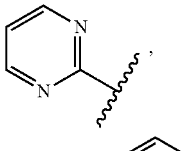 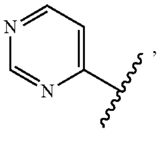

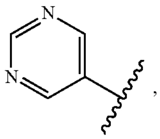 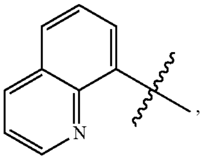

-continued

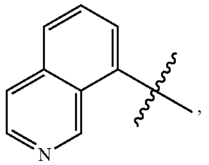 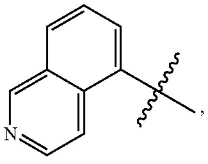

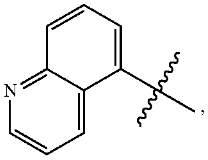 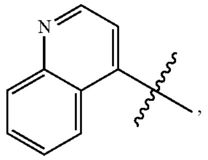

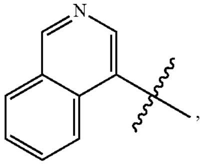 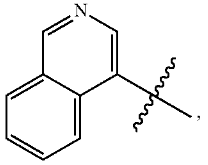

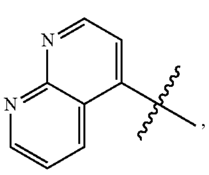 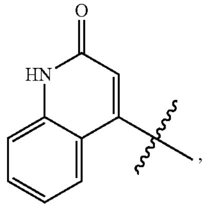

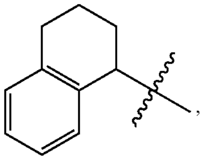 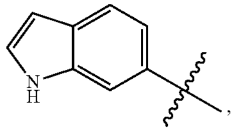

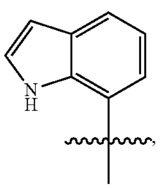 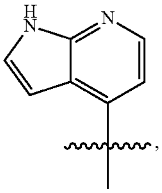 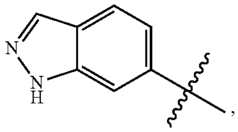

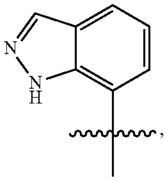 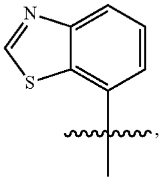 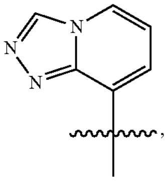

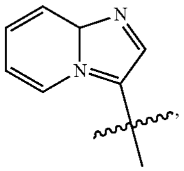 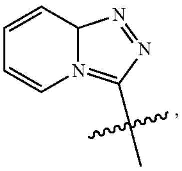 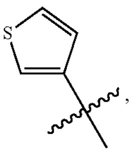

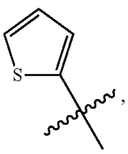 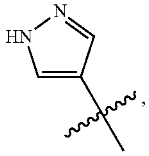 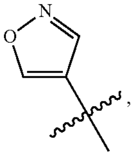 and

-continued

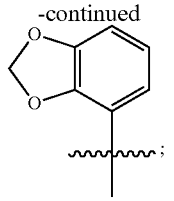

and; wherein each A is independently optionally substituted with one to six $R^A$.

In some embodiments of formula (I), (II), (IIa), (IIb), (IIc), (IId), (IIe), (IIf), (IIg), (III), (IIIa), (IIIb), (IIIc), (IV), (IVa), (IVb), (IVc), (V), (Va), (Vb), (Vc), (VI), (VIa), (VIb), (VIc), or (VII), A is independently substituted with one to three $R^A$, and each $R^A$ is independently selected from halo, $C_{1-4}$alkyl, $C_{1-4}$haloalkyl, and —$NR^{a1}R^{a2}$. In some embodiments, each $R^A$ is independently selected from F, Cl, —$CH_3$, —$CF_3$, and —$NH_2$.

In some embodiments of formula (I), or (VII), wherein "A-L" is selected from:

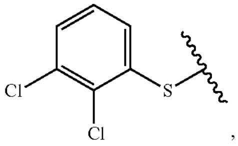, 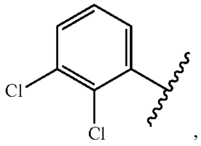, 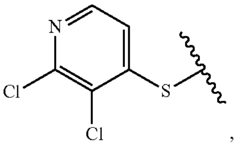, 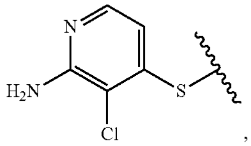, 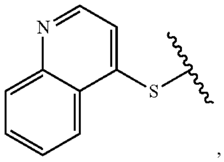, 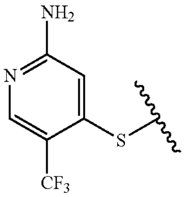, 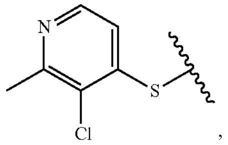, 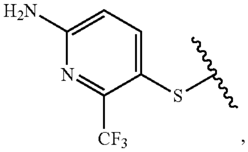, 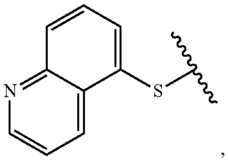, 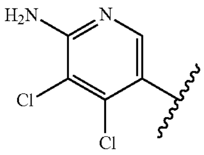, 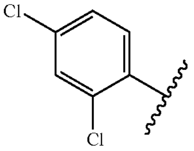, 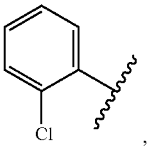, 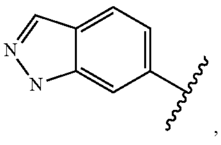, 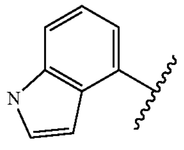, -continued

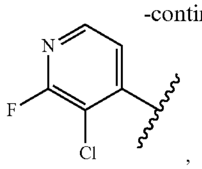, 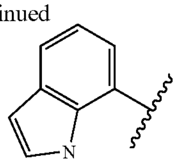, 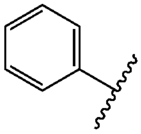, 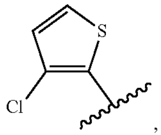, 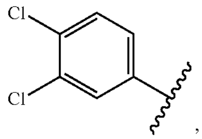, 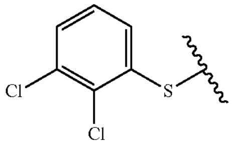, 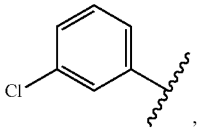, 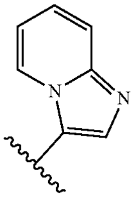, 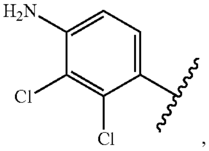, 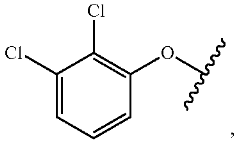, 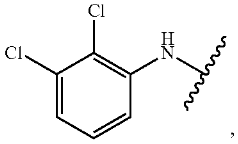, 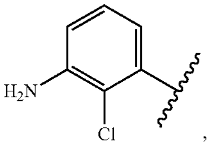, 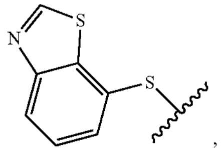, 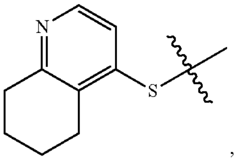, and 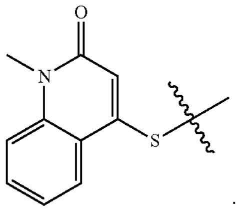.

In some embodiments of formula (I), or (VII), wherein "A-L" is selected from:

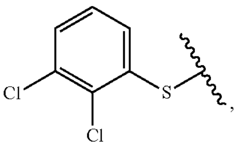, 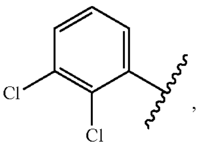, 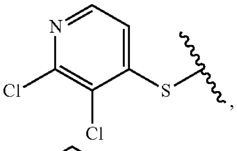, 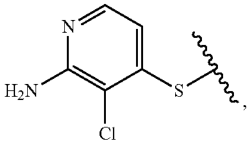, 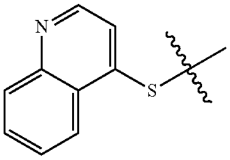, 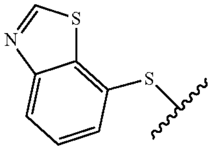, and

-continued

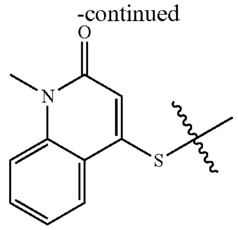

.

In some embodiments of formula (I), (II), (IIa), (IIb), (IIc), (IIg), (III), (IIIa), (IIIb), (IV), (IVa), (IVb), (V), (Va), (Vb), (VI), (VIa), (VIb), or (VII), $Z^1$ and $Z^2$ are $CR^3$. In some embodiments, $Z^1$ and $Z^2$ are CH. In some embodiments, $Z^1$ is N, and $Z^2$ is $CR^3$. In some embodiments, $Z^1$ is $CR^3$, and $Z^2$ is N. In some embodiments, $R^3$ is selected from H, halo, hydroxyl, cyano, $C_{1-4}$alkyl, $C_{1-4}$haloalkyl, $C_{1-4}$alkoxyl, $C_{1-4}$alkylene-OH, —$NR^{c1}R^{c2}$, —C(O)$OR^{c1}$. In some embodiments, $R^3$ is selected from H, F, Cl, CN, OH, —$NH_2$, —$CH_3$, —$CH_2F$, —$CHF_2$, —$CF_3$, —$OCH_3$, and —$OCF_3$. In some embodiments, $R^3$ is Cl.

In some embodiments of formula (I), (II), (IIa), (Ib), (IIc), (IId), (IIe), (IIf), (IIg), (III), (IIIa), (IIIb), (IIIc), (IV), (IVa), (IVb), (Ivc), (V), (Va), (Vb), (Vc), (VI), (VIa), (VIb), (VIc) or (VII), $R^1$ is selected from H, halo, and $C_{1-4}$alkyl. In some embodiments, $R^1$ is selected from Cl, and —$CH_3$. In some embodiments, $R^1$ is Cl.

In some embodiments of formula (I), (II), (IIa), (IIIa), (IVa), (Va), or (VIa), $X^1$ is selected from —$CR^2{}_2$—, —$CHR^2$—, $CH_2$, and O. In some embodiments, $X^1$ is $CH_2$. In some embodiments, $X^1$ is O.

In some embodiments of formula (I), (II), (IIa), (IIIa), (IVa), (Va), or (VIa), n is 1 or 2. In some embodiments, n is 2.

In some embodiments of formula (I), (II), (IIa), (IIIa), (IVa), (Va), or (VIa), m is selected from 0, 1, and 2. In some embodiments, m is 0. In some embodiments, m is 1. In some embodiments, m is 2.

In some embodiments of formula (I), (II), (IIa), (IIb), (IIc), (IId), (IIg), (III), (IIIa), (IIIb), (IIIc), (IV), (IVa), (IVb), (IVc), (V), (Va), (Vb), (Vc), (VI), (VIa), (VIb), (VIc) or (VII), $R^2$ is selected from halo, $C_{1-6}$alkyl, $C_{1-6}$haloalkyl, —$C_{1-4}$alkylene-$NR^{c1}R^{c2}$, and —$NR^{c1}R^{c2}$. In some embodiments, $R^2$ is selected from halo, $C_{1-4}$alkyl, and —$CH_2$—$NR^{c1}R^{c2}$. In some embodiments, $R^2$ is selected from $NH_2$, —$CH_3$, and —$CH_2NH_2$. In some embodiments, $R^2$ is $NH_2$.

In some embodiments of formula (II), (IIa), or (Ib), each $A^1$, $A^2$, $A^3$, $A^4$, and $A^5$ is independently selected from N, and $CR^{AA}$. In some embodiments, $A^1$, $A^2$, $A^3$, $A^4$, and $A^5$ are each $CR^{AA}$. In some embodiments, $A^3$ is N, and $A^1$, $A^2$, $A^4$, and $A^5$ are each $CR^{AA}$. In some embodiments, $A^4$ is N, and $A^1$, $A^2$, $A^3$, and $A^5$ are each $CR^{AA}$. In some embodiments, $A^2$, and $A^4$ are N, and $A^1$, $A^3$, and $A^5$ are each $CR^{AA}$.

In some embodiments of formula (II), (IIa), (Ib), (IIc), (IId), (IIe), (IIf), or (IIg), one of $A^3$, and $A^4$ is N. In some embodiments, $A^3$ is N, and $A^4$ is $CR^{AA}$. In some embodiments, $A^4$ is N, and $A^3$ is $CR^{AA}$.

In some embodiments of formula (III), (IIIa), (IIIb), or (IIIc), at least one of $A^1$, $A^4$, $A^5$, $A^6$, $A^7$, $A^8$, and $A^9$ is N. In some embodiments, at least two of $A^1$, $A^4$, $A^5$, $A^6$, $A^7$, $A^8$, and $A^9$ are N.

In some embodiments of formula (IV), (IVa), (IVb), or (IVc), at least one of $A^3$, $A^4$, $A^5$, $A^6$, $A^7$, $A^8$, and $A^9$ is N. In some embodiments, at least two of $A^3$, $A^4$, $A^5$, $A^6$, $A^7$, $A^8$, and $A^9$ are N. In some embodiments, $A^3$ is N, and $A^4$, $A^5$, $A^6$, $A^7$, $A^8$, and $A^9$ are each $CR^{AA}$. In some embodiments, $A^6$ is N, and $A^3$, $A^4$, $A^5$, $A^7$, $A^8$, and $A^9$ are each $CR^{AA}$.

In some embodiments of formula (V), (Va), (Vb), (Vc), (VI), (VIa), (VIb), or (VIc), at least one of $A^{10}$, $A^{11}$, $A^{12}$, $A^{13}$, $A^{14}$, $A^{15}$, $A^{16}$, and $A^{17}$ is N. In some embodiments, at least two of $A^{10}$, $A^{11}$, $A^{12}$, $A^{13}$, $A^{14}$, $A^{15}$, $A^{16}$, and $A^{17}$ are N. In some embodiments, at least one of $A^{15}$, $A^{16}$, and $A^{17}$ is S. In some embodiments, $A^{17}$ is N, and $A^{10}$, $A^{11}$, $A^{12}$, $A^{13}$, $A^{14}$, $A^{15}$, and $A^{16}$ are each $CR^{AA}$. In some embodiments, $A^{11}$, $A^{16}$ and $A^{17}$ are N, and $A^{10}$, $A^{12}$, $A^{13}$, $A^{14}$, and $A^{15}$ are each $CR^{AA}$.

In some embodiments of formula (V), (Va), (Vb), (Vc), (VI), (VIa), (VIb), or (VIc), at least one of $A^{10}$, $A^{11}$, $A^{12}$, $A^{13}$, $A^{14}$, $A^{15}$, $A^{16}$, and $A^{17}$ is N. In some embodiments, at least two of $A^{10}$, $A^{11}$, $A^{12}$, $A^{13}$, $A^{14}$, $A^{15}$, $A^{16}$, and $A^{17}$ are N. In some embodiments, at least one of $A^{15}$, $A^{16}$, and $A^{17}$ is S. In some embodiments, $A^{17}$ is N, and $A^{10}$, $A^{11}$, $A^{12}$, $A^{13}$, $A^{14}$, $A^{15}$, and $A^{16}$ are each $CR^{AA}$. In some embodiments, $A^{11}$, $A^{16}$ and $A^{17}$ are N, and $A^{10}$, $A^{12}$, $A^{13}$, $A^{14}$, and $A^{15}$ are each $CR^{AA}$. In some embodiments, $A^{16}$ and $A^{17}$ are N, and $A^{10}$, $A^{11}$, $A^{12}$, $A^{13}$, $A^{14}$, and $A^{15}$ are each $CR^{AA}$.

In some embodiments of formula (I), (II), (IIc), (IId), (IIe), (IIf), (IIg), (IIIb), (IIIc), (IV), (IVb), (IVc), (V), (Vb), (Vc), (VI), (VIb), (VIc) or (VII), q is 1 or 2. In some embodiments, q is 1. In some embodiments, q is 2.

In some embodiments of formula (I), (II), (IIc), (IId), (IIe), (IIg), (IIIa), (IIIb), (IIc), (IV), (IVb), (IVc), (V), (Vb), (Vc), or (VI), p is selected from 0, 1, and 2. In some embodiments, p is 1.

In some embodiments of formula (I), (II), (IIc), (IId), (IIe), (IIf), (IIIa), (IIIb), (IIIc), (IV), (IVb), (IVc), (V), (Vb), (Vc), (VI), (VIb), or (VIc), $X^2$ is O or $CH_2$. In some embodiments, $X^2$ is O. In some embodiments, $X^2$ is $CH_2$.

In some embodiments of formula (I), (II), (IIc), (IId), (IIe), (IIf), ((IIg), (IIIa), (IIIb), (IIIc), (IV), (IVb), (IVc), (V), (Vb), (Vc), (VI), (VIb), (VIc), or (VII), each $R^{22}$ is selected from halo, hydroxyl, $C_{1-6}$alkyl, $C_{1-6}$haloalkyl, —$C_{1-4}$alkylene-$NR^{c1}R^{c2}$, and —$NR^{c1}R^{c2}$. In some embodiments, each $R^{22}$ is selected from $CH_3$, and $CH_2NH_2$, $NH_2$, and OH. In some embodiments, $R^{22}$ is $NH_2$.

In some embodiments of formula (I), (II), (IIIa), (IV), (V), and (VI), B is selected from:

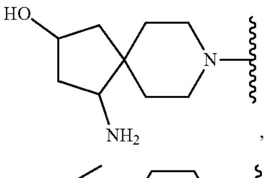

,

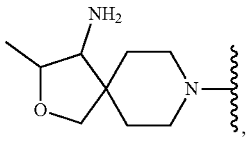

,

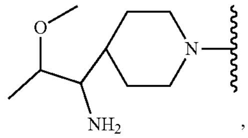

,

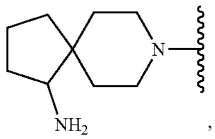

,

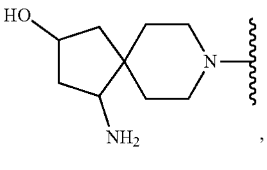

,

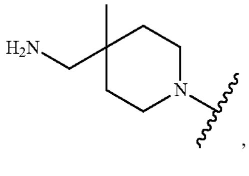

,

-continued

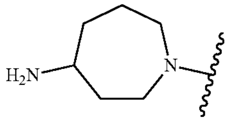,
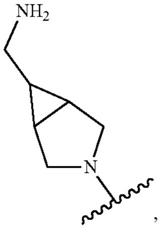,
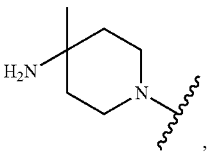,
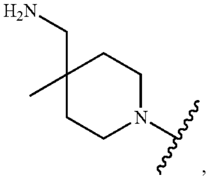,
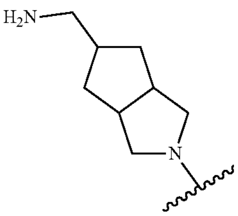,
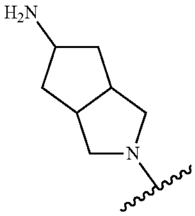,
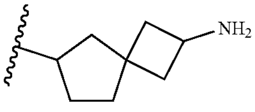,
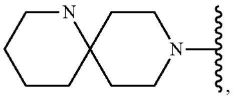,
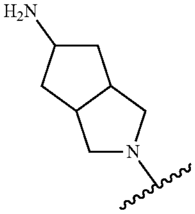,
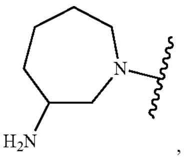, and
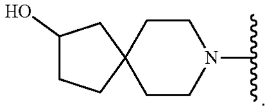.

In some embodiments, B is selected from:

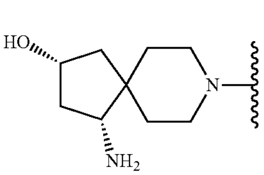,
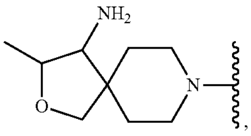,
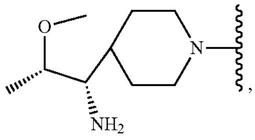,
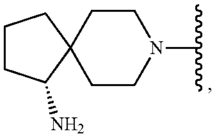,
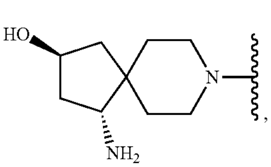,
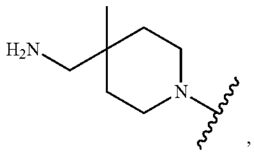,

-continued

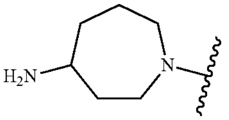,
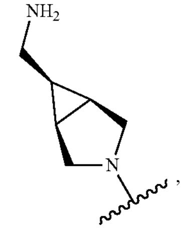,
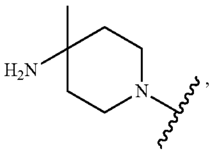,
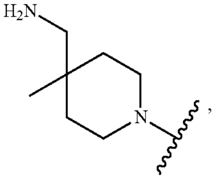,
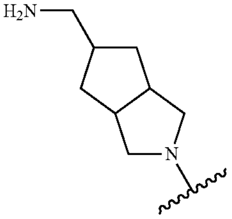,
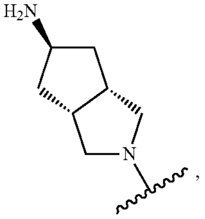,
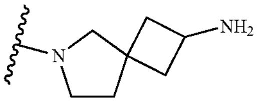,
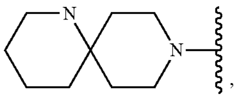,
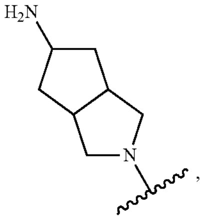,
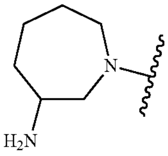, and
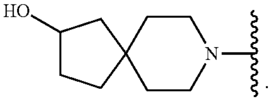.

In some embodiments of formula (VII), $X^3$, $X^4$, $X^5$, and $X^6$ are each $CR^{xx}$. In some embodiments, $X^3$, $X^4$, $X^5$, and $X^6$ are each CH. In some embodiments, at least one of $X^3$, $X^4$, $X^5$, and $X^6$ is N.

In some embodiments, the compound of the present disclosure is selected from examples 1-86.

In some embodiments, the compound of the present disclosure is selected from examples 87-149.

In some embodiments, the compound of the present disclosure is selected from:

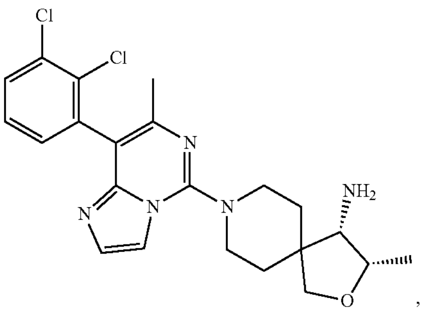,

-continued
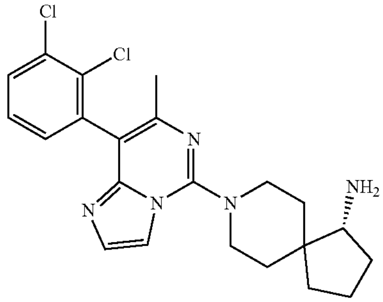
,
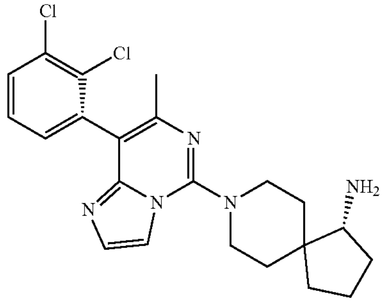
,
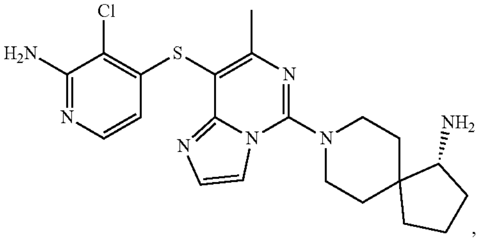
,
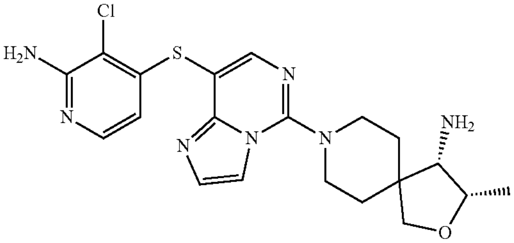
,
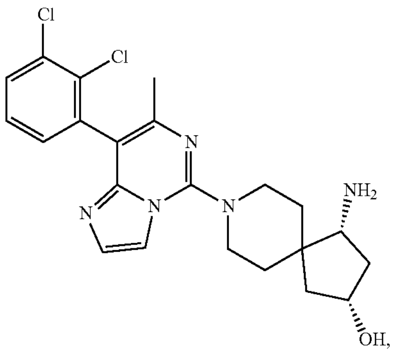
-continued
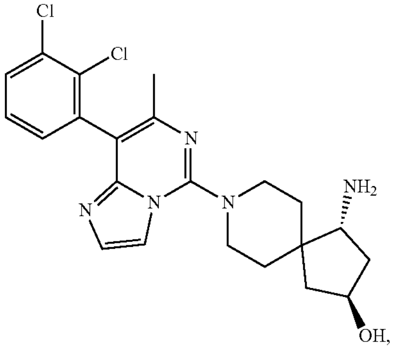
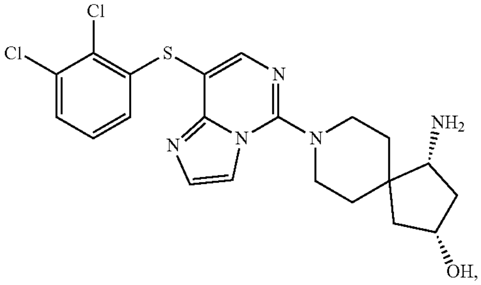
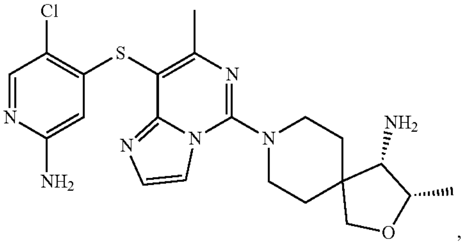
,
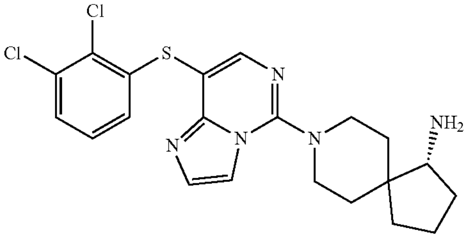
,
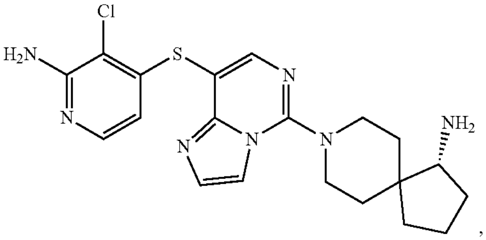
,
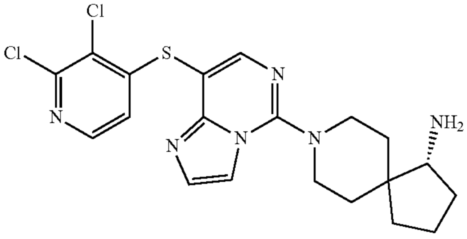
, -continued
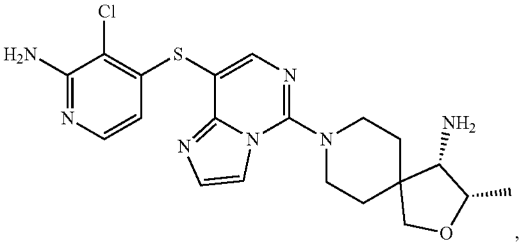
,
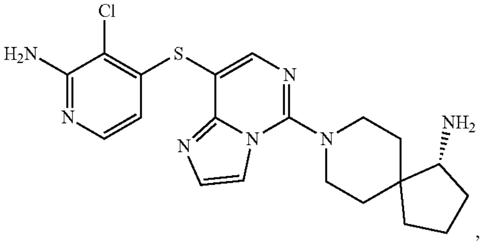
,
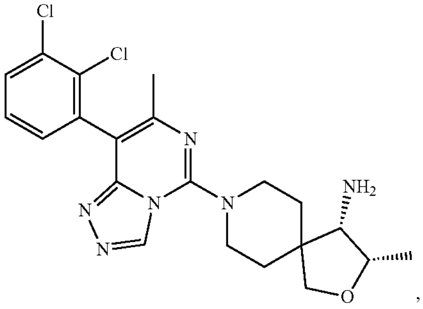
,
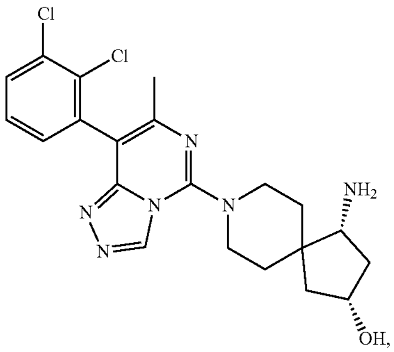
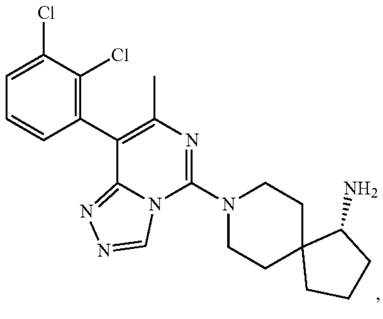
,
-continued
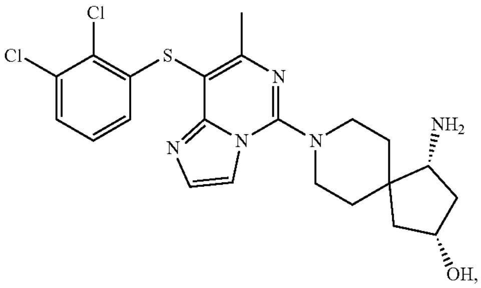
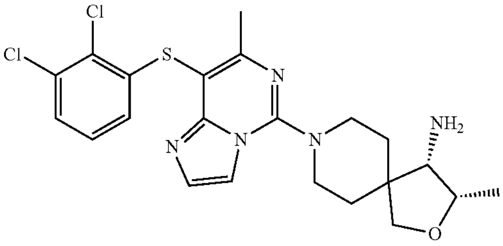
,
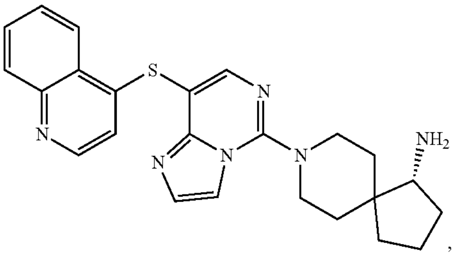
, and
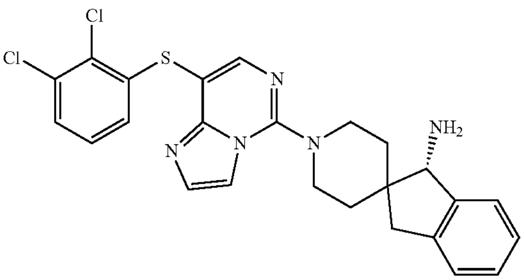
In some embodiments, the compound of the present disclosure is selected from:
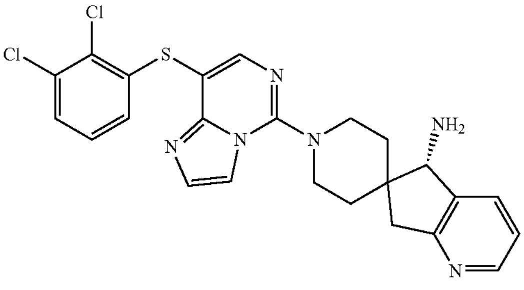
, and -continued

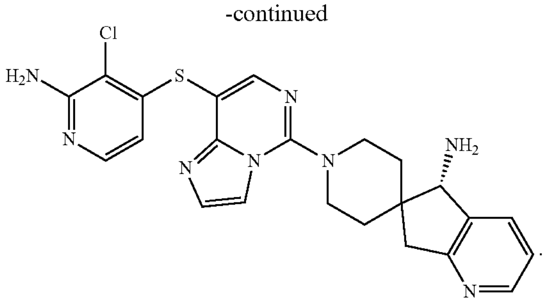

In some embodiments, provided is a pharmaceutical composition comprising a compound of the present disclosure and at least one pharmaceutically acceptable carrier.

In some embodiments, provided is a method for treating a disease or condition associated with SHP2 modulation comprising administrating to a subject an effective amount of the compound of the present disclosure or a pharmaceutically acceptable salt thereof, or a composition of the present disclosure. In some embodiments, the disease or condition is selected from Noonan Syndrome, Leopard Syndrome, juvenile myelomonocytic leukemias (JMML), neuroblastoma, melanoma, acute myeloid leukemia (AML), myelodysplastic syndrome (MDS), B cell acute lymphoblastic leukemia (B-ALL), breast cancer, esophageal cancer, lung cancer, colon cancer, head cancer, gastric carcinoma, squamous-cell carcinoma of the head and neck, anaplastic large-cell lymphoma and glioblastoma. In some embodiments, the method further comprises administration of an additional therapeutic compound.

In some embodiments, provided is a use of a compound of the present disclosure, or a pharmaceutical composition of the present disclosure, in the manufacture of a medicament for treating a disease or condition associated with SHP2 modulation. In some embodiments, provided is a use of the pharmaceutical composition of the present disclosure for use in treating or preventing a disease associated with SHP2 modulation.

Provided are also compounds described herein or pharmaceutically acceptable salts, isomer, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

In certain embodiments, provided are optical isomers, racemates, or other mixtures thereof of the compounds described herein or pharmaceutically acceptable salts or a mixture thereof. In those situations, the single enantiomer or diastereomer, i.e., optically active form, can be obtained by asymmetric synthesis or by resolution of the racemate. Resolution of racemates can be accomplished, for example, by conventional methods such as crystallization in the presence of a resolving agent, or chromatography, using, for example a chiral high pressure liquid chromatography (HPLC) column. In addition, provided are also Z- and E-forms (or cis- and trans-forms) of the hydroxyamidine compounds described herein. Specifically, Z- and E-forms are included even if only one designation is named for both carbon-carbon double bonds as well as the hydroxyamidine bond.

Where chirality is not specified but is present, it is understood that the embodiment is directed to either the specific diastereomerically or enantiomerically enriched form; or a racemic or scalemic mixture of such compound (s).

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

In certain embodiments, provided herein are also crystalline and amorphous forms of the compounds described herein or pharmaceutically acceptable salts, isomer, or a mixture thereof.

In certain embodiments, provided are also chelates, non-covalent complexes, and mixtures thereof, of the compounds described herein or pharmaceutically acceptable salts, isomer, or a mixture thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

Compositions and Kits

Compounds provided herein are usually administered in the form of pharmaceutical compositions. Thus, provided herein are also pharmaceutical compositions that comprise one or more of the compounds provided herein or pharmaceutically acceptable salts, isomer, or a mixture thereof and one or more pharmaceutically acceptable vehicles selected from carriers, adjuvants and excipients. The compounds provided herein may be the sole active ingredient or one of the active ingredients of the pharmaceutical compositions. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

In one aspect, provided herein are pharmaceutical compositions comprising a compound provided, or a pharmaceutically acceptable salt thereof, and a pharmaceutically acceptable excipient or carrier. In some embodiments, the pharmaceutical compositions comprise a therapeutically effective amount of a compound provided herein, or a pharmaceutically acceptable salt thereof, and a pharmaceutically acceptable excipient or carrier.

In some embodiments, the pharmaceutical compositions provided herein further comprise one or more (e.g., one, two, three, four, one or two, one to three, or one to four) additional therapeutic agents, or a pharmaceutically acceptable salt thereof. In some embodiments, the pharmaceutical compositions further comprise a therapeutically effective amount of the one or more (e.g., one, two, three, four, one or two, one to three, or one to four) additional therapeutic agents, or a pharmaceutically acceptable salt thereof.

In some embodiments, the one or more additional therapeutic agents include agents that are therapeutic for a hepatitis B virus (HBV) infection, human immunodeficiency virus (HIV) infection, cancer, or a hyper-proliferative disease. In some embodiments, agents that are therapeutic for cancer or hyper-proliferative disease include PD1 inhibitors and/or PDL1 inhibitors.

In some embodiments, the one or more additional therapeutic agents is selected from the group consisting of: adefovir (Hepsera®), tenofovir disoproxil fumarate+emtricitabine (Truvada®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (Axxo), Alfaferone, interferon alfa-2b, Feron, interferon-alpha 2 (CJ), Bevac, Laferonum, Vipeg, Blauferon-B, Blauferon-A, Intermax Alpha, Realdiron, Lanstion, Pegaferon, PDferon-B, alfainterferona 2b, Kalferon, Pegnano, Feronsure, PegiHep, Optipeg A, Realfa 2B, Reliferon, peginterferon alfa-2b, Reaferon-EC, Proquiferon, Uniferon, Urifron, interferon alfa-2b, Anterferon, Shanferon, MOR-22, interleukin-2 (IL-2), recombinant human interleukin-2 (Shenzhen Neptunus), Layfferon, Ka Shu Ning, Shang Sheng Lei Tai, Intefen, Sinogen, Fukangtai, Alloferon and celmoleukin, or a pharmaceutically acceptable salt of any of the foregoing, or any combinations thereof.

In some embodiments, the one or more additional therapeutic agents is selected from the group consisting of: 4'-ethynyl-2-fluoro-2'-deoxyadenosine, bictegravir or a pharmaceutically acceptable salt thereof, abacavir sulfate, tenofovir, tenofovir disoproxil, tenofovir disoproxil fumarate, tenofovir disoproxil hemifumarate, tenofovir alafenamide, tenofovir alafenamide hemifumarate, emtricitabine, and lamivudine, or a pharmaceutically acceptable salt of any of the foregoing, or any combinations thereof.

In some embodiments, the one or more additional therapeutic agents is selected from the group consisting of: nivolumab, lambrolizumab, pembrolizumab, pidilizumab, PDR001, TSR-001, atezolizumab, durvalumab, or avelumab, or a pharmaceutically acceptable salt of any of the foregoing, or any combinations thereof.

In some embodiments, the one or more additional therapeutic agents is selected from the group consisting of: rituxan, doxorubicin, gemcitabine, pidilizumab, TSR-042, BMS-986016, ruxolitinib, N-(cyanomethyl)-4-[2-(4-morpholinoanilino)pyrimidin-4-yl]benzamide, XL147, BKM120, GDC-0941, BAY80-6946, PX-866, CH5132799, XL756, BEZ235, and GDC-0980, wortmannin, LY294002, PI3K II, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, ZSTK474, AS252424, TGX221, TG100115, IC87114, IPI-549, INCB050465, (S)-2-(1-((9H-purin-6-yl)amino)propyl)-5-fluoro-3-phenylquinazolin-4(3H)-one, (S)-2-(1-((9H-purin-6-yl)amino)ethyl)-6-fluoro-3-phenylquinazolin-4(3H)-one, (S)-2-(1-((9H-purin-6-yl)amino)ethyl)-3-(2,6-difluorophenyl)quinazolin-4(3H)-one, (S)-4-amino-6-((1-(5-chloro-4-oxo-3-phenyl-3,4-dihydroquinazolin-2-yl)ethyl)amino)pyrimidine-5-carbonitrile, and ipilimumab, or a pharmaceutically acceptable salt of any of the foregoing, or any combinations thereof.

In some embodiments, the one or more additional therapeutic agents is selected from the group consisting of idelalisib, tirabrutinib, momelotinib, and entospletinib, or a pharmaceutically acceptable salt of any of the foregoing, or any combinations thereof.

The pharmaceutical compositions may be administered in either single or multiple doses. The pharmaceutical compositions may be administered by various methods including, for example, rectal, buccal, intranasal and transdermal routes. In some embodiments, the pharmaceutical compositions may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds provided herein. Administration may be via, for example, capsule or enteric coated tablets. In making the pharmaceutical compositions that include at least one compound provided herein or pharmaceutically acceptable salts, isomer, or a mixture thereof, the active ingredient (such as a compound provided herein) is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose or any combinations thereof. The pharmaceutical compositions can additionally include lubricating agents such as talc, magnesium stearate, and mineral oil; wetting agents; emulsifying and suspending agents; preserving agents such as methyl and propylhydroxy-benzoates; sweetening agents; and flavoring agents; or any combinations thereof.

The pharmaceutical compositions that include at least one compound described herein or pharmaceutically acceptable salts, isomer, or a mixture thereof can be formulated so as to provide quick, sustained or delayed release of the active ingredient (such as a compound provided herein) after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds provided herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or pharmaceutically acceptable salts, isomer, or a mixture thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with materials such as shellac, cetyl alcohol, and cellulose acetate.

Pharmaceutical compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In one aspect, provided herein are kits that comprise a compound provided herein, or a pharmaceutically acceptable salt, stereoisomer, prodrug, or solvate thereof, and suitable packaging. In some embodiments, the kit further comprises instructions for use. In some embodiments, the kit comprises a compound provided herein, or a pharmaceutically acceptable salt, stereoisomer, prodrug, or solvate thereof, and a label and/or instructions for use of the compounds in the treatment of the indications, including the diseases or conditions, described herein.

In some embodiments, the kits further comprise one or more (e.g., one, two, three, four, one or two, one to three, or one to four) additional therapeutic agents, or a pharmaceutically acceptable salt thereof.

In one aspect, provided herein are articles of manufacture that comprise a compound described herein or pharmaceutically acceptable salts, isomer, or a mixture thereof in a suitable container. In some embodiments, the container may be a vial, jar, ampoule, preloaded syringe, or intravenous bag.

Methods

The methods provided herein may be applied to cell populations in vivo or ex vivo. "In vivo" means within a living individual, as within an animal or human. In this context, the methods provided herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the present disclosure may be used for a variety of purposes, including therapeutic and experimental purposes. For example, the present disclosure may be used ex vivo to determine the optimal schedule and/or dosing of administration of a SHP-2 inhibitor for a given indication, cell type, individual, and other parameters. Information gleaned from such use may be used for experimental purposes or in the clinic to set protocols for in vivo treatment. Other ex vivo uses for which the present disclosure may be suited are described below or will become apparent to those skilled in the art. The selected compounds may be further characterized to examine the safety or tolerance dosage in human or non-human subjects. Such properties may be examined using commonly known methods to those skilled in the art.

In one aspect, the present disclosure provides methods of inhibiting SHP-2 activity in a subject in need thereof, comprising administering to the subject a therapeutically effective amount of a compound provided herein, or a pharmaceutically acceptable salt thereof, or a pharmaceutical composition provided herein.

In one aspect, the present disclosure provides methods of treating a disease or disorder associated with SHP-2 activity in a subject in need thereof, comprising administering to the subject a therapeutically effective amount of a compound provided herein, or a pharmaceutically acceptable salt thereof, or a pharmaceutical composition provided herein.

In one aspect, the present disclosure provides methods of increasing T-cell activation in a subject in need thereof, comprising administering to the subject a therapeutically effective amount of a compound provided herein, or a pharmaceutically acceptable salt thereof, or a pharmaceutical composition provided herein.

In one aspect, the present disclosure provides methods of treating a disease or disorder associated with SHP-2 modulation in a subject in need thereof, comprising administering to the subject a therapeutically effective amount of a compound provided herein, or a pharmaceutically acceptable salt thereof, or a pharmaceutical composition provided herein.

In some embodiments, the disease or disorder associated with SHP-2 modulation is Noonan Syndrome, or Leopard Syndrome.

In one aspect, the present disclosure provides methods of treating cancer in a subject in need thereof, comprising administering to the subject a therapeutically effective amount of a compound provided herein, or a pharmaceutically acceptable salt thereof, or a pharmaceutical composition provided herein.

In some embodiments, the cancer is selected from the group consisting of bladder cancer, breast cancer, colorectal cancer, gastric cancer, head and neck squamous cell carcinoma, Hodgkin lymphoma, Merkel-cel carcinoma, mesothelioma, melanoma, non-small cell lung cancer, lung cancer, ovarian cancer, pancreatic cancer, prostate cancer, renal cell carcinoma, small cell lung cancer, transitional cell carcinoma, juvenile myelomonocytic leukemia's, neuroblastoma, acute myeloid leukemia, glioblastoma, esophageal cancer, colon cancer, head cancer, anaplastic large-cell lymphoma, and urothelial cancer.

In one aspect, the present disclosure provides methods of inhibiting the growth or proliferation of cancer cells in a subject in need thereof, comprising administering to the subject a therapeutically effective amount of a compound provided herein, or a pharmaceutically acceptable salt thereof, or a pharmaceutical composition provided herein.

In some embodiments, the above methods further comprise administering a therapeutically effective amount of one or more additional therapeutic agents, or a pharmaceutically acceptable salt thereof.

In some embodiments, the one or more additional therapeutic agents is selected from the group consisting of: Inducible T-cell costimulator (ICOS) agonists, cytotoxic T-lymphocyte antigen 4 (CTLA-4)-blocking antibodies, PD1 and/or PD-L1 inhibitors, Cluster of Differentiation 47 (CD47) inhibitors, OX40 agonists, GITR agonists, CD27 agonists, CD28 agonists, CD40 agonists, CD137 agonists, Toll-like receptor 8 (TLR8) agonists, T cell immunoglobulin and mucin domain-3 (TIM-3) inhibitors, lymphocyte activation gene 3 (LAG-3) inhibitors, CEACAM1 inhibitors, T cell immunoreceptor with Ig and ITIM domains (TIGIT) inhibitors, V-domain immunoglobulin (Ig)-containing suppressor of T-cell activation (VISTA) inhibitors, anti-Killer IgG-like receptors (KIR) inhibitors, STING agonists, C—X—C chemokine receptor type 4 (CXCR-4) inhibitors, B7-H3 inhibitors, CD73 inhibitors, inhibitory RNA, IL2/15/17 fusion proteins, MKNK1/2 inhibitors, JAK inhibitors, and PI3K inhibitors, or a pharmaceutically acceptable salt of any of the foregoing, or any combinations thereof.

In some embodiments, the one or more additional therapeutic agents is selected from the group consisting of: rituxan, doxorubicin, gemcitabine, nivolumab, pembrolizumab, pidilizumab, PDR001, TSR-001, atezolizumab, durvalumab, avelumab, pidilizumab, TSR-042, BMS-986016, ruxolitinib, N-(cyanomethyl)-4-[2-(4-morpholinoanilino) pyrimidin-4-yl]benzamide, XL147, BKM120, GDC-0941, BAY80-6946, PX-866, CH5132799, XL756, BEZ235, and GDC-0980, wortmannin, LY294002, PI3K II, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, ZSTK474, AS252424, TGX221, TG100115, IC87114, IPI-549, INCB050465, (S)-2-(1-((9H-purin-6-yl)amino)propyl)-5-fluoro-3-phenylquinazolin-4(3H)-one, (S)-2-(1-((9H-purin-6-yl)amino)ethyl)-6-fluoro-3-phenylquinazolin-4(3H)-one, (S)-2-(1-((9H-purin-6-yl)amino)ethyl)-3-(2,6-difluorophenyl)quinazolin-4(3H)-one, (S)-4-amino-6-((1-(5-chloro-4-oxo-3-phenyl-3,4-dihydroquinazolin-2-yl) ethyl)amino)pyrimidine-5-carbonitrile, and ipilimumab, or a pharmaceutically acceptable salt of any of the foregoing, or any combinations thereof.

In some embodiments, the one or more additional therapeutic agents is selected from the group consisting of idelalisib, tirabrutinib, momelotinib, and entospletinib, or a pharmaceutically acceptable salt of any of the foregoing, or any combinations thereof.

In one aspect, the present disclosure provides methods of treating or preventing a hepatitis B virus (HBV) infection in a subject in need thereof, comprising administering to the subject a therapeutically effective amount of a compound provided herein, or a pharmaceutically acceptable salt thereof, or a pharmaceutical composition provided herein.

In some embodiments, the method of treating or preventing a HBV infection further comprises administering a therapeutically effective amount of one or more additional therapeutic agents, or a pharmaceutically acceptable salt thereof.

In some embodiments, the one or more additional therapeutic agents is selected from the group consisting of HBV combination drugs, HBV vaccines, HBV DNA polymerase inhibitors, immunomodulators, toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucelotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1 agonists, Bruton's tyrosine kinase (BTK) inhibitors, KDM inhibitors, HBV replication inhibitors, arginase inhibitors, and other HBV drugs, or a pharmaceutically acceptable salt of any of the foregoing, or any combinations thereof.

In some embodiments, the one or more additional therapeutic agents is selected from the group consisting of adefovir (Hepsera®), tenofovir disoproxil fumarate+emtricitabine (Truvada®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (Axxo), Alfaferone, interferon alfa-2b, Feron, interferon-alpha 2 (CJ), Bevac, Laferonum, Vipeg, Blauferon-B, Blauferon-A, Intermax Alpha, Realdiron, Lanstion, Pegaferon, PDferon-B, alfainterferona 2b, Kalferon, Pegnano, Feronsure, PegiHep, Optipeg A, Realfa 2B, Reliferon, peginterferon alfa-2b, Reaferon-EC, Proquiferon, Uniferon, Urifron, interferon alfa-2b, Anterferon, Shanferon, MOR-22, interleukin-2 (IL-2), recombinant human interleukin-2 (Shenzhen Neptunus), Layfferon, Ka Shu Ning, Shang Sheng Lei Tai, Intefen, Sinogen, Fukangtai, Alloferon and celmoleukin, or a pharmaceutically acceptable salt of any of the foregoing, or any combinations thereof.

In some embodiments, the one or more additional therapeutic agents is selected from the group consisting of entecavir, adefovir, tenofovir disoproxil fumarate, tenofovir alafenamide, tenofovir, tenofovir disoproxil, tenofovir alafenamide fumarate, tenofovir alafenamide hemifumarate, telbivudine and lamivudine, or a pharmaceutically acceptable salt of any of the foregoing, or any combinations thereof.

In some embodiments, the one or more additional therapeutic agents is selected from the group consisting of tenofovir alafenamide, tenofovir alafenamide fumarate, and tenofovir alafenamide hemifumarate, or a pharmaceutically acceptable salt of any of the foregoing, or any combinations thereof.

In one aspect, the present disclosure provides methods of treating or preventing a human immunodeficiency virus (HIV) infection in a subject in need thereof, comprising administering to the subject a therapeutically effective amount of a compound provided herein, or a pharmaceutically acceptable salt thereof, or a pharmaceutical composition provided herein.

In some embodiments, the method of treating or preventing a HIV infection further comprises administering a therapeutically effective amount of one or more additional therapeutic agents, or a pharmaceutically acceptable salt thereof.

In some embodiments, the one or more additional therapeutic agents is selected from the group consisting of: combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or a pharmaceutically acceptable salt of any of the foregoing, or any combinations thereof.

In some embodiments, the one or more additional therapeutic agents is selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or a pharmaceutically acceptable salt of any of the foregoing, or any combinations thereof.

In some embodiments, the one or more additional therapeutic agents is selected from the group consisting of 4'-ethynyl-2-fluoro-2'-deoxyadenosine, bictegravir, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt of any of the foregoing, or any combinations thereof.

In some embodiments, the one or more additional therapeutic agents is selected from the group consisting of 4'-ethynyl-2-fluoro-2'-deoxyadenosine, bictegravir, tenofovir alafenamide, tenofovir alafenamide fumarate and tenofovir alafenamide hemifumarate, or a pharmaceutically acceptable salt of any of the foregoing, or any combinations thereof.

In some embodiments, the one or more additional therapeutic agents is selected from the group consisting of 4'-ethynyl-2-fluoro-2'-deoxyadenosine, bictegravir, tenofovir disoproxil, tenofovir disoproxil hemifumarate, and tenofovir disoproxil fumarate, or a pharmaceutically acceptable salt of any of the foregoing, or any combinations thereof.

In some embodiments, the one or more additional therapeutic agents is selected from the group consisting of emtricitabine and lamivudine, or a pharmaceutically acceptable salt of each thereof.

In some embodiments, the one or more additional therapeutic agents is emtricitabine or a pharmaceutically acceptable salt thereof.

In some embodiments, the method of treating or preventing a HIV infection further comprises administering one or more additional therapeutic agents selected from the group consisting of 4'-ethynyl-2-fluoro-2'-deoxyadenosine, bictegravir, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt of any of the foregoing, or any combinations thereof, and further comprises administering another therapeutic agent selected from the group consisting of emtricitabine and lamivudine, or a pharmaceutically acceptable salt of each thereof.

In some embodiments, the method of treating or preventing a HIV infection further comprises administering one or more additional therapeutic agents selected from the group consisting of 4'-ethynyl-2-fluoro-2'-deoxyadenosine, bictegravir, tenofovir alafenamide, and tenofovir alafenamide hemifumarate, or a pharmaceutically acceptable salt of any of the foregoing, or any combinations thereof, and further comprises administering another therapeutic agent selected from the group consisting of emtricitabine and lamivudine, or a pharmaceutically acceptable salt of each thereof.

In some embodiments, the method of treating or preventing a HIV infection further comprises administering one or more additional therapeutic agents selected from the group consisting of 4'-ethynyl-2-fluoro-2'-deoxyadenosine, bictegravir, tenofovir disoproxil, tenofovir disoproxil fumarate, and tenofovir disoproxil hemifumarate, or a pharmaceutically acceptable salt of any of the foregoing, or any combinations thereof, and further comprises administering another therapeutic agent selected from the group consisting of emtricitabine and lamivudine, or a pharmaceutically acceptable salt thereof.

In some embodiments, the methods described herein comprise administering a therapeutically effective amount of a compound provided herein, or a pharmaceutically acceptable salt thereof. In some embodiments, the methods described herein comprise administering a therapeutically effective amount of a pharmaceutical composition provided herein.

Administration

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In some embodiments, the compound is administered on a daily or intermittent schedule for the duration of the individual's life.

The specific dose level of a compound of the present disclosure for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound provided herein, or a pharmaceutically acceptable salt or pharmaceutically acceptable tautomer thereof, may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

The dosage or dosing frequency of a compound of the present disclosure may be adjusted over the course of the treatment, based on the judgment of the administering physician.

The compounds of the present disclosure may be administered to an individual (e.g., a human) in a therapeutically effective amount. In some embodiments, the compound is administered once daily.

The compounds provided herein can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day. In some embodiments, a therapeutically effective amount of the compounds provided herein include from about 0.3 mg to about 30 mg per day, or from about 30 mg to about 300 mg per day, or from about 0.3 μg to about 30 mg per day, or from about 30 μg to about 300 μg per day.

A compound of the present disclosure may be combined with one or more additional therapeutic agents in any dosage amount of the compound of the present disclosure (e.g., from 1 mg to 1000 mg of compound). Therapeutically effective amounts may include from about 0.1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose, or such as from about 0.01 mg per dose to about 1000 mg per dose, or such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose, or such as from about 1 mg per dose to about 1000 mg per dose. Other therapeutically effective amounts of the compound provided herein are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of the present disclosure are about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 mg per dose.

In some embodiments, the methods described herein comprise administering to the subject an initial daily dose of about 1 to 500 mg of a compound p herein and increasing the dose by increments until clinical efficacy is achieved. Increments of about 5, 10, 25, 50, or 100 mg can be used to increase the dose. The dosage can be increased daily, every other day, twice per week, once per week, once every two weeks, once every three weeks, or once a month.

When administered orally, the total daily dosage for a human subject may be between about 1 mg and 1,000 mg, between about 10-500 mg/day, between about 50-300 mg/day, between about 75-200 mg/day, or between about 100-150 mg/day.

A single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound disclosed herein is administered once daily in a method disclosed herein. In some embodiments, a compound disclosed herein is administered twice daily in a method disclosed herein.

The frequency of dosage of the compound of the present disclosure will be determined by the needs of the individual patient and can be, for example, once per day or twice, or more times, per day. Administration of the compound continues for as long as necessary to treat the HBV infection, HIV infection, cancer, hyper-proliferative disease, or any other indication described herein. For example, a compound can be administered to a human being infected with HBV for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

The compounds of the present disclosure or the pharmaceutical compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

Combination Therapy

In some embodiments, a compound of the present disclosure, or a pharmaceutically acceptable salt thereof, is combined with one, two, three, four or more additional therapeutic agents. In some embodiments, a compound of the present disclosure, or a pharmaceutically acceptable salt thereof, is combined with two additional therapeutic agents. In some embodiments, a compound of the present disclosure, or a pharmaceutically acceptable salt thereof, is combined with three additional therapeutic agents. In some embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In some embodiments, when a compound of the present disclosure is combined with one or more additional therapeutic agents as described herein, the components of the composition are administered as a simultaneous or sequential regimen. When administered sequentially, the combination may be administered in two or more administrations.

In some embodiments, a compound of the present disclosure is combined with one or more additional therapeutic agents in a unitary dosage form for simultaneous administration to a patient, for example as a solid dosage form for oral administration.

In some embodiments, a compound of the present disclosure is co-administered with one or more additional therapeutic agents.

Co-administration includes administration of unit dosages of the compounds disclosed herein before or after administration of unit dosages of one or more additional therapeutic agents. The compounds disclosed herein may be administered within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In some embodiments a compound provided herein, is formulated as a tablet, which may optionally contain one or more other compounds useful for treating the disease being treated. In certain embodiments, the tablet can contain another active ingredient for treating a HBV infection, HIV infection, cancer, or a hyper-proliferative disease. In some embodiments, such tablets are suitable for once daily dosing.

Also provided herein are methods of treatment in which a compound provided herein or a tautomer or pharmaceutically acceptable salt thereof, is given to a patient in combination with one or more additional therapeutic agents or therapy.

HIV Combination Therapy

In certain embodiments, a method for treating or preventing an HIV infection in a human or animal having or at risk of having the infection is provided, comprising administering to the human or animal a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human or animal having or at risk of having the infection is provided, comprising administering to the human or animal a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent, or excipient are provided.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, the compounds disclosed herein are formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, or any combinations thereof.

In certain embodiments, such tablets are suitable for once daily dosing.

In some embodiments, the additional therapeutic agent may be an anti-HIV agent. In some embodiments, the additional therapeutic agent is selected from the group consisting of HIV combination drugs, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T), latency reversing agents, compounds that target the HIV capsid (including capsid inhibitors), immune-based therapies, phosphatidylinositol 3-kinase (PI3K) inhibitors, alpha-4/beta-7 antagonists, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and other HIV therapeutic agents, or any combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, or any combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY® (bictegravir, emtricitabine, tenofovir alafenamide); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; Vacc-4x and romidepsin; and APH-0812, or any combinations thereof.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, ACC-007, AIC-292, KM-023, PC-1005, and VM-1500.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, MK-8504 and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs.

Examples of gp120 inhibitors include Radha-108 (receptol) 3B3-PE38, BanLec, bentonite-based nanomedicine, fostemsavir tromethamine, IQP-0831, and BMS-663068.

Examples of CXCR4 inhibitors include plerixafor, ALT-1188, N15 peptide, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), AM-0015, ALT-803, NIZ-985, NKTR-255, IL-15 modulating antibodies, JQ1, disulfiram, amphotericin B, and ubiquitin inhibitors such as largazole analogs, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series.

Immune-Based Therapies

Examples of immune-based therapies include toll-like receptors modulators such as TLR1, TLR2, TLR3, TLR4, TLR5, TLR6, TLR7, TLR8, TLR9, TLR10, TLR11, TLR12, and TLR13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107; interleukin-15/Fc fusion protein; normferon; peginterferon alfa-2a; peginterferon alfa-2b; recombinant interleukin-15; RPI-MN; GS-9620; STING modulators; RIG-I modulators; NOD2 modulators; and IR-103.

Examples of TLR8 modulators include motolimod, resiquimod, 3M-051, 3M-052, MCT-465, IMO-4200, VTX-763, VTX-1463 and those disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Novira therapeutics), U.S. Pat. No. 9,670,205 (Gilead Sciences Inc.), US20160289229 (Gilead Sciences Inc.), U.S. patent application Ser. No. 15/692,161 (Gilead Sciences Inc.), and U.S. patent application Ser. No. 15/692,093 (Gilead Sciences Inc.).

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-Like" Therapeutic Proteins.

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, and MB-66.

Further examples include bavituximab, UB-421, C2F5, 2G12, C4E10, C2F5+C2G12+C4E10, 8ANC195, 3BNC117, 3BNC60, 10-1074, PGT145, PGT121, PGT-151, PGT-133, MDX010 (ipilimumab), DH511, N6, VRC01 PGDM1400, A32, 7B2, 10E8, 10E8v4, CAP256-VRC26.25, DRVIA7, VRC-07-523, VRC-HIVMAB080-00-AB, VRC-HIVMAB060-00-AB, MGD-014 and VRC07.

Additional examples of HIV bispecific antibodies include MGD014.

Pharmacokinetic Enhancers

Examples of pharmacokinetic enhancers include cobicistat and ritonavir.

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3NSSP ISA-51, poly-ICLC adjuvanted vaccines, Tatlmmune, GTU-multiHIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI, and MVA.HTI.

Additional HIV Therapeutic Agents

Examples of additional HIV therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

Examples of other drugs for treating HIV include acemannan, alisporivir, BanLec, deferiprone, Gamimune, metenkefalin, naltrexone, Prolastin, REP 9, RPI-MN, VSSP, H1viral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

Gene Therapy and Cell Therapy

Gene therapy and cell therapy include the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; and genetic approaches to modify cellular activity to further alter endogenous immune responsiveness against the infection.

Examples of dendritic cell therapy include AGS-004.

Gene Editors

Examples of gene editing systems include a CRISPR/Cas9 system, a zinc finger nuclease system, a TALEN system, a homing endonucleases system, and a meganuclease system.

Examples of HIV targeting CRISPR/Cas9 systems include EBT101.

CAR-T Cell Therapy

CAR-T cell therapy includes a population of immune effector cells engineered to express a chimeric antigen receptor (CAR), wherein the CAR comprises an HIV antigen-binding domain. The HIV antigens include an HIV envelope protein or a portion thereof, gp120 or a portion thereof, a CD4 binding site on gp120, the CD4-induced binding site on gp120, N glycan on gp120, the V2 of gp120, and the membrane proximal region on gp41. In some embodiments, the immune effector cell is a T cell or an NK cell. In some embodiments, the T cell is a CD4+ T cell, a CD8+ T cell, or a combination thereof.

Examples of HIV CAR-T cell therapy include VC-CAR-T.

TCR-T Cell Therapy

TCR-T cell therapy includes T cells engineered to target HIV derived peptides present on the surface of virus-infected cells.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY® (bictegravir, emtricitabine, tenofovir alafenamide); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, tenofovir alafenamide hemifumarate, or bictegravir.

In a particular embodiment, a compound disclosed herein, or a pharmaceutically acceptable salt thereof, is combined with tenofovir, tenofovir disoproxil, tenofovir disoproxil fumarate, tenofovir alafenamide, tenofovir alafenamide hemifumarate, or bictegravir.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, tenofovir alafenamide hemifumarate, and bictegravir and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, tenofovir alafenamide hemifumarate, and bictegravir and a second additional therapeutic agent, wherein the second additional therapeutic agent is emtricitabine.

A compound as disclosed herein may be combined with one or more additional therapeutic agents in any dosage amount of the compound (e.g., from 1 mg to 500 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein may be combined with the agents provided herein in any dosage amount of the compound (e.g., from 1 mg to 500 mg of compound) as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein may be combined with the agents provided herein in any dosage amount of the compound (e.g., from 1 mg to 500 mg of compound) as if each combination of dosages were specifically and individually listed.

Nonalcoholic Steatohepatitis (NASH) Combination Therapy

In some embodiments, the therapeutic agent, or combination of therapeutic agents, are a(n) ACE inhibitor, Acetyl CoA carboxylase inhibitor, Adenosine A3 receptor agonist, Adiponectin receptor agonist, AKT protein kinase inhibitor, AMP-activated protein kinases (AMPK), Amylin receptor agonist, Angiotensin II AT-1 receptor antagonist, Autotaxin inhibitors, Bioactive lipid, Calcitonin agonist, Caspase inhibitor, Caspase-3 stimulator, Cathepsin inhibitor, Caveolin 1 inhibitor, CCR2 chemokine antagonist, CCR3 chemokine antagonist, CCR5 chemokine antagonist, Chloride channel stimulator, CNR1 inhibitor, Cyclin D1 inhibitor, Cytochrome P450 7A1 inhibitor, DGAT1/2 inhibitor, Dipeptidyl peptidase IV inhibitor, Endosialin modulator, Eotaxin ligand inhibitor, Extracellular matrix protein modulator, Farnesoid X receptor agonist, Fatty acid synthase inhibitors, FGF1 receptor agonist, Fibroblast growth factor (FGF-15, FGF-19, FGF-21) ligands, Galectin-3 inhibitor, Glucagon receptor agonist, Glucagon-like peptide 1 agonist, G-protein coupled bile acid receptor 1 agonist, Hedgehog (Hh) modulator, Hepatitis C virus NS3 protease inhibitor, Hepatocyte nuclear factor 4 alpha modulator (HNF4A), Hepatocyte growth factor modulator, HMG CoA reductase inhibitor, IL-10 agonist, IL-17 antagonist, Ileal sodium bile acid cotransporter inhibitor, Insulin sensitizer, integrin modulator, intereukin-1 receptor-associated kinase 4 (IRAK4) inhibitor, Jak2 tyrosine kinase inhibitor, Klotho beta stimulator, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, Matrix metalloproteinases (MMPs) inhibitor, MEKK-5 protein kinase inhibitor, Membrane copper amine oxidase (VAP-1) inhibitor, Methionine aminopeptidase-2 inhibitor, Methyl CpG binding protein 2 modulator, MicroRNA-21 (miR-21) inhibitor, Mitochondrial uncoupler, Myelin basic protein stimulator, NACHT LRR PYD domain protein 3 (NLRP3) inhibitor, NAD-dependent deacetylase sirtuin stimulator, NADPH oxidase inhibitor (NOX), Nicotinic acid receptor 1 agonist, P2Y13 purinoceptor stimulator, PDE 3 inhibitor, PDE 4 inhibitor, PDE 5 inhibitor, PDGF receptor beta modulator, Phospholipase C inhibitor, PPAR alpha agonist, PPAR delta agonist, PPAR gamma agonist, PPAR gamma modulator, Protease-activated receptor-2 antagonist, Protein kinase modulator, Rho associated protein kinase inhibitor, Sodium glucose transporter-2 inhibitor, SREBP transcription factor inhibitor, STAT-1 inhibitor, Stearoyl CoA desaturase-1 inhibitor, Suppressor of cytokine signalling-1 stimulator, Suppressor of cytokine signalling-3 stimulator, Transforming growth factor β (TGF-β), Transforming growth factor 3 activated Kinase 1 (TAK1), Thyroid hormone receptor beta agonist, TLR-4 antagonist, Transglutaminase inhibitor, Tyrosine kinase receptor modulator, GPCR modulator, nuclear hormone receptor modulator, WNT modulators, or YAP/TAZ modulator.

Non-limiting examples of therapeutic agents and targets comprise:

- ACE inhibitors, such as enalapril;
- Acetyl CoA carboxylase (ACC) inhibitors, such as NDI-010976 (firsocostat), DRM-01, gemcabene, PF-05175157, QLT-091382, PF-05221304;
- Adenosine receptor agonists, such as CF-102 (namodenoson), CF-101, CF-502, CGS21680;
- Adiponectin receptor agonists, such as ADP-355;
- Amylin/calcitonin receptor agonists, such as KBP-042;
- AMP activated protein kinase stimulators, such as O-304;
- Angiotensin II AT-1 receptor antagonists, such as irbesartan;
- Autotaxin inhibitors, such as PAT-505, PAT-048, GLPG-1690, X-165, PF-8380, AM-063;
- Bioactive lipids, such as DS-102;
- Cannabinoid receptor type 1 (CNR1) inhibitors, such as namacizumab, GWP-42004;
- Caspase inhibitors, such as emricasan;
- Pan cathepsin B inhibitors, such as VBY-376;
- Pan cathepsin inhibitors, such as VBY-825;
- CCR2/CCR5 chemokine antagonists, such as cenicriviroc;
- CCR2 chemokine antagonists, such as propagermanium;
- CCR3 chemokine antagonists, such as bertilimumab;
- Chloride channel stimulators, such as cobiprostone;
- Diglyceride acyltransferase 2 (DGAT2) inhibitors, such as IONIS-DGAT2Rx, PF-06865571;
- Diglyceride acyltransferase 1 (DGAT1) inhibitors, such as GSK-3008356;
- Dipeptidyl peptidase IV inhibitors, such as linagliptin, evogliptin;
- Eotaxin ligand inhibitors, such as bertilimumab;
- Extracellular matrix protein modulators, such as CNX-024;
- Farnesoid X receptor (FXR) agonists, such as AGN-242266, AKN-083, EDP-305, GNF-5120, GS-9674, LJN-452 (tropifexor), LMB-763, obeticholic acid, Px-102, Px-103, M790, M780, M450, M480, PX20606, EYP-001, INT-2228;
- Farnesoid X receptor (FXR)/G-protein coupled bile acid receptor 1(TGR5) agonists, such as INT-767;
- Fatty acid synthase inhibitors, such as TVB-2640;
- Fibroblast growth factor 19 (rhFGF19)/cytochrome P450 (CYP) 7A1 inhibitors, such as NGM-282;
- Fibroblast growth factor 21(FGF-21) ligand, such as BMS-986171,
- BMS-986036;
- Fibroblast growth factor 21(FGF-21)/glucagon like peptide 1 (GLP-1) agonist, such as YH-25723;
- Galectin-3 inhibitors, such as GR-MD-02;
- Glucagon-like peptide 1(GLP1R) agonists, such as AC-3174, liraglutide, semaglutide;
- G-protein coupled bile acid receptor 1(TGR5) agonists, such as RDX-009, INT-777;
- Heat shock protein 47 (HSP47) inhibitors, such as ND-L02-s0201;
- HMG CoA reductase inhibitors, such as atorvastatin, fluvastatin, pitavastatin, pravastatin, rosuvastatin, simvastatin;
- IL-10 agonists, such as peg-ilodecakin;
- Ileal sodium bile acid cotransporter inhibitors, such as A-4250, volixibat potassium ethanolate hydrate (SHP-262), GSK2330672;
- Insulin sensitizers, such as, KBP-042, MSDC-0602K, Px-102, RG-125 (AZD4076), VVP-100X;
- beta Klotho (KLB)-FGF1c agonist, such as NGM-313;
- 5-Lipoxygenase inhibitors, such as tipelukast (MN-001);
- Lipoprotein lipase inhibitors, such as CAT-2003;
- LPL gene stimulators, such as alipogene tiparvovec;
- Liver X receptor (LXR) inhibitors, such as PX-L603, PX-L493, BMS-852927, T-0901317, GW-3965, SR-9238;
- Lysophosphatidate-1 receptor antagonists, such as BMT-053011, UD-009. AR-479, ITMN-10534, BMS-986020, KI-16198;
- Lysyl oxidase homolog 2 inhibitors, such as simtuzumab;
- MEKK-5 protein kinase (ASK-1) inhibitors, such as GS-4997;
- Semicarbazide-Sensitive Amine OxidaseNascular Adhesion Protein-1 (SSAO/VAP-1) Inhibitors, such as PXS-4728A;
- Methionine aminopeptidase-2 inhibitors, such as ZGN-839;
- Methyl CpG binding protein 2 modulators, such as mercaptamine;
- Mineralocorticoid receptor antagonists (MCRA), such as MT-3995;
- Mitochondrial uncouplers, such as 2,4-dinitrophenol;
- Myelin basic protein stimulators, such as olesoxime;
- Myeloperoxidase inhibitors, such as PF-06667272;
- NADPH oxidase 1/4 inhibitors, such as GKT-831;
- Nicotinic acid receptor 1 agonists, such as ARI-3037MO;
- NACHT LRR PYD domain protein 3 (NLRP3) inhibitors, such as KDDF-201406-03, NBC-6;

Nuclear receptor modulators, such as DUR-928;

P2Y13 purinoceptor stimulators, such as CER-209;

PDE 3/4 inhibitors, such as tipelukast (MN-001);

PDE 5 inhibitors, such as sildenafil;

PDGF receptor beta modulators, such as BOT-191, BOT-509;

PPAR agonists, such as elafibranor (GFT-505), MBX-8025, deuterated pioglitazone R-enantiomer, pioglitazone, DRX-065, saroglitazar, IVA-337;

Protease-activated receptor-2 antagonists, such as PZ-235;

Protein kinase modulators, such as CNX-014;

Rho associated protein kinase (ROCK) inhibitors, such as KD-025;

Sodium glucose transporter-2(SGLT2) inhibitors, such as ipragliflozin, remogliflozin etabonate, ertugliflozin, dapagliflozin, sotagliflozin;

SREBP transcription factor inhibitors, such as CAT-2003, MDV-4463;

Stearoyl CoA desaturase-1 inhibitors, such as aramchol;

Thyroid hormone receptor beta agonists, such as MGL-3196, MGL-3745, VK-2809;

TLR-4 antagonists, such as JKB-121;

Tyrosine kinase receptor modulators, such as CNX-025;

GPCR modulators, such as CNX-023; and

Nuclear hormone receptor modulators, such as Px-102.

In some embodiments, the therapeutic agent, or combination of therapeutic agents, are A-4250, AC-3174, acetylsalicylic acid, AK-20, alipogene tiparvovec, aramchol, ARI-3037MO, ASP-8232, bertilimumab, Betaine anhydrous, BI-1467335, BMS-986036, BMS-986171, BMT-053011, BOT-191, BTT-1023, CAT-2003, cenicriviroc, CER-209, CF-102, CGS21680, CNX-014, CNX-023, CNX-024, CNX-025, cobiprostone, colesevelam, dapagliflozin, deuterated pioglitazone R-enantiomer, 2,4-dinitrophenol, DRX-065, DS-102, DUR-928, EDP-305, elafibranor (GFT-505), emricasan, enalapril, ertugliflozin, evogliptin, F-351, GKT-831, GNF-5120, GRI-0621, GR-MD-02, GS-4997, GS-9674, hydrochlorothiazide, icosapent ethyl ester, IMM-124-E, INT-767, IONIS-DGAT2Rx, ipragliflozin, Irbesarta, propagermanium, IVA-337, JKB-121, KB-GE-001, KBP-042, KD-025, M790, M780, M450, metformin, sildenafil, LC-280126, linagliptin, liraglutide, LJN-452, LMB-763, MBX-8025, MDV-4463, mercaptamine, MGL-3196, MGL-3745, MSDC-0602K, namacizumab, NC-101, NDI-010976, ND-L02-s0201, NGM-282, NGM-313, NGM-386, NGM-395, norursodeoxycholic acid, 0-304, obeticholic acid, 25HC3S, olesoxime, PAT-505, PAT-048, peg-ilodecakin, pioglitazone, pirfenidone, PRI-724, PX20606, Px-102, PX-L603, PX-L493, PXS-4728A, PZ-235, RDX-009, remogliflozin etabonate, RG-125 (AZD4076), saroglitazar, semaglutide, simtuzumab, solithromycin, sotagliflozin, statins (atorvastatin, fluvastatin, pitavastatin, pravastatin, rosuvastatin, simvastatin), TCM-606F, TEV-45478, tipelukast (MN-001), TLY-012, TRX-318, TVB-2640, UD-009, ursodeoxycholic acid, VBY-376, VBY-825, VK-2809, vismodegib, volixibat potassium ethanolate hydrate (SHP-626), VVP-100X, WAV-301, WNT-974, or ZGN-839.

Cancer and/or Hyper-Proliferative Disease Combination Therapy

In one embodiment, the compound provided herein may be employed with other therapeutic methods of cancer treatment. Preferably, combination therapy with chemotherapeutic, hormonal, antibody, surgical and/or radiation treatments are contemplated.

In some embodiments, the further anti-cancer therapy is surgery and/or radiotherapy. In some embodiments, the further anti-cancer therapy is at least one additional cancer medicament.

In some embodiments, there is provided a combination comprising a compound provided herein, or a pharmaceutically acceptable salt thereof and at least one further cancer medicament.

In some embodiments, there is provided a combination comprising a compound provided herein, or a pharmaceutically acceptable salt thereof and at least one further cancer medicament, for use in therapy.

In some embodiments, there is provided the use of a combination comprising a compound provided herein, or a pharmaceutically acceptable salt thereof and at least one cancer medicament, in the manufacture of a medicament for the treatment of cancer.

Examples of further cancer medicaments include intercalating substances such as anthracycline, doxorubicin, idarubicin, epirubicin, and daunorubicin; topoisomerase inhibitors such as irinotecan, topotecan, camptothecin, lamellarin D, etoposide, teniposide, mitoxantrone, amsacrine, ellipticines and aurintricarboxylic acid; nitrosourea compounds such as carmustine (BCNU), lomustine (CCNU), and streptozocin; nitrogen mustards such as cyclophosphamide, mechlorethamine, uramustine, bendamustine, melphalan, chlorambucil, mafosfamide, trofosfamid and ifosfamide; alkyl sulfonates such as busulfan and treosulfan; alkylating agents such as procarbazin, dacarbazin, temozolomid and thiotepa; platinum analogues such as cisplatin, carboplatin, nedaplatin, oxaliplatin, satraplatin, and triplatin tetranitrate; microtubule disruptive drugs such as vinblastine, colcemid and nocodazole; antifolates like methotrexate, aminopterin, dichloromethotrexat, pemetrexed, raltitrexed and pralatrexate: purine analogues like azathioprine, mercaptopurine, thioguanine, fludarabine, fludarabine phosphate, pentostatin and cladribine; pyrimidine analogues like 5-fluorouracil, floxuridine, cytarabine, 6-azauracil, gemcitabine; steroids such as gestagene, androgene, glucocorticoids, dexamethasone, prednisolone, and prednisone; anti-cancer antibodies such as monoclonal antibodies, e.g., alemtuzumab, apolizumab, cetuximab, epratuzumab, galiximab, gemtuzumab, ipilimumab, labetuzumab, panitumumab, rituximab, trastuzumab, nimotuzumab, mapatumumab, matuzumab, rhMab ICR62 and pertuzumab, radioactively labeled antibodies and antibody-drug conjugates; anti-cancer peptides such as radioactively labeled peptides and peptide-drug conjugates; and taxane and taxane analogues such as paclitaxel and docetaxel.

In certain embodiments, a method for treating or preventing a cancer or hyper-proliferative disease in a human or animal having or at risk of having the cancer or hyper-proliferative disease is provided, comprising administering to the human or animal a therapeutically effective amount of a compound provided herein as disclosed herein, or a pharmaceutically acceptable salt thereof, in combination with a therapeutically effective amount of one or more (e.g., one, two, three, one or two, or one to three) additional therapeutic agents. In one embodiment, a method for treating a cancer or hyper-proliferative disease in a human or animal having or at risk of having the cancer or hyper-proliferative disease is provided, comprising administering to the human or animal a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In certain embodiments, the present disclosure provides a method for treating a cancer or hyper-proliferative disease, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating cancer or hyper-proliferative disease.

The compounds described herein may be used or combined with one or more of a chemotherapeutic agent, an anti-cancer agent, an anti-angiogenic agent, an anti-fibrotic agent, an immunotherapeutic agent, a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a radiotherapeutic agent, an anti-neoplastic agent, an anti-proliferation agent, an oncolytic virus, a gene modifier or editor (such as CRISPR/Cas9, zinc finger nucleases or synthetic nucleases, TALENs), a CAR (chimeric antigen receptor) T-cell immunotherapeutic agent, an engineered T cell receptor (TCR-T), or any combination thereof. These therapeutic agents may be in the forms of compounds, antibodies, polypeptides, or polynucleotides. In one embodiment, provided herein is a product comprising a compound described herein and an additional therapeutic agent as a combined preparation for simultaneous, separate, or sequential use in therapy.

The one or more additional therapeutic agents include, but are not limited to, an inhibitor, agonist, antagonist, ligand, modulator, stimulator, blocker, activator or suppressor of a gene, ligand, receptor, protein, or factor. Non-limiting examples of additional therapeutic agents include:

Abelson murine leukemia viral oncogene homolog 1 gene (ABL, such as ABL1), Acetyl-CoA carboxylase (such as ACC1/2), activated CDC kinase (ACK, such as ACK1), Adenosine deaminase, adenosine receptor (such as A2B, A2a, A3), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Bruton's tyrosine kinase (BTK), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1, CHK2), chemokine (C—C motif) receptor (such as CCR2, CCR4, CCR5), chemokine (C—X—C motif) receptor (such as CXCR4, CXCR1 and CXCR2), Chemokine CC21 ligand, Cholecystokinin CCK2 receptor, Chorionic gonadotropin, c-Kit (tyrosine-protein kinase Kit or CD117), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e, CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement C3, Connective tissue growth factor, COP9 signalosome subunit 5, CSF-1 (colony-stimulating factor 1 receptor), CSF2 gene, CTLA-4 (cytotoxic T-lymphocyte protein 4) receptor, Cyclin D1, Cyclin G1, cyclin-dependent kinases (CDK, such as CDK1, CDK1B, CDK2-9), cyclooxygenase (such as 1, 2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, Delta-like protein ligand (such as 3, 4), Deoxyribonuclease, Dickkopf-1 ligand, dihydrofolate reductase (DHFR), Dihydropyrimidine dehydrogenase, Dipeptidyl peptidase IV, discoidin domain receptor (DDR, such as DDR1), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, echinoderm microtubule like protein 4, EGFR tyrosine kinase receptor, Elastase, Elongation factor 1 alpha 2, Elongation factor 2, Endoglin, Endonuclease, Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Factor (such as Xa, VIIa), farnesoid x receptor (FXR), Fas ligand, Fatty acid synthase (FASN), Ferritin, FGF-2 ligand, FGF-5 ligand, fibroblast growth factor (FGF, such as FGF1, FGF2, FGF4), Fibronectin, Fms-related tyrosine kinase 3 (Flt3), focal adhesion kinase (FAK, such as FAK2), folate hydrolase prostate-specific membrane antigen 1 (FOLH 1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Ganglioside GD2, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releaseing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOT1L), histone deacetylase (HDAC, such as 1, 2, 3, 6, 10, 11), Histone H1, Histone H3, HLA class I antigen (A-2 alpha), HLA class II antigen, Homeobox protein NANOG, HSPB1 gene, Human leukocyte antigen (HLA), Human papillomavirus (such as E6, E7) protein, Hyaluronic acid, Hyaluronidase, Hypoxia inducible factor-1 alpha (HIF1$\alpha$), Imprinted Maternally Expressed Transcript (H19) gene, mitogen-activated protein kinase kinase kinase kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, G1, G2, K, M), Immunoglobulin Fc receptor, Immunoglobulin gamma Fc receptor (such as I, III, IIIA), indoleamine 2,3-dioxygenase (IDO, such as IDO1), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KiSS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), lysyl oxidase-like protein (LOXL, such as LOXL2), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Major vault protein, MAPK-activated protein kinase (such as MK2), Mas-related G-protein coupled receptor, matrix metalloprotease (MMP, such as MMP2, MMP9), Mcl-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2, 3, 6), Membrane copper amine oxidase, Mesothelin, MET tyrosine kinase, Metabotropic glutamate receptor 1, Metalloreductase STEAP1 (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1,2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyltransferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, Noradrenaline transporter, Notch (such as Notch-2 receptor, Notch-3 receptor, Notch-4 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Ornithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly ADP ribose polymerase (PARP, such as PARP1, 2 and 3), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase)gene, Ros1 tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Semaphorin-4D, Serine protease, serine/threonine kinase (STK), serine/threonine-protein kinase (TBK, such as TBK1), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Son of sevenless (SOS), Specific protein 1 (Sp1) transcription factor, Sphingomyelin synthase, Sphingosine kinase (such as 1, 2), Sphingosine-1-phosphate receptor-1, spleen tyrosine kinase (SYK), SRC gene, Src tyrosine kinase, STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, TGF beta 2 ligand, Thrombopoietin receptor, Thymidine kinase, Thymidine phosphorylase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, Transferrin, Transforming growth factor (TGF, such as beta) kinase, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E21 (UBE21, UBC9), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase Yes, Wee-1 protein kinase, Wilms' tumor antigen 1, Wilms' tumor protein, X-linked inhibitor of apoptosis protein, Zinc finger protein transcription factor, or any combinations thereof.

Non-limiting examples of additional therapeutic agents may be categorized by their mechanism of action into, for example, the following groups:

anti-metabolites/anti-cancer agents, such as pyrimidine analogs floxuridine, capecitabine, cytarabine, CPX-351 (liposomal cytarabine, daunorubicin), and TAS-118;

purine analogs, folate antagonists (such as pralatrexate), and related inhibitors;

antiproliferative/antimitotic agents including natural products, such as vinca alkaloids (vinblastine, vincristine) and microtubule disruptors such as taxane (paclitaxel, docetaxel), vinblastin, nocodazole, epothilones, vinorelbine (NAVELBINE®), and epipodophyllotoxins (etoposide, teniposide);

DNA damaging agents, such as actinomycin, amsacrine, busulfan, carboplatin, chlorambucil, cisplatin, cyclophosphamide (CYTOXAN®), dactinomycin, daunorubicin, doxorubicin, epirubicin, iphosphamide, melphalan, merchlorethamine, mitomycin C, mitoxantrone, nitrosourea, procarbazine, taxol, Taxotere, teniposide, etoposide, and triethylenethiophosphoramide;

DNA-hypomethylating agents, such as guadecitabine (SGI-110) and ASTX727;

antibiotics such as dactinomycin, daunorubicin, doxorubicin, idarubicin, anthracyclines, mitoxantrone, bleomycins, and plicamycin (mithramycin);

enzymes such as L-asparaginase which systemically metabolizes L-asparagine and deprives cells which do not have the capacity to synthesize their own asparagine;

antiplatelet agents;

DNAi oligonucleotides targeting Bcl-2, such as PNT2258;

agents that activate or reactivate latent human immunodeficiency virus (HIV), such as panobinostat and romidepsin;

asparaginase stimulators, such as crisantaspase (Erwinase®) and GRASPA (ERY-001, ERY-ASP), and calaspargase pegol;

pan-Trk, ROS1 and ALK inhibitors, such as entrectinib and TPX-0005;

anaplastic lymphoma kinase (ALK) inhibitors, such as alectinib and ceritinib;

antiproliferative/antimitotic alkylating agents, such as nitrogen mustard cyclophosphamide and analogs (melphalan, chlorambucil, hexamethylmelamine, thiotepa), alkyl nitrosoureas (carmustine) and analogs, streptozocin, and triazenes (dacarbazine);

antiproliferative/antimitotic antimetabolites, such as folic acid analogs (methotrexate);

platinum coordination complexes (cisplatin, oxiloplatinim, and carboplatin), procarbazine, hydroxyurea, mitotane, and aminoglutethimide;

hormones, hormone analogs (estrogen, tamoxifen, goserelin, bicalutamide, and nilutamide), and aromatase inhibitors (letrozole and anastrozole);

anticoagulants such as heparin, synthetic heparin salts, and other inhibitors of thrombin;

fibrinolytic agents such as tissue plasminogen activator, streptokinase, urokinase, aspirin, dipyridamole, ticlopidine, and clopidogrel;

antimigratory agents;

antisecretory agents (breveldin);

immunosuppressives, such as tacrolimus, sirolimus, azathioprine, and mycophenolate;

growth factor inhibitors, and vascular endothelial growth factor inhibitors;

fibroblast growth factor inhibitors, such as FPA14;

anti-VEGFR antibodies, such as IMC-3C5, GNR-011 and tanibirumab;
anti-VEGF/DDL4 antibodies, such as ABT-165;
anti-cadherins antibodies, such as HKT-288;
anti-CD70 antibodies, such as AMG-172; anti-leucine-rich repeat containing 15 (LRRC15) antibodies, such as ABBV-085 and ARGX-110;
angiotensin receptor blockers and nitric oxide donors;
antisense oligonucleotides, such as AEG35156, IONIS-KRAS-2.5Rx, EZN-3042, RX-0201, IONIS-AR-2.5Rx, BP-100 (prexigebersen), and IONIS-STAT3-2.5Rx;
DNA interference oligonucleotides, such as PNT2258 and AZD-9150;
anti-ANG-2 antibodies, such as MED13617, and LY3127804;
anti-ANG-1/ANG-2 antibodies, such as AMG-780;
anti-MET/EGFR antibodies, such as LY3164530;
anti-EGFR antibodies, such as ABT-414, AMG-595, necitumumab, ABBV-221, depatuxizumab mafodotin (ABT-414), tomuzotuximab, ABT-806, vectibix, modotuximab, and RM-1929;
anti-CSF1R antibodies, such as emactuzumab, LY3022855, AMG-820, and FPA-008 (cabiralizumab);
anti-CD40 antibodies, such as RG7876, SEA-CD40, APX-005M, and ABBV-428;
anti-endoglin antibodies, such as TRC105 (carotuximab);
anti-CD45 antibodies, such as 1311-BC8 (lomab-B);
anti-HER3 antibodies, such as LJM716, and GSK2849330;
anti-HER2 antibodies, such as margetuximab, MED14276, and BAT-8001;
anti-HLA-DR antibodies, such as IMMU-114;
anti-IL-3 antibodies, such as JNJ-56022473;
anti-OX40 antibodies, such as MED16469, MED16383, MED10562 (tavolixizumab), MOXR0916, PF-04518600, RG-7888, GSK-3174998, INCAGN1949, BMS-986178, GBR-8383, and ABBV-368;
anti-EphA3 antibodies, such as KB-004;
anti-CD20 antibodies, such as obinutuzumab, IGN-002;
anti-CD20/CD3 antibodies, such as RG7828;
anti-CD37 antibodies, such as AGS67E, and otlertuzumab (TRU-016);
anti-ENPP3 antibodies, such as AGS-16C3F;
anti-FGFR-3 antibodies, such as LY3076226, and B-701;
anti-FGFR-2 antibodies, such as GAL-F2;
anti-C5 antibodies, such as ALXN-1210;
anti-CD27 antibodies, such as varlilumab (CDX-1127);
anti-TROP-2 antibodies, such as IMMU-132
anti-NKG2a antibodies, such as monalizumab;
anti-VISTA antibodies, such as HMBD-002;
anti-PVRIG antibodies, such as COM-701;
anti-EpCAM antibodies, such as VB4-845;
anti-BCMA antibodies, such as GSK-2857916
anti-CEA antibodies, such as RG-7813;
anti-cluster of differentiation 3 (CD3) antibodies, such as MGD015;
anti-folate receptor alpha antibodies, such as IMGN853;
MCL-1 inhibitors, such as AMG-176, S-64315, AZD-5991, 483-LM, A-1210477, UMI-77, and JKY-5-037;
epha2 inhibitors, such as MM-310;
anti LAG-3 antibodies, such as relatlimab (ONO-4482), LAG-525, MK-4280, and REGN-3767;
raf kinase/VEGFR inhibitors, such as RAF-265;
polycomb protein (EED) inhibitors, such as MAK683;
anti-fibroblast activation protein (FAP)/IL-2R antibodies, such as RG7461;
anti-fibroblast activation protein (FAP)/TRAIL-$R^2$ antibodies, such as RG7386;
anti-fucosyl-GM1 antibodies, such as BMS-986012;
p38 MAP kinase inhibitors, such as ralimetinib;
PRMT1 inhibitors, such as MS203;
Sphingosine kinase 2 (SK2) inhibitors, such as opaganib;
FLT3-ITD inhibitors, such as BCI-332;
Nuclear erythroid 2-related factor 2 stimulators, such as omaveloxolone (RTA-408);
Tropomyosin receptor kinase (TRK) inhibitors, such as LOXO-195, and ONO-7579;
anti-ICOS antibodies, such as JTX-2011, and GSK3359609;
anti-DR5 (TRAIL2) antibodies, such as DS-8273;
anti-GD2 antibodies, such as APN-301;
anti-interleukin-17 (IL-17) antibodies, such as CJM-112;
anti-carbonic anhydrase IX antibodies, such as TX-250;
anti-CD38-attenukine, such as TAK573;
anti-Mucin 1 antibodies, such as gatipotuzumab;
Mucin 1 inhibitors, such as GO-203-2C;
MARCKS protein inhibitors, such as BIO-11006;
Folate antagonists, such as arfolitixorin;
Galectin-3 inhibitors, such as GR-MD-02;
Phosphorylated P68 inhibitors, such as RX-5902;
CD95/TNF modulators, such as ofranergene obadenovec;
PI3K/Akt/mTOR inhibitors, such as ABTL-0812;
pan-PIM kinase inhibitors, such as INCB-053914;
IL-12 gene stimulators, such as EGEN-001, and tavokinogene telseplasmid;
Heat shock protein HSP90 inhibitors, such as TAS-116, and PEN-866;
VEGF/HGF antagonists, such as MP-0250;
SYK tyrosine kinase/FLT3 tyrosine kinase inhibitors, such as TAK-659;
SYK tyrosine kinase/JAK tyrosine kinase inhibitors, such as ASN-002;
FLT3 tyrosine kinase, such as FF-10101, and CDX-301;
FLT3/MEK1 inhibitors, such as E-6201;
IL-24 antagonist, such as AD-IL24;
RIG-I agonists, such as RGT-100;
Aerolysin stimulators, such as topsalysin;
P-Glycoprotein 1 inhibitors, such as HM-30181A;
CSF-1 antagonists, such as ARRY-382, and BLZ-945;
anti-Mesothelin antibodies, such as SEL-403;
Thymidine kinase stimulators, such as aglatimagene besadenovec;
Polo-like kinase 1 inhibitors, such as PCM-075;
TLR-7 agonists, such as TMX-101 (imiquimod);
NEDD8 inhibitors, such as pevonedistat (MLN-4924), and TAS-4464;
Pleiotropic pathway modulators, such as avadomide (CC-122);
FoxM1 inhibitors, such as thiostrepton;
Anti-MUC1 antibodies, such as Mab-AR-20.5;
anti-CD38 antibodies, such as isatuximab, and MOR-202;
UBA1 inhibitors, such as TAK-243;
Src tyrosine kinase inhibitors, such as VAL-201;
VDAC/HK inhibitors, such as VDA-1102;
BRAF/PI3K inhibitors, such as ASN-003;
Elf4a inhibitors, such as rohinitib, eFT226;
TP53 gene stimulators, such as ad-p53;
PD-L1/EGFR inhibitors, such as GNS-1480;
Retinoic acid receptor alpha (RARα) inhibitors, such as SY-1425;
SIRT3 inhibitors, such as YC8-02;

Stromal cell-derived factor 1 ligand inhibitors, such as olaptesed pegol (NOX-A12);

IL-4 receptor modulators, such as MDNA-55;

Arginase-I stimulators, such as pegzilarginase;

Topoisomerase I inhibitor/hypoxia inducible factor-1 alpha inhibitors, such as PEG-SN38 (firtecan pegol);

Hypoxia inducible factor-1 alpha inhibitors, such as PT-2977, and PT-2385;

CD122 agonists such as NKTR-214;

p53 tumor suppressor protein stimulators such as kevetrin;

Mdm4/Mdm2 p53-binding protein inhibitors, such as ALRN-6924;

kinesin spindle protein (KSP) inhibitors, such as filanesib (ARRY-520);

CD80-fc fusion protein inhibitors, such as FPT-155;

Menin and mixed lineage leukemia (MLL) inhibitors such as KO-539;

Liver x receptor agonists, such as RGX-104;

IL-10 agonists, such as AM-0010;

EGFR/ErbB-2 inhibitors, such as varlitinib;

VEGFR/PDGFR inhibitors, such as vorolanib;

IRAK4 inhibitors, such as CA-4948;

anti-TLR-2 antibodies, such as OPN-305;

Calmodulin modulators, such as CBP-501;

Glucocorticoid receptor antagonists, such as relacorilant (CORT-125134);

Second mitochondria-derived activator of caspases (SMAC) protein inhibitors, such as BI-891065;

Lactoferrin modulators, such as LTX-315;

Kit tyrosine kinase/PDGF receptor alpha antagonists such as DCC-2618;

KIT inhibitors, such as PLX-9486;

Exportin 1 inhibitors, such as eltanexor;

EGFR/ErbB2/Ephb4 inhibitors, such as tesevatinib;

anti-CD33 antibodies, such as IMGN-779;

anti-KMA antibodies, such as MDX-1097;

anti-TIM-3 antibodies, such as TSR-022, LY-3321367, and MBG-453;

anti-CD55 antibodies, such as PAT-SC1;

anti-PSMA antibodies, such as ATL-101;

anti-CD100 antibodies, such as VX-15;

anti-EPHA3 antibodies, such as fibatuzumab;

anti-Erbb antibodies, such as CDX-3379, HLX-02, and seribantumab;

anti-APRIL antibodies, such as BION-1301;

Anti-Tigit antibodies, such as BMS-986207, and RG-6058;

CHST15 gene inhibitors, such as STNM-01;

RAS inhibitors, such as NEO-100;

Somatostatin receptor antagonist, such as OPS-201;

CEBPA gene stimulators, such as MTL-501;

DKK3 gene modulators, such as MTG-201;

p70s6k inhibitors, such as MSC2363318A;

methionine aminopeptidase 2 (MetAP2) inhibitors, such as M8891, and APL-1202;

arginine N-methyltransferase 5 inhibitors, such as GSK-3326595;

anti-programmed cell death protein 1 (anti-PD-1) antibodies, such as nivolumab (OPDIVO®, BMS-936558, MDX-1106), pembrolizumab (KEYTRUDA®, MK-3477, SCH-900475, lambrolizumab, CAS Reg. No. 1374853-91-4), pidilizumab, PF-06801591, BGB-A317, GLS-010 (WBP-3055), AK-103 (HX-008), MGA-012, BI-754091, REGN-2810 (cemiplimab), AGEN-2034, JS-001, JNJ-63723283, genolimzumab (CBT-501), LZM-009, BCD-100, LY-3300054, SHR-1201, BAT-1306, and anti-programmed death-ligand 1 (anti-PD-L1) antibodies such as BMS-936559, atezolizumab (MPDL3280A), durvalumab (MED14736), avelumab, CK-301, (MSB0010718C), MED10680, CX-072, CBT-502, PDR-001 (spartalizumab), TSR-042 (dostarlimab), JTX-4014, BGB-A333, SHR-1316, CS-1001 (WBP-3155, KN-035, IBI-308, FAZ-053, and MDX1105-01;

PD-L1/VISTA antagonists such as CA-170;

anti-PD-L1/TGFβ antibodies, such as M7824;

anti-transferrin antibodies, such as CX-2029;

anti-IL-8 (Interleukin-8) antibodies, such as HuMax-Inflam;

ATM (ataxia telangiectasia) inhibitors, such as AZD0156;

CHK1 inhibitors, such as GDC-0575, LY2606368 (prexasertib), SRA737, and RG7741 (CHK1/2);

CXCR4 antagonists, such as BL-8040, LY2510924, burixafor (TG-0054), X4P-002, and X4P-001-IO;

EXH2 inhibitors, such as GSK2816126;

HER2 inhibitors, such as neratinib, and tucatinib (ONT-380);

KDM1 inhibitors, such as ORY-1001, IMG-7289, INCB-59872, and GSK-2879552;

CXCR2 antagonists, such as AZD-5069;

GM-CSF antibodies, such as lenzilumab;

DNA dependent protein kinase inhibitors, such as MSC2490484A (nedisertib), VX-984, and AsiDNA (DT-01);

protein kinase C (PKC) inhibitors, such as LXS-196, and sotrastaurin;

Selective estrogen receptor downregulators (SERD), such as fulvestrant (Faslodex®), RG6046, RG6047, elacestrant (RAD-1901) and AZD9496;

Selective estrogen receptor covalent antagonists (SERCAs), such as H3B-6545;

selective androgen receptor modulator (SARM), such as GTX-024, and darolutamide;

transforming growth factor-beta (TGF-beta) kinase antagonists, such as galunisertib;

anti-transforming growth factor-beta (TGF-beta) antibodies, such as LY3022859, NIS793, and XOMA 089;

bispecific antibodies, such as MM-141 (IGF-1/ErbB3), MM-111 (Erb2/Erb3), JNJ-64052781 (CD19/CD3), PRS-343 (CD-137/HER2), AFM26 (BCMA/CD16A), JNJ-61186372 (EGFR/cMET), AMG-211 (CEA/CD3), RG7802 (CEA/CD3), ERY-974 (CD3/GPC3) vancizumab (angiopoietins/VEGF), PF-06671008 (Cadherins/CD3), AFM-13 (CD16/CD30), APV0436 (CD123/CD3), flotetuzumab (CD123/CD3), REGN-1979 (CD20/CD3), MCLA-117 (CD3/CLEC12A), MCLA-128 (HER2/HER3), JNJ-0819, JNJ-7564 (CD3/heme), AMG-757 (DLL3-CD3), MGD-013 (PD-1/LAG-3), AK-104 (CTLA-4/PD-1), AMG-330 (CD33/CD3), AMG-420 (BCMA/CD3), BI-836880 (VEFG/ANG2), JNJ-63709178 (CD123/CD3), MGD-007 (CD3/gpA33), MEDI-5752 (PD-1/CTLA-4), XENP-20053 (PD-1/CTLA-4), AK-104 (CTLA-4/PD-1) and MGD-009 (CD3/B7H3);

Mutant selective EGFR inhibitors, such as PF-06747775, EGF816 (nazartinib), ASP8273, ACEA-0010, and BI-1482694;

Anti-GITR (glucocorticoid-induced tumor necrosis factor receptor-related protein) antibodies, such as MEDI1873, FPA-154, INCAGN-1876, TRX-518, BMS-986156, MK-1248, and GWN-323;

anti-delta-like protein ligand 3 (DDL3) antibodies, such as rovalpituzumab tesirine;

anti-clusterin antibodies, such as AB-16B5;
anti-Ephrin-A4 (EFNA4) antibodies, such as PF-06647263;
anti-RANKL antibodies, such as denosumab;
anti-mesothelin antibodies, such as BMS-986148, and Anti-MSLN-MMAE;
anti-sodium phosphate cotransporter 2B (NaP2B) antibodies, such as lifastuzumab
anti-c-Met antibodies, such as ABBV-399;
Adenosine A2A receptor antagonists, such as CPI-444, AZD-4635, preladenant, and PBF-509;
Alpha-ketoglutarate dehydrogenase (KGDH) inhibitors, such as CPI-613;
XPO1 inhibitors, such as selinexor (KPT-330);
Isocitrate dehydrogenase 2 (IDH2) inhibitors, such as enasidenib (AG-221);
IDH1 inhibitors such as AG-120, and AG-881 (IDH1 and IDH2), IDH-305, and BAY-1436032;
interleukin-3 receptor (IL-3R) modulators, such as SL-401;
Arginine deiminase stimulators, such as pegargiminase (ADI-PEG-20);
antibody-drug conjugates, such as MLN0264 (anti-GCC, guanylyl cyclase C), T-DM1 (trastuzumab emtansine, Kadcycla), milatuzumab-doxorubicin (hCD74-DOX), brentuximab vedotin, DCDT2980S, polatuzumab vedotin, SGN-CD70A, SGN-CD19A, inotuzumab ozogamicin, lorvotuzumab mertansine, SAR3419, isactuzumab govitecan, enfortumab vedotin (ASG-22ME), ASG-15ME, DS-8201 ((trastuzumab deruxtecan), 225Ac-lintuzumab, U3-1402, 177Lu-tetraxetan-tetuloma, tisotumab vedotin, anetumab ravtansine, CX-2009, SAR-566658, W-0101, polatuzumab vedotin, and ABBV-085;
claudin-18 inhibitors, such as claudiximab;
β-catenin inhibitors, such as CWP-291;
anti-CD73 antibodies, such as MEDI-9447 (oleclumab), CPX-006, IPH-53, and BMS-986179;
CD73 antagonists, such as AB-680, PSB-12379, PSB-12441, and PSB-12425;
CD39/CD73 antagonists, such as PBF-1662;
chemokine receptor 2 (CCR) inhibitors, such as PF-04136309, CCX-872, and BMS-813160 (CCR2/CCR5)
thymidylate synthase inhibitors, such as ONX-0801;
ALK/ROS1 inhibitors, such as lorlatinib;
tankyrase inhibitors, such as G007-LK;
Mdm2 p53-binding protein inhibitors, such as CMG-097, and HDM-201;
c-PIM inhibitors, such as PIM447;
BRAF inhibitors, such as dabrafenib, vemurafenib, encorafenib (LGX818), and PLX8394;
sphingosine kinase-2 (SK2) inhibitors, such as Yeliva® (ABC294640);
cell cycle inhibitors, such as selumetinib (MEK1/2), and sapacitabine;
AKT inhibitors such as MK-2206, ipatasertib, afuresertib, AZD5363, ARQ-092, capivasertib, and triciribine;
anti-CTLA-4 (cytotoxic T-lymphocyte protein-4) inhibitors, such as tremelimumab, AGEN-1884, and BMS-986218, ipilimumab, BMS-986249, CS_1002, REGN-4659, BCD-145;
c-MET inhibitors, such as AMG-337, savolitinib, tivantinib (ARQ-197), capmatinib, and tepotinib, ABT-700, AG213, AMG-208, JNJ-38877618 (OMO-1), merestinib, and HQP-8361;
c-Met/VEGFR inhibitors, such as BMS-817378, and TAS-115;
c-Met/RON inhibitors, such as BMS-777607;
BRAF/EGFR inhibitors, such as BGB-283;
bcr/abl inhibitors, such as rebastinib, and asciminib;
MNK1/MNK2 inhibitors, such as eFT-508;
mTOR inhibitor/cytochrome P450 3A4 stimulators, such as TYME-88
lysine-specific demethylase-1 (LSD1) inhibitors, such as CC-90011;
Pan-RAF inhibitors, such as LY3009120, LXH254, and TAK-580;
Raf/MEK inhibitors, such as RG7304;
CSF1R/KIT and FLT3 inhibitors, such as pexidartinib (PLX3397);
kinase inhibitors, such as vandetanib;
E selectin antagonists, such as GMI-1271;
differentiation inducers, such as tretinoin;
epidermal growth factor receptor (EGFR) inhibitors, such as osimertinib (AZD-9291);
topoisomerase inhibitors, such as doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), and irofulven (MGI-114);
corticosteroids, such as cortisone, dexamethasone, hydrocortisone, methylprednisolone, prednisone, and prednisolone;
growth factor signal transduction kinase inhibitors;
nucleoside analogs, such as DFP-10917;
Axl inhibitors, such as BGB-324 (bemcentinib), and SLC-0211;
BET inhibitors, such as INCB-054329, INCB057643, TEN-010, AZD-5153, ABT-767, BMS-986158, CC-90010, GSK525762 (molibresib), NHWD-870, ODM-207, GSK-2820151, GSK-1210151A, ZBC246, ZBC260, ZEN3694, FT-1101, RG-6146, CC-90010, mivebresib, BI-894999, PLX-2853, PLX-51107, CPI-0610, and GS-5829;
PARP inhibitors, such as olaparib, rucaparib, veliparib, talazoparib, ABT-767, and BGB-290;
Proteasome inhibitors, such as ixazomib, carfilzomib (Kyprolis®), and marizomi;
Glutaminase inhibitors, such as CB-839;
Vaccines, such as peptide vaccine TG-01 (RAS), GALE-301, GALE-302, nelipepimut-s, SurVaxM, DSP-7888, TPIV-200, PVX-410, VXL-100, DPX-E7, ISA-101, 6MHP, OSE-2101, galinpepimut-S, SVN53-67/M57-KLH, IMU-131;
bacterial vector vaccines such as CRS-207/GVAX, axalimogene filolisbac (ADXS11-001); adenovirus vector vaccines such as nadofaragene firadenovec; autologous Gp96 vaccine; dendritic cells vaccines, such as CVactm, stapuldencel-T, eltrapuldencel-T, SL-701, BSK01TM, rocapuldencel-T (AGS-003), DCVAC, CVactm, stapuldencel-T, eltrapuldencel-T, SL-701, BSK01™ ADXS31-142; oncolytic vaccines such as, talimogene laherparepvec, pexastimogene devacirepvec, GL-ONC1, MG1-MA3, parvovirus H-1, ProstAtak, enadenotucirev, MG1MA3, ASN-002 (TG-1042); therapeutic vaccines, such as CVAC-301, CMP-001, PF-06753512, VBI-1901, TG-4010, ProscaVax™; tumor cell vaccines, such as Vigil® (IND-14205), Oncoquest-L vaccine; live attenuated, recombinant, serotype 1 poliovirus vaccine, such as PVS-RIPO;

Adagloxad simolenin; MEDI-0457; DPV-001 a tumor-derived, autophagosome enriched cancer vaccine; RNA vaccines such as, CV-9209, LV-305; DNA vaccines, such as MEDI-0457, MVI-816, INO-5401; modified vaccinia virus Ankara vaccine expressing p53, such as MVA-p53; DPX-Survivac; BriaVax™; GI-6301; GI-6207; and GI-4000;

anti-DLL4 (delta like ligand 4) antibodies, such as demcizumab; STAT-3 inhibitors, such as napabucasin (BBI-608); ATPase p97 inhibitors, such as CB-5083;

smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole;

interferon alpha ligand modulators, such as interferon alpha-2b, interferon alpha-2a biosimilar (Biogenomics), ropeginterferon alfa-2b (AOP-2014, P-1101, PEG IFN alpha-2b), Multiferon (Alfanative, Viragen), interferon alpha ib, Roferon-A (Canferon, Ro-25-3036), interferon alfa-2a follow-on biologic (Biosidus)(Inmutag, Inter 2A), interferon alfa-2b follow-on biologic (Biosidus—Bioferon, Citopheron, Ganapar, Beijing Kawin Technology—Kaferon), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-n1 (Humoferon, SM-10500, Sumiferon);

interferon gamma ligand modulators, such as interferon gamma (OH-6000, Ogamma 100);

IL-6 receptor modulators, such as tocilizumab, siltuximab, and AS-101 (CB-06-02, IVX-Q-101);

Telomerase modulators, such as, tertomotide (GV-1001, HR-2802, Riavax) and imetelstat (GRN-163, JNJ-63935937);

DNA methyltransferases inhibitors, such as temozolomide (CCRG-81045), decitabine, guadecitabine (S-110, SGI-110), KRX-0402, RX-3117, RRx-001, and azacitidine;

DNA gyrase inhibitors, such as pixantrone and sobuzoxane;

Bcl-2 family protein inhibitors, such as ABT-263, venetoclax (ABT-199), ABT-737, and AT-101;

Notch inhibitors, such as LY3039478 (crenigacestat), tarextumab (anti-Notch2/3), and BMS-906024;

anti-myostatin inhibitors, such as landogrozumab;

hyaluronidase stimulators, such as PEGPH-20;

Wnt pathway inhibitors, such as SM-04755, PRI-724, and WNT-974;

gamma-secretase inhibitors, such as PF-03084014, MK-0752, and RO-4929097;

Grb-2 (growth factor receptor bound protein-2) inhibitors, such as BP1001;

TRAIL pathway-inducing compounds, such as ONC201, and ABBV-621;

Focal adhesion kinase inhibitors, such as VS-4718, defactinib, and GSK2256098;

hedgehog inhibitors, such as saridegib, sonidegib (LDE225), glasdegib and vismodegib;

Aurora kinase inhibitors, such as alisertib (MLN-8237), and AZD-2811, AMG-900, barasertib, and ENMD-2076;

HSPB1 modulators (heat shock protein 27, HSP27), such as brivudine, and apatorsen;

ATR inhibitors, such as BAY-937, AZD6738, AZD6783, VX-803, VX-970 (berzosertib) and VX-970;

mTOR inhibitors, such as sapanisertib and vistusertib (AZD2014), and ME-344;

mTOR/PI3K inhibitors, such as gedatolisib, GSK2141795, omipalisib, and RG6114;

Hsp90 inhibitors, such as AUY922, onalespib (AT13387), SNX-2112, and SNX5422;

Murine double minute (mdm2) oncogene inhibitors, such as DS-3032b, RG7775, AMG-232, HDM201, and idasanutlin (RG7388);

CD137 agonists, such as urelumab, and utomilumab (PF-05082566);

STING agonists, such asADU-S100 (MIW-815), SB-11285, MK-1454, SR-8291, AdVCA0848, GSK-532, SYN-STING, MSA-1, and SR-8291;

FGFR inhibitors, such as FGF-401 (roblitinib), INCB-054828, BAY-1163877, AZD4547, JNJ-42756493, LY2874455, SAR-439115, BLU-554, H3B-6527, ABSK-011, ABK-356, HM-81422, INCB-62079, and Debio-1347;

fatty acid synthase (FASN) inhibitors, such as TVB-2640;

Anti-KIR monoclonal antibodies, such as lirilumab (IPH-2102), and IPH-4102;

Antigen CD19 inhibitors, such as MOR208, MEDI-551, AFM-11, and inebilizumab;

CD44 binders, such as A6;

protein phosphatease 2A (PP2A) inhibitors, such as LB-100;

CYP17 inhibitors, such as seviteronel (VT-464), ASN-001, ODM-204, CFG920, and abiraterone acetate;

RXR agonists, such as IRX4204;

hedgehog/smoothened (hh/Smo) antagonists, such as taladegib, and patidegib;

complement C3 modulators, such as Imprime PGG;

IL-15 agonists, such as ALT-803, NKTR-255, and hetIL-15;

EZH2 (enhancer of zeste homolog 2) inhibitors, such as tazemetostat, CPI-1205, and GSK-2816126;

Oncolytic viruses, such as pelareorep, CG-0070, MV-NIS therapy, HSV-1716, DS-1647, VCN-01, ONCOS-102, TBI-1401, tasadenoturev (DNX-2401), vocimagene amiretrorepvec, RP-1, CVA21, Celyvir, LOAd-703, and OBP-301;

DOT1L (histone methyltransferase) inhibitors, such as pinometostat (EPZ-5676);

toxins such as Cholera toxin, ricin, *Pseudomonas* exotoxin, *Bordetella pertussis* adenylate cyclase toxin, diphtheria toxin, and caspase activators;

DNA plasmids, such as BC-819

PLK inhibitors of PLK 1, 2, and 3, such as volasertib (PLK1);

WEE1 inhibitors, such as AZD1775 (adavosertib);

Rho kinase (ROCK) inhibitors, such as AT13148, and KD025;

ERK inhibitors, such as GDC-0994, LY3214996, and MK-8353;

IAP inhibitors, such as ASTX660, debio-1143, birinapant, APG-1387, and LCL-161;

RNA polymerase inhibitors, such as lurbinectedin (PM-1183), and CX-5461;

Tubulin inhibitors, such as PM-184, BAL-101553 (lisavanbulin), OXI-4503, fluorapacin (AC-0001), and plinabulin;

Toll-like receptor 4 (TL4) agonists, such as G100, GSK1795091, and PEPA-10;

Elongation factor 1 alpha 2 inhibitors, such as plitidepsin;

CD95 inhibitors, such as APG-101, APO-010, and asunercept;

- WT1 inhibitors, such as DSP-7888;
- splicing factor 3B subunit1 (SF3B1) inhibitors, such as H3B-8800
- PDGFR alpha/KIT mutant-specific inhibitors such as BLU-285;
- SHP-2 inhibitors, such as PHPS-1, TNO155 (SHP-099), RMC-4630, and RMC-4550; and
- retinoid Z receptor gamma (RORγ) agonists, such as LYC-55716.

In some embodiments, provided herein are methods of treating or preventing a cancer or hyper-proliferative disease in a human or animal having or at risk of having the cancer or hyper-proliferative disease is provided, comprising administering to the human or animal a therapeutically effective amount of a compound provided herein as disclosed herein, or a pharmaceutically acceptable salt thereof, in combination with a therapeutically effective amount of one or more (e.g., one, two, three, one or two, or one to three) additional therapeutic agents selected from the group consisting of apoptosis signal-regulating kinase (ASK) inhibitors; Bruton's tyrosine kinase (BTK) inhibitors; cluster of differentiation 47 (CD47) inhibitors; cyclin-dependent kinase (CDK) inhibitors; discoidin domain receptor (DDR) inhibitors; histone deacetylase (HDAC) inhibitors; indoleamine-pyrrole-2,3-dioxygenase (IDO1) inhibitors; Janus kinase (JAK) inhibitors; lysyl oxidase-like protein (LOXL) inhibitors; matrix metalloprotease (MMP) inhibitors; mitogen-activated protein kinase (MEK) inhibitors; phosphatidylinositol 3-kinase (PI3K) inhibitors; spleen tyrosine kinase (SYK) inhibitors; toll-like receptor 8 (TLR8) inhibitors; toll-like receptor 9 (TLR9) inhibitors; tyrosine-kinase inhibitors (TKIs), or a pharmaceutically acceptable salt of any of the foregoing, or any combinations thereof. Non-limiting examples include:

- Apoptosis Signal-Regulating Kinase (ASK) Inhibitors: ASK inhibitors include ASK1 inhibitors. Examples of ASK1 inhibitors include, but are not limited to, those described in WO 2011/008709 (Gilead Sciences) and WO 2013/112741 (Gilead Sciences);
- Bruton's Tyrosine Kinase (BTK) Inhibitors: Examples of BTK inhibitors include, but are not limited to, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib, M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, and TAS-5315;
- Cluster of Differentiation 47 (CD47) inhibitors: Examples of CD47 inhibitors include, but are not limited to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621;
- Cyclin-dependent Kinase (CDK) Inhibitors: CDK inhibitors include inhibitors of CDK 1, 2, 3, 4, 6, 7 and 9, such as abemaciclib, alvocidib (HMR-1275, flavopiridol), AT-7519, dinaciclib, ibrance, FLX-925, LEE001, palbociclib, ribociclib, rigosertib, selinexor, UCN-01, SY1365, CT-7001, SY-1365, G1T38, milciclib, trilaciclib, and TG-02;
- Discoidin Domain Receptor (DDR) Inhibitors: DDR inhibitors include inhibitors of DDR1 and/or DDR2. Examples of DDR inhibitors include, but are not limited to, those disclosed in WO 2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO 2013/034933 (Imperial Innovations);
- Histone Deacetylase (HDAC) Inhibitors: Examples of HDAC inhibitors include, but are not limited to, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, and entinostat;
- Indoleamine-pyrrole-2,3-dioxygenase (IDO1) inhibitors: Examples of IDO1 inhibitors include, but are not limited to, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, and LY-3381916;
- Janus Kinase (JAK) Inhibitors: JAK inhibitors inhibit JAK1, JAK2, and/or JAK3. Examples of JAK inhibitors include, but are not limited to, AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB1518), peficitinib (ASP015K), ruxolitinib, tofacitinib (formerly tasocitinib), INCB052793, and XL019;
- Lysyl Oxidase-Like Protein (LOXL) Inhibitors: LOXL inhibitors include inhibitors of LOXL1, LOXL2, LOXL3, LOXL4, and/or LOXL5. Examples of LOXL inhibitors include, but are not limited to, the antibodies described in WO 2009/017833 (Arresto Biosciences). Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics);
- Matrix Metalloprotease (MMP) Inhibitors: MMP inhibitors include inhibitors of MMP1 through 10. Examples of MMP9 inhibitors include, but are not limited to, marimastat (BB-2516), cipemastat (Ro 32-3555), GS-5745 (andecaliximab) and those described in WO 2012/027721 (Gilead Biologics); Mitogen-activated Protein Kinase (MEK) Inhibitors: MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, LNP-3794, HL-085, and refametinib;
- Phosphatidylinositol 3-kinase (PI3K) Inhibitors: PI3K inhibitors include inhibitors of PI3Kγ, PI3Kδ, PI3Kβ, PI3Kα, and/or pan-PI3K. Examples of PI3K inhibitors include, but are not limited to, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences);

Spleen Tyrosine Kinase (SYK) Inhibitors: Examples of SYK inhibitors include, but are not limited to, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Conn.) and those described in U.S. 2015/0175616;

Toll-like receptor 8 (TLR8) inhibitors: Examples of TLR8 inhibitors include, but are not limited to, E-6887, IMO-4200, IMO-8400, IMO-9200, MCT-465, MEDI-9197, motolimod, resiquimod, VTX-1463, and VTX-763;

Toll-like receptor 9 (TLR9) inhibitors: Examples of TLR9 inhibitors include, but are not limited to, AST-008, IMO-2055, IMO-2125, lefitolimod, litenimod, MGN-1601, and PUL-042; and Tyrosine-kinase Inhibitors (TKIs): TKIs may target epidermal growth factor receptors (EGFRs) and receptors for fibroblast growth factor (FGF), platelet-derived growth factor (PDGF), and vascular endothelial growth factor (VEGF). Examples of TKIs include, but are not limited to, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, tivoanib, TH-4000, and MEDI-575 (anti-PDGFR antibody).

As used herein, the term “chemotherapeutic agent” or “chemotherapeutic” (or “chemotherapy” in the case of treatment with a chemotherapeutic agent) is meant to encompass any non-proteinaceous (i.e., non-peptidic) chemical compound useful in the treatment of cancer. Examples of chemotherapeutic agents include but are not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, especially bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammall and calicheamicin phill), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-tricUorotriemylamine; urethane; vindesine; dacarbazine; mannomustine; mitobronitol; mitolactol; pipobroman; gacytosine; arabinoside (“Ara-C”); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFIRI (fluorouracil, leucovorin, and irinotecan); and pharmaceutically acceptable salts, acids, or derivatives of any of the above.

Also included in the definition of “chemotherapeutic agent” are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Anti-Hormonal Agents

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, and ODM-204.

Examples of progesterone receptor antagonist include onapristone.

Anti-Angiogenic Agents

Anti-angiogenic agents include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as I-azetidine-2-carboxylic acid (LACA), cishydroxyproline, d,l-3,4-dehydroproline, thiaproline, α,α'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, and inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents

Anti-fibrotic agents include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Immunotherapeutic Agents

Examples of immunotherapeutic agents include but are not limited to therapeutic antibodies suitable for treating patients. Some examples of therapeutic antibodies include abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, and 3F8. Rituximab can be used for treating indolent B-cell cancers, including marginal-zone lymphoma, WM, CLL and small lymphocytic lymphoma. In some embodiments, a combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

Cancer Gene Therapy and Cell Therapy

Cancer gene therapy and cell therapy include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; and genetic approaches to modify cellular activity to further alter endogenous immune responsiveness against cancer.

Gene Editors

Examples of genome editing system include a CRISPR/Cas9 system, a zinc finger nuclease system, a TALEN system, a homing endonucleases system, and a meganuclease system.

CAR-T Cell Therapy and TCR-T Cell Therapy

CAR-T cell therapy includes a population of immune effector cells engineered to express a chimeric antigen receptor (CAR), wherein the CAR comprises a tumor antigen-binding domain. The immune effector cell is a T cell or an NK cell. TCR-T cell therapy includes TCR-T cells that are engineered to target tumor derived peptides present on the surface of tumor cells. Cells can be autologous or allogeneic.

In some embodiments, the CAR comprises an antigen binding domain, a transmembrane domain, and an intracellular signaling domain.

In some embodiments, the intracellular domain comprises a primary signaling domain, a costimulatory domain, or both of a primary signaling domain and a costimulatory domain.

In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon Rib), CD79a, CD79b, Fcgamma RIIa, DAP10, and DAP12.

In some embodiments, the costimulatory domain comprises a functional domain of one or more proteins selected from the group consisting of CD27, CD28, 4-1BB(CD137), OX40, CD30, CD40, PD-1, ICOS, lymphocyte function-associated antigen-1 (LFA-I), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD 1 Id, ITGAE, CD103, ITGAL, CD 1 Ia, LFA-1, ITGAM, CD1 Ib, ITGAX, CD1 Ic, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD1 Ia, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R u, ITGA1, VLA1, CD49a, ITGA4, IA4, CD49D, ITGA6, VLA-6, CD49f, ITGAD, CD1 Id, ITGAE, CD103, ITGAL, CD1 Ia, LFA-1, ITGAM, CD1 Ib, ITGAX, CD1 Ic, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the antigen binding domain binds a tumor antigen.

In some embodiments, the tumor antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvIII); ganglioside G2 (GD2); ganglioside GD3 (aNeuSAc(2-8)aNeuSAc(2-3)bD-Gaip(1-4)bDGlcp(1-1)Cer); TNF receptor family member B cell maturation (BCMA); Tn antigen ((Tn Ag) or (GalNAcu-Ser/Thr)); prostate-specific membrane antigen (PSMA); Receptor tyrosine kinase-like orphan receptor 1 (RORI); Fms-Like, Tyrosine Kinase 3 (FLT3); Tumor-associated glycoprotein 72 (TAG72); CD38; CD44v6; Carcinoembryonic antigen (CEA); Epithelial cell adhesion molecule (EP-CAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y)antigen; CD24; Platelet-derived growth factor receptor beta (PDGFR-beta); Stage-specificembryonic antigen-4 (SSEA-4); CD20; delta like 3 (DLL3); Folate receptor alpha; Receptor tyrosine-protein kinase, ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murineleukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeuSAc(2-3)bDGalp(1-4)bDGlcp(1-1)Cer); transglutaminase 5 (TGS5); high molecular weight-melanomaassociatedantigen (HMWMAA); o-acetyl-GD2 ganglioside (OAcGD2); Folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (ORS IE2); TCR Gamma Alternate Reading Frame Protein (TARP); Wilms tumor protein (WT1); Cancer/testis antigen 1 (NY-ESO-1); Cancer/testis antigen 2 (LAGE-Ia); Melanomaassociated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); Fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1 B1 (CYP IBI); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRI); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like modulecontaining mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the tumor antigen is selected from CD150, 5T4, ActRIIA, B7, BMCA, CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, GD2, GD3, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, LI-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-RI (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acethycholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, and Fc Receptor-like 5 (FcRL5).

Non limiting examples of cell therapies include Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CAR T cells, autologous 4H11-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, and CSG-005.

In some embodiments, the tumor targeting antigen includes: Alphafetoprotein, such as ET-1402, and AFP-TCR; Anthrax toxin receptor 1, such as anti-TEM8 CAR T-cell therapy; B cell maturation antigens (BCMA), such as bb-2121, UCART-BCMA, ET-140, KITE-585, MCM-998, LCAR-B38M, CART-BCMA, SEA-BCMA, BB212, UCART-BCMA, ET-140, P-BCMA-101, and AUTO-2 (APRIL-CAR; Anti-CLL-1 antibodies, such as KITE-796; B7 homolog 6, such as CAR-NKp30 and CAR-B7H6; B-lymphocyte antigen CD19, such as TBI-1501, CTL-119 huCART-19 T cells, JCAR-015 U.S. Pat. No. 7,446,190, JCAR-014, JCAR-017, (WO2016196388, WO2016033570, WO2015157386), axicabtagene ciloleucel (KTE-C19), U.S. Pat. Nos. 7,741,465, 6,319,494, UCART-19, EBV-CTL, T tisagenlecleucel-T (CTL019), WO2012079000, WO2017049166, CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, and IM19 CAR-T; B-lymphocyte antigen CD20, such as ATTCK-20; B-lymphocyte cell adhesion, such as UCART-22, and JCAR-018 (WO2016090190); NY-ESO-1, such as GSK-3377794, and TBI-1301; Carbonic anhydrase, such as DC-Ad-GMCAIX; Caspase 9 suicide gene, such as CaspaCIDe DLI, and BPX-501; CCR5, such as SB-728; CDw123, such as MB-102, and UCART-123; CD20m such as CBM-C20.1; CD4, such as ICG-122; CD30, such as CART30 (CBM-C30.1; CD33, such as CIK-CAR.CD33; CD38, such as T-007, and UCART-38; CD40 ligand, such as BPX-201; CEACAM protein 4 modulators, such as MG7-CART; Claudin 6, such as CSG-002; EBV targeted, such as CMD-003; EGFR, such as autologous 4H11-28z/fIL-12/EFGRt T cell; Endonuclease, such as PGN-514, and PGN-201; Epstein-Barr virus specific T-lymphocytes, such as TT-10; Erbb2, such as CST-102 and CIDeCAR; Ganglioside (GD2), such as 4SCAR-GD2; Glutamate carboxypeptidase II, such as CIK-CAR.PSMA, CART-PSMA-TGFßRDN, and P-PSMA-101; Glypican-3 (GPC3), such as TT-16 and GLYCAR; Hemoglobin, such as PGN-236; Hepatocyte growth factor receptor, such as anti-cMet RNA CAR T; Human papillomavirus E7 protein, such as KITE-439; Immunoglobulin gamma Fc receptor III, such as ACTR087; IL-12, such as DC-RTS-IL-12; IL-12 agonist/mucin 16, such as JCAR-020; IL-13 alpha 2, such as MB-101; IL-2, such as CST-101; K-Ras GTPase, such as anti-KRAS G12V mTCR cell therapy; Neural cell adhesion molecule L1 L1CAM (CD171), such as JCAR-023; Latent membrane protein 1/Latent membrane protein 2, such as Ad5f35-LMPd1-2-transduced autologous dendritic cells; Melanoma associated antigen 10, such as MAGE-A10C796T and MAGE-A10 TCR; Melanoma associated antigen 3/Melanoma associated antigen 6 (MAGE A3/A6) such as KITE-718; Mesothelin, such as CSG-MESO and TC-210; NKG2D, such as NKR-2; Ntrkr1 tyrosine kinase receptor, such as JCAR-024; T cell receptors, such as BPX-701 and IMCgp100; T-lymphocyte, such as TT-12; Tumor infiltrating lymphocytes, such as LN-144 and LN-145; and Wilms tumor protein, such as JTCR-016, WT1-CTL.

Lymphoma or Leukemia Combination Therapy

In some embodiments, the additional therapeutic agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17-AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R-MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCI-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), and venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The above-mentioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and non-myeloablative allogeneic hematopoietic stem cell transplantation.

Non-Hodgkin's Lymphomas Combination Therapy

In some embodiments, the additional therapeutic agents are suitable for treating non-Hodgkin's lymphomas (NHL), especially those of B cell origin, which include monoclonal antibodies, standard chemotherapy approaches (e.g., CHOP, CVP, FCM, MCP, and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP, R-FCM, R-CVP, and R-MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

In some embodiments, the additional therapeutic agents are suitable for treating mantle cell lymphoma (MCL), which include combination chemotherapies such as CHOP, hyperCVAD, and FCM. These regimens can also be supplemented with the monoclonal antibody rituximab to form combination therapies R-CHOP, hyperCVAD-R, and R-FCM. Any of the above-mentioned therapies may be combined with stem cell transplantation or ICE in order to treat MCL.

Other examples of therapeutic agents suitable for treating MCL include:

- immunotherapy, such as monoclonal antibodies (like rituximab) and cancer vaccines, such as GTOP-99, which are based on the genetic makeup of an individual patient's tumor;
- radioimmunotherapy, wherein a monoclonal antibody is combined with a radioisotope particle, such as iodine-131 tositumomab (BEXXAR®), yttrium-90 ibritumomab tiuxetan (ZEVALIN®), and BEXXAR® in sequential treatment with CHOP;
- autologous stem cell transplantation coupled with high-dose chemotherapy, administering proteasome inhibitors such as bortezomib (VELCADE® or PS-341), or administering antiangiogenesis agents such as thalidomide, especially in combination with rituximab;
- drugs that lead to the degradation of Bcl-2 protein and increase cancer cell sensitivity to chemotherapy, such as oblimersen, in combination with other chemotherapeutic agents;
- mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents; and other agents such as flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CCI-779), everolimus (RAD001), BMS-345541, curcumin, SAHA, thalidomide, lenalidomide (REVLIMID®, CC-5013), and geldanamycin (17-AAG).

Waldenstrom's Macroglobulinemia Combination Therapy

In some embodiments, the additional therapeutic agents are suitable for treating Waldenstrom's Macroglobulinemia (WM), which include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combinations thereof.

Other examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma Combination Therapy

In some embodiments, the additional therapeutic agents are suitable for treating diffuse large B-cell lymphoma (DLBCL), which include cyclophosphamide, doxorubicin, vincristine, prednisone, anti-CD20 monoclonal antibodies, etoposide, bleomycin, many of the agents listed for WM, and any combination thereof, such as ICE and R-ICE.

Chronic Lymphocytic Leukemia Combination Therapy

In some embodiments, the additional therapeutic agents are suitable for treating chronic lymphocytic leukemia (CLL), which include chlorambucil, cyclophosphamide, fludarabine, pentostatin, cladribine, doxorubicin, vincristine, prednisone, prednisolone, alemtuzumab, many of the agents listed for WM, and combination chemotherapy and chemo-immunotherapy, including the following common combination regimens: CVP, R-CVP, ICE, R-ICE, FCR, and FR.

Myelofibrosis Combination Therapy

In some embodiments, the additional therapeutic agents are suitable for treating myelofibrosis, which include hedgehog inhibitors, histone deacetylase (HDAC) inhibitors, and tyrosine kinase inhibitors. Non-limiting examples of hedgehog inhibitors are saridegib and vismodegib.

Examples of HDAC inhibitors include, but are not limited to, pracinostat and panobinostat.

Non-limiting examples of tyrosine kinase inhibitors include lestaurtinib, bosutinib, imatinib, gilteritinib, radotinib, and cabozantinib.

Hyperproliferative Disease Combination Therapy

In some embodiments, the additional therapeutic agents are suitable for treating a hyper-proliferative disease, which include gemcitabine, nab-paclitaxel, and gemcitabine/nab-paclitaxel with a JAK inhibitor and/or PI3Kδ inhibitor.

Bladder Cancer Combination Therapy

In some embodiments, the additional therapeutic agents are suitable for treating bladder cancer, which include atezolizumab, carboplatin, cisplatin, docetaxel, doxorubicin, fluorouracil (5-FU), gemcitabine, idosfamide, Interferon alfa-2b, methotrexate, mitomycin, nab-paclitaxel, paclitaxel, pemetrexed, thiotepa, vinblastine, and any combinations thereof.

Breast Cancer Combination Therapy

In some embodiments, the additional therapeutic agents are suitable for treating breast cancer, which include albumin-bound paclitaxel, anastrozole, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, Letrozole, methotrexate, mitoxantrone, paclitaxel, pegylated liposomal doxorubicin, pertuzumab, tamoxifen, toremifene, trastuzumab, vinorelbine, and any combinations thereof.

Triple Negative Breast Cancer Combination Therapy

In some embodiments, the additional therapeutic agents are suitable for treating triple negative breast cancer, which include cyclophosphamide, docetaxel, doxorubicin, epirubicin, fluorouracil, paclitaxel, and combinations thereof.

Colorectal Cancer Combination Therapy

In some embodiments, the additional therapeutic agents are suitable for treating colorectal cancer, which include bevacizumab, capecitabine, cetuximab, fluorouracil, irinotecan, leucovorin, oxaliplatin, panitumumab, ziv-aflibercept, and any combinations thereof.

Castration-Resistant Prostate Cancer Combination Therapy

In some embodiments, the additional therapeutic agents are suitable for treating castration-resistant prostate cancer, which include abiraterone, cabazitaxel, docetaxel, enzalutamide, prednisone, sipuleucel-T, and any combinations thereof.

Esophageal and Esophagogastric Junction Cancer Combination Therapy

In some embodiments, the additional therapeutic agents are suitable for treating esophageal and esophagogastric junction cancer, which include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof.

Gastric Cancer Combination Therapy

In some embodiments, the additional therapeutic agents are suitable for treating gastric cancer, which include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head & Neck Cancer Combination Therapy

In some embodiments, the additional therapeutic agents are suitable for treating head & neck cancer, which include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Hepatobiliary Cancer Combination Therapy

In some embodiments, the additional therapeutic agents are suitable for treating hepatobiliary cancer, which include capecitabine, cisplatin, fluoropyrimidine, 5-fluorourcil, gemecitabine, oxaliplatin, sorafenib, and any combinations thereof.

Hepatocellular Carcinoma Combination Therapy

In some embodiments, the additional therapeutic agents are suitable for treating hepatocellular carcinoma, which include capecitabine, doxorubicin, gemcitabine, sorafenib, and any combinations thereof.

Non-Small Cell Lung Cancer Combination Therapy

In some embodiments, the additional therapeutic agents are suitable for treating non-small cell lung cancer (NSCLC), which include afatinib, albumin-bound paclitaxel, alectinib, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof.

Small Cell Lung Cancer Combination Therapy

In some embodiments, the additional therapeutic agents are suitable for treating small cell lung cancer (SCLC), which include bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof.

Melanoma Combination Therapy

In some embodiments, the additional therapeutic agents are suitable for treating melanoma, which include albumin bound paclitaxel, carboplatin, cisplatin, cobiemtinib, dabrafenib, dacrabazine, IL-2, imatinib, interferon alfa-2b, ipilimumab, nitrosourea, nivolumab, paclitaxel, pembrolizumab, pilimumab, temozolomide, trametinib, vemurafenib, vinblastine, and any combinations thereof.

Ovarian Cancer Combination Therapy

In some embodiments, the additional therapeutic agents are suitable for treating ovarian cancer, which include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcibabine, ifosfamide, irinotecan, letrozole, leuprolide acetate, liposomal doxorubicin, megestrol acetate, melphalan, olaparib, oxaliplatin, paclitaxel, Pazopanib, pemetrexed, tamoxifen, topotecan, vinorelbine, and any combinations thereof.

Pancreatic Cancer Combination Therapy

In some embodiments, the additional therapeutic agents are suitable for treating pancreatic cancer, which include 5-fluorourcil, albumin-bound paclitaxel, capecitabine, cisplatin, docetaxel, erlotinib, fluoropyrimidine, gemcitabine, irinotecan, leucovorin, oxaliplatin, paclitaxel, and any combinations thereof.

Renal Cell Carcinoma Combination Therapy

In some embodiments, the additional therapeutic agents are suitable for treating renal cell carcinoma, which include axitinib, bevacizumab, cabozantinib, erlotinib, everolimus, levantinib, nivolumab, pazopanib, sorafenib, sunitinib, temsirolimus, and any combinations thereof.

EXAMPLES

Methods for preparing the novel compounds described herein will be apparent to those of skill in the art with suitable procedures being described, for example, in the reaction schemes and examples below.

Abbreviations

Ace-Cl—1-Chloroethyl chloroformate
ACN—Acetonitrile
$Ac_2O$—Acetic Anhydride
AcOH—Acetic Acid
Bis-pin—Bis(pinacolato)diboron
$B_2Pin_2$—Bis(pinacolato)diboron
BnBr—benzyl bromide
$[BnNMe_3]Cl$—Benzyltrimethylammonium chloride
$[BnEt_3N]Cl$—Benzyltriethylammonium chloride
$BnNEt_3Cl$—Benzyltriethylammonium chloride
Bredereck's Reagent—tert-Butoxy bis(dimethylamino) methane
Boc—tert-Butoxycarbonyl
$Boc_2O$—di-tert-Butyl Dicarbonate
$(Boc)_2O$—di-tert-Butyl Dicarbonte
Cbz—Benzyloxycarbonyl
CbzCl—Benzyl Chloroformate
conc—concentrated
DCM—Dichloromethane
DIBAL-H—Diisobutylaluminum hydride
DIEA—Diisopropylethylamine
Dioxane—more specifically: 1,4-Dioxane
DIPEA—N,N-Diisopropylethylamine
DMA—N,N-Dimethylacetamide
DMF—Dimethylformamide
DMP—Dess-Martin periodinane: 1,1,1-Triacetoxy-1,1-dihydro-1,2-benziodoxol-3(1H)-one
EtOAc—Ethyl Acetate
EtOH—Ethanol
Grubbs II Catalyst—(1,3-Bis(2,4,6-trimethylphenyl)-2-imidazolidinylidene)dichloro (phenylmethylene)(tricyclohexylphosphine)ruthenium, Benzylidene[1,3-bis(2,4,6-trimethylphenyl)-2-imidazolidinylidene]dichloro (tricyclohexylphosphine) ruthenium, Dichloro[1,3-bis(2,4,6-trimethylphenyl)-2-imidazolidinylidene] (benzylidene)(tricyclohexylphosphine)ruthenium (II)
$H_2$—Hydrogen
HCl—Hydrogen Chloride
Hex—Hexanes
HPLC—High-pressure liquid chromatography
Hunig's Base—Diisopropylethylamine
$K_2CO_3$—Potassium Carbonate
KOAc—Potassium Acetate
$K_3PO_4$—Potassium Phosphate
LCMS—Liquid chromatography/mass spectrometry
LDA—Lithium Diisopropylamide
$LiBH_4$—Lithium Borohydride
MeCN—Acetonitrile
$Me_4$ t-BuXphos—2-Di-tert-butylphosphino-3,4,5,6-tetramethyl-2',4',6'-triisopropyl-1-1'-biphenyl
mCPBA—3-Chloroperbenzoic acid
m-CPBA—3-Chloroperbenzoic acid
MeOH—Methanol MTBE—tert-Butyl MethylEether
$NaBH_4$—Sodium Borohydride
NaOEt—Sodium Ethoxide
NaOH—Sodium Hydroxide
$Na_2SO_4$—Sodium Sulfate
$NEt_3$—Triethylamine
$NH_4Cl$—Ammonium Chloride
NMP—N-Methyl Pyrrolidinone
NMR—Nuclear Magnetic Resonance
Palau'chlor—2-Chloro-1,3-bis(methoxycarbonyl)guanidine
Parkins Catalyst—Hydrido(dimethylphosphinous acid KP) [hydrogen bis(dimethylphosphinito-κP)]platinum (II)
$PBr_3$—Phosphorous tribromide
PhMe—Toluene
$POCl_3$—Phosphorus (V) Oxychloride
Pd/C—Palladium on Carbon
$PdCl_2$(dppf)—Dichloro bis(1,1'-diphenylphosphinoferrocene)-Palladium(II)
$Pd(dba)_2$—Palladium(O) bis(dibenzylideneacetone)
$Pd_2(dba)_3$—Tris(dibenzylideneacetone)dipalladium(0)
PyBroP—Bromotripyrrolidinophosphonium Hexafluorophosphate
RT—room temperature
SFC—Supercritical Fluid Chromatography
Sphos Pd G4—Methanesulfonyloxy(2-dicyclohexylphosphino-2',6'-dimethoxy-1,1'-biphenyl)[2-(2'-methylamino-1,1'-biphenyl)]palladium(II)
(S)-TolBINAP—(S)-(−)-2,2'-p-tolyl-phosphino)-1,1'-binaphthyl
TASF—Tris(dimethylamino)sulfonium difluorotrimethylsilicate
TBDMSCl—tert-Butyldimethylchlorosilane
TBDMS-Cl—tert-Butyldimethylchlorosilane
TBS—tert-Butyldimethylsilyl
TBSCl—tert-Butyldimethylsilyl chloride
t-BuONa—Sodium tert-Butoxide
TeocOSuc—1-[2-(Trimethylsilyl)ethoxycarbonyloxy]pyrrolidin-2,5-dione
$Ti(OEt)_4$—Titanium Ethoxide
THF—Tetrahydrofuran
XantPhos—4,5-Bis(diphenylphosphino)-9,9-dimethylxanthene General Schemes Typical embodiments of compounds in accordance with the present disclosure may be synthesized using the general reaction schemes and/or examples described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods for synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

General Scheme I depicts a general route used to synthesize compounds of Formula AA. Intermediates FA1 and FA2 were treated with base, giving a nucleophilic aromatic substitution ($S_NAr$) product FA3 having an $R^1$ group as defined in the present disclosure. Treatment of RA3 with an acid, commonly as solvent, provided FA4. Usually FA4 was converted to its derived aryl chloride FA5 using phosphorous (V) oxychloride with a variety of additives including but not limited to benzyltrialkylammonium chlorides. FA5 was treated with FA6 to give $S_NAr$ product FA7, optionally substituted with a variety of $X^2$ and $R^{22}$ groups as defined in the present disclosure. C—S bond coupling with FA8 gave sulfide FA9 bearing a variety of groups A as defined in the present disclosure. In some cases, A-SNa (the sodium salt) was used as a form of FA8 to make FA9. Commonly, a protecting group (PG) was then removed to afford Examples of Formula AA. The Examples were isolated by conventional means.

General Scheme I

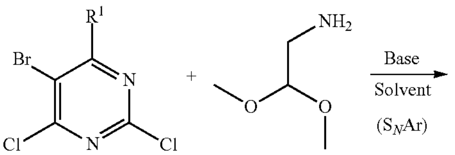

FA1 FA2

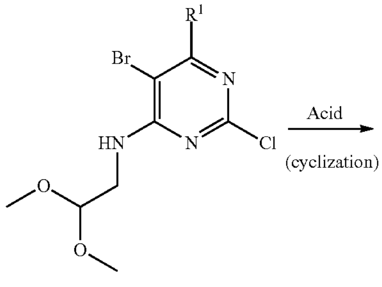

FA3

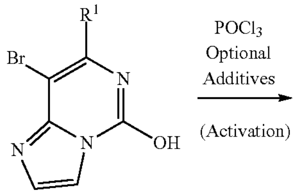

FA4

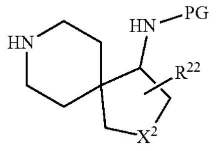

FA6

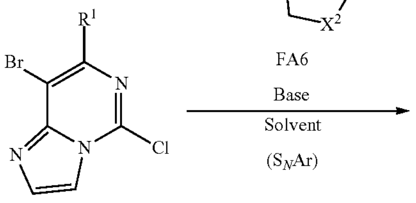

FA5

-continued

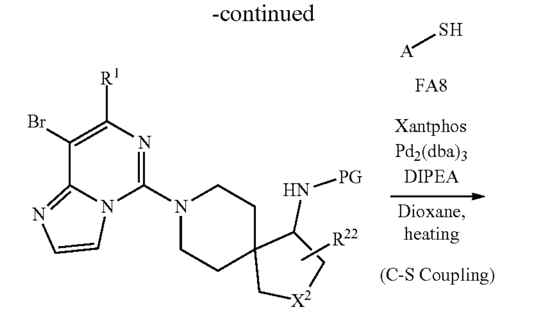

FA7

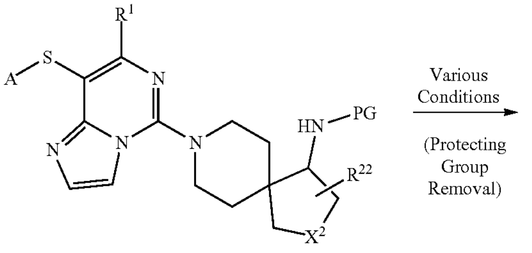

FA9

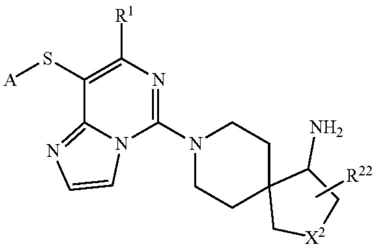

Formula AA

General Scheme II depicts a general route used to synthesize compounds of Formula BB. Intermediates FB1 and FB2 were treated with base, giving a nucleophilic aromatic substitution ($S_NAr$) product FB3 having an $R^1$ group as defined in the present disclosure. Treatment of RB3 with an acid, commonly as solvent, provided FB4. By treating compound FB4 with FB5 in the presence of base, often with a transition metal catalyst, FB6 was obtained with a variety of groups A as defined in the present disclosure. Usually, compound FB6 was activated with a phosphorous (V) reagent, with optional use of additives to install the Leaving Group (LG) present in FB7. The leaving group LG could be a halide, or other suitable functionality able to undergo $S_NAr$ reactions; such functionality would be known to those skilled in the art. Either with or without isolation of FB7 directly, treatment with amine FB8 with groups $R^2$ (as defined in the present disclosure) in the presence of base provided compounds having the Formula BB via an $S_NAr$-type reaction.

General Scheme II

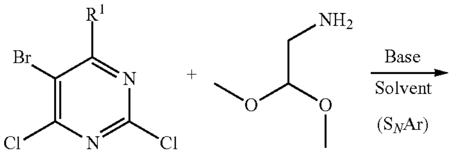

FB1 FB2

-continued

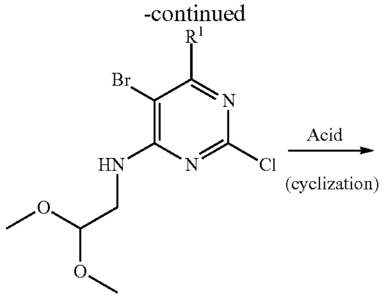

FB3

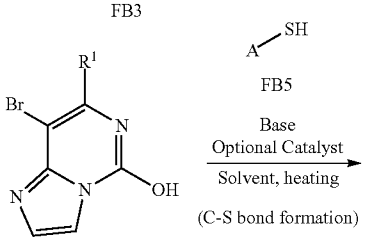

FB4

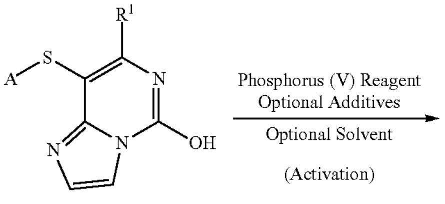

FB6

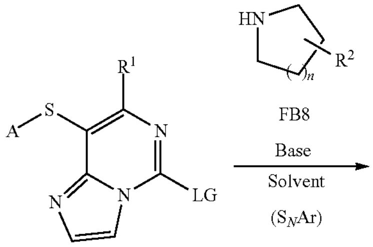

FB7

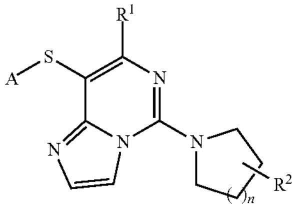

Formula BB

General Scheme III depicts a general route used to synthesize compounds of Formula C. Intermediate FC1 and hydrazine were combined, optionally in the presence of base, giving a nucleophilic aromatic substitution ($S_NAr$) product FC2. Once treated with a trialkylorthoformate in the presence of acid, FC2 could be cyclized to provide FC3. Commonly FC3 was activated to convert group G into a suitable Leaving Group (LG), giving compound FC4. G can be a halide such as chloro, or a methylthio group. The leaving group $LG^2$ could be a halide, methylthio-S-oxide, methyl-S-dioxide, or other suitable functionality able to undergo $S_NAr$ reactions; such functionality would be known to those skilled in the art. Intermediate FC4 was not always isolated but rather used directly in the subsequent $S_NAr$ reaction with FC5 (containing groups $X^2$ and $R^{22}$ as defined in the present disclosure) to provide FC6. When G was Cl, FC3 itself, upon treatment with FC5, could directly be converted to FC6. In many cases, FC6 underwent a coupling reaction with boron-derivative FC7 (Having group A as defined in the present disclosure) to give FC8. Commonly, FC7 was a boronic acid, but could also be in the form of a derived boronate ester. Removal of the protecting group (PG) on FC8 gave compounds Formula CC.

General Scheme III

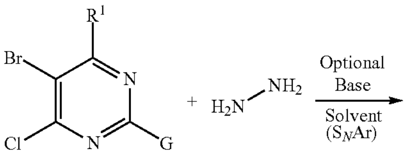

FC1

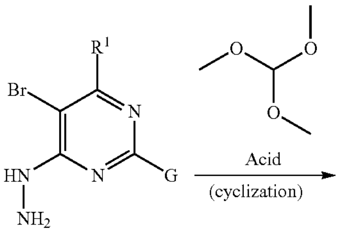

FC2

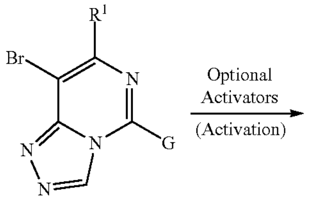

FC3

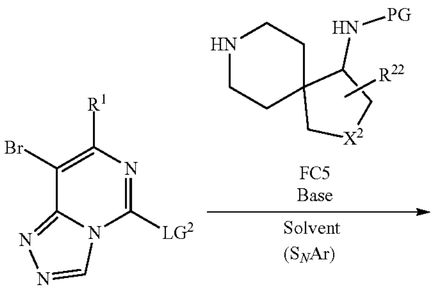

FC4

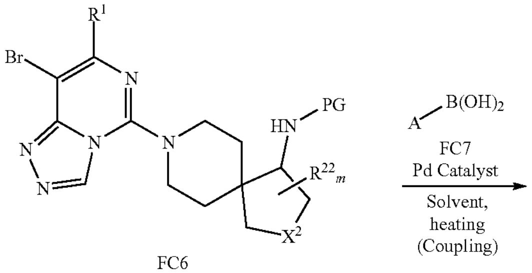

FC6

-continued

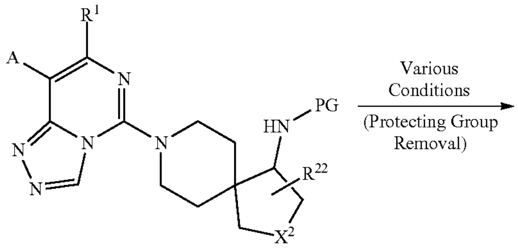

FC8

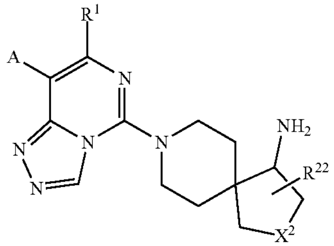

Formula CC

General Scheme IV

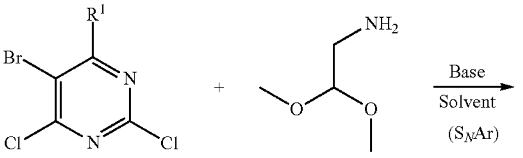

FD1 FD2

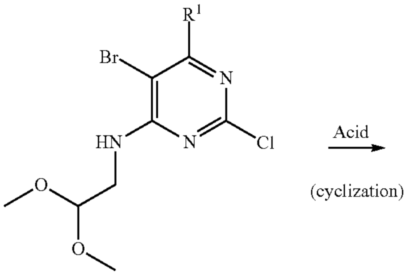

FD3

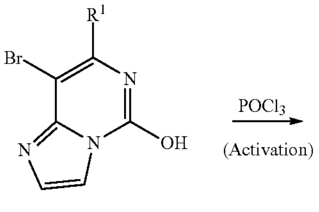

FD4

-continued

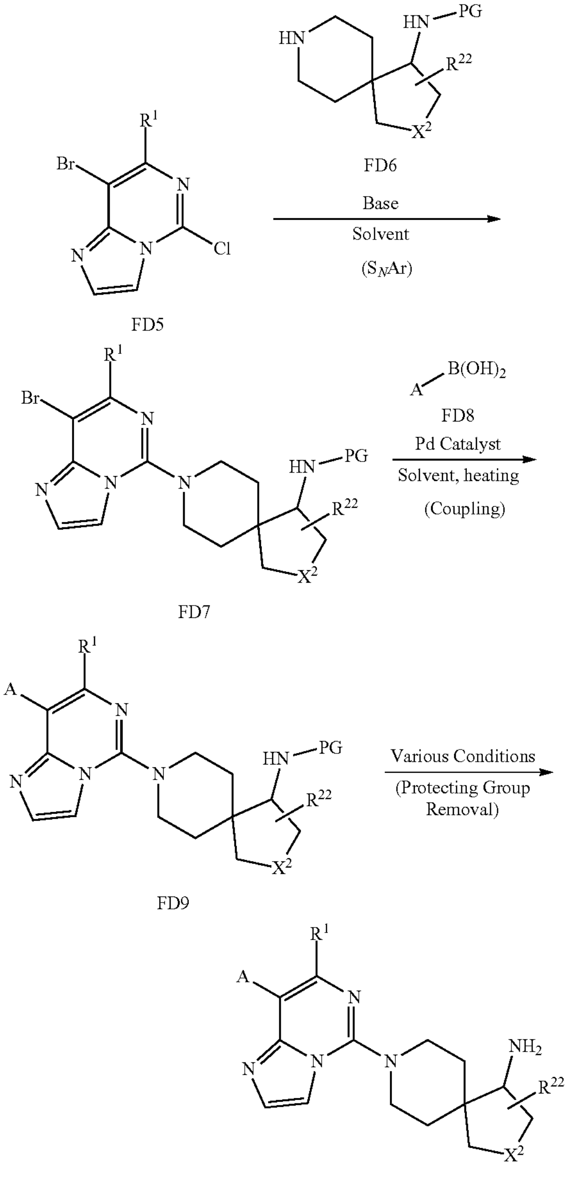

FD5, FD6, FD7, FD8, FD9, Formula DD

General Scheme IV depicts a general route used to synthesize compounds of Formula DD. Intermediates FD1 and FD2 were treated with base, giving a nucleophilic aromatic substitution ($S_NAr$) product FD3, being optionally substituted with an $R^1$ group as defined in the present disclosure. Treatment of RD3 with an acid, commonly as solvent, provided FD4. Usually FD4 was converted to its derived aryl chloride FD5 using phosphorous (V) oxychloride with a variety of additives including but not limited to benzyltrialkylammonium chlorides. FD5 was treated with FD6 (having groups $X^2$ and $R^{22}$ as defined in the present disclosure) to give $S_NAr$ product FD7. C—C bond coupling with boronic acid compound FD8 gave biaryl compound FD9 having group A as defined in the present disclosure. Commonly, FD8 was a boronic acid, but could also be in the form of a derived boronate ester. Often, a protecting group (PG) was then removed to afford Examples of Formula DD. The Examples were isolated by conventional means.

Synthesis of Intermediates

Compound Q1y

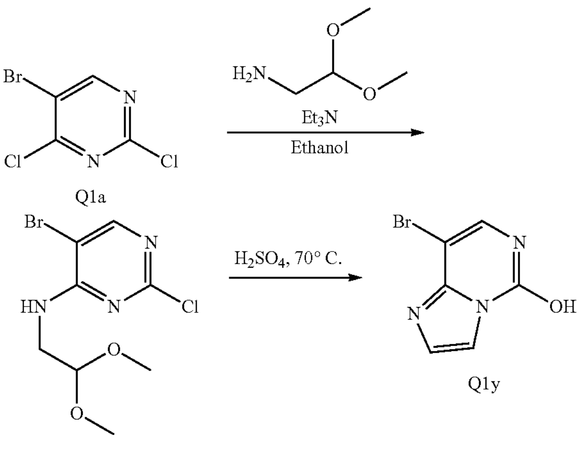

Q1a, Q1b, Q1y

Compound Q1b: To Compound Q1a (10 g) in ethanol (100 mL) at 0° C. was added triethylamine (12.0 mL, 88 mmol, 2 equiv.) and aminoacetaldehyde dimethyl acetal (6.2 mL, 57.1 mmol, 1.3 equiv.). After 15 min, the reaction was warmed to ambient temperature. After 16 h, the reaction was concentrated in vacuo. The resulting slurry was diluted with diethyl ether, cooled to 0° C., and stirred for 30 min. The mixture was then filtered through Celite, rinsed with diethyl ether, and the filtrate was dried with sodium sulfate, and concentrated in vacuo to afford Compound Q1b. $^1H$ NMR (400 MHz, DMSO-$d_6$) δ 8.27 (s, 1H), 7.67 (t, J=5.9 Hz, 1H), 4.58 (t, J=5.4 Hz, 1H), 3.47 (t, J=5.7 Hz, 2H), 3.28 (s, 6H). LCMS $ESI^+$ calc'd for $C_8H_{11}BrClN_3O_2$: 298.0 [M+$H^+$]; found: 297.9 [M+$H^+$].

Compound Q1y: of Compound Q1b (6.4 g) was dissolved in concentrated sulfuric acid (65 mL) and heated to 75° C. After 2 h, the reaction was poured into ice and slowly basified with 5 M aqueous sodium hydroxide to ~pH 6 while maintaining the reaction at room temp. The resulting suspension was filtered and the solids were dried to give Compound Q1y. $^1H$ NMR (400 MHz, DMSO-$d_6$) δ 11.90 (s, 1H), 7.89 (d, J=1.5 Hz, 1H), 7.64 (s, 1H), 7.42 (d, J=1.5 Hz, 1H). LCMS $ESI^+$ calc'd for $C6H_4BrN_3O$: 214.0 [M+$H^+$]. found: 214.0 [M+$H^+$].

Compound Q1z

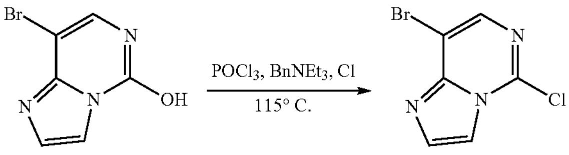

Q1y, Q1z

Compound Q1z: To Compound Q1y (3.5 g) was added phosphorus(V) oxychloride (50 mL) and benzyltriethylammonium chloride (11.2 g) and the mixture was heated to 115° C. After 3 h, the mixture was concentrated in vacuo and the slurry was coevaporated with EtOAc. The resulting material was diluted with EtOAc and slowly treated with saturated sodium bicarbonate solution. The layers were separated and the organics were washed with brine, dried over sodium sulfate, and concentrated in vacuo. The solids were then suspended in DCM and filtered. The mother liquor was concentrated in vacuo and subjected to flash chromatography (0-100% EtOAc in hexanes) to afford Compound Q1z. $^1$H NMR (400 MHz, DMSO-d$_6$) δ 8.20 (d, J=1.5 Hz, 1H), 8.19 (s, 1H), 7.84 (d, J=1.5 Hz, 1H). LCMS ESI$^+$ calc'd for $C_6H_3BrClN_3$: 233.9 [M+H$^+$]. found: 233.9 [M+H$^+$].

Compound Q2

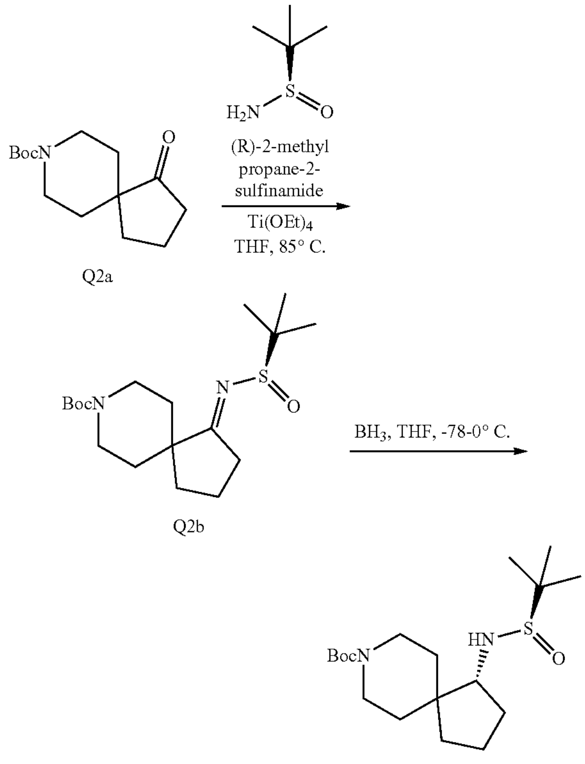

Q2a

Q2b

Q2

Compound Q2b: To Compound Q2a (2.15 g) and (R)-2-methylpropane-2-sulfinamide (2.05 g) in THF (42 mL) was added titanium(IV) ethoxide (7.0 mL) and the mixture was heated to 85° C. After 48 hrs, the mixture was cooled to ambient temperature and, under vigorous stirring, was added water. After 15 min, the suspension was filtered through celite and the solids were rinsed with EtOAc. The filtrate was dried over sodium sulfate and concentrated in vacuo. The resulting material was purified by flash chromatography (0-100% EtOAc in hexanes) to give Compound Q2b. $^1$H NMR (400 MHz, Chloroform-d) δ 3.92 (d, J=13.4 Hz, 2H), 3.12-2.95 (m, 3H), 2.78-2.59 (m, 1H), 1.96-1.80 (m, 2H), 1.80-1.65 (m, 4H), 1.46 (s, 9H), 1.45-1.35 (m, 2H), 1.24 (s, 9H). LCMS ESI$^+$ calc'd for $C_{18}H_{32}N_2O_3S$: 357.2 [M+H$^+$]. found: 356.8 [M+H$^+$].

Compound Q2: To Compound Q2b (100 mg) in THF (2.8 mL) at −78° C. was added borane tetrahydrofuran complex solution (0.47 mL, 1 M) dropwise. After 1 h, the reaction was warmed to 0° C. After 3 h, the reaction was quenched with MeOH and warmed to ambient temperature. After stirring for 30 min, the mixture was concentrated in vacuo and purified by flash chromatography (0-100% EtOAc in hexanes) to give Compound Q2. $^1$H NMR (400 MHz, Chloroform-d) δ 3.94 (d, J=14.2 Hz, 2H), 3.35-3.23 (m, 1H), 3.15 (d, J=4.7 Hz, 1H), 2.85 (td, J=12.9, 2.9 Hz, 2H), 2.15-1.99 (m, 1H), 1.85-1.71 (m, 1H), 1.70-1.60 (m, 4H), 1.51 (td, J=12.7, 12.2, 4.5 Hz, 2H), 1.45 (s, 9H), 1.27 (d, J=10.6 Hz, 2H), 1.21 (s, 9H). LCMS ESI$^+$ calc'd for $C_{18}H_{34}N_2O_3S$: 381.2 [M+Na$^+$]. found: 381.1 [M+Na$^+$].

Compound Q3

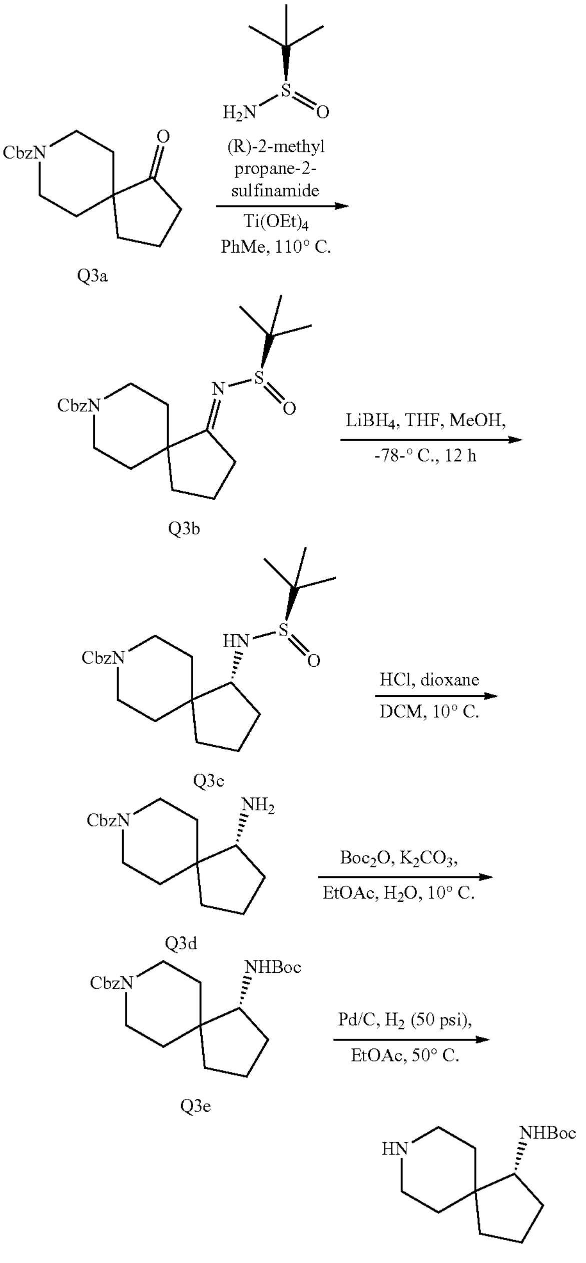

Q3a

Q3b

Q3c

Q3d

Q3e

Q3

Compound Q3b: To a mixture of Compound Q3a (140 g) and (R)-2-methylpropane-2-sulfinamide (88.6 g) in toluene (1000 mL) at 10° C. was added titanium(IV) ethoxide (505 mL) in one portion and the mixture was heated to 110° C. After 12 h, water was added drop-wise and the mixture was cooled to 10° C. After 30 min, then the mixture was filtered, rinsed with EtOAc, and the filtrate was concentrated under reduce pressure. The residue was purified by column chromatography (1-100% EtOAc in petroleum ether) at give Compound Q3b.

Compound Q3c: To Compound Q3b (160 g) in THF (1000 mL) and MeOH (100 mL) was added $LiBH_4$ (35.7 g) at −78° C. The mixture was stirred at −60° C. for 12 h. To above mixture was added aq. $NH_4Cl$ drop-wise, extracted with EtOAc, and concentrated under reduced pressure. The residue was purified by column chromatography (5-50% EtOAc in petroleum ether) to give Compound Q3c.

Compound Q3d: To Compound Q3c (120 g) in DCM (450 mL) was added HCl in 1,4-dioxane (229 mL, 4 M) in one portion at 10° C. and stirred for 1 h. The mixture was concentrated under reduce pressure to give Compound Q3d.

Compound Q3e: To Compound Q3d (95 g) and $Boc_2O$ (76.6 g) in EtOAc (500 mL) was added $K_2CO_3$ (60.6 g) in water (500 mL) drop-wise at 10° C. and stirred for 2 h. The mixture was extracted with EtOAc and concentrated under reduce pressure. The residue was purified by column chromatography (5-100% EtOAc in petroleum ether) to give Compound Q3e. $^1H$ NMR (400 MHz, Chloroform-d) δ 7.39-7.27 (m, 4H), 5.12 (s, 2H), 4.35 (brd, J=9.0 Hz, 1H), 3.95 (brd, J=13.0 Hz, 2H), 3.77-3.64 (m, 1H), 3.07-2.88 (m, 2H), 2.09-2.01 (m, 1H), 1.68-1.59 (m, 4H), 1.48-1.40 (m, 11H), 1.28-1.24 (m, 2H), 0.89-0.84 (m, 2H).

Compound Q3: To Compound Q3e (90 g) in EtOAc (1800 mL) was added Pd/C (30.0 g). The suspension was degassed under vacuum and purged with $H_2$ several times. The mixture was stirred under $H_2$ (50 psi) at 50° C. for 12 h. The mixture was filtered and concentrated under reduce pressure to give Compound Q3. $^1H$ NMR (400 MHz, Chloroform-d) δ 4.44 (br d, J=9.2 Hz, 1H), 3.63 (q, J=8.3 Hz, 1H), 2.98-2.87 (m, 2H), 2.75-2.60 (m, 2H), 1.99 (dt, J=7.9, 12.7 Hz, 1H), 1.82-1.67 (m, 2H), 1.65-1.52 (m, 3H), 1.48-1.31 (m, 12H), 1.29-1.16 (m, 2H). LCMS $ESI^+$ calc'd for $C_{14}H_{26}N_2O_2$: 255.2 [M+H$^+$]. found: 255.1 [M+H$^+$].

Compound Q4y

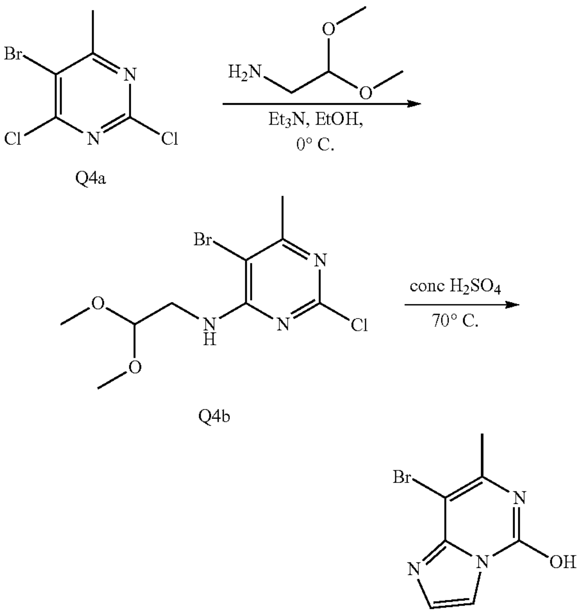

Q4a

Q4b

Q4y

Compound Q4b: To Compound Q4a (15 g, 62 mmol) at 0° C. was added $Et_3N$ and aminoacetaldehyde dimethyl acetal (9.8 g, 93 mmol), the reaction mixture was then warmed to RT, stirred at RT for 12 h. Crashed out product was then filtered, washed with hexane, dried over high vacuum to afford crude product Compound Q4b. LCMS $ESI^+$ calc'd for $C_9H_{13}BrClN_3O_2$: 310.0 [M+H$^+$]. found: 310.1 [M+H$^+$].

Compound Q4y: To Compound Q4b (18 g, 58 mmol) was added conc. $H_2SO_4$ (53 mL) to form a yellow solution with some solids remaining, heated to 75° C. for 1 h, reaction was then slowly cooled to 0° C. Then NaOH (5 N) solution was slowly added to ~pH6. The crashed out solid was filtered and dried to afford Compound Q4y. LCMS $ESI^+$ calc'd for $C_7H_6BrN_3O$: 228.0 [M+H$^+$]. found: 228.1 [M+H$^+$].

Compound Q4z

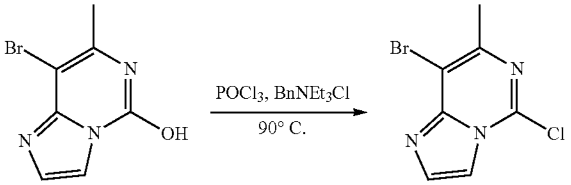

Q4y Q4z

Compound Q4z: To Compound Q4y (7 g, 30.7 mmol) in round bottle flask was added $POCl_3$ (70.6 g, 460.43 mmol) and benzyltriethylammonium chloride (8.39 g, 36.83 mmol) at 0° C., heated reaction mixture to 115° C. for 1 h. $POCl_3$ was evaporated and the residue was dissolved in DCM and directly purified with combi-flash column without work-up to afford Compound Q4z. LCMS $ESI^+$ calc'd for $C_7H_5BrClN_3$: 246.0 [M+H$^+$]. found: 246.1 [M+H$^+$].

Compound Q5

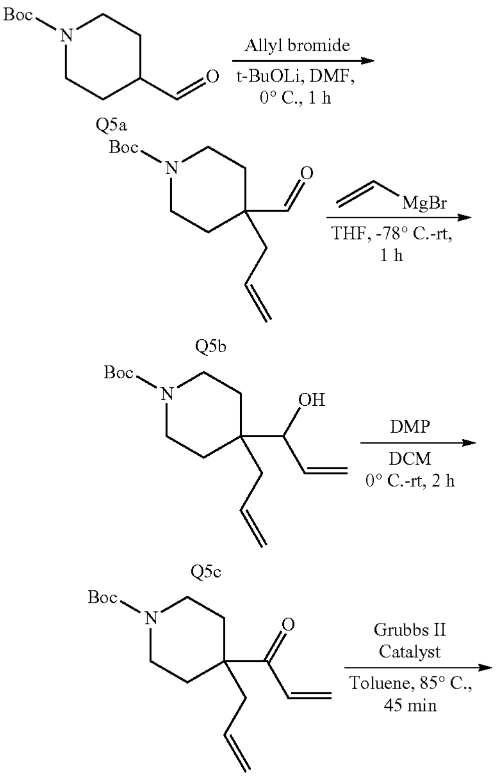

Q5a

Q5b

Q5c

Q5d

-continued

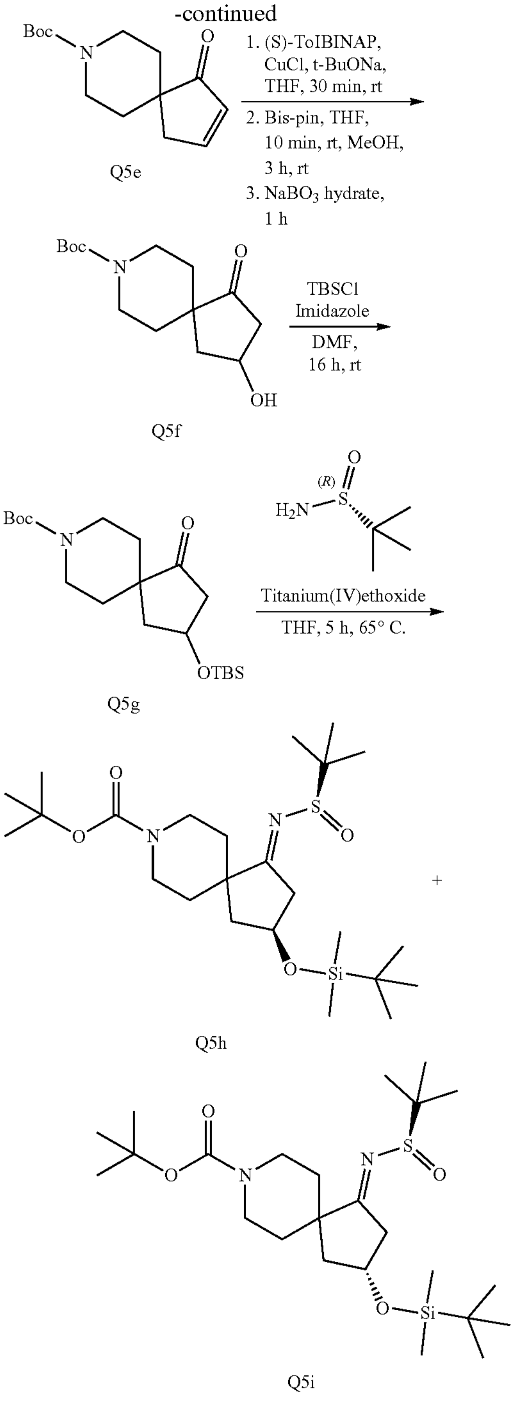

Q5e

Q5f

Q5g

Q5h

Q5i

Compound Q5b: To a solution of Compound Q5a (125 g) in DMF (1.25 L) was added t-BuOLi (32.8 g) followed by dropwise addition of allyl bromide (50.6 mL) at 0° C. The resulting reaction mixture was stirred at 0° C. for 1 h. The reaction mixture was quenched with aq $NH_4Cl$ solution (1.2 L), extracted with EtOAc (2×500 mL). The combined organic layers were washed with saturated aqueous NaCl solution (250 mL), dried over anhydrous sodium sulphate, filtered and concentrated under reduced pressure to afford Compound Q5b. $^1H$ NMR (400 MHz, Chloroform-d) δ 9.50 (s, 1H), 5.63-5.60 (m, 1H), 5.12-5.05 (m, 2H), 3.78 (s, 2H), 2.98-2.92 (m, 2H), 2.24 (d, J=6.4 Hz, 2H), 1.95 (d, J=2.8 Hz, 2H), 1.58 (s, 9H), 1.49 (s, 1H), 1.48-1.46 (m, 1H).

Compound Q5c: To a stirred solution of Compound Q5b (60 g) in THF (600 mL) was added vinyl magnesium bromide (1.0 M in THF, 592 mL) at −78° C. The reaction mixture was stirred at −78° C. for 1 h. The reaction mixture was quenched with aq $NH_4Cl$ solution (500 mL), and extracted with ethyl acetate (2×500 mL). The combined organic layers were washed with saturated aqueous NaCl solution (1000 mL), dried over anhydrous sodium sulfate, filtered and concentrated under reduced pressure to afford Compound Q5c. The crude product was used in the next step without further purification.

Compound Q5d: To a stirred solution of Compound Q5c (55 g) in DCM (550 mL) at 0° C. was added DMP (91.3 g) in a portion-wise manner. The resulting reaction mixture was stirred at 0° C. for 2 h. The reaction mixture was quenched with $NaHCO_3$:$Na_2SO_3$ (2000 mL, 1:1 ratio) and extracted with ethyl acetate (2×1000 mL). The combined organic layers were washed with saturated aqueous NaCl solution (1000 mL), dried over anhydrous sodium sulfate, filtered and concentrated under reduced pressure to afford Compound Q5d. The crude product was used in the next step without further purification.

Compound Q5e: To a stirred solution of Compound Q5d (52 g) in toluene (1.56 L) degassed with argon gas for 10 min at RT was added Grubbs II Catalyst (4.7 g). The resulting reaction mixture was stirred at 85° C. for 45 min. The mixture was cooled to RT, concentrated under reduced pressure and the residue was purified by flash column chromatography to afford Compound Q5e. $^1H$ NMR (400 MHz, Chloroform-d) δ 7.68-7.65 (m, 1H), 6.20-6.17 (m, 1H), 4.10 (s, 2H), 2.93-2.87 (m, 2H), 2.61 (s, 2H), 1.80-1.75 (m, 2H), 1.60 (s, 9H), 11.28 (d, J=12.0 Hz, 2H).

Compound Q5f: A mixture of CuCl (118 mg), (S)-TolBINAP (807 mg) and t-BuONa (114 mg) in THF (50 mL) was stirred for 30 min at rt. Bis-pin (11.1 g) in THF (16 mL) was added and the resulting mixture was stirred for 10 min at RT. A solution of Compound Q5e (10 g) in THF (41 mL v) was added drop wise at 20° C. followed by addition of MeOH. The resulting mixture was stirred for 3 h at RT. Water (125 mL) was then added to the reaction mixture and cooled to 20° C., sodium perborate was added in a portion wise, the resulting reaction mixture was vigorously stirred for 1 h at RT. The reaction mixture was then quenched with aqueous saturated $Na_2SO_3$ (500 mL) and $NaHCO_3$ solution (500 mL) and extracted with EtOAc (2×500 mL). The combined organic layer was washed with saturated aqueous NaCl solution (1000 mL), dried over anhydrous sodium sulfate, filtered and concentrated under reduced pressure to afford Compound Q5f. The crude product was used in the next step without further purification.

Compound Q5g: To a stirred solution of Compound Q5f (10.7 g) in DMF (107 mL) was added imidazole at 0° C., followed by addition of TBSCl (7.2 g) as a portion wise at 0° C., the resulting reaction mixture was stirred for 16 h at RT. The reaction mixture was quenched with aqueous $NH_4Cl$ (200 mL) solution, and extracted with EtOAc (2×500 mL). The combined organic layer was washed with saturated aqueous NaCl solution (1000 mL), dried over anhydrous sodium sulfate, filtered and concentrated under reduced pressure to afford Compound Q5g. LCMS $ESI^+$ calc'd for $C_{20}H_{37}NO_4Si$: 384.2 [M+H$^+$]. found: 384.3 [M+H$^+$].

Compound Q5h: To a solution of Compound Q5g (13 g) in THF (130 mL) was added (R)-2-methylpropane-2-sulfinamide (8.2 g) at RT followed by the addition of $Ti(OEt)_4$ (30 mL) and the resulting reaction mixture was stirred at 65° C. for 5 h. The reaction mixture was quenched with aqueous $NH_4Cl$ (200 mL) solution, and extracted with EtOAc (2×500 mL). The combined organic layer was washed with saturated aqueous NaCl solution (1000 mL), dried over anhydrous sodium sulfate, filtered and concentrated under reduced pressure. The residue was purified by flash column to afford Compound Q5h and Compound Q5i. LCMS ESI$^+$ calc'd for $C_{24}H_{46}N_2O_4SSi$: 487.2 [M+H$^+$]. found: 487.5 [M+H$^+$].

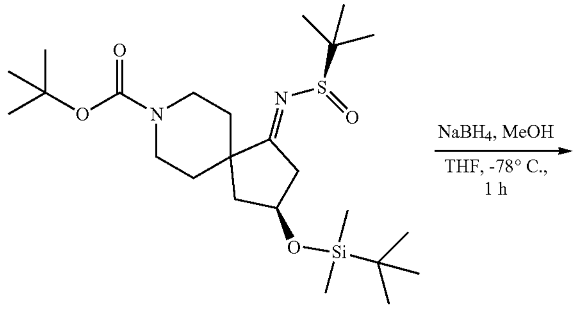

Q5h

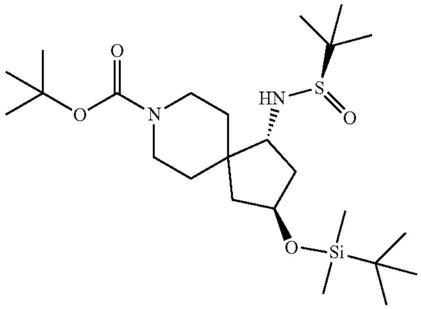

Q5

Compound Q5: To a stirred solution of Compound Q5h (7 g) in THF (70 mL) and MeOH (7 mL) was added $NaBH_4$ (1.6 g) portion-wise at −78° C. The resulting reaction mixture stirred for 1 h at −78° C. The reaction mixture was cooled to room temperature, quenched with 10% $NH_4Cl$ solution (25 mL) and extracted with EtOAc (2×250 mL). The combined organic layer was washed with saturated aqueous NaCl solution (100 mL), dried over anhydrous sodium sulfate, filtered and concentrated under reduced pressure. The residue was purified by column chromatography to afford Compound Q5. $^1$H NMR (400 MHz, Chloroform-d) δ 5.03 (d, J=9.2 Hz, 1H). 4.2-4.21 (m, 1H), 3.82-3.79 (m, 2H), 3.39-3.30 (m, 1H), 2.71 (s, 2H), 1.98-1.70 (m, 4H), 1.41 (s, 1H), 1.37 (s, 9H), 1.22 (d, J=12.8 Hz, 1H), 1.20 (s, 9H), 0.87 (s, 9H), 0.00 (s, 6H). LCMS ESI$^+$ calc'd for $C_{24}H_{48}N_2O_4SSi$: 489.3 [M+H$^+$]. found: 489.4 [M+H$^+$].

Compound Q6

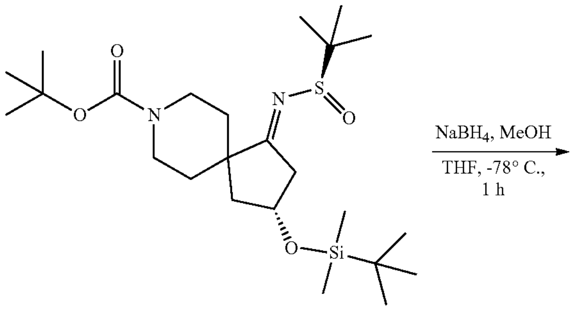

Q5i

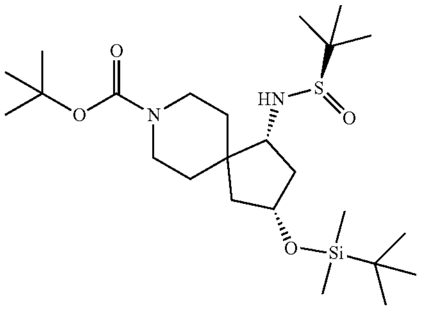

Q6

Compound Q6: To Compound Q5i (7.3 g) in THF (73 mL) and MeOH (7.3 mL) was added $NaBH_4$ (1.7 g) portion-wise at −78° C. The resulting reaction mixture stirred for 1 h at −78° C. The reaction mixture was cooled to room temperature, quenched with 10% $NH_4Cl$ solution (25 mL) and extracted with EtOAc (2×250 mL). The combined organic layer was washed with saturated aqueous NaCl solution (100 mL), dried over anhydrous sodium sulfate, filtered and concentrated under reduced pressure. The residue was purified by column chromatography to afford Compound Q6. $^1$H NMR (400 MHz, Chloroform-d) δ 5.05-5.03 (m, 1H). 3.88-3.78 (m, 1H), 3.12-3.02 (m, 1H), 2.71 (s, 2H), 2.22-2.14 (m, 1H), 1.75-1.61 (m, 4H), 1.49 (s, 2H), 1.39 (s, 9H), 1.11 (s, 9H), 0.87 (s, 9H), 0.00 (s, 6H). LCMS ESI$^+$ calc'd for $C_{24}H_{48}N_2O_4SSi$: 489.3 [M+H$^+$]. found: 489.4 [M+H$^+$].

Compound Q7

Compound Q7b: To a stirred solution of ethyl Compound Q7a (215.0 g, 1.82 moles) in toluene (1075 mL) was added imidazole (148.7 g, 2.18 moles) in one lot at room temperature. Cooled the reaction mixture to 0° C., TBDMS-Cl (301.9 g, 2.00 moles) dissolved in toluene (430 ml) was added drop wise at 0° C. After completion of addition, reaction mixture was allowed to warm to room temperature and stirred at room temperature for 16 h. The reaction mixture was then diluted with water and stirred for 15 min. The layers were separated, and the organic layer was dried over anhydrous sodium sulphate, filtered and concentrated under reduced pressure. The crude compound was purified through column to afford Compound Q7b. $^1$H NMR (400 MHz, Chloroform-d) δ 4.29 (t, J=2.4 Hz, 1H), 4.17 (d, J=7.6 Hz, 2H), 1.39 (d, J=6.8 Hz, 3H), 1.27 (t, J=6.8 Hz, 3H), 0.90 (s, 9H), 0.08 (d, J=10.8 Hz, 6H).

Compound Q7c: To a stirred solution of Compound Q7b (100.0 g, 0.43 moles) in diethyl ether was added DIBAL-H (1.0 M in Toluene) drop wise at −78° C. under argon gas atmosphere. After completion of addition, reaction mixture was stirred for additional 4 h at the same temperature. The reaction mixture was then quenched with water followed by 15% NaOH solution. After completion of quenching, reaction mixture was allowed to warm to room temperature and filter through celite pad and concentrated the filtrate at 20° C. (bath temperature) under reduced pressure to afford Compound Q7c. $^1$H NMR (400 MHz, Chloroform-d) δ 9.61 (d, J=1.2 Hz, 1H), 4.12-4.07 (m, 1H), 1.28 (d, J=6.8 Hz, 3H), 0.93 (s, 9H), 0.91 (d, J=4.0 Hz, 6H).

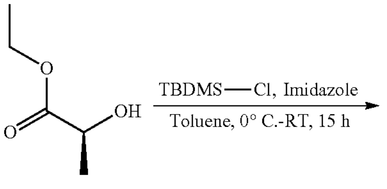

Q7a

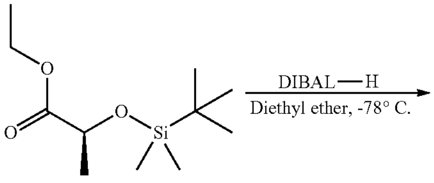

Q7b

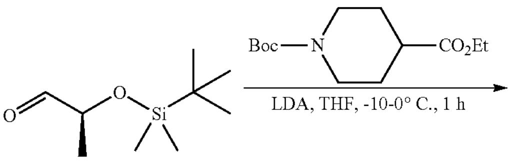

Q7c

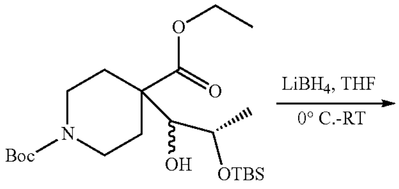

Q7d

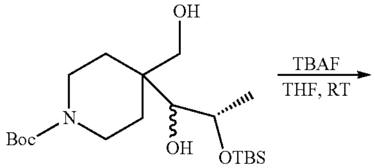

Q7e

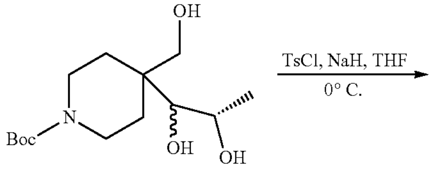

Q7f

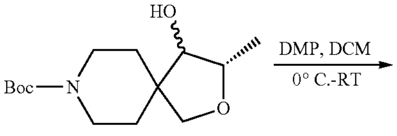

Q7g

-continued

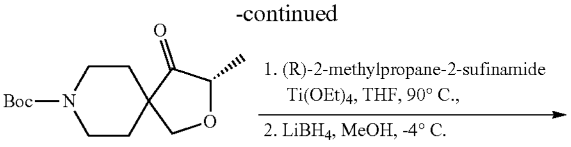

Q7h

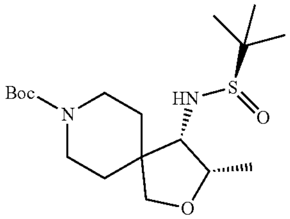

Q7

Compound Q7d: To a stirred solution of 1-(tert-butyl) 4-ethyl piperidine-1,4-dicarboxylate (100.0 g, 0.388 moles) in THF (1000 ml) was added LDA (291.4 ml, 0.588 moles, 2.0 M in THF) drop wise at 0° C. under $N_2$ atmosphere. After completion of addition, reaction mixture was stirred for 30 min at the same temperature. Compound Q7c (124.2 g, 0.588 moles) in THF (300 ml) was added drop wise at 0° C. under $N_2$ atmosphere. After completion of addition, reaction mixture was stirred for additional 1 h at the same temperature. The reaction was then quenched with sat. $NaHCO_3$ solution and extracted with ethyl acetate. Organic layer was washed with water followed by brine solution. Organic layer was dried over anhydrous $Na_2SO_4$, filter and concentrated under reduced pressure. The crude compound was purified through column to afford Compound Q7d. $^1$H NMR (400 MHz, Chloroform-d) δ 4.23-4.11 (m, 2H), 3.83-3.82 (m, 3H), 3.56-3.54 (m, 1H), 2.80 (s, 1H), 2.04 (s, 1H), 1.74-1.68 (m, 2H), 1.34 (s, 9H), 1.29-1.26 (m, 4H), 1.13 (d, J=6.4 Hz, 3H), 0.88 (s, 9H), 0.09 (s, 6H).

Compound Q7e: To a stirred solution of Compound Q7d (99.5 g, 0.246 moles) in THF (995 ml) was added $LiBH_4$ (8.05 g, 0.364 moles) portion wise at 0° C. After completion of addition, reaction mixture was allowed to warm to room temperature and stirred for 16 h. The reaction was then quenched with sat. $NH_4Cl$ solution and extracted with ethyl acetate. Organic layer was washed with brine solution. Organic layer was dried over anhydrous $Na_2SO_4$, filter and concentrated under reduced pressure. The crude compound was purified through column chromatography to afford Compound Q7e. $^1$H NMR (400 MHz, Chloroform-d) δ 4.04-4.01 (m, 1H), 3.88-3.85 (m, 1H), 3.84-3.62 (m, 4H), 3.60-3.55 (m, 1H), 2.64 (d, J=3.2 Hz, 1H), 1.78-1.65 (m, 1H), 1.68-1.61 (m, 1H), 1.28 (s, 9H), 1.27 (d, J=4.8 Hz, 3H), 0.90 (s, 9H), 0.09 (s, 3H), 0.08 (s, 3H).

Compound Q7f: To a stirred solution of Compound Q7e (65.0 g, 0.161 moles) in THF (650 mL) was added TBAF (241.5 mL, 1.0 M in THF) at room temperature. After completion of addition, reaction mixture was stirred at room temperature for 2 h. The reaction was then quenched with water and extracted with ethyl acetate. Organic layer was washed with excess of water followed brine solution. Organic layer was dried over anhydrous $Na_2SO_4$, filter and concentrated under reduced pressure. The crude compound was purified through column chromatography to afford Compound Q7f. $^1$H NMR (400 MHz, Chloroform-d) δ 4.02-3.98 (m, 1H), 3.86-3.82 (m, 1H), 3.74-3.66 (m, 3H), 3.45 (t, J=8.0 Hz, 1H), 3.18-3.06 (m, 2H), 2.60 (d, J=8.4 Hz, 1H), 2.19 (s, 1H), 1.73-1.60 (m, 3H), 1.58 (s, 9H), 1.35 (d, J=8.8 Hz, 3H).

Compound Q7g: To a stirred suspension of NaH (33.0 g, 1.377 moles) in THF (300 mL) was added Compound Q7f (59.8 g, 0.206 moles) in THF (350 ml) at 0° C. as drop wise under $N_2$ atmosphere. After completion of addition, reaction mixture was stirred for 15 min at the same temperature. Tosyl chloride (39.3 g, 0.206 moles) in THF (350 mL) was added drop wise at the same temperature and stirred for additional 1 h at the same temperature. The reaction was then quenched with sat. $NH_4Cl$ solution and extracted with ethyl acetate. Organic layer was washed with water followed by brine solution. Organic layer was dried over anhydrous $Na_2SO_4$, filter and concentrated under reduced pressure. The crude compound was purified through column chromatography to afford Compound Q7g. $^1H$ NMR (400 MHz, Chloroform-d) δ 3.83-3.67 (m, 5H), 3.44 (t, J=5.2 Hz, 1H), 3.07-2.97 (m, 2H), 1.73-1.66 (m, 2H), 1.60-1.56 (m, 2H), 1.46 (s, 9H), 1.34 (d, J=6.4 Hz, 3H).

Compound Q7h: To a stirred solution of Compound Q7g (19.5 g, 0.072 moles) and (R)-2-methylpropane-2-sulfinamide (17.5 g, 0.144 moles) in THF was added $Ti(OEt)_4$ (66.0 g, 0.289 moles) at room temperature under $N_2$ atmosphere. Heated the reaction mixture to 90° C. and stirred for 24 h at the same temperature. The reaction mixture was then cooled down to −4° C. and quenched with methanol. $LiBH_4$ (1.57 g, 0.072 moles) was added portion wise 0° C. After completion of addition, reaction mixture was stirred for additional 2 h at the same temperature. The reaction was then quenched with sat. $NH_4Cl$ solution and diluted with ethyl acetate. Filtered the reaction mixture through celite pad and separated both the layers. Organic layer was washed with water followed by brine solution. Organic layer was dried over anhydrous $Na_2SO_4$, filter and concentrated under reduced pressure. The crude compound was purified through column chromatography to afford Compound Q7h. $^1H$ NMR (400 MHz, Chloroform-d) δ 4.21-4.19 (m, 1H), 3.95-3.90 (m, 4H), 3.16-3.10 (m, 1H), 3.04-2.97 (m, 1H), 1.82-1.78 (m, 1H), 1.61-1.58 (m, 3H), 1.46 (s, 9H), 1.31 (d, J=4.0 Hz, 3H).

Compound Q7: To a stirred solution of Compound Q7h (19.5 g, 0.072 moles) and (R)-2-methylpropane-2-sulfinamide (17.5 g, 0.144 moles) in THF was added $Ti(OEt)_4$ (66.0 g, 0.289 moles) at room temperature under $N_2$ atmosphere. The reaction mixture was heated to 90° C. and stirred for 24 h at the same temperature. The reaction mixture was cooled down to −4° C. and quenched with methanol. $LiBH_4$ (1.57 g, 0.072 moles) was added portion wise at 0° C. After completion of addition, reaction mixture was stirred for additional 2 h at the same temperature. The reaction was then quenched with sat. $NH_4Cl$ solution and diluted with ethyl acetate. Filtered the reaction mixture through celite pad and separated both the layers. Organic layer was washed with water followed by brine solution. Organic layer was dried over anhydrous $Na_2SO_4$, filter and concentrated under reduced pressure. The crude compound was purified through column chromatography to afford Compound Q7. $^1H$ NMR (400 MHz, Chloroform-d) δ 4.21-4.15 (m, 1H), 3.90-3.84 (m, 3H), 3.63 (s, 1H), 3.46-3.43 (m, 1H), 3.31-3.29 (m, 1H), 2.92 (s, 2H), 1.81 (s, 2H), 1.60 (s, 1H), 1.44 (s, 9H), 1.25 (s, 9H), 1.20 (d, J=6.4 Hz, 3H). LCMS $ESI^+$ calc'd for $C_{18}H_{34}BrN_2O_4S$: 375.2 [M+H$^+$]. found: 375.7 [M+H$^+$].

Compound Q8

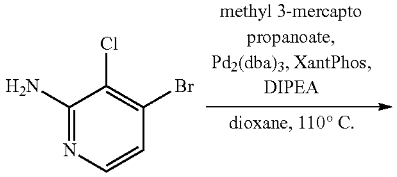

Q8a

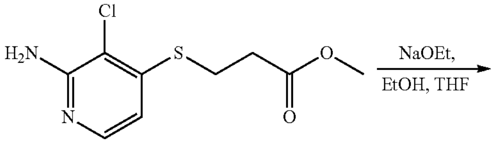

Q8b

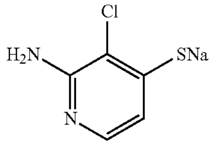

Q8

Compound Q8b: To a solution of Compound Q8a (870.7 mg, 3.174 mmol) in 1,4-dioxane (10.8 mL) was added $Pd_2(dba)_3$ (583.3 mg, 0.635 mmol), XantPhos (734.7 mg, 1.270 mmol), methyl 3-mercaptopropanoate (0.372 mL, 3.492 mmol), and DIPEA (1.106 mL, 6.348 mmol), then the reaction was heated to 110° C. for 2 h. The reaction mixture was diluted with EtOAc, filtered through Celite, the filtrate was concentrated in vacuo, and purified by column chromatography (0-20% MeOH in DCM) to give Compound Q8b. $^1H$ NMR (400 MHz, DMSO-$d_6$) δ 77.80 (d, J=5.4 Hz, 1H), 6.56 (d, J=5.4 Hz, 1H), 6.24 (s, 2H), 3.63 (s, 3H), 3.21 (t, J=7.0 Hz, 2H), 2.72 (t, J=7.0 Hz, 2H). LCMS $ESI^+$ calc'd for $C_9H_{11}ClN_2O_2S$: 247.0 [M+H$^+$]. found: 247.1 [M+H$^+$].

Compound Q8: To a solution of Compound Q8b (485 mg, 1.96 mmol) in THF (6.55 mL) was added sodium ethoxide solution (0.77 mL, 21 wt % in ethanol) at 0° C. After 20 min, the mixture was the solution was suspended in DCM (5 mL) and MTBE (5 mL). Hexanes (10 mL) were added inducing precipitation of the product. The solids were collected by filtration and used without further purification, to give Compound Q8. $^1H$ NMR (400 MHz, DMSO-$d_6$) δ 7.02 (d, J=5.4 Hz, 1H), 6.45 (d, J=5.3 Hz, 1H), 5.00 (s, 2H). LCMS $ESI^+$ calc'd for $C_5H_5ClN_2S$: 161.0 [M+H$^+$]. found: 160.9 [M+H$^+$].

Compound Q9

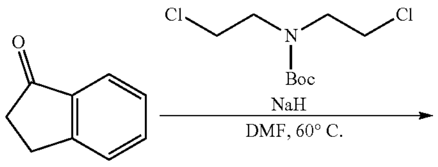

Q9a

-continued

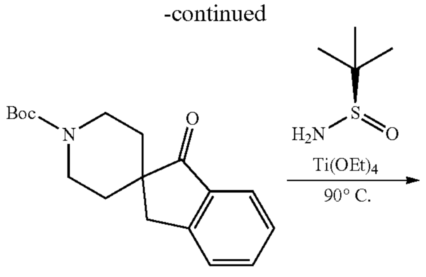

Q9b

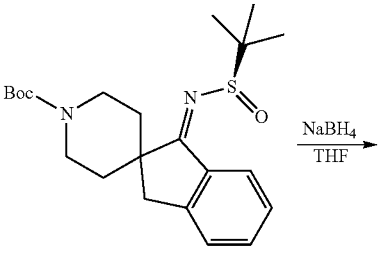

Q9c

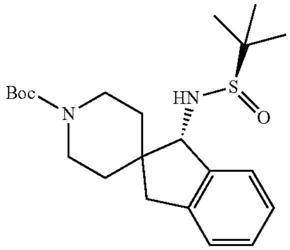

Q9

Compound Q9b: NaH (7.24 g, 181.60 mmol, 60% in mineral oil) was added into the solution of Compound Q9a (8.00 g, 60.54 mmol) in DMF (160 mL). The mixture was stirred for 1 h at room temperature. Tert-butyl bis (2-chloroethyl) carbamate (16.12 g, 66.58 mmol) was dropwise added. And then the mixture was stirred for 16 h at 60° C. The mixture was quenched with brine (300 mL), extracted with EtOAc (200 mL×2). The organic layers were combined and washed with brine (150 mL×2), dried over anhydrous $Na_2SO_4$. After concentration, the residue was purified by column chromatography to afford Compound Q9b. $^1H$ NMR (400 MHz, $CDCl_3$) δ: 7.76 (d, J=8.0 Hz, 1H), 7.64-7.60 (m, 1H), 7.47 (d, J=8.0 Hz, 1H), 7.41-7.38 (m, 1H), 4.12 (s, broad, 2H), 3.08-2.98 (m, 4H), 1.95-1.88 (m, 2H), 1.52 (s, 9H), 1.48-1.40 (m, 2H). LCMS $ESI^+$ calc'd for $C_{13}H_{26}N_2OS$: 259.1 [$M+H^+$]. found: 259.0.

Compound Q9c: A mixture of Compound Q9b (8.5 g, 28.24 mmol) and (R)-2-methylpropane-2-sulfinamide (8.59 g, 84.71 mmol) in Titanium ethoxide (90 g) was stirred for 19 hours at 90° C. The mixture was poured into EtOAc (300 mL), and brine (200 mL) was added. After stirred for 15 mins, the solid was filtrated out. The liquid was separated. The organic layer was washed with brine (150 mL×2), dried over anhydrous $Na_2SO_4$. After concentration, the residue was purified by column chromatography to afford Compound Q9c. $^1H$ NMR (400 MHz, $CDCl_3$) δ: 7.76 (d, J=8.0 Hz, 1H), 7.64-7.60 (m, 1H), 7.47 (d, J=8.0 Hz, 1H), 7.41-7.38 (m, 1H), 4.12 (s, broad, 2H), 3.08-2.98 (m, 4H), 1.95-1.88 (m, 2H), 1.52 (s, 9H), 1.48-1.40 (m, 2H). LCMS $ESI^+$ calc'd for $C_{22}H_{32}N_2O_3S$: 405.2 [$M+H^+$]. found: 405.3.

Compound Q9: $NaBH_4$ (1.17 g, 30.79 mmol) was added into the solution of Compound Q9c (7.5 g, 18.57 mmol) in THF (150 mL) at −50° C. The mixture was stirred for 16 hours with natural warming to room temperature. The mixture was quenched with brine (100 mL), extracted with EtOAc (150 mL×2). The organic layers were combined and washed with brine (100 mL×2), dried over anhydrous $Na_2SO_4$. After concentration, the residue was purified by column chromatography to Compound Q9. $^1H$ NMR (400 MHz, $CDCl_3$) δ: 7.31-7.30 (m, 1H), 7.25-7.19 (m, 2H), 4.50 (d, J=7.2 Hz, 1H), 4.03-4.00 (m, 2H), 3.53 (s, broad, 1H), 3.03-2.98 (m, 3H), 2.72-2.68 (m, 1H), 2.10 (br s, 1H), 1.73-1.70 (m, 1H), 1.61-1.45 (m, 10H), 1.41-1.26 (m, 10H). LCMS $ESI^+$ calc'd for $C_{22}H_{34}N_2O_3S$: 407.2 [$M+H^+$]. found: 407.1.

Compound Q10y and Compound Q10z

Compound Q10b: A solution of Compound Q10a (500 g, 4.76 mol), $K_2CO_3$ (1426 g, 10.32 mol) and (bromomethyl) benzene (814 g, 4.76 mol) in acetone (12 L) was stirred at 60° C. for overnight. After cooling to RT, the reaction mixture was filtered and washed with acetone (3×1 L). The filtrate was concentrated under reduced pressure. Water (3000 mL) was added and adjusted pH to 9~10 with $Na_2CO_3$ and extracted with DCM:MeOH=10:1 (5×1 L). The combined organic layers were dried with $Na_2SO_4$, concentrated to give a crude residue, which was purified by silica gel chromatography to give Compound Q10b. $^1H$ NMR (400 M, $CDCl_3$) δ 7.33-7.25 (m, 5H), 3.71 (s, 2H), 3.62 (t, J=5.6 Hz, 4H), 3.04 (broad, 2H), 2.71 (t, J=5.6 Hz, 4H). LCMS $ESI^+$ calc'd for $C_{11}H_{17}NO_2$: 196.1 [$M+H^+$]. found: 196.1.

Compound Q10c: To a solution of Compound Q10b (500 g, 2.56 mol) in $CHCl_3$ (4400 mL) was added phosphorus tribromide (1386 g, 5.1 mol) by dropwise. The resulting mixture was stirred at 65° C. for 2 h. Cooled to 0° C. and then ice-water (2000 mL) was carefully added by drop wise. Adjusted pH to 7~8 with $Na_2CO_3$ and phases were separated. The aqueous phase was extracted with DCM (3×1000 mL), the organic layers combined and dried over anhydrous $Na_2SO_4$ and filtered. The filtrate was concentrated under reduced pressure to give crude compound 5 (750 g). The crude product was purified by a short silica gel to give Compound Q10c. $^1H$ NMR (400 M, $CDCl_3$) δ 7.37-7.28 (m, 5H), 3.76 (s, 2H), 3.39-3.35 (m, 4H), 3.03-2.99 (q, J=7.6 Hz, 4H).

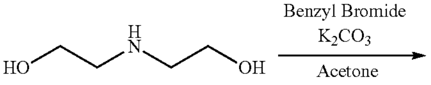

Q10a

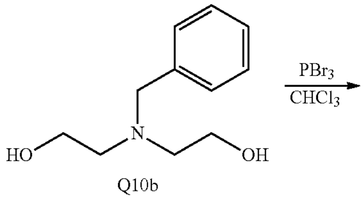

Q10b

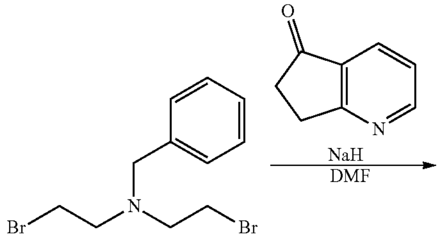

Q10c

-continued

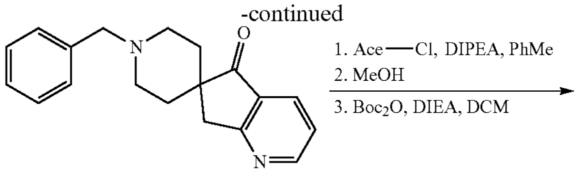

Q10d

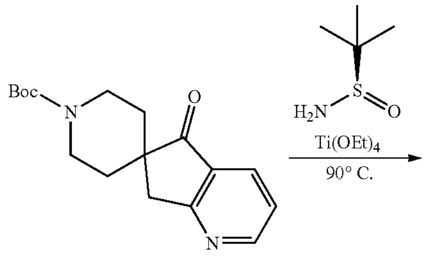

Q10e

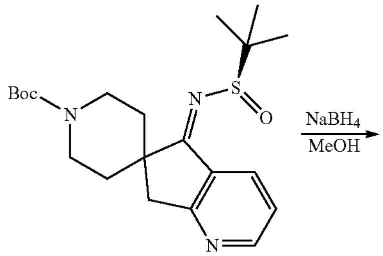

Q10f

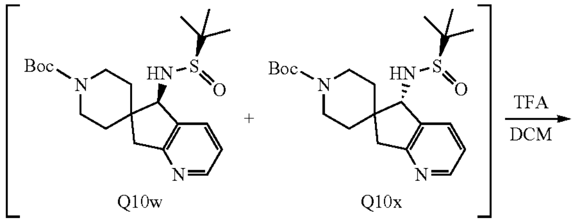

Q10w Q10x

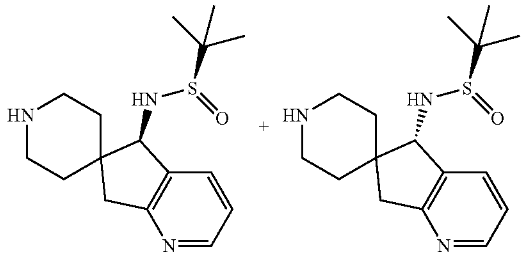

Q10y Q10z

Compound Q10d: To a solution of Compound Q10c (65 g, 0.488 mol) in DMF (780 mL) was added NaH (60% dispersion in mineral oil, 45 g, 1.12 mol) by portion wise at 0° C. under nitrogen atmosphere. After that the mixture was heated to 30° C., stirred for 1 h at this temperature. Then a solution of 6,7-dihydro-5H-cyclopenta[b]pyridin-5-one (172.4 g, 0.527 mol) in DMF (260 mL) was added by drop wise at 30~35° C. The mixture was stirred at 30~35° C. for overnight. After cooling to 0° C., the reaction mixture was poured into water (2000 mL), a large amount of solid was formed, adjusted pH with 2 N HCl until all solid was dissolved. The pH was adjusted to 7~8 with 2 N NaOH and extracted with EtOAc (3×3000 mL). The combined organic layers were washed with water (3×3000 mL), dried over anhydrous $Na_2SO_4$, filtered and concentrated under reduced pressure. The resulting residue was purified by silica chromatography to give Compound Q10d. $^1$H NMR (400 M, $CDCl_3$) δ 8.74 (dd, J=1.6, 4.8 Hz, 1H), 7.94 (dd, J=1.6, 7.8 Hz, 1H), 7.30-7.16 (m, 6H), 3.50 (s, 2H), 3.08 (s, 2H), 2.88-2.81 (m, 2H), 2.15-1.97 (m, 4H), 1.37-1.19 (dm, 2H). LCMS ESI$^+$ calc'd for $C_{19}H_{20}N_2O$: 293.1 [M+H$^+$]. found: 293.2.

Compound Q10e: 1—Chloroethyl chloroformate (104.06 g, 0.73 mol) was added to a solution of Compound Q10d (26.6 g, 91 mmol) and DIEA (94.06 g, 0.73 mol) in toluene (1621 mL). The reaction mixture was stirred for 2 h at 100° C. The reaction mixture was concentrated under reduced pressure to give a crude residue, which was dissolved in methanol (1307 mL) and heated to reflux. After stirred for 12 h, the reaction mixture was cooled to room temperature, concentrated under reduced pressure to give a crude residue, then dissolved in dichloromethane (1621 mL). Di-tert-butyl dicarbonate (99.3 g, 0.45 mol) and triethylamine (46 g, 0.45 mol) were added. The reaction mixture was stirred for 12 h at room temperature. The reaction mixture was concentrated under reduced pressure to give a crude residue, which was purified by silica gel column to give Compound Q10e. $^1$H NMR (400 M, $CDCl_3$) δ 8.77-8.76 (m, 1H), 7.98-7.96 (m, 1H), 7.30-7.21 (m, 1H), 4.09-4.07 (m, 2H), 3.12 (s, 2H), 2.98-2.96 (m, 2H), 1.91-1.83 (m, 2H), 1.36-1.34 (m, 11H). LCMS ESI$^+$ calc'd for $C_{17}H_{22}N_2O_3$: 303.1 [M+H$^+$]. found: 303.0.

Compound Q10f: $Ti(OEt)_4$ (207.8 g, 911 mmol) was heated at 90° C., then Compound Q10e (21 g, 69.45 mmol) and (R)-(+)-2-methylpropane-2-sulfinamide (10.1 g, 83.34 mmol) were added. Stirred at 90° C. for the 2 h. After cooling to room temperature, ethyl acetate (700 mL) and brine (800 mL) was added. A large amount of solid was formed. Filtered through a pad of Celite. Washed with EtOAc (200 mL*3). Phases were separated and extracted with ethyl acetate. The organic phase was dried over $Na_2SO_4$ and evaporated to give Compound Q10f, which was used without further purification. $^1$H NMR (400 M, $CDCl_3$) δ 8.70 (d, J=7.2 Hz, 1H), 8.61 (dd, J=1.2, 4.8 Hz, 1H), 7.24 (dd, J=4.8, 8.0 Hz, 1H), 4.09-4.02 (m, 2H), 3.11 (s, 2H), 2.92-2.87 (m, 2H), 1.97-1.91 (m, 2H), 1.37 (s, 9H), 1.21 (s, 9H). LCMS ESI$^+$ calc'd for $C_{21}H_{31}N_3O_3S$: 406.2 [M+H$^+$]. found: 406.2.

Compound Q10w and Compound Q10x: To a solution of Compound Q10f (11 g, 27.12 mmol) in MeOH (110 mL) was added sodium borohydride (3.08 g, 81.37 mmol) by portion wise at −78° C. under $N_2$. The mixture was stirred at −78° C. for 1 h and then warmed to room temperature and stirred another 1 h. The mixture was poured into a saturated solution of saturated aqueous ammonium chloride (200 mL) slowly and stirred for 30 mins. Concentrated under reduced pressure to give a crude residue, then extracted with ethyl acetate (3×100 mL), the combined organic phases were dried over anhydrous $Na_2SO_4$. The solvent was evaporated under reduced pressure to give a mixture of crude Compound Q10w and Compound Q10x, which was used without further purification.

Compound Q10y and Compound Q10z: To a solution of a mixture of Compound Q10w and Compound Q10x (33 g) in DCM (118 mL) was added TFA (49.6 g, 0.43 mol) by drop wise at room temperature. The mixture was stirred for 1.5 h at 25° C. The mixture was concentrated to give a crude product, which was purified by reverse-phase chromatography to give the title compounds. Compound Q10y: $^1$H NMR (400 M, DMSO-d6) δ 8.60 (broad, 1H), 8.48 (broad, 1H), 8.40 (d, J=4.8 Hz, 1H), 7.87 (d, J=7.6 Hz, 1H), 7.27 (dd, J=7.6, 4.8 Hz, 1H), 5.72 (d, J=10.4 Hz, 1H), 4.50 (d, J=10.0 Hz, 1H), 3.29-2.98 (m, 5H), 2.98-2.85 (m, 1H), 1.86-1.71 (m, 3H), 1.42-1.39 (m, 1H), 1.23 (s, 9H). LCMS ESI$^+$ calc'd for $C_{16}H_{25}N_3OS$: 308.2 [M+H$^+$]. found: 308.1. Compound Q10z: $^1$H NMR (400 M, DMSO-d6) δ 9.20-8.60 (broad, 1H), 8.40 (d, J=4.8 Hz, 1H), 7.64 (d, J=7.6 Hz, 1H), 7.23 (dd, J=7.6, 4.8 Hz, 1H), 5.95 (d, J=10.4 Hz, 1H), 4.51 (d, J=10.0 Hz, 1H), 3.26-2.99 (m, 5H), 2.86-2.82 (m, 1H), 2.00-1.92 (m, 1H), 1.90-1.86 (m, 1H), 1.70-1.66 (m, 1H), 1.51-1.47 (m, 1H), 1.23 (s, 9H). LCMS ESI$^+$ calc'd for $C_{16}H_{25}N_3OS$: 308.2 [M+H$^+$]. found: 308.2.

Compound N1

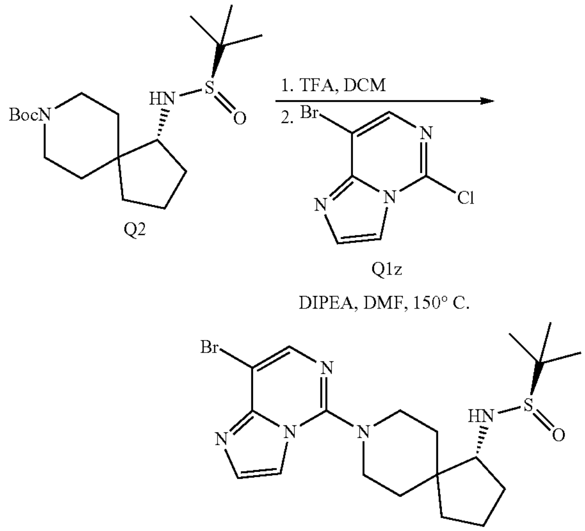

Q2

Q1z

N1

Compound N1: To a solution of Compound Q2 (2.37 g) in DCM (50 mL) was added TFA (5 mL). After 2.5 h, the reaction was concentrated in vacuo and coevaporated with toluene. To the crude residue in DMF (20 mL) was added DIPEA (4 mL) and stirred for 10 min. To the mixture was added Compound Q1z (1.13 g) in DMF (10 mL) and the reaction was heated to 50° C. for 3 h. The mixture was diluted with EtOAc, successively washed with brine, dried over sodium sulfate, diluted with ethanol, and concentrated in vacuo to give Compound N1. $^1$H NMR (400 MHz, DMSO-$d_6$) δ 7.94 (s, 1H), 7.76 (d, J=1.5 Hz, 1H), 7.67 (d, J=1.4 Hz, 1H), 4.98 (d, J=8.0 Hz, 1H), 3.73 (td, J=8.3, 4.0 Hz, 2H), 3.20 (q, J=7.7 Hz, 1H), 3.05 (dtd, J=19.0, 12.3, 2.1 Hz, 2H), 2.04 (td, J=12.7, 4.0 Hz, 1H), 1.93 (q, J=8.9 Hz, 1H), 1.82 (dt, J=13.3, 7.3 Hz, 2H), 1.70-1.58 (m, 2H), 1.55 (dq, J=9.0, 4.8, 3.8 Hz, 1H), 1.46 (tt, J=9.2, 4.8 Hz, 1H), 1.40-1.29 (m, 2H), 1.13 (s, 9H). LCMS ESI$^+$ calc'd for $C_{19}H_{28}BrN_5OS$: 454.1 [M+H$^+$]. found: 454.2 [M+H$^+$].

Compound N2

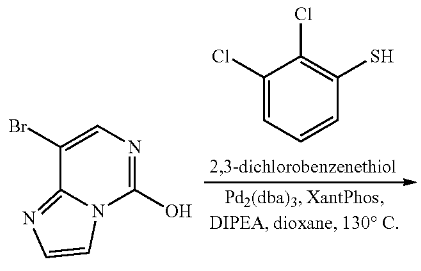

Q1y

-continued

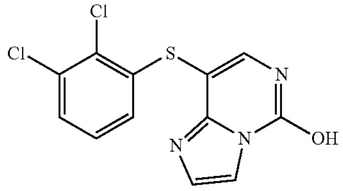

N2

Compound N2: A solution of Compound Q1y (0.301 g), 2,3-dichlorobenzenethiol (0.503 g), $Pd_2(dba)_3$ (0.260 g), and XantPhos (0.333 g) in 1,4-dioxane (14 mL) was added DIPEA (1.0 mL) and heated in a microwave reactor to 130° C. for 1 h. The reaction was diluted with EtOAc, filtered through Celite, and the filtrate was concentrated in vacuo. Precipitation with DCM and hexane was used to give Compound N2. $^1$H NMR (400 MHz, DMSO-$d_6$) δ 12.14 (s, 1H), 7.85 (d, J=1.4 Hz, 1H), 7.81 (s, 1H), 7.40 (dd, J=8.0, 1.4 Hz, 1H), 7.32 (d, J=1.5 Hz, 1H), 7.13 (t, J=8.1 Hz, 1H), 6.91 (dd, J=8.2, 1.3 Hz, 1H). LCMS ESI$^+$ calc'd for $C_{12}H_7C_2N_3OS$: 312.0 [M+H$^+$]. found: 312.1 [M+H$^+$].

Compound N3

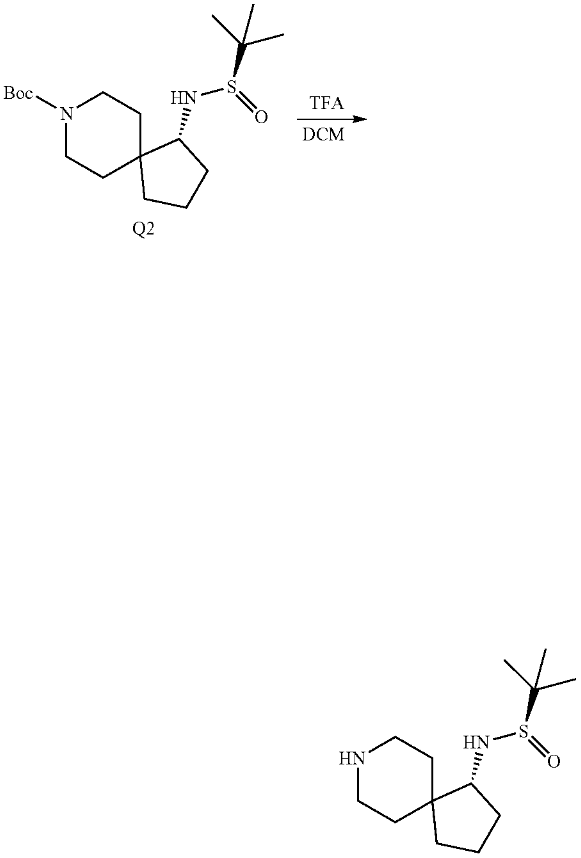

Q2

N3

Compound N3: To a solution of Compound Q2 (2100 mg, 5.857 mmol) in DCM (5.0 mL) was added TFA (2 mL), then the reaction was stirred at RT for 20 min. The solvent was then evaporated to afford crude product Compound N3. LCMS ESI$^+$ calc'd for $C_{13}H_{26}N_2OS$: 259.1 [M+H$^+$]. found: 259.0.

Compound N4

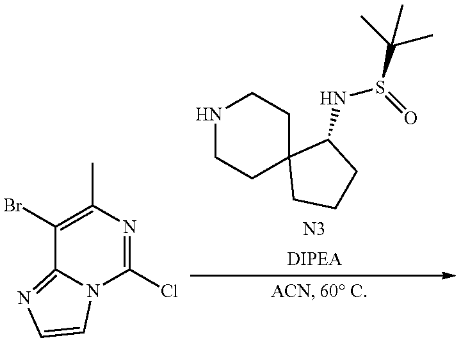

Q4z

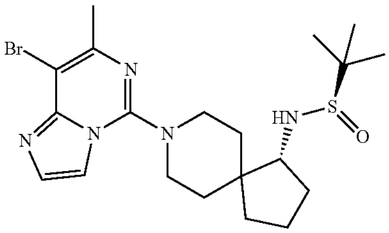

N4

Compound N4: To a solution of Compound Q4z (0.218 g, 0.884 mmol)) and Compound N3 (0.274 g, 1.061 mmol) in ACN (5 mL) was added DIPEA (0.92 mL). The reaction mixture was heated at 60° C. for 1 h, the mixture was diluted with EtOAc, washed with brine, the organic solvent was concentrated in vacuo, and then purified with Combi-Flash column to afford Compound N4. LCMS ESI$^+$ calc'd for $C_{20}H_{30}BrN_5OS$: 468.1 [M+H$^+$]. found: 468.0 [M+H$^+$].

Compound N5x:

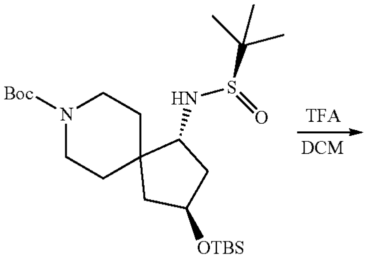

Q5

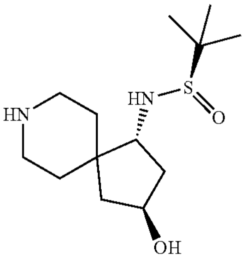

N5x

Compound N5x: To a solution of Compound Q5 (200 mg, 0.41 mmol) in DCM (3.0 mL) was added TFA (0.5 mL), then the reaction was stirred at RT for 20 min. The solvent was then evaporated to afford crude product Compound N5x. LCMS ESI$^+$ calc'd for $C_{13}H_{26}N_2O_2S$: 275.1 [M+H$^+$]. found: 275.2.

Compound N5y:

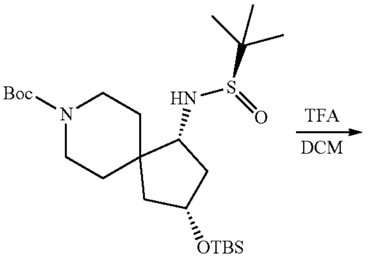

Q6

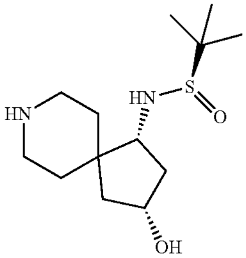

N5y

Compound N5y: To a solution of Compound Q6 (200 mg, 0.41 mmol) in DCM (3.0 mL) was added TFA (0.5 mL), then the reaction was stirred at RT for 20 min. The solvent was then evaporated to afford crude product Compound N5y. LCMS ESI$^+$ calc'd for $C_{13}H_{26}N_2O_2S$: 275.1 [M+H$^+$]. found: 275.2.

Compound N5z:

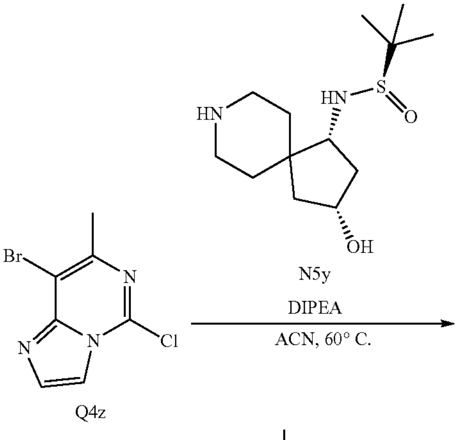

Q4z

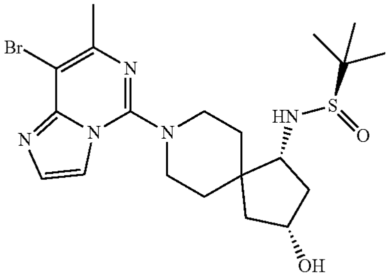

N5z

Compound N5z: To a solution of Compound Q4z (400 mg, 2 mmol) and Compound N5y (757 mg, 2 mmol) in ACN (3 mL) was added DIPEA (0.8 mL). The reaction mixture was heated at 70° C. for 1 h, the mixture was diluted with EtOAc, washed with brine and TFA at 23° C., the organic solvent was concentrated in vacuo, and then purified with Combi-Flash column to afford Compound N5z. LCMS ESI$^+$ calc'd for $C_{20}H_{30}BrN_5O_2S$: 484.1 [M+H$^+$]. found: 484.2 [M+H$^+$].

Compound N6

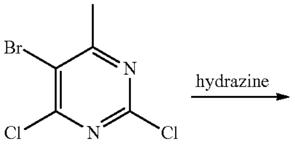

N6a

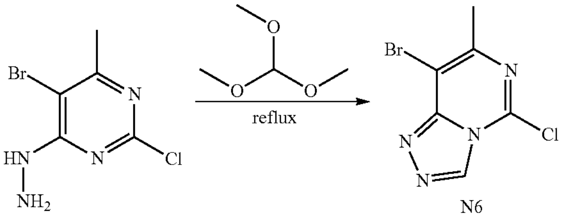

N6b

N6

Compound N6b: To a solution of Compound N6a (5.86 g, 24 mmol) in EtOH (30.0 mL) was added hydrazine (1.6 g, 48 mmol), then the reaction was stirred at RT overnight. The solution turned to white slurry mixture. The white precipitate was then filtered to afford crude product Compound N6b. LCMS ESI$^+$ calc'd for $C_5H_6BrClN_4$: 237.0 [M+H$^+$]. found: 237.1 [M+H$^+$].

Compound N6: Mixed Compound N6b (2 g, 8.4 mmol) with trimethoxymethane (17.8 g, 168 mmol) and then the reaction mixture was heated at reflux for 3 h. The reaction mixture was then cooled down and the white precipitate was then filtered, followed with washing with hexane to afford crude product Compound N6. LCMS ESI$^+$ calc'd for $C_6H_4BrClN_4$: 247.0 [M+H$^+$]. found: 247.1 [M+H$^+$].

Compound N7

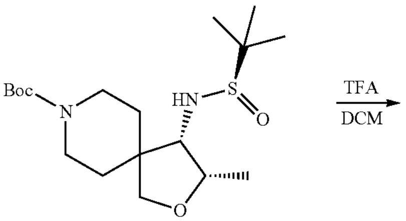

Q6

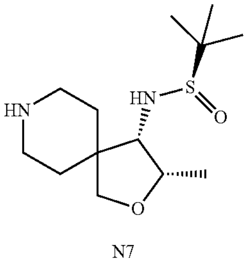

N7

Compound N7: To a solution of Compound Q7 (213 mg, 0.57 mmol) in DCM (3.0 mL) was added TFA (0.5 mL), then the reaction was stirred at RT for 20 min. The solvent was then evaporated to afford crude product Compound N7. LCMS ESI$^+$ calc'd for $C_{13}H_{26}N_2O_2S$: 275.1 [M+H$^+$]. found: 275.0 [M+H$^+$].

Compound N8

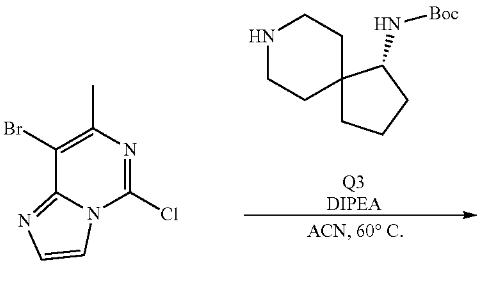

Q4z

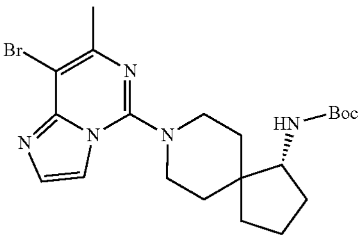

N8

Compound N8: To a solution of Compound Q4z (0.218 g, 0.884 mmol)) and Compound Q3 (0.274 g, 1.061 mmol) in ACN (5 mL) was added DIPEA (0.92 mL). The reaction mixture was heated at 60° C. for 1 h, the mixture was diluted with EtOAc, washed with brine, the organic solvent was concentrated in vacuo, and then purified with Combi-Flash column to afford Compound N8. LCMS ESI$^+$ calc'd for $C_{20}H_{30}BrN_5OS$: 468.1 [M+H$^+$]. found: 468.0 [M+H$^+$].

Compound N9

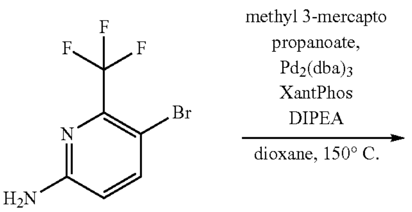

N9a

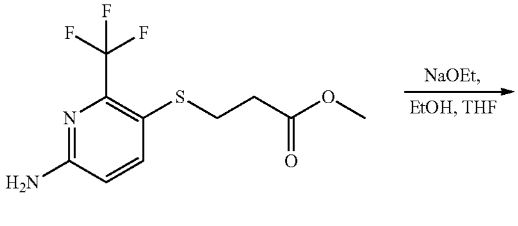

N9b

-continued

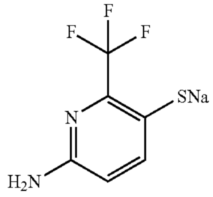

N9

Compound N9b: To a solution of Compound N9a (0.350 mg) in 1,4-dioxane (4.8 mL) was added $Pd_2(dba)_3$ (0.270 g), XantPhos (0.1960 g), methyl 3-mercaptopropanoate (0.17 mL), and DIPEA (0.50 mL), then the reaction was heated to 150° C. for 1 h in a microwave reactor. The reaction mixture was diluted with EtOAc, filtered through Celite, the filtrate was concentrated in vacuo, and purified by column chromatography (0-100% EtOAc in hexanes) to give Compound N9b. $^1H$ NMR (400 MHz, DMSO-$d_6$) δ 7.70 (d, J=8.7 Hz, 1H), 6.69 (s, 2H), 6.66 (d, J=8.7 Hz, 1H), 3.56 (s, 3H), 2.98 (t, J=7.0 Hz, 2H), 2.53 (t, J=7.0 Hz, 2H). $^{19}F$ NMR (376 MHz, DMSO-$d_6$) δ −62.65. LCMS $ESI^+$ calc'd for $C_{10}H_{11}F_3N_2O_2S$: 281.1 [M+H$^+$]. found: 281.0 [M+H$^+$].

Compound N9: To a solution of Compound N9b (0.399 g) in THF (4.7 mL) was added sodium ethoxide solution (0.57 mL, 21 wt % in ethanol). After 2 h, the mixture was diluted with DCM, sonicated, filtered, and the solids were dried to give Compound N9. $^1H$ NMR (400 MHz, DMSO-$d_6$) δ 7.96 (d, J=8.5 Hz, 1H), 6.64 (d, J=8.5 Hz, 1H), 6.27 (s, 2H). $^{19}F$ NMR (376 MHz, DMSO-$d_6$) δ −61.26. LCMS $ESI^+$ calc'd for $C_6H_5F_3N_2S$: 195.0 [M+H$^+$]. found: does not ionize.

Compound N10

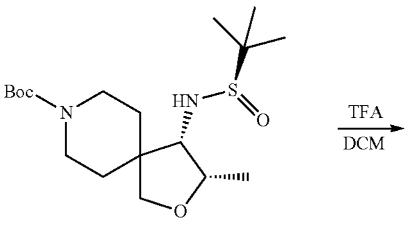

Q6

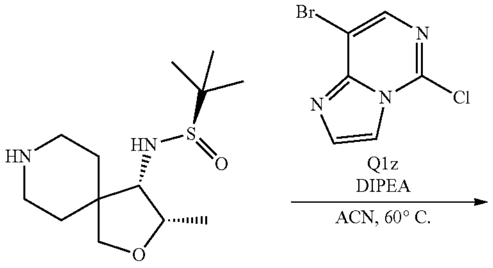

N7

-continued

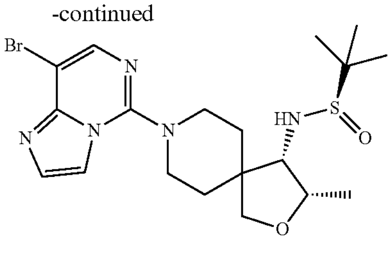

N10

Compound N7: To a solution of Compound Q7 (213 mg, 0.57 mmol) in DCM (3.0 mL) was added TFA (0.5 mL), then the reaction was stirred at RT for 20 min. The solvent was then evaporated to afford crude product Compound N7. LCMS $ESI^+$ calc'd for $C_{13}H_{26}N_2O_2S$: 275.1 [M+H$^+$]. found: 275.0 [M+H$^+$].

Compound N10: To a solution of Compound Q1z (500 mg, 2.15 mmol) and Compound N7 (767 mg, 2.80 mmol) in ACN (5 mL) was added DIPEA (2.5 mL). The reaction mixture was heated at 80° C. for 1 h, the mixture was diluted with EtOAc, washed with brine, the organic solvent was concentrated in vacuo, and then purified with Combi-Flash column to afford Compound N10. LCMS $ESI^+$ calc'd for $C_{19}H_{28}BrN_5O_2S$: 470.1 [M+H$^+$]. found: 470.1 [M+H$^+$].

Compound N11

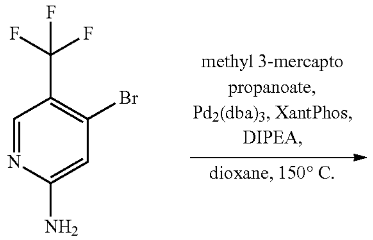

N11a

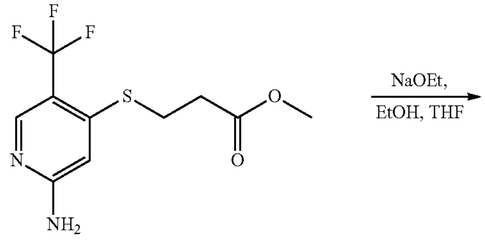

N11b

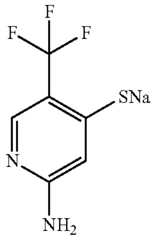

N11

Compound N11b: To a solution of Compound N11a (0.402 mg) in 1,4-dioxane (4.6 mL) was added $Pd_2(dba)_3$ (0.259 g), XantPhos (0.322 g), methyl 3-mercaptopropanoate (0.17 mL), and DIPEA (0.48 mL), then the reaction was heated to 150° C. for 1 h in a microwave reactor. The reaction mixture was diluted with EtOAc, filtered through Celite, the filtrate was concentrated in vacuo, and purified by column chromatography (0-100% EtOAc in hexanes) to give Compound N11b. $^{1}$H NMR (400 MHz, DMSO-$d_6$) δ 8.07 (s, 1H), 6.69 (s, 2H), 6.48 (s, 1H), 3.63 (s, 3H), 3.20 (t, J=7.2 Hz, 2H), 2.75 (t, J=7.2 Hz, 2H). $^{19}$F NMR (376 MHz, DMSO-$d_6$) δ −58.89. LCMS ESI$^+$ calc'd for $C_{10}H_{11}F_3N_2O_2S$: 281.1 [M+H$^+$]. found: 281.0 [M+H$^+$].

Compound N11: To a solution of Compound N1b (0.214 g) in THF (2.5 mL) was added sodium ethoxide solution (0.30 mL, 21 wt % in ethanol). After 2 h, the mixture was concentrated in vacuo, diluted with DCM and MTBE, sonicated, and concentrated in vacuo to give Compound N11. $^{1}$H NMR (400 MHz, DMSO-$d_6$) δ 8.42 (s, 1H), 6.46 (s, 1H), 6.29 (s, 3H). $^{19}$F NMR (376 MHz, DMSO-$d_6$) δ −59.33. LCMS ESI$^+$ calc'd for $C_6H_5F_3N_2S$: 195.0 [M+H$^+$]. found: does not ionize.

Compound N12

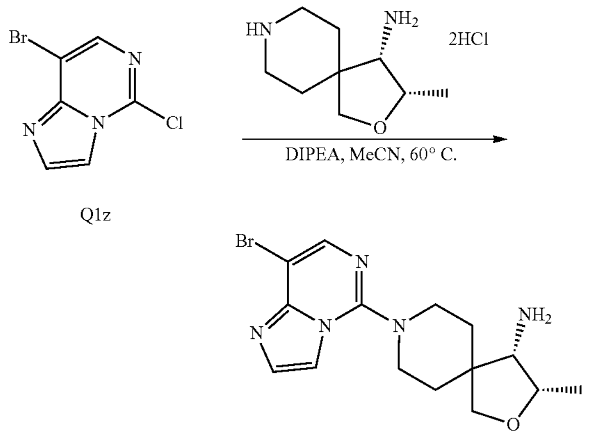

Q1z

N12

Compound N12: To Compound Q1z (0.253 g) in MeCN (7.5 mL) was added (3S, 4S)-3-methyl-2-oxa-8-azaspiro [4.5]decan-4-amine dihydrochloride (0.324 g) and DIPEA (1.1 mL), and heated to 60° C. After 3 h, the reaction was diluted with EtOAc, washed with brine, dried over sodium sulfate, and dried in vacuo to give Compound N12. $^{1}$H NMR (400 MHz, DMSO-$d_6$) δ 7.95 (s, 1H), 7.85 (d, J=1.5 Hz, 1H), 7.67 (d, J=1.4 Hz, 1H), 4.13-4.06 (m, 1H), 3.69 (d, J=8.5 Hz, 1H), 3.61-3.48 (m, 3H), 3.30-3.12 (m, 2H), 2.98 (d, J=5.0 Hz, 1H), 1.98-1.88 (m, 1H), 1.87-1.77 (m, 1H), 1.72-1.56 (m, 2H), 1.10 (d, J=6.4 Hz, 3H). LCMS ESI$^+$ calc'd for $C_{15}H_{20}BrN_5O$: 366.1 [M+H$^+$]. found: 366.2 [M+H$^+$].

Compound N13y

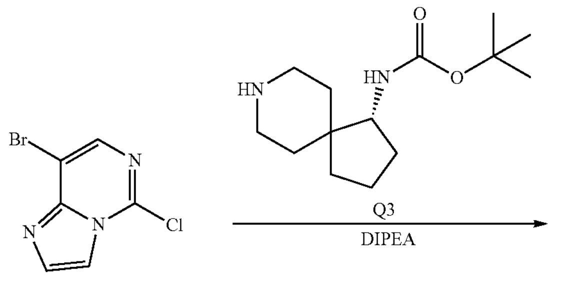

Q1z

-continued

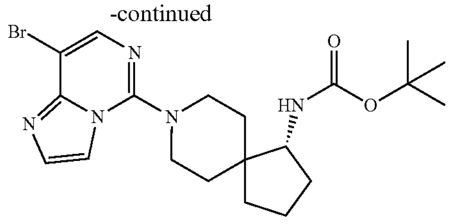

N13y

Compound N13y: Compound Q1z (5.671 g, 24.39 mmol) and Compound Q3 (6.205 g, 24.39 mmol) were dissolved in 1,4 Dioxane (40 mL) and DIPEA was added (8.498 ml, 48.79 mmol) the reaction stirred at r.t. for 2 h. The mixture was diluted with EtOAc, successively washed with brine, dried over magnesium sulfate, and concentrated in vacuo. The residue was reconstituted in toluene and purified by column chromatography (0-100% EtOAc in hexanes). This provided Compound N13y. LCMS ESI$^+$ calc'd for $C_{20}H_{28}BrN_5O_2$: 450.1 [M+H$^+$]. found: [M+H$^+$] 450.2.

Compound N13z

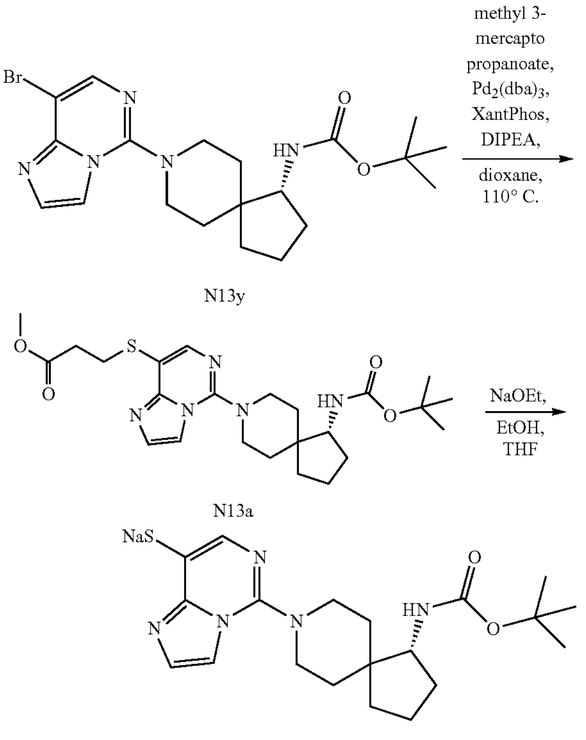

N13y

N13a

N13z

Compound N13a: To a solution of Compound N13y (2.073 g, 4.60 mmol) in 1,4-dioxane (15 mL) was added $Pd_2(dba)_3$ (84.3 mg, 0.092 mmol), XantPhos (106.5 mg, 0.184 mmol), methyl 3-mercaptopropanoate (1 mL, 9.229 mmol), and DIPEA (1.6 mL, 9.206 mmol), then the reaction was heated to 110° C. for 2 h. The reaction mixture was diluted with EtOAc, filtered through Celite, the filtrate was concentrated in vacuo, and purified by column chromatography (0-100% EtOAc in Hexanes) to give Compound N13a. LCMS ESI$^+$ calc'd for $C_{24}H_{35}N_5O_4S$: 490.2 [M+H$^+$]. found: 490.2 [M+H$^+$].

Compound N13z: To a solution of Compound N13a (2.153 g, 4.397 mmol) in THF (15 mL) was added sodium ethoxide solution (1.76 mL, 21 wt % in ethanol). After 20 min, the mixture was the solution was suspended in DCM (15 ml), MTBE (15 ml), followed by the addition of hexanes (30 ml), inducing precipitation of the product. The solids were collected by filtration and used without further purification, to give Compound N13z. LCMS ESI+ calc'd for $C_{20}H_{29}N_5O_2S$: 404.2 [M+H+]; found 404.1 [M+H+].

Compound N14:

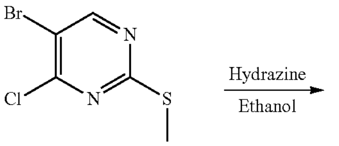

N14a

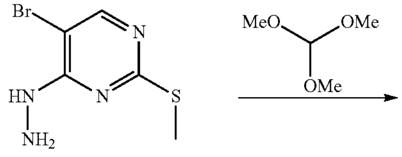

N14b

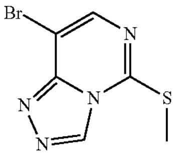

N14

Compound N14b: Compound N14a (2 g, 8.3 mmol) was dissolved in EtOH (40 mL) at room temperature. Hydrazine (0.556 mL, 17.54 mmol) was added dropwise. Reaction became very thick white slurry in 10 min. EtOH (10 mL) was added to the reaction mixture to assist stirring. Reaction was stirred at room temperature for 4 hours. Some solid crashed out of reaction mixture. Filtration followed with washing with hexane (100 mL) to afford Compound N14a. LCMS ESI+ calc'd for $C_5H_7BrN_4S$: 259.0 [M+Na+]. found: 259 [M+Na+].

Compound N14: Compound N14b (1.9 g, 8.08 mmol) was mixed with trimethoxymethane (25.7 g, 242.5 mmol). The resulting reaction mixture was heated at reflux for 3 hours. Reaction was then cooled down to room temperature. Solid crashed out of solution. Filtration afforded Compound N14. LCMS ESI+ calc'd for $C_6H_5BrN_4S$: 245.0 [M+H+]. found: 245.1 [M+H+].

Compound N15:

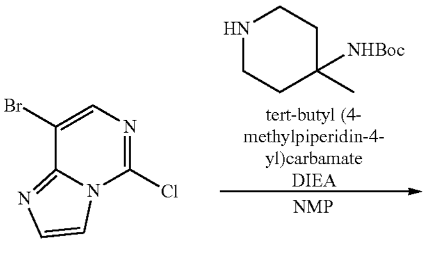

Q1z

-continued

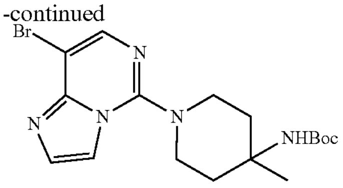

N15

Compound N15: In a 10 mL reaction vial Compound Q1z (100 mg, 0.430 mmol) and tert-butyl (4-methylpiperidin-4-yl)carbamate (276.6 mg, 1.29 mmol) were dissolved in NMP (1.5 mL) at room temperature. DIEA (0.5 mL, 2.88 mmol) was added. Reaction mixture was purged with argon for 5 min and was then heated under microwave at 110° C. for 1 hour. Reaction mixture was then diluted with EtOAc (20 mL) and was then treated with saturated aqueous $NH_4Cl$ solution (30 mL). Organic phase was separated and was then washed with saturated brine (20 mL) and water (20 mL). Organic phase was separated and concentrated to dryness. The residue was purified on silica gel directly with 0-100% EtOAc in hexanes to afford Compound N15. LCMS ESI+ calc'd for $C_{17}H_{24}BrN_5O_2$: 410.1 [M+H+]. found: 410.2 [M+H+].

Compound N16:

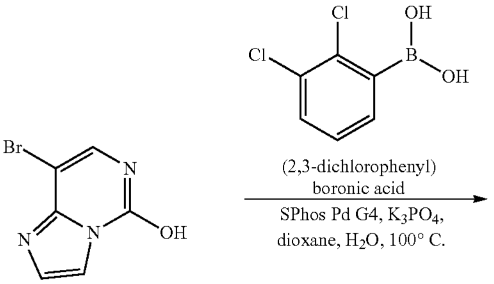

Q1y

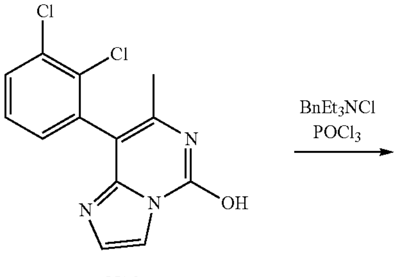

N16a

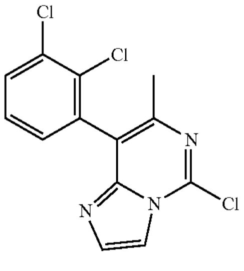

N16

Compound N16a: A solution of Compound Q1y (2.0 g, 8.8 mmol), (2,3-dichlorophenyl)boronic acid (2.5 g, 13.16 mmol), SPhos Pd G4 (0.348 mg, 0.44 mmol), potassium phosphate tribasic (5.6 g, 26 mmol) were added to 1,4-dioxane (19 mL) and water (1 mL). The reaction vessel was purged with argon and heated to 100° C. for 60 min. The mixture was diluted with EtOAc and washed with water, dried over magnesium sulfate, filtered through Celite, and concentrated in vacuo. The residue was reconstituted in toluene and purified by column chromatography (0-20% MeOH in DCM). This provided Compound N16a. LCMS ESI$^+$ calc'd for $C_{13}H_9C_{12}N_3O$: 294.0 [M+H$^+$]. found: 294.1 [M+H$^+$].

Compound N16: Benzyltriethylammonium chloride (0.804 g, 3.529 mmol) to a suspension of Compound N16a (0.346 g, 1.17 mmol) in phosphorous(V) oxychloride (5 ml) and heated to 120° C. for 16 h. The reaction was concentrated in vacuo and purified directly by column chromatography (0-100% EtOAc in Hexanes) to provide Compound N16. The material was used without further purification. LCMS ESI$^+$ calc'd for $C_{13}H_8Cl_{13}N_3$: 312.0 [M+H$^+$]. found: 312.1 [M+H$^+$].

Compound N17

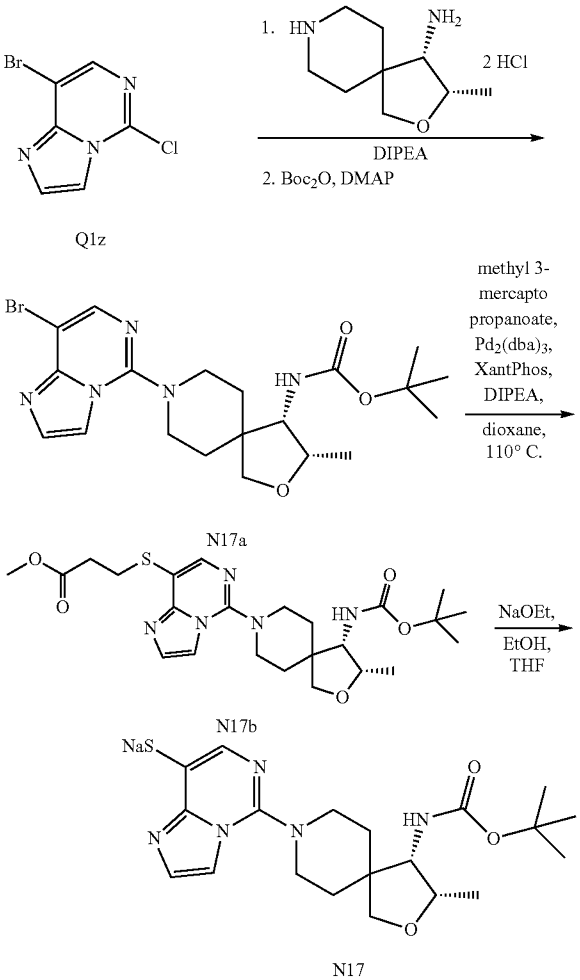

Q1z
N17a
N17b
N17

Compound N17a: Compound Q1z (9.560 g, 41.12 mmol) and tert-butyl (R)-(8-azaspiro[4.5]decan-1-yl)carbamate (10.0 g, 41.12 mmol) were dissolved in DMA (137 mL) and DIPEA (35.8 ml, 205.6 mmol) was added the reaction stirred at r.t. for 2 h. DMAP (525.5 mg, 4.302 mmol) and $Boc_2O$ (26.93 g, 123.37 mmol) were added to the solution and stirred for an additional 1 h. The mixture was diluted with EtOAc, successively washed with brine, dried over magnesium sulfate, and concentrated in vacuo. The residue was reconstituted in toluene and purified by column chromatography (0-100% EtOAc in Hexanes). This provided Compound N17a. LCMS ESI$^+$ calc'd for $C_{20}H_{28}BrN_5O_3$: 466.1 [M+H$^+$]. found: 466.2 [M+H$^+$].

Compound N17b: To a solution of Compound N17a (8.000 g, 17.15 mmol) in 1,4-dioxane (57.2 mL) was added $Pd_2(dba)_3$ (314.2 mg, 0.343 mmol), XantPhos (397 mg, 0.686 mmol), methyl 3-mercaptopropanoate (3.72 mL, 34.31 mmol), and DIPEA (5.97 mL, 34.31 mmol), then the reaction was heated to 110° C. for 2 h. The reaction mixture was diluted with EtOAc, filtered through Celite, the filtrate was concentrated in vacuo, and purified by column chromatography (0-100% EtOAc in Hexanes) to give Compound N17b. LCMS ESI$^+$ calc'd for $C_{24}H_{35}N_5O_5S$: 506.2 [M+H$^+$]. found: 506.2 [M+H$^+$].

Compound N17: To a solution of Compound N17b (7.730 g, 15.3 mmol) in THF (76.4 mL) was added sodium ethoxide solution (21 w/w in ethanol, 6.12 mL). After 20 min, the mixture was the solution was suspended in DCM (51 mL), MTBE (51 mL), followed by the addition of hexanes (30 mL), inducing precipitation of the product. The solids were collected by filtration and used without further purification, to give Compound N17. LCMS ESI$^+$ calc'd for $C_{20}H_{28}N_5O_3S$: 420.2 [M+H$^+$]; found 420.2 [M+H$^+$].

Compound N18:

Compound N18x: To a solution of Compound Q9 (5000 mg, 12.3 mmol) in DCM (15.0 mL) was added TFA (2 mL), then the reaction was stirred at RT for 20 min. The solvent was then evaporated to afford crude product Compound N18x. LCMS ESI$^+$ calc'd for $C_{17}H_{26}N_2OS$: 307.1 [M+H$^+$]. found: 307.0 [M+H$^+$].

Compound N18y: To a solution of Compound Q1z (5.03 g, 0.022 mol)) and Compound N18x (7 g, 0.017 mol) in ACN (25 mL) was added DIEA (7.3 mL). The reaction mixture was heated at 70° C. for 30 mins, the mixture was diluted with EtOAc, washed with brine, the organic solvent was concentrated in vacuo, and then purified with CombiFlash column to afford Compound N18y. LCMS ESI$^+$ calc'd for $C_{23}H_{28}BrN_5OS$: 502.1 [M+H$^+$]. found: 502.2 [M+H$^+$].

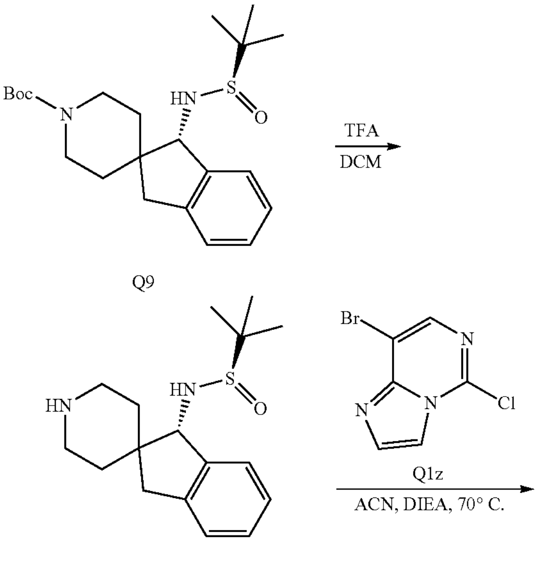

Q9
Q1z
N18x

-continued

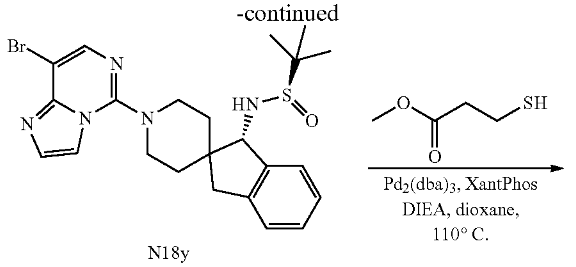

N18y

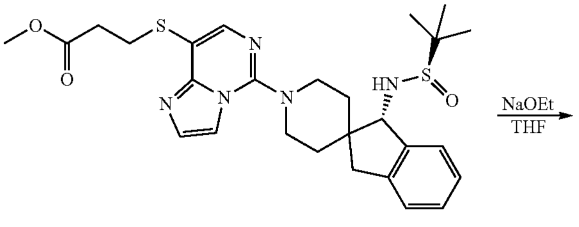

N18z

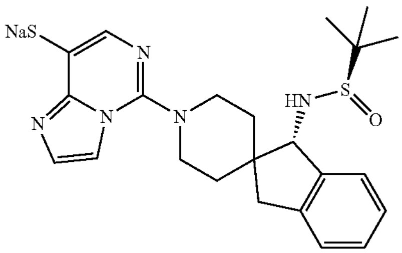

N18

Compound N18z: A solution of Compound N18y (2 g, 3.98 mmol), methyl 3-mercaptopropanoate (0.96 g, 7.96 mmol), $Pd_2(dba)_3$ (109 mg, 0.2 mmol), Xantphos (138 mg, 0.24 mmol), DIEA (1.03 g, 7.96 mmol) were added to 1,4-dioxane (11 mL). The reaction mixture was heated to 110° C. for 2 h. The mixture was then diluted with EtOAc, washed with brine, the organic solvent was concentrated in vacuo, and then purified with Combi-Flash column to Compound N18z. LCMS $ESI^+$ calc'd for $C_{27}H_{35}N_5O_3S_2$: 542.2 $[M+H^+]$. found: 542.1 $[M+H^+]$.

Compound N18: A solution of Compound N18z (1 g, 1.85 mmol) was dissolved in THF (5 mL). The reaction mixture was then cooled to 0° C. and sodium ethoxide (0.7 mL, 21 wt % in EtOH) was added and stirred for 2 h. Then MTBE and hexane were added to reaction mixture and the resulting precipitate was then filtered to afford Compound N18. LCMS $ESI^+$ calc'd for $C_{23}H_{28}N_5NaOS$: 456.1 $[M-Na+H^+]$. found: 456.0 $[M-Na+H^+]$.

Compound N19:

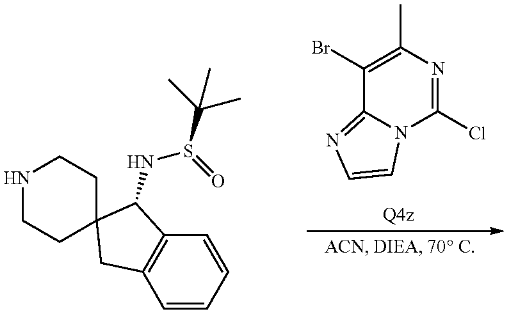

N18x

-continued

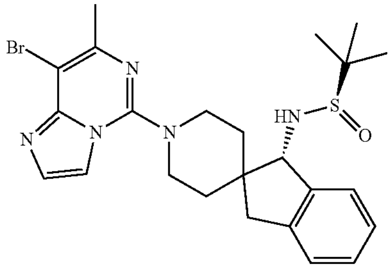

N19

Compound N19: To a solution of Compound Q4z (53 mg, 0.02 mol)) and Compound N18x (90 mg, 0.02 mol) in ACN (2.5 mL) was added DIEA (0.09 mL). The reaction mixture was heated at 70° C. for 30 mins, the mixture was diluted with EtOAc, washed with brine, the organic solvent was concentrated in vacuo, and then purified with Combi-Flash column to afford Compound N19 (45 mg). LCMS $ESI^+$ calc'd for $C_{24}H_{30}BrN_5OS$: 516.1 $[M+H^+]$. found: 516.2 $[M+H^+]$.

Compound N20:

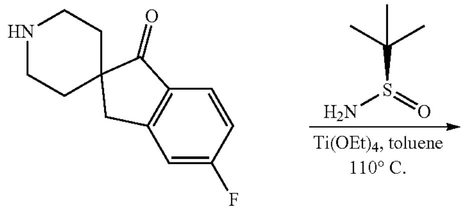

N20x

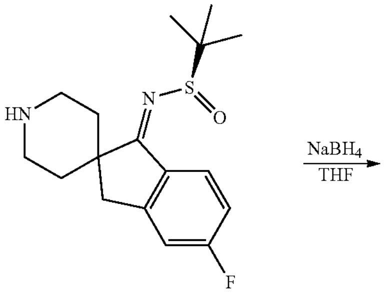

N20y

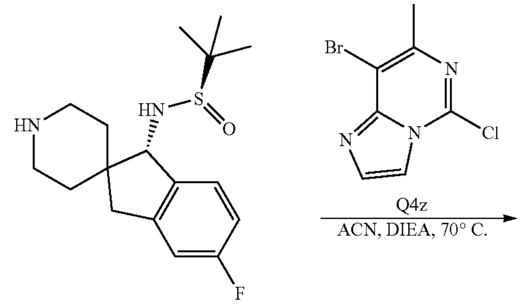

N20z

-continued

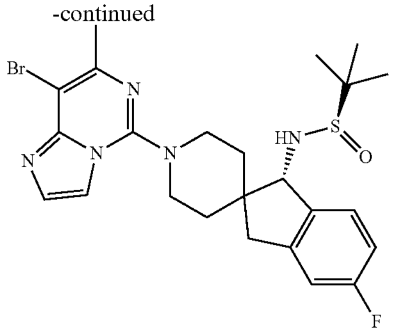

N20

Compound N20y: To a solution of Compound N20x (248 mg, 0.7 mmol) in toluene (5.0 mL) was added (R)-2-methylpropane-2-sulfinamide (471 mg, 4 mmol), then followed by the addition of $Ti(OEt)_4$ (354 mg, 2 mmol). The reaction was heated at 110° C. overnight. the mixture was diluted with EtOAc, washed with $NaHCO_3$ solution, the organic solvent was concentrated in vacuo, and then purified with Combi-Flash column to afford Compound N20y. LCMS $ESI^+$ calc'd for $C_{17}H_{23}N_2OS$: 323.1 [$M+H^+$]; found: 323.0 [$M+H^+$].

Compound N20z: To a solution of Compound N20y (69 mg, 0.16 mmol) in THF (2.0 mL) at −50° C. was added $NaBH_4$ (9 mg, 0.25 mmol), then followed by the addition of $Ti(OEt)_4$ (354 mg, 2 mmol). The reaction was allowed to warm to RT and stirred at RT overnight. the mixture was diluted with EtOAc, washed with aq $NH_4Cl$ solution, the organic solvent was concentrated in vacuo, and then purified with Combi-Flash column to afford Compound N20z. LCMS $ESI^+$ calc'd for $C_{17}H_{25}FN_2OS$: 325.1 [$M+H^+$]. found: 325.0 [$M+H^+$].

Compound N20: To a solution of Compound Q4z (34 mg, 0.14 mmol) and Compound N20z (15 mg, 0.05 mmol) in ACN (2.5 mL) was added DIEA (0.03 mL). The reaction mixture was heated at 70° C. for 30 mins, the mixture was diluted with EtOAc, washed with brine, the organic solvent was concentrated in vacuo, and then purified with Combi-Flash column to afford Compound N20. LCMS $ESI^+$ calc'd for $C_{24}H_{29}BrN_5OS$: 534.1 [$M+H^+$]. found: 534.2 [$M+H^+$].

Example 1: (3S,4S)-8-(8-(2,3-dichlorophenyl)-7-methylimidazo[1,2-c]pyrimidin-5-yl)-3-methyl-2-oxa-8-azaspiro[4.5]decan-4-amine

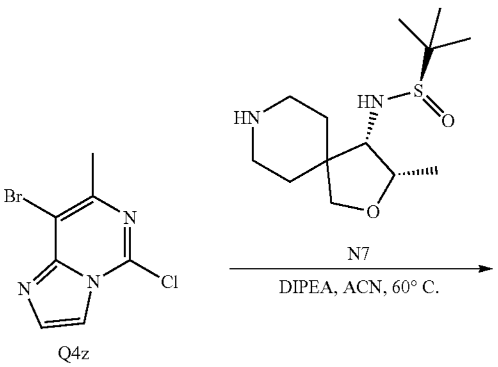

Q4z

N7

-continued

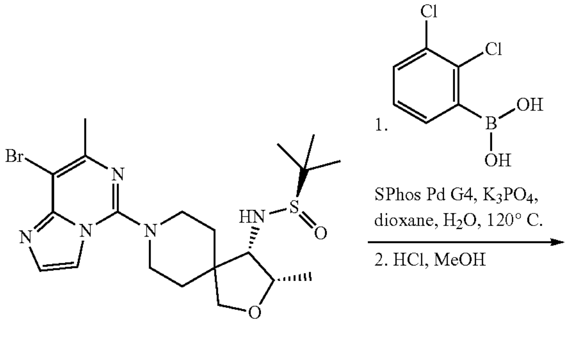

E1a

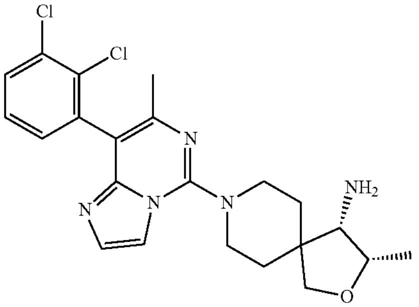

Example 1

Compound E1a: To a solution of Compound Q4z (110 mg, 0.446 mmol) and Compound N7 (153 mg, 0.558 mmol) in ACN (3 mL) was added DIPEA (0.47 mL). The reaction mixture was heated at 60° C. for 1 h, the mixture was diluted with EtOAc, washed with brine, the organic solvent was concentrated in vacuo, and then purified with Combi-Flash column to afford Compound E1a. LCMS $ESI^+$ calc'd for $C_{20}H_{30}BrN_5O_2S$: 484.1 [$M+H^+$]. found: 484.1 [$M+H^+$].

Example 1: A solution of Compound E1a (30 mg, 0.06 mmol), (2,3-dichlorophenyl)boronic acid (35 mg, 0.18 mmol), SPhos Pd G4 (10 mg, 0.012 mmol), potassium phosphate tribasic (53 mg, 0.25 mmol) were added to 1,4-dioxane (2 mL) and water (2 mL). The reaction mixture was heated to 120° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 1. $^1H$ NMR (400 MHz, Methanol-d4) δ 8.06 (d, J=2.4 Hz, 1H), 7.94 (d, J=2.4 Hz, 1H), 7.83 (dd, J=8.1, 1.5 Hz, 1H), 7.56 (t, J=7.9 Hz, 1H), 7.50-7.39 (m, 1H), 4.43-4.28 (m, 1H), 4.19-3.99 (m, 3H), 3.95 (dd, J=9.2, 1.8 Hz, 1H), 3.55 (d, J=4.2 Hz, 1H), 3.51-3.34 (m, 2H), 2.35 (s, 3H), 2.23-1.92 (m, 3H), 1.87 (d, J=13.4 Hz, 1H), 1.37 (d, J=6.5 Hz, 3H). LCMS $ESI^+$ calc'd for $C_{22}H_{25}Cl_2N_5O$: 446.1 [$M+H^+$]. found: 446.2 [$M+H^+$].

Example 2: (R)-8-(8-(1H-indol-4-yl)-7-methylimidazo[1,2-c]pyrimidin-5-yl)-8-azaspiro[4.5]decan-1-amine

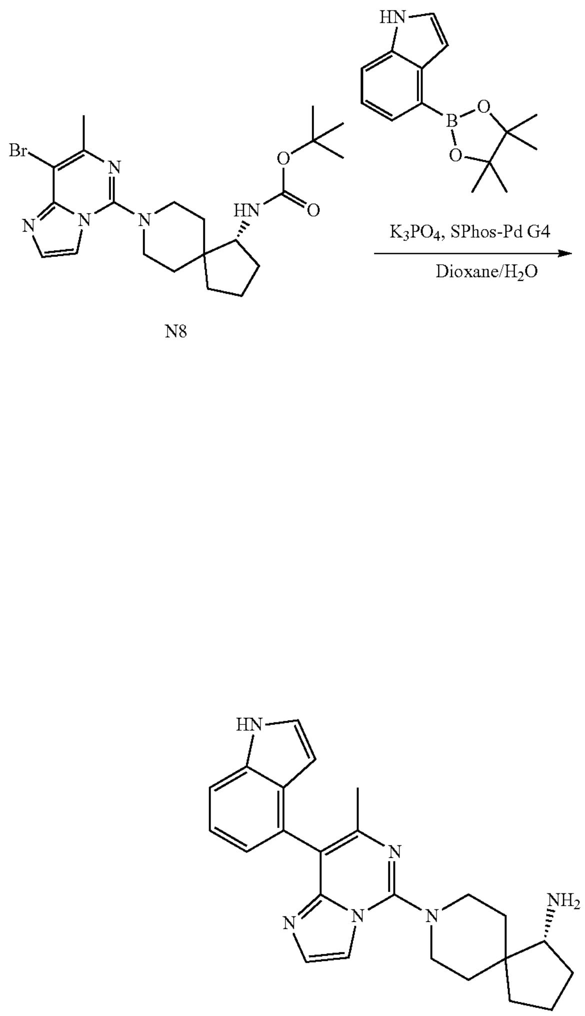

N8

Example 2

Example 2: A microwave tube was charged with Compound N8 (55 mg), 4-(4,4,5,5-tetramethyl-1,3,2-dioxaborolan-2-yl)-1H-indole (58 mg), $K_3PO_4$ (75 mg), SPhos-Pd G4 (5 mg), dioxane (3.0 mL), and $H_2O$ (1.0 mL). The mixture was purged with Argon. The vessel was sealed and heated under microwave irradiation at 100° C. for 30 min. The Boc group was found to have been removed during the course of the reaction. The reaction was cooled to 23° C. and directly purified on a C18 column via reversed-phase HPLC (0.1% TFA in $H_2O$/CH3CN with gradient elution 95:5 to 0:100) giving the desired product after lyophilization. This provided Example 2. $^1$H NMR (400 MHz, MeOH-$d_4$) δ 7.99 (d, J=2.4 Hz, 1H), 7.80 (d, J=2.3 Hz, 1H), 7.64 (dt, J=8.1, 1.0 Hz, 1H), 7.40-7.31 (m, 2H), 7.12 (dt, J=7.2, 0.9 Hz, 1H), 6.14 (dd, J=3.2, 1.0 Hz, 1H), 4.12-3.98 (m, 2H), 3.45 (t, J=12.7 Hz, 2H), 3.38 (t, J=6.5 Hz, −10H), 2.39 (s, 3H), 2.30 (ddd, J=13.1, 7.4, 4.3 Hz, 1H), 2.10-1.88 (m, 4H), 1.86-1.66 (m, 2H). LCMS ESI$^+$ calc'd for $C_{24}H_{28}N_6$: 401.2 [M+H$^+$]. found: 401.3 [M+H$^+$].

Example 3: R)-8-(8-(1H-indol-7-yl)-7-methylimidazo[1,2-c]pyrimidin-5-yl)-8-azaspiro[4.5]decan-1-amine

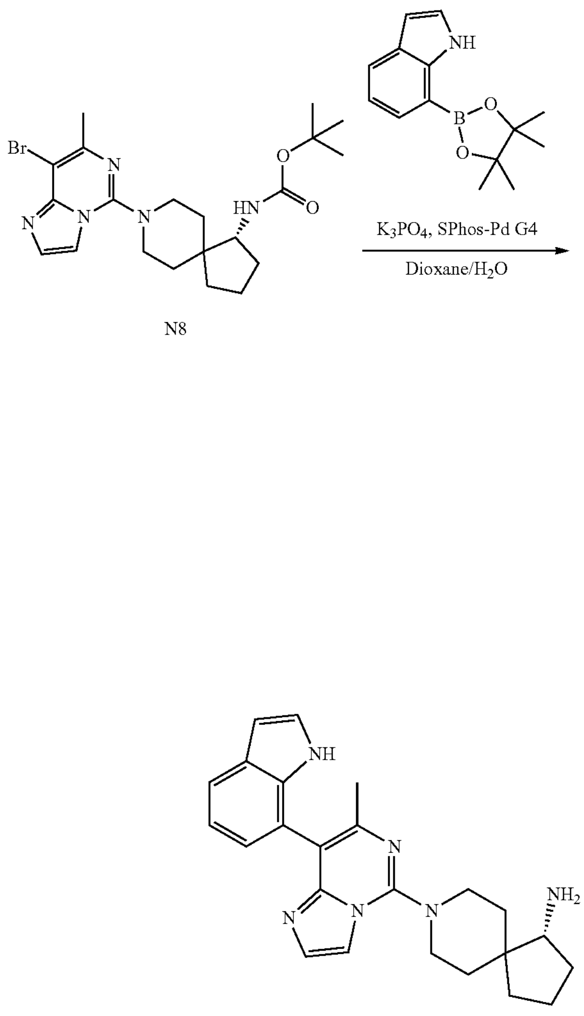

N8

Example 3

Example 3: A microwave tube was charged with Compound N8 (40 mg), 7-(4,4,5,5-tetramethyl-1,3,2-dioxaborolan-2-yl)-1H-indole (42 mg), $K_3PO_4$ (55 mg), SPhos-Pd G4 (3 mg), dioxane (3.0 mL), and $H_2O$ (1.0 mL). The vessel was sealed and heated under microwave irradiation at 100° C. for 30 min. The Boc group was removed during the course of the reaction. The reaction was cooled to 23° C. and directly purified on a C18 column via reversed-phase HPLC (0.1% TFA in $H_2O$/CH3CN with gradient elution 95:5 to 0:100) giving the desired product after lyophilization. This provided Example 3 as a mixture of atropdiastereomers. $^1$H NMR (400 MHz, MeOH-$d_4$, mixture of atropdiastereomers) δ 8.07-7.96 (m, 2H), 7.94 (dd, J=6.2, 2.5 Hz, 1H), 7.89-7.69 (m, 3H), 7.65 (s, 1H), 7.37-7.12 (m, 5H), 7.07 (t, J=9.2 Hz, 1H), 6.96-6.82 (m, 2H), 6.64 (d, J=3.2 Hz, 1H), 5.32 (dd, J=17.5, 8.8 Hz, 1H), 4.21-3.81 (m, 3H), 3.63 (d, J=10.1 Hz, 1H), 2.52-2.45 (m, 2H), 2.40 (d, J=26.2 Hz, 2H). LCMS ESI$^+$ calc'd for $C_{24}H_{28}N_6$: 401.2 [M+H$^+$]. found: 401.5 [M+H$^+$].

Example 4: (R)-8-(7-methyl-8-(pyridin-4-yl)imidazo[1,2-c]pyrimidin-5-yl)-8-azaspiro[4.5]decan-1-amine

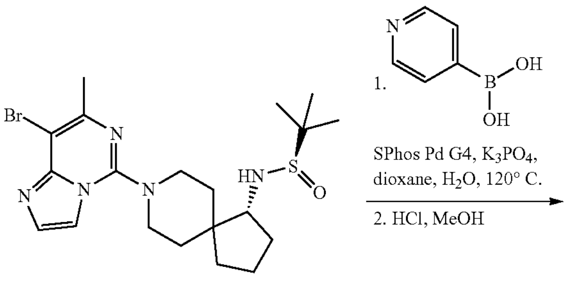

N4

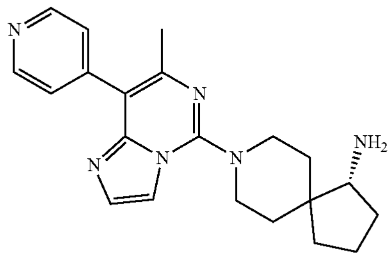

Example 4

Example 4: A solution of Compound N4 (30 mg, 0.06 mmol), (2,3-dichlorophenyl)boronic acid (35 mg, 0.18 mmol), SPhos Pd G4 (10 mg, 0.012 mmol), potassium phosphate tribasic (53 mg, 0.25 mmol) were added to 1,4-dioxane (2 mL) and water (2 mL). The reaction mixture was heated to 120° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 4. $^1$H NMR (400 MHz, Methanol-d4) δ 8.94 (dt, J=5.1, 1.0 Hz, 2H), 7.99 (td, J=3.2, 1.5 Hz, 3H), 7.90-7.84 (m, 1H), 4.11 (dd, J=22.3, 13.9 Hz, 2H), 3.68 (t, J=5.3 Hz, 0H), 3.45 (ddt, J=14.1, 11.9, 2.8 Hz, 2H), 3.36 (d, J=6.7 Hz, 1H), 2.47 (s, 3H), 2.36-2.22 (m, 1H), 2.08-1.96 (m, 1H), 2.01-1.76 (m, 5H), 1.70 (t, J=14.4 Hz, 2H). LCMS ESI$^+$ calc'd for $C_{21}H_{26}N_6$: 363.2 [M+H$^+$]; found: 363.2 [M+H$^+$].

Example 5: (R)-8-(7-methyl-8-phenylimidazo[1,2-c]pyrimidin-5-yl)-8-azaspiro[4.5]decan-1-amine

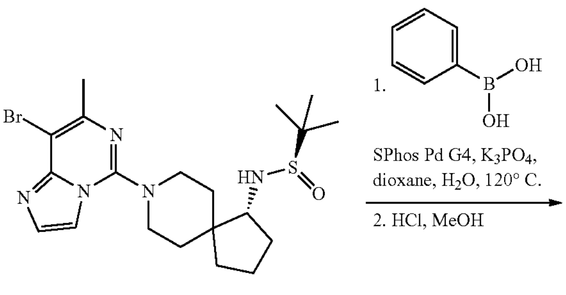

N4

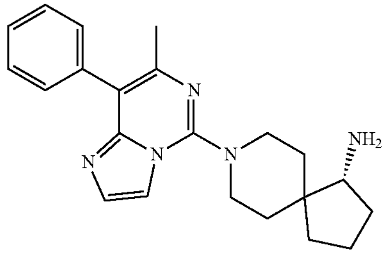

Example 5

Example 5: A solution of Compound N4 (51 mg, 0.11 mmol), phenylboronic acid (40 mg, 0.33 mmol), SPhos Pd G4 (17 mg, 0.02 mmol), potassium phosphate tribasic (92 mg, 0.44 mmol) were added to 1,4-dioxane (2 mL) and water (2 mL). The reaction mixture was heated to 120° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 5. $^1$H NMR (400 MHz, Methanol-d4) (7.98 (d, J=2.4 Hz, 1H), 7.87 (d, J=2.3 Hz, 1H), 7.70-7.55 (m, 3H), 7.52-7.44 (m, 2H), 4.09-3.95 (m, 2H), 3.49-3.33 (m, 3H), 2.42 (s, 3H), 2.28 (ddd, J=10.1, 7.2, 4.2 Hz, 1H), 2.17 (s, 0H), 2.08-1.76 (m, 6H), 1.70 (t, J=13.9 Hz, 2H). LCMS ESI$^+$ calc'd for $C_{22}H_{27}N_5$: 362.2 [M+H$^+$]; found: 362.2 [M+H$^+$].

Example 6: (R)-8-(7-methyl-8-(pyridin-2-yl)imidazo[1,2-c]pyrimidin-5-yl)-8-azaspiro[4.5]decan-1-amine

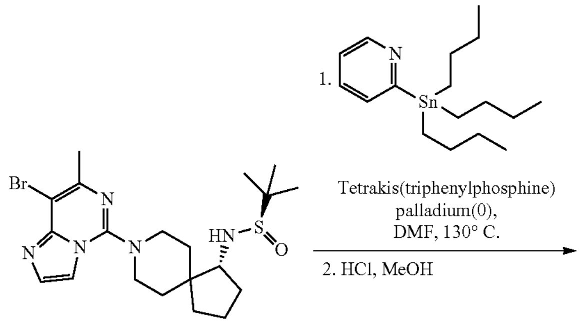

N4

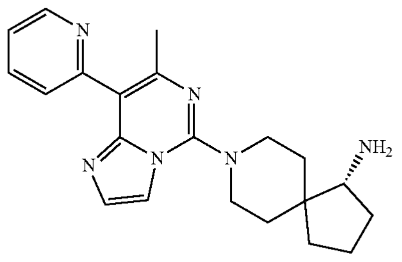

Example 6

Example 6: A solution of Compound N4 (46 mg, 0.098 mmol), 2-(tributylstannyl)pyridine (72 mg, 0.2 mmol), Tetrakis(triphenylphosphine)palladium(0) (11 mg, 0.01 mmol) were added to DMF (2 mL). The reaction mixture was heated to 130° C. overnight. The mixture was diluted with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 6. $^{1}$H NMR (400 MHz, Methanol-d4) (8.91-8.79 (m, 1H), 8.12 (td, J=7.7, 1.8 Hz, 1H), 8.03 (d, J=2.4 Hz, 1H), 7.93 (d, J=2.3 Hz, 1H), 7.83-7.77 (m, 1H), 7.68-7.56 (m, 1H), 4.06 (ddd, J=41.6, 24.8, 14.2 Hz, 2H), 3.46 (ddd, J=14.2, 8.5, 2.6 Hz, 2H), 3.40-3.35 (m, 1H), 2.59 (s, 3H), 2.29 (dtd, J=15.0, 8.3, 7.9, 5.0 Hz, 1H), 2.09-1.58 (m, 9H). LCMS ESI$^{+}$ calc'd for $C_{21}H_{26}N_6$: 363.2 [M+H$^{+}$]. found: 363.2 [M+H$^{+}$].

Example 7: (R)-8-(7-methyl-8-(3-(trifluoromethyl)phenyl)imidazo[1,2-c]pyrimidin-5-yl)-8-azaspiro[4.5]decan-1-amine

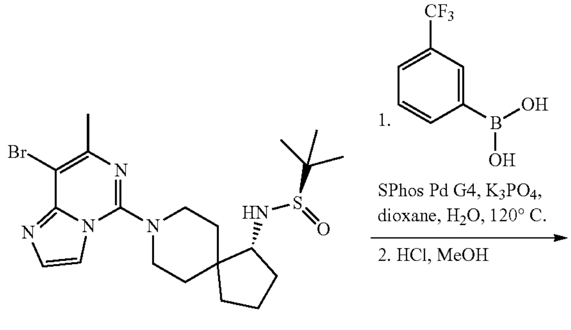

N4

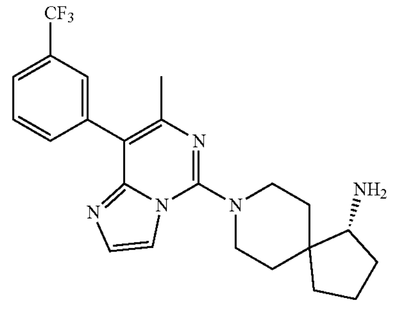

Example 7

Example 7: A solution of Compound N4 (48 mg, 0.1 mmol), (3-(trifluoromethyl)phenyl)boronic acid (58 mg, 0.3 mmol), SPhos Pd G4 (16 mg, 0.02 mmol), potassium phosphate tribasic (87 mg, 0.4 mmol) were added to 1,4-dioxane (2 mL) and water (2 mL). The reaction mixture was heated to 120° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 7. $^{1}$H NMR (400 MHz, Methanol-d4) δ 8.01 (d, J=2.4 Hz, 1H), 7.96-7.80 (m, 4H), 7.76 (d, J=7.7 Hz, 1H), 4.15-3.95 (m, 2H), 3.50-3.39 (m, 2H), 3.37 (d, J=6.7 Hz, 2H), 2.40 (s, 3H), 2.34-2.20 (m, 1H), 2.07-1.76 (m, 7H), 1.70 (t, J=14.0 Hz, 2H). $^{19}$F NMR (376 MHz, Methanol-$d_4$) δ −64.71 (s, 3F), −77.70 (s, 6F). LCMS ESI$^{+}$ calc'd for $C_{23}H_{26}F_3N_5$: 430.2 [M+H$^{+}$]. found: 430.2 [M+H$^{+}$].

Example 8: (R)-8-(8-(2-chlorophenyl)-7-methylimidazo[1,2-c]pyrimidin-5-yl)-8-azaspiro[4.5]decan-1-amine

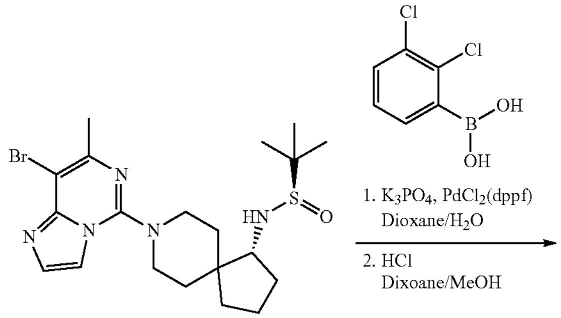

N4

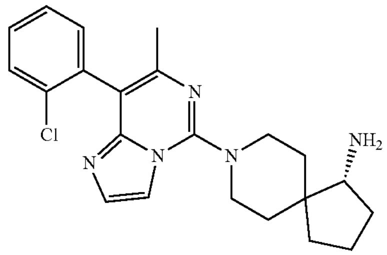

Example 8

Example 8: A microwave tube was charged with Compound N4 (100 mg), (2,3-dichlorophenyl)boronic acid (81 mg), K3P04 (136 mg), $PdCl_2$(dppf) (17 mg), dioxane (3.0 mL), and $H_2O$ (1.0 mL). The mixture was degassed with argon. The vessel was sealed and heated under microwave irradiation at 100° C. for 30 min. The reaction was cooled to 23° C. and diluted with brine. The system was extracted with EtOAc. The organic phase was concentrated and the residue was subjected to chromatography on silica gel (Eluent: MeOH gradient in DCM). The desired product was treated with MeOH, followed by and HCl (4.0 M in dioxane), then stirred for 10 min at 23° C. The reaction was concentrated under reduced pressure. The residue was subjected to purification on a C18 column via reversed-phase HPLC (0.1% TFA in $H_2O$/CH3CN with gradient elution 95:5 to 0:100) giving Example 8. $^1$H NMR (400 MHz, MeOH-$d_4$) δ 7.94 (d, J=2.3 Hz, 1H), 7.83 (d, J=2.2 Hz, 1H), 7.61 (dd, J=5.1, 1.1 Hz, 2H), 7.54 (q, J=1.4 Hz, 1H), 7.46-7.35 (m, 1H), 4.13-3.88 (m, 2H), 3.53-3.34 (m, 2H), 2.41 (s, 3H), 2.36-2.19 (m, 1H), 2.09-1.57 (m, 9H). LCMS ESI$^+$ calc'd for $C_{22}H_{26}ClN_5$: 396.2 [M+H$^+$]. found: 396.2 [M+H$^+$].

Example 9: (R)-8-(8-(2,3-dichlorophenyl)-7-methylimidazo[1,2-c]pyrimidin-5-yl)-8-azaspiro[4.5]decan-1-amine

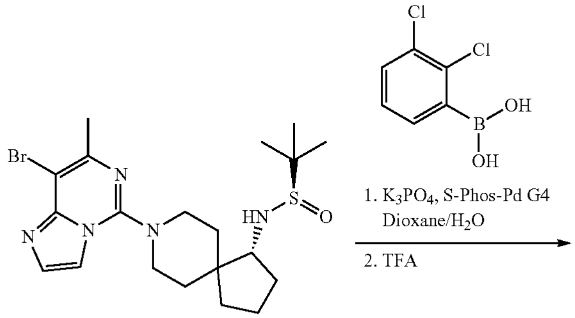

N4

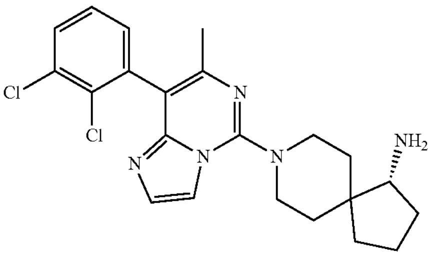

Example 9

Example 9: A microwave tube was charged with Compound N4 (103 mg), (2,3-dichlorophenyl)boronic acid (126 mg), $K_3PO_4$ (140 mg), S-Phos-Pd G4 (35 mg), dioxane (2.0 mL), and $H_2O$ (2.0 mL). The mixture was degassed with argon. The vessel was sealed and heated under microwave irradiation at 120° C. for 30 min. The reaction was cooled to 23° C. and diluted with brine. The system was extracted with EtOAc. The organic phase was concentrated and the residue was subjected to chromatography on silica gel (Eluent: MeOH gradient in DCM). The desired product was treated with TFA (neat), then stirred for 10 min at 23° C. The reaction was concentrated under reduced pressure. The residue was subjected to purification on a C18 column via reversed-phase HPLC (0.1% TFA in $H_2O$/CH3CN with gradient elution 95:5 to 0:100) giving Example 9. $^1$H NMR (400 MHz, MeOH-$d_4$) δ 7.96 (d, J=2.2 Hz, 1H), 7.83 (d, J=2.2 Hz, 1H), 7.80 (dd, J=8.1, 1.6 Hz, 1H), 7.54 (t, J=7.9 Hz, 1H), 7.42 (dt, J=7.6, 1.3 Hz, 1H), 4.06 (dd, J=14.5, 9.7 Hz, 2H), 2.32 (s, 4H), 2.12-1.59 (m, 10H). LCMS ESI$^+$ calc'd for $C_{22}H_{25}Cl_2N_5$: 430.2 [M+H$^+$]. found: 430.2 [M+H$^+$].

Example 10: ($S_{axial}$,R)-8-(8-(2,3-dichlorophenyl)-7-methylimidazo[1,2-c]pyrimidin-5-yl)-8-azaspiro[4.5]decan-1-amine and Example 11: ($R_{axial}$,R)-8-(8-(2,3-dichlorophenyl)-7-methylimidazo[1,2-c]pyrimidin-5-yl)-8-azaspiro[4.5]decan-amine

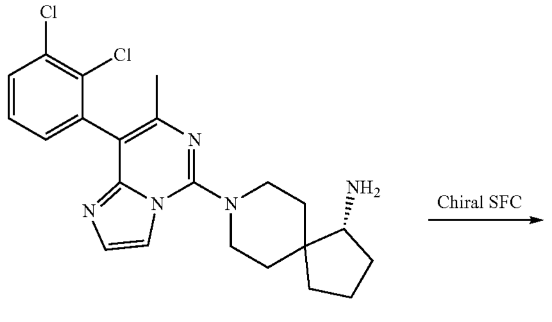

Example 9

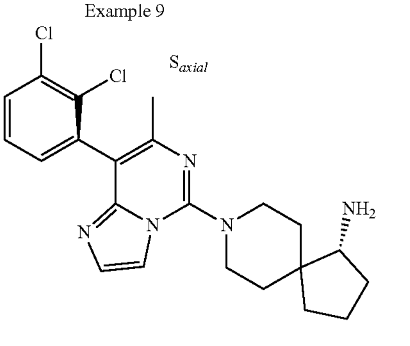

Example 10
Peak 1

+

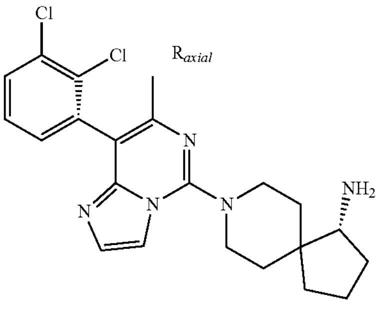

Example 11
Peak 2

Example 10: ($S_{axial}$) and Example 11: ($R_{axial}$): A sample of Example 9 was subjected to purification via Chiral SFC. was subjected to chiral SFC using supercritical $CO_2$ and EtOH as a mobile phase on an IG-H column at 40° C. (100 mm×4.6 mm; 5 μm) column with isocratic elution at 20% EtOH (doped with 0.1% TFA) in $CO_2$. Two peaks were obtained, corresponding to the two atropdiastereomers of Example 9. Axial chiralities of the two atropdiastereomeric products were assigned arbitrarily. The first product peak to elute was Example 10 ($S_{axial}$). $^1$H NMR (400 MHz, $CD_3CN$) (7.76 (dd, J=8.1, 1.5 Hz, 1H), 7.73 (d, J=2.3 Hz, 1H), 7.70 (d, J=2.2 Hz, 1H), 7.50 (t, J=7.9 Hz, 1H), 7.36 (dd, J=7.7, 1.6 Hz, 1H), 3.96 (dd, J=28.9, 13.5 Hz, 3H), 3.47-3.25 (m, 4H), 1.93-1.13 (m, 16H). The second product peak to elute was Example 11 ($R_{axial}$). $^1$H NMR (400 MHz, $CD_3CN$) (7.72 (dd, J=8.1, 1.6 Hz, 1H), 7.68 (d, J=2.1 Hz, 1H), 7.64 (d, J=2.0 Hz, 1H), 7.47 (t, J=7.9 Hz, 1H), 7.35 (dd, J=7.6, 1.6 Hz, 1H), 3.92 (dd, J=18.6, 14.1 Hz, 3H), 3.47-3.22 (m, 4H), 2.23-2.00 (m, 2H), 1.94-1.56 (m, 10H), 1.42-1.19 (m, 2H).

Example 12: (R)-8-(8-(3-chlorothiophen-2-yl)-7-methylimidazo[1,2-c]pyrimidin-5-yl)-8-azaspiro[4.5]decan-1-amine

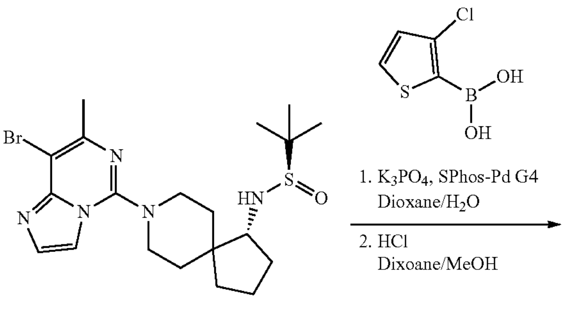

N4

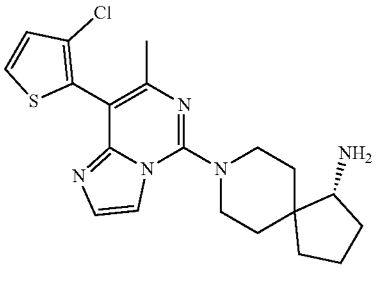

Example 12

Example 12: A microwave tube was charged with Compound N4 (30 mg), (3-chlorothiophen-2-yl)boronic acid (31 mg), $K_3PO_4$ (41 mg), SPhos-Pd G4 (10 mg), dioxane (3.0 mL), and $H_2O$ (1.0 mL). The mixture was degassed with argon. The vessel was sealed and heated under microwave irradiation at 100° C. for 30 min. The reaction was cooled to 23° C. and diluted with brine. The system was extracted with EtOAc. The organic phase was concentrated and the residue was subjected to chromatography on silica gel (Eluent: MeOH gradient in EtOAc). The desired product was treated with MeOH, followed by and HCl (4.0 M in dioxane), then stirred for 10 min at 23° C. The reaction was concentrated under reduced pressure. The residue was subjected to purification on a C18 column via reversed-phase HPLC (0.1% TFA in $H_2O$/CH3CN with gradient elution 95:5 to 0:100) giving Example 12. $^1$H NMR (400 MHz, MeOH-$d_4$) δ 8.00 (d, J=2.4 Hz, 1H), 7.92 (d, J=2.3 Hz, 1H), 7.87 (d, J=5.5 Hz, 1H), 7.28 (d, J=5.5 Hz, 1H), 4.13 (dd, J=24.9, 13.6 Hz, 3H), 3.61-3.39 (m, 2H), 2.43 (s, 3H), 2.37-2.19 (m, 1H), 2.09-1.54 (m, 9H). LCMS ESI$^+$ calc'd for $C_{20}H_{24}ClN_5S$: 402.1 [M+H$^+$]; found: 402.2 [M+H$^+$].

Example 13: (R)-8-(8-(1,5-dimethyl-1H-pyrazol-4-yl)-7-methylimidazo[1,2-c]pyrimidin-5-yl)-8-azaspiro[4.5]decan-1-amine

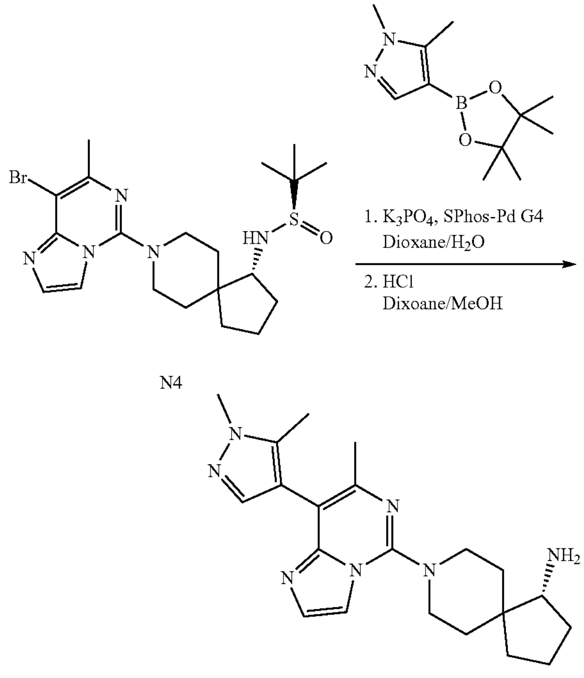

N4

Example 13

Example 13: A microwave tube was charged with Compound N4 (38 mg), 1,5-dimethyl-4-(4,4,5,5-tetramethyl-1,3,2-dioxaborolan-2-yl)-1H-pyrazole (54 mg), K3P04 (52 mg), SPhos-Pd G4 (13 mg), dioxane (3.0 mL), and $H_2O$ (1.0 mL). The vessel was sealed and heated under microwave irradiation at 145° C. for 30 min. The reaction was cooled to 23° C. and diluted with brine. The system was extracted with EtOAc. The organic phase was concentrated and the residue was subjected to chromatography on silica gel (Eluent: MeOH gradient in DCM). The desired product was treated with MeOH, followed by and HCl (4.0 M in dioxane), then stirred for 10 min at 23° C. The reaction was concentrated under reduced pressure. The residue was subjected to purification on a C18 column via reversed-phase HPLC (0.1% TFA in $H_2O$/CH3CN with gradient elution 95:5 to 0:100) giving Example 13. $^1$H NMR (400 MHz, MeOH-$d_4$) δ 7.97 (d, J=2.3 Hz, 1H), 7.88 (d, J=2.3 Hz, 1H), 7.55 (s, 1H), 4.09-4.01 (m, 2H), 3.93 (s, 3H), 3.50-3.32 (m, 3H), 2.42 (s, 3H), 2.34-2.22 (m, 2H), 2.19 (s, 3H), 2.06-1.75 (m, 6H), 1.75-1.63 (m, 2H). LCMS ESI$^+$ calc'd for $C_{21}H_{29}N_7$: 380.3 [M+H$^+$]. found: 380.3 [M+H$^+$].

Example 14: (R)-8-(8-(1,4-dimethyl-1H-pyrazol-5-yl)-7-methylimidazo[1,2-c]pyrimidin-5-yl)-8-azaspiro[4.5]decan-1-amine Example 14: A microwave tube was charged with Compound N4 (38 mg), 1,4-dimethyl-5-(4,4,5,5-tetramethyl-1,3,2-dioxaborolan-2-yl)-1H-pyrazole (54 mg), $K_3PO_4$ (52 mg), SPhos-Pd G4 (13 mg), dioxane (3.0 mL), and $H_2O$ (1.0 mL). The vessel was sealed and heated under microwave irradiation at 100° C. for 30 min. The reaction was cooled to 23° C. and directly purified on a C18 column via reversed-phase HPLC (0.1% TFA in $H_2O$/CH3CN with gradient elution 95:5 to 0:100) giving the desired product after lyophilization. The desired product was treated with MeOH, followed by and HCl (4.0 M in dioxane), then stirred for 10 min at RT. The solution was directly purified on a C18 column via reversed-phase HPLC (0.1% TFA in $H_2O$/CH3CN with gradient elution 95:5 to 0:100) giving Example 14. $^1$H NMR (400 MHz, MeOH-$d_4$) δ 8.04 (d, J=2.4 Hz, 1H), 7.91 (d, J=2.3 Hz, 1H), 7.51 (s, 1H), 4.19-4.10 (m, 2H), 3.68 (s, 3H), 3.55-3.44 (m, 2H), 3.41-3.28 (m, 1H), 2.34 (s, 3H), 2.34-2.22 (m, 2H), 2.06-1.75 (m, 6H), 1.96 (s, 3H), 1.75-1.63 (m, 2H). LCMS ESI$^+$ calc'd for $C_{21}H_{29}N_7$: 380.2 [M+H$^+$]. found: 380.3 [M+H$^+$].

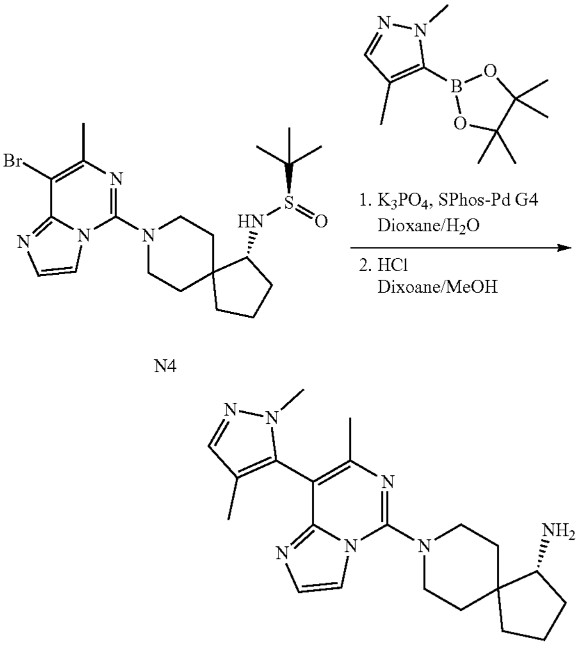

N4

Example 14

Example 15: (R)-8-(8-(imidazo[1,2-a]pyridin-3-yl)-7-methylimidazo[1,2-c]pyrimidin-5-yl)-8-azaspiro[4.5]decan-1-amine

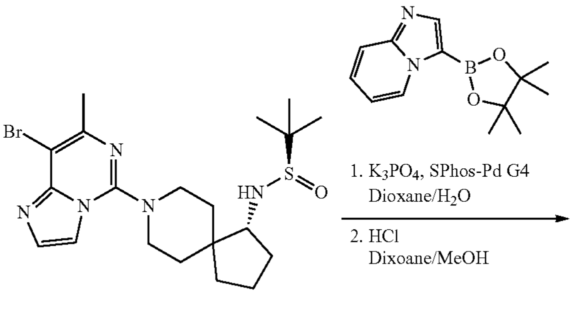

N14

-continued

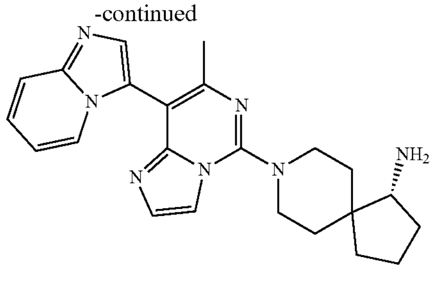

Example 15

Example 15: A microwave tube was charged with Compound N4 (40 mg), 3-(4,4,5,5-tetramethyl-1,3,2-dioxaborolan-2-yl)imidazo[1,2-a]pyridine (63 mg), $K_3PO_4$ (54 mg), SPhos-Pd G4 (3 mg), dioxane (3.0 mL), and $H_2O$ (1.0 mL). The vessel was sealed and heated under microwave irradiation at 100° C. for 30 min. The reaction was cooled to 23° C. and directly purified on a C18 column via reversed-phase HPLC (0.1% TFA in $H_2O$/CH3CN with gradient elution 95:5 to 0:100) giving the desired product after lyophilization. The desired product was treated with MeOH, followed by and HCl (4.0 M in dioxane), then stirred for 10 min at RT. The solution was directly purified on a C18 column via reversed-phase HPLC (0.1% TFA in $H_2O$/CH3CN with gradient elution 95:5 to 0:100) giving Example 15. $^1$H NMR (400 MHz, MeOH-$d_4$) δ 8.37-8.27 (m, 2H), 8.13-8.05 (m, 2H), 7.89 (d, J=1.9 Hz, 1H), 7.66 (d, J=1.9 Hz, 1H), 7.47 (ddd, J=6.8, 5.6, 2.5 Hz, 1H), 4.15 (t, J=17.5 Hz, 2H), 3.50-3.33 (m, 2H), 2.43 (s, 3H), 2.35-2.25 (m, 1H), 2.09-1.96 (m, 3H), 1.96-1.81 (m, 4H), 1.81-1.66 (m, 3H). LCMS ESI$^+$ calc'd for $C_{23}H_{27}N_7$: 402.2 [M+H$^+$]. found: 402.3 [M+H$^+$].

Example 16: (R)-8-(8-(2-amino-5-chloropyridin-4-yl)-7-methylimidazo[1,2-c]pyrimidin-5-yl)-8-azaspiro[4.5]decan-1-amine

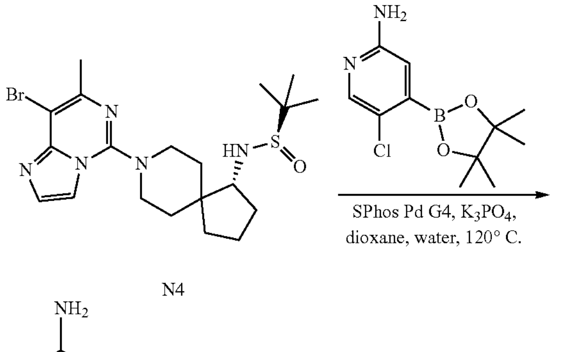

N4

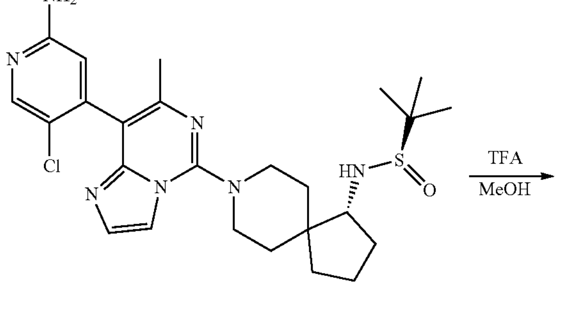

E16a

-continued

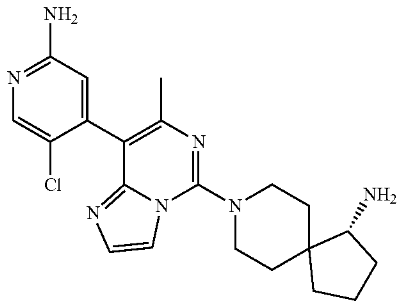

Example 16

Compound E16a: A solution of Compound N4 (0.028 g), 5-chloro-4-(4,4,5,5-tetramethyl-1,3,2-dioxaborolan-2-yl)pyridin-2-amine (0.051 g), SPhos Pd G4 (0.010 g), and potassium phosphate tribasic (0.0570 g) in 1,4-dioxane (1.5 mL) and water (1.5 mL) was heated in a microwave reactor to 120° C. for 30 min. The reaction was diluted with EtOAc, washed with brine, dried over sodium sulfate, and concentrated in vacuo. The residue was subjected to column chromatography (0-25% MeOH in DCM) to give Compound E16a. $^1$H NMR (400 MHz, DMSO-$d_6$) δ 8.04 (s, 1H), 7.61 (d, J=1.5 Hz, 1H), 7.48 (d, J=1.4 Hz, 1H), 6.43 (s, 1H), 6.21 (s, 2H), 5.03 (d, J=8.1 Hz, 1H), 3.88-3.66 (m, 2H), 3.28-3.15 (m, 1H), 3.15-2.96 (m, 2H), 2.15 (s, 3H), 2.13-2.02 (m, 1H), 1.99-1.89 (m, 1H), 1.89-1.79 (m, 2H), 1.72-1.62 (m, 2H), 1.62-1.54 (m, 1H), 1.51-1.46 (m, 1H), 1.44-1.32 (m, 2H), 1.14 (s, 9H). LCMS ESI$^+$ calc'd for $C_{25}H_{34}ClN_7OS$: 516.2 [M+H$^+$]. found: 516.3 [M+H$^+$].

Example 16: To a solution of Compound E16a (0.018 g) in MeOH (0.5 mL) was added HCl in 1,4-dioxane (0.5 mL, 4 M). After 30 min, the reaction was diluted with water and purified by preparatory HPLC (10-70% MeCN in water with 0.1% TFA, Gemini) to give Example 16. $^1$H NMR (400 MHz, DMSO-$d_6$) δ 8.19 (s, 1H), 7.89 (d, J=9.3 Hz, 6H), 6.58 (s, 1H), 3.87 (t, J=16.8 Hz, 2H), 3.39-3.18 (m, 3H), 2.24 (s, 3H), 2.19-2.00 (m, 1H), 1.94-1.63 (m, 7H), 1.59 (d, J=13.1 Hz, 1H), 1.52 (d, J=13.6 Hz, 1H). $^{19}$F NMR (376 MHz, DMSO-$d_6$) δ −75.09. LCMS ESI$^+$ calc'd for $C_{21}H_{26}ClN_7$: 412.2 [M+H$^+$]. found: 412.3 [M+H$^+$].

Example 17: (R)-8-(8-((6-amino-2-(trifluoromethyl)pyridin-3-yl)thio)-7-methylimidazo[1,2-c]pyrimidin-5-yl)-8-azaspiro[4.5]decan-1-amine

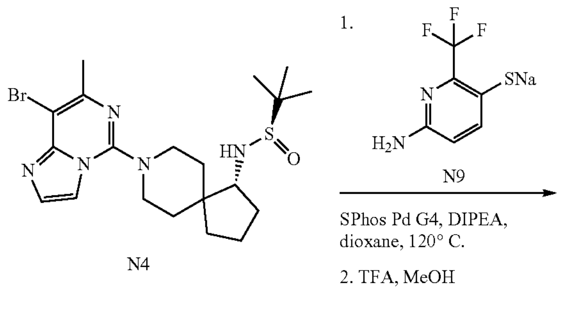

N4

-continued

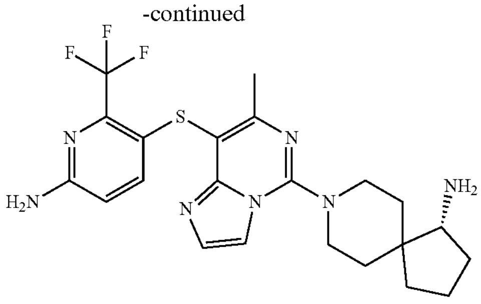

Example 17

Example 17: A solution of Compound N4 (0.100 g), Compound N9 (0.098 g), and SPhos Pd G4 (0.040 g) in 1,4-dioxane (4.4 mL) was added DIPEA (0.20) and heated in a microwave reactor to 120° C. for 30 min. The reaction filtered through Celite, rinsed with EtOAc, and the filtrate was concentrated in vacuo. To the crude in MeOH (1.0 mL) was added HCl in 1,4-dioxane (0.25 mL, 4 M). After 30 min, the reaction was diluted with water and MeOH, and purified by preparatory HPLC (5-50% MeCN in water with 0.1% TFA, Gemini) to give Example 17. $^1$H NMR (400 MHz, DMSO-$d_6$) δ 7.84 (s, 4H), 7.78 (s, 1H), 7.16 (d, J=8.8 Hz, 1H), 6.71-6.35 (m, 3H), 3.92-3.83 (m, 2H), 3.33-3.19 (m, 3H), 2.47 (s, 3H), 2.17-2.00 (m, 1H), 1.95-1.70 (m, 5H), 1.70-1.61 (m, 2H), 1.53 (dd, J=26.1, 13.2 Hz, 2H). $^{19}$F NMR (376 MHz, DMSO-$d_6$) δ −63.28 (s, 3F), −74.67 (s 6F). LCMS ESI$^+$ calc'd for $C_{22}H_{26}F_3N_7S$: 478.2 [M+H$^+$]. found: 478.2 [M+H$^+$].

Example 18: (R)-8-(8-((2-amino-3-chloropyridin-4-yl)thio)-7-methylimidazo[1,2-c]pyrimidin-5-yl)-8-azaspiro[4.5]decan-1-amine

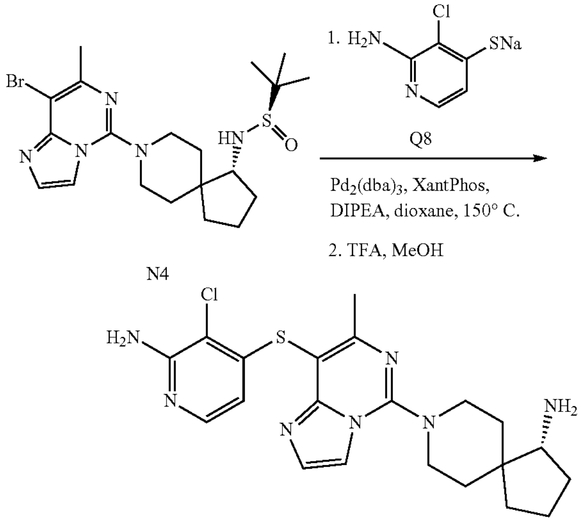

Q8

N4

Example 18

Example 18: A solution of Compound N4 (0.052 g), Compound Q8 (0.041 g), $Pd_2(dba)_3$ (0.023 g), and XantPhos (0.026 g) in 1,4-dioxane (2.2 mL) was added DIPEA (0.10) and heated in a microwave reactor to 150° C. for 1 h. The reaction filtered through Celite, rinsed with 1,4-dioxane and EtOAc, and the filtrate was concentrated in vacuo. To the crude in MeOH (1.0 mL) was added HCl in 1,4-dioxane (0.25 mL, 4 M). After 30 min, the reaction was diluted with water and MeOH, and purified by preparatory HPLC (5-50% MeCN in water with 0.1% TFA, Gemini) to give Example 18. $^1$H NMR (400 MHz, DMSO-$d_6$) δ 7.87 (s, 4H), 7.74 (s, 1H), 7.60 (d, J=5.8 Hz, 1H), 7.02 (s, 2H), 5.95 (d, J=5.8 Hz, 1H), 4.01-3.90 (m, 2H), 3.40-3.29 (m, 2H), 3.29-3.20 (m, 2H), 2.49 (s, 3H), 2.16-2.03 (m, 1H), 1.89-1.71 (m, 5H), 1.71-1.62 (m, 2H), 1.62-1.48 (m, 2H). $^{19}$F NMR (376 MHz, DMSO-$d_6$) δ −74.81. LCMS ESI$^+$ calc'd for $C_{21}H_{26}ClN_7S$: 444.2 [M+H$^+$]. found: 444.2 [M+H$^+$].

Example 19: (R)-8-(7-methyl-8-(2-(trifluoromethyl)pyridin-3-yl)imidazo[1,2-c]pyrimidin-5-yl)-8-azaspiro[4.5]decan-1-amine

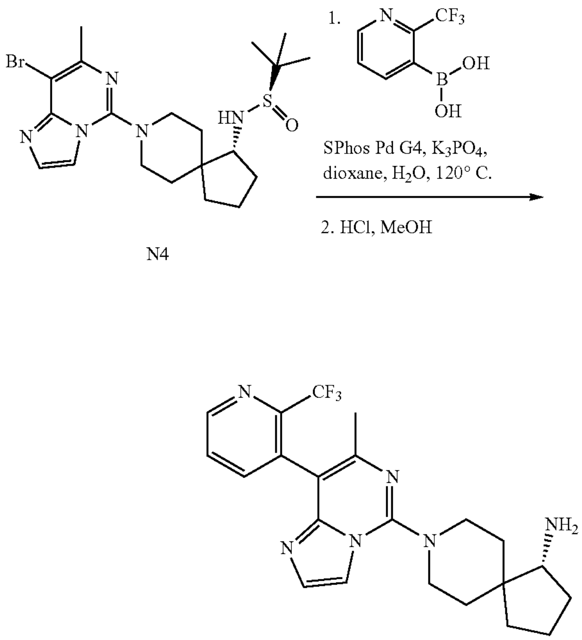

N4

Example 19

Example 19: A solution of (86 mg, 0.18 mmol), (2-(trifluoromethyl)pyridin-3-yl)boronic acid (105 mg, 0.55 mmol), SPhos Pd G4 (29 mg, 0.037 mmol), potassium phosphate tribasic (156 mg, 0.7 mmol) were added to 1,4-dioxane (2 mL) and water (2 mL). The reaction mixture was heated to 120° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 19. $^1$H NMR (400 MHz, Methanol-$d_4$) δ 8.94 (dd, J=4.8, 1.6 Hz, 1H), 8.08-7.99 (m, 2H), 7.97-7.87 (m, 2H), 4.20-4.07 (m, 2H), 3.56-3.42 (m, 2H), 3.37 (d, J=6.7 Hz, 1H), 2.36-2.23 (m, 2H), 2.27 (s, 3H), 1.96 (s, 4H), 2.10-1.79 (m, 2H), 1.83-1.64 (m, 2H). $^{19}$F NMR (376 MHz, Methanol-$d_4$) δ −66.94 (2 lines, 3F), −77.91 (s, 6F). LCMS ESI$^+$ calc'd for $C_{22}H_{25}F_3N_6$: 431.2 [M+H$^+$]. found: 431.2 [M+H$^+$].

Example 20: (R)-8-(8-(3,5-dimethylisoxazol-4-yl)-7-ethylimidazo[1,2-c]pyrimidin-5-yl)-8-azaspiro[4.5]decan-1-amine

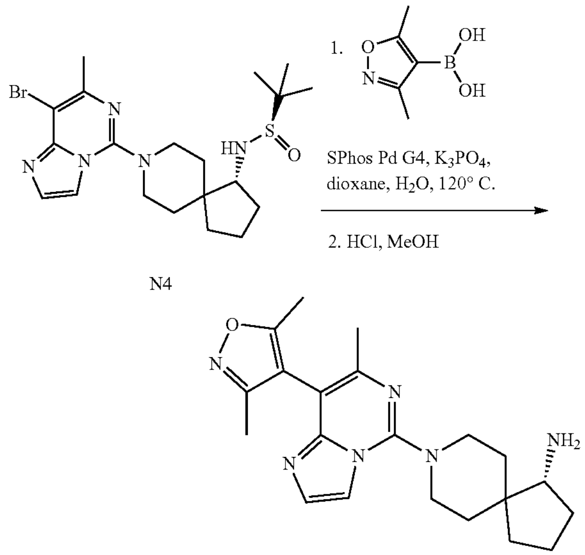

Example 20

Example 20: A solution of Compound N4 (60 mg, 0.13 mmol), (3,5-dimethylisoxazol-4-yl)boronic acid (54 mg, 0.38 mmol), SPhos Pd G4 (20 mg, 0.03 mmol), potassium phosphate tribasic (109 mg, 0.5 mmol) were added to 1,4-dioxane (2 mL) and water (2 mL). The reaction mixture was heated to 120° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 20. $^1$H NMR (400 MHz, Methanol-$d_4$) δ 7.99 (d, J=2.3 Hz, 1H), 7.90 (d, J=2.3 Hz, 1H), 4.08 (dd, J=23.3, 13.6 Hz, 2H), 3.45 (ddt, J=13.9, 11.3, 2.4 Hz, 2H), 3.37 (d, J=6.5 Hz, 1H), 2.39 (s, 3H), 2.33 (s, 3H), 2.30-2.22 (m, 1H), 2.14 (s, 3H), 2.06-1.63 (m, 9H). LCMS ESI$^+$ calc'd for $C_{21}H_{28}N_6O$: 381.2 [M+H$^+$]. found: 381.1 [M+H$^+$].

Example 21: (R)-8-(7-methyl-8-(2-(trifluoromethyl)phenyl) imidazo[1,2-c]pyrimidin-5-yl)-8-azaspiro[4.5]decan-1-amine

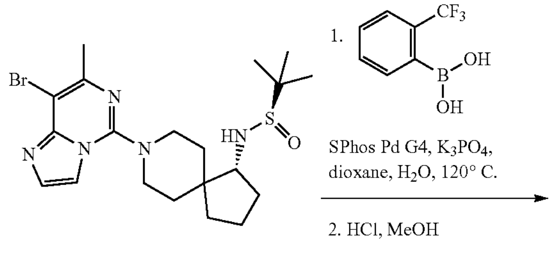

N4

-continued

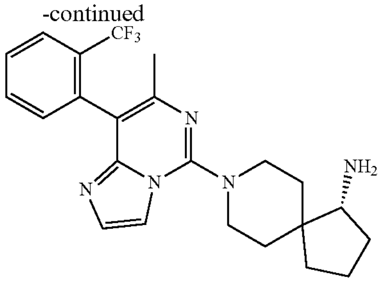

Example 21

Example 21: A solution of Compound N4 (0.052 g, 0.11 mmol), (2-(trifluoromethyl)phenyl)boronic acid (0.063 g, 0.33 mmol), SPhos Pd G4 (0.018 g, 0.022 mmol), potassium phosphate tribasic (0.094 g, 0.44 mmol) were added to 1,4-dioxane (2 mL) and water (2 mL). The reaction mixture was heated to 120° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 21. $^1$H NMR (400 MHz, Methanol-$d_4$) δ 8.02 (q, J=2.6, 1.9 Hz, 2H), 7.93-7.78 (m, 3H), 7.53 (d, J=7.5 Hz, 1H), 4.18-4.02 (m, 2H), 3.47 (td, J=12.4, 11.3, 3.7 Hz, 2H), 3.37 (d, J=6.7 Hz, 1H), 2.36-2.25 (m, 1H), 2.25 (s, 3H), 2.10-1.98 (m, 1H), 2.00-1.87 (m, 4H), 1.92-1.78 (m, 1H), 1.82-1.65 (m, 2H). $^{19}$F NMR (376 MHz, DMSO-$d_6$) δ −61.88, −73.58. LCMS ESI$^+$ calc'd for $C_{23}H_{26}F_3N_5$: 430.2 [M+H$^+$]. found: 430.2 [M+H$^+$].

Example 22: (R)-8-(7-methyl-8-(pyridin-3-yl)imidazo[1,2-c]pyrimidin-5-yl)-8-azaspiro[4.5]decan-1-amine

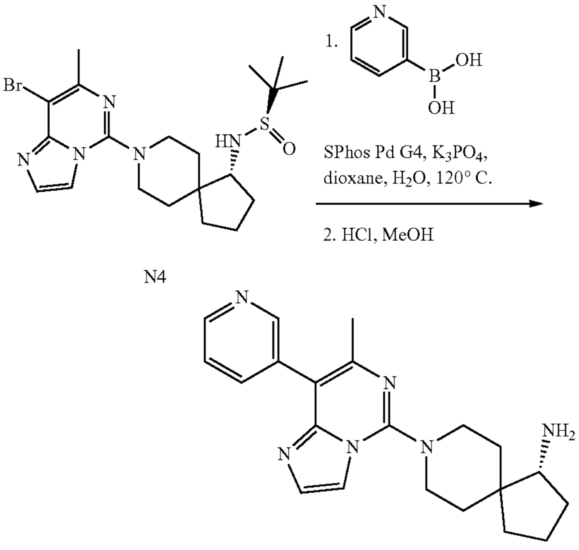

Example 22

Example 22: A solution of Compound N4 (57 mg, 0.12 mmol), pyridin-3-ylboronic acid (45 mg, 0.37 mmol), SPhos Pd G4 (19 mg, 0.024 mmol), potassium phosphate tribasic (103 mg, 0.49 mmol) were added to 1,4-dioxane (2 mL) and water (2 mL). The reaction mixture was heated to 120° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 22. $^1$H NMR (400 MHz, Methanol-$d_4$) δ 8.88-8.77 (m, 2H), 8.21 (dt, J=7.9, 1.9 Hz, 1H), 8.00 (d, J=2.3 Hz, 1H), 7.92-7.82 (m, 2H), 4.15-4.01 (m, 2H), 3.51-3.33 (m, 3H), 2.42 (s, 3H), 2.36-2.23 (m, OH), 2.28 (s, 1H), 2.08-1.79 (m, 5H), 1.82-1.64 (m, 2H). LCMS ESI$^+$ calc'd for $C_{21}H_{26}N_6$: 363.2 [M+H$^+$]. found: 363.2 [M+H$^+$].

Example 23: (R)-8-(8-(3-chlorophenyl)-7-methylimidazo[1,2-c]pyrimidin-5-yl)-8-azaspiro[4.5]decan-1-amine

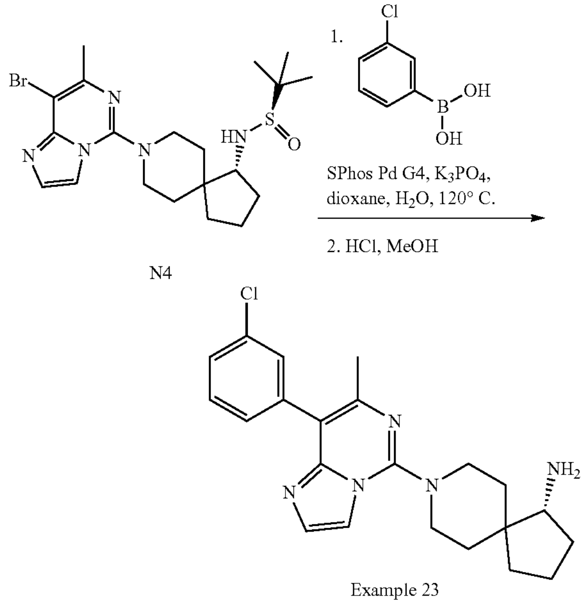

N4

Example 23

Example 23: A solution of Compound N4 (58 mg, 0.12 mmol), (3-chlorophenyl)boronic acid (58 mg, 0.37 mmol), SPhos Pd G4 (20 mg, 0.024 mmol), potassium phosphate tribasic (105 mg, 0.49 mmol) were added to 1,4-dioxane (2 mL) and water (2 mL). The reaction mixture was heated to 120° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 23. $^1$H NMR (400 MHz, Methanol-d4) δ 7.99 (d, J=2.4 Hz, 1H), 7.88 (d, J=2.3 Hz, 1H), 7.67-7.59 (m, 2H), 7.55 (q, J=1.4 Hz, 1H), 7.46-7.34 (m, 1H), 4.03 (dd, J=22.6, 13.9 Hz, 2H), 3.43 (t, J=12.1 Hz, 2H), 3.36 (t, J=6.5 Hz, 1H), 2.41 (s, 3H), 2.36-2.21 (m, 1H), 2.07-1.76 (m, 7H), 1.70 (t, J=13.3 Hz, 2H). LCMS ESI$^+$ calc'd for $C_{22}H_{26}ClN_5$: 396.1 [M+H$^+$]. found: 396.2 [M+H$^+$].

Example 24: (R)-8-(7-methyl-8-(2-(trifluoromethyl)pyridin-4-yl)imidazo[1,2-c]pyrimidin-5-yl)-8-azaspiro[4.5]decan-1-amine

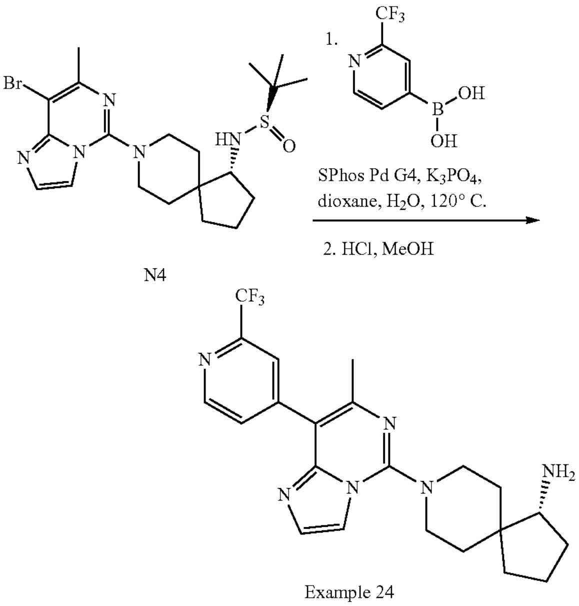

N4

Example 24

Example 24: A solution of Compound N4 (50 mg, 0.11 mmol), (2-(trifluoromethyl)pyridin-4-yl)boronic acid (61 mg, 0.32 mmol), SPhos Pd G4 (17 mg, 0.02 mmol), potassium phosphate tribasic (91 mg, 0.43 mmol) were added to 1,4-dioxane (2 mL) and water (2 mL). The reaction mixture was heated to 120° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 24. $^1$H NMR (400 MHz, Methanol-$d_4$) δ 8.97 (d, J=5.0 Hz, 1H), 8.01 (d, J=2.1 Hz, 2H), 7.90 (d, J=2.3 Hz, 1H), 7.81 (dd, J=4.9, 1.5 Hz, 1H), 4.17-3.97 (m, 2H), 3.46 (dd, J=13.8, 11.5 Hz, 2H), 3.36 (t, J=6.5 Hz, 1H), 2.43 (s, 3H), 2.28 (ddd, J=13.1, 7.5, 4.4 Hz, 1H), 2.10-1.76 (m, 7H), 1.70 (t, J=13.8 Hz, 2H). $^{19}$F NMR (376 MHz, Methanol-$d_4$) δ −70.03 (s, 3F), −77.80 (s, 6F). LCMS ESI$^+$ calc'd for $C_{22}H_{25}F_3N_6$: 431.2 [M+H$^+$]. found: 431.2 [M+H$^+$].

Example 25: (R)-8-(8-(3,4-dichlorophenyl)-7-methylimidazo[1,2-c]pyrimidin-5-yl)-8-azaspiro[4.5]decan-1-amine

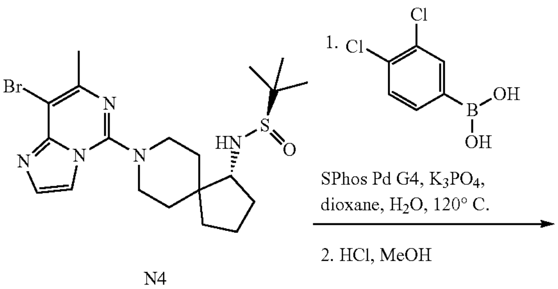

N4

-continued

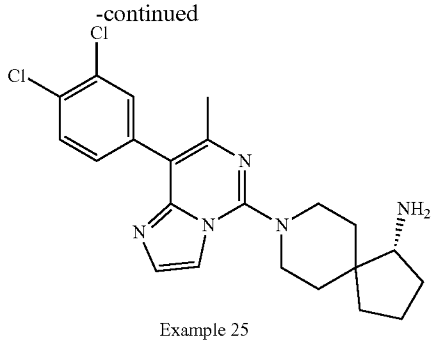

Example 25

Example 25: A solution of Compound N4 (58 mg, 0.12 mmol), (3,4-dichlorophenyl)boronic acid (71 mg, 0.37 mmol), SPhos Pd G4 (20 mg, 0.024 mmol), potassium phosphate tribasic (105 mg, 0.49 mmol) were added to 1,4-dioxane (2 mL) and water (2 mL). The reaction mixture was heated to 120° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 25. $^1$H NMR (400 MHz, Methanol-$d_4$) δ 7.96 (d, J=2.3 Hz, 1H), 7.86 (d, J=2.3 Hz, 1H), 7.79 (d, J=8.3 Hz, 1H), 7.70 (d, J=2.0 Hz, 1H), 7.42 (dd, J=8.2, 2.1 Hz, 1H), 4.14-3.90 (m, 2H), 3.53-3.34 (m, 3H), 2.41 (s, 3H), 2.35-2.21 (m, 1H), 2.07-1.74 (m, 7H), 1.69 (t, J=13.2 Hz, 2H). LCMS ESI$^+$ calc'd for $C_{22}H_{25}Cl_2N_5$: 430.1 [M+H$^+$]. found: 430.1 [M+H$^+$].

Example 26: (R)-8-(8-(2,4-dichlorophenyl)-7-methylimidazo[1,2-c]pyrimidin-5-yl)-8-azaspiro[4.5]decan-1-amine

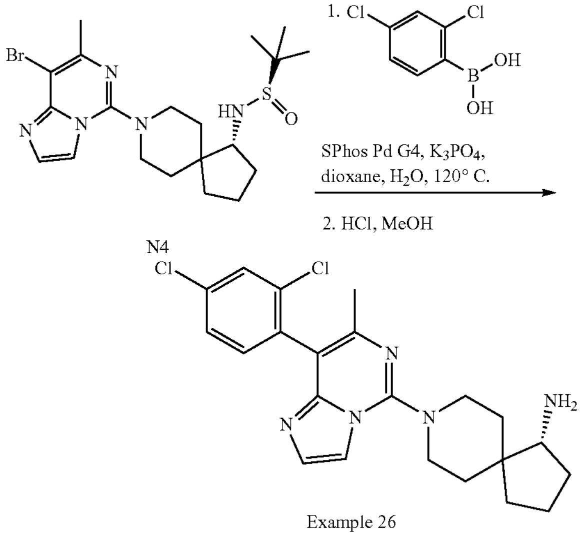

Example 26

Example 26: A solution of Compound N4 (65 mg, 0.14 mmol), (2,4-dichlorophenyl)boronic acid (80 mg, 0.42 mmol), SPhos Pd G4 (22 mg, 0.028 mmol), potassium phosphate tribasic (119 mg, 0.56 mmol) were added to 1,4-dioxane (2 mL) and water (2 mL). The reaction mixture was heated to 120° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 26. $^1$H NMR (400 MHz, Methanol-$d_4$) € 8.00 (d, J=2.4 Hz, 1H), 7.89 (d, J=2.3 Hz, 1H), 7.81 (d, J=2.1 Hz, 1H), 7.60 (dd, J=8.3, 2.1 Hz, 1H), 7.48 (d, J=8.3 Hz, 1H), 4.09 (dd, J=22.5, 13.9 Hz, 2H), 3.45 (t, J=12.8 Hz, 2H), 3.37 (d, J=6.7 Hz, 1H), 2.34 (s, 3H), 2.31-2.22 (m, 1H), 2.09-1.76 (m, 7H), 1.70 (t, J=14.6 Hz, 2H). LCMS ESI$^+$ calc'd for $C_{22}H_{25}Cl_2N_5$: 430.1 [M+H$^+$]. found: 430.2 [M+H$^+$].

Example 27: (R)-8-(8-(4-amino-2,3-dichlorophenyl)-7-methylimidazo[1,2-c]pyrimidin-5-yl)-8-azaspiro[4.5]decan-1-amine

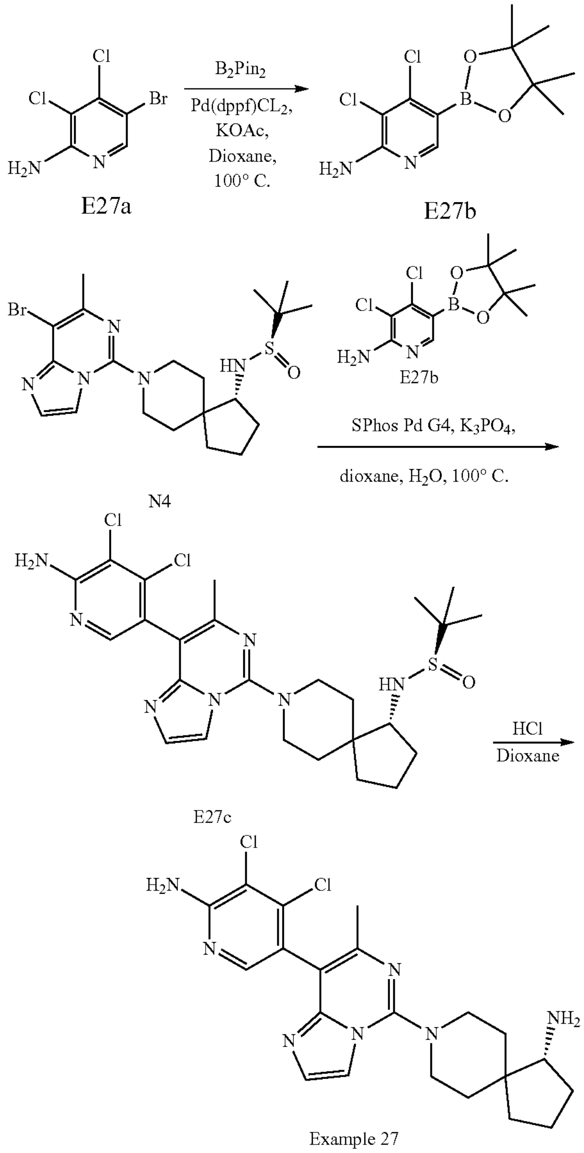

Example 27

Compound E27b: Compound E27a (2.00 g, 8.27 mmol), Pd(dppf)$Cl_2$ DCM complex (0.308 g, 0.413 mmol), bis (pinacolato)diboron (4.20 g, 16.5 mmol), and potassium acetate (2.43 g, 24.8 mmol) were dissolved in 1,4-dioxane (20 mL). The reaction vessel was purged with argon and heated to 100° C. for 16 hours. The mixture was diluted with EtOAc and washed with water, dried over magnesium sulfate, filtered through Celite, and concentrated in vacuo. The residue was purified by column chromatography (0-100% EtOAc in Hexanes). This provided Compound E27b. LCMS $ESI^+$ calc'd for $C_{11}H_{15}BCl_2N_2O$: 289.0 [M+$H^+$]. found: 289.1 [M+$H^+$].

Compound E27c: A solution of Compound N4 (0.080 g, 0.16 mmol), Compound E27b (0.095 g, 0.329 mmol), SPhos Pd G4 (1.3 mg, 0.002 mmol), potassium phosphate tribasic (0.140 g, 0.659 mmol) were added to 1,4-dioxane (2 mL) and water (0.2 mL). The reaction vessel was purged with argon and heated to 100° C. for 60 min. The mixture was diluted with EtOAc and washed with water, dried over magnesium sulfate, filtered through Celite, and concentrated in vacuo. The residue was reconstituted in toluene and purified by column chromatography (0-20% MeOH in DCM). This provided Compound E27c. LCMS $ESI^+$ calc'd for $C_{25}H_{33}Cl_2N_7OS$: 550.2 [M+$H^+$]. found: 550.1 [M+$H^+$].

Example 27: Compound E27c (0.100 g, 0.256 mmol) was dissolved in DCM (5 mL), and 4N HCl in 1,4 dioxane (1 mL). The resulting suspension was stirred for 30 min. The solution was concentrated and reconstituted in water and DMF and the purified by preparatory HPLC (10-100% MeCN in water with 0.1% TFA, Gemini). This provided Example 27. $^1H$ NMR (400 MHz, DMSO-$d_6$) δ 8.04-7.74 (m, 6H), 6.94 (s, 2H), 3.86 (dt, J=17.5 Hz, 2H), 3.28 (m, 3H), 2.23 (s, 3H), 2.07 (m, 1H), 1.68 (m, 9H). LCMS $ESI^+$ calc'd for $C_{21}H_{25}Cl_2N_7$: 446.1 [M+$H^+$]. found: 446.2 [M+$H^+$].

Example 28: (R)-8-(8-(3-chloro-2-fluoropyridin-4-yl)-7-methylimidazo[1,2-c]pyrimidin-5-yl)-8-azaspiro[4.5]decan-1-amine

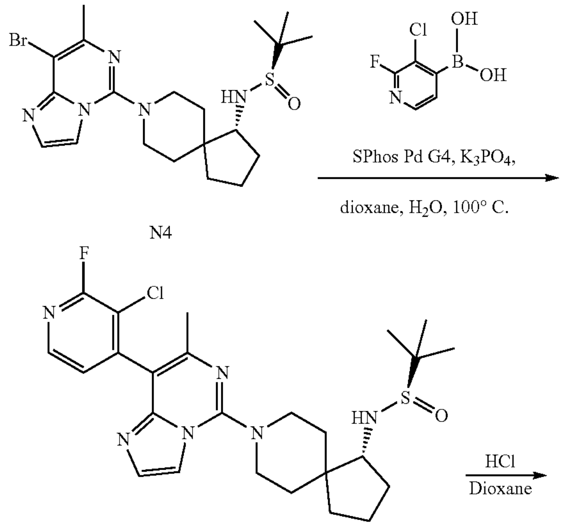

N4

E28a

-continued

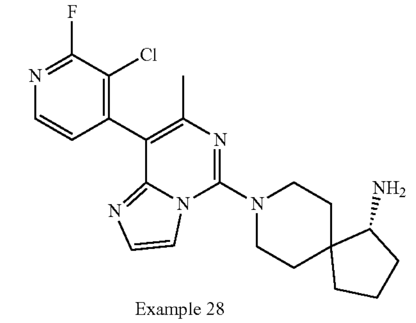

Example 28

Compound E28a: A solution of Compound N4 (0.310 g, 0.662 mmol), (3-chloro-2-fluoropyridin-4-yl)boronic acid (0.128 g, 0.728 mmol), SPhos Pd G4 (0.105 g, 0.132 mmol), potassium phosphate tribasic (0.562 g, 2.65 mmol) were added to 1,4-dioxane (4 mL) and water (4 mL). The reaction vessel was purged with argon and heated to 100° C. for 60 min. The mixture was diluted with EtOAc and washed with water, dried over magnesium sulfate, filtered through Celite, and concentrated in vacuo. The residue was reconstituted in toluene and purified by column chromatography (0-20% MeOH in DCM). This provided Compound E28a. LCMS $ESI^+$ calc'd for $C_{25}H_{32}ClFN_6OS$: 519.2 [M+$H^+$]. found: 519.1 [M+$H^+$].

Example 28: Compound E28a (0.072 g, 0.139 mmol) was dissolved in DCM (5 mL), and 4N HCl in 1,4 dioxane (1 mL). The resulting suspension was stirred for 30 min. The solution was concentrated and reconstituted in water and DMF and purified by preparatory HPLC (10-100% MeCN in water with 0.1% TFA, Gemini). This provided Example 28 as TFA salt. $^1H$ NMR (400 MHz, DMSO-$d_6$) δ 8.32 (d, J=5.0 Hz, 1H), 7.98-7.77 (m, 4H), 7.73 (s, 1H), 7.47 (dd, J=5.0, 2.3 Hz, 1H), 3.84 (d, J=15.1 Hz, 2H), 3.25 (d, J=10.4 Hz, 4H), 2.19 (s, 3H), 2.15-1.98 (m, 1H), 1.93-1.42 (m, 9H). $^{19}F$ NMR (376 MHz, DMSO-$d_6$) δ −71.56, −74.91. LCMS $ESI^+$ calc'd for $C_{21}H_{24}ClFN_6$: 415.2 [M+$H^+$]. found: 415.2 [M+$H^+$].

Example 29: (R)-8-(8-(2-amino-3-chloropyridin-4-yl)-7-methylimidazo[1,2-c]pyrimidin-5-yl)-8-azaspiro[4.5]decan-1-amine

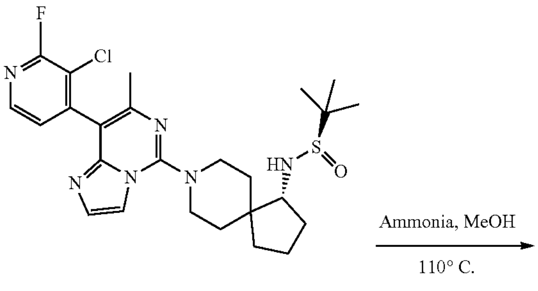

E28a

-continued

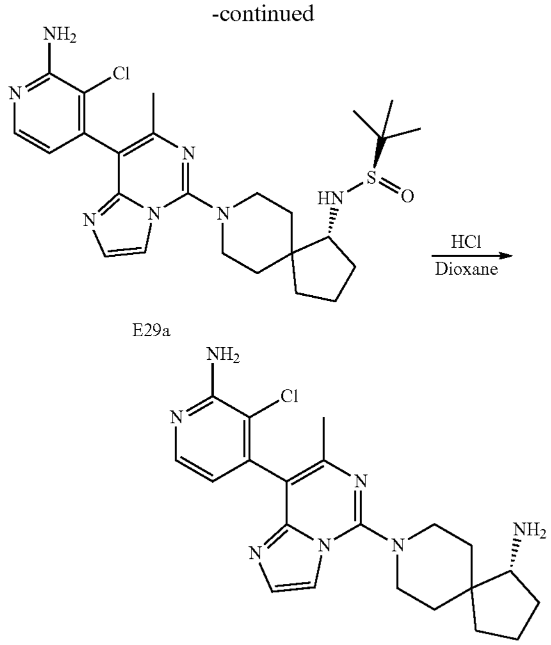

E29a

Example 29

Compound E29a: A solution of Compound E28a (0.310, 0.662 mmol), was dissolved in 7N Ammonia in MeOH sealed in a microwave vial and heated to 110° C. for 72 h. The solvent was removed in vacuo to afford Compound E29a. The material was carried forward without further purification. LCMS ESI+ calc'd for $C_{25}H_{34}ClN_7OS$: 516.2 [M+H+]. found: 516.1 [M+H+].

Example 29: All of the material from the previous step, Compound E29a, was dissolved in DCM (5 mL), and 4N HCl in 1,4 dioxane (1 mL). The resulting suspension was stirred for 30 min. The solution was concentrated and reconstituted in water and DMF and purified by preparatory HPLC (10-100% MeCN in water with 0.1% TFA, Gemini). This provided Example 29. $^1$H NMR (400 MHz, DMSO-$d_6$) δ 8.01 (d, J=5.2 Hz, 1H), 7.83 (s, 5H), 6.59 (dd, J=5.1, 2.2 Hz, 1H), 3.25 (s, 3H), 2.19 (s, 3H), 2.15-2.00 (m, 1H), 1.92-1.43 (m, 9H). LCMS ESI+ calc'd for $C_{21}H_{26}ClN_7$: 412.2 [M+H+]; found: 412.3 [M+H+].

Example 30: (R)-8-(8-(3-chloro-2-fluoropyridin-4-yl)-7-methylimidazo[1,2-c]pyrimidin-5-yl)-8-azaspiro[4.5]decan-1-amine Compound E30b: Compound E30a (1.00 g, 4.15 mmol), Pd(dppf)$Cl_2$ DCM complex (0.310 g, 0.415 mmol), bis (pinacolato)diboron (3.162 g, 12.5 mmol), and potassium acetate (1.22 g, 12.5 mmol) were dissolved in 1,4-dioxane (20 mL). The reaction vessel was purged with argon and heated to 100° C. for 16 hours. The mixture was diluted with EtOAc and washed with water, dried over magnesium sulfate, filtered through Celite, and concentrated in vacuo. The residue was purified by column chromatography (0-100% EtOAc in Hexanes). This provided Compound E30b. LCMS ESI+ calc'd for $C_{12}H_{16}BCl_2NO_2$ 288.1: [M+H+]. found: 288.1 [M+H+].

Compound E30c: A solution of Compound N4 (75 mg, 0.16 mmol), Compound E30b (92 mg, 0.32 mmol), SPhos Pd G4 (25 mg, 0.032 mmol), potassium phosphate tribasic (0.136 g, 0.640 mmol) were added to 1,4-dioxane (4 mL) and water (4 mL). The reaction vessel was purged with argon and heated to 100° C. for 60 min. The mixture was diluted with EtOAc and washed with water, dried over magnesium sulfate, filtered through Celite, and concentrated in vacuo. The residue was reconstituted in toluene and purified by column chromatography (0-20% MeOH in DCM). This provided Compound E30c. LCMS ESI+ calc'd for $C_{26}H_{34}Cl_2N_6OS$: 549.2 [M+H+]. found: 549.1 [M+H+].

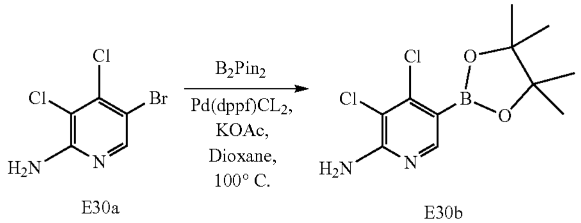

E30a E30b

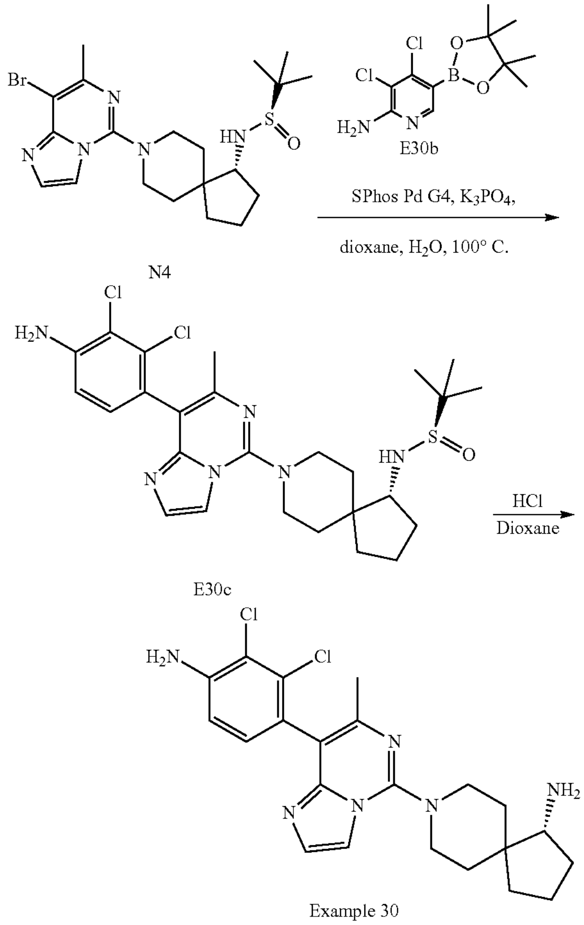

N4 E30b E30c

Example 30

Example 30: Compound E30c (12.6 mg, 0.028 mmol) was dissolved in DCM (5 ml), and 4N HCl in 1,4 dioxane (1 ml). The resulting suspension was stirred for 30 min. The solution was concentrated and reconstituted in water and DMF and purified by preparatory HPLC (10-100% MeCN in water with 0.1% TFA, Gemini). This provided Example 30. $^1$H NMR (400 MHz, DMSO-$d_6$) δ 7.86 (m, 5H), 7.02 (dd, J=8.4, 1.9 Hz, 1H), 6.87 (d, J=8.4 Hz, 1H), 3.83 (t, J=17.2 Hz, 4H), 3.27 (t, J=12.0 Hz, 4H), 2.18 (s, 3H), 2.14-2.00 (m, 1H), 1.93-1.42 (m, 10H). LCMS ESI+ calc'd for $C_{22}H_{26}Cl_2N_6$: 445.2 [M+H+]. found: 445.2 [M+H+].

Example 31: (3S,4S)-8-(8-((2-amino-3-chloropyridin-4-yl)thio)imidazo[1,2-c]pyrimidin-5-yl)-3-methyl-2-oxa-8-azaspiro[4.5]decan-4-amine

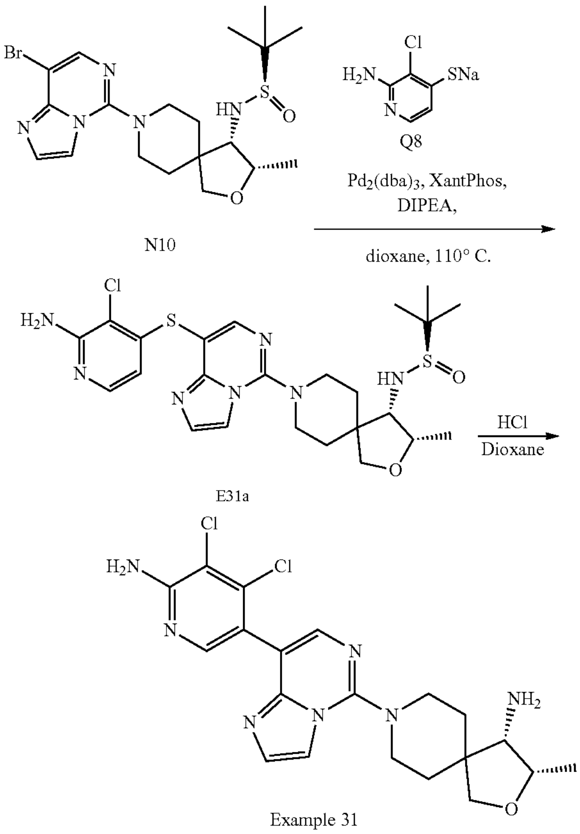

Compound E31a: Compound N10 (200 mg, 0.425 mmol) in 1,4-dioxane (5 mL) was added $Pd_2(dba)_3$ (77.6 mg, 0.085 mmol), XantPhos (98.4 mg, 0.170 mmol), Compound Q8 (116.5 mg, 0.638 mmol), and DIPEA (0.222 mL, 1.28 mmol). The reaction vessel was purged with argon, sealed, and heated to 110° C. until complete consumption of starting materials. The reaction mixture was cooled to room temperature, diluted with EtOAc and washed with water followed by brine. The organic partition was dried over magnesium sulfate, and filtered through Celite. The resulting solution was concentrated and purified by column chromatography (0-100% EtOAc in Hexanes). This provided Compound E31a. LCMS $ESI^+$ calc'd for $C_{24}H_{32}ClN_7O_2S_2$: 551.2 [$M+H^+$]. found: 551.1 [$M+H^+$].

Example 31: Compound E31a (115 mg, 0.260 mmol) was dissolved in DCM (10 mL), and 4N HCl in 1,4 dioxane (2 mL). The resulting suspension was stirred for 30 min. The solution was concentrated and reconstituted in water and DMF and purified by preparatory HPLC (10-100% MeCN in water with 0.1% TFA, Gemini). This provided Example 31. $^1H$ NMR (400 MHz, DMSO-$d_6$) δ 7.86 (m, 5H), 7.02 (dd, J=8.4, 1.9 Hz, 1H), 6.87 (d, J=8.4 Hz, 1H), 3.83 (t, J=17.2 Hz, 4H), 3.27 (t, J=12.0 Hz, 4H), 2.18 (s, 3H), 2.14-2.00 (m, 1H), 1.93-1.42 (m, 10H). LCMS $ESI^+$ calc'd for $C_{20}H_{24}ClN_7OS$: 446.2 [$M+H^+$]. found: 446.2 [$M+H^+$].

Example 32: (R)-8-(8-(3-chloro-2-fluoropyridin-4-yl)-7-methylimidazo[1,2-c]pyrimidin-5-yl)-8-azaspiro[4.5]decan-1-amine

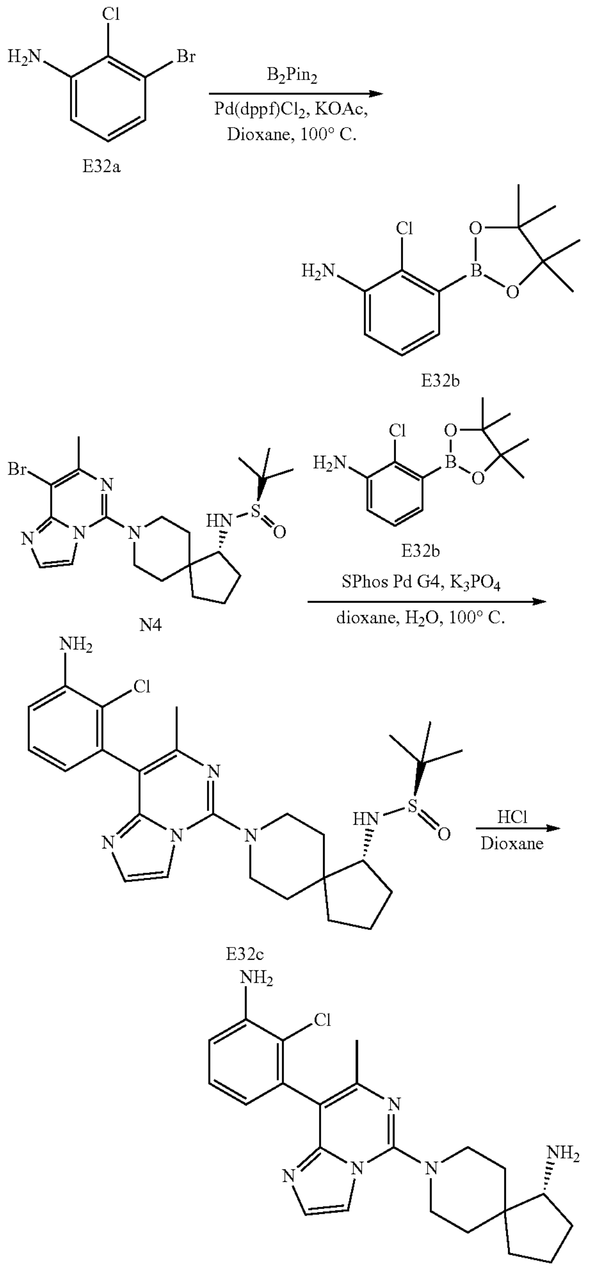

Compound E32b: Compound E32a (1.00 g, 4.84 mmol), $Pd(dppf)Cl_2$ DCM complex (0.361 g, 0.484 mmol), bis (pinacolato)diboron (3.70 g, 14.5 mmol), and potassium acetate (1.43 g, 14.5 mmol) were dissolved in 1,4-dioxane (20 mL). The reaction vessel was purged with argon and heated to 100° C. for 16 hours. The mixture was diluted with EtOAc and washed with water, dried over magnesium sulfate, filtered through Celite, and concentrated in vacuo. The residue was purified by column chromatography (0-100% EtOAc in Hexanes). This provided Compound E32b. LCMS ESI+ calc'd for $C_{12}H_{17}BClNO_2$: 254.1 [M+H+]. found: 254.1 [M+H+].

Compound E32c: A solution of Compound N4 (130 mg, 0.278 mmol), Compound E32b (141 mg, 0.555 mmol), SPhos Pd G4 (44 mg, 0.055 mmol), potassium phosphate tribasic (0.237 g, 1.11 mmol) were added to 1,4-dioxane (4 mL) and water (4 mL). The reaction vessel was purged with argon and heated to 100° C. for 60 min. The mixture was diluted with EtOAc and washed with water, dried over magnesium sulfate, filtered through Celite, and concentrated in vacuo. The residue was reconstituted in toluene and purified by column chromatography (0-20% MeOH in DCM). This provided Compound E32c. LCMS ESI+ calc'd for $C_{26}H_{35}ClN_6OS$: 515.2 [M+H+]. found: 515.1 [M+H+].

Example 32: Compound E32c (12.6 mg, 0.028 mmol) was dissolved in DCM (5 mL), and 4N HCl in 1,4 dioxane (1 mL). The resulting suspension was stirred for 30 min. The solution was concentrated and reconstituted in water and DMF and purified by preparatory HPLC (10-100% MeCN in water with 0.1% TFA, Gemini). This provided Example 32. $^1$H NMR (400 MHz, DMSO-$d_6$) δ 8.17-7.92 (m, 5H), 7.18 (t, J=7.8 Hz, 1H), 6.95 (dd, J=8.2, 1.5 Hz, 1H), 6.56 (dt, J=7.4, 1.6 Hz, 1H), 3.81 (m, 1H), 3.28 (dd, J=27.0, 15.8 Hz, 3H), 2.20 (s, 3H), 2.14-1.98 (m, 1H), 1.97-1.36 (m, 10H). LCMS ESI+ calc'd for $C_{22}H_{27}ClN_6$: 411.2 [M+H+]. found: 411.2 [M+H+].

Example 33: (2R,4R)-4-amino-8-(8-(2,3-dichlorophenyl)-7-methylimidazo[1,2-c]pyrimidin-5-yl)-8-azaspiro[4.5]decan-2-ol

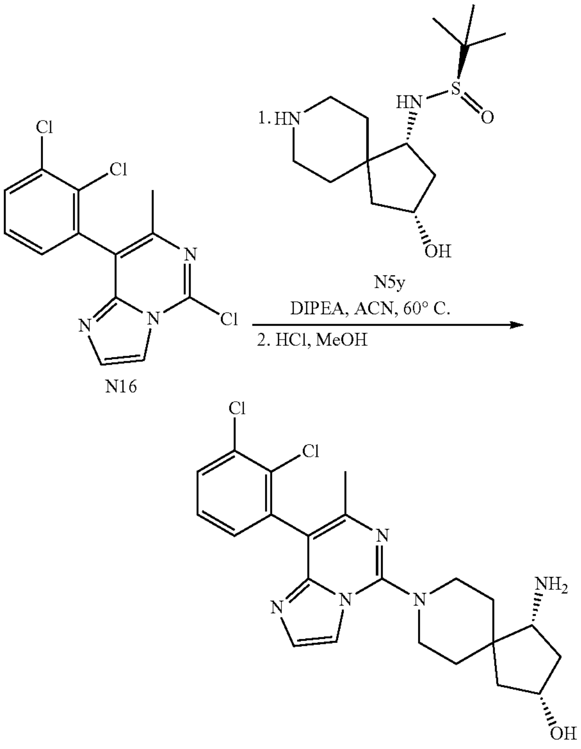

N16

Example 33

Example 33: To a solution of Compound N16 (39 mg, 0.1 mmol) and Compound N5y (116 mg, 0.3 mmol) in ACN (3 mL) was added DIPEA (0.1 mL). The reaction mixture was heated at 60° C. for 1 h, the mixture was diluted with EtOAc, washed with brine, the organic solvent was concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 33. $^1$H NMR (400 MHz, Methanol-$d_4$) δ 8.03 (d, J=2.3 Hz, 1H), 7.91 (d, J=2.3 Hz, 1H), 7.82 (dd, J=8.1, 1.5 Hz, 1H), 7.55 (q, J=9.0, 8.5 Hz, 1H), 7.45 (dd, J=7.7, 1.6 Hz, 1H), 4.48 (dd, J=6.0, 3.0 Hz, 1H), 4.18 (d, J=13.7 Hz, 1H), 4.07 (d, J=13.7 Hz, 1H), 3.42 (td, J=13.3, 12.0, 8.0 Hz, 3H), 2.51-2.38 (m, 1H), 2.34 (s, 3H), 2.24-2.13 (m, 1H), 1.99 (ddd, J=34.0, 12.6, 4.1 Hz, 5H), 1.68 (d, J=12.6 Hz, 1H). LCMS ESI+ calc'd for $C_{22}H_{25}Cl_2N_5O$: 446.1 [M+H+]. found: 446.2 [M+H+].

Example 34: (2S,4R)-4-amino-8-(8-(2,3-dichlorophenyl)-7-methylimidazo[1,2-c]pyrimidin-5-yl)-8-azaspiro[4.5]decan-2-ol

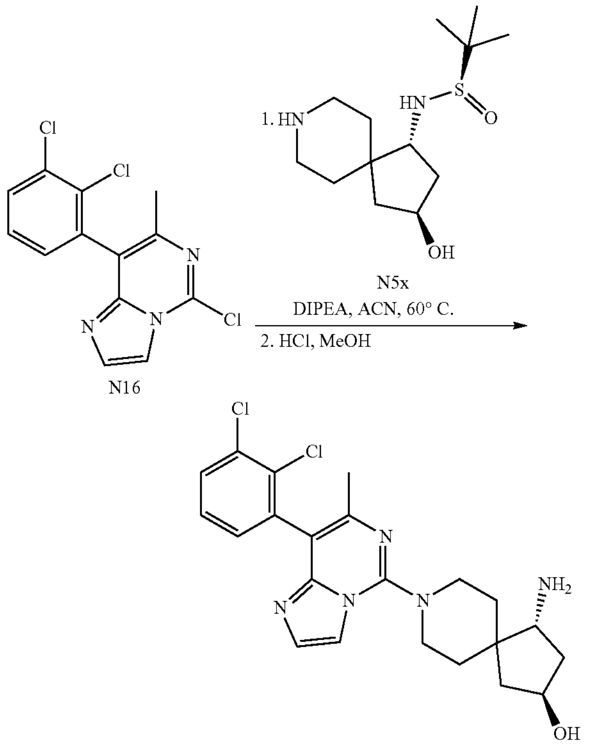

N16

Example 34

Example 34: (2R,4R)-4-amino-8-(8-(2,3-dichlorophenyl)-7-methylimidazo[1,2-c]pyrimidin-5-yl)-8-azaspiro[4.5]decan-2-ol: To a solution of Compound N16 (39 mg, 0.1 mmol) and Compound N5x (116 mg, 0.3 mmol) in ACN (3 mL) was added DIPEA (0.1 mL). The reaction mixture was heated at 60° C. for 1 h, the mixture was diluted with EtOAc, washed with brine, the organic solvent was concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 34. $^1$H NMR (400 MHz, Methanol-$d_4$) δ

7.98 (d, J=2.2 Hz, 1H), 7.86 (d, J=2.2 Hz, 1H), 7.83-7.75 (m, 1H), 7.62-7.48 (m, 1H), 7.47-7.37 (m, 1H), 4.48 (dq, J=5.9, 2.9 Hz, 1H), 4.14 (t, J=14.4 Hz, 2H), 3.59 (dd, J=9.1, 7.1 Hz, 1H), 3.45-3.35 (m, 1H), 2.33 (s, 3H), 2.29-1.58 (m, 8H). LCMS ESI$^+$ calc'd for $C_{22}H_{25}Cl_2N_5O$: 446.1 [M+H$^+$]. found: 446.2 [M+H$^+$].

Example 35: (2R,4R)-4-amino-8-(8-((2,3-dichlorophenyl)thio)imidazo[1,2-c]pyrimidin-5-yl)-8-azaspiro[4.5]decan-2-ol

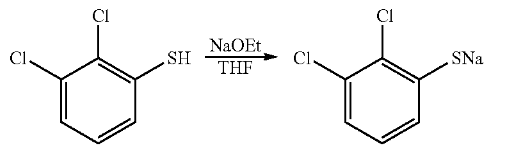

E35a

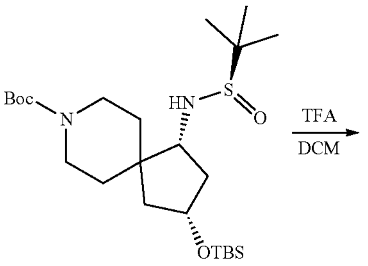

Q6

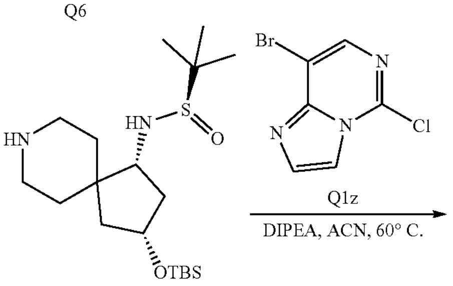

E35b

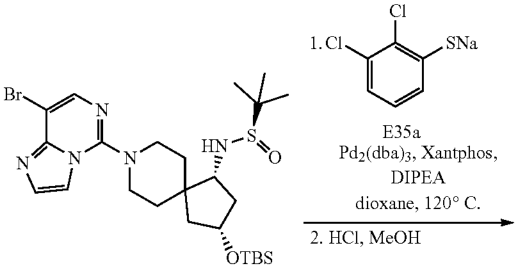

E35c

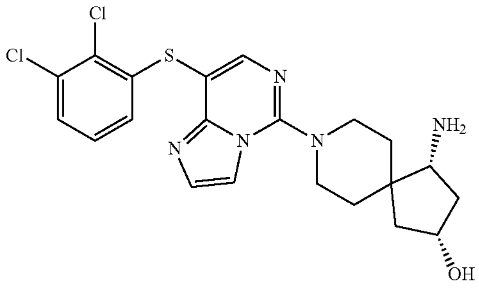

Example 35

Compound E35a: To a solution of 2,3-dichlorobenzenethiol (4 g, 22.34 mmol) in THF (20.0 mL) was added NaOEt (21% wt in EtOH, 8.4 mL), then the reaction was stirred at RT for 20 min. DCM (20 mL) was the added to reaction mixture, followed by addition of MTBE (30 mL) and hexane (60 mL). The precipitate was then filtered, rinsed with hexane and dried on high vacuum to afford Compound E35a. LCMS ESI$^+$ calc'd for $C_6H_3Cl_2NaS$: 176.9 [M−Na]. found: 176.7.

Compound E35b: To a solution of Compound Q6 (527 mg, 0.41 mmol) in DCM (3.0 mL) was added TFA (0.5 mL), then the reaction was stirred at RT for 20 min. The solvent was then evaporated to afford crude product Compound 35b. LCMS ESI$^+$ calc'd for $C_{19}H_{40}N_2O_2SSi$: 389.3 [M+H$^+$]. found: 389.4 [M+H$^+$].

Compound E35c: To a solution of Compound E35b (0.41 g, 1.03 mmol)) and Compound Q1z (0.24 g, 1.03 mmol) in ACN (3 mL) was added DIPEA (1.1 mL). The reaction mixture was heated at 60° C. for 1 h, the mixture was diluted with EtOAc, washed with brine, the organic solvent was concentrated in vacuo, and then purified with Combi-Flash column to afford Compound E35c. LCMS ESI$^+$ calc'd for $C_{25}H_{42}BrN_5O_2SSi$: 584.2 [M+H$^+$]. found: 584.0 [M+H$^+$].

Example 35: To a solution of Compound E35c (74 mg, 0.09 mmol) and sodium 2,3-dichlorobenzenethiolate (39 mg, 0.19 mmol) in dioane (2 mL) was added $Pd_2(dba)_3$ (16 mg, 0.018 mmol), Xantphos (21 mg, 0.035 mmol) and DIPEA (0.08 mL). The reaction mixture was heated at 120° C. for 1 h, the mixture was diluted with EtOAc, washed with brine, and the organic solvent was concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 35. $^1$H NMR (400 MHz, Methanol-d$_4$) δ 8.30 (s, 1H), 8.00 (d, J=2.0 Hz, 1H), 7.81 (d, J=2.0 Hz, 1H), 7.38 (dd, J=8.0, 1.3 Hz, 1H), 7.10 (t, J=8.1 Hz, 1H), 6.78 (dd, J=8.1, 1.3 Hz, 1H), 4.48 (tt, J=6.1, 3.1 Hz, 1H), 4.22 (d, J=13.6 Hz, 1H), 4.12 (d, J=13.9 Hz, 1H), 3.53-3.36 (m, 3H), 2.50-2.36 (m, 1H), 2.18 (dd, J=14.3, 6.2 Hz, 1H), 2.10-1.80 (m, 5H), 1.68 (d, J=12.4 Hz, 1H). LCMS ESI$^+$ calc'd for $C_{21}H_{23}Cl_2N_5OS$: 464.4 [M+H$^+$]. found: 464.2 [M+H$^+$].

Example 36: 1-(8-((2,3-dichlorophenyl)thio)imidazo[1,2-c]pyrimidin-5-yl)azepan-4-amine

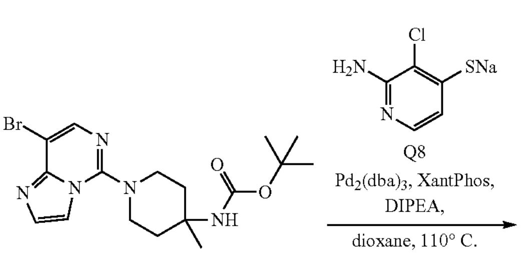

N15

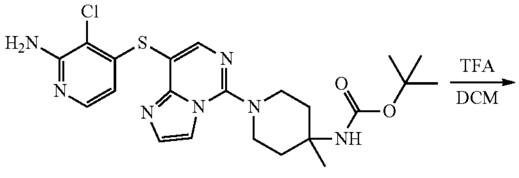

E36a

-continued

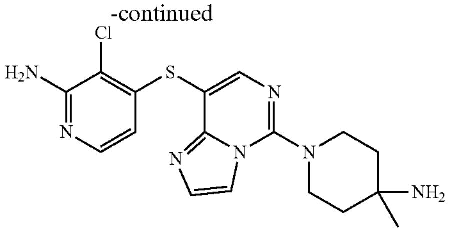

Example 36

Compound E36a: To a solution of Compound N15 (0.106 g, 0.15 mmol) in 1,4-dioxane (2 ml) was added $Pd_2(dba)_3$ (11 mg, 0.012 mmol), XantPhos (13 mg, 0.024 mmol), Compound Q8 (74 mg, 0.29 mmol), and DIPEA (0.123 mL, 0.705 mmol). The reaction vessel was purged with argon, sealed, and heated to 110° C. until complete consumption of starting materials. The reaction was cooled to 23° C. and directly purified on a C18 column via reversed-phase HPLC (0.1% TFA in $H_2O$/CH3CN with gradient elution 95:5 to 0:100) giving the desired Compound E36a product after lyophilization. LCMS ESI$^+$ calc'd for $C_{22}H_{28}ClN_7O_2S$: 490.1 [M+H$^+$]. found: 490.1 [M+H$^+$].

Example 36: The above Compound E36a, (54 mg, 0.11 mmol) was dissolved in 3 mL DCM and 3 mL TFA was added. The reaction was stirred for 3 h at which time volatiles were removed and the resulting solid product rinsed with diethyl ether to obtain Example 36. $^1$H NMR (400 MHz, methanol-d$_4$) δ 8.17 (s, 1H), 7.90 (d, J=1.7 Hz, 1H), 7.64 (d, J=1.7 Hz, 1H), 7.49 (d, J=6.8 Hz, 1H), 6.21 (d, J=6.8 Hz, 1H), 4.02 (d, J=14.0 Hz, 2H), 3.62-3.51 (m, 2H), 2.14-1.96 (m, 4H), 1.55 (s, 3H). LCMS ESI$^+$ calc'd for $C_{17}H_{20}ClN_7S$: 390.1 [M+H$^+$]. found: 390.1 [M+H$^+$].

Example 37: (3S,4S)-8-(8-((6-amino-2-(trifluoromethyl)pyridin-3-yl)thio)imidazo[1,2-c]pyrimidin-5-yl)-3-methyl-2-oxa-8-azaspiro[4.5]decan-4-amine

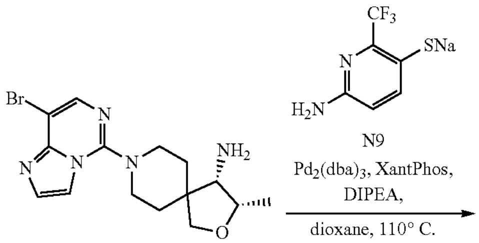

N12

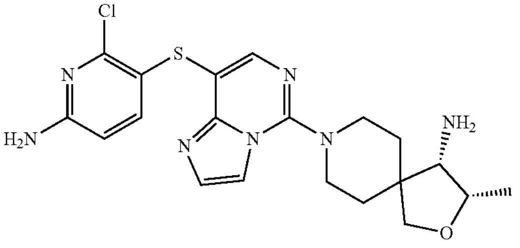

Example 37

Example 37: To a solution of Compound N12 (0.062 g, 0.15 mmol) in 1,4-dioxane (2 ml) was added $Pd_2(dba)_3$ (11 mg, 0.012 mmol), XantPhos (13 mg, 0.024 mmol), Compound N9 (63 mg, 0.29 mmol), and DIPEA (0.123 mL, 0.705 mmol). The reaction vessel was purged with argon, sealed, and heated to 110° C. until complete consumption of starting materials. The reaction was cooled to 23° C. and directly purified on a C18 column via reversed-phase HPLC (0.1% TFA in $H_2O$/CH3CN with gradient elution 95:5 to 0:100) giving the desired Example 37 after lyophilization. $^1$H NMR (400 MHz, Methanol-d$_4$) δ 7.92 (d, J=1.8 Hz, 1H), 7.86 (s, 1H), 7.74 (s, 1H), 7.61 (d, J=8.8 Hz, 1H), 6.66 (d, J=8.7 Hz, 1H), 4.41-4.16 (m, 2H), 4.11-3.80 (m, 5H), 3.72 (p, J=6.6 Hz, 2H), 3.48 (d, J=4.0 Hz, 2H), 3.28-3.14 (m, 2H), 2.17-1.86 (m, 4H), 1.78 (d, J=13.3 Hz, 2H), 1.50-1.22 (m, 7H). LCMS ESI$^+$ calc'd for $C_{21}H_{24}F_3N_4OS$: 480.2 [M+H$^+$]. found: 480.1 [M+H$^+$].

Example 38: (3S,4S)-8-(8-((2-amino-5-(trifluoromethyl)pyridin-4-yl)thio)imidazo[1,2-c]pyrimidin-5-yl)-3-methyl-2-oxa-8-azaspiro[4.5]decan-4-amine

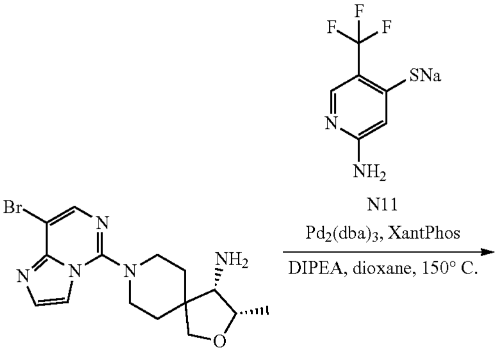

N12

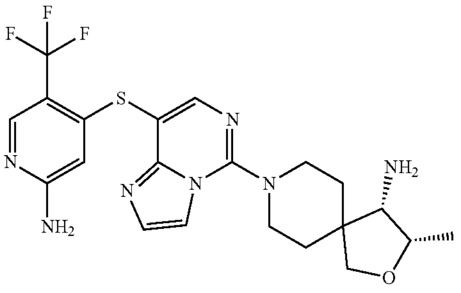

Example 38

Example 38: A solution of Compound N12 (0.180 g), Compound N11 (0.095 g), $Pd_2(dba)_3$ (0.081 g), and XantPhos (0.102 g) in 1,4-dioxane (10 mL) was added DIPEA (0.32) and heated in a microwave reactor to 150° C. for 1 h. The reaction filtered through Celite, rinsed with EtOAc, and the filtrate was concentrated in vacuo. The material was purified by preparatory HPLC (5-75% MeCN in water with 0.1% TFA, Gemini) to give Example 38. $^1$H NMR (400 MHz, DMSO-d$_6$) δ 8.24 (s, 1H), 8.14 (d, J=1.2 Hz, 1H), 8.01 (s, 3H), 7.92 (s, 1H), 7.70 (d, J=1.6 Hz, 1H), 5.98 (s, 1H), 4.30-4.20 (m, 1H), 4.02-3.88 (m, 3H), 3.74 (d, J=9.1 Hz, 1H), 3.54-3.44 (m, 1H), 3.37-3.24 (m, 2H), 2.04-1.91 (m, 2H), 1.83 (d, J=13.9 Hz, 1H), 1.71 (d, J=13.6 Hz, 1H), 1.24 (d, J=6.3 Hz, 4H). $^{19}$F NMR (376 MHz, DMSO-d$_6$) δ −59.09 (s, 3F), −75.22 (s, 6F). LCMS ESI$^+$ calc'd for $C_{21}H_{24}F_3N_7OS$: 480.2 [M+H$^+$]. found: 480.3 [M+H$^+$].

Example 39: (3S,4S)-8-(8-((2-amino-5-(trifluoromethyl)pyridin-4-yl)thio)imidazo[1,2-c]pyrimidin-5-yl)-3-methyl-2-oxa-8-azaspiro[4.5]decan-4-amine

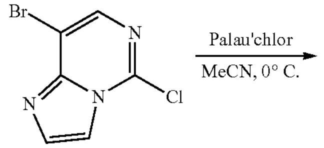

Q1z

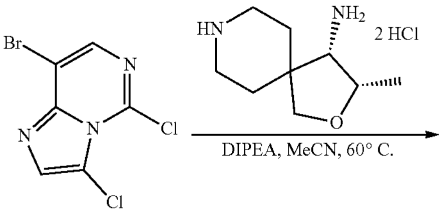

E39a

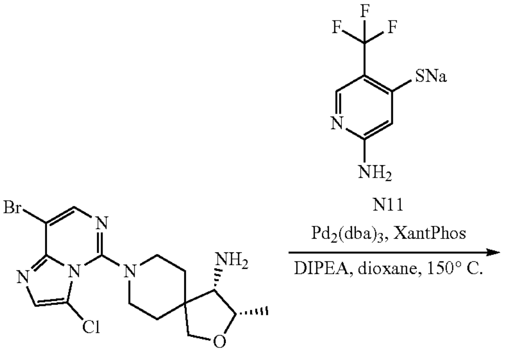

E39b

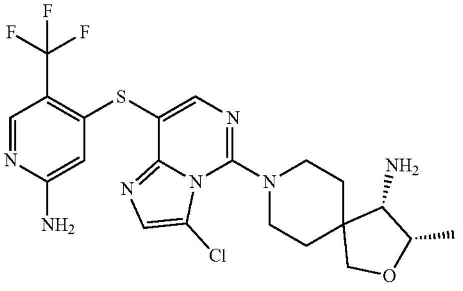

Example 39

Compound E39a: To Compound Q1z (0.250 g) in MeCN (2.2 mL) at 0° C. was added Palau'chlor (0.225 g). After 90 min, the reaction was concentrated in vacuo and purified by column chromatography (0-100% EtOAc in hexanes) to give Compound E39a. $^1$H NMR (400 MHz, DMSO-$d_6$) δ 8.16 (s, 1H), 7.90 (s, 1H). LCMS ESI$^+$ calc'd for $C_6H_2BrCl_2N_3$: 267.9 [M+H$^+$]. found: 268.0 [M+H$^+$].

Compound E39b: To Compound E39a (0.346 g) in MeCN (10 mL) was added (3S,4S)-3-methyl-2-oxa-8-azaspiro[4.5]decan-4-amine dihydrochloride (0.394 g) and DIPEA (1.4 mL), and heated to 60° C. After 90 min, the reaction was diluted with EtOAc, washed with brine, dried over sodium sulfate, and dried in vacuo to give Compound E39b. $^1$H NMR (400 MHz, DMSO-$d_6$) δ 7.94 (s, 1H), 7.72 (s, 1H), 4.07 (td, J=7.3, 6.8 Hz, 1H), 3.67 (d, J=8.4 Hz, 1H), 3.51 (d, J=9.0 Hz, 1H), 2.98 (d, J=4.9 Hz, 1H), 1.98-1.89 (m, 1H), 1.89-1.79 (m, 1H), 1.74-1.52 (m, 2H), 1.09 (d, J=6.1 Hz, 3H). LCMS ESI$^+$ calc'd for $C_{15}H_{19}BrClN_5O$: 402.0 [M+H$^+$]. found: 402.1 [M+H$^+$].

Example 39: A solution of Compound E39b (0.129 g), Compound N11 (0.069 g), $Pd_2(dba)_3$ (0.059 g), and Xant-Phos (0.074 g) in 1,4-dioxane (3.2 mL) was added DIPEA (0.22) and heated in a microwave reactor to 150° C. for 1 h. The reaction filtered through Celite, rinsed with EtOAc, and the filtrate was concentrated in vacuo. The material was purified by preparatory HPLC (5-75% MeCN in water with 0.1% TFA, Gemini) to give Example 39. $^1$H NMR (400 MHz, DMSO-$d_6$) δ 8.18 (s, 1H), 8.09 (s, 1H), 7.98 (s, 3H), 7.71 (s, 1H), 6.73 (s, 2H), 5.85 (s, 1H), 4.29-4.15 (m, 1H), 3.88 (d, J=9.1 Hz, 1H), 3.77-3.67 (m, 2H), 3.62 (d, J=13.2 Hz, 1H), 3.55-3.43 (m, 1H), 3.25-2.83 (m, 2H), 2.18-1.93 (m, 2H), 1.84 (d, J=13.4 Hz, 1H), 1.68 (d, J=13.2 Hz, 1H), 1.23 (d, J=6.5 Hz, 3H). $^{19}$F NMR (376 MHz, DMSO-$d_6$) δ −58.65 (s, 3F), −74.89 (s, 6F). LCMS ESI$^+$ calc'd for $C_{21}H_{23}ClF_3N_7OS$: 514.1 [M+H$^+$]. found: 514.2 [M+H$^+$].

Example 40: 2-(8-((2,3-dichlorophenyl)thio)imidazo[1,2-c]pyrimidin-5-yl)octahydrocyclopenta[c]pyrrol-5-amine

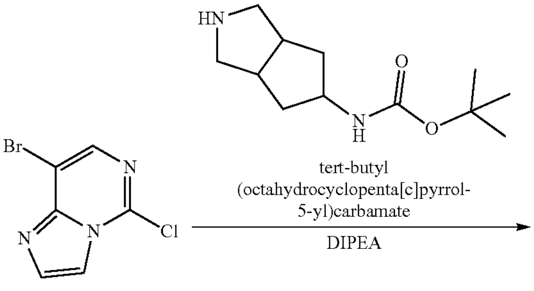

Q1z

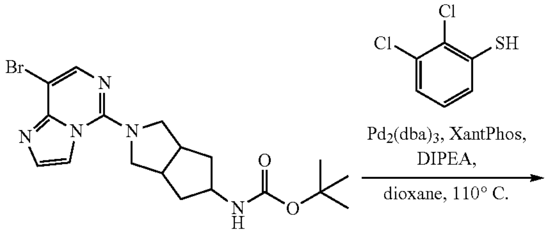

E40a

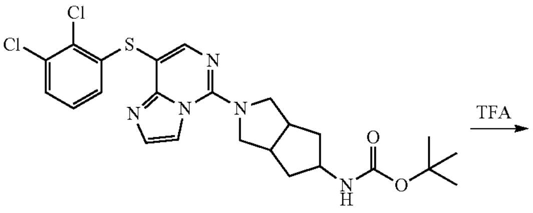

E40b

-continued

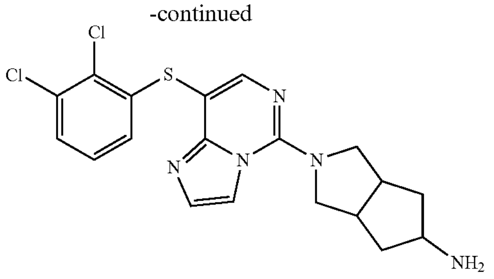

Example 40

Compound E40a: Compound Q1z (0.258 g, 1.11 mmol) was dissolved in 1,4 dioxane (2.5 mL), and tert-butyl (octahydrocyclopenta[c]pyrrol-5-yl)carbamate (254 mg, 1.121 mmol) and DIPEA (0.387 mL, 2.22 mmol) was added. The solution was stirred at room temperature until starting materials were consumed. The solution was diluted with ethyl acetate and washed with water and brine. The organic partitions were dried over magnesium sulfate and concentrated in vacuo. The residue was reconstituted in toluene and purified by column chromatography (0-100% EtOAc in Hexanes). This provided 8 Compound E40a. LCMS ESI$^+$ calc'd for $C_{13}H_9Cl_2N_{30}$: 422.1 [M+H$^+$]. found: 422.1 [M+H$^+$].

Compound E40b: Compound E40a (200 mg, 0.474 mmol) in 1,4-dioxane (2 ml) was added $Pd_2(dba)_3$ (110 mg, 0.189 mmol), XantPhos (70 mg, 0.076 mmol), 2,3-dichlorobenzenethiol (93 mg, 0.521 mmol), and DIPEA (0.222 mL, 1.28 mmol). The reaction vessel was purged with argon, sealed, and heated to 110° C. until complete consumption of starting materials. The reaction mixture was cooled to room temperature, diluted with EtOAc and washed with water followed by brine. The organic partition was dried over magnesium sulfate, and filtered through Celite. The resulting solution was concentrated and purified by column chromatography (0-100% EtOAc in Hexanes). This provided Compound E40b. LCMS ESI$^+$ calc'd for $C_{24}H_{32}ClN_7O_2S_2$: 520.1 [M+H$^+$]. found: 520.0 [M+H$^+$].

Example 40: Compound E40b (0.100 g, 0.256 mmol) was dissolved in DCM (5 ml), and TFA (1 ml) was added. The solution was concentrated and reconstituted in water and DMF and the solution was purified on preparatory HPLC (10-100% MeCN in water with 0.1% TFA, Gemini). This provided Example 40. $^1$H NMR (400 MHz, DMSO-d$_6$) δ 8.30 (d, J=2.0 Hz, 1H), 8.09 (s, 1H), 7.93 (s, 3H), 7.70 (s, 1H), 7.40 (dd, J=8.0, 1.4 Hz, 1H), 7.12 (t, J=8.1 Hz, 1H), 6.70 (dd, J=8.1, 1.4 Hz, 1H), 4.09 (dd, J=11.2, 7.1 Hz, 2H), 3.79 (dd, J=11.5, 4.0 Hz, 3H), 2.97 (m, 2H), 2.02 (m, 2H), 1.89 (m, 2H). LCMS ESI$^+$ calc'd for $C_{19}H_{19}Cl_2N_5S$: 420.1 [M+H$^+$]. found: 420.1 [M+H$^+$].

Example 41: (2-(8-((2,3-dichlorophenyl)thio)imidazo[1,2-c]pyrimidin-5-yl)octahydrocyclopenta[c]pyrrol-5-yl)methanamine

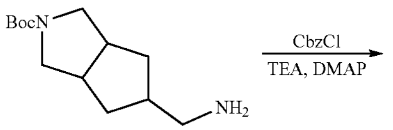

E41a

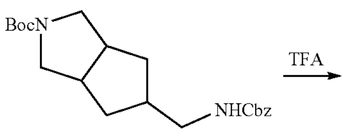

E41b

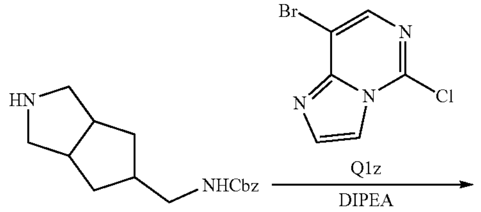

E41c

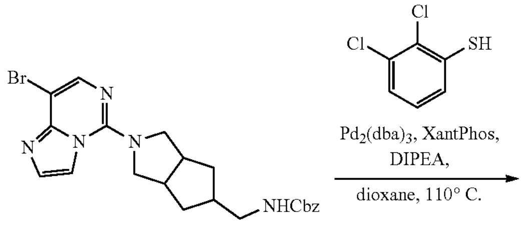

E41d

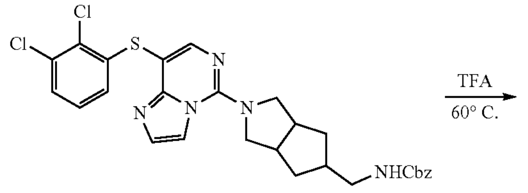

E41e

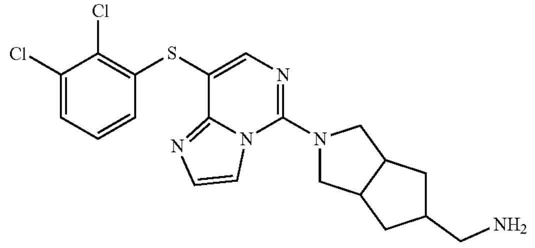

Example 41

Compound E41b: Compound E41a (560 mg, 2.33 mmol) was dissolved in DCM, DMAP was added followed by TEA, and CbzCl was added dropwise. The resulting solution was stirred at room temperature for 1 h. The reaction was diluted with water and EtOAc. The organic partition was dried over magnesium sulfate, concentrated in vacuo, and purified by column chromatography (0-100% EtOAc in hexanes) to provide Compound E41b. LCMS ESI$^+$ calc'd for $C_{21}H_{30}N_2O_4$: 318.2 [M-isobutylene+H$^+$]. found: 318.9 [M-isobutylene+H$^+$].

Compound E41c: Compound E41b (170 mg, 0.454 mmol) was dissolved in DCM (5 ml) and TFA (1 ml) was added. The resulting solution was stirred at room temperature for 30 min. Upon consumption of the starting material, the reaction was concentrated in vacuo. This provided Compound E41c. LCMS ESI$^+$ calc'd for $C_{16}H_{22}N_2O_2$: 275.2 [M+H$^+$]. found: 275.1 [M+H$^+$].

Compound E41d: Compound Q1z (95 mg, 0.409 mmol) and Compound E41c (125 mg, 0.454 mmol) were dissolved in 1,4 Dioxane (2 mL) and DIPEA was added (0.072 mL, 0.413 mmol) the reaction stirred at r.t. for 2 h. The mixture was diluted with EtOAc, successively washed with brine, dried over magnesium sulfate, and concentrated in vacuo. The residue was reconstituted in toluene and purified by column chromatography (0-100% EtOAc in Hexanes). This provided Compound E41e. LCMS $ESI^+$ calc'd for $C_{22}H_{24}BrN_5O_2$: 470.1 [$M+H^+$]. found: 470.3 [$M+H^+$].

Compound E41e: Compound E41d (220 mg, 0.468 mmol) in 1,4-dioxane (2 mL) was added $Pd_2(dba)_3$ (86 mg, 0.094 mmol), XantPhos (109 mg, 0.187 mmol), 2,3-dichlorobenzenethiol (167 mg, 0.935 mmol), and DIPEA (0.163 mL, 0.742 mmol). The reaction vessel was purged with argon, sealed, and heated to 110° C. until complete consumption of starting materials. The reaction mixture was cooled to room temperature, diluted with EtOAc and washed with water followed by brine. The organic partition was dried over magnesium sulfate, and filtered through Celite. The resulting solution was concentrated and used in the next step without purification. This provided Compound E41e. LCMS $ESI^+$ calc'd for $C_{28}H_{27}Cl_2N_5O_2S$: 568.1 [$M+H^+$]. found: 568.2 [$M+H^+$].

Example 41: Compound E41e was dissolved in TFA (2 mL) and heated to 60° C. for 6 h. The solution was concentrated and reconstituted in water and DMF and the solution was purified on preparatory HPLC (10-100% MeCN in water with 0.1% TFA, Gemini). This provided Example 41 as a TFA salt. $^1H$ NMR (400 MHz, DMSO-$d_6$) δ 8.30 (s, 1H), 8.07 (s, 1H), 7.71 (d, J=37.7 Hz, 4H), 7.40 (dd, J=8.0, 1.4 Hz, 1H), 7.12 (t, J=8.1 Hz, 1H), 6.69 (dd, J=8.1, 1.3 Hz, 1H), 4.18-4.00 (m, 2H), 3.84 (dd, J=11.5, 3.6 Hz, 1H), 3.72 (dd, J=11.3, 3.8 Hz, 1H), 2.94-2.72 (m, 4H), 2.45-2.18 (m, 1H), 2.15-2.00 (m, 1H), 1.79 (ddd, J=13.2, 7.4, 2.7 Hz, 1H), 1.60 (dt, J=13.0, 7.5 Hz, 1H), 1.27 (td, J=12.4, 6.5 Hz, 1H). LCMS $ESI^+$ calc'd for $C_{20}H_{21}Cl_2N_5S$: 434.1 [$M+H^+$]. found: 434.2 [$M+H^+$].

Example 42: ((1R,5S,6r)-3-(8-((2,3-dichlorophenyl)thio)imidazo[1,2-c]pyrimidin-5-yl)-3-azabicyclo[3.1.0]hexan-6-yl)methanamine Compound E42a: Benzyltriethylammonium chloride (0.341 g, 1.50 mmol) to a suspension of Compound N2 (0.155 g, 0.499 mmol) in phosphorous(V) oxychloride (1.6 mL) and heated to 120° C. for 16 h. The reaction was concentrated in vacuo and purified directly by column chromatography (0-100% EtOAc in hexanes) to provide Compound E42a. LCMS $ESI^+$ calc'd for $C_{12}H_6Cl_3N_3S$: 329.9 [$M+H^+$]. found: 330.1 [$M+H^+$].

Compound E42c: Compound E42b (0.540 g, 2.544 mmol) was dissolved in DCM, DMAP (0.015 g, 0.127 mmol) was added followed by DIPEA (0.822 g, 6.359 mmol) and CbzCl (0.430 mL, 0.430 mmol) was added dropwise. The resulting solution was stirred at room temperature for 1 h. The reaction was diluted with water and EtOAc. The organic partition was dried over magnesium sulfate, concentrated in vacuo, and purified by column chromatography (0-100% EtOAc in hexanes). This provided Compound E42c. $^1H$ NMR (400 MHz, DMSO-$d_6$) δ 7.41-7.21 (m, 5H), 4.99 (s, 2H), 3.37 (d, J=10.8 Hz, 2H), 3.21 (t, J=12.6 Hz, 2H), 2.98-2.83 (m, 2H), 1.40 (t, J=3.1 Hz, 2H), 1.35 (s, 8H), 0.61 (tt, J=6.8, 3.3 Hz, 1H). LCMS $ESI^+$ calc'd for $C_{19}H_{26}N_2O_4$: 346.2 [$M+H^+$]. found: Compound does not ionize.

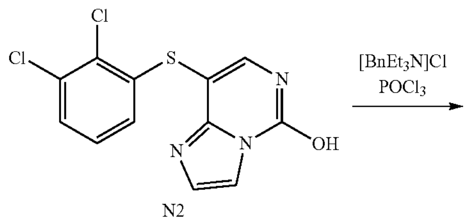

N2

-continued

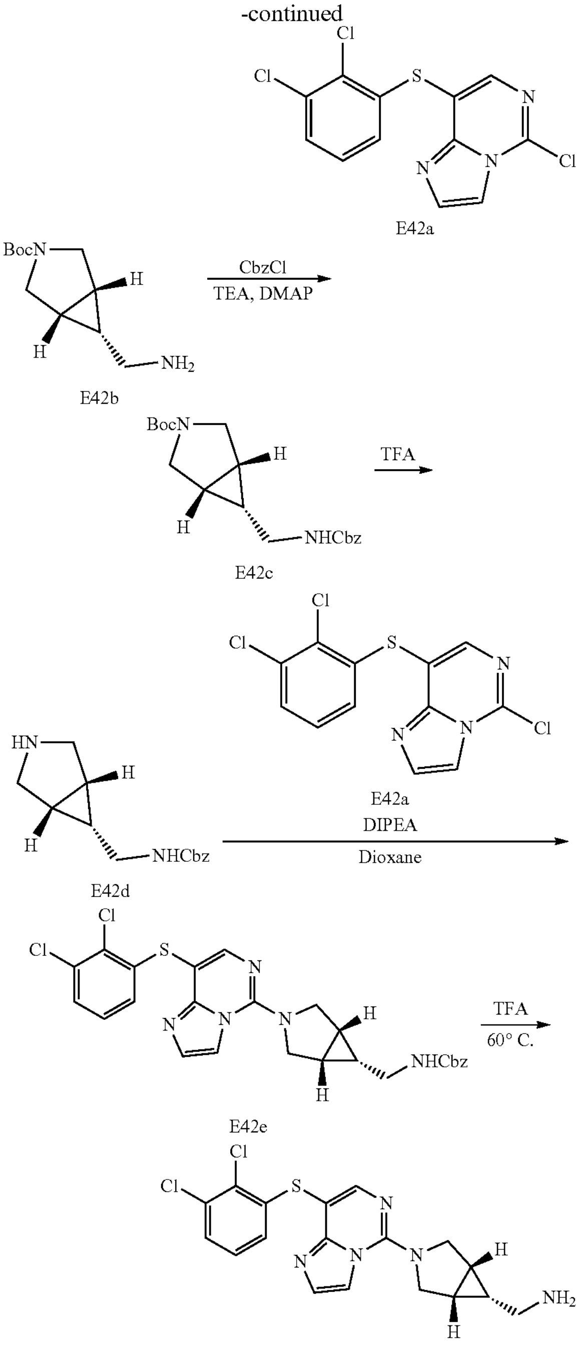

Compound E42d: Compound E42c (170 mg, 0.454 mmol) was dissolved in DCM (5 mL) and TFA (1 mL) was added. The resulting solution was stirred at room temperature for 30 min. Upon consumption of the starting material, the reaction was concentrated in vacuo, and used directly in the next step without purification. This provided Compound E42d. LCMS $ESI^+$ calc'd for $C_{14}H_{18}N_2O_2$: 247.1 [$M+H^+$]. found: 247.1 [$M+H^+$].

Compound E42e: Compound E42a (0.030 g, 0.091 mmol) and Compound E42d (0.102 g, 0.294 mmol) were dissolved in 1,4 dioxane (2 mL) and DIPEA was added (0.158 mL, 0.907 mmol) the reaction stirred at r.t. for 2 h. The mixture was diluted with EtOAc, successively washed with brine, dried over magnesium sulfate, and concentrated in vacuo, and used in the next step without purifying. This provided Compound E42e. LCMS ESI+ calc'd for $C_{26}H_{23}Cl_2N_5O_2S$: 540.1 [M+H+]. found: 540.1 [M+H+].

Example 42: Compound E42e was dissolved in TFA (2 mL) and heated to 60° C. for 6 h. The solution was concentrated and reconstituted in water and DMF and the solution was purified on preparatory HPLC (10-100% MeCN in water with 0.1% TFA, Gemini). This provided Example 42 as a TFA salt. $^1$H NMR (400 MHz, DMSO-$d_6$) δ 8.23 (d, J=1.8 Hz, 1H), 7.98 (s, 1H), 7.77 (s, 3H), 7.57 (s, 1H), 7.39 (dd, J=8.0, 1.4 Hz, 1H), 7.11 (t, J=8.0 Hz, 1H), 6.66 (dd, J=8.1, 1.4 Hz, 1H), 4.25 (d, J=11.0 Hz, 2H), 4.01 (m, 1H), 3.99 (m, 1H), 2.78 (q, J=6.1 Hz, 2H), 1.85 (m, 2H), 0.92 (p, J=4.1 Hz, 1H). LCMS ESI+ calc'd for $C_{18}H_{17}Cl_2N_5S$: 406.1 [M+H+]. found: 406.1 [M+H+].

Example 43: (1-(8-((2,3-dichlorophenyl)thio)imidazo[1,2-c]pyrimidin-5-yl)-4-methylpiperidin-4-yl) methanamine

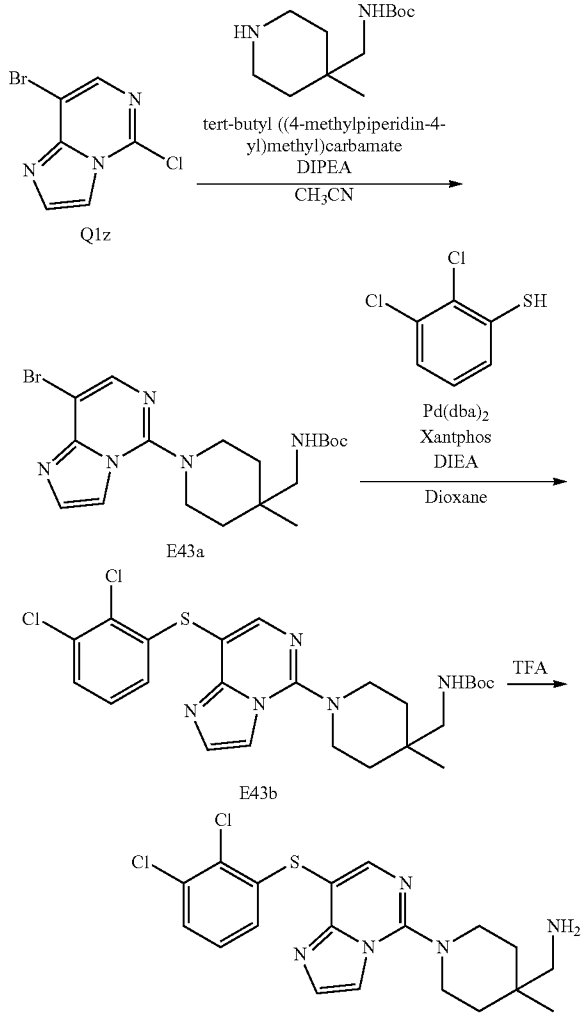

Q1z

E43a

E43b

Example 43

Compound E43a: In a 10 mL reaction vial Compound Q1z (50 mg, 0.215 mmol) and tert-butyl ((4-methylpiperidin-4-yl)methyl)carbamate (147.3 mg, 0.645 mmol) were dissolved in CH3CN (1.5 mL) at rt. DIEA (0.25 mL, 1.44 mmol) was added. Reaction mixture was purged with argon for 5 min and was then heated under microwave at 90° C. for 1 hour. Reaction mixture was purified on silica gel directly with 0-100% EtOAc in Hex to afford product Compound E43a. LCMS ESI+ calc'd for $C_{18}H_{26}BrN_5O_2$: 424.1 [M+H+]. found: 424.2 [M+H+].

Compound E43b: In a 10 mL reaction vial Compound E43a (25 mg, 0.059 mmol), 2,3-dichlorobenzenethiol (26.4 mg, 0.147 mmol) and Xantphos (13.6 mg, 0.024 mmol) were dissolved in dioxane (3 mL) at room temperature. DIEA (0.041 mL, 0.236 mmol) was added dropwise. Pd(dba)$_2$ (6.8 mg, 0.012 mmol) was added. The resulting reaction mixture was purged with argon for 5 min and then heated under microwave at 115° C. for 2 hours. Reaction mixture was cooled down and then was purified directly on silica gel column with 0-100% EtOAc in Hex to afford Compound E43b. LCMS ESI+ calc'd for $C_{24}H_{29}Cl_2N_5O_2S$: 522.1 [M+H+]. found: 522.2 [M+H+].

Example 43: In a 5 mL reaction vial, Compound E43b (7 mg, 0.013 mmol) was dissolved in TFA (1 mL). Reaction mixture was stirred at room temperature for 5 min and then was concentrated to dryness. The residue was dissolved in methanol (2 mL) and was then purified with reverse phase prep-HPLC with water (containing 0.5% TFA) and acetonitrile (containing 0.5% TFA) to afford Example 43 as a TFA salt. $^1$H NMR (400 MHz, Acetonitrile-d3) δ 8.10 (s, 1H), 7.69 (d, J=1.6 Hz, 1H), 7.57 (d, J=1.6 Hz, 1H), 7.41 (br, 3H), 7.34 (dd, J=8.0, 1.3 Hz, 1H), 7.05 (t, J=8.0 Hz, 1H), 6.77 (dd, J=8.1, 1.4 Hz, 1H), 3.77 (dt, J=13.7, 4.7 Hz, 2H), 3.51 (ddd, J=13.3, 9.5, 3.2 Hz, 2H), 3.01 (s, 2H), 1.80 (ddd, J=13.5, 9.4, 3.8 Hz, 2H), 1.68 (ddd, J=13.9, 6.0, 3.7 Hz, 2H), 1.20 (s, 3H). LCMS ESI+ calc'd for $C_{19}H_{21}Cl_2N_5S$: 421.1 [M+H+]. found: 422.2 [M+H+].

Example 44: (R)-8-(8-((2,3-dichlorophenyl)thio) imidazo[1,2-c]pyrimidin-5-yl)-8-azaspiro[4.5]decan-1-amine

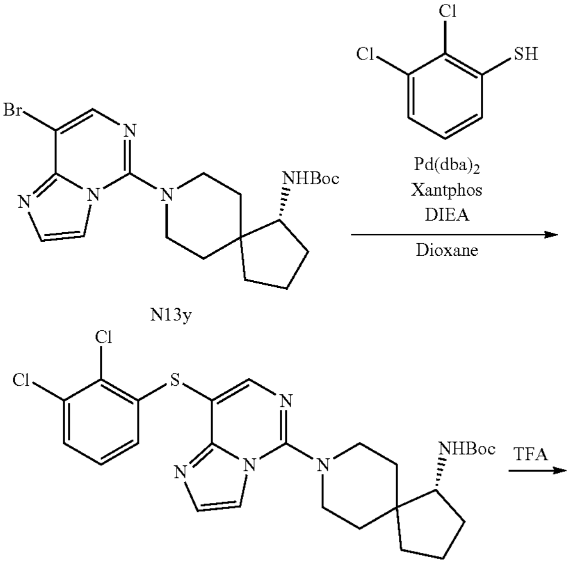

N13y

E44a

-continued

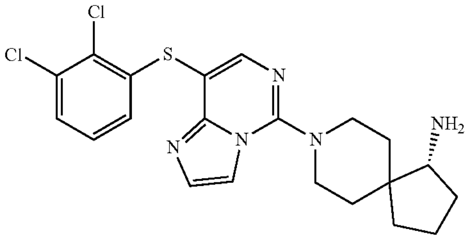

Example 44

Compound E44a: In a 10 mL reaction vial Compound N13y (30 mg, 0.067 mmol), 2,3-dichlorobenzenethiol (23.5 mg, 0.142 mmol) and Xantphos (15.4 mg, 0.027 mmol) were dissolved in dioxane (1.5 mL) at room temperature. DIEA (0.046 mL, 0.266 mmol) was added dropwise. $Pd(dba)_2$ (7.66 mg, 0.013 mmol) was then added. The resulting reaction mixture was purged with argon for 5 min and then heated under microwave at 115° C. for 2 hours. Reaction mixture was cooled down and then was purified directly on silica gel column with 0-100% EtOAc in Hex to afford Compound E44a. LCMS $ESI^+$ calc'd for $C_{26}H_{31}Cl_2N_5O_2S$: 548.2 [M+H$^+$]. found: 548.2 [M+H$^+$].

Example 44: In a 5 mL reaction vial, Compound E44a (30 mg, 0.055 mmol) was dissolved in TFA (1 mL). Reaction mixture was stirred at room temperature for 5 min and then was concentrated to dryness. The residue was dissolved in methanol (2 mL) and was then purified with reverse phase prep-HPLC with water (containing 0.5% TFA) and acetonitrile (containing 0.5% TFA) to afford Example 44 as a TFA salt. $^1$H NMR (400 MHz, Acetonitrile-d3) δ 8.25 (s, 1H), 7.75 (d, J=2.0 Hz, 1H), 7.64 (d, J=1.9 Hz, 1H), 7.39 (s, broad, 3H), 7.36 (dd, J=8.0, 1.3 Hz, 1H), 7.08 (t, J=8.0 Hz, 1H), 6.79 (dd, J=8.1, 1.3 Hz, 1H), 4.14-3.91 (m, 2H), 3.51-3.29 (m, 2H), 2.35-2.15 (m, 1H), 1.94-1.76 (m, 8H), 1.75-1.68 (m, 1H), 1.61 (dt, J=13.6, 2.6 Hz, 1H). LCMS $ESI^+$ calc'd for $C_{21}H_{23}Cl_2N_5S$: 448.1 [M+H$^+$]. found: 448.3 [M+H$^+$].

Example 45: (R)-8-(8-((2-amino-3-chloropyridin-4-yl)thio)imidazo[1,2-c]pyrimidin-5-yl)-8-azaspiro[4.5]decan-1-amine

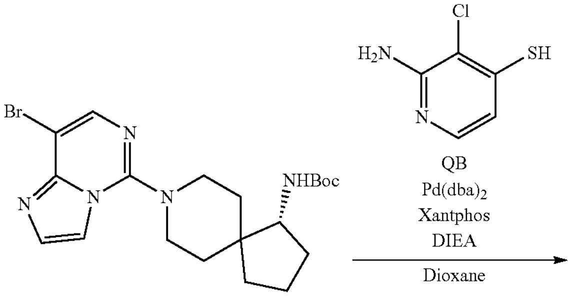

N13y

-continued

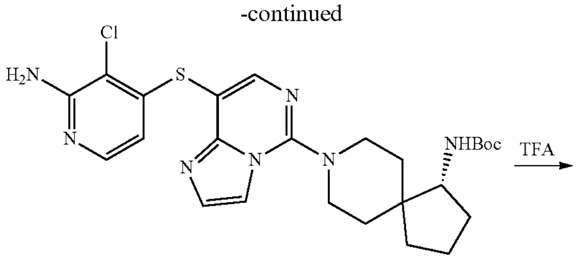

E45a

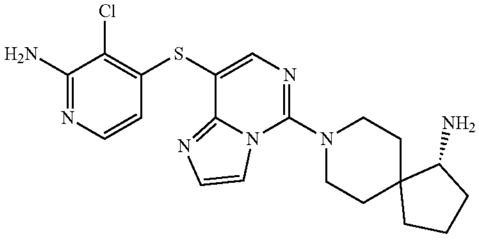

Example 45

Compound E45a: In a 10 mL reaction vial Compound N13y (24 mg, 0.053 mmol), Compound Q8 (42 mg, 0.230 mmol) and Xantphos (12 mg, 0.021 mmol) were dissolved in dioxane (1.5 mL) at room temperature. DIEA (0.037 mL, 0.210 mmol) was added dropwise. $Pd(dba)_2$ (6.1 mg, 0.011 mmol) was then added. The resulting reaction mixture was purged with argon for 5 min and then heated under microwave at 115° C. for 2 hours. Reaction mixture was cooled down and then was purified directly on silica gel column with 0-100% EtOAc in Hex and then 10% MeOH in EtOAc to afford Compound E45a. LCMS $ESI^+$ calc'd for $C_{25}H_{32}ClN_7O_2S$: 530.2 [M+H$^+$]. found: 530.2 [M+H$^+$].

Example 45: In a 5 mL reaction vial, Compound E45a (20 mg, 0.038 mmol) was dissolved in TFA (1 mL). Reaction mixture was stirred at room temperature for 5 min and then was concentrated to dryness. The residue was dissolved in methanol (2 mL) and was then purified with reverse phase prep-HPLC with water (containing 0.5% TFA) and acetonitrile (containing 0.5% TFA) to afford Example 45 as a TFA salt. $^1$H NMR (400 MHz, acetonitrile-d3) δ 8.22 (s, 1H), 8.23-7.89 (br, 2H), 7.75 (d, J=1.8 Hz, 1H), 7.69 (d, J=1.8 Hz, 1H), 7.48 (d, J=6.7 Hz, 1H), 7.08 (s, 3H), 6.27 (d, J=6.6 Hz, 1H), 4.13-4.01 (m, 2H), 3.40 (ddd, J=14.0, 11.6, 2.7 Hz, 2H), 2.23 (dt, J=14.4, 7.6 Hz, 1H), 1.93-1.54 (m, 10H). LCMS $ESI^+$ calc'd for $C_{20}H_{24}ClN_7S$: 430.2 [M+H$^+$]. found: 430.2 [M+H$^+$].

Example 46: (R)-8-(8-((2,3-dichloropyridin-4-yl)thio)imidazo[1,2-c]pyrimidin-5-yl)-8-azaspiro[4.5]decan-1-amine

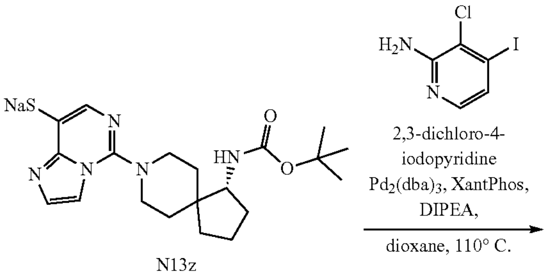

N13z

-continued

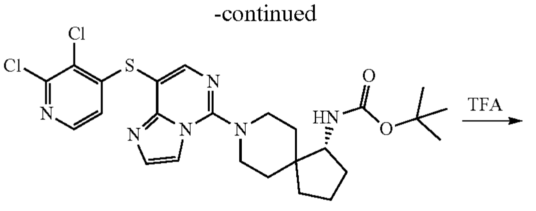

E46a

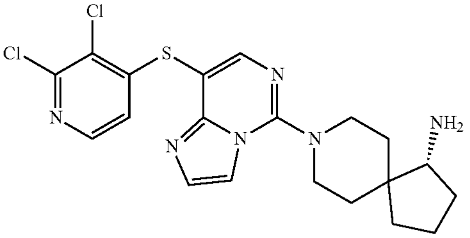

Example 46

Compound E46a: Compound N13z (135 mg, 318 mmol) in 1,4-dioxane (3 mL) was added $Pd_2(dba)_3$ (14.5 mg, 0.0159 mmol), XantPhos (18.4 mg, 0.0318 mmol), 2,3-dichloro-4-iodopyridine (109 mg, 0.397 mmol), and DIPEA (0.166 mL, 0.954 mmol). The reaction vessel was purged with argon, sealed, and heated to 110° C. until complete consumption of starting materials. The reaction mixture was cooled to room temperature, diluted with EtOAc and washed with water followed by brine. The organic partition was dried over magnesium sulfate, and filtered through Celite. The resulting solution was concentrated and purified by column chromatography (0-100% EtOAc in hexanes). This provided Compound E46a. LCMS $ESI^+$ calc'd for $C_{25}H_{30}Cl_2N_6O_2S$: 549.2 $[M+H^+]$. found: 549.2 $[M+H^+]$.

Example 46: Compound E46a was dissolved in DCM (5 mL), and TFA (1 mL) was added. The solution was concentrated and reconstituted in water and DMF and the solution was purified on preparatory HPLC (10-100% MeCN in water with 0.1% TFA, Gemini). This provided Example 46. $^1H$ NMR (400 MHz, DMSO-de) δ 8.16 (s, 1H), 7.99 (d, J=5.3 Hz, 1H), 7.96-7.88 (m, 3H), 7.87 (d, J=1.7 Hz, 1H), 7.68 (d, J=1.6 Hz, 1H), 6.73 (d, J=5.3 Hz, 1H), 3.95 (t, J=14.6 Hz, 2H), 3.39-3.27 (m, 2H), 3.23 (d, J=6.4 Hz, 1H), 2.16-1.99 (m, 1H), 1.92-1.61 (m, 7H), 1.53 (dd, J=29.2, 13.4 Hz, 2H). LCMS $ESI^+$ calc'd for $C_{20}H_{22}Cl_2N_6S$: 449.1 $[M+H^+]$. found: 449.1 $[M+H^+]$.

Example 47: (R)-8-(8-((3-chloro-2-methylpyridin-4-yl)thio)imidazo[1,2-c]pyrimidin-5-yl)-8-azaspiro[4.5]decan-1-amine

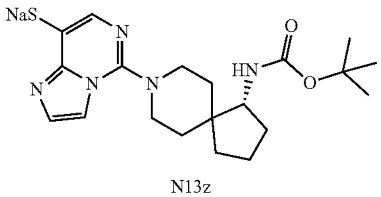

N13z

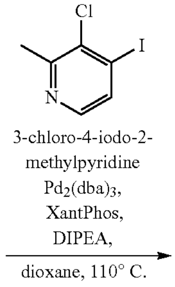

-continued

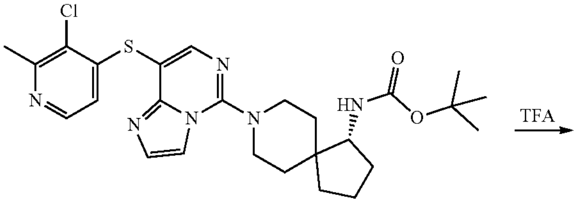

E47a

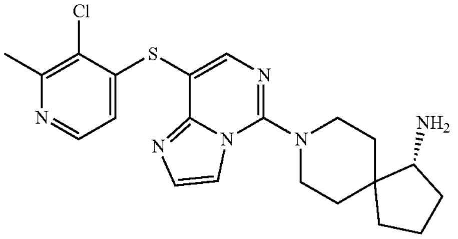

Example 47

Compound E47a: Compound N13z (100 mg, 0.235 mmol) in 1,4-dioxane (2 ml) was added $Pd_2(dba)_3$ (11 mg, 0.012 mmol), XantPhos (13 mg, 0.024 mmol), 3-chloro-4-iodo-2-methylpyridine (74 mg, 0.294 mmol), and DIPEA (0.123 ml, 0.705 mmol). The reaction vessel was purged with argon, sealed, and heated to 110° C. until complete consumption of starting materials. The reaction mixture was cooled to room temperature, diluted with EtOAc and washed with water followed by brine. The organic partition was dried over magnesium sulfate, and filtered through Celite. The resulting solution was concentrated and purified by column chromatography (0-100% EtOAc in Hexanes). This provided Compound E47a. LCMS $ESI^+$ calc'd for $C_{26}H_{33}ClN_6O_2S$: 529.2 $[M+H^+]$. found: 529.9 $[M+H^+]$.

Example 47: Compound E47a in DCM (5 mL) was added TFA (2 mL). After 30 min, the mixture was diluted with water and DMF and purified and preparatory HPLC (10-100% MeCN in water 0.1% TFA). This provided Example 47. $^1H$ NMR (400 MHz, DMSO-$d_6$) δ 8.20 (s, 1H), 8.07 (d, J=5.5 Hz, 1H), 8.02-7.81 (m, 4H), 7.76 (d, J=1.7 Hz, 1H), 6.68-6.62 (m, 1H), 3.96 (t, J=14.9 Hz, 2H), 3.43-3.16 (m, 3H), 2.57 (s, 3H), 2.08 (td, J=9.5, 8.4, 5.2 Hz, 1H), 1.91-1.43 (m, 9H). LCMS $ESI^+$ calc'd for $C_{21}H_{25}ClN_6S$: 429.2 $[M+H^+]$. found: 429.2 $[M+H^+]$.

Example 48: 1-(8-((2,3-dichlorophenyl)thio)imidazo[1,2-c]pyrimidin-5-yl)-4-methylpiperidin-4-amine

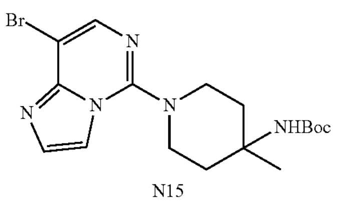

N15

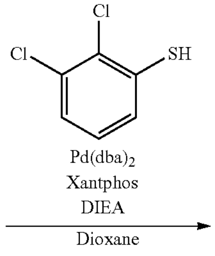

-continued

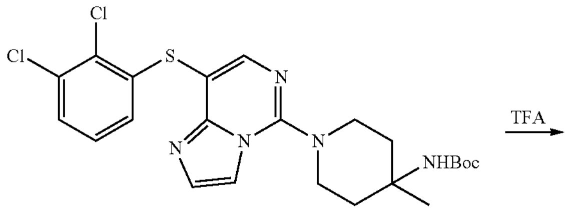

E48a

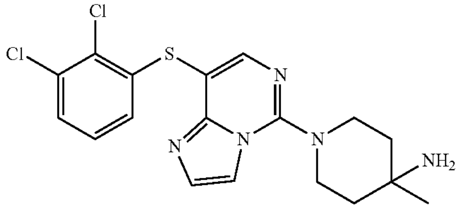

Example 48

Compound E48a: In a 10 mL reaction vial Compound N15 (30 mg, 0.073 mmol), 2,3-dichlorobenzenethiol (50 mg, 0.276 mmol) and Xantphos (17 mg, 0.029 mmol) were dissolved in dioxane (1.5 mL) at room temperature. DIEA (0.051 mL, 0.292 mmol) was added dropwise. Then $Pd(dba)_2$ (8.4 mg, 0.015 mmol) was added. The resulting reaction mixture was purged with argon for 5 min and then heated under microwave at 115° C. for 90 min. Reaction mixture was cooled down and then was purified directly on silica gel column with 0-100% EtOAc in Hex to afford Compound E48a. LCMS $ESI^+$ calc'd for $C_{23}H_{27}Cl_2N_5O_2S$: 508.1 $[M+H^+]$. found: 508.1 $[M+H^+]$.

Example 48: In a 5 mL reaction vial, Compound E48a (30 mg, 0.059 mmol) was dissolved in TFA (1 mL). Reaction mixture was stirred at room temperature for 5 min and then was concentrated to dryness. The residue was dissolved in methanol (2 mL) and was then purified with reverse phase prep-HPLC with water (containing 0.5% TFA) and acetonitrile (containing 0.5% TFA) to afford Example 48 as a TFA salt. $^1H$ NMR (400 MHz, acetonitrile-d3) δ 8.21 (s, 1H), 7.74 (d, J=1.9 Hz, 1H), 7.65 (br, 3H), 7.62 (d, J=1.9 Hz, 1H), 7.36 (dd, J=8.0, 1.4 Hz, 1H), 7.07 (t, J=8.1 Hz, 1H), 6.78 (dd, J=8.1, 1.4 Hz, 1H), 3.96 (dt, J=14.2, 4.6 Hz, 2H), 3.53 (ddd, J=13.7, 10.0, 3.2 Hz, 2H), 2.18 (ddd, J=13.9, 10.0, 4.1 Hz, 2H), 2.11-2.00 (m, 2H), 1.57 (s, 3H). LCMS $ESI^+$ calc'd for $C_{18}H_{19}Cl_2N_5S$: 408.1 $[M+H^+]$. found: 408.1 $[M+H^+]$.

Example 49: 4-methyl-1-(8-(phenylthio)imidazo[1,2-c]pyrimidin-5-yl)piperidin-4-amine

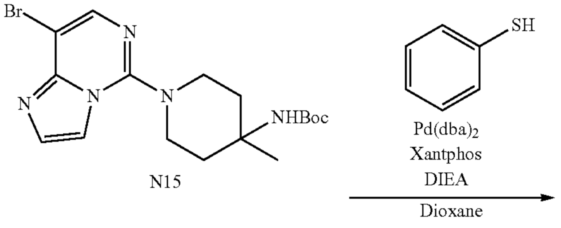

N15

-continued

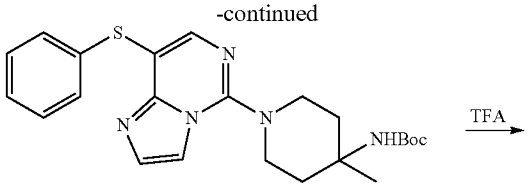

E49a

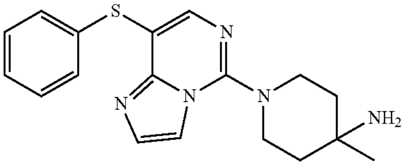

Example 49

Compound E49a: In a 10 mL reaction vial Compound N15 (20 mg, 0.049 mmol), benzenethiol (21.5 mg, 0.195 mmol) and Xantphos (11.3 mg, 0.019 mmol) were dissolved in dioxane (1.5 mL) at room temperature. DIEA (0.034 mL, 0.195 mmol) was added dropwise. Then $Pd(dba)_2$ (5.6 mg, 0.010 mmol) was added. The resulting reaction mixture was purged with argon for 5 min and then heated under microwave at 120° C. for 90 min. Reaction mixture was cooled down and then was purified directly on silica gel column with 0-100% EtOAc in Hex to afford Compound E49a. LCMS $ESI^+$ calc'd for $C_{23}H_{29}N_5O_2S$: 440.2 $[M+H^+]$. found: 440.2 $[M+H^+]$.

Example 49: In a 5 mL reaction vial, Compound E49a (20 mg, 0.045 mmol) was dissolved in TFA (1 mL). Reaction mixture was stirred at room temperature for 5 min and then was concentrated to dryness. The residue was dissolved in methanol (2 mL) and was then purified with reverse phase prep-HPLC with water (containing 0.5% TFA) and acetonitrile (containing 0.5% TFA) to afford Example 49 as a TFA salt. $^1H$ NMR (400 MHz, Acetonitrile-d3) δ 8.24 (s, 1H), 7.76 (d, J=2.0 Hz, 1H), 7.73 (d, J=2.0 Hz, 1H), 7.65 (br, 3H), 7.40-7.22 (m, 5H), 3.96 (dt, J=14.2, 4.6 Hz, 2H), 3.50 (ddd, J=13.7, 10.0, 3.1 Hz, 2H), 2.16 (ddd, J=13.9, 10.0, 3.9 Hz, 2H), 2.05-1.98 (m, 2H). LCMS $ESI^+$ calc'd for $C_{18}H_{21}N_5S$: 340.2 $[M+H^+]$. found: 340.2 $[M+H^+]$.

Example 50: (R)-8-(8-((6-amino-4-(trifluoromethyl)pyridin-3-yl)thio)imidazo[1,2-c]pyrimidin-5-yl)-8-azaspiro[4.5]decan-1-amine

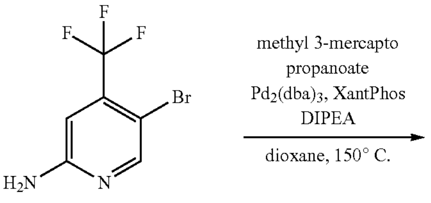

E50a

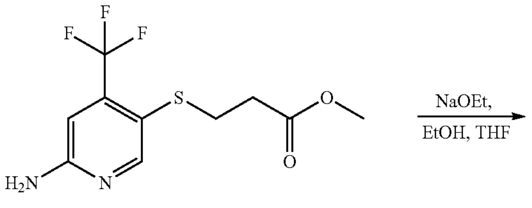

E50b

-continued

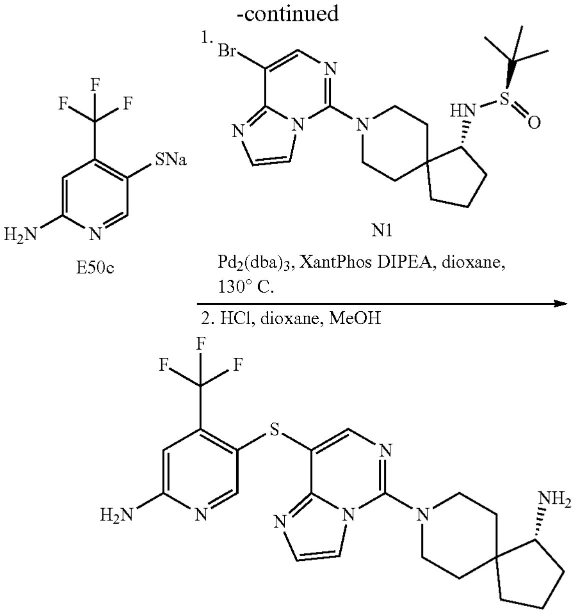

Example 50

Compound E50b: To a solution of Compound E50a (0.199 mg) in 1,4-dioxane (3.0 mL) was added $Pd_2(dba)_3$ (0.157 g), XantPhos (0.1960 g), methyl 3-mercaptopropanoate (0.20 mL), and DIPEA (0.30 mL), then the reaction was heated to 150° C. for 1 h in a microwave reactor. The reaction mixture was diluted with EtOAc, filtered through Celite, the filtrate was concentrated in vacuo, and purified by column chromatography (0-10% MeOH in DCM) to give Compound E50b. $^1$H NMR (400 MHz, DMSO-$d_6$) δ 8.18 (s, 1H), 6.83 (s, 2H), 6.79 (s, 1H), 3.56 (s, 3H), 2.91 (t, J=7.0 Hz, 2H), 2.53 (d, J=6.9 Hz, 3H). $^{19}$F NMR (376 MHz, DMSO-$d_6$) δ −62.65 (s). LCMS ESI$^+$ calc'd for $C_{10}H_{11}F_3N_2O_2S$: 281.1 [M+H$^+$]. found: 281.0 [M+H$^+$].

Compound E50c: To a solution of Compound E50b (0.214 g) in THF (2.5 mL) was added sodium ethoxide solution (0.30 mL, 21 wt % in ethanol). After 1 h, the mixture was concentrated in vacuo, the residue was suspended in DCM and MTBE, concentrated in vacuo, and was used without further purification, to give Compound E50c. $^1$H NMR (400 MHz, DMSO-$d_6$) δ 8.42 (s, 1H), 6.46 (s, 1H), 6.29 (s, 3H). $^{19}$F NMR (376 MHz, DMSO-$d_6$) δ −59.33 (s). LCMS ESI$^+$ calc'd for $C_6H_5F_3N_2S$: 195.0 [M+H$^+$]; found: does not ionize.

Example 50: A solution of Compound N1 (0.100 g), Compound E50c (0.100 g), $Pd_2(dba)_3$ (0.049 g), XantPhos (0.054 g), and DIPEA (0.20 mL) in 1,4-dioxane (4.4 mL) was heated to 150° C. for 1 h in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 1 h. The reaction was diluted with water and purified by preparatory HPLC (10-75% MeCN in water with 0.1% TFA, Gemini) to give Example 50. $^1$H NMR (400 MHz, DMSO-$d_6$) δ 8.37 (s, 1H), 7.79 (s, 3H), 7.73 (d, J=1.6 Hz, 1H), 7.69 (d, J=1.5 Hz, 1H), 7.23 (s, 1H), 7.00 (s, 2H), 6.86 (s, 1H), 3.69 (t, J=12.6 Hz, 2H), 3.29-3.16 (m, 1H), 3.11 (t, J=12.0 Hz, 2H), 2.17-1.93 (m, 1H), 1.89-1.56 (m, 7H), 1.48 (dd, J=25.3, 13.5 Hz, 2H). $^{19}$F NMR (376 MHz, DMSO-$d_6$) δ −62.55 (s, 3F), −74.78 (s, 6F). LCMS ESI$^+$ calc'd for $C_{21}H_{24}F_3N_7S$: 464.2 [M+H$^+$]. found: 464.2 [M+H$^+$].

Example 51: (R)-8-(8-((6-amino-2-(trifluoromethyl)pyridin-3-yl)thio)imidazo[1,2-c]pyrimidin-5-yl)-8-azaspiro[4.5]decan-1-amine

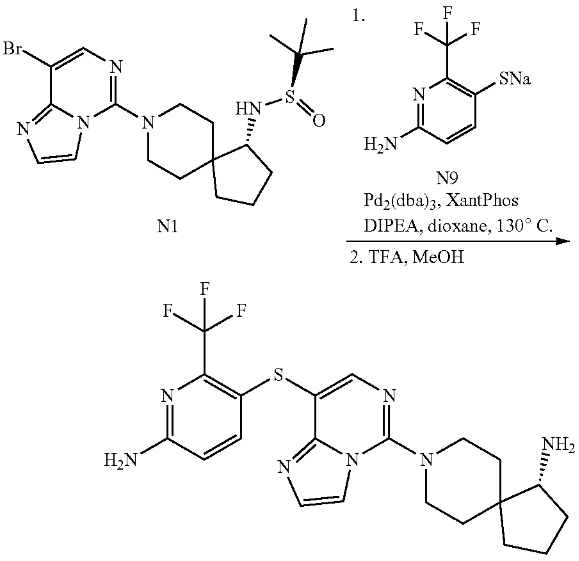

Example 51

Example 51: A solution of Compound N1 (0.102 g), Compound N9 (0.100 g), $Pd_2(dba)_3$ (0.041 g), and XantPhos (0.052 g) in 1,4-dioxane (4.4 mL) was added DIPEA (0.20 mL) and heated in a microwave reactor to 130° C. for 1 h. The reaction filtered through Celite, rinsed with EtOAc, and the filtrate was concentrated in vacuo. To the crude in MeOH (1.0 mL) was added HCl in 1,4-dioxane (0.25 mL, 4 M). After 30 min, the reaction was diluted with water and MeOH, and purified by preparatory HPLC (10-75% MeCN in water with 0.1% TFA, Gemini) to give Example 51. $^1$H NMR (400 MHz, DMSO-$d_6$) δ 7.81 (s, 3H), 7.75 (d, J=1.6 Hz, 1H), 7.68 (d, J=1.4 Hz, 1H), 7.61 (d, J=8.7 Hz, 1H), 7.43 (s, 1H), 6.81 (s, 2H), 6.61 (d, J=8.7 Hz, 1H), 3.73 (t, J=13.7 Hz, 2H), 3.28-3.20 (m, 1H), 3.15 (t, J=12.1 Hz, 2H), 2.20-1.97 (m, 1H), 1.97-1.59 (m, 7H), 1.50 (dd, J=25.4, 13.2 Hz, 2H). $^{19}$F NMR (376 MHz, DMSO-$d_6$) δ −62.99 (s, 3F), −74.81 (s, 6F). LCMS ESI$^+$ calc'd for $C_{21}H_{24}F_3N_7S$: 464.2 [M+H$^+$]. found: 464.2 [M+H$^+$].

Example 52: (R)-8-(8-(2,3-dichlorophenyl)imidazo[1,2-c]pyrimidin-5-yl)-8-azaspiro[4.5]decan-1-amine

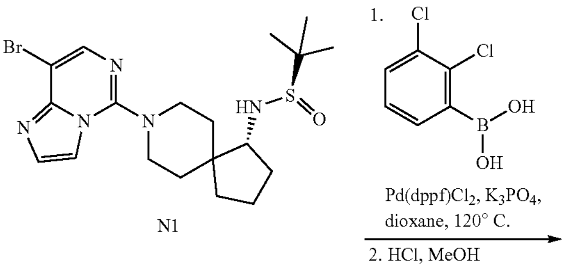

-continued

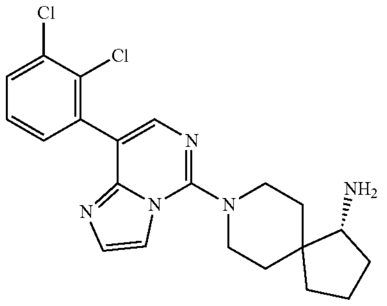

Example 52

Example 52: A solution of Compound N1 (43 mg, 0.095 mmol), (2,3-dichlorophenyl)boronic acid (36 mg, 0.19 mmol), Pd(dppf)$Cl_2$ (8 mg, 0.01 mmol), potassium phosphate tribasic (60 mg, 0.28 mmol) were added to 1,4-dioxane (3 mL). The reaction mixture was heated to 120° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 52. $^1$H NMR (400 MHz, Methanol-$d_4$) δ 8.25 (s, 1H), 8.10 (d, J=2.3 Hz, 1H), 8.02 (d, J=2.3 Hz, 1H), 7.84-7.73 (m, 1H), 7.58-7.39 (m, 2H), 4.22-4.00 (m, 2H), 3.49 (ddt, J=14.2, 12.1, 2.9 Hz, 2H), 2.36-2.20 (m, 1H), 2.06-1.59 (m, 10H). LCMS ESI$^+$ calc'd for $C_{21}H_{23}Cl_2N_5$: 416.1 [M+H$^+$]. found: 416.1 [M+H$^+$].

Example 53: (R)-8-(8-((2-amino-5-(trifluoromethyl)pyridin-4-yl)thio)imidazo[1,2-c]pyrimidin-5-yl)-8-azaspiro[4.5]decan-1-amine

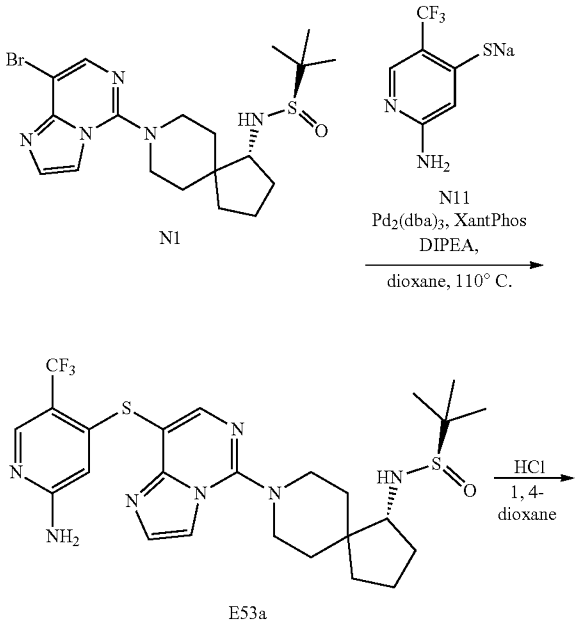

-continued

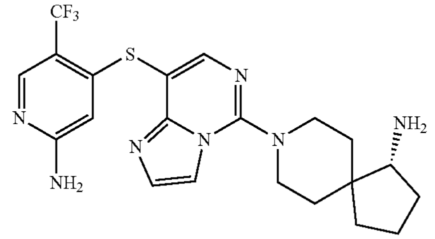

Example 53

Compound E53a: To a solution of Compound N1 (0.062 g, 0.15 mmol) in 1,4-dioxane (2 ml) was added $Pd_2(dba)_3$ (11 mg, 0.012 mmol), XantPhos (13 mg, 0.024 mmol), Compound N11 (74 mg, 0.29 mmol), and DIPEA (0.123 mL, 0.705 mmol). The reaction vessel was purged with argon, sealed, and heated to 110° C. until complete consumption of starting materials. The reaction was cooled to 23° C. and directly purified on a C18 column via reversed-phase HPLC (0.1% TFA in $H_2O$/CH3CN with gradient elution 95:5 to 0:100) giving Compound E53a product after lyophilization. LCMS ESI$^+$ calc'd for $C_{26}H_{32}F_3N_7OS$: 548.2 [M+H$^{+1}$. found: 548.1 [M+H$^+$].

Example 53: The above Compound E53a (54 mg, 0.11 mmol) was dissolved in 3 mL 4N HCl in dioxane. The reaction was stirred for 3 h at which time volatiles were removed and the resulting solid product rinsed with diethyl ether to obtain Example 53. $^1$H NMR (400 MHz, Methanol-$d_4$) δ 8.20 (d, J=6.5 Hz, 2H), 7.93 (d, J=1.8 Hz, 1H), 7.71 (d, J=1.7 Hz, 1H), 6.29 (s, 1H), 4.26-3.97 (m, 2H), 3.55-3.33 (m, 2H), 2.24 (dd, J=12.0, 7.3 Hz, 1H), 2.09-1.77 (m, 6H), 1.77-1.53 (m, 2H). LCMS ESI$^+$ calc'd for $C_{21}H_{32}F_3N_7OS$: 464.2 [M+H$^+$]. found: 464.2 [M+H$^+$].

Example 54: (R)-8-(8-((4-(trifluoromethyl)pyrimidin-5-yl)thio)imidazo[1,2-c]pyrimidin-5-yl)-8-azaspiro[4.5]decan-1-amine

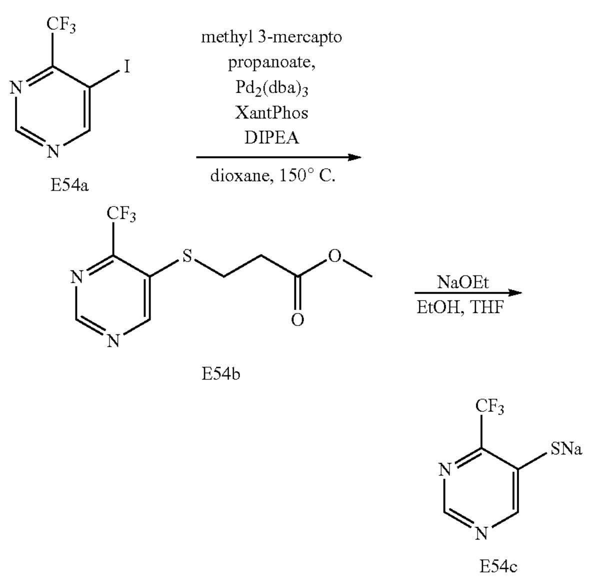

-continued

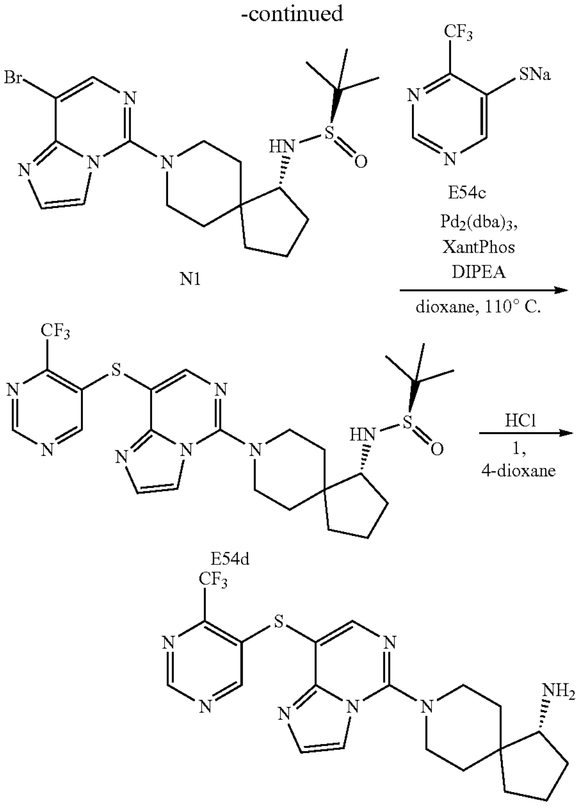

Example 54

Compound E54b: To a solution of Compound E54a (0.200 mg) in 1,4-dioxane (3.0 mL) was added $Pd_2(dba)_3$ (0.157 g), XantPhos (0.1960 g), methyl 3-mercaptopropanoate (0.20 mL), and DIPEA (0.30 mL). The reaction was heated to 150° C. for 1 h in a microwave reactor. The reaction mixture was diluted with EtOAc, filtered through Celite, the filtrate was concentrated in vacuo, and purified by column chromatography (0-10% MeOH in DCM) to give Compound E54b. LCMS $ESI^+$ calc'd for $C_9H_9F_3N_2O_2S$: 267.1 $[M+H^+]$. found: 267.4 $[M+H^+]$.

Compound E54c: To a solution of Compound E54b (0.200 g) in THF (2.5 mL) was added sodium ethoxide solution (0.30 mL, 21 wt % in ethanol). After 1 h, the mixture was concentrated in vacuo, the residue was suspended in DCM and MTBE, concentrated in vacuo, and was used without further purification, to give Compound E54c, the sodium salt of 4-(trifluoromethyl)pyrimidine-5-thiol. LCMS $ESI^+$ calc'd for $C_5H_3F_3N_2S$: 204.0 $[M+Na^+]$. found: 204.0 $[M+Na^+]$.

Compound E54d: To a solution of Compound N1 (0.068 g, 0.15 mmol) in 1,4-dioxane (2 ml) was added $Pd_2(dba)_3$ (11 mg, 0.012 mmol), XantPhos (13 mg, 0.024 mmol), Compound E54c (59 mg, 0.29 mmol), and DIPEA (0.123 ml, 0.705 mmol). The reaction vessel was purged with argon, sealed, and heated to 110° C. until complete consumption of starting materials. The reaction was cooled to 23° C. and directly purified on a C18 column via reversed-phase HPLC (0.1% TFA in $H_2O$/CH3CN with gradient elution 95:5 to 0:100) giving Compound E54d product after lyophilization. LCMS $ESI^+$ calc'd for $C_{24}H_{30}F_3N_7O_2S$: 554.2 $[M+H^+]$. found: 554.4 $[M+H^+]$.

Example 54: The above Compound E36d (54 mg, 0.11 mmol) was dissolved in 3 mL 4N HCl in 1,4-dioxane. The reaction was stirred for 3 h at which time volatiles were removed and the resulting solid product rinsed with diethyl ether to obtain Example 54. $^1H$ NMR (400 MHz, Methanol-$d_4$) δ 7.92 (d, J=1.8 Hz, 1H), 7.86 (s, 1H), 7.74 (s, 1H), 7.61 (d, J=8.8 Hz, 1H), 6.66 (d, J=8.7 Hz, 1H), 4.35-4.24 (m, 1H), 4.02-3.84 (m, 4H), 3.72 (p, J=6.6 Hz, 1H), 3.48 (d, J=4.0 Hz, 1H), 3.29-3.17 (m, 2H), 2.09-1.98 (m, 2H), 1.93 (d, J=13.8 Hz, 1H), 1.78 (d, J=13.3 Hz, 1H), 1.40-1.28 (m, 8H). LCMS $ESI^+$ calc'd for $C_{20}H_{22}F_3N_7S$: 450.2 $[M+H^+]$. found: 450.3 $[M+H^+]$.

Example 55: (3S,4S)-8-(8-((2,3-dichlorophenyl)thio)imidazo[1,2-c]pyrimidin-5-yl)-3-methyl-2-oxa-8-azaspiro[4.5]decan-4-amine

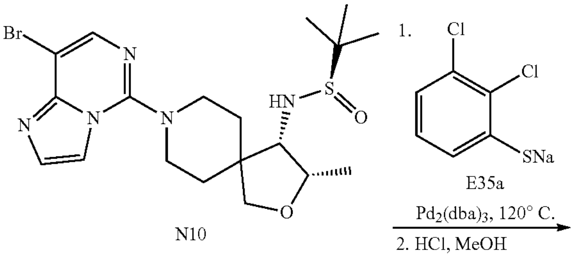

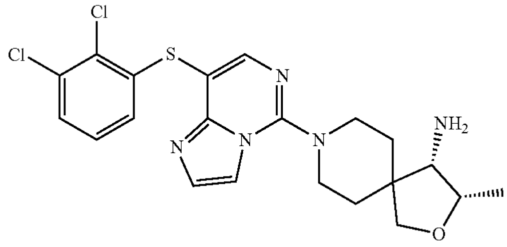

Example 55

Example 55: To a solution of Compound N10 (85 mg, 0.14 mmol) and Compound E35a (37 mg, 0.18 mmol) in dioxane (2 mL) was added $Pd_2(dba)_3$ (26 mg, 0.029 mmol), Xantphos (33 mg, 0.058 mmol) and DIPEA (0.12 mL). The reaction mixture was heated to 120° C. for 60 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 55. $^1H$ NMR (400 MHz, Methanol-$d_4$) δ 8.42 (s, 1H), 8.10 (d, J=2.2 Hz, 1H), 7.93 (d, J=2.2 Hz, 1H), 7.40 (dd, J=8.0, 1.4 Hz, 1H), 7.13 (t, J=8.1 Hz, 1H), 6.83 (dd, J=8.1, 1.4 Hz, 1H), 4.36 (qd, J=6.5, 4.1 Hz, 1H), 4.26-4.09 (m, 2H), 4.05 (d, J=9.3 Hz, 1H), 3.94 (d, J=9.3 Hz, 1H), 3.61-3.38 (m, 3H), 2.19-1.79 (m, 4H), 1.36 (d, J=6.5 Hz, 3H). LCMS $ESI^+$ calc'd for $C_{21}H_{23}Cl_2N_5OS$: 464.1 $[M+H^+]$. found: 464.2 $[M+H^+]$.

Example 56: 1-(8-((2,3-dichlorophenyl)thio)imidazo[1,2-c]pyrimidin-5-yl)azepan-4-amine

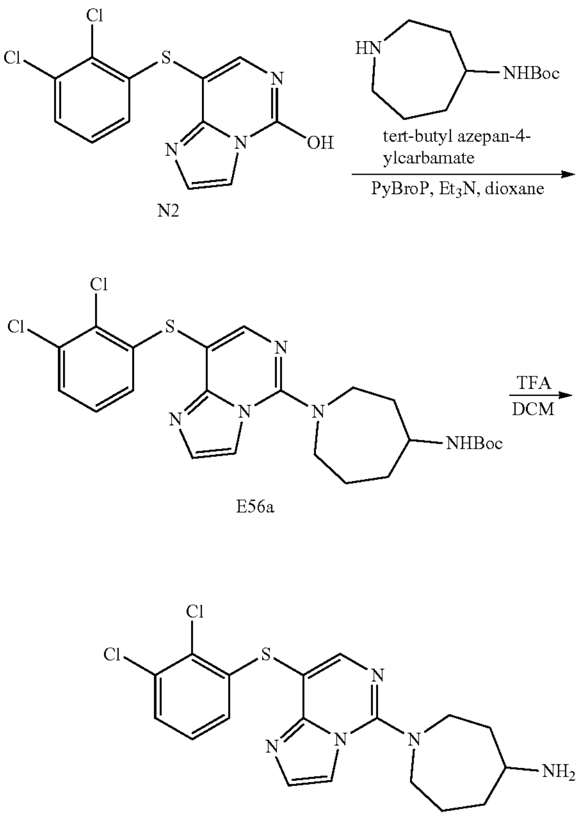

N2

E56a

Example 56

Compound E56a: To Compound N2 (0.049 g) and tert-butyl azepan-4-ylcarbamate (0.048 g) in 1,4-dioxane (1.5 mL) was added PyBroP (0.093 g) and triethylamine (0.4 mL), After 16 h, the reaction was diluted with EtOAc, washed with saturated sodium bicarbonate and brine, dried over sodium sulfate, concentrated in vacuo, and purified by column chromatography (0-100% EtOAc in hexanes) to give Compound E56a. $^1$H NMR (400 MHz, DMSO-$d_6$) δ 7.94 (s, 1H), 7.93 (d, J=1.7 Hz, 1H), 7.47 (d, J=1.6 Hz, 1H), 7.39 (dd, J=8.0, 1.4 Hz, 1H), 7.12 (t, J=8.1 Hz, 1H), 6.94 (d, J=7.8 Hz, 1H), 6.66 (dd, J=8.1, 1.4 Hz, 1H), 4.00-3.82 (m, 2H), 3.82-3.60 (m, 2H), 3.60-3.44 (m, 1H), 2.16-2.03 (m, 1H), 2.03-1.91 (m, 1H), 1.91-1.73 (m, 3H), 1.53 (q, J=11.5, 10.6 Hz, 1H), 1.38 (s, 9H). LCMS ESI$^+$ calc'd for $C_{23}H_{27}Cl_2N_5O_2S$: 508.1 [M+H$^+$]. found: 508.2 [M+H$^+$].

Example 56: A solution of Compound E56a (0.047 g) in DCM (2.0 mL) was added TFA (0.5 mL). After 30 min, the reaction was concentrated in vacuo and the residue was lyophilized from water to give Example 56. $^1$H NMR (400 MHz, DMSO-$d_6$) δ 8.01 (s, 2H), 7.83 (s, 3H), 7.57 (s, 1H), 7.41 (dd, J=8.0, 1.4 Hz, 1H), 7.13 (t, J=8.1 Hz, 1H), 6.69 (dd, J=8.1, 1.4 Hz, 1H), 4.07-3.94 (m, 2H), 3.85-3.74 (m, 1H), 3.74-3.62 (m, 1H), 3.41-3.20 (m, 1H), 2.26-2.14 (m, 1H), 2.11-1.95 (m, 3H), 1.95-1.82 (m, 1H), 1.61 (q, J=11.8, 11.0 Hz, 1H). $^{19}$F NMR (376 MHz, DMSO-$d_6$) δ -74.61 (d, J=5.5 Hz). LCMS ESI$^+$ calc'd for $C_{18}H_{19}Cl_2N_5S$: 408.1 [M+H$^+$]. found: 408.1 [M+H$^+$].

Example 57: 9-(8-((2,3-dichlorophenyl)thio)imidazo[1,2-c]pyrimidin-5-yl)-1,9-diazaspiro[5.5]undecane

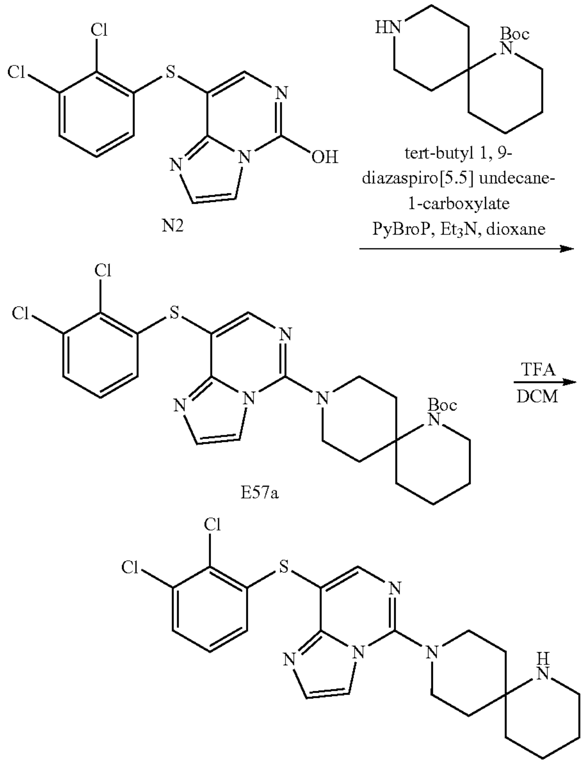

N2

E57a

Example 57

Compound E57a: To Compound N2 (0.050 g) and tert-butyl 1,9-diazaspiro[5.5]undecane-1-carboxylate (0.053 g) in 1,4-dioxane (1.5 mL) was added PyBroP (0.098 g) and triethylamine (0.4 mL), After 16 h, the reaction was diluted with EtOAc, washed with saturated sodium bicarbonate and brine, dried over sodium sulfate, concentrated in vacuo, and purified by column chromatography (0-100% EtOAc in hexanes) to give Compound E57a. $^1$H NMR (400 MHz, DMSO-$d_6$) δ 8.02 (s, 1H), 7.88 (d, J=1.5 Hz, 1H), 7.54 (d, J=1.4 Hz, 1H), 7.40 (dd, J=8.0, 1.4 Hz, 1H), 7.11 (t, J=8.1 Hz, 1H), 6.68 (dd, J=8.1, 1.4 Hz, 1H), 3.72-3.59 (m, 2H), 3.59-3.51 (m, 2H), 3.48 (t, J=5.9 Hz, 2H), 2.85 (ddd, J=12.9, 8.3, 3.6 Hz, 2H), 1.81-1.57 (m, 6H), 1.52 (dt, J=12.7, 5.9 Hz, 2H), 1.39 (s, 9H). LCMS ESI$^+$ calc'd for $C_{26}H_{31}Cl_2N_5O_2S$: 548.2 [M+H$^+$]. found: 548.3 [M+H$^+$].

Example 57: A solution of Compound E57a (0.043 g) in DCM (2.0 mL) was added TFA (0.5 mL). After 30 min, the reaction was concentrated in vacuo and the residue was lyophilized from MeCN and water to give Example 57. $^1$H NMR (400 MHz, DMSO-$d_6$) δ 8.63 (s, 2H), 8.09 (s, 1H), 7.94 (d, J=1.6 Hz, 1H), 7.65 (d, J=1.6 Hz, 1H), 7.43 (dd, J=8.0, 1.4 Hz, 1H), 7.13 (t, J=8.0 Hz, 1H), 6.73 (dd, J=8.1, 1.4 Hz, 1H), 3.89 (d, J=14.0 Hz, 2H), 3.43 (t, J=12.0 Hz, 2H), 3.11 (s, 2H), 2.08 (d, J=13.5 Hz, 2H), 1.98 (t, J=11.3 Hz, 2H), 1.87 (s, 2H), 1.66 (s, 4H). $^{19}$F NMR (376 MHz, DMSO-$d_6$) δ -74.86 (d, J=4.6 Hz). LCMS ESI$^+$ calc'd for $C_{21}H_{23}Cl_2N_5S$: 448.1 [M+H$^+$]; found: 448.2 [M+H$^+$].

Example 58: 6-(8-((2,3-dichlorophenyl)thio)imidazo[1,2-c]pyrimidin-5-yl)-6-azaspiro[3.4]octan-2-amine

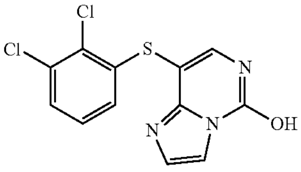

N2

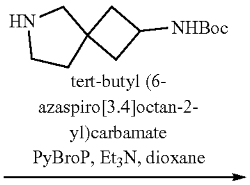

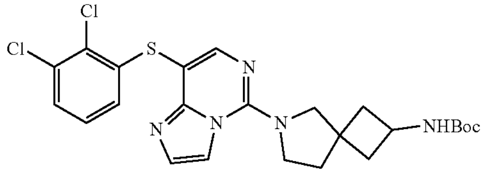

E58a

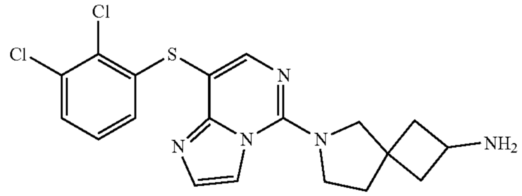

Example 58

Compound E58a: To Compound N2 (0.049 g) and tert-butyl (6-azaspiro[3.4]octan-2-yl)carbamate (0.038 g) in 1,4-dioxane (1.5 mL) was added PyBroP (0.092 g) and triethylamine (0.4 mL), After 16 h, the reaction was diluted with EtOAc, washed with saturated sodium bicarbonate and brine, dried over sodium sulfate, concentrated in vacuo, and purified by column chromatography (0-100% EtOAc in hexanes) to give Compound E58a. $^1$H NMR (400 MHz, DMSO-$d_6$) δ 8.17 (dd, J=10.6, 1.7 Hz, 1H), 7.88 (d, J=1.0 Hz, 1H), 7.42 (d, J=1.7 Hz, 1H), 7.38 (dd, J=8.0, 1.4 Hz, 1H), 7.19 (t, J=6.7 Hz, 1H), 7.11 (td, J=8.0, 2.1 Hz, 1H), 6.64 (dd, J=8.1, 1.4 Hz, 1H), 4.09-3.97 (m, 1H), 3.92 (d, J=11.4 Hz, 2H), 3.84 (dd, J=13.3, 6.4 Hz, 2H), 2.39-2.19 (m, 2H), 1.96 (dq, J=18.4, 7.5, 5.2 Hz, 4H), 1.37 (s, 9H). LCMS ESI$^+$ calc'd for $C_{24}H_{27}Cl_2N_5O_2S$: 520.1 [M+H$^+$]. found: 520.2 [M+H$^+$].

Example 58: A solution of Compound E58a (0.045 g) in DCM (2.0 mL) was added TFA (0.5 mL). After 30 min, the reaction was concentrated in vacuo and the residue was lyophilized from water to give Example 58. $^1$H NMR (400 MHz, DMSO-$d_6$) δ 8.63 (s, 2H), 8.09 (s, 1H), 7.94 (d, J=1.6 Hz, 1H), 7.65 (d, J=1.6 Hz, 1H), 7.43 (dd, J=8.0, 1.4 Hz, 1H), 7.13 (t, J=8.0 Hz, 1H), 6.73 (dd, J=8.1, 1.4 Hz, 1H), 3.89 (d, J=14.0 Hz, 2H), 3.43 (t, J=12.0 Hz, 2H), 3.11 (s, 2H), 2.08 (d, J=13.5 Hz, 2H), 1.98 (t, J=11.3 Hz, 2H), 1.87 (s, 2H), 1.66 (s, 4H). $^{19}$F NMR (376 MHz, DMSO-$d_6$) δ −74.86 (d, J=4.6 Hz). LCMS ESI$^+$ calc'd for $C_{19}H_{19}Cl_2N_5S$: 420.1 [M+H$^+$]. found: 420.2 [M+H$^+$].

Example 59: 1-(8-((2,3-dichlorophenyl)thio)imidazo[1,2-c]pyrimidin-5-yl)azepan-3-amine

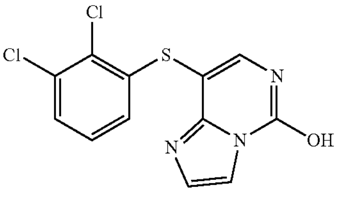

N2

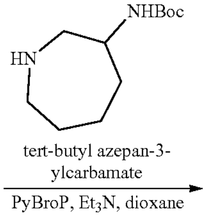

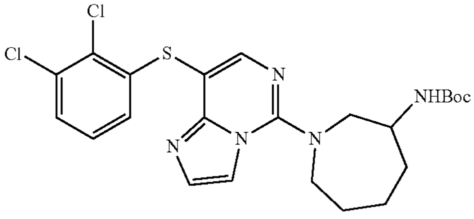

E59a

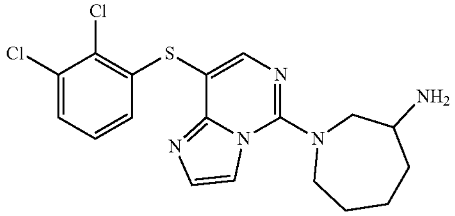

Example 59

Compound E59a: To Compound N2 (0.034 g) and tert-butyl azepan-3-ylcarbamate (0.033 g) in 1,4-dioxane (1.5 mL) was added PyBroP (0.052 g) and triethylamine (0.05 mL), After 16 h, the reaction was diluted with EtOAc, washed with saturated sodium bicarbonate and brine, dried over sodium sulfate, concentrated in vacuo, and purified by column chromatography (0-100% EtOAc in hexanes) to give Compound E59a. $^1$H NMR (400 MHz, DMSO-$d_6$) δ 8.05 (s, 1H), 7.94 (s, 1H), 7.49 (d, J=1.6 Hz, 1H), 7.39 (dd, J=8.0, 1.4 Hz, 1H), 7.11 (t, J=8.0 Hz, 1H), 7.01 (d, J=8.3 Hz, 1H), 6.67 (dd, J=8.1, 1.4 Hz, 1H), 4.08 (dd, J=14.6, 4.4 Hz, 1H), 4.00-3.80 (m, 2H), 3.72-3.61 (m, 1H), 3.61-3.48 (m, 1H), 2.00-1.86 (m, 1H), 1.86-1.74 (m, 3H), 1.66-1.42 (m, 2H), 1.37 (s, 9H). LCMS ESI$^+$ calc'd for $C_{23}H_{27}Cl_2N_5O_2S$: 508.1 [M+H$^+$]; found: 508.2 [M+H$^+$].

Example 59: A solution of Compound E59a (0.027 g) in DCM (2.0 mL) was added TFA (0.5 mL). After 2 h, the reaction was concentrated in vacuo and the residue was lyophilized from MeCN and water to give Example 59. $^1$H NMR (400 MHz, DMSO-$d_6$) δ 8.00 (s, 1H), 7.98 (s, 1H), 7.92 (s, 3H), 7.58 (s, 1H), 7.42 (dd, J=8.0, 1.3 Hz, 1H), 7.14 (t, J=8.0 Hz, 1H), 6.73 (dd, J=8.0, 0.9 Hz, 1H), 4.03 (d, J=5.4 Hz, 2H), 4.00-3.90 (m, 1H), 3.81-3.54 (m, 2H), 2.13-1.89 (m, 2H), 1.89-1.76 (m, 2H), 1.73-1.44 (m, 2H). $^{19}$F NMR (376 MHz, DMSO-$d_6$) δ −74.79 (d, J=38.7 Hz). LCMS ESI$^+$ calc'd for $C_{18}H_{19}Cl_2N_5S$: 408.1 [M+H$^+$]. found: 408.2 [M+H$^+$].

Example 60: (R)-8-(8-(2,3-dichlorophenyl)-7-methyl-[1,2,4]triazolo[1,5-c]pyrimidin-5-yl)-8-azaspiro[4.5]decan-1-amine

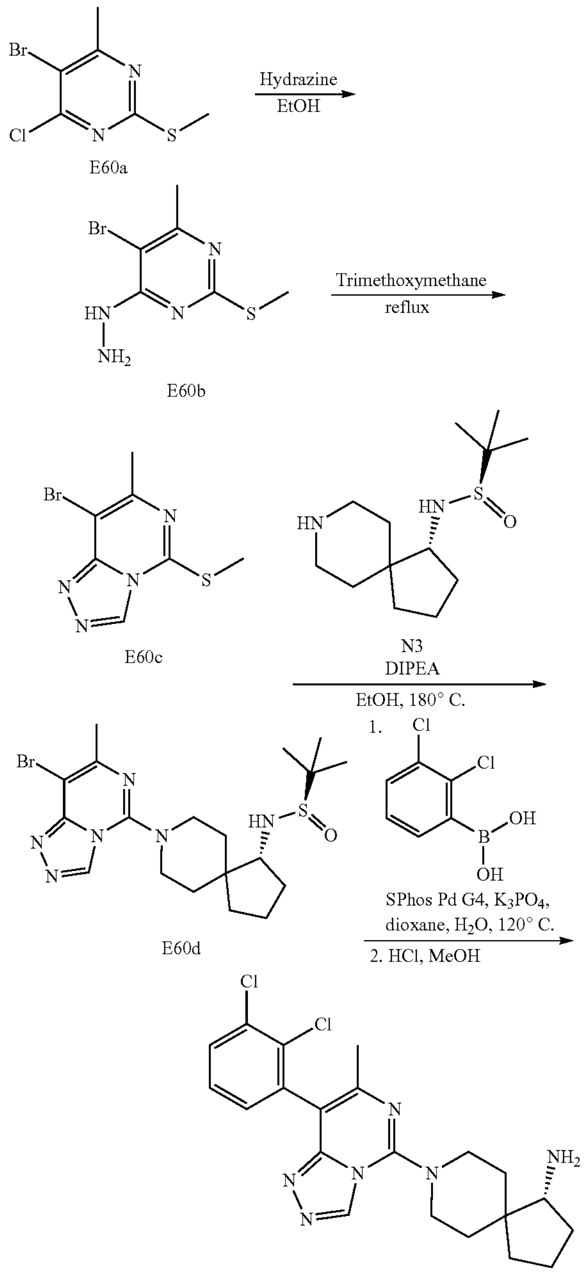

E60a, E60b, E60c, E60d, Example 60

Compound E60b: To a solution of Compound E60a (8 g, 31.5 mmol) in EtOH (50.0 mL) was added hydrazine (2.1 g, 2.1 mmol), then the reaction was stirred at RT for 4 h. Solid crashed out of reaction mixture and the precipitate was then filtered, rinsed with hexane and dried on high vacuum to afford Compound E60b. LCMS ESI$^+$ calc'd for $C_6H_9BrN_4S$: 248.9 [M+H]. found: 248.9.

Compound E60c: Compound E60b (0.52 g, 2.1 mmol) was mixed with trimethoxymethane (4.4 g, 41.2 mmol), then the reaction was heated at reflux for 3 h. The reaction mixture was then cooled down and white solid crashed out of reaction mixture. The precipitate was then filtered, rinsed with hexane and dried on high vacuum to afford Compound E60c. LCMS ESI$^+$ calc'd for $C_7H_7BrN_4S$: 258.9 [M+H]. found: 258.9.

Compound E60d: To a solution of Compound E60c (150 mg, 0.58 mmol) and Compound N3 (299 mg, 1.16 mmol) in EtOH (5 mL) was added DIPEA (0.6 mL). The reaction mixture was heated at 180° C. for 3 h, the mixture was diluted with EtOAc, washed with brine, the organic solvent was concentrated in vacuo, and then purified with Combi-Flash column to afford Compound E60d. LCMS ESI$^+$ calc'd for $C_{19}H_{29}BrN_6OS$: 469.1 [M+H$^+$]. found: 469.0 [M+H$^+$].

Example 60: A solution of Compound E60d (14 mg, 0.03 mmol), 2,3-dichlorophenyl)boronic acid (17 mg, 0.09 mmol), SPhos Pd G4 (5 mg, 0.006 mmol), potassium phosphate tribasic (25 mg, 0.1 mmol) were added to 1,4-dioxane (2 mL) and water (2 mL). The reaction mixture was heated to 120° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 60. $^1$H NMR (400 MHz, Methanol-d$_4$) δ 8.26 (s, 1H), 7.68 (dd, J=8.1, 1.6 Hz, 1H), 7.45 (t, J=7.9 Hz, 1H), 7.34 (dd, J=7.7, 1.6 Hz, 1H), 5.14 (s, 2H), 3.57-3.39 (m, 2H), 3.29 (d, J=6.9 Hz, 1H), 2.28 (dd, J=8.1, 3.9 Hz, 1H), 2.24 (s, 3H), 2.03-1.57 (m, 9H). LCMS ESI$^+$ calc'd for $C_{21}H_{24}Cl_2N_6$: 431.1 [M+H$^+$]. found: 431.2 [M+H$^+$].

Example 61: 1-(8-((2,3-dichlorophenyl)thio)-[1,2,4]triazolo[4,3-c]pyrimidin-5-yl)-4-methylpiperidin-4-amine

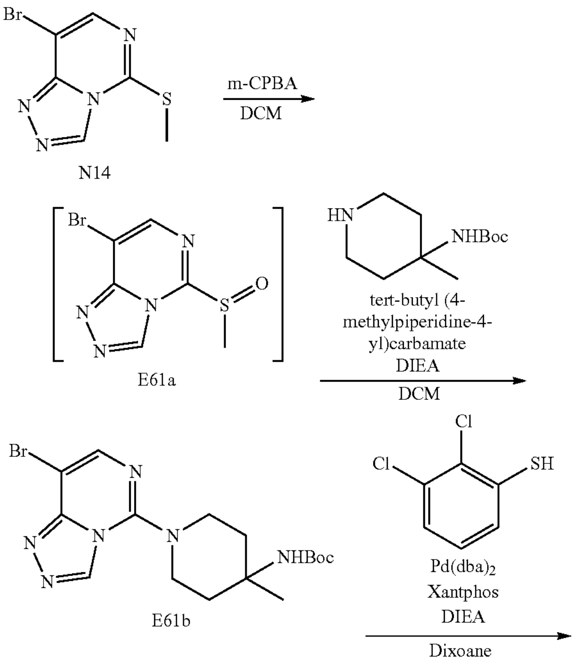

N14, E61a, E61b

-continued

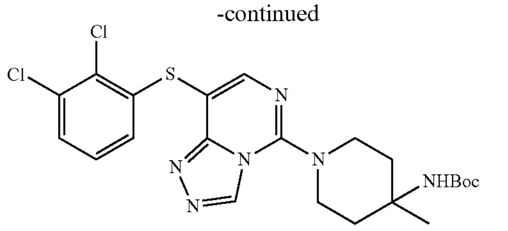

E61c

+

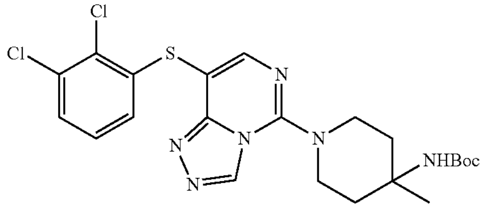

E61d

Compound E61a: In a 10 mL reaction vial Compound N14 (210 mg, 0.857 mmol) was dissolved in DCM (10 mL) at room temperature. Then the solution was cooled down to 0° C. A solution of m-CPBA (max 77%) (384 mg, 1.71 mmol) in DCM (5 mL) was added dropwise over 2 min. The resulting reaction mixture was stirred at 0° C. for 20 min. Then another solution of m-CPBA (max 77%) (95.6 mg, 0.43 mmol) in DCM (5 mL) was added dropwise. The reaction mixture was stirred without re-charged cold bath for 90 min. The resulting sulfoxide intermediate Compound E61a in DCM solution can be used directly for next step without purification. LCMS ESI$^+$ calc'd for $C_6H_5BrN_4OS$: 260.9 [M+H$^+$]. found: 261.0 [M+H$^+$].

Compound E61b: To the pre-formed sulfoxide intermediate Compound E61a in DCM, was added tert-butyl (4-methylpiperidin-4-yl)carbamate (580 mg, 2.7 mmol) and DIEA (1 mL, 5.8 mmol) was added. Reaction mixture was stirred at room temperature for 17 hours. Solvent was removed under vacuum. The residue was diluted with EtOAc (30 mL) and was then treated with saturated aqueous $NH_4Cl$ solution (30 mL). The organic phase was separated and was washed with saturated brine solution (30 mL). The organic phase was separated and concentrated to dryness. The residue was purified on silica gel directly with 0-100% EtOAc in Hex to afford product Compound E61b. LCMS ESI$^+$ calc'd for $C_{16}H_{23}BrN_6O_2$: 411.1 [M+H$^+$]. found: 411.2 [M+H$^+$].

Compound E61c and Compound E61d: In a 10 mL reaction vial Compound E61b (28 mg, 0.068 mmol), 2,3-dichlorobenzenethiol (45.1 mg, 0.252 mmol) and Xantphos (15.8 mg, 0.027 mmol) were dissolved in dioxane (1.5 mL) at room temperature. DIEA (0.047 mL, 0.272 mmol) was added dropwise. $Pd(dba)_2$ (7.8 mg, 0.014 mmol) was added. The resulting reaction mixture was purged with argon for 5 min and then heated under microwave at 115° C. for 90 min. Reaction mixture was cooled down and then was purified directly on silica gel column with 0-100% EtOAc in Hex to afford two products as isomers due to Dimroth rearrangement. The first to elute was the Dimroth Rearrangement product: Compound E61d. LCMS ESI$^+$ calc'd for $C_{22}H_{26}Cl_2N_6O_2S$: 509.1 [M+H$^+$]. found: 509.1 [M+H$^+$]. The second to elute with more polarity on silica gel was Compound E61c (12 mg). LCMS ESI$^+$ calc'd for $C_{22}H_{26}Cl_2N_6O_2S$: 509.1 [M+H$^+$]. found: 509.1 [M+H$^+$].

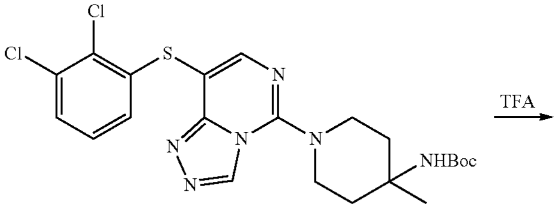

E61c

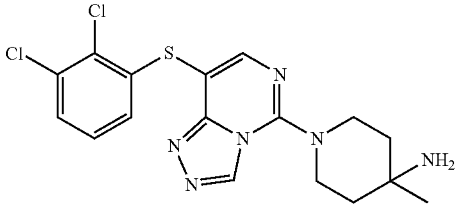

Example 61

Example 61: In a 5 mL reaction vial, Compound E61c (12 mg, 0.024 mmol) was dissolved in TFA (1 mL). Reaction mixture was stirred at room temperature for 5 min and then was concentrated to dryness. The residue was dissolved in methanol (2 mL) and was then purified with reverse phase prep-HPLC with water (containing 0.5% TFA) and acetonitrile (containing 0.5% TFA) to afford Example 61 as a TFA salt. $^1$H NMR (400 MHz, Acetonitrile-d3) δ 8.98 (s, 1H), 7.97 (s, 1H), 7.46 (s, 3H), 7.37 (dd, J=8.0, 1.4 Hz, 1H), 7.08 (t, J=8.0 Hz, 1H), 6.89 (dd, J=8.1, 1.4 Hz, 1H), 3.99 (dt, J=14.3, 4.7 Hz, 2H), 3.55 (ddd, J=13.8, 10.0, 3.3 Hz, 2H), 2.14 (ddd, J=14.0, 9.9, 4.1 Hz, 2H), 2.06-1.98 (m, 2H), 1.55 (s, 3H). LCMS ESI$^+$ calc'd for $C_{17}H_{18}Cl_2N_6S$: 409.1 [M+H$^+$]. found: 409.1 [M+H$^+$].

Example 62: 1-(8-((2,3-dichlorophenyl)thio)-[1,2,4]triazolo[1,5-c]pyrimidin-5-yl)-4-methylpiperidin-4-amine

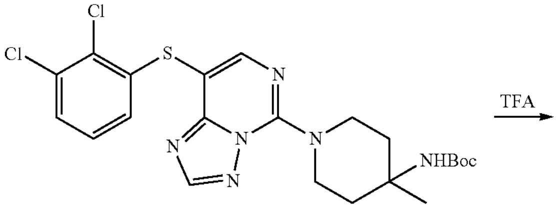

E61d

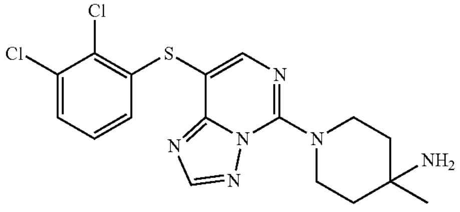

Example 62

Example 62: In a 5 mL reaction vial, Compound E61d (20 mg, 0.039 mmol) was dissolved in TFA (1 mL). Reaction mixture was stirred at room temperature for 5 min and then was concentrated to dryness. The residue was dissolved in methanol (2 mL) and was then purified with reverse phase prep-HPLC with water (containing 0.5% TFA) and acetonitrile (containing 0.5% TFA) to afford Example 62 as a TFA salt. $^1H$ NMR (400 MHz, Methanol-d4) δ 8.36 (s, 1H), 8.23 (s, 1H), 7.30 (dd, J=8.0, 1.4 Hz, 1H), 7.04 (t, J=8.1 Hz, 1H), 6.69 (dd, J=8.1, 1.4 Hz, 1H), 4.93-4.87 (m, 2H), 3.84 (ddd, J=14.0, 8.6, 5.0 Hz, 2H), 2.00 (q, J=4.4 Hz, 4H), 1.55 (s, 3H). LCMS ESI$^+$ calc'd for $C_{17}H_{18}Cl_2N_6S$: 409.1 [M+H$^+$]. found: 409.0 [M+H$^+$].

Example 63: (R)-8-(8-((2-amino-3-chloropyridin-4-yl)thio)-[1,2,4]triazolo[4,3-c]pyrimidin-5-yl)-8-azaspiro[4.5]decan-1-amine

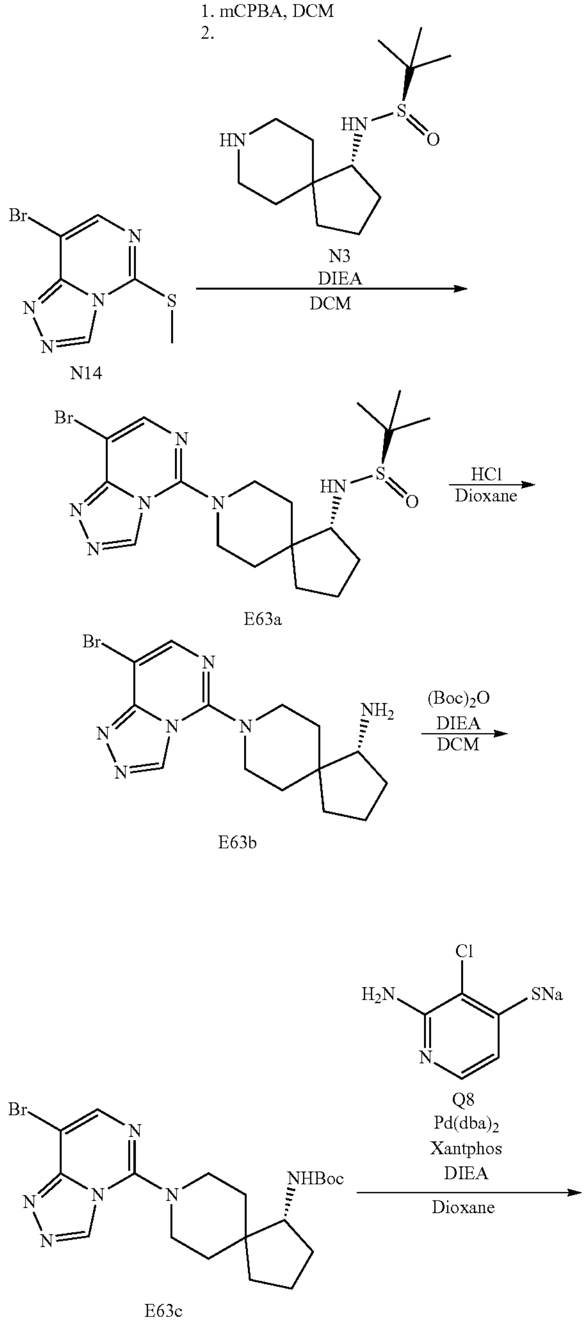

-continued

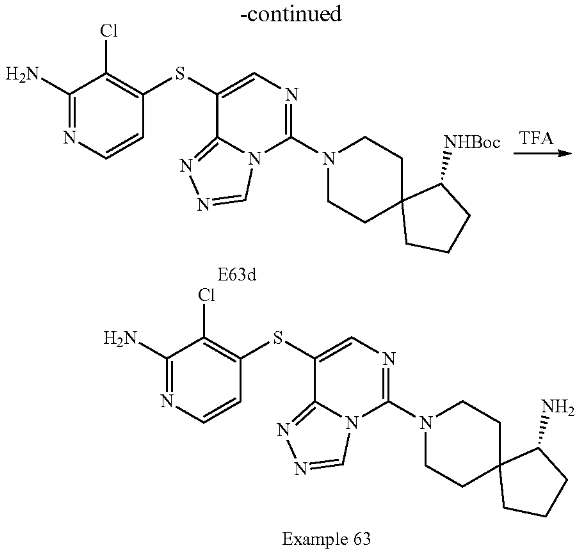

Compound E63a: Compound N14 (300 mg, 1.244 mmol) was dissolved in DCM (10 mL) at room temperature. The solution was cooled down to 0° C. Then a solution of m-CPBA (77% purity) (548 mg, 2.45 mmol) in DCM (5 mL) was added dropwise. In 20 min, another portion of m-CPBA (77% purity) (136 mg, 0.612 mmol) in DCM (2 mL) was added dropwise. The resulting reaction mixture was stirred at 0° C. for 30 min and then stirred recharged cold bath for 1.5 hours. To this pre-formed sulfoxide, was added a solution of Compound N3 (937 mg, 3.6 mmol) in DCM (5 mL). DIEA (3 mL) was added to reaction mixture. The resulting reaction mixture was then stirred at room temperature for 17 hours. Reaction mixture was concentrated to dryness. The residue was treated with EtOAc (50 mL) and water (50 mL). Saturated aqueous $NaHCO_3$ solution (30 mL) was added. Organic phase was separated and then concentrated to dryness. Residue was purified on silica gel column with 0-100% EtOAc in Hex to afford Compound E63a. LCMS ESI$^+$ calc'd for $C_{18}H_{27}BrN_6OS$: 455.1 [M+H$^+$]; found: 455.1 [M+H$^+$].

Compound E63b: Compound E63a (250 mg, 0.55 mmol) was treated with HCl (4 M in dioxane, 7.8 mL) at room temperature. The resulting reaction mixture was stirred at room temperature for 1 hour. The reaction mixture was concentrated to dryness to afford product Compound E63b as an HCl salt. LCMS ESI$^+$ calc'd for $C_{14}H_{19}BrN_6$: 351.1 [M+H$^+$]. found: 351.1 [M+H$^+$].

Compound E63c: Compound E63b (190 mg, 0.55 mmol) was dissolved in DCM (10 mL) at room temperature. $Boc_2O$ (120 mg, 0.55 mmol) and DIEA (0.9 mL, 5.5 mmol) were added sequentially. The reaction mixture was stirred at room temperature for 2 hours. Reaction mixture was then concentrated to dryness. The residue was loaded on silica gel column with solid loading method and was purified with 0-100% EtOAc/Hex to afford product Compound E63c. LCMS ESI$^+$ calc'd for $C_{19}H_{27}BrN_6O_2$: 451.1 [M+H$^+$]. found: 451.2 [M+H$^+$].

Compound E63d: In a 10 mL reaction vial Compound E63c (47 mg, 0.104 mmol), Compound Q8 (70 mg, 0.385 mmol) and Xantphos (24 mg, 0.042 mmol) were dissolved in dioxane (3 mL) at room temperature. DIEA (0.072 mL, 0.417 mmol) was added dropwise. $Pd(dba)_2$ (12 mg, 0.021 mmol) was then added. The resulting reaction mixture was purged with argon for 5 min and then heated under microwave at 115° C. for 2 hours. Reaction mixture was cooled down and then was purified directly on silica gel column with 0-100% EtOAc in Hex and then 10% MeOH in EtOAc to afford Compound E63d. LCMS ESI$^+$ calc'd for $C_{24}H_{31}ClN_8O_2S$: 531.2 [M+H$^+$]. found: 531.2 [M+H$^+$].

Example 63: In a 5 mL reaction vial, Compound E63d (23 mg, 0.043 mmol) was dissolved in TFA (1 mL). Reaction mixture was stirred at room temperature for 5 min and then was concentrated to dryness. The residue was dissolved in methanol (2 mL) and was then purified with reverse phase prep-HPLC with water (containing 0.5% TFA) and acetonitrile (containing 0.5% TFA) to afford Example 63 as a TFA salt. $^1$H NMR (400 MHz, Acetonitrile-d3) δ 9.01 (s, 1H), 8.14 (br, 2H), 7.99 (s, 1H), 7.48 (d, J=6.8 Hz, 1H), 7.11 (br, 3H), 6.31 (d, J=6.7 Hz, 1H), 4.26-4.06 (m, 2H), 3.61-3.34 (m, 2H), 2.31-2.17 (m, 1H), 1.94-1.75 (m, 8H), 1.74-1.55 (m, 2H). LCMS ESI$^+$ calc'd for $C_{19}H_{23}ClN_8S$: 431.2 [M+H$^+$]. found: 431.1 [M+H$^+$].

Example 64: (1-(8-((2,3-dichlorophenyl)thio)-3-methyl-[1,2,4]triazolo[4,3-c]pyrimidin-5-yl)-4-methylpiperidin-4-yl)methanamine

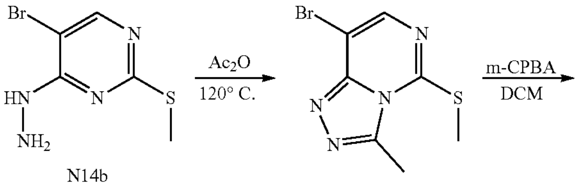

N14b

E64a

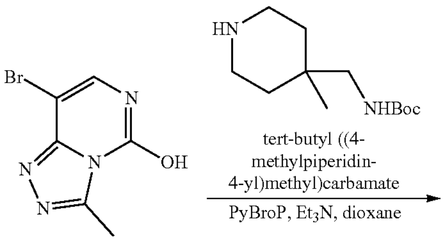

E64b

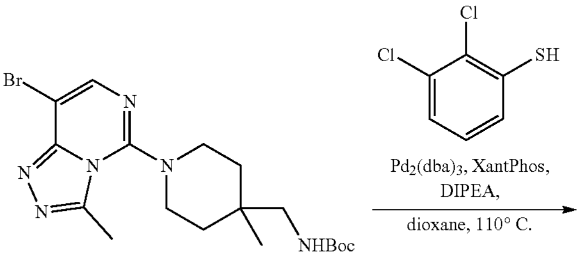

E64c

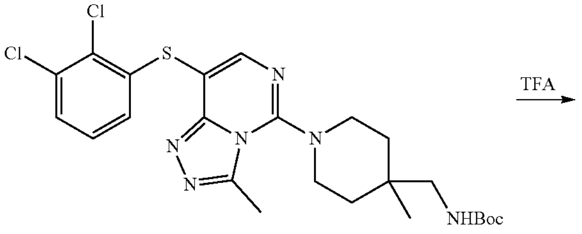

E64d

-continued

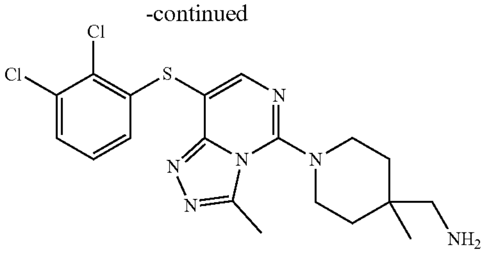

Example 64

Compound E64a: Compound N14b (0.755 g, 3.21 mmol) was dissolved in Acetic anhydride (2 mL) and heated to 120° C. for 4 h. The solution was cooled to room temperature and concentrated in vacuo. The residue was dissolved in EtOAc and a saturated sodium bicarbonate solution was added, and the biphasic solution was stirred for 1 h. The organic partition was washed with brine, dried over magnesium sulfate, and concentrated in vacuo. The residue was reconstituted in toluene and purified by column chromatography (0-100% EtOAc in Hexanes). This provided Compound E64a. LCMS ESI$^+$ calc'd for $C_7H_7BrN_4S$: 259.0 [M+H$^+$]. found: 259.0 [M+H$^+$].

Compound E64b: Compound E64a (0.403 g, 1.55 mmol) was dissolved in DCM (5 mL) and cooled to 0° C. A solution was made of mCPBA (0.697 g, 3.11 mmol) dissolved in DCM (5 mL) and added dropwise to the solution of Compound E64a. The solution was warmed to room temperature. After 3 h the product had precipitated from the solution. The solids were collected by filtration. This provided Compound E64b. LCMS ESI$^+$ calc'd for $C_6H_5BrN_4S$: 229.0 [M+H$^+$]. found: 228.9 [M+H$^+$].

Compound E64c: To Compound E64b (150 mg, 0.655 mmol) and tert-butyl ((4-methylpiperidin-4-yl)methyl)carbamate (194.4 mg, 0.851 mmol) in 1,4-dioxane (5 mL) was added PyBroP (366.4 mg, 0.786 mmol) and triethylamine (0.23 mL, 1.6 mmol), After 3 h, the reaction was diluted with EtOAc, dried over sodium sulfate, concentrated in vacuo, and purified by column chromatography (0-100% EtOAc in hexanes) to give Compound E64c. LCMS ESI$^+$ calc'd for $C_{18}H_{27}BrN_6O_2$: 439.1 [M+H$^+$]. found: 438.9 [M+H$^+$].

Compound E64d: Compound E64c (52 mg, 0.118 mmol) in 1,4-dioxane (2 ml) was added $Pd_2(dba)_3$ (17 mg, 0.019 mmol), XantPhos (27 mg, 0.047 mmol), 2,3-dichlorobenzenethiol (37 mg, 0.207 mmol), and DIPEA (0.041 ml, 0.237 mmol). The reaction vessel was purged with argon, sealed, and heated to 110° C. until complete consumption of starting materials. The reaction mixture was cooled to room temperature, diluted with EtOAc and washed with water followed by brine. The organic partition was dried over magnesium sulfate, and filtered through Celite. The resulting solution was concentrated and used in the next step without purification. This provided Compound E64d. LCMS ESI$^+$ calc'd for $C_{24}H_{32}ClN_7O_2S_2$: 537.1 [M+H$^+$]. found: 537.1 [M+H$^+$].

Example 64: Compound E64d was dissolved in DCM (5 ml), and TFA (1 ml) was added. The solution was concentrated and reconstituted in water and DMF and the solution was purified on preparatory HPLC (10-100% MeCN in water with 0.1% TFA, Gemini). This provided Example 64 as TFA salt. $^1$H NMR (400 MHz, DMSO-d$_6$) δ 8.17 (s, 1H), 7.73 (s, 3H), 7.39 (dd, J=8.0, 1.4 Hz, 1H), 7.12 (t, J=8.1 Hz, 1H), 6.69 (dd, J=8.1, 1.4 Hz, 1H), 4.51 (d, J=13.8 Hz, 2H), 3.83 (t, J=10.9 Hz, 2H), 2.81 (d, J=6.0 Hz, 2H), 2.40 (s, 3H), 1.71-1.41 (m, 4H), 1.10 (s, 3H). LCMS $ESI^+$ calc'd for $C_{19}H_{22}Cl_2N_6S$: 437.1 [$M+H^+$]. found: 437.1 [$M+H^+$].

Example 65: (R)-8-(8-(2,3-dichlorophenyl)-7-methyl[1,2,4]triazolo[4,3-c]pyrimidin-5-yl)-8-azaspiro[4.5]decan-1-amine

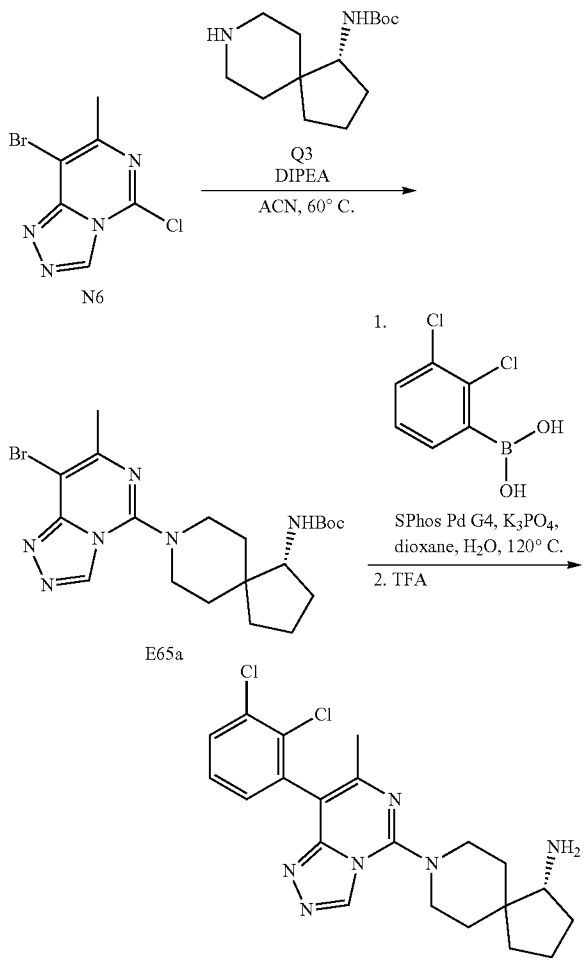

Example 65

Compound E65a: To a solution of Compound N6 (100 mg, 0.4 mmol) and Compound Q3 (113 mg, 0.44 mmol) in ACN (5 mL) was added DIPEA (0.2 mL). The reaction mixture was heated at 80° C. for 10 min, the mixture was diluted with EtOAc, washed with brine, the organic solvent was concentrated in vacuo, and then purified with Combi-Flash column to afford Compound E65a. LCMS $ESI^+$ calc'd for $C_{20}H_{29}BrN_6O_2$: 465.1 [$M+H^+$]. found: 465.1 [$M+H^+$].

Example 65: A solution of Compound E65a (47 mg, 0.1 mmol), 2,3-dichlorophenyl)boronic acid (58 mg, 0.3 mmol), SPhos Pd G4 (16 mg, 0.02 mmol), potassium phosphate tribasic (86 mg, 0.4 mmol) were added to 1,4-dioxane (2 mL) and water (2 mL). The reaction mixture was heated to 70° C. for 30 min in a microwave reactor. The mixture was dilute with EtOAc, filtered through Celite, and concentrated in vacuo. The crude material was dissolved in TFA (1 mL) and stirred for 5 min. The reaction solvent was evaporated and the residue was purified by preparatory HPLC (10-75% MeCN in water with 0.1% TFA, Gemini) to afford Example 65. $^1H$ NMR (400 MHz, Methanol-d4) δ 9.24 (s, 1H), 7.73 (dd, J=8.1, 1.6 Hz, 1H), 7.49 (t, J=7.9 Hz, 1H), 7.39 (dd, J=7.7, 1.6 Hz, 1H), 4.14 (t, J=16.4 Hz, 2H), 3.45 (ddt, J=13.5, 7.4, 4.8 Hz, 2H), 3.35 (d, J=6.3 Hz, 1H), 2.29 (td, J=7.7, 3.9 Hz, 1H), 2.24 (s, 3H), 2.09-1.74 (m, 7H), 1.68 (t, J=13.2 Hz, 2H). LCMS $ESI^+$ calc'd for $C_{21}H_{24}Cl_2N_6$: 431.1 [$M+H^+$]; found: 431.2 [$M+H^+$].

Example 66: (R)-8-(8-(6-amino-4,5-dichloropyridin-3-yl)-7-methyl-[1,2,4]triazolo[4,3-c]pyrimidin-5-yl)-8-azaspiro[4.5]decan-1-amine

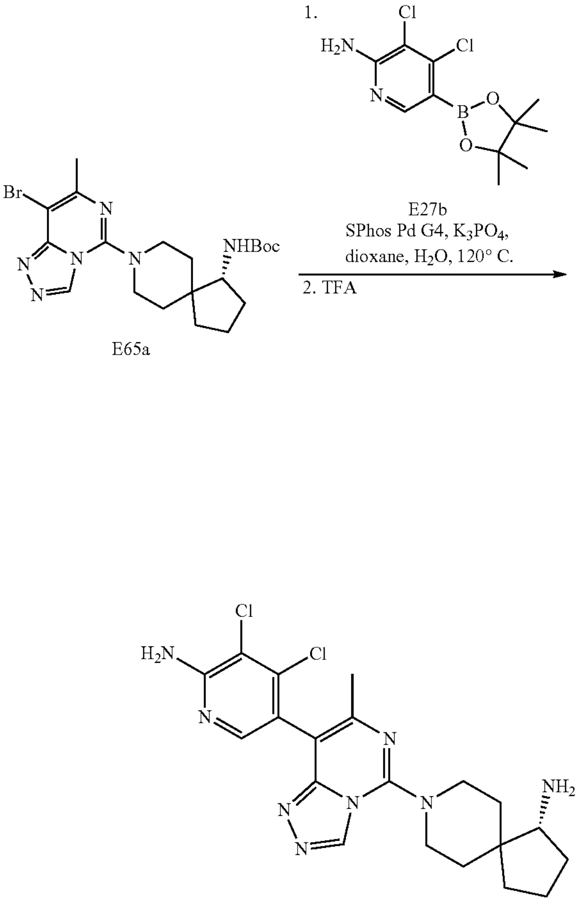

Example 66

Example 66: A solution of Compound E65a (51 mg, 0.1 mmol), Compound E27b (70 mg, 0.24 mmol), SPhos Pd G4 (17 mg, 0.02 mmol), potassium phosphate tribasic (93 mg, 0.44 mmol) were added to 1,4-dioxane (1 mL) and water (1 mL). The reaction mixture was heated to 70° C. for 30 min in a microwave reactor. The mixture was dilute with EtOAc, filtered through Celite, and concentrated in vacuo. The crude material was dissolved in TFA (1 mL) and stirred for 5 min. The reaction solvent was evaporated and the residue was purified by preparatory HPLC (10-75% MeCN in water with 0.1% TFA, Gemini) to afford Example 66. $^1H$ NMR (400 MHz, Methanol-d4) δ 9.26 (s, 1H), 7.93 (s, 1H), 4.28-4.06 (m, 2H), 3.48 (tdd, J=13.6, 6.9, 3.0 Hz, 2H), 3.35 (d, J=6.5 Hz, 1H), 2.31 (s, 4H), 2.09-1.75 (m, 7H), 1.74-1.60 (m, 2H). LCMS $ESI^+$ calc'd for $C_{20}H_{24}Cl_2N_8$: 447.1 [$M+H^+$]. found: 447.2 [$M+H^+$].

Example 67: (3S,4S)-8-(8-(2,3-dichlorophenyl)-7-methyl-[1,2,4]triazolo[4,3-c]pyrimidin-5-yl)-3-methyl-2-oxa-8-azaspiro[4.5]decan-4-amine

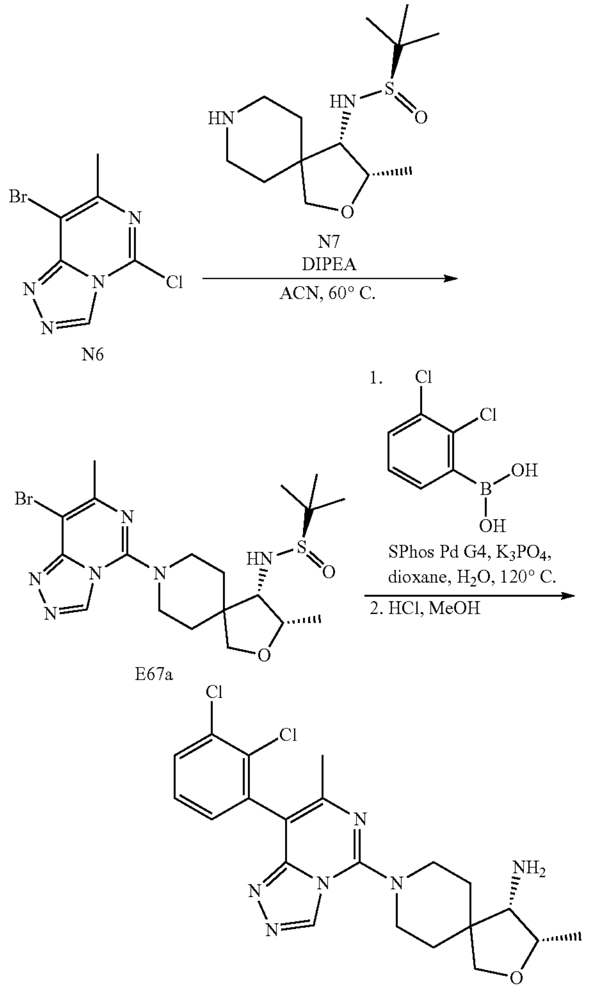

N6

E67a

Example 67

Compound E67a: To a solution of Compound N6 (110 mg, 0.44 mmol) and Compound N7 (171 mg, 0.62 mmol) in ACN (2.5 mL) was added DIPEA (0.2 mL). The reaction mixture was heated at 80° C. for 10 min, the mixture was diluted with EtOAc, washed with brine, the organic solvent was concentrated in vacuo, and then purified with Combi-Flash column to afford Compound E67a. LCMS ESI$^+$ calc'd for $C_{19}H_{29}BrN_6O_2S$: 485.1[M+H$^+$]. found: 485.1 [M+H$^+$].

Example 67: A solution of Compound E67a (91 mg, 0.19 mmol), 2,3-dichlorophenyl)boronic acid (107 mg, 0.56 mmol), SPhos Pd G4 (30 mg, 0.04 mmol), potassium phosphate tribasic (159 mg, 0.75 mmol) were added to 1,4-dioxane (2 mL) and water (2 mL). The reaction mixture was heated to 70° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 67. $^1$H NMR (400 MHz, Methanol-d4) δ 9.25 (d, J=0.6 Hz, 1H), 7.73 (dd, J=8.1, 1.6 Hz, 1H), 7.49 (t, J=7.9 Hz, 1H), 7.39 (dd, J=7.7, 1.6 Hz, 1H), 4.43-4.27 (m, 1H), 4.19-4.02 (m, 3H), 3.95 (d, J=9.1 Hz, 1H), 3.53 (d, J=4.0 Hz, 1H), 3.49-3.35 (m, 2H), 2.25 (s, 3H), 2.18-1.93 (m, 3H), 1.85 (d, J=13.3 Hz, 1H), 1.36 (d, J=6.5 Hz, 3H). LCMS ESI$^+$ calc'd for $C_{21}H_{24}Cl_2N_6O$: 447.1 [M+H$^+$]. found: 447.2 [M+H$^+$].

Example 68: (2R,4R)-4-amino-8-(8-(2,3-dichlorophenyl)-7-methyl-[1,2,4]triazolo[4,3-c]pyrimidin-5-yl)-8-azaspiro[4.5]decan-2-ol

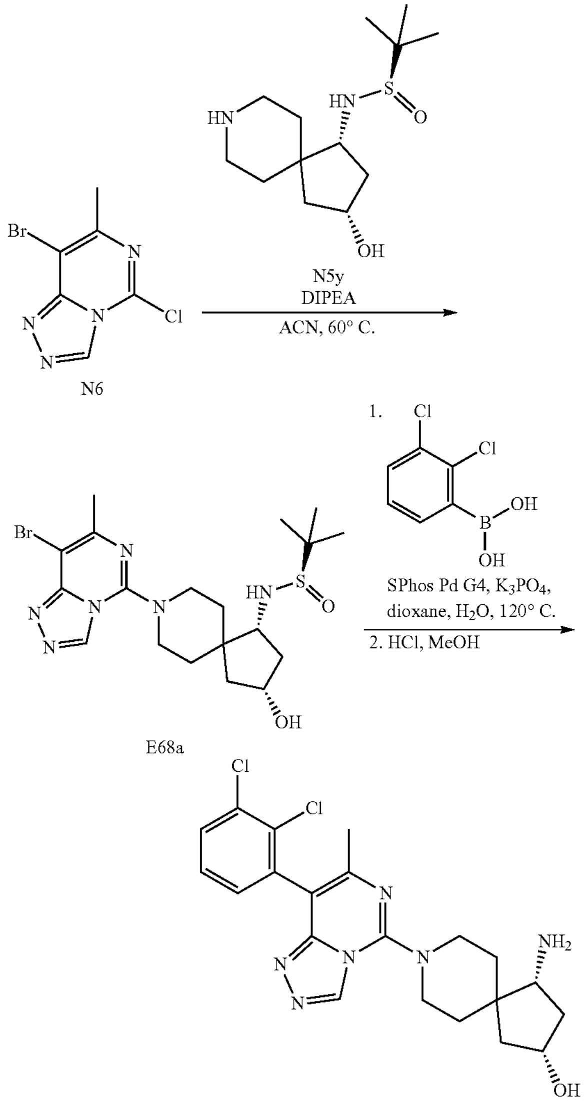

N6

E68a

Example 68

Compound E68a: To a solution of Compound N6 (380 mg, 2 mmol) and Compound N5y (836 mg, 3 mmol) in ACN (2.5 mL) was added DIPEA (0.8 mL). The reaction mixture was heated at 80° C. for 10 min, the mixture was diluted with EtOAc, washed with brine, the organic solvent was concentrated in vacuo, and then purified with Combi-Flash column to afford Compound E68a. LCMS ESI$^+$ calc'd for $C_{19}H_{29}BrN_6O_2S$: 485.1 [M+H$^+$]. found: 485.1 [M+H$^+$].

Example 68: A solution of Compound E68a (96 mg, 0.2 mmol), 2,3-dichlorophenyl)boronic acid (113 mg, 0.6 mmol), SPhos Pd G4 (31 mg, 0.04 mmol), potassium phosphate tribasic (168 mg, 0.8 mmol) were added to 1,4-dioxane (2 mL) and water (2 mL). The reaction mixture was heated to 70° C. for 30 min in a microwave reactor. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 68. $^1$H NMR (400 MHz, Methanol-d4) δ 9.25 (s, 1H), 7.73 (dd, J=8.1, 1.5 Hz, 1H), 7.49 (t, J=7.9 Hz, 1H), 7.40 (dd, J=7.7, 1.6 Hz, 1H), 4.48 (tt, J=6.1, 3.1 Hz, 1H), 4.30-4.16 (m, 1H), 4.12 (d, J=13.8 Hz, 1H), 3.54-3.35 (m, 3H), 2.53-2.36 (m, 1H), 2.25 (s, 3H), 2.20-2.12 (m, 1H), 2.08-1.83 (m, 5H), 1.67 (dd, J=13.1, 2.7 Hz, 1H). LCMS ESI$^+$ calc'd for $C_{21}H_{24}Cl_2N_6O$: 447.1 [M+H$^+$]. found: 447.2 [M+H$^+$].

Example 69: (R)-8-(7-chloro-8-(2,3-dichlorophenyl) imidazo[1,2-c]pyrimidin-5-yl)-8-azaspiro[4.5]decan-1-amine

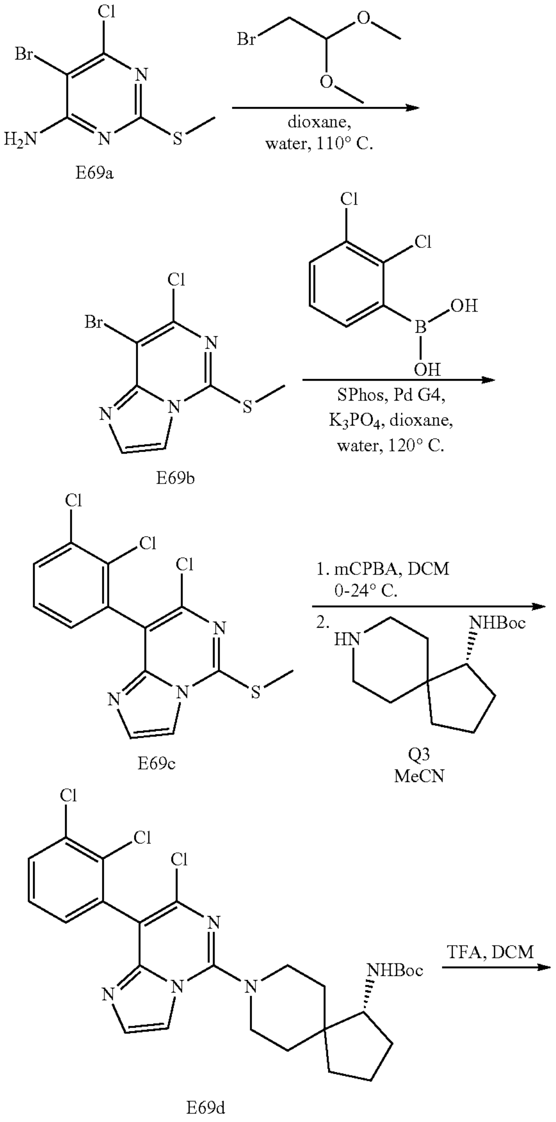

-continued

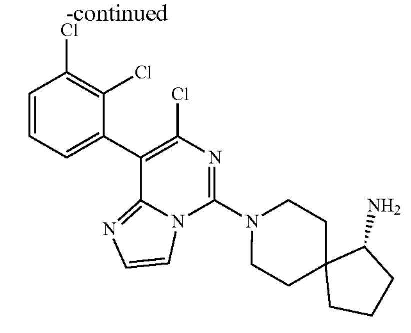

Example 69

Compound E69b: To Compound E69a (1.00 g) in 1,4-dioxane (8.0 mL) and water (2.0 mL) was added 2-bromo-1,1-dimethoxyethane (0.60 mL), then heated to 110° C. for 2 h. The mixture was the cooled to 0° C., diluted with MTBE, filtered, and the solids dried to give Compound E69b. $^1$H NMR (400 MHz, DMSO-d$_6$) δ 11.91 (s, 1H), 7.89 (d, J=1.6 Hz, 1H), 7.65 (s, 1H), 7.43 (t, J=1.3 Hz, 1H). LCMS ESI$^+$ calc'd for $C_7H_5BrClN_3S$: 279.9 [M+H$^+$]. found: 280.0 [M+H$^+$].

Compound E69c: A solution of Compound E69b (0.248 g), (2,3-dichlorophenyl) boronic acid (1.32 g), SPhos Pd G4 (0.133 g), and potassium phosphate tribasic (0.679 g) in 1,4-dioxane (8.0 mL) and water (8.0 mL) was heated in a microwave reactor to 120° C. for 30 min. The reaction was diluted with EtOAc, washed with brine, dried over sodium sulfate, and concentrated in vacuo. The residue was subjected to column chromatography (0-100% EtOAc in hexanes) to give Compound E69c. $^1$H NMR (400 MHz, DMSO-d$_6$) δ 8.01 (d, J=1.5 Hz, 1H), 7.80 (dd, J=7.8, 1.8 Hz, 1H), 7.68 (d, J=1.5 Hz, 1H), 7.53 (t, J=7.8 Hz, 1H), 7.49 (dd, J=7.7, 1.8 Hz, 1H), 2.83 (s, 3H). LCMS ESI$^+$ calc'd for $C_{13}H_8Cl_3N_3S$: 344.0 [M+H$^+$]. found: 344.1 [M+H$^+$].

Compound E69d: To a solution of Compound E69c (0.118 g), in DCM (0.7 mL) at 0° C. was added mCPBA in DCM (0.42 mL, 1 M) and after 5 min the reaction was warmed to ambient temperature. After 24 h, Compound Q3 (0.193 g) in MeCN (1.4 mL) was added and the mixture was stirred for 90 min. The reaction was then diluted with EtOAc, washed sequentially with saturated sodium thiosulfate, saturated sodium bicarbonate and brine, dried over sodium sulfate, and concentrated in vacuo. The residue was subjected to column chromatography (0-100% EtOAc in hexanes) to give Compound E69d. $^1$H NMR (400 MHz, Chloroform-d) δ 7.58-7.51 (m, 2H), 7.45 (d, J=1.5 Hz, 1H), 7.33 (td, J=7.6, 0.9 Hz, 1H), 7.29 (dt, J=7.7, 2.1 Hz, 1H), 3.95-3.79 (m, 3H), 3.21 (dp, J=22.7, 12.3, 11.7 Hz, 2H), 2.19-2.07 (m, 1H), 2.03-1.56 (m, 9H), 1.47 (s, 9H). LCMS ESI$^+$ calc'd for $C_{26}H_{30}Cl_3N_5O_2$: 550.2 [M+H$^+$]. found: 550.3 [M+H$^+$].

Example 69: To a solution of Compound E69d (0.017 g) in DCM (1.0 mL) was added TFA (0.25 mL). After 15 min, the reaction was diluted with MeCN and water and purified by preparatory HPLC (10-70% MeCN in water with 0.1% TFA, Gemini) to give Example 69. $^1$H NMR (400 MHz, DMSO-d$_6$) δ 7.82 (d, J=6.5 Hz, 4H), 7.77 (dd, J=8.0, 1.6 Hz, 1H), 7.61 (s, 1H), 7.50 (t, J=7.9 Hz, 1H), 7.42 (dt, J=7.7, 1.8 Hz, 1H), 3.91 (t, J=14.2 Hz, 2H), 3.38-3.19 (m, 3H), 2.17-2.04 (m, 1H), 1.92-1.71 (m, 5H), 1.71-1.62 (m, 2H), 1.55 (dd, J=25.9, 13.4 Hz, 2H). $^{19}$F NMR (376 MHz, DMSO-d$_6$) δ -74.95. LCMS ESI$^+$ calc'd for $C_{21}H_{22}Cl_3N_5$: 450.1 [M+H$^+$]. found: 450.3 [M+H$^+$].

Example 70: (R)-8-(8-(isoquinolin-4-ylthio)imidazo[1,2-c]pyrimidin-5-yl)-8-azaspiro[4.5]decan-1-amine

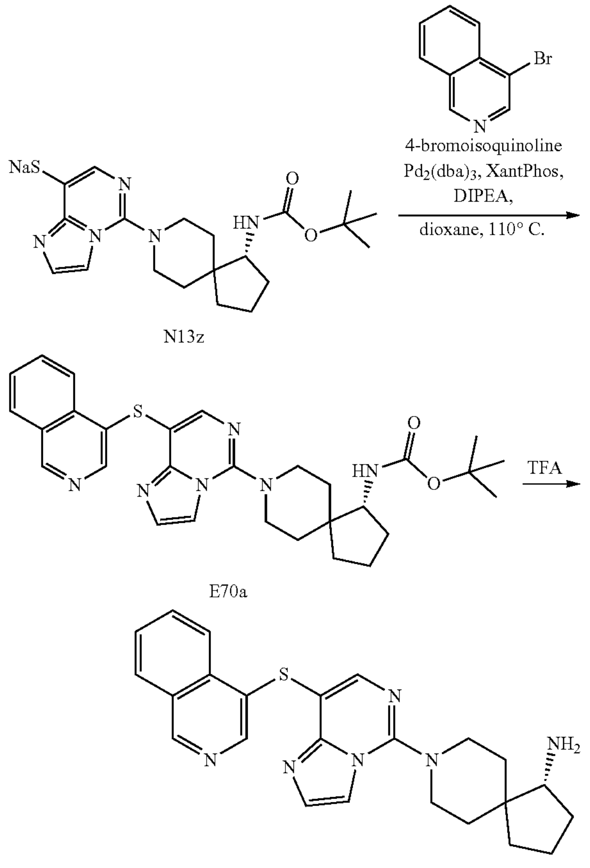

N13z

E70a

Example 70

Compound E70a: Compound N13z: (47.3 mg, 0.111 mmol) in 1,4-dioxane (2 mL) was added $Pd_2(dba)_3$ (22 mg, 0.0216 mmol), XantPhos (28 mg, 0.04839 mmol), 4-bromoisoquinoline (47.3 mg, 0.149 mmol), and DIPEA (61.4 μL, 0.353 mmol). The reaction vessel was degassed with argon, sealed, and heated to 110° C. overnight. The reaction mixture was then cooled to room temperature, filtered through Celite®, and concentrated. The resulting residue was concentrated, diluted with 1:1 acetonitrile and water each containing 0.1% TFA and purified on preparatory HPLC (0 to 100% acetonitrile in water each containing 0.1% TFA). This provided Compound E70a as a TFA salt. LCMS $ESI^+$ calc'd for $C_{29}H_{34}N_6O_2S$: 531.3 [$M+H^+$]. found: 531.3 [$M+H^+$].

Example 70: Compound E70a TFA salt was mixed with TFA (2 mL). After 4 h, the mixture was concentrated on rotovap, diluted with 1:1 acetonitrile and water each containing 0.1% TFA and purified on preparatory HPLC (0 to 100% acetonitrile in water each containing 0.1% TFA). This provided Example 70 as a TFA salt. $^1H$ NMR (400 MHz, $MeOH-d_4$) δ 9.38 (s, 1H), 8.57 (d, J=8.4 Hz, 1H), 8.37 (d, J=8.4 Hz, 1H), 8.28 (s, 1H), 8.25 (s, 1H), 8.15 (ddd, J=8.4, 7.0, 1.3 Hz, 1H), 8.03-7.94 (m, 2H), 7.84 (d, J=2.0 Hz, 1H), 4.16-4.03 (m, 2H), 3.49-3.38 (m, 2H), 3.36-3.30 (m, 1H), 2.28 (d, J=8.5 Hz, 2H), 2.04-1.74 (m, 6H), 1.68 (t, J=12.3 Hz, 2H). LCMS $ESI^+$ calc'd for $C_{24}H_{26}N_6S$: 431.2 [$M+H^+$]. found: 431.2 [$M+H^+$].

Example 71: (3S,4S)-8-(8-(2,3-dichlorophenoxy)imidazo[1,2-c]pyrimidin-5-yl)-3-methyl-2-oxa-8-azaspiro[4.5]decan-4-amine

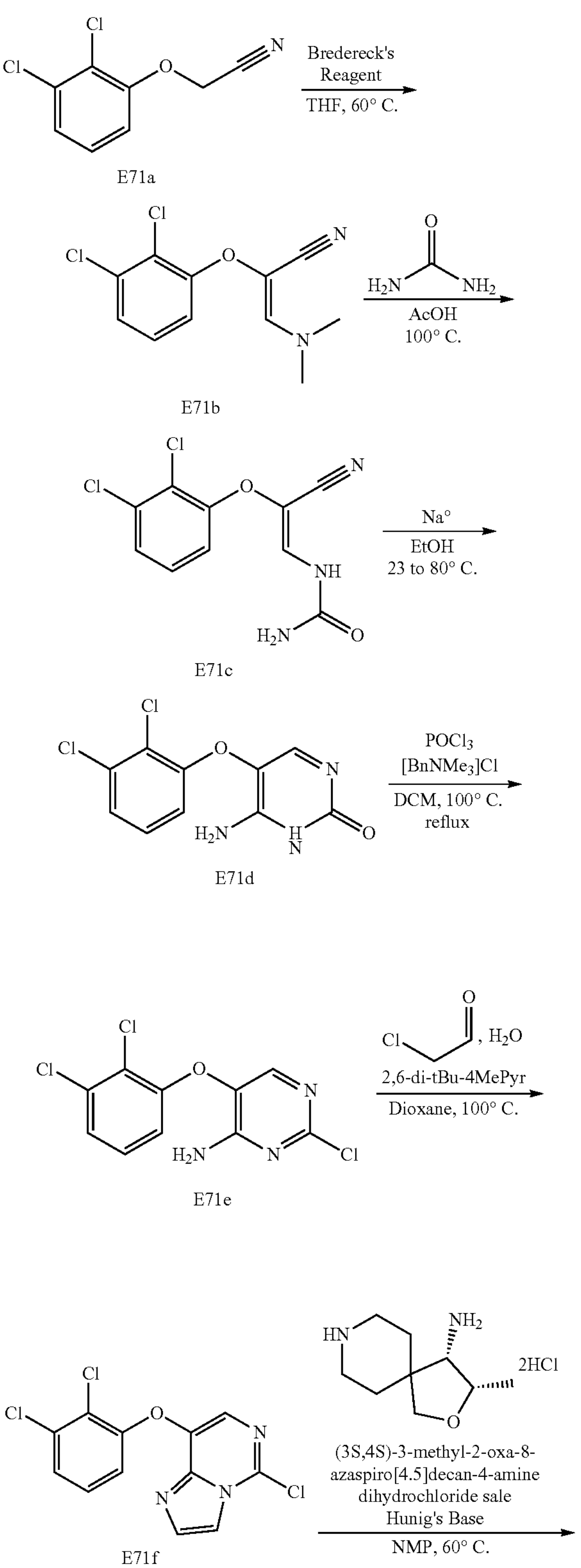

E71a

E71b

E71c

E71d

E71e

E71f

-continued

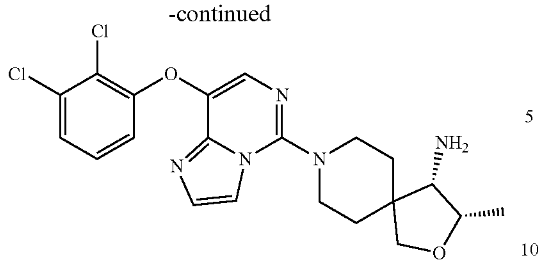

Example 71

Compound E71b: A flask was charged with Compound E71a (832 mg), THF (10 mL), and Bredereck's Reagent (1.2 g). The flask was fitted with a reflux condenser, and the reaction was heated to 60° C. for 1 h. The reaction was concentrated under reduced pressure to remove most of the THF. The resulting mixture was treated with PhMe. The resulting solution was purified directly via chromatography on silica gel (Eluent: EtOAc gradient in hexane) giving Compound E71b. LCMS ESI$^+$ calc'd for $C_{11}H_{10}Cl_2N_2O_3$: 257.0 [M+H$^+$]. found: 256.9 [M+H$^+$].

Compound E71c: A flask containing Compound E71b (700 mg) in glacial AcOH (7 mL) was treated with Urea (530 mg). The reaction was stirred at 100° C. for 16 h. The reaction was partially concentrated at 70° C. under reduced pressure to remove as much AcOH as possible. The resulting material was treated with PhMe/EtOAc/MeOH 5:4:1 (v:v:v, 5 mL total). The resulting solution was purified directly via chromatography on silica gel (Eluent: EtOAc gradient in hexane followed by MeOH gradient in EtOAc) providing Compound E71c. LCMS ESI$^+$ calc'd for $C_{10}H_7Cl_2N_3O_2$: 272.0 [M+H$^+$]. found: 272.0 [M+H$^+$].

Compound E71d: A flask equipped with a bubbler was charged with a solution of Compound E71c (270 mg) in absolute EtOH (20 mL) was treated with freshly-cut sodium metal (200 mg in portions) at 23° C. Once all of the sodium had reacted and bubbling (in the bubbler) had ceased, the reaction was stirred for 6 h at 23° C., then heated to 80° C. for 24 h. The reaction was cooled to 23° C. and a precipitate developed. A solid was captured via filtration, washed with absolute EtOH, then air-dried. This gave Compound E71d. NMR (400 MHz, MeOH-d$_4$) δ 7.46 (s, 1H), 7.24-7.17 (m, 2H), 6.84 (dd, J=6.5, 3.2 Hz, 1H). LCMS ESI$^+$ calc'd for $C_{10}H_7Cl_2N_3O_2$: 272.0 [M+H$^+$]. found: 272.1 [M+H$^+$].

Compound E71e: A flask containing Compound E71d (202 mg) and benzyltrimethylammonium chloride (202 mg) was treated with $POCl_3$ (5.0 mL), followed by DCM (5.0 mL). The reaction was fitted with a reflux condenser and bubbler, then heated to 100° C. All solids dissolved. After 16 h, the reaction was cooled to 23° C. and decanted carefully onto crushed ice (100 mL volume). The slurry was agitated until only one liquid phase was detected, giving a solid brown precipitate. At this point, the system was allowed to stand for 30 min. The mixture was extracted with DCM (2×50 mL). The aq phase was kept. Combined organic extracts were dried ($Na_2SO_4$) and filtered. The filtrate was concentrated, and the resulting residue was treated with PhMe and EtOAc followed by enough MeOH to induce solution. The solution was purified via chromatography on silica gel (Eluent: EtOAc gradient in hexane) giving Compound E71e. The aforementioned aq layer was cooled to 0° C. in an ice bath and adjusted to pH=12 via addition of solid NaOH in portions. The resulting suspension was filtered. The filtrate was extracted with EtOAc thoroughly. The combined organic extracts were dried ($Na_2SO_4$) and filtered. Concentration of the filtrate provided additional Compound E71e. $^1$H NMR (400 MHz, MeOH-d$_4$) δ 7.49 (s, 1H), 7.44 (dd, J=8.1, 1.4 Hz, 1H), 7.35 (t, J=8.2 Hz, 1H), 7.10 (dd, J=8.2, 1.5 Hz, 1H). LCMS ESI$^+$ calc'd for $C_{10}H_6Cl_3N_3O$: 290.0 [M+H$^+$]. found: 290.1 [M+H$^+$].

Compound E71f: A vial containing Compound E71e (150 mg) in dioxane (8 mL) was treated with 2,6-di-tert-butyl-4-methylpyridine (500 mg), followed by 45% (w/v) chloroacetaldehyde in $H_2O$ (200 μL). The vessel was sealed and heated to 100° C. for 1 h. More 45% (w/v) chloroacetaldehyde in $H_2O$ (200 μL) was added and heating was continued for 7 h at 100° C. The reaction was cooled to 23° C. and diluted with $H_2O$ (50 mL) and brine (5 mL). The system was extracted with EtOAc (50 mL). The organic phase was dried ($Na_2SO_4$) and filtered. The filtrate was concentrated, and the resulting residue was treated with PhMe. This gave a suspension, which was filtered. The filtrate was purified directly via chromatography on silica gel (Eluent: EtOAc gradient in hexane) giving Compound E71f. $^1$H NMR (400 MHz, $CD_3CN$) δ 7.88 (d, J=1.6 Hz, 1H), 7.65 (d, J=1.7 Hz, 1H), 7.56 (d, J=1.2 Hz, 1H), 7.41-7.37 (m, 1H), 7.28-7.21 (m, 1H), 7.03-6.97 (m, 1H). LCMS ESI$^+$ calc'd for $C_{12}H_6Cl_3N_{30}$: 314.0 [M+H$^+$]. found: 314.1 [M+H$^+$].

Example 71: A vial containing (3S,4S)-3-methyl-2-oxa-8-azaspiro[4.5]decan-4-amine dihydrochloride salt (36 mg) and NMP (1 mL) was treated with Hunig's Base (100 μL). After all solids had dissolved, Compound E71f (23 mg) was added with stirring at 23° C. The reaction was heated to 60° C. for 30 min. The reaction was cooled to 23° C. $H_2O$ (1 mL) and CH3CN (1 mL) were added, followed by TFA (50 μL). The solution was purified on a C18 column via reversed-phase HPLC (0.1% TFA in $H_2O$/CH3CN with gradient elution 95:5 to 0:100) giving Example 71. $^1$H NMR (400 MHz, $CD_3CN$) δ 7.75-7.67 (m, 3H), 7.37-7.32 (m, 1H), 7.22 (td, J=8.3, 1.6 Hz, 1H), 6.94 (dd, J=8.4, 1.8 Hz, 1H), 4.27 (ddt, J=10.9, 7.2, 3.3 Hz, 1H), 3.96 (d, J=9.2 Hz, 1H), 3.80 (d, J=9.5 Hz, 1H), 3.77-3.65 (m, 1H), 3.57 (d, J=4.2 Hz, 1H), 3.41-3.32 (m, 1H), 3.23-3.04 (m, 2H), 2.26 (t, J=8.1 Hz, 1H), 2.14-1.78 (m, 2H), 1.37-1.31 (m, 1H), 1.29 (dd, J=6.5, 1.5 Hz, 3H). LCMS ESI$^+$ calc'd for $C_{21}H_{23}Cl_2N_5O_2$: 448.1 [M+H$^+$]. found: 448.2 [M+H$^+$].

Example 72: (R)-8-(8-((2,3-dichlorophenyl)amino)imidazo[1,2-c]pyrimidin-5-yl)-8-azaspiro[4.5]decan-1-amine

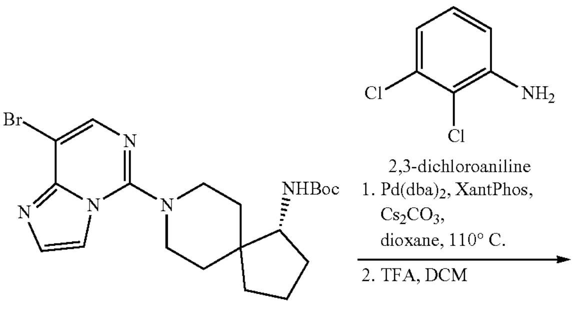

N13y

-continued

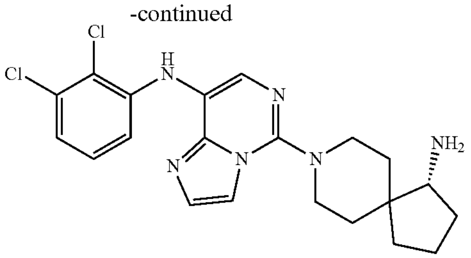

Example 72

Example 72: To a suspension of Compound N13y (100 mg, 0.22 mmol), 2,3-dichloroaniline (54 mg, 0.33, 1.5 eq), and $Cs_2CO_3$ (86 mg, 0.266 mmol, 1.2 eq) in 2 mL dioxane was degassed by bubbling $N_2$ through for 30 minutes. 4,5-Bis(diphenylphosphino)-9,9-dimethylxanthene (13 mg, 0.022 mmol, 0.1 eq) and Bis(dibenzylideneacetone)palladium(13 mg, 0.022 mmol, 0.1 eq) was added to mixture. The reaction mixture was then heated 90° C. for 6 h. The reaction mixture was then concentrated and purified by silica chromatography eluting with 10% EA:Hex. 32 mg of boc protected product was collected. The 17 mg of this product was dissolved in 10 mL DCM and 0.5 mL of TFA was added. The reaction was stirred at room temperature for 16 h and concentrated. This provided Example 72 as a TFA salt. $^1H$ NMR (400 MHz, Methanol-$d_4$) δ 8.07 (s, 1H), 7.98 (d, J=2.1 Hz, 1H), 7.87 (d, J=2.1 Hz, 1H), 7.15-7.02 (m, 2H), 6.73 (dd, J=7.9, 1.7 Hz, 1H), 3.92 (dd, J=18.9, 14.2 Hz, 2H), 3.43-3.35 (m, 2H), 2.44-2.20 (m, 1H), 2.10-2.01 (m, 1H), 1.99-1.75 (m, 5H), 1.76-1.61 (m, 2H), 1.32 (d, J=7.3 Hz, 2H). LCMS $ESI^+$ calc'd for $C_{21}H_{24}Cl_2N_6$: 431.1 [$M+H^+$]; found: 431.1 [$M+H^+$].

Example 73: (R)-8-(8-(1H-indazol-6-yl)-7-methylimidazo[1,2-c]pyrimidin-5-yl)-8-azaspiro[4.5]decan-1-amine

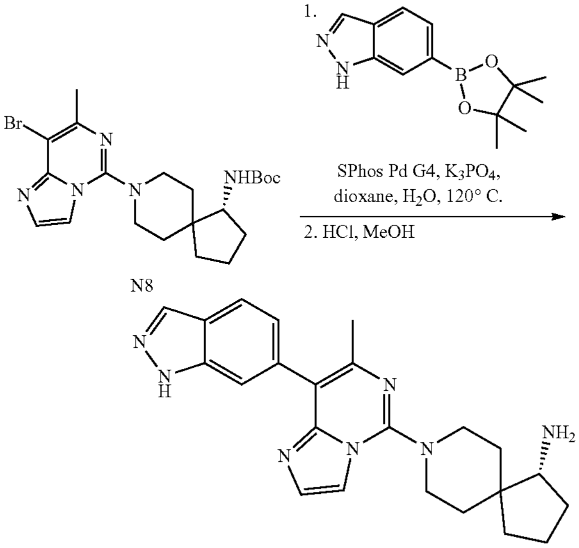

N8

Example 73

Example 73: A solution of Compound N8 (100 mg, 0.21 mmol), 6-(4,4,5,5-tetramethyl-1,3,2-dioxaborolan-2-yl)-1H-indazole (105 mg, 0.43 mmol), SPhos Pd G4 (34 mg, 0.04 mmol), potassium phosphate tribasic (183 mg, 0.86 mmol) were added to 1,4-dioxane (2 mL) and water (2 mL). The reaction mixture was heated to 120° C. for 30 min in a microwave reactor. The mixture was dilute with EtOAc, filtered through Celite, and concentrated in vacuo. The crude material was dissolved in TFA (1 mL) and stirred for 5 min. The reaction solvent was evaporated and the residue was purified by preparatory HPLC (10-75% MeCN in water with 0.1% TFA, Gemini) to afford Example 73. 1H NMR (400 MHz, Methanol-d4) δ 8.21 (d, J=1.0 Hz, 1H), 8.04 (dd, J=8.3, 0.9 Hz, 1H), 8.00 (d, J=2.4 Hz, 1H), 7.86 (d, J=2.3 Hz, 1H), 7.70 (q, J=1.1 Hz, 1H), 7.21 (dd, J=8.3, 1.4 Hz, 1H), 4.12-3.95 (m, 2H), 3.45 (ddt, J=14.3, 11.4, 2.3 Hz, 2H), 3.38 (d, J=6.6 Hz, 1H), 2.45 (s, 3H), 2.36-2.20 (m, 1H), 2.12-1.76 (m, 7H), 1.71 (tt, J=16.0, 2.8 Hz, 2H). LCMS $ESI^+$ calc'd for $C_{23}H_{27}N_7$: 402.2 [$M+H^+$]. found: 402.2 [$M+H^+$].

Example 74: (R)-8-(8-(2,2-difluorobenzo[d][1,3]dioxol-5-yl)-7-methylimidazo[1,2-c]pyrimidin-5-yl)-8-azaspiro[4.5]decan-1-amine

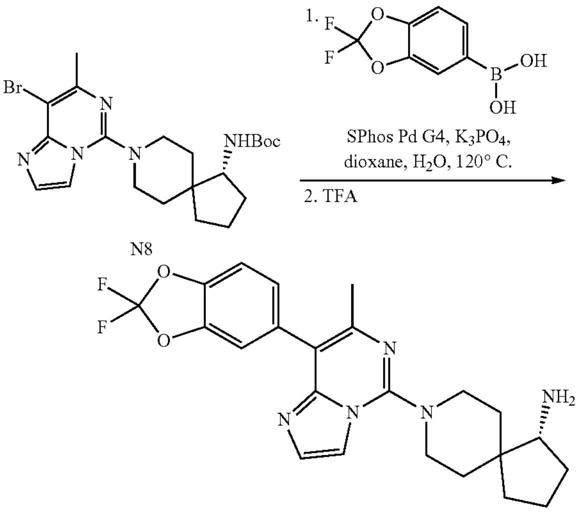

N8

Example 74

Example 74: A solution of Compound N8 (124 mg, 0.27 mmol), (2,2-difluorobenzo[d][1,3]dioxol-5-yl)boronic acid (108 mg, 0.53 mmol), SPhos Pd G4 (42 mg, 0.05 mmol), potassium phosphate tribasic (227 mg, 1 mmol) were added to 1,4-dioxane (2 mL) and water (2 mL). The reaction mixture was heated to 120° C. for 30 min in a microwave reactor. The mixture was dilute with EtOAc, filtered through Celite, and concentrated in vacuo. The crude material was dissolved in TFA (1 mL) and stirred for 5 min. The reaction solvent was evaporated and the residue was purified by preparatory HPLC (10-75% MeCN in water with 0.1% TFA, Gemini) to afford Example 74. $^1H$ NMR (400 MHz, Methanol-$d_4$) δ 7.98 (d, J=2.3 Hz, 1H), 7.89 (d, J=2.3 Hz, 1H), 7.47 (d, J=8.3 Hz, 1H), 7.38 (d, J=1.6 Hz, 1H), 7.28 (dd, J=8.2, 1.7 Hz, 1H), 4.12-3.92 (m, 2H), 3.48-3.39 (m, 2H), 3.37 (d, J=6.7 Hz, 1H), 2.42 (s, 3H), 2.29 (dddd, J=10.6, 7.8, 6.0, 3.1 Hz, 1H), 2.06-1.76 (m, 7H), 1.75-1.64 (m, 2H). LCMS $ESI^+$ calc'd for $C_{23}H_{25}F_2N_5O_2$: 442.1 [$M+H^+$]. found: 442.2 [$M+H^+$].

Example 75: (2R,4R)-4-amino-8-(8-((2,3-dichlorophenyl)thio)-7-methylimidazo[1,2-c]pyrimidin-5-yl)-8-azaspiro[4.5]decan-2-ol

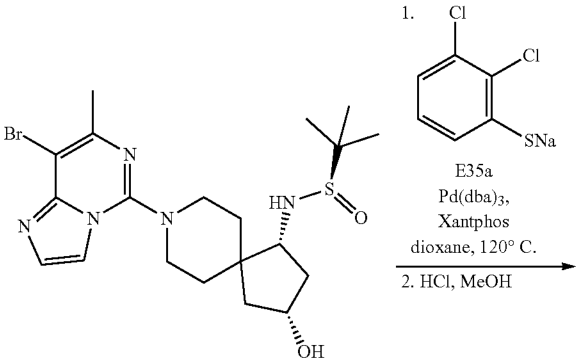

N5z

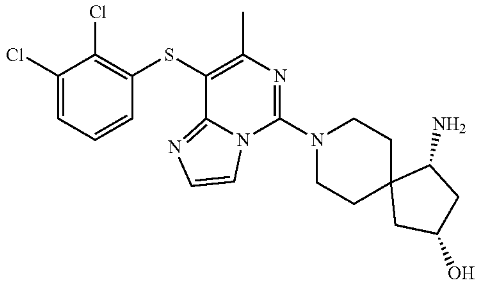

Example 75

Example 75: A solution of Compound N5z (315 mg, 0.65 mmol), sodium Compound E35a (261 mg, 1.3 mmol), in dioxane (3 mL) was added $Pd_2(dba)_3$ (60 mg, 0.065 mmol), Xantphos (75 mg, 0.13 mmol) and DIPEA (0.3 mL). The reaction mixture was heated to 120° C. overnight. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 75. $^1H$ NMR (400 MHz, Methanol-$d_4$) δ 8.02 (d, J=2.3 Hz, 1H), 7.85 (d, J=2.3 Hz, 1H), 7.40 (dd, J=8.0, 1.4 Hz, 1H), 7.13 (t, J=8.0 Hz, 1H), 6.71 (dd, J=8.1, 1.3 Hz, 1H), 4.48 (tt, J=6.2, 3.2 Hz, 1H), 4.24 (dd, J=45.6, 13.8 Hz, 2H), 3.49 (tdd, J=14.1, 11.9, 2.8 Hz, 2H), 3.41 (dd, J=6.7, 4.6 Hz, 1H), 2.64 (s, 3H), 2.44 (ddd, J=14.3, 6.7, 5.6 Hz, 1H), 2.19 (dd, J=14.2, 6.2 Hz, 1H), 2.09-1.86 (m, 5H), 1.69 (dd, J=13.4, 2.7 Hz, 1H). LCMS ESI$^+$ calc'd for $C_{22}H_{25}Cl_2N_5OS$: 478.1 [M+H$^+$]. found: 478.2 [M+H$^+$].

Example 76: (3S,4S)-8-(8-((2,3-dichlorophenyl)thio)-7-methylimidazo[1,2-c]pyrimidin-5-yl)-3-methyl-2-oxa-8-azaspiro[4.5]decan-4-amine

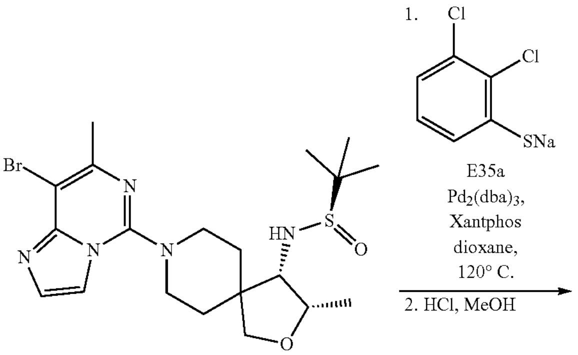

N4

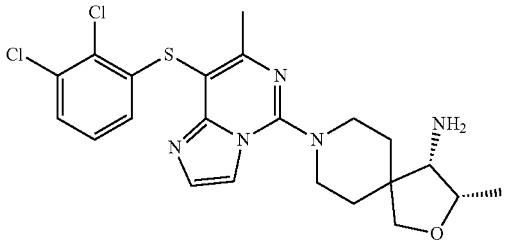

Example 76

Example 76: A solution of Compound N4 (296 mg, 0.6 mmol), sodium 2,3-dichlorobenzenethiolate (246 mg, 1.2 mmol), in dioxane (3 mL) was added $Pd_2(dba)_3$ (56 mg, 0.06 mmol), Xantphos (71 mg, 0.12 mmol) and DIPEA (0.3 mL). The reaction mixture was heated to 120° C. overnight. The mixture was dilute with EtOAc, filtered through Celite, and concentrated in vacuo. The crude material was dissolved in MeOH (1 mL) and treated with HCl solution (0.25 mL, 4 M in 1,4-dioxane) and stirred for 5 min. The reaction solvent was evaporated and the residue was purified by preparatory HPLC (10-75% MeCN in water with 0.1% TFA, Gemini) to afford Example 76. $^1H$ NMR (400 MHz, Methanol-$d_4$) δ 8.05 (d, J=2.4 Hz, 1H), 7.87 (d, J=2.3 Hz, 1H), 7.40 (dd, J=8.0, 1.3 Hz, 1H), 7.14 (t, J=8.0 Hz, 1H), 6.73 (dd, J=8.1, 1.3 Hz, 1H), 4.36 (qd, J=6.5, 4.1 Hz, 1H), 4.29-4.11 (m, 2H), 4.06 (d, J=9.2 Hz, 1H), 3.94 (d, J=9.2 Hz, 1H), 3.56 (d, J=4.0 Hz, 1H), 3.55-3.41 (m, 2H), 2.65 (s, 3H), 2.22-1.94 (m, 3H), 1.88 (ddt, J=13.3, 4.7, 2.4 Hz, 1H), 1.37 (d, J=6.5 Hz, 3H). LCMS ESI$^+$ calc'd for $C_{22}H_{25}Cl_2N_5OS$: 478.1 [M+H$^+$]. found: 478.3 [M+H$^+$].

Example 77: (R)-8-(8-((1H-indazol-6-yl)thio)imidazo[1,2-c]pyrimidin-5-yl)-8-azaspiro[4.5]decan-1-amine

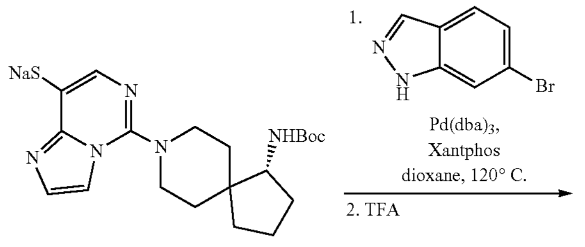

N13z

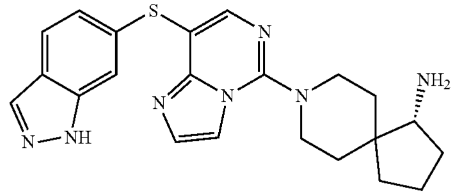

Example 77

Example 77: A solution of Compound N13z (50 mg, 0.12 mmol), 6-bromo-1H-indazole (37 mg, 0.19 mmol), in dioxane (3 mL) was added $Pd_2(dba)_3$ (11 mg, 0.012 mmol), Xantphos (14 mg, 0.024 mmol) and DIPEA (0.06 mL). The reaction mixture was heated to 120° C. overnight. The mixture was dilute with EtOAc, filtered through Celite, and concentrated in vacuo. The crude material was dissolved in TFA (1 mL) and stirred for 5 min. The reaction solvent was evaporated and the residue was purified by preparatory HPLC (10-75% MeCN in water with 0.1% TFA, Gemini) to Example 77. $^1$H NMR (400 MHz, Methanol-$d_4$) δ 8.31 (s, 1H), 8.03 (d, J=1.0 Hz, 1H), 7.99 (d, J=2.1 Hz, 1H), 7.89 (d, J=2.1 Hz, 1H), 7.73 (dd, J=8.5, 0.8 Hz, 1H), 7.57 (dt, J=1.7, 0.9 Hz, 1H), 7.14 (dd, J=8.5, 1.6 Hz, 1H), 4.17-3.97 (m, 2H), 3.52-3.38 (m, 2H), 2.40-2.17 (m, 1H), 2.06-1.74 (m, 8H), 1.72-1.62 (m, 2H). LCMS ESI$^+$ calc'd for $C_{22}H_{25}N_7S$: 420.1 [M+H$^+$]. found: 420.2 [M+H$^+$].

Example 78: (R)-8-(8-(quinolin-4-ylthio)imidazo[1,2-c]pyrimidin-5-yl)-8-azaspiro[4.5]decan-1-amine

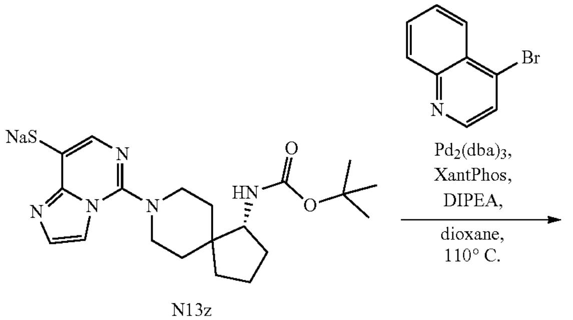

N13z

-continued

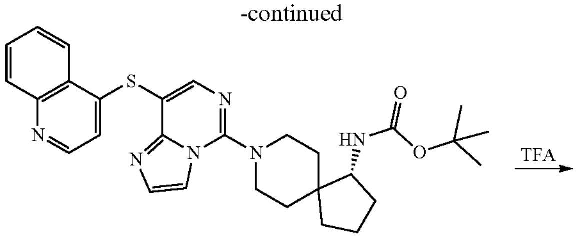

E78a

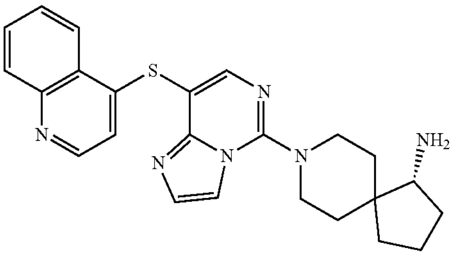

Example 78

Compound E78a: Compound N13z (24.45 mg, 0.118 mmol) in 1,4-dioxane (2 ml) was added $Pd_2(dba)_3$ (10.76 mg, 0.012 mmol), XantPhos (13.6 mg, 0.0235 mmol), 4-bromoquinoline (50 mg, 0.118 mmol), and DIPEA (61.4 μL, 0.353 mmol). The reaction vessel was degassed with argon, sealed, and heated to 110° C. overnight. The reaction mixture was then cooled to room temperature, filtered through Celite®, and concentrated. The resulting residue was concentrated, diluted with 1:1 acetonitrile and water each containing 0.1% TFA and purified on preparatory HPLC (0 to 100% acetonitrile in water each containing 0.1% TFA). This provided Compound E78a as a TFA salt. LCMS ESI$^+$ calc'd for $C_{29}H_{34}N_6O_2S$: 531.3 [M+H$^+$]. found: 531.2 [M+H$^+$].

Example 78: Compound E78a TFA salt was mixed with TFA (2 ml). After 4 h, the mixture was concentrated on rotovap, diluted with 1:1 acetonitrile and water each containing 0.1% TFA and purified on preparatory HPLC (0 to 100% acetonitrile in water each containing 0.1% TFA). This provided Example 78 as a TFA salt. $^1$H NMR (400 MHz, MeOH-$d_4$) δ 8.68-8.64 (m, 2H), 8.36 (s, 1H), 8.21 (d, broad, J=3.8 Hz, 2H), 8.04 (dt, J=8.4, 4.1 Hz, 1H), 7.98 (d, J=1.8 Hz, 1H), 7.71 (d, J=1.8 Hz, 1H), 7.31 (d, J=6.1 Hz, 1H), 4.20 (dd, broad, J=19.8, 14.4 Hz, 2H), 3.49 (tt, J=12.8, 3.4 Hz, 2H), 3.37 (t, J=6.7 Hz, 1H), 2.33-2.26 (m, 2H), 2.03-1.81 (m, 6H), 1.72 (t, broad, J=13.0 Hz, 2H). LCMS ESI$^+$ calc'd for $C_{24}H_{26}N_6S$: 431.2 [M+H$^+$]. found: 431.2 [M+H$^+$].

Example 79: (R)-8-(8-(cyclohexylthio)imidazo[1,2-c]pyrimidin-5-yl)-8-azaspiro[4.5]decan-1-amine

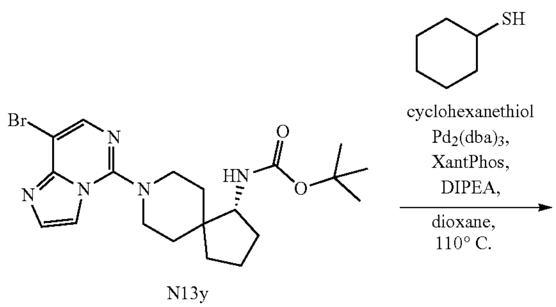

N13y

-continued

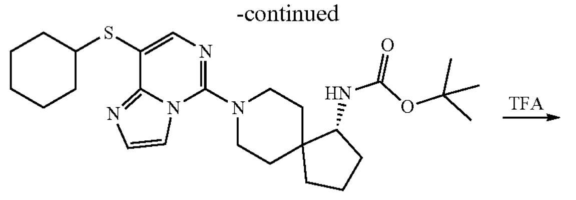

E79a

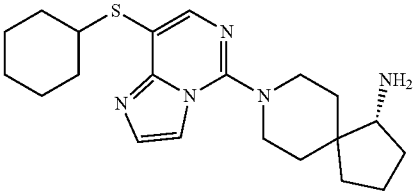

Example 79

Compound E79a: Compound N13y (106 mg, 0.235 mmol) in 1,4-dioxane (2 ml) was added $Pd_2(dba)_3$ (10.8 mg, 0.0118 mmol), XantPhos (13.6 mg, 0.0235 mmol), cyclohexanethiol (54.7 mg, 0.471 mmol), and DIPEA (0.123 ml, 0.706 mmol). The reaction vessel was purged with argon, sealed, and heated to 110° C. until complete consumption of starting materials. The reaction mixture was cooled to room temperature, diluted with EtOAc and washed with water followed by brine. The organic partition was dried over magnesium sulfate, and filtered through Celite. The resulting solution was concentrated and purified by column chromatography (0-100% EtOAc in Hexanes). This provided Compound E79a LCMS ESI$^+$ calc'd for $C_{24}H_{32}ClN_7O_2S_2$: 486.3 [M+H$^+$]. found: 486.3 [M+H$^+$].

Example 79: Compound E79a was dissolved in DCM (10 ml), and 4N HCl in 1,4 dioxane (2 ml). The resulting suspension was stirred for 30 min. The solution was concentrated and reconstituted in water and DMF and purified by preparatory HPLC (10-100% MeCN in water with 0.1% TFA, Gemini). This provided Example 79. $^1$H NMR (400 MHz, DMSO-$d_6$) δ 8.08-7.69 (m, 6H), 3.78 (t, J=14.8 Hz, 2H), 3.39 (dd, J=15.4, 5.2 Hz, 1H), 3.30-3.10 (m, 3H), 2.15-1.98 (m, 1H), 1.94-1.58 (m, 10H), 1.58-1.39 (m, 3H), 1.37-1.10 (m, 5H). LCMS ESI$^+$ calc'd for $C_{20}H_{24}ClN_7OS$: 386.2 [M+H$^+$]. found: 386.3 [M+H$^+$].

Example 80: (R)-8-(8-((2,3-dimethylpyridin-4-yl)thio)imidazo[1,2-c]pyrimidin-5-yl)-8-azaspiro[4.5]decan-1-amine

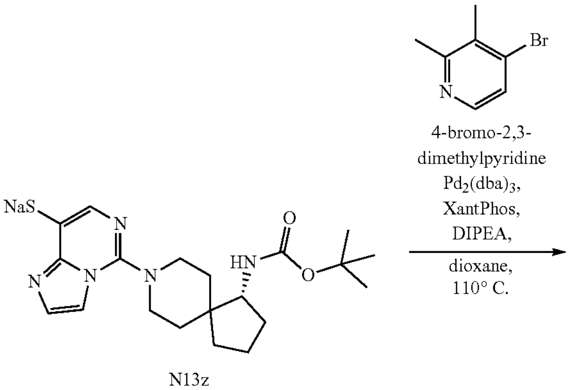

N13z

-continued

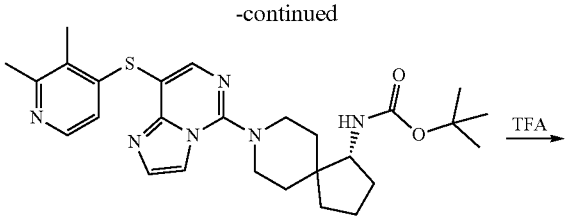

E80a

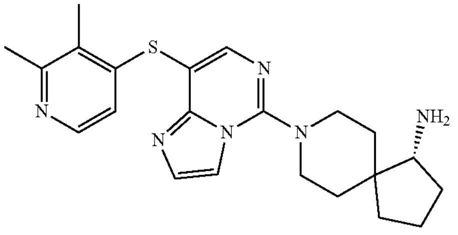

Example 80

Compound E80a: Compound N13z (100 mg, 235 mmol) in 1,4-dioxane (2 mL) was added $Pd_2(dba)_3$ (11 mg, 0.012 mmol), XantPhos (24 mg, 0.024 mmol), 4-bromo-2,3-dimethylpyridine (131 mg, 0.705 mmol), and DIPEA (0.123 mL, 0.705 mmol). The reaction vessel was purged with argon, sealed, and heated to 110° C. until complete consumption of starting materials. The reaction mixture was cooled to room temperature, diluted with EtOAc and washed with water followed by brine. The organic partition was dried over magnesium sulfate, and filtered through Celite. The resulting solution was concentrated and purified by column chromatography (0-100% EtOAc in Hexanes). This provided Compound E80a. LCMS ESI$^+$ calc'd for $C_{27}H_{36}N_6O_2S$: 509.3 [M+H$^+$]. found: 509.2 [M+H$^+$].

Example 80: Compound E80a was dissolved in DCM (5 ml), and TFA (1 ml) was added. The solution was concentrated and reconstituted in water and DMF and the solution was purified on preparatory HPLC (10-100% MeCN in water with 0.1% TFA, Gemini). This provided Example 80. $^1$H NMR (400 MHz, DMSO-$d_6$) δ 8.17 (d, J=6.5 Hz, 1H), 8.14 (s, 1H), 7.96 (s, 3H), 7.86 (d, J=1.7 Hz, 1H), 7.63 (d, J=1.5 Hz, 1H), 7.01 (d, J=6.5 Hz, 1H), 3.95 (t, J=14.3 Hz, 2H), 3.41-3.10 (m, 3H), 2.66 (s, 3H), 2.44 (s, 3H), 2.15-2.01 (m, 1H), 1.93-1.46 (m, 10H). LCMS ESI$^+$ calc'd for $C_{22}H_{28}N_6S$: 409.2 [M+H$^+$]. found: 409.3 [M+H$^+$].

Example 81: (R)-8-(8-((2-chloro-3-methylpyridin-4-yl)thio)imidazo[1,2-c]pyrimidin-5-yl)-8-azaspiro[4.5]decan-1-amine

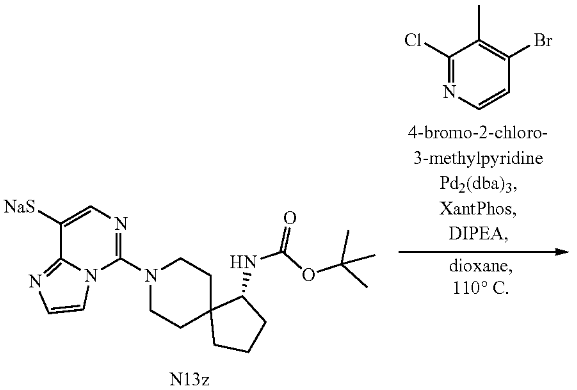

N13z

-continued

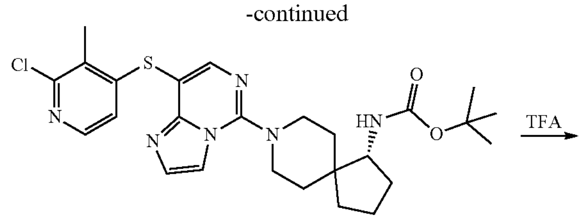

E81a

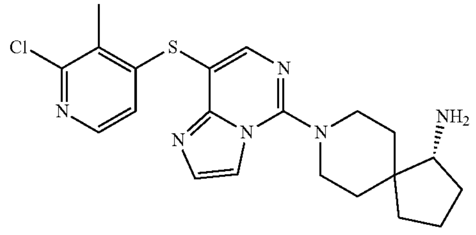

Example 81

Compound E81a: Compound N13z (100 mg, 235 mmol) in 1,4-dioxane (2 mL) was added $Pd_2(dba)_3$ (11 mg, 0.012 mmol), XantPhos (24 mg, 0.024 mmol), 4-bromo-2-chloro-3-methylpyridine (131 mg, 0.705 mmol), and DIPEA (0.123 mL, 0.705 mmol). The reaction vessel was purged with argon, sealed, and heated to 110° C. until complete consumption of starting materials. The reaction mixture was cooled to room temperature, diluted with EtOAc and washed with water followed by brine. The organic partition was dried over magnesium sulfate, and filtered through Celite. The resulting solution was concentrated and purified by column chromatography (0-100% EtOAc in Hexanes). This provided Compound E81a. LCMS $ESI^+$ calc'd for $C_{26}H_{33}ClN_6O_2S$: 529.2 $[M+H^+]$. found: 529.2 $[M+H^+]$.

Example 81: Compound E81a was dissolved in DCM (5 mL), and TFA (1 mL) was added. The solution was concentrated and reconstituted in water and DMF and the solution was purified on preparatory HPLC (10-100% MeCN in water with 0.1% TFA, Gemini). This provided Example 81. $^1H$ NMR (400 MHz, DMSO-$d_6$) δ 8.10 (s, 1H), 7.94-7.73 (m, 5H), 7.65 (d, J=1.5 Hz, 1H), 6.63 (d, J=5.3 Hz, 1H), 3.93 (t, J=14.6 Hz, 3H), 3.36-3.14 (m, 3H), 2.44 (s, 3H), 2.06 (d, J=13.4 Hz, 1H), 1.90-1.42 (m, 9H). LCMS $ESI^+$ calc'd for $C_{21}H_{25}ClN_6S$: 429.2 $[M+H^+]$. found: 429.3 $[M+H^+]$.

Example 82; (R)-8-(8-((5,6,7,8-tetrahydroquinolin-4-yl)thio)imidazo[1,2-c]pyrimidin-5-yl)-8-azaspiro[4.5]decan-1-amine

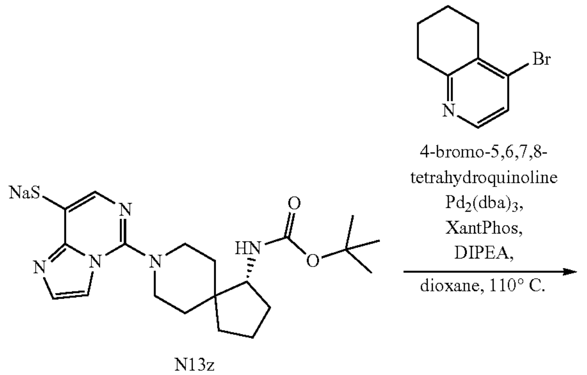

N13z

-continued

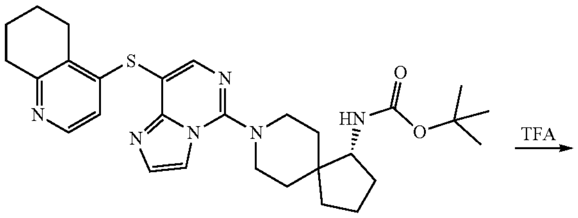

E82a

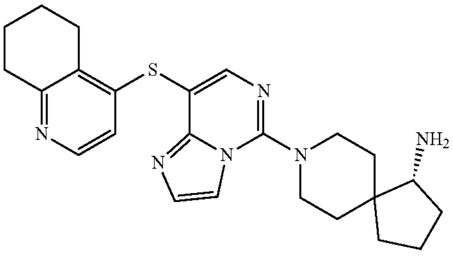

Example 82

Compound E82a: Compound N13z (50 mg, 118 mmol) in 1,4-dioxane (1 mL) was added $Pd_2(dba)_3$ (5.8 mg, 0.0058 mmol), XantPhos (6.8 mg, 0.011 mmol), 4-bromo-5,6,7,8-tetrahydroquinoline (131 mg, 0.705 mmol), and DIPEA (0.061 mL, 352 mmol). The reaction vessel was purged with argon, sealed, and heated to 110° C. until complete consumption of starting materials. The reaction mixture was cooled to room temperature, diluted with EtOAc and washed with water followed by brine. The organic partition was dried over magnesium sulfate, and filtered through Celite. The resulting solution was concentrated and purified by column chromatography (0-100% EtOAc in Hexanes). This provided Compound E82a. LCMS $ESI^+$ calc'd for $C_{29}H_{38}N_6O_2S$: 535.3 $[M+H^+]$. found: 535.3 $[M+H^+]$.

Example 82: Compound E82a was dissolved in DCM (5 mL), and TFA (1 mL) was added. The solution was concentrated and reconstituted in water and DMF and the solution was purified on preparatory HPLC (10-100% MeCN in water with 0.1% TFA, Gemini). This provided Example 82. $^1H$ NMR (400 MHz, DMSO-$d_6$) δ 8.14 (d, J=6.3 Hz, 1H), 8.09 (s, 1H), 7.83 (d, J=1.7 Hz, 4H), 7.59 (d, J=1.5 Hz, 1H), 6.88 (s, 1H), 3.94 (t, J=13.9 Hz, 2H), 3.24 (m, 2H) 2.97 (s, 2H), 2.79 (s, 2H), 2.09 (s, 1H), 1.97-1.38 (m, 14H). LCMS $ESI^+$ calc'd for $C_{24}H_{30}N_6S$: 435.2 $[M+H^+]$. found: 435.3 $[M+H^+]$.

Example 83: (R)-8-(8-([1,2,4]triazolo[4,3-a]pyridin-8-ylthio)imidazo[1,2-c]pyrimidin-5-yl)-8-azaspiro[4.5]decan-1-amine

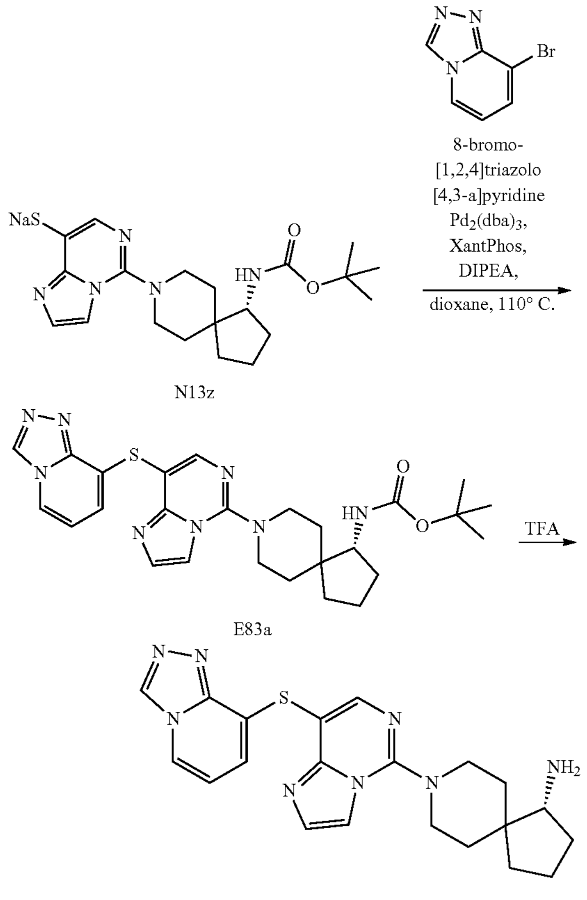

N13z

E83a

Example 83

Compound E83a: Compound N13z (23.27 mg, 0.118 mmol) in 1,4-dioxane (2 ml) was added $Pd_2(dba)_3$ (5.38 mg, 0.006 mmol), XantPhos (6.8 mg, 0.01175 mmol), 8-bromo-[1,2,4]triazolo[4,3-a]pyridine (50 mg, 0.118 mmol), and DIPEA (61.4 μL, 0.353 mmol). The reaction vessel was degassed with argon, sealed, and heated to 110° C. overnight. The reaction mixture was then cooled to room temperature, filtered through Celite®, and concentrated. The resulting residue was concentrated, diluted with 1:1 acetonitrile and water each containing 0.1% TFA and purified on preparatory HPLC (0 to 100% acetonitrile in water each containing 0.1% TFA). This provided Compound E83a as a TFA salt. LCMS $ESI^+$ calc'd for $C_{26}H_{36}N_8O_2S$: 521.2 $[M+H^+]$. found: 521.2 $[M+H^+]$.

Example 83: Compound E83a TFA salt was mixed with TFA (2 mL). After 4 h, the mixture was concentrated on rotovap, diluted with 1:1 acetonitrile and water each containing 0.1% TFA and purified on preparatory HPLC (0 to 100% acetonitrile in water each containing 0.1% TFA). This provided Example 83 as a TFA salt. $^1H$ NMR (400 MHz, $MeOH-d_4$) δ 9.26 (s, 1H), 8.46 (s, 1H), 8.43 (dd, J=6.9, 0.9 Hz, 1H), 8.03 (d, J=2.2 Hz, 1H), 7.90 (d, J=2.1 Hz, 1H), 7.17 (dd, J=7.1, 0.9 Hz, 1H), 6.92 (t, J=7.0 Hz, 1H), 4.20-4.11 (m, 2H), 3.53-3.45 (m, 2H), 3.36 (t, J=6.7 Hz, 1H, partially covered by solvent peak), 2.31-2.24 (m, 2H), 2.05-1.77 (m, 6H), 1.69 (t, broad, J=13.0 Hz, 2H). LCMS $ESI^+$ calc'd for $C_{21}H_{24}N_8S$: 431.2 $[M+H^+]$. found: 431.2 $[M+H^+]$.

Example 84: (R)-8-(8-([1,2,4]triazolo[4,3-a]pyridin-8-ylthio)imidazo[1,2-c]pyrimidin-5-yl)-8-azaspiro[4.5]decan-1-amine

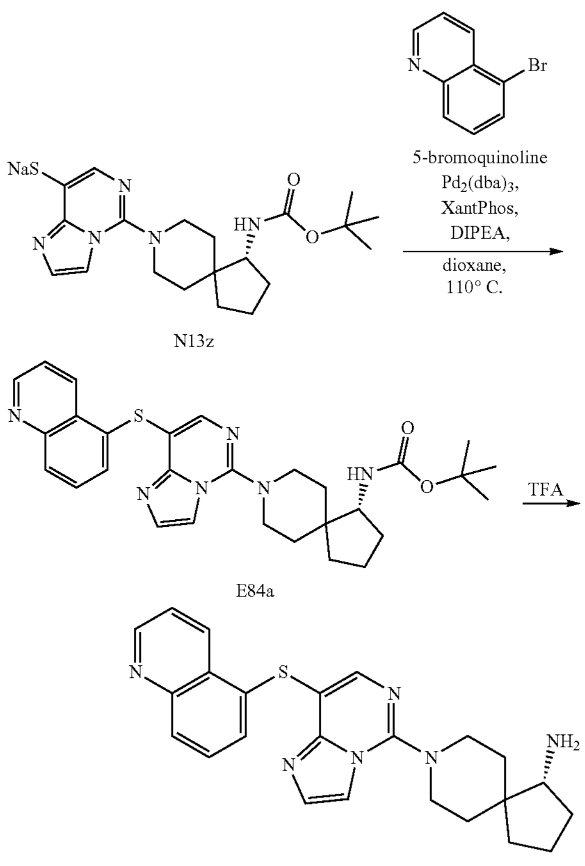

N13z

E84a

Example 84

Compound E84a: Compound N13z (24.45 mg, 0.118 mmol) in 1,4-dioxane (2 ml) was added $Pd_2(dba)_3$ (10.76 mg, 0.012 mmol), XantPhos (13.6 mg, 0.0235 mmol), 5-bromoquinoline (50 mg, 0.118 mmol), and DIPEA (61.4 μL, 0.353 mmol). The reaction vessel was degassed with argon, sealed, and heated to 110° C. overnight. The reaction mixture was then cooled to room temperature, filtered through Celite®, and concentrated. The resulting residue was concentrated, diluted with 1:1 acetonitrile and water each containing 0.1% TFA and purified on preparatory HPLC (0 to 100% acetonitrile in water each containing 0.1% TFA). This provided Compound E84a as a TFA salt. LCMS $ESI^+$ calc'd for $C_{29}H_{34}N_6O_2S$: 531.3 $[M+H^+]$. found: 531.3 $[M+H^+]$.

Example 84: Compound E84a TFA salt was mixed with TFA (2 mL). After 4 h, the mixture was concentrated on rotovap, diluted with 1:1 acetonitrile and water each containing 0.1% TFA and purified on preparatory HPLC (0 to 100% acetonitrile in water each containing 0.1% TFA). This provided Example 84 as a TFA salt. $^1H$ NMR (400 MHz, $MeOH-d_4$) δ 9.20 (dt, J=8.6, 1.2 Hz, 1H), 9.09 (dd, J=4.7, 1.6 Hz, 1H), 8.19 (s, 1H), 8.03 (dt, J=8.6, 1.0 Hz, 1H), 7.97 (d, J=2.0 Hz, 1H), 7.87 (dd, J=8.6, 4.7 Hz, 1H), 7.82 (d, J=2.0 Hz, 1H), 7.77 (dd, J=8.6, 7.5 Hz, 1H), 7.56 (dd, J=7.5, 1.0 Hz, 1H), 4.13-4.02 (m, 2H), 3.47-3.38 (m, 2H), 3.36-3.30 (m, 1H, partially covered by the solvent peak), 2.33-2.24 (m, 2H), 2.01-1.76 (m, 6H), 1.68 (t, broad, J=13.0 Hz, 2H). LCMS $ESI^+$ calc'd for $C_{24}H_{26}N_6S$: 431.2 $[M+H^+]$. found: 431.2 $[M+H^+]$.

Example 85: (S)-1'-(8-((2,3-dichlorophenyl)thio)imidazo[1,2-c]pyrimidin-5-yl)-1,3-dihydrospiro[indene-2,4'-piperidin]-1-amine Compound E85a: A flask was charged with Compound Q1z (97 mg) and spiro[indene-2,4'-piperidin]-1(3H)-one, HCl salt (100 mg) was treated with NMP (2.0 mL), and Hunig's Base (300 μL). The reaction was heated to 60° C. for 20 min. The reaction was then cooled to 23° C. and treated with EtOAc (40 mL). The system was washed with $H_2O$ (3×30 mL). The final organic phase was dried ($Na_2SO_4$) and filtered. The filtrate was concentrated, giving Compound E85a, which was used without further purification. LCMS $ESI^+$ calc'd for $C_{19}H_{17}BrN_4O$: 397.1 $[M+H^+]$. found: 397.3 $[M+H^+]$.

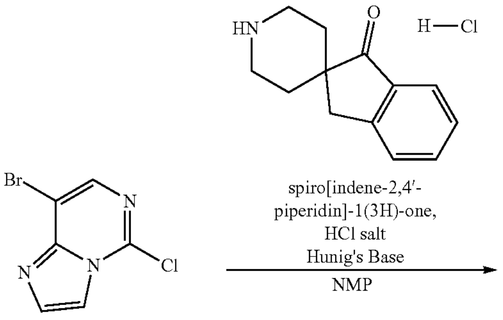

Q1z

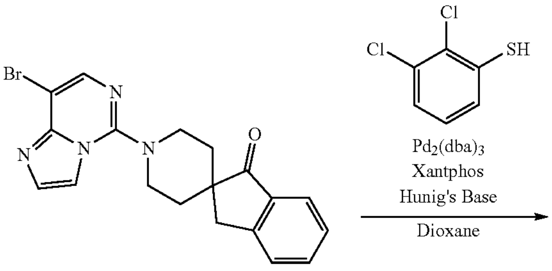

E85a

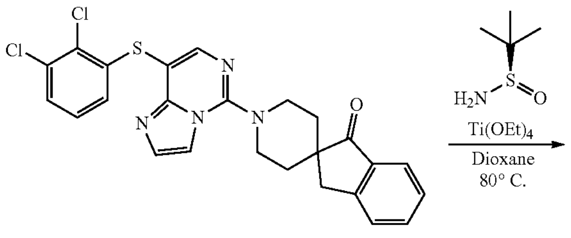

E85b

-continued

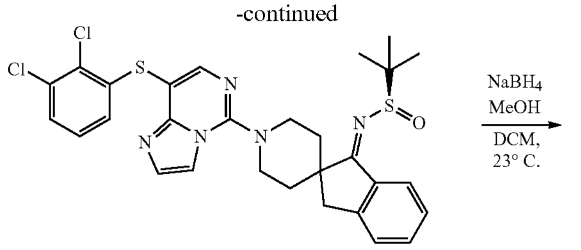

E85c

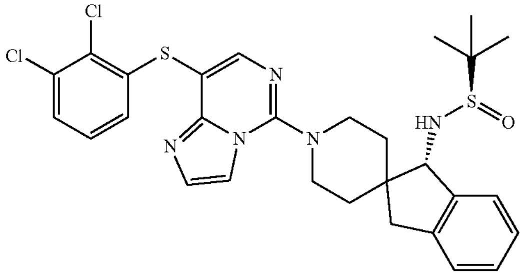

+

E85d

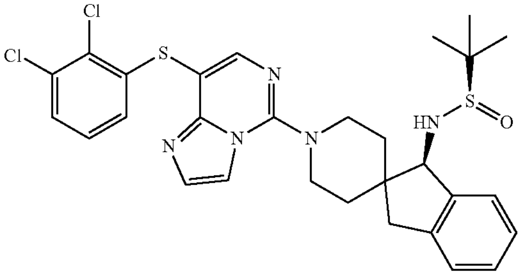

E85e

Compound E85b: A flask containing Compound E85a (173 mg), 2,3-dichlorobenzenethiol (78 mg), $Pd_2(dba)_3$ (21 mg), and Xantphos (25 mg) was treated with dioxane (6 mL) followed by Hunig's Base (400 μL). The reaction was stirred at 23° C. for 5 min. The system was stirred at 110° C. for 20 h, then heated to 130° C. for 2 h. The reaction was cooled to 23° C. Additional $Pd_2(dba)_3$ (30 mg) and Xantphos (34 mg) were added. Heating was resumed at 130° C. for 1 h. The reaction was cooled to 23° C. and diluted with $H_2O$ (40 mL). The system was extracted with EtOAc (40 mL). The organic phase was washed with brine and subsequently filtered through a short plug of Celite®. The resulting organic phase of the filtrate was dried ($Na_2SO_4$) and filtered. The filtrate was concentrated, giving a residue, which was treated with PhMe. The resulting solution purified via chromatography on silica gel (Eluent: EtOAc gradient in hexane) giving Compound E85b. LCMS $ESI^+$ calc'd for $C_{25}H_{20}Cl_2N_4OS$: 495.1 $[M+H^+]$. found: 495.3 $[M+H^+]$.

Compound E85c: A flask containing Compound E85b (61 mg) and (R)-2-methylpropane-2-sulfinamide (200 mg) was treated with dioxane (8 mL). The reaction was heated to 80° C., and all solids dissolved. $Ti(OEt)_4$ (500 μL) was added. Reaction was stirred at 80° C. for 72 h. The reaction was cooled to 23° C. and added dropwise to brine (20 mL) over a 5 min period. After stirring for 5 min, EtOAc (40 mL) was added. The resulting slurry was stirred for 1 h then filtered. The organic phase of the filtrate was collected. The aq phase of the filtrate was extracted with EtOAc (20 mL). Combined organic phases were dried ($Na_2SO_4$), and filtered. The filtrate was concentrated and the resulting residue was treated with PhMe. The solution was purified via chromatography on silica gel (Eluent: EtOAc gradient in hexane) giving Compound E85c. LCMS ESI+ calc'd for $C_{29}H_{29}Cl_2N_5OS_2$: 598.1 [M+H+]. found: 598.0 [M+H+].

Compound E85d and Compound E85e: A vial containing Compound E85c (74 mg) was treated with DCM (2.0 mL) and MeOH (2.0 mL). $NaBH_4$ (100 mg) was added. After stirring for 1 h, the reaction was quenched with aq NaOH (1.0 M, 1 mL) with stirring at 23° C. for 3 h. The system was concentrated under reduced pressure to remove the DCM and MeOH. $H_2O$ (20 mL) was added and the system was extracted with EtOAc (2×20 mL). Combined organic phases were washed with brine, dried ($Na_2SO_4$), and filtered. The filtrate was concentrated under reduced pressure. $H_2O$ (2 mL) and $CH_3CN$ (2 mL) were added, followed by TFA (30 μL). The resulting solution was purified on a C18 column via reversed-phase HPLC (0.1% TFA in $H_2O/CH_3CN$ with gradient elution 95:5 to 0:100) giving Compound E85d (first to elute). LCMS ESI+ calc'd for $C_{29}H_{31}Cl_2N_5OS_2$: 600.1 [M+H+]. found: 600.1 [M+H+] and Compound E85e (second to elute). LCMS ESI+ calc'd for $C_{29}H_{31}Cl_2N_5OS_2$: 600.1 [M+H+]. found: 600.1 [M+H+].

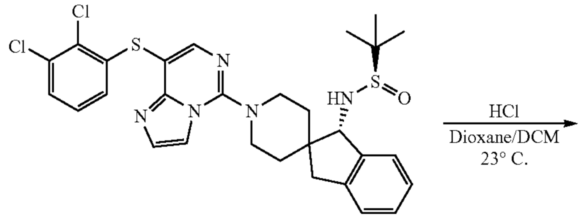

E85d

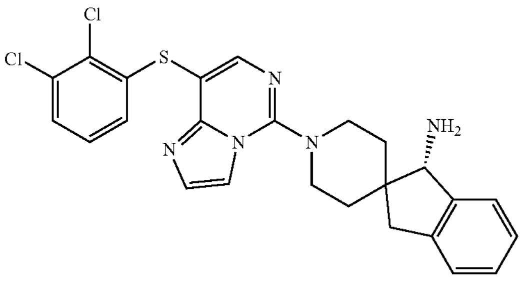

Example 85

Example 85: A flask containing Compound E85d (all of the material from the previous reaction, first peak to elute) and DCM (1 mL) was treated with HCl (4.0 M in dioxane, 0.5 mL) at 23° C. for 5 min. The reaction was concentrated under reduced pressure. $H_2O$ (2 mL) and $CH_3CN$ (2 mL) were added. The resulting solution was purified on a C18 column via reversed-phase HPLC (0.1% TFA in $H_2O/CH_3CN$ with gradient elution 95:5 to 0:100) giving Example 85. $^1H$ NMR (400 MHz, $CD_3CN$) δ 8.17 (s, 1H), 7.70 (d, J=1.9 Hz, 1H), 7.61-7.50 (m, 2H), 7.45-7.26 (m, 4H), 7.05 (t, J=8.1 Hz, 1H), 6.76 (dd, J=8.1, 1.4 Hz, 1H), 4.54 (s, 1H), 4.01 (dd, J=38.6, 13.5 Hz, 2H), 3.45 (qd, J=11.2, 2.7 Hz, 2H), 3.32-3.06 (m, 2H), 2.21-1.98 (m, 2H), 1.91-1.62 (m, 2H). LCMS ESI+ calc'd for $C_{25}H_{23}Cl_2N_5S$: 496.1 [M+H+]. found: 496.2 [M+H+].

Example 86: (R)-1'-(8-((2,3-dichlorophenyl)thio)imidazo[1,2-c]pyrimidin-5-yl)-1,3-dihydrospiro[indene-2,4'-piperidin]-1-amine

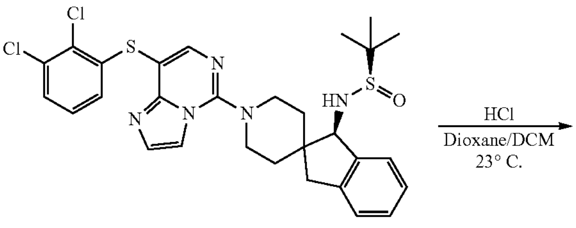

E85e

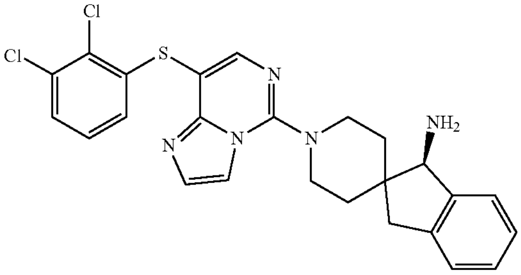

Example 86

Example 86: A flask containing Compound E85e (all of the material from the previous reaction, second peak to elute) and DCM (1 mL) was treated with HCl (4.0 M in dioxane, 0.5 mL) at 23° C. for 5 min. The reaction was concentrated under reduced pressure. $H_2O$ (2 mL) and $CH_3CN$ (2 mL) were added. The resulting solution was purified on a C18 column via reversed-phase HPLC (0.1% TFA in $H_2O/CH_3CN$ with gradient elution 95:5 to 0:100) giving Example 86. $^1H$ NMR (400 MHz, $CD_3CN$) δ 8.12 (s, 1H), 7.69 (d, J=1.8 Hz, 1H), 7.61-7.50 (m, 2H), 7.46-7.28 (m, 4H), 7.04 (t, J=8.0 Hz, 1H), 6.77 (dd, J=8.1, 1.4 Hz, 1H), 4.54 (s, 1H), 4.09-3.85 (m, 2H), 3.42 (qd, J=10.9, 2.7 Hz, 2H), 3.30-3.10 (m, 2H), 2.21-1.97 (m, 2H), 1.90-1.59 (m, 2H). LCMS ESI+ calc'd for $C_{25}H_{23}Cl_2N_5S$: 496.1 [M+H+]. found: 496.2 [M+H+].

Example 87: (R)-8-(8-(isoquinolin-4-ylthio)imidazo[1,2-c]pyrimidin-5-yl)-8-azaspiro[4.5]decan-1-amine

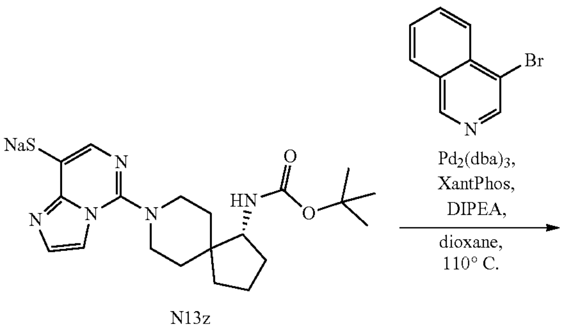

N13z

-continued

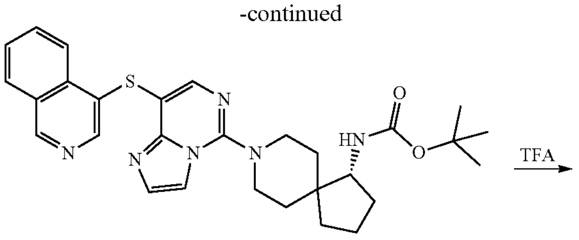

E87a

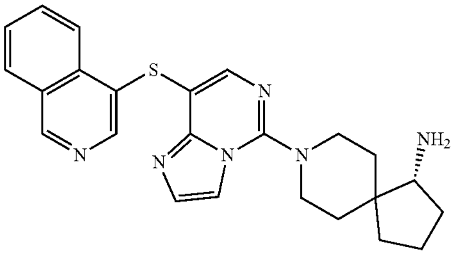

Example 87

Compound E87a: Compound N13z (47 mg, 0.111 mmol) in 1,4-dioxane (2 ml) was added $Pd_2(dba)_3$ (22 mg, 0.024 mmol), XantPhos (28 mg, 0.048 mmol), 4-bromoisoquinoline (31 mg, 0.15 mmol), and DIPEA (58 μL, 0.333 mmol). The reaction vessel was degassed with argon, sealed, and heated to 110° C. overnight. The reaction mixture was then cooled to room temperature, filtered through Celite®, and concentrated. The resulting residue was concentrated, diluted with 1:1 acetonitrile and water each containing 0.1% TFA and purified on preparatory HPLC (0 to 100% acetonitrile in water each containing 0.1% TFA). This provided Compound E87a as a TFA salt.

Example 87: Compound E87a was mixed with TFA (2 ml). After 4 h, the mixture was concentrated on rotovap, diluted with 1:1 acetonitrile and water each containing 0.1% TFA and purified on preparatory HPLC (0 to 100% acetonitrile in water each containing 0.1% TFA). This provided Example 87 as a TFA salt. $^1$H NMR (400 MHz, Methanol-$d_4$) δ 9.38 (s, 1H), 8.60-8.53 (m, 1H), 8.37 (d, J=8.5 Hz, 1H), 8.27 (d, J=14.5 Hz, 2H), 8.15 (ddd, J=8.4, 7.0, 1.3 Hz, 1H), 8.02-7.93 (m, 2H), 7.84 (d, J=2.0 Hz, 1H), 4.17-4.03 (m, 2H), 3.44 (t, J=12.7 Hz, 2H), 2.34-2.19 (m, 1H), 2.01-1.63 (m, 10H). LCMS $ESI^+$ calc'd for $C_{24}H_{26}N_6S$: 431.2 [M+H$^+$]. found: 431.2 [M+H$^+$].

Example 88: (R)-4-((5-(1-amino-8-azaspiro[4.5]decan-8-yl)imidazo[1,2-c]pyrimidin-8-yl)thio)quinoline-8-carbonitrile

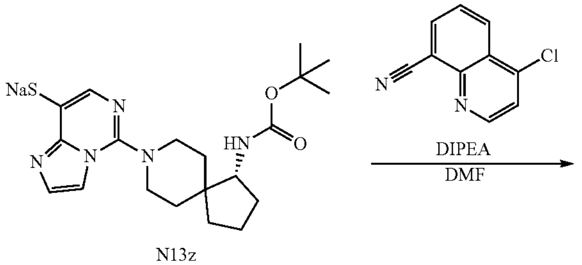

N13z

-continued

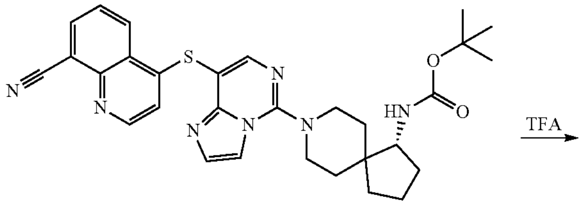

E88a

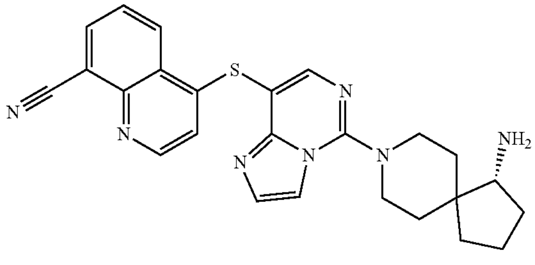

Example 88

Compound E88a: Compound N13z (40 mg, 0.094 mmol) in DMF (1 ml) was added to 4-bromoquinoline-8-carbonitrile (22 mg, 0.118 mmol) and DIPEA (0.592 ml, 3.40 mmol). The reaction vessel was to 110° C. until complete consumption of starting materials. The reaction mixture was cooled to room temperature, diluted with EtOAc and washed with water followed by brine. The organic partition was dried over magnesium sulfate, and filtered through Celite. The resulting solution was concentrated and purified by column chromatography (0-100% EtOAc in Hexanes). This provided Compound E88a. LCMS $ESI^+$ calc'd for $C_{31}H_{36}N_6O_5S$: 556.2 [M+H$^+$]. found: 556.2 [M+H$^+$].

Example 88: The compound was prepared in a manner similar to Example 84 using Compound E88a as the starting material. $^1$H NMR (400 MHz, DMSO-$d_6$) δ 8.67 (d, J=4.9 Hz, 1H), 8.59 (dd, J=8.6, 1.3 Hz, 1H), 8.44 (dd, J=7.2, 1.3 Hz, 1H), 8.15 (s, 1H), 7.85 (dd, J=8.5, 7.3 Hz, 1H), 7.83-7.74 (m, 4H), 7.58 (d, J=1.5 Hz, 1H), 6.99 (d, J=4.9 Hz, 1H), 3.94 (t, J=14.4 Hz, 2H), 3.41 (s, 130H), 2.07 (d, J=15.1 Hz, 1H), 1.91-1.60 (m, 6H), 1.60-1.44 (m, 1H). LCMS $ESI^+$ calc'd for $C_{25}H_{25}N_7S$ [M+H$^+$]: 456.2. found: 456.3 [M+H$^+$].

Example 89: (R)-4-((5-(1-amino-8-azaspiro[4.5]decan-8-yl)imidazo[1,2-c]pyrimidin-8-yl)thio)quinolin-2(1H)-one

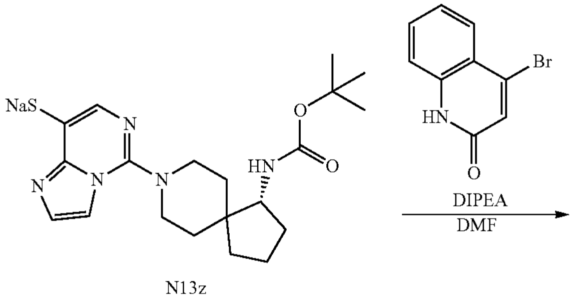

N13z

-continued

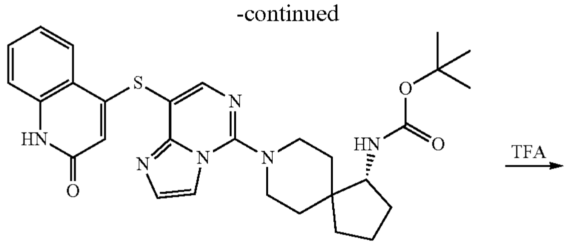

E89a

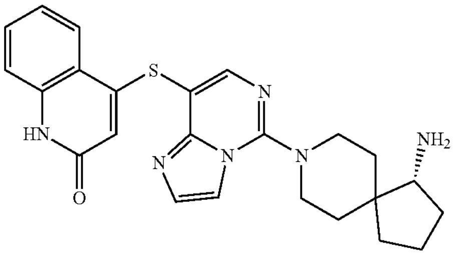

Example 89

Compound E89a: The compound was prepared in a similar manner to Compound E88a using Compound N13z and 4-bromoquinolin-2(1H)-one.

Example 89: This example was prepared in a manner similar to Example 84 using Compound E89a as the starting material. $^{1}$H NMR (400 MHz, Methanol-$d_4$) δ 8.38 (s, 1H), 8.07 (dd, J=8.2, 1.2 Hz, 1H), 8.03 (d, J=2.1 Hz, 1H), 7.84 (d, J=2.0 Hz, 1H), 7.67 (ddd, J=8.5, 7.2, 1.3 Hz, 1H), 7.45-7.36 (m, 2H), 5.91 (s, 1H), 4.20 (dd, J=22.0, 13.8 Hz, 2H), 3.63-3.43 (m, 2H), 3.36 (t, J=6.6 Hz, 1H), 2.29 (dt, J=12.2, 8.3 Hz, 1H), 2.07-1.76 (m, 8H), 1.71 (t, J=13.7 Hz, 2H). LCMS ESI$^+$ calc'd for $C_{24}H_{26}N_6OS$ [M+H$^+$]: 447.2. found: 447.3 [M+H$^+$].

Example 90: (R)-8-(8-((1,8-naphthyridin-4-yl)thio)imidazo[1,2-c]pyrimidin-5-yl)-8-azaspiro[4.5]decan-1-amine Compound E90A: The compound was prepared in a similar manner to Compound E78a using Compound N13z and 4-bromo-1,8-naphthyridine.

Example 90: The compound was prepared in a manner similar to Example 84 using Compound E90a as the starting material. $^{1}$H NMR (400 MHz, DMSO-$d_6$) δ 9.29 (dd, J=4.4, 1.7 Hz, 1H), 9.06 (dd, J=8.5, 1.7 Hz, 1H), 8.77 (d, J=5.7 Hz, 1H), 8.40 (s, 1H), 8.02 (d, J=2.0 Hz, 1H), 7.98 (dd, J=8.5, 4.4 Hz, 1H), 7.78 (d, J=1.9 Hz, 1H), 7.29 (d, J=5.6 Hz, 1H), 4.22 (dd, J=22.0, 13.7 Hz, 2H), 3.52 (tt, J=13.5, 2.9 Hz, 2H), 3.37 (dd, J=7.6, 5.7 Hz, 1H), 2.30 (dt, J=12.2, 7.9 Hz, 1H), 2.06-1.66 (m, 9H). LCMS ESI$^+$ calc'd for $C_{23}H_{25}N_7S$ [M+H$^+$]: 432.2. found: 432.3 [M+H$^+$].

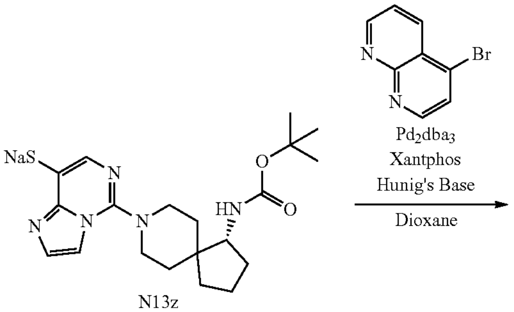

N13z

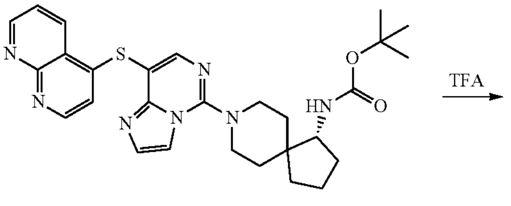

E90a

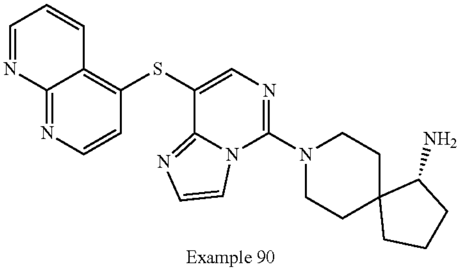

Example 90

Example 91: (S)-1-(1-(8-((2,3-dichlorophenyl)thio)imidazo[1,2-c]pyrimidin-5-yl)piperidin-4-yl)ethan-1-amine

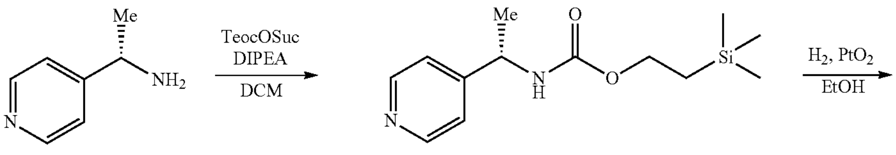

E91a

E91b

-continued

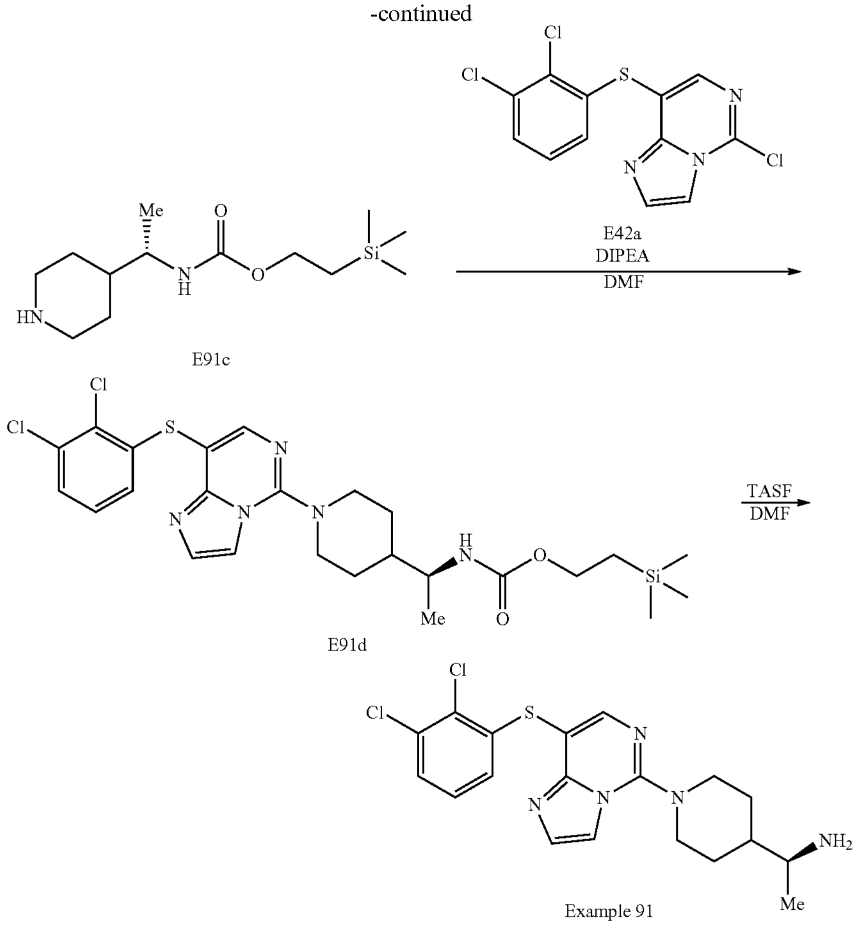

Compound E91b: Compound E91a (473 mg, 3.872 mmol) and TeocOSuc (1.19 g, 4.589 mmol) were dissolved in dichloromethane and stirred at room temperature as DIPEA (0.876 mL, 5.0 mmol) was added. Stirred for 24 h. The reaction mixture was washed with water and organic phase was concentrated, product chromatographed with 0 to 10% MeOH in $CH_2Cl_2$ gradient, product eluting at 5-7% MeOH. Obtained Compound E91b. $^1H$ NMR (400 MHz, Chloroform-d) δ 8.61-8.55 (m, 2H), 7.28-7.21 (m, 2H), 4.96 (s, 1H), 4.83 (s, 1H), 4.21-4.09 (m, 2H), 1.48 (d, J=7.0 Hz, 3H), 0.99 (s, broad, 2H).

Compound E91c: Compound E91b (937 mg, 4.0 mmol) was dissolved in ethanol (20 mL) and platinum oxide (IV) (400 mg, 1.761 mmol) was added, followed by 6N HCl (0.5 mL) and stirred under 1 atm of hydrogen overnight. The sample was filtered and concentrated, giving Compound E91c. LCMS $ESI^+$ calc'd for $C_{13}H_{28}N_2O_2Si$: 273.2 [$M+H^+$]. found: 273.2 [$M+H^+$].

Example 91: Compound E91c (30 mg, 0.091 mmol) and Compound E42a (43 mg, 0.14 mmol) were dissolved in DMF (1 mL) and DIPEA (0.047 mL, 0.272 mmol) was added. Stirring overnight at room temperature gave a reaction containing Compound E91d. At that time, TASF (74 mg, 0.27 mmol) was added to the solution, and the solution was heated to 60° C. for 12 h. The mixture was concentrated under reduced pressure, diluted with 1:1 acetonitrile and water each containing 0.1% TFA, and purified on preparatory HPLC (0 to 100% acetonitrile in water each containing 0.1% TFA). This provided Example 91 as a TFA salt. $^1H$ NMR (400 MHz, Methanol-$d_4$) δ 8.37 (s, 1H), 8.06 (d, J=2.2 Hz, 1H), 7.87 (d, J=2.2 Hz, 1H), 7.39 (dd, J=8.0, 1.4 Hz, 1H), 7.12 (t, J=8.0 Hz, 1H), 6.82 (dd, J=8.1, 1.3 Hz, 1H), 4.36 (d, broad, J=13.2 Hz, 1H), 3.35-3.25 (m, 5H), 2.05-1.90 (m, 2H), 1.77-1.60 (m, 2H), 1.37 (d, J=6.7 Hz, 3H). LCMS $ESI^+$ calc'd for $C_{19}H_{21}Cl_2N_5S$: 422.1 [$M+H^+$]. found: 422.0 [$M+H^+$].

Example 92: 4-((5-((3S,4S)-4-amino-3-methyl-2-oxa-8-azaspiro[4.5]decan-8-yl)imidazo[1,2-c]pyrimidin-8-yl)thio)-1-methylquinolin-2(1H)-one Compound E92a: The compound was prepared in a similar manner to Compound E88a using Compound N17 and 4-bromo-1-methylquinolin-2(1H)-one.

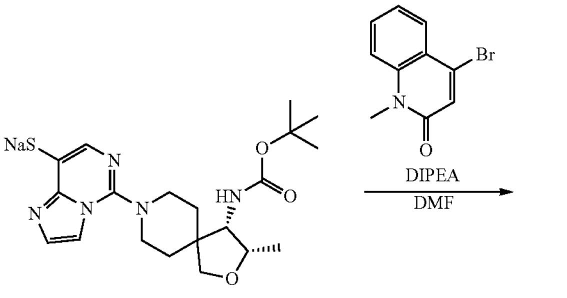

N17

-continued

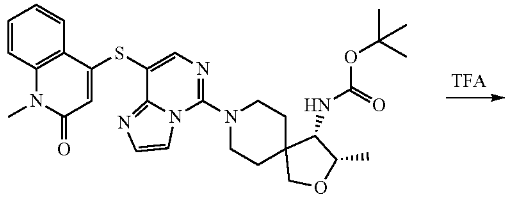

E92a

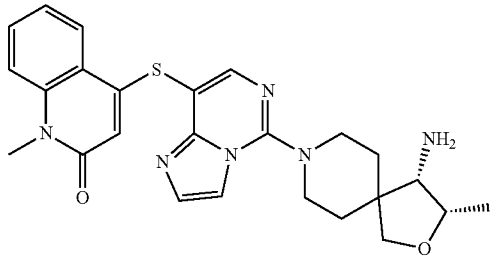

Example 92

Example 92: The compound was prepared in a manner similar to Example 88 using Compound E92a as the starting material. $^1$H NMR (400 MHz, methanol-$d_4$) δ 8.42 (s, 1H), 8.14 (dd, J=8.1, 1.4 Hz, 1H), 8.07 (d, J=2.1 Hz, 1H), 7.88 (d, J=2.1 Hz, 1H), 7.80 (ddd, J=8.7, 7.2, 1.4 Hz, 1H), 7.73-7.60 (m, 1H), 7.46 (ddd, J=8.2, 7.2, 1.1 Hz, 1H), 6.00 (s, 1H), 4.48-4.30 (m, 1H), 4.28-4.11 (m, 2H), 4.07 (d, J=9.2 Hz, 1H), 3.96 (d, J=9.2 Hz, 1H), 3.71 (s, 3H), 3.56 (d, J=4.0 Hz, 1H), 3.54-3.42 (m, 2H), 2.19-2.00 (m, 3H), 1.91-1.85 (m, 1H), 1.37 (d, J=6.5 Hz, 3H). LCMS ESI$^+$ calc'd for $C_{25}H_{28}N_6O_2S$ [M+H$^+$]: 477.2. found: 477.3 [M+H$^+$].

Example 93: (3S,4S)-3-methyl-8-(8-(isoquinolin-4-ylthio)imidazo[1,2-c]pyrimidin-5-yl)-2-oxa-8-azaspiro[4.5]decan-4-amine

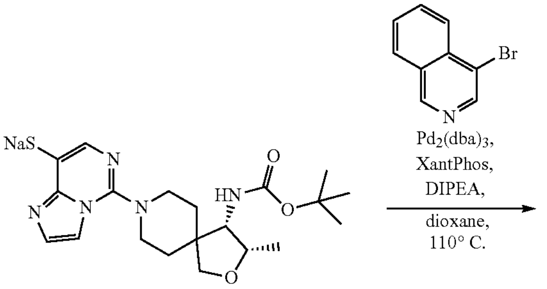

N17

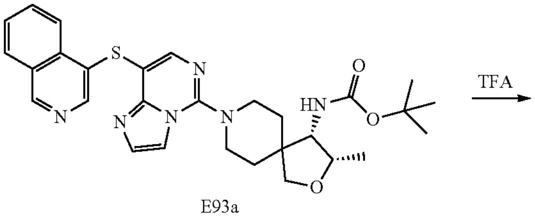

E93a

-continued

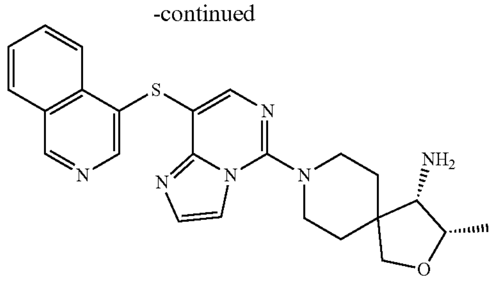

Example 93

Compound E93a: Compound N17 (47 mg, 0.106 mmol) in 1,4-dioxane (2 ml) was added $Pd_2(dba)_3$ (10 mg, 0.011 mmol), XantPhos (13 mg, 0.022 mmol), 4-bromoisoquinoline (22 mg, 0.106 mmol), and DIPEA (32 μL, 0.18 mmol). The reaction vessel was degassed with argon, sealed, and heated to 110° C. overnight. The reaction mixture was then cooled to room temperature, filtered through Celite®, and concentrated. The resulting residue was concentrated, diluted with 1:1 acetonitrile and water each containing 0.1% TFA and purified on preparatory HPLC (0 to 100% acetonitrile in water each containing 0.1% TFA). This Compound E93a as a TFA salt. LCMS ESI$^+$ calc'd for $C_{29}H_{34}N_6O_3S$: 547.2 [M+H$^+$]. found: 547.2 [M+H$^+$].

Example 93: Compound E93a was mixed with TFA (2 ml). After 4 h, the mixture was concentrated on rotovap, diluted with 1:1 acetonitrile and water each containing 0.1% TFA and purified on preparatory HPLC (0 to 100% acetonitrile in water each containing 0.1% TFA). This provided Example 93 (33 mg) as a TFA salt. $^1$H NMR (400 MHz, Methanol-$d_4$) δ 9.7 (s, 1H), 8.61 (dq, J=8.2, 1.0 Hz, 1H), 8.44 (dt, J=8.2, 1.0 Hz, 1H), 8.41 (s, 1H), 8.28-8.19 (m, 2H), 8.08-7.99 (m, 2H), 7.90 (d, J=2.1 Hz, 1H), 4.40-4.30 (m, 1H), 4.20-4.07 (m, 2H), 4.04 (d, J=9.2 Hz, 1H), 3.94 (d, J=9.3 Hz, 1H), 3.54 (d, J=4.1 Hz, 1H), 3.51-3.34 (m, 2H), 2.18-1.97 (m, 3H), 1.85 (d, J=13.3 Hz, 1H), 1.36 (d, J=6.5 Hz, 3H). LCMS ESI$^+$ calc'd for $C_{24}H_{26}N_6OS$: 447.2 [M+H$^+$]. found: 447.2 [M+H$^+$].

Example 94: (R)-1-(1-(8-((2,3-dichlorophenyl)thio)imidazo[1,2-c]pyrimidin-5-yl)piperidin-4-yl)ethan-1-amine Example 94 was obtained similarly to Example 91, but using (R)-1-(pyridin-4-yl)ethan-1-amine instead of (S)-1-(pyridin-4-yl)ethan-1-amine in the first step. Thus, Example 94 was obtained as a TFA salt. $^1$H NMR (400 MHz, Methanol-$d_4$) δ 8.42 (s, 1H), 8.10 (d, J=2.2 Hz, 1H), 7.92 (d, J=2.2 Hz, 1H), 7.40 (dd, J=8.0, 1.4 Hz, 1H), 7.13 (t, J=8.1 Hz, 1H), 6.84 (dd, J=8.1, 1.3 Hz, 1H), 4.39 (broad d, J=13.2 Hz, 1H), 3.40-3.20 (m, 5H), 2.11-1.91 (m, 2H), 1.77-1.58 (m, 2H), 1.37 (d, J=6.8 Hz, 3H). LCMS ESI$^+$ calc'd for $C_{19}H_{21}Cl_2N_5S$: 422.1 [M+H$^+$]. found: 422.1 [M+H$^+$].

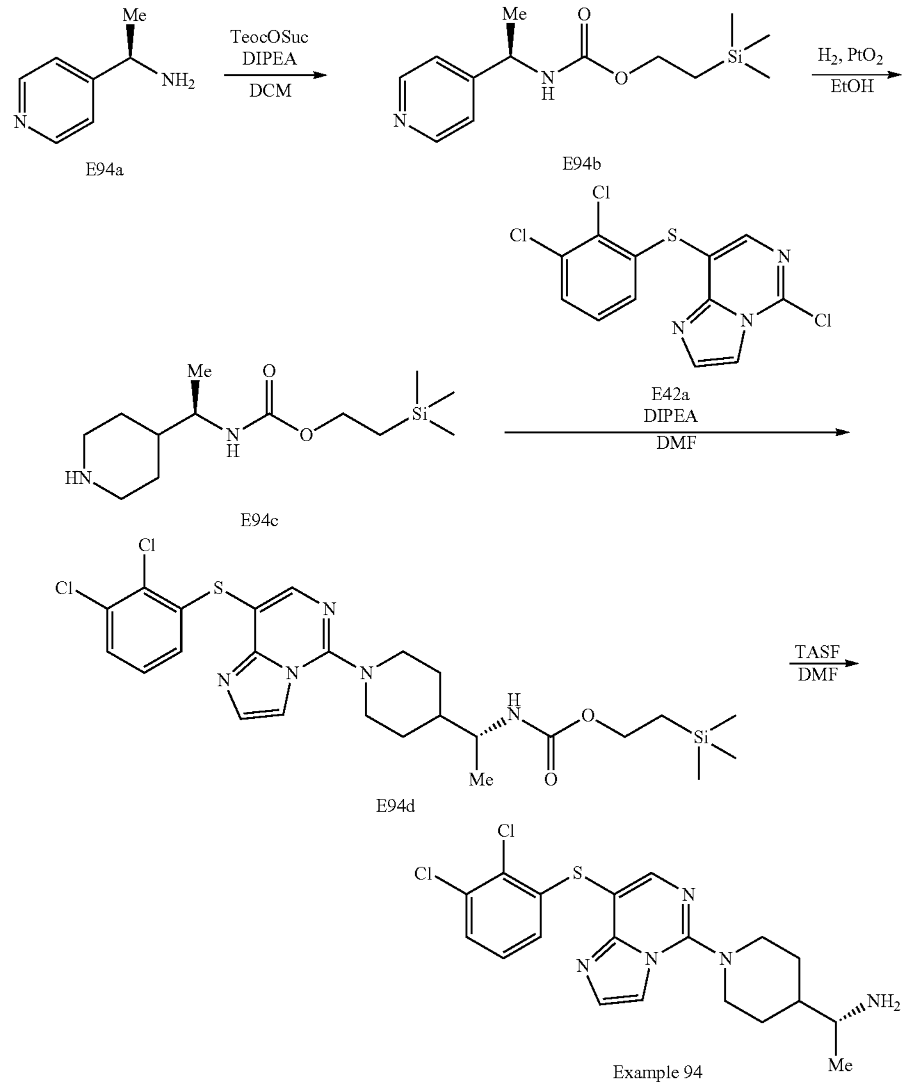
E94a E94b E94c E94d Example 94
Example 95: (3S,4S)-8-(8-(benzo[d]thiazol-7-ylthio) imidazo[1,2-c]pyrimidin-5-yl)-3-methyl-2-oxa-8-azaspiro[4.5]decan-4-amine
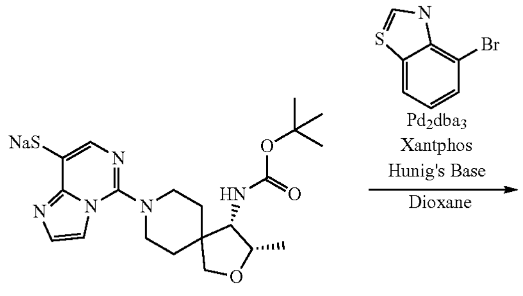
N17
-continued
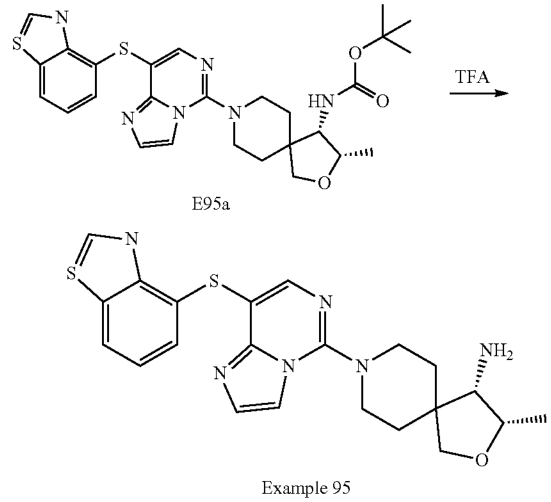
E95a
Example 95

Compound E95a: The compound was prepared in a similar manner to Compound E87a using Compound N17 and 7-bromobenzo[d]thiazole. LCMS $ESI^+$ calc'd for $C_{22}H_{24}N_6OS_2$ [M+$H^+$]: 453.2. found: 453.4 [M+$H^+$].

Example 95: The compound was prepared in a manner similar to Example 84 using Compound E95a as the starting material. $^1$H NMR (400 MHz, methanol-$d_4$) δ 9.12 (s, 1H), 8.05 (s, 1H), 8.04-7.96 (m, 1H), 7.65-7.58 (m, 2H), 7.49-7.41 (m, 2H), 4.26 (dd, J=6.6, 4.4 Hz, 1H), 4.06 (d, J=7.1 Hz, 1H), 3.94 (d, J=9.3 Hz, 1H), 3.92-3.81 (m, 1H), 3.79 (d, J=9.2 Hz, 1H), 3.60 (s, 1H), 3.56 (d, J=4.3 Hz, 1H), 3.22 (ddd, J=26.0, 11.9, 8.9 Hz, 2H), 2.11-1.99 (m, 2H), 1.91-1.71 (m, 2H), 1.28 (d, J=6.5 Hz, 3H). LCMS $ESI^+$ calc'd for $C_{22}H_{24}N_6OS_2$ [M+$H^+$]: 453.2; Found: 453.4 [M+$H^+$].

Example 96: 7-((5-((3S,4S)-4-amino-3-methyl-2-oxa-8-azaspiro[4.5]decan-8-yl)imidazo[1,2-c]pyrimidin-8-yl)thio)benzo[b]thiophene-3-carbaldehyde

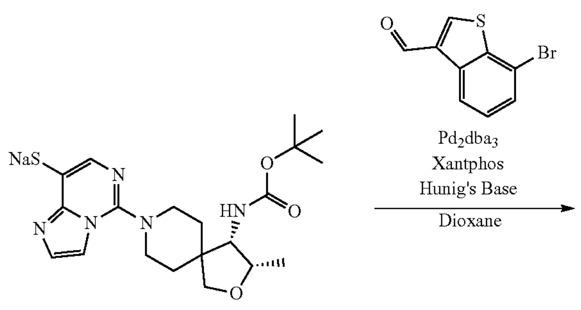

N17

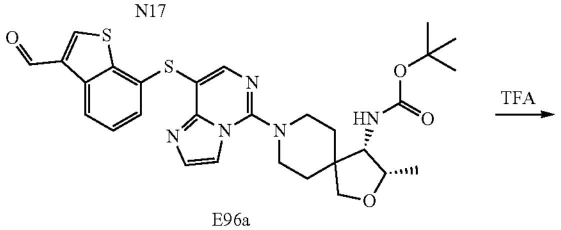

E96a

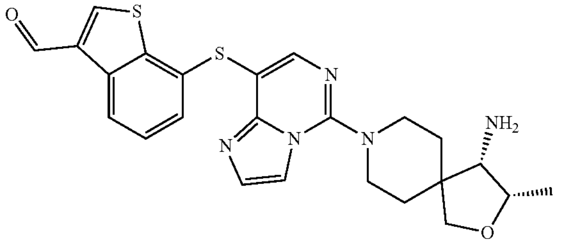

Example 96

Compound E96a: The compound was prepared in a similar manner to Compound E78a using $N_{17}$ and 7-bromobenzo[b]thiophene-3-carbaldehyde. $ESI^+$ m/z Calc'd for $C_{29}H_{33}N_5O_4S_2$ [M+$H^+$]: 580.2; Found: 580.2 [M+$H^+$].

Example 96: The compound was prepared in a manner similar to Example 84 using Compound E96a as the starting material. $^1$H NMR (400 MHz, Methanol-$d_4$) δ 10.10 (s, 1H), 8.62 (s, 1H), 8.54 (dd, J=7.9, 1.2 Hz, 1H), 7.94 (s, 1H), 7.63-7.57 (m, 2H), 7.57-7.52 (m, 1H), 7.48 (d, J=7.8 Hz, 1H), 4.35-4.17 (m, 1H), 3.93 (d, J=9.3 Hz, 1H), 3.89-3.73 (m, 2H), 3.55 (d, J=4.2 Hz, 1H), 3.17 (dd, J=14.0, 3.3 Hz, 1H), 2.08-1.69 (m, 6H), 1.27 (d, J=6.5 Hz, 3H). (LCMS): $ESI^+$ m/z Calc'd for $C_{24}H_{25}N_5O_4S_2$[M+$H^+$]: 480.2. found: 480.2 [M+$H^+$].

Example 97: (3S,4S)-8-(8-((6,7-dihydro-5H-cyclopenta[b]pyridin-4-yl)thio)imidazo[1,2-c]pyrimidin-5-yl)-3-methyl-2-oxa-8-azaspiro[4.5]decan-4-amine

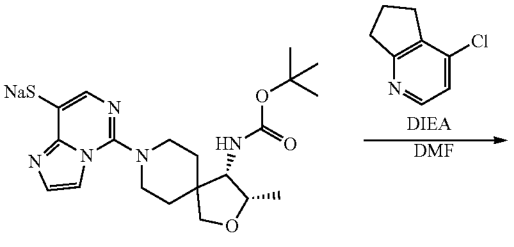

N17

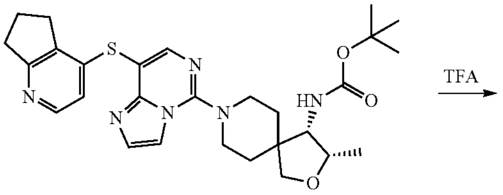

E97a

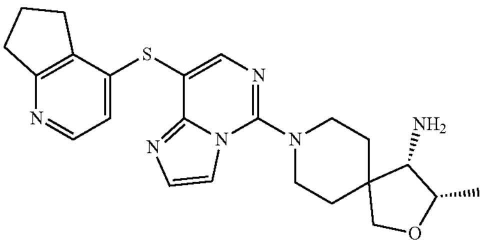

Example 97

Compound E97a: The compound was prepared in a similar manner to Compound E88a using Compound N17 and 4-chloro-6,7-dihydro-5H-cyclopenta[b]pyridine.

Example 97: The compound was prepared in a manner similar to Example 84 using Compound E97a as the starting material. $^1$H NMR (400 MHz, Methanol-$d_4$) δ 8.30 (s, 1H), 8.15 (d, J=6.5 Hz, 1H), 7.99 (d, J=1.9 Hz, 1H), 7.76 (d, J=1.8 Hz, 1H), 7.09 (d, J=6.5 Hz, 1H), 4.42-4.30 (m, 1H), 4.16 (dd, J=20.8, 15.1 Hz, 2H), 4.06 (d, J=9.2 Hz, 1H), 3.94 (d, J=9.2 Hz, 1H), 3.56 (d, J=4.1 Hz, 1H), 3.51-3.37 (m, 2H), 3.35 (d, J=5.4 Hz, 1H), 3.20 (t, J=7.5 Hz, 2H), 2.46 (p, J=7.8 Hz, 2H), 2.21-1.79 (m, 4H), 1.37 (d, J=6.5 Hz, 3H). LCMS $ESI^+$ calc'd for $C_{23}H_{28}N_6OS$ [M+$H^+$]: 437.2. Found: 437.3 [M+$H^+$].

Example 98: (3S,4S)-3-methyl-8-(8-(pyrazolo[1,5-a]pyridin-4-ylthio)imidazo[1,2-c]pyrimidin-5-yl)-2-oxa-8-azaspiro[4.5]decan-4-amine Compound E98a: The compound was prepared in a similar manner to Compound E88a using Compound N17 and 4-bromopyrazolo[1,5-a]pyridine.

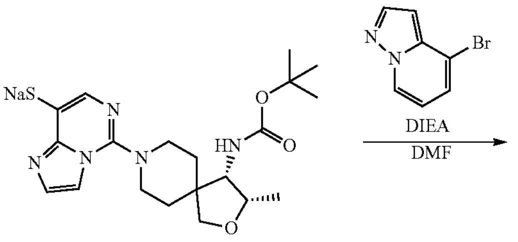

N17

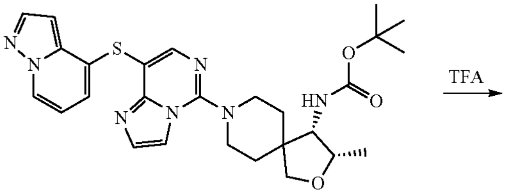

E98a

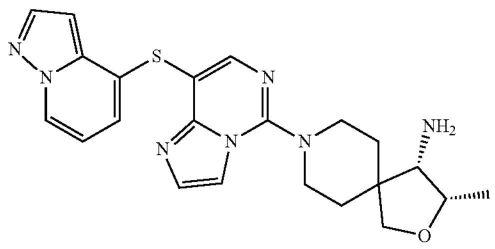

Example 98

Example 98: The compound was prepared in a manner similar to Example 84 using Compound E98a as the starting material. $^1H$ NMR (400 MHz, Methanol-$d_4$) δ 8.48 (dt, J=6.9, 0.9 Hz, 1H), 8.46 (s, 1H), 8.12-7.90 (m, 3H), 7.07 (dd, J=7.2, 0.8 Hz, 1H), 6.86-6.74 (m, 2H), 4.35 (qd, J=6.4, 4.0 Hz, 1H), 4.20-4.06 (m, 2H), 4.04 (d, J=9.3 Hz, 1H), 3.92 (d, J=9.2 Hz, 1H), 3.54 (d, J=4.1 Hz, 1H), 3.45 (dddd, J=27.7, 13.9, 11.1, 2.9 Hz, 2H), 2.20-2.06 (m, 2H), 1.99 (d, J=13.9 Hz, 1H), 1.86 (d, J=13.3 Hz, 1H), 1.36 (d, J=6.5 Hz, 3H). LCMS $ESI^+$ calc'd for $C_{22}H_{25}N_7OS$ [M+H$^+$]: 436.1; Found: 436.2 [M+H$^+$].

Example 99: (3S,4S)-8-(8-(benzo[b]thiophen-7-ylthio)imidazo[1,2-c]pyrimidin-5-yl)-3-methyl-2-oxa-8-azaspiro[4.5]decan-4-amine

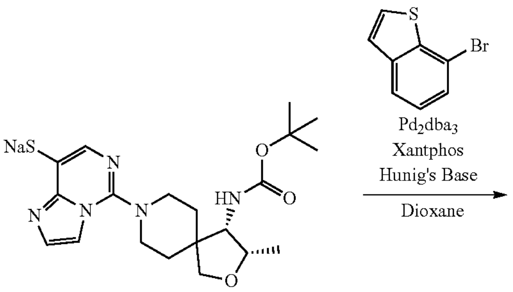

N17

-continued

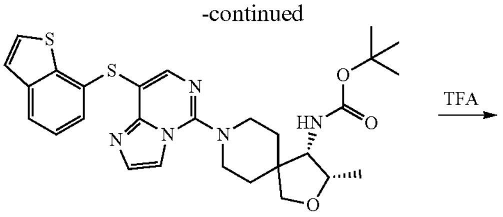

E99a

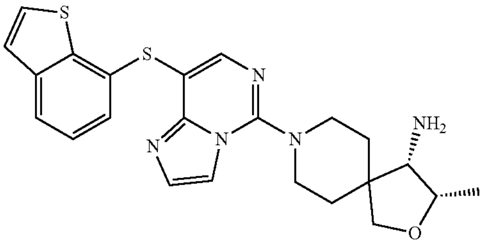

Example 99

Compound E99a: The compound was prepared in a similar manner to Compound E78a using Compound N17 and 7-bromobenzo[b]thiophene. $ESI^+$ m/z Calc'd for $C_{28}H_{33}N_5O_3S_2$[M+H$^+$]: 552.2. found: 552.3 [M+H$^+$].

Example 99: The compound was prepared in a manner similar to Example 84 using Compound E99a as the starting material. $^1H$ NMR (400 MHz, $CD_3CN$) δ 7.97 (s, 1H), 7.81 (dd, J=7.9, 1.1 Hz, 1H), 7.63-7.54 (m, 3H), 7.44 (d, J=5.5 Hz, 1H), 7.40 (dd, J=7.5, 1.1 Hz, 1H), 7.33 (t, J=7.7 Hz, 1H), 4.34-4.18 (m, 1H), 3.94 (d, J=9.2 Hz, 1H), 3.89-3.80 (m, 1H), 3.81-3.70 (m, 1H), 3.55 (d, J=4.4 Hz, 1H), 3.18 (dddd, J=16.8, 13.6, 10.9, 2.8 Hz, 1H), 2.13-1.71 (m, 6H), 1.28 (d, J=6.5 Hz, 3H). (LCMS): $ESI^+$ m/z Calc'd for $C_{23}H_{25}N_5OS_2$ [M+H$^+$]: 452.2. found: 452.2 [M+H$^+$].

Example 100: (3S,4S)-8-(8-((2-aminobenzo[d]thiazol-7-yl)thio)imidazo[1,2-c]pyrimidin-5-yl)-3-methyl-2-oxa-8-azaspiro[4.5]decan-4-amine

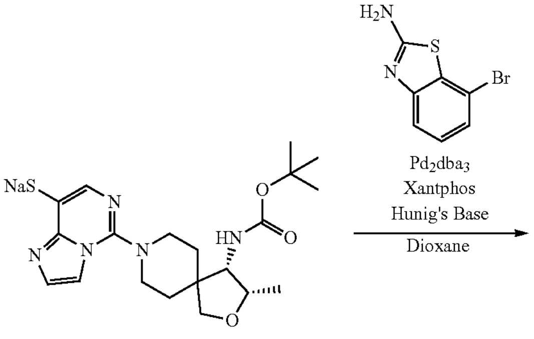

N17

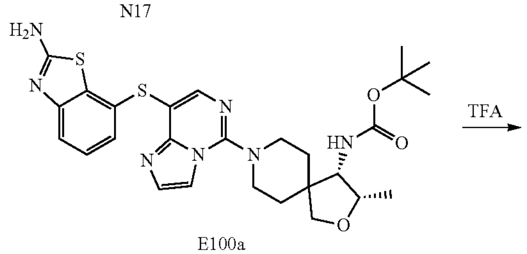

E100a

-continued

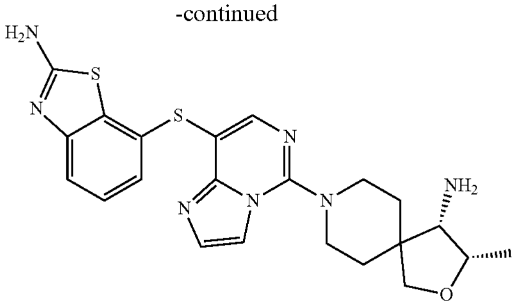

Example 100

Compound E100a: The compound was prepared in a similar manner to Compound E78a using Compound N17 and 7-bromobenzo[d]thiazol-2-amine. ESI$^+$ m/z Calc'd for $C_{27}H_{33}N_7O_3S_2$[M+H$^+$]: 568.2. found: 568.2 [M+H$^+$].

Example 100: The compound was prepared in a manner similar to Example 84 using Compound E100a as the starting material. $^1$H NMR (400 MHz, $CD_3CN$) δ 8.15 (s, 1H), 7.62 (d, J=2.0 Hz, 1H), 7.48 (d, J=1.9 Hz, 1H), 7.36-7.26 (m, 2H), 7.19 (dd, J=7.1, 1.6 Hz, 1H), 4.30-4.17 (m, 1H), 4.08-3.86 (m, 2H), 3.79 (d, J=9.4 Hz, 1H), 3.57 (d, J=4.5 Hz, 1H), 3.26 (q, J=11.2 Hz, 1H), 2.18-1.77 (m, 6H), 1.28 (d, J=6.4 Hz, 3H). (LCMS): ESI$^+$ m/z Calc'd for $C_{22}H_{25}N_7OS_2$ [M+H$^+$]: 468.2; Found: 468.3 [M+H$^+$].

Example 101: (3S,4S)-3-methyl-8-(8-((2-(methylthio)phenyl)thio)imidazo[1,2-c]pyrimidin-5-yl)-2-oxa-8-azaspiro[4.5]decan-4-amine

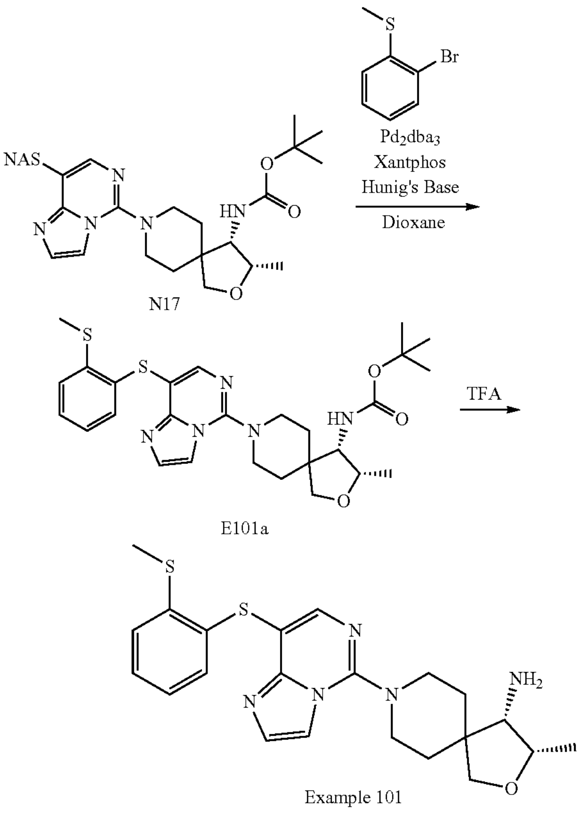

N17

E101a

Example 101

Compound E101a: The compound was prepared in a similar manner to Compound E78a using Compound N17 and (2-bromophenyl)(methyl)sulfane. ESI$^+$ m/z Calc'd for $C_{27}H_{35}N_5O_3S_2$[M+H$^+$]: 542.2; Found: 542.3 [M+H$^+$].

Example 101: The compound was prepared in a manner similar to Example 84 using Compound E101a as the starting material. $^1$H NMR (400 MHz, $CD_3CN$) δ 7.98 (s, 1H), 7.71-7.57 (m, 2H), 7.33 (dd, J=7.9, 1.3 Hz, 1H), 7.25 (ddd, J=7.9, 6.8, 1.9 Hz, 1H), 7.12-6.96 (m, 2H), 4.33-4.18 (m, 1H), 3.96 (d, J=9.3 Hz, 1H), 3.93-3.82 (m, 1H), 3.81 (s, 1H), 3.57 (d, J=4.4 Hz, 1H), 3.33-3.13 (m, 1H), 2.50 (s, 3H), 2.16-1.66 (m, 6H), 1.29 (d, J=6.5 Hz, 3H). (LCMS): ESI$^+$ m/z Calc'd for $C_{22}H_{27}N_5OS_2$ [M+H$^+$]: 480.2. found: 442.3 [M+H$^+$].

Example 102: (3S,4S)-3-methyl-8-(8-(thieno[2,3-b]pyridin-4-ylthio)imidazo[1,2-c]pyrimidin-5-yl)-2-oxa-8-azaspiro[4.5]decan-4-amine

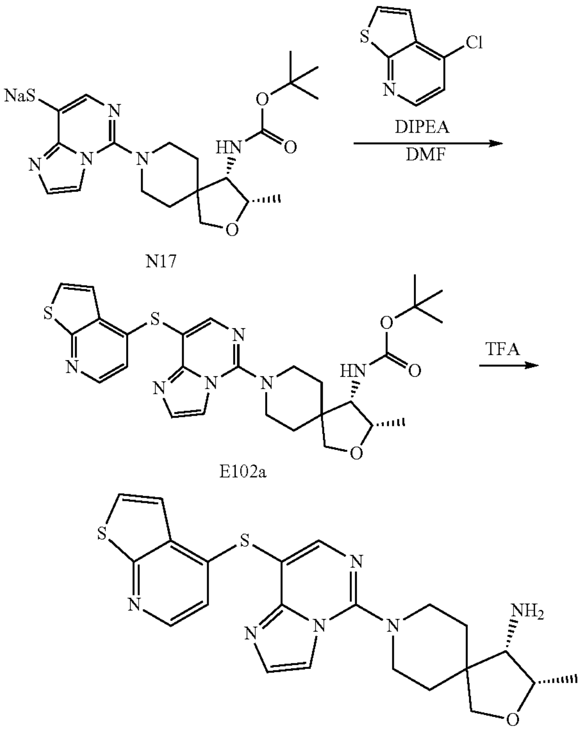

N17

E102a

Example 102

Compound E102a: The compound was prepared in a similar manner to Compound E88a using Compound N17 and 4-chlorothieno[2,3-b]pyridine.

Example 102: The compound was prepared in a manner similar to Example 84 using Compound E102a as the starting material. $^1$H NMR (400 MHz, methanol-$d_4$) δ 8.41 (s, 1H), 8.24 (d, J=5.2 Hz, 1H), 8.05 (d, J=2.1 Hz, 1H), 7.89 (d, J=6.1 Hz, 1H), 7.84 (d, J=2.0 Hz, 1H), 7.64 (d, J=6.1 Hz, 1H), 6.84 (d, J=5.2 Hz, 1H), 4.45-4.31 (m, 1H), 4.24-4.09 (m, 2H), 4.06 (d, J=9.2 Hz, 1H), 3.96 (d, J=9.2 Hz, 1H), 3.58-3.35 (m, 4H), 2.23-1.95 (m, 3H), 1.37 (d, J=6.5 Hz, 3H). LCMS ESI$^+$ calc'd for $C_{22}H_{24}N_6OS_2$ [M+H$^+$]: 453.1. found: 453.2 [M+H$^+$].

Example 103: (3S,4S)-3-methyl-8-(8-(naphthalen-1-ylthio)imidazo[1,2-c]pyrimidin-5-yl)-2-oxa-8-azaspiro[4.5]decan-4-amine

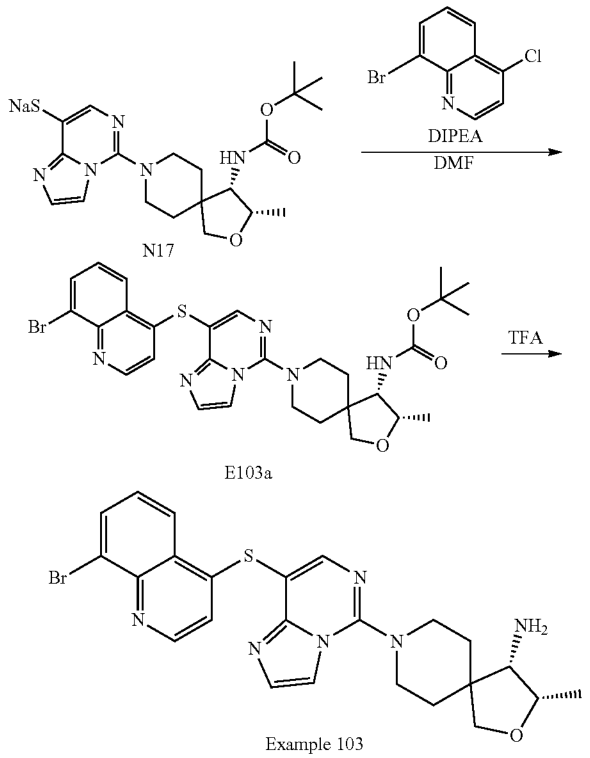

N17
E103a
Example 103

Compound E103a: The compound was prepared in a similar manner to Compound E88a using Compound N17 and 8-bromo-4-chloroquinoline.

Example 103: The compound was prepared in a manner similar to Example 84 using Compound E103a as the starting material. $^1$H NMR (400 MHz, DMSO-$d_6$) δ 8.61 (d, J=4.8 Hz, 1H), 8.29 (dd, J=8.4, 1.2 Hz, 1H), 8.25-8.16 (m, 2H), 7.97 (s, 3H), 7.90 (d, J=1.7 Hz, 1H), 7.67 (d, J=1.5 Hz, 1H), 7.63 (dd, J=8.4, 7.5 Hz, 1H), 6.95 (d, J=4.8 Hz, 1H), 4.28-4.16 (m, 4H), 4.01-3.84 (m, 3H), 3.74 (d, J=9.0 Hz, 1H), 3.48 (s, 1H), 3.30 (q, J=12.7 Hz, 2H), 1.97 (t, J=12.2 Hz, 2H), 1.83 (d, J=13.6 Hz, 1H), 1.76-1.64 (m, 1H), 1.22 (d, J=6.5 Hz, 3H). LCMS ESI$^+$ calc'd for $C_{24}H_{25}BrN_6OS$ [M+H$^+$]: 525.1. found: 525.3 [M+H$^+$].

Example 104: (3S,4S)-8-(8-((8-aminoquinolin-4-yl)thio)imidazo[1,2-c]pyrimidin-5-yl)-3-methyl-2-oxa-8-azaspiro[4.5]decan-4-amine Compound E104a: Compound N17 (100 mg, 0.226 mmol) in 1,4-dioxane (2 ml) was added $Pd_2(dba)_3$ (10 mg, 0.011 mmol), XantPhos (13.1 mg, 0.023 mmol), methyl 4-bromoquinolin-8-amine (152 mg, 0.679 mmol), and DIPEA (0.118 ml, 0.679 mmol). The reaction vessel was purged with argon, sealed, and heated to 110° C. until complete consumption of starting materials. The reaction mixture was cooled to room temperature, diluted with EtOAc and washed with water followed by brine. The organic partition was dried over magnesium sulfate, and filtered through Celite. The resulting solution was concentrated and purified by column chromatography (0-100% EtOAc in Hexanes). This provided Compound E104a. LCMS ESI$^+$ calc'd for $C_{31}H_{36}N_6O_5S$: 562.2 [M+H$^+$]. found: 562.2 [M+H$^+$].

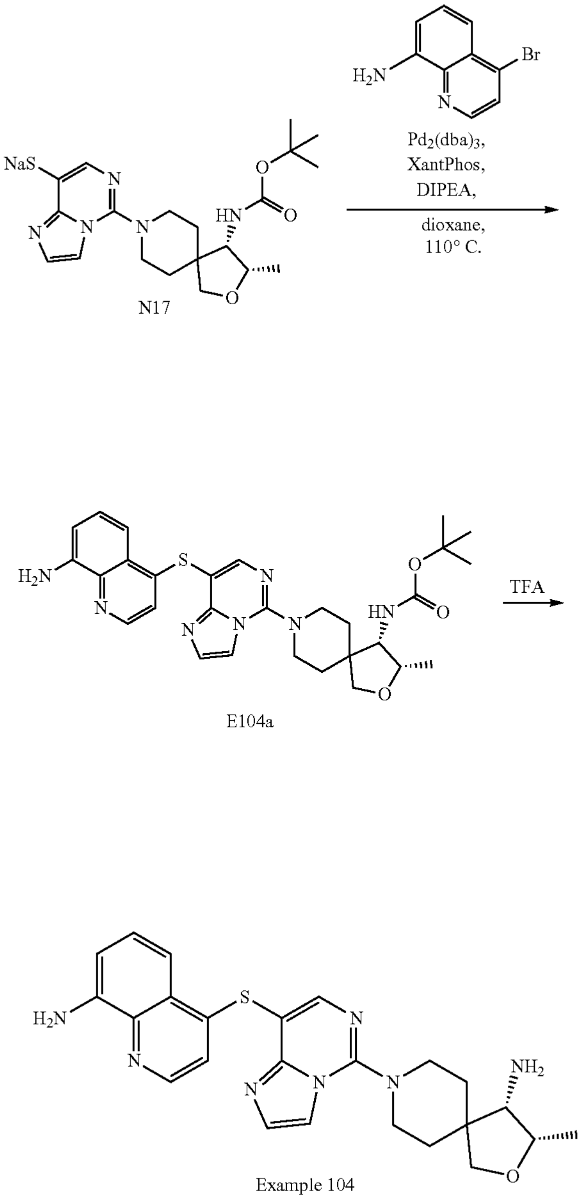

N17
E104a
Example 104

Example 104: Compound E104a was dissolved in DCM (5 ml), and TFA (1 ml) was added. The solution was concentrated and reconstituted in water and DMF and the solution was purified on preparatory HPLC (10-100% MeCN in water with 0.1% TFA, Gemini). This provided Example 104. $^1$H NMR (400 MHz, DMSO-$d_6$) δ 8.37 (d, J=4.8 Hz, 1H), 8.22 (s, 1H), 8.04 (s, 3H), 7.93 (d, J=1.8 Hz, 1H), 7.73 (d, J=1.6 Hz, 1H), 7.43 (dd, J=8.3, 7.4 Hz, 1H), 7.37 (dd, J=8.3, 1.4 Hz, 1H), 7.01 (dd, J=7.5, 1.4 Hz, 1H), 6.82 (d, J=4.8 Hz, 1H), 4.30-4.18 (m, 1H), 4.01-3.85 (m, 3H), 3.74 (d, J=9.0 Hz, 1H), 3.48 (s, 1H), 3.31 (q, J=12.3 Hz, 2H), 2.03-1.90 (m, 2H), 1.83 (d, J=13.8 Hz, 1H), 1.71 (d, J=13.4 Hz, 1H), 1.23 (d, J=6.5 Hz, 3H). LCMS ESI$^+$ calc'd for $C_{26}H_{28}N_6O_3S$: 462.2 [M+H$^+$]. found: 462.3 [M+H$^+$].

Example 105: methyl 4-((5-((3S,4S)-4-amino-3-methyl-2-oxa-8-azaspiro[4.5]decan-8-yl)imidazo[1,2-c]pyrimidin-8-yl)thio)quinoline-8-carboxylate

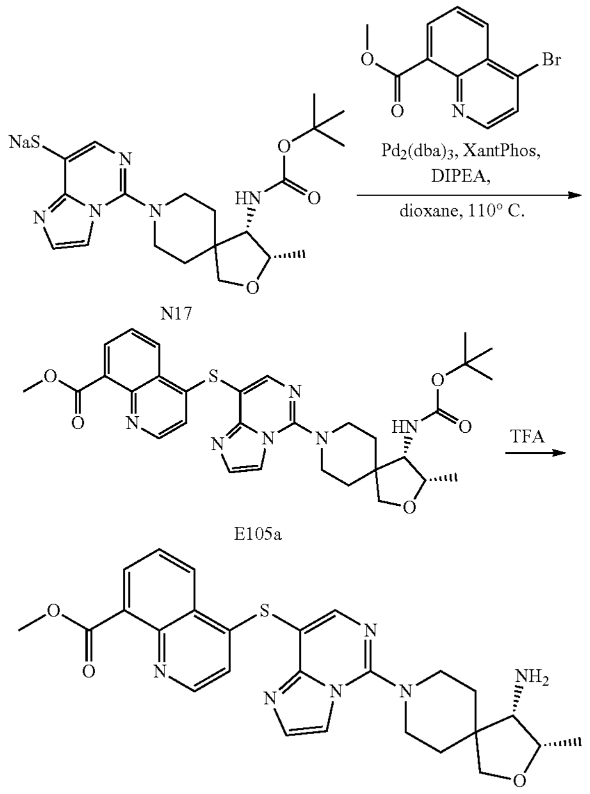

N17

E105a

Example 105

Compound E105a: Compound N17 (500 mg, 1.132 mmol) in 1,4-dioxane (12 ml) was added $Pd_2(dba)_3$ (52 mg, 0.057 mmol), XantPhos (65.3 mg, 0.113 mmol), methyl 4-bromoquinoline-8-carboxylate (603 mg, 2.265 mmol), and DIPEA (0.592 ml, 3.40 mmol). The reaction vessel was purged with argon, sealed, and heated to 110° C. until complete consumption of starting materials. The reaction mixture was cooled to room temperature, diluted with EtOAc and washed with water followed by brine. The organic partition was dried over magnesium sulfate, and filtered through Celite. The resulting solution was concentrated and purified by column chromatography (0-100% EtOAc in Hexanes). This provided Compound E105a. LCMS ESI$^+$ calc'd for $C_{31}H_{36}N_6O_5S$: 604.3 [M+H$^+$]. found: 604.3 [M+H$^+$].

Example 105: Compound E105a was dissolved in DCM (5 ml), and TFA (1 ml) was added. The solution was concentrated and reconstituted in water and DMF and the solution was purified on preparatory HPLC (10-100% MeCN in water with 0.1% TFA, Gemini). This provided Example 105. $^1$H NMR (400 MHz, DMSO-d$_6$) δ 8.59 (d, J=5.0 Hz, 1H), 8.44 (dd, J=8.4, 1.4 Hz, 1H), 8.22 (s, 1H), 8.06 (dd, J=7.1, 1.4 Hz, 1H), 7.98 (s, 3H), 7.91 (d, J=1.7 Hz, 1H), 7.80 (dd, J=8.4, 7.2 Hz, 1H), 7.68 (d, J=1.6 Hz, 1H), 6.97 (d, J=4.9 Hz, 1H), 4.24 (p, J=6.4 Hz, 1H), 4.01-3.91 (m, 2H), 3.74 (d, J=9.1 Hz, 1H), 3.48 (d, J=6.3 Hz, 1H), 3.30 (q, J=12.3 Hz, 2H), 1.97 (t, J=12.5 Hz, 2H), 1.83 (d, J=13.7 Hz, 1H), 1.76-1.63 (m, 1H), 1.22 (d, J=6.5 Hz, 3H). LCMS ESI$^+$ calc'd for $C_{26}H_{28}N_6O_3S$: 505.2 [M+H$^+$]. found: 505.2 [M+H$^+$].

Example 106: (3S,4S)-3-methyl-8-(8-(thieno[3,2-b]pyridin-7-ylthio)imidazo[1,2-c]pyrimidin-5-yl)-2-oxa-8-azaspiro[4.5]decan-4-amine

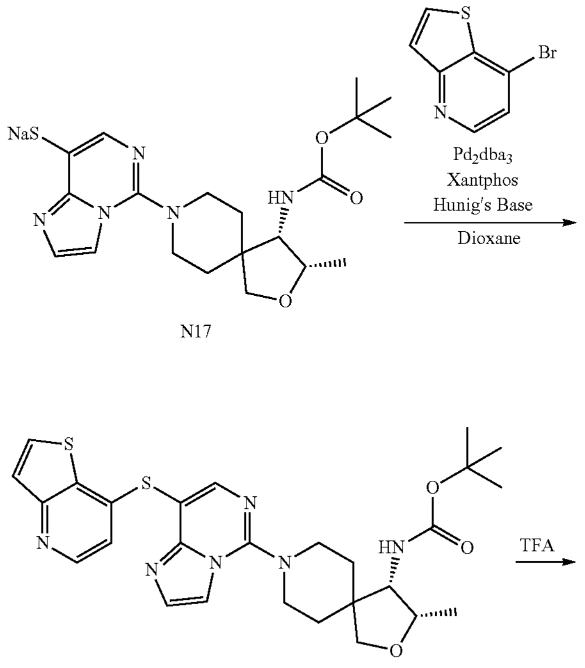

N17

E106a

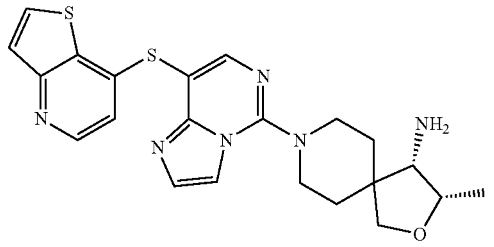

Example 106

Compound E106a: The compound was prepared in a similar manner to Compound E78a using Compound N17 and 7-bromothieno[3,2-b]pyridine. ESI$^+$ m/z Calc'd for $C_{27}H_{32}N_6O_3S_2$[M+H$^+$]: 553.2; Found: 553.2 [M+H$^+$].

Example 106: The compound was prepared in a manner similar to Example 84 using Compound E106a as the starting material. $^1$H NMR (400 MHz, $CD_3CN$) δ 8.39 (d, J=5.9 Hz, 1H), 8.30 (s, 1H), 8.21 (d, J=5.6 Hz, 1H), 7.74 (d, J=5.6 Hz, 1H), 7.68 (d, J=1.9 Hz, 1H), 7.54 (d, J=1.9 Hz, 1H), 7.06 (d, J=5.9 Hz, 1H), 4.36-4.18 (m, 1H), 4.11-3.95 (m, 2H), 3.82 (d, J=9.2 Hz, 1H), 3.59 (d, J=4.5 Hz, 1H), 3.35 (dddd, J=16.5, 13.7, 11.0, 2.7 Hz, 1H), 2.22-1.75 (m, 6H), 1.30 (d, J=6.6 Hz, 3H). (LCMS): ESI$^+$ m/z Calc'd for $C_{22}H_{24}N_6OS_2$ [M+H$^+$]: 453.2; Found: 453.3 [M+H$^+$].

Example 107: (3S,4S)-8-(8-(benzo[d]isothiazol-7-ylthio)imidazo[1,2-c]pyrimidin-5-yl)-3-methyl-2-oxa-8-azaspiro[4.5]decan-4-amine

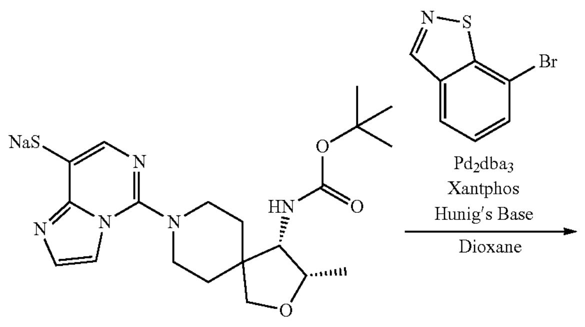

N17

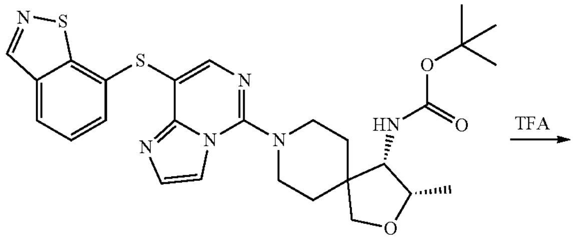

E107a

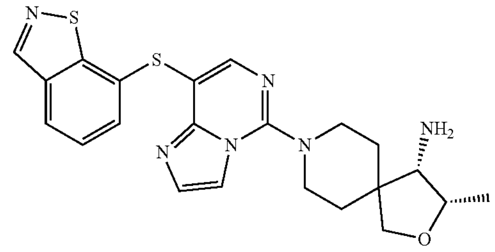

Example 107

Compound E107a: The compound was prepared in a similar manner to Compound E78a using Compound N17 and 7-bromobenzo[d]isothiazole. ESI$^+$ m/z Calc'd for $C_{27}H_{32}N_6O_3S_2$[M+H$^+$]: 553.2. found: 553.2 [M+H$^+$].

Example 107: The compound was prepared in a manner similar to Example 84 using Compound E107a as the starting material. $^1$H NMR (400 MHz, $CD_3CN$) δ 8.96 (s, 1H), 8.16 (s, 1H), 8.06 (dd, J=8.0, 1.0 Hz, 1H), 7.63-7.50 (m, 3H), 7.47-7.31 (m, 1H), 4.26 (qd, J=6.5, 4.4 Hz, 1H), 3.95 (d, J=9.3 Hz, 1H), 3.94-3.75 (m, 2H), 3.56 (d, J=4.4 Hz, 1H), 3.23 (dddd, J=18.3, 13.7, 11.0, 2.8 Hz, 1H), 2.14-1.70 (m, 6H), 1.28 (d, J=6.5 Hz, 3H). (LCMS): ESI$^+$ m/z Calc'd for $C_{22}H_{24}N_6OS_2$ [M+H$^+$]: 453.2; Found: 453.2 [M+H$^+$].

Example 108: (3S,4S)-8-(8-((3-chloro-2-(methylthio)phenyl)thio)imidazo[1,2-c]pyrimidin-5-yl)-3-methyl-2-oxa-8-azaspiro[4.5]decan-4-amine Compound E108a: The compound was prepared in a similar manner to Compound E78a using Compound N17 and (2-bromo-6-chlorophenyl)(methyl)sulfane. ESI$^+$ m/z Calc'd for $C_{27}H_{34}ClN_5O_3S_2$ [M+H$^+$]: 576.2; found: 576.2 [M+H$^+$].

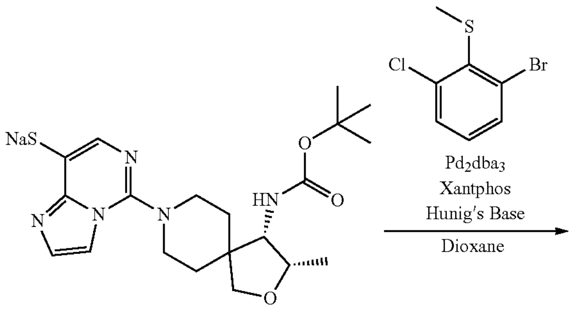

N17

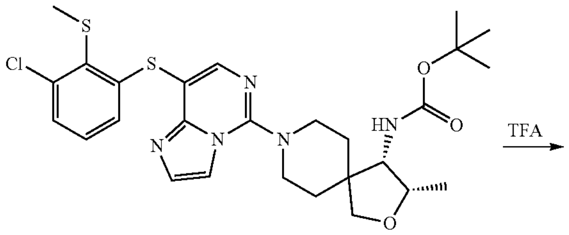

E108a

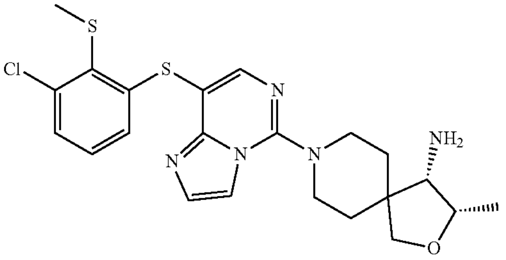

Example 108

Example 108: The compound was prepared in a manner similar to Example 84 using Compound E108a as the starting material. $^1$H NMR (400 MHz, $CD_3CN$) δ 8.19 (s, 1H), 7.69 (d, J=2.0 Hz, 1H), 7.57 (d, J=1.9 Hz, 1H), 7.26 (dd, J=8.0, 1.2 Hz, 1H), 7.03 (t, J=8.0 Hz, 1H), 6.59 (dd, J=8.1, 1.2 Hz, 1H), 4.29 (dd, J=6.6, 4.5 Hz, 1H), 4.10-3.86 (m, 2H), 3.81 (d, J=9.2 Hz, 1H), 3.58 (d, J=4.5 Hz, 1H), 3.32 (dddd, J=19.4, 13.7, 11.0, 2.6 Hz, 1H), 2.20-1.77 (m, 6H), 1.30 (d, J=6.5 Hz, 3H). (LCMS): ESI$^+$ m/z Calc'd for $C_{22}H_{26}ClN_5OS_2$ [M+H$^+$]: 476.1. found: 476.2 [M+H$^+$].

Example 109: (3S,4S)-8-(8-((8-(1H-1,2,4-triazol-1-yl)quinolin-4-yl)thio)imidazo[1,2-c]pyrimidin-5-yl)-3-methyl-2-oxa-8-azaspiro[4.5]decan-4-amine

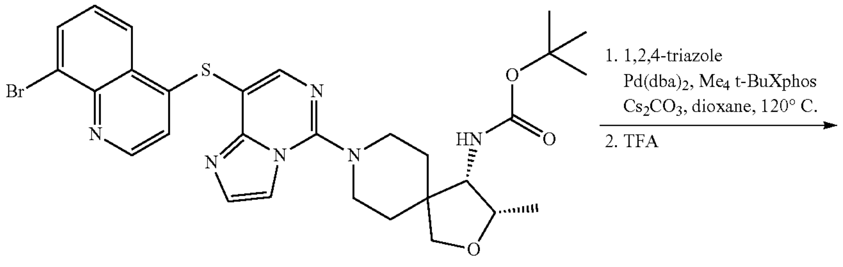

E103a

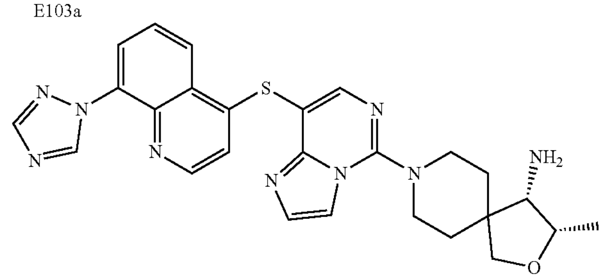

Example 109

Example 109: Compound E103a (70 mg, 0.112 mmol), 1,2,4-triazole (10 mg, 0.14 mmol), $Pd(dba)_2$ (6 mg, 0.011 mmol), $Me_4$ t-BuXphos (13 mg, 0.027 mmol) and $Cs_2CO_3$ (73 mg, 0.224 mmol) were mixed in dioxane (2.0 mL) and the reaction mixture was heated at 90° C. overnight. The mixture was filtered, the filtrate was concentrated in vacuo, and then the residue was dissolved in TFA and stirred at RT for 5 mins. The solvent was then evaporated and the residue was purified with Prep HPLC to afford Example 109. $^1H$ NMR (400 MHz, Methanol-$d_4$) δ 9.53 (s, 1H), 8.64 (d, J=4.9 Hz, 1H), 8.48 (dd, J=8.5, 1.3 Hz, 1H), 8.46 (s, 1H), 8.34 (dd, J=7.6, 1.3 Hz, 1H), 8.28 (s, 1H), 8.07 (d, J=2.1 Hz, 1H), 7.91 (dd, J=8.5, 7.6 Hz, 1H), 7.86 (d, J=2.1 Hz, 1H), 7.05 (d, J=4.9 Hz, 1H), 4.42-4.31 (m, 1H), 4.19 (dd, J=24.4, 13.7 Hz, 2H), 4.07 (d, J=9.2 Hz, 1H), 3.97 (d, J=9.2 Hz, 1H), 3.60-3.38 (m, 3H), 2.18-1.81 (m, 4H), 1.37 (d, J=6.5 Hz, 3H). LCMS $ESI^+$ calc'd for $C_{26}H_{27}N_9OS$: 514.2 [$M+H^+$]. found: 514.2.

Example 110: 4-((5-((3S,4S)-4-amino-3-methyl-2-oxa-8-azaspiro[4.5]decan-8-yl)imidazo[1,2-c]pyrimidin-8-yl)thio)quinoline-8-carboxylic acid

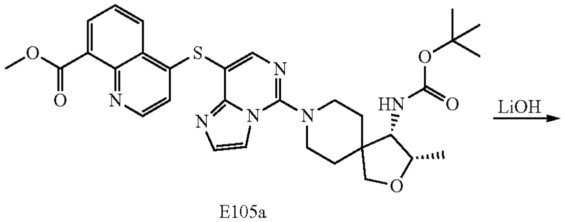

E105a

-continued

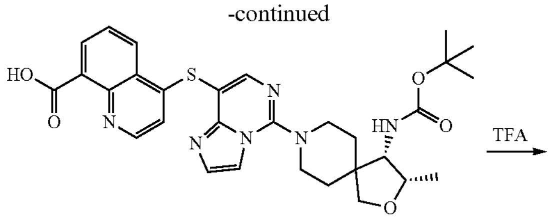

E110a

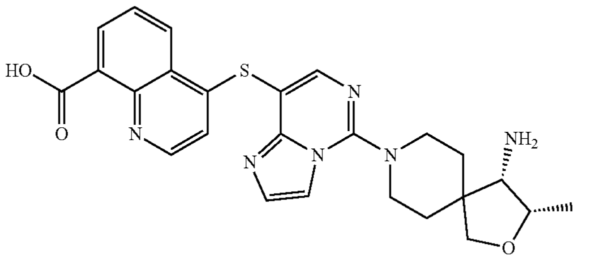

Example 110

Compound E110a: Compound E105a (219 mg, 0.362 mmol) was dissolved in THF and LiOH (46 mg, 1.086 mmol) was added and stirred at r.t. for 16 h. The resulting solution was concentrated providing Compound E110a. LCMS $ESI^+$ calc'd for $C_{30}H_{34}N_6O_5S$: 591.2 [$M+H^+$]. found: 591.2 [$M+H^+$].

Example 110: Compound E110a was dissolved in DCM (5 ml), and TFA (1 ml) was added. The solution was concentrated and reconstituted in water and DMF and the solution was purified on preparatory HPLC (10-100% MeCN in water with 0.1% TFA, Gemini). This provided Example 110. $^1H$ NMR (400 MHz, DMSO-$d_6$) δ 8.69-8.63 (m, 2H), 8.62 (dd, J=8.5, 1.4 Hz, 1H), 8.20 (s, 1H), 8.03-7.90 (m, 4H), 7.88 (d, J=1.6 Hz, 1H), 7.62 (d, J=1.5 Hz, 1H), 7.07 (d, J=5.2 Hz, 1H), 4.29-4.19 (m, 1H), 4.00-3.87 (m, 3H), 3.74 (d, J=9.0 Hz, 1H), 3.48 (s, 1H), 3.39-3.21 (m, 2H), 1.97

(t, J=11.9 Hz, 2H), 1.83 (d, J=13.7 Hz, 1H), 1.71 (t, J=9.9 Hz, 1H), 1.23 (d, J=6.5 Hz, 3H). LCMS ESI$^+$ calc'd for $C_{25}H_{26}N_6O_3S$: 491.2 [M+H$^+$]. found: 491.2 [M+H$^+$].

Example 111: (3S,4S)-8-(8-((2-aminoquinolin-4-yl)thio)imidazo[1,2-c]pyrimidin-5-yl)-3-methyl-2-oxa-8-azaspiro[4.5]decan-4-amine

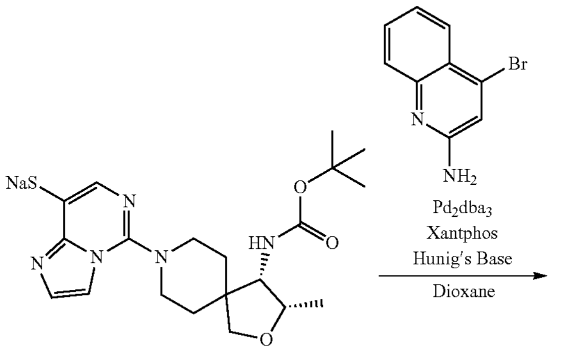

N17

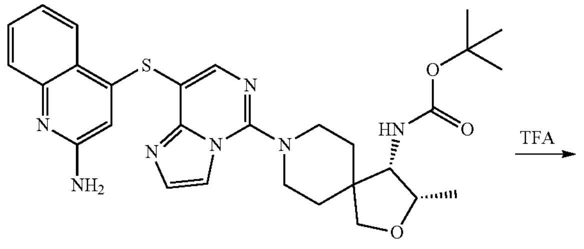

E111a

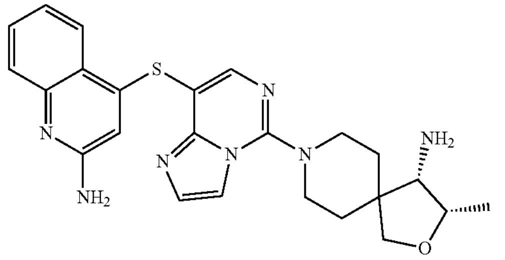

Example 111

Compound E111a: The compound was prepared in a similar manner to Compound E78a using Compound N17 and 4-bromoquinolin-2-amine.

Example 111: The compound was prepared in a manner similar to Example 84 using Compound E111a as the starting material. $^1$H NMR (400 MHz, DMSO-d$_6$) δ 8.19 (s, 1H), 8.17-8.12 (m, 1H), 8.01 (s, 2H), 7.91 (d, J=1.6 Hz, 1H), 7.88-7.81 (m, 1H), 7.68 (d, J=8.4 Hz, 1H), 7.65 (d, J=1.4 Hz, 1H), 7.62-7.53 (m, 1H), 6.24 (s, 1H), 4.30-4.17 (m, 1H), 4.00-3.85 (m, 4H), 3.74 (d, J=9.1 Hz, 1H), 3.48 (s, 1H), 3.29 (q, J=12.1 Hz, 2H), 1.96 (t, J=12.4 Hz, 2H), 1.77 (dd, J=48.3, 13.4 Hz, 2H), 1.23 (d, J=6.5 Hz, 3H). LCMS ESI$^+$ calc'd for $C_{24}H_{27}N_7OS$ [M+H$^+$]: 462.2. found: 462.3 [M+H$^+$].

Example 112: N-(4-((5-((3S,4S)-4-amino-3-methyl-2-oxa-8-azaspiro[4.5]decan-8-yl)imidazo[1,2-c]pyrimidin-8-yl)thio)quinolin-8-yl)acetamide

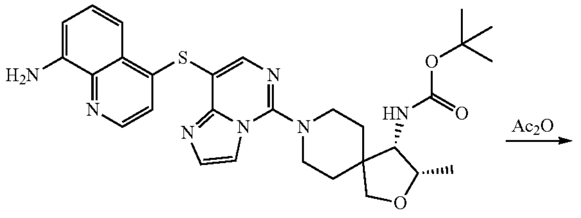

E104a

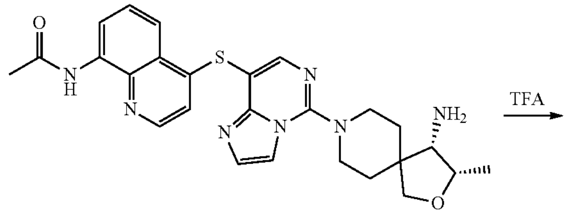

E112a

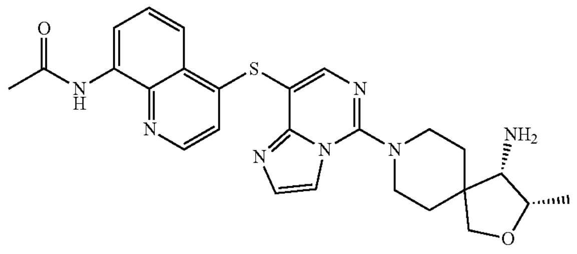

Example 112

Compound E112a: Compound E105a (100 mg, 0.178 mmol) was dissolved in DCM (5 ml), DIPEA (0.1 ml, 0.574 mmol) and DMAP (0.2 mg, 0.002 mmol) were added followed by $Ac_2O$ (0.34 ml, 0.356 mmol). The resulting solution was stirred at room temperature for 2 h. The solution was concentrated and used directly without purification. This provided Compound E112a. LCMS ESI$^+$ calc'd for $C_{31}H_{37}N_7O_4S$: 604.3 [M+H$^+$]. found: 604.3 [M+H$^+$].

Example 112: Compound E112a was dissolved in DCM (5 ml), and TFA (1 ml) was added. The solution was concentrated and reconstituted in water and DMF and the solution was purified on preparatory HPLC (10-100% MeCN in water with 0.1% TFA, Gemini). This provided Example 112. $^1$H NMR (400 MHz, DMSO-d$_6$) δ 10.08 (s, 1H), 8.66 (d, J=7.8 Hz, 1H), 8.52 (d, J=4.8 Hz, 1H), 8.19 (s, 1H), 7.97 (s, 3H), 7.92-7.81 (m, 2H), 7.74-7.59 (m, 2H), 6.91 (d, J=4.8 Hz, 1H), 4.32-4.16 (m, 1H), 3.94 (d, J=14.8 Hz, 2H), 3.90 (d, J=9.2 Hz, 2H), 3.74 (d, J=9.0 Hz, 1H), 3.47 (d, J=6.3 Hz, 1H), 3.29 (q, J=12.3 Hz, 2H), 2.24 (s, 3H), 1.97 (t, J=12.3 Hz, 2H), 1.83 (d, J=13.9 Hz, 1H), 1.71 (t, J=10.1 Hz, 1H), 1.22 (d, J=6.5 Hz, 3H). LCMS ESI$^+$ calc'd for $C_{26}H_{29}N_7O_2S$: 504.2 [M+H$^+$]. found: 504.2 [M+H$^+$].

Example 113: 4-((5-((3S,4S)-4-amino-3-methyl-2-oxa-8-azaspiro[4.5]decan-8-yl)imidazo[1,2-c]pyrimidin-8-yl)thio)quinoline-8-carboxamide

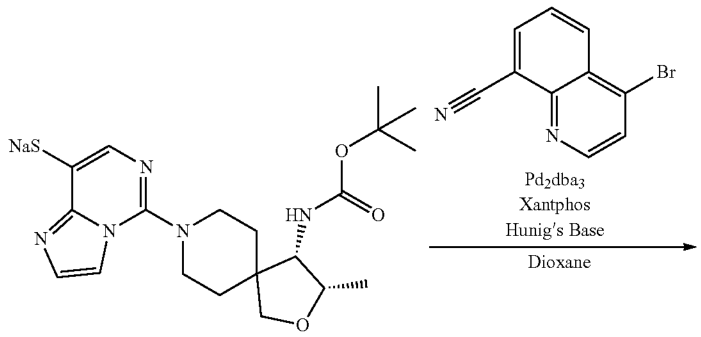

N17

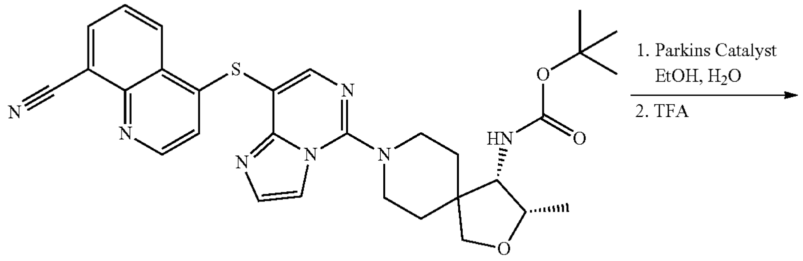

E111a

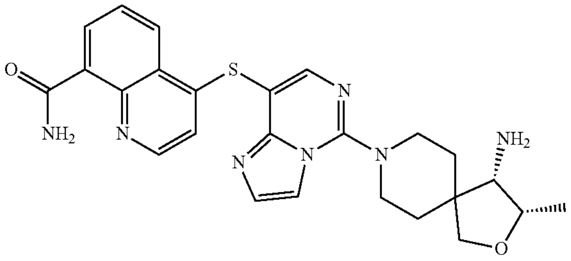

Example 113

Compound E113a: The compound was prepared in a similar manner to Compound E78a using Compound N17 and 4-bromoquinoline-8-carbonitrile.

Example 113: To a solution of Compound E113a (20 mg, 0.035 mmol) in EtOH (1.8 mL) and water (0.2 mL) was added Parkins Catalyst (15 mg, 0.035 mmol). The reaction was heated at 80° C. for 20 mins. the mixture was filtered, the filtrate was concentrated in vacuo, and then the residue was dissolved in TFA and stirred at RT for 5 min. The solvent was then evaporated and the residue was purified with Prep HPLC to afford Example 113. $^1$H NMR (400 MHz, Methanol-d4) δ 8.79-8.71 (m, 2H), 8.68 (d, J=5.5 Hz, 1H), 8.39 (s, 1H), 8.04-7.96 (m, 2H), 7.76 (d, J=1.8 Hz, 1H), 7.23 (d, J=5.6 Hz, 1H), 4.44-4.29 (m, 1H), 4.18 (dd, J=22.0, 13.9 Hz, 2H), 4.07 (d, J=9.2 Hz, 1H), 3.97 (d, J=9.2 Hz, 1H), 3.57 (d, J=4.1 Hz, 1H), 3.53-3.37 (m, 2H), 2.21-1.81 (m, 4H), 1.37 (d, J=6.5 Hz, 3H). LCMS ESI$^+$ calc'd for $C_{25}H_{27}N_7O_2S$: 490.1 [M+H$^+$]. found: 490.2 [M+H$^+$].

Example 114: (3S,4S)-3-methyl-8-(8-(quinolin-4-ylthio)imidazo[1,2-c]pyrimidin-5-yl)-2-oxa-8-azaspiro[4.5]decan-4-amine Compound E114a: Compound N17 (51 mg, 0.116 mmol) in 1,4-dioxane (2 ml) was added $Pd_2(dba)_3$ (10 mg, 0.011 mmol), XantPhos (13 mg, 0.022 mmol), 4-bromoquinoline (27 mg, 0.130 mmol), and DIPEA (34 μL, 0.2 mmol). The reaction vessel was degassed with argon, sealed, and heated to 110° C. overnight. The reaction mixture was then cooled to room temperature, filtered through Celite®, and concentrated. The resulting residue was concentrated, diluted with 1:1 acetonitrile and water each containing 0.1% TFA and purified on preparatory HPLC (0 to 100% acetonitrile in water each containing 0.1% TFA). This provided Compound E114a as a TFA salt. LCMS ESI$^+$ calc'd for $C_{29}H_{34}N_6O_3S$: 547.2 [M+H$^+$]. found: 547.2 [M+H$^+$].

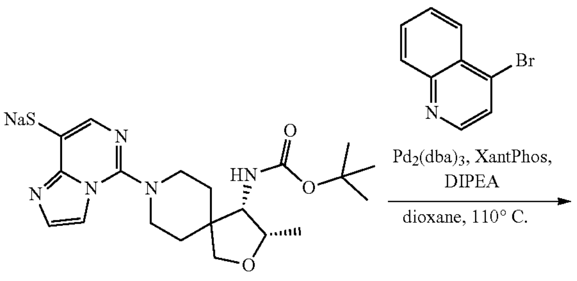

N17

-continued

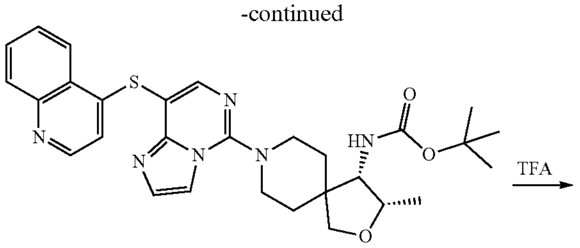

E114a

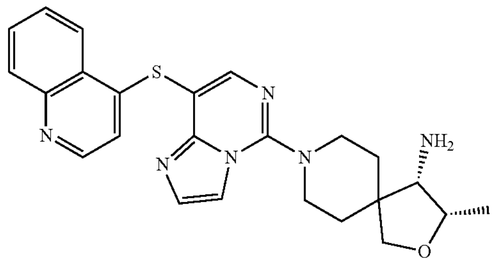

Example 114

Example 114: Compound E114a was mixed with TFA (2 ml). After 4 h, the mixture was concentrated on rotovap, diluted with 1:1 acetonitrile and water each containing 0.1% TFA and purified on preparatory HPLC (0 to 100% acetonitrile in water each containing 0.1% TFA). This provided Compound E114 (50 mg) as a TFA salt. $^1$H NMR (400 MHz, Methanol-$d_4$) δ 8.69 (d, J=6.1 Hz, 1H), 8.66 (dt, J=8.4, 0.9 Hz, 1H), 8.41 (s, 1H), 8.26-8.18 (m, 2H), 8.12-8.05 (m, 1H), 8.04 (d, J=2.0 Hz, 1H), 7.77 (d, J=1.8 Hz, 1H), 7.37 (d, J=6.1 Hz, 1H), 4.43-4.32 (m, 1H), 4.27-4.13 (m, 2H), 4.07 (d, J=9.2 Hz, 1H), 3.96 (d, J=9.2 Hz, 1H), 3.57 (d, J=4.0 Hz, 1H), 3.48 (dt, J=25.8, 11.9 Hz, 2H), 2.15 (t, J=12.3 Hz, 2H), 2.05 (d, J=13.3 Hz, 1H), 1.89 (d, J=13.3 Hz, 1H), 1.38 (d, J=6.5 Hz, 3H). LCMS ESI$^+$ calc'd for $C_{24}H_{26}N_6OS$: 447.2 [M+H$^+$]. found: 447.2 [M+H$^+$].

Example 115: (3S,4S)-8-(8-((6-fluoroquinolin-4-yl)thio)imidazo[1,2-c]pyrimidin-5-yl)-3-methyl-2-oxa-8-azaspiro[4.5]decan-4-amine

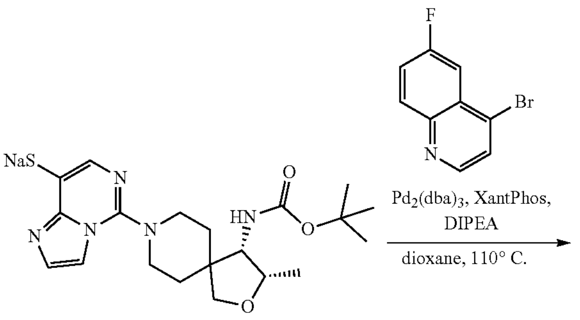

N17

-continued

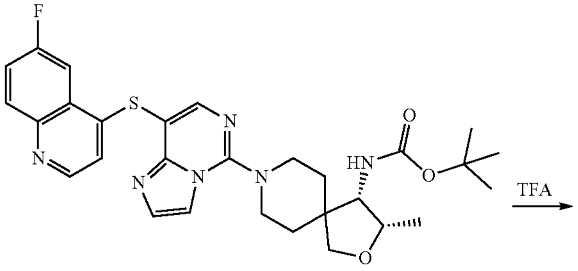

E115a

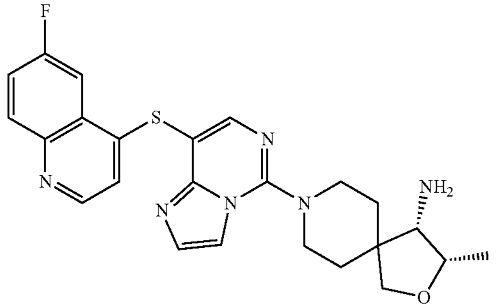

Example 115

Compound E115a: Compound N17 (51 mg, 0.116 mmol) in 1,4-dioxane (2 ml) was added $Pd_2(dba)_3$ (10 mg, 0.011 mmol), XantPhos (13 mg, 0.022 mmol), 4-bromo-6-fluoroquinoline (27 mg, 0.130 mmol), and DIPEA (34 μL, 0.2 mmol). The reaction vessel was degassed with argon, sealed, and heated to 110° C. overnight. The reaction mixture was then cooled to room temperature, filtered through Celite®, and concentrated. The resulting residue was concentrated, diluted with 1:1 acetonitrile and water each containing 0.1% TFA and purified on preparatory HPLC (0 to 100% acetonitrile in water each containing 0.1% TFA). This provided Compound E115a as a TFA salt.

Example 115: Compound E115a was mixed with TFA (2 ml). After 4 h, the mixture was concentrated on rotovap, diluted with 1:1 acetonitrile and water each containing 0.1% TFA and purified on preparatory HPLC (0 to 100% acetonitrile in water each containing 0.1% TFA). This provided Example 115 as a TFA salt. $^1$H NMR (400 MHz, Methanol-$d_4$) δ 8.62 (d, J=5.7 Hz, 1H), 8.41 (s, 1H), 8.32-8.21 (m, 2H), 8.04 (d, J=1.9 Hz, 1H), 7.97 (ddd, J=9.6, 8.1, 2.7 Hz, 1H), 7.79 (d, J=1.9 Hz, 1H), 7.26 (d, J=5.5 Hz, 1H), 4.37 (qd, J=6.5, 4.1 Hz, 1H), 4.19 (ddt, J=22.3, 13.9, 4.2 Hz, 2H), 4.07 (d, J=9.2 Hz, 1H), 3.96 (d, J=9.1 Hz, 1H), 3.57 (d, J=4.1 Hz, 2H), 3.47 (ddd, J=13.8, 11.3, 2.7 Hz, 1H), 2.21-2.08 (m, 2H), 2.08-2.00 (m, 1H), 1.89 (d, J=13.1 Hz, 1H), 1.37 (d, J=6.5 Hz, 3H). LCMS ESI$^+$ calc'd for $C_{25}H_{28}N_6O_2S$: 465.2 [M+H$^+$]. found: 465.1 [M+H$^+$].

Example 116: (3S,4S)-8-(8-((7-fluoroquinolin-4-yl)thio)imidazo[1,2-c]pyrimidin-5-yl)-3-methyl-2-oxa-8-azaspiro[4.5]decan-4-amine

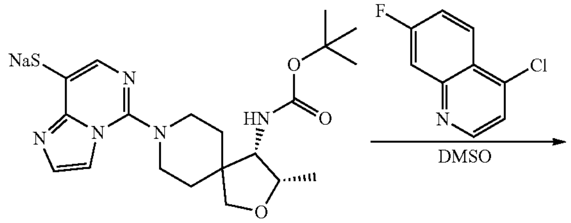

N17

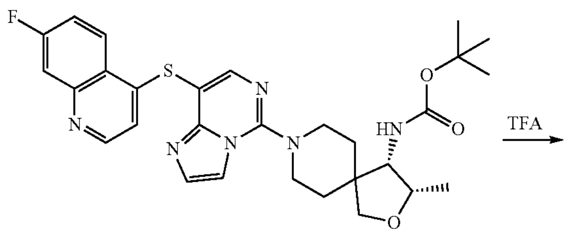

E116a

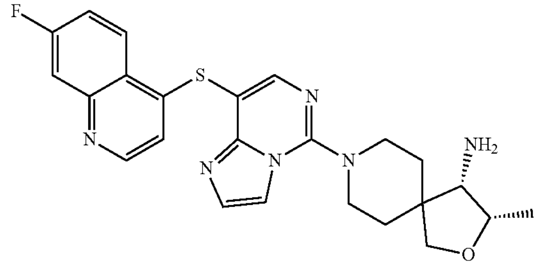

Example 116

Compound E116A: A solution of Compound N17 (20.0 mg, 0.0453 mmol) and 4-chloro-7-fluoro-quinoline (0.0112 g, 0.0616 mmol) in DMSO (1 mL) was heated at 100° C. for 1 h. The reaction was purified by reverse phase column chromatography, eluting with 0.1% TFA water and $CH_3CN$, giving Compound E116A, which was used in the next reaction.

Example 116: The Compound E116a from the previous reaction was dissolved in 10 mL DCM and TFA (0.5 mL) was added. The reaction was stirred for 16 h and then concentrated, giving Example 116. $^1H$ NMR (400 MHz, Methanol-$d_4$) δ 8.72 (d, J=5.8 Hz, 1H), 8.70-8.65 (m, 1H), 8.48 (s, 1H), 8.10 (d, J=2.1 Hz, 1H), 7.93 (dd, J=9.0, 2.5 Hz, 1H), 7.90-7.81 (m, 2H), 7.35 (d, J=6.0 Hz, 1H), 4.38 (tt, J=6.7, 3.3 Hz, 1H), 4.35-4.15 (m, 2H), 4.08 (d, J=9.2 Hz, 1H), 3.96 (d, J=9.2 Hz, 1H), 3.58 (d, J=4.2 Hz, 1H), 3.56 (s, OH), 2.28-2.13 (m, 2H), 2.04 (d, J=13.9 Hz, 1H), 1.90 (d, J=13.4 Hz, 1H), 1.38 (d, J=6.5 Hz, 3H). LCMS ESI$^+$ calc'd for $C_{24}H_{25}FN_6OS$ [M+H$^+$]: 465.2. found: 465.2 [M+H$^+$].

Example 117: (3S,4S)-3-methyl-8-(8-(quinazolin-4-ylthio)imidazo[1,2-c]pyrimidin-5-yl)-2-oxa-8-azaspiro[4.5]decan-4-amine

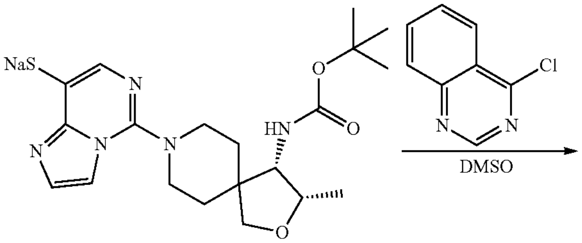

N17

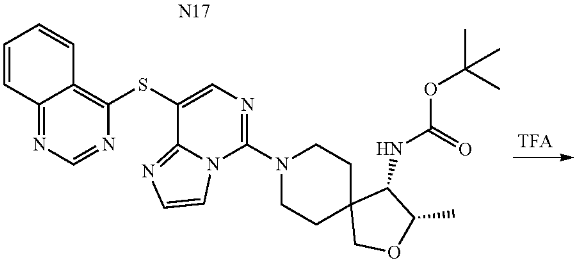

E117a

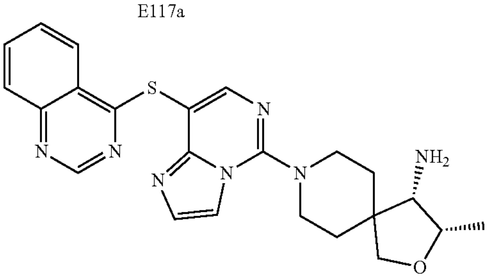

Example 117

Compound E117a: The compound was prepared in a similar manner to Compound E116a using Compound N17 and 4-chloroquinazoline.

Example 117: The compound was prepared in a manner similar to Example 116 using Compound E117a as the starting material. $^1H$ NMR (400 MHz, methanol-$d_4$) δ 8.71 (s, 1H), 8.51 (s, 1H), 8.40 (dt, J=8.3, 1.0 Hz, 1H), 8.18 (d, J=2.5 Hz, 1H), 8.11 (ddd, J=8.3, 6.9, 1.3 Hz, 1H), 8.07-7.99 (m, 2H), 7.89 (ddd, J=8.2, 6.8, 1.3 Hz, 1H), 4.45-4.33 (m, 1H), 4.23 (dd, J=24.8, 14.1 Hz, 1H), 4.08 (d, J=9.2 Hz, 1H), 3.96 (d, J=9.2 Hz, 1H), 3.64-3.41 (m, 3H), 2.29-2.09 (m, 3H), 2.04 (d, J=14.1 Hz, 1H), 1.92 (dd, J=17.2, 14.1 Hz, 1H), 1.37 (d, J=6.5 Hz, 4H). LCMS ESI$^+$ calc'd for $C_{23}H_{23}N_7OS$ [M+H$^+$]: 448.2. found: 448.2 [M+H$^+$].

Example 118: (3S,4S)-8-(8-(isoquinolin-1-ylthio)imidazo[1,2-c]pyrimidin-5-yl)-3-methyl-2-oxa-8-azaspiro[4.5]decan-4-amine Compound E118a: The compound was prepared in a similar manner to Compound E116a using Compound N17 and 1-chloroisoquinoline.

Example 118: The compound was prepared in a manner similar to Example 116 using Compound E118a as the starting material. $^1H$ NMR (400 MHz, methanol-$d_4$) δ8.51 (s, 1H), 8.44-8.38 (m, 1H), 8.16 (d, J=2.4 Hz, 1H), 8.02 (d, J=5.8 Hz, 1H), 7.99 (q, J=3.5, 3.0 Hz, 2H), 7.89 (ddd, J=8.2, 6.9, 1.2 Hz, 1H), 7.82 (ddd, J=8.3, 6.9, 1.3 Hz, 1H), 7.63 (dd, J=5.9, 0.8 Hz, 1H), 4.53-4.29 (m, 1H), 4.19 (dt, J=24.4, 9.3 Hz, 2H), 4.08 (d, J=9.2 Hz, 1H), 3.95 (d, J=9.3 Hz, 1H), 3.58 (p, J=3.9, 3.5 Hz, 2H), 3.54-3.43 (m, 1H), 2.23-2.08 (m, 2H), 2.03 (d, J=13.9 Hz, 1H), 1.90 (d, J=13.3 Hz, 1H), 1.37 (d, J=6.5 Hz, 4H). LCMS ESI$^+$ calc'd for $C_{24}H_{26}N_6OS$ [M+H$^+$]: 447.2. found: 447.1 [M+H$^+$].

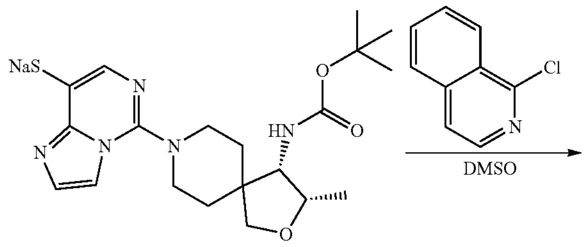

N17

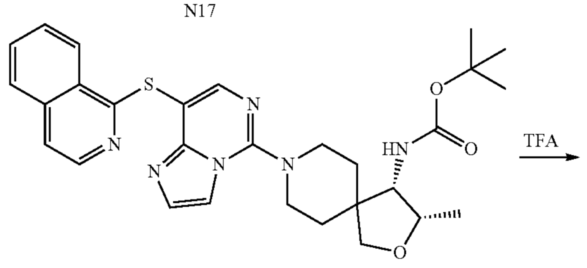

E118a

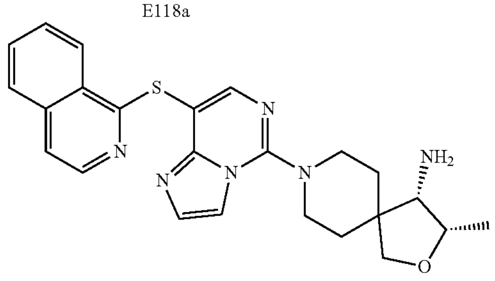

Example 118

Example 119: (1-(8-((2,3-dichlorophenyl)thio)imidazo[1,2-c]pyrimidin-5-yl)piperidin-4-yl)methanamine

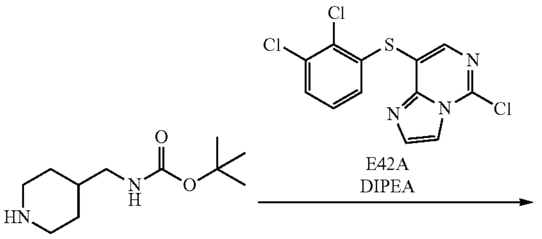

E119a

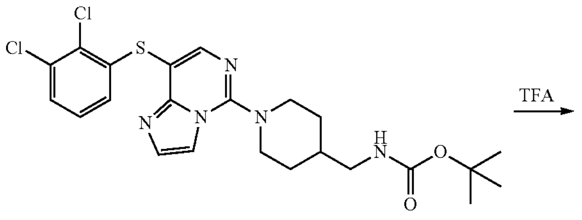

E119b

-continued

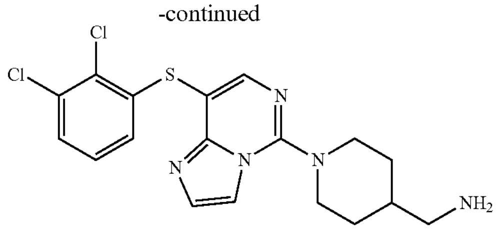

Example 119

Example 119: The compound was prepared in a manner similar to Example 42 using Compound E119a as the starting material instead of Compound E42e. $^1$H NMR (400 MHz, methanol-d$_4$) δ 8.25 (s, 1H), 7.97 (d, J=2.0 Hz, 1H), 7.77 (d, J=2.0 Hz, 1H), 7.37 (dd, J=8.0, 1.4 Hz, 1H), 7.09 (t, J=8.1 Hz, 1H), 6.76 (dd, J=8.1, 1.4 Hz, 1H), 4.27 (d, J=13.1 Hz, 2H), 3.32-3.19 (m, 7H), 2.97 (d, J=6.9 Hz, 2H), 2.08 (dt, J=7.5, 4.0 Hz, 0H), 2.01 (d, J=13.8 Hz, 2H), 1.73-1.52 (m, 2H). LCMS ESI$^+$ calc'd for $C_{18}H_{19}Cl_2N_5S$ [M+H$^+$]: 408.1. found: 408.1 [M+H$^+$].

Example 120: 4-((5-((3S,4S)-4-amino-3-methyl-2-oxa-8-azaspiro[4.5]decan-8-yl)imidazo[1,2-c]pyrimidin-8-yl)thio)-1-naphthamide

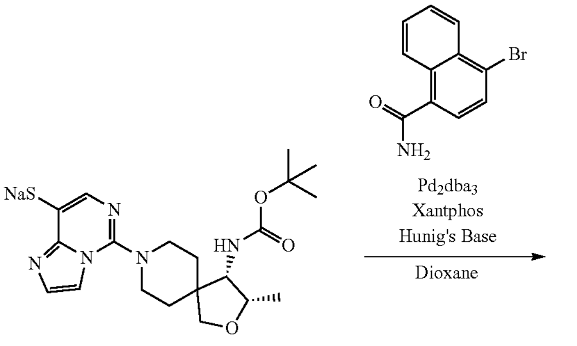

N17

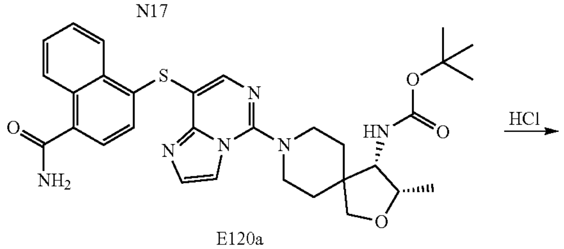

E120a

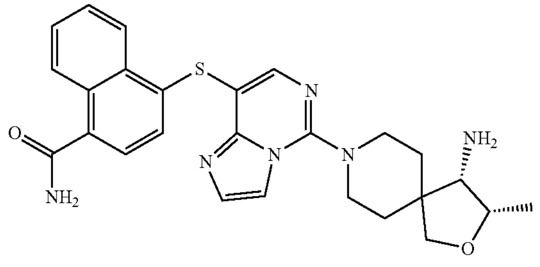

Example 120

Compound E120A: The compound was prepared in a similar manner to Compound E78a using Compound N17 and 4-bromo-1-naphthamide.

Example 120: The compound was prepared in a manner similar to Example 85 using Compound E120a as the starting material. $^1H$ NMR (400 MHz, methanol-$d_4$) δ 8.53-8.43 (m, 1H), 8.43-8.31 (m, 1H), 8.11 (s, 1H), 8.00 (d, J=2.1 Hz, 1H), 7.84 (d, J=2.0 Hz, 1H), 7.75-7.63 (m, 2H), 7.54 (d, J=7.6 Hz, 1H), 7.32 (d, J=7.6 Hz, 1H), 4.46-4.27 (m, 1H), 4.12-3.97 (m, 3H), 3.93 (d, J=9.2 Hz, 1H), 3.53 (d, J=4.0 Hz, 1H), 3.46-3.35 (m, 1H), 2.16-1.94 (m, 4H), 1.84 (d, J=13.2 Hz, 1H), 1.39-1.27 (m, 4H). LCMS $ESI^+$ calc'd for $C_{26}H_{28}N_6O_2S$ [M+H$^+$]: 489.2. found: 489.3 [M+H$^+$].

Example 121: (S)-1'-(8-((2-amino-3-chloropyridin-4-yl)thio)imidazo[1,2-c]pyrimidin-5-yl)-1,3-dihydrospiro[indene-2,4'-piperidin]-1 amine

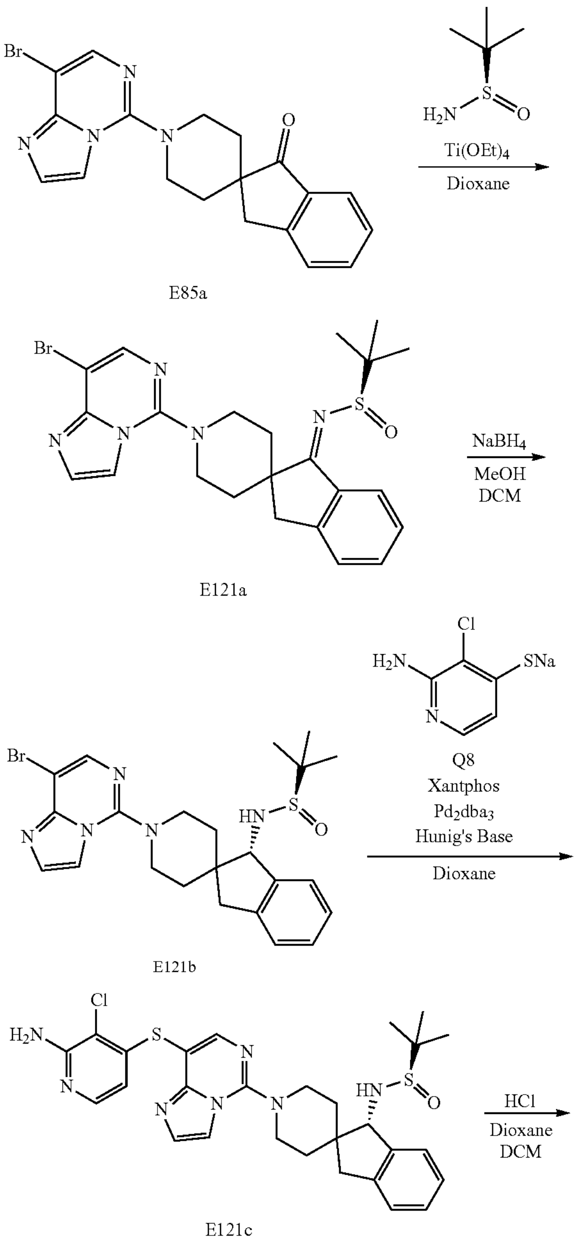

E85a

E121a

E121b

E121c

-continued

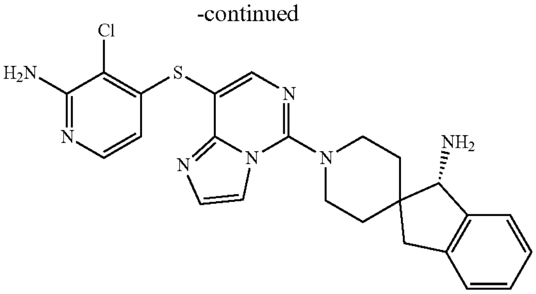

Example 121

Compound E121a: A flask containing Compound E85a (350 mg) and (R)-2-methylpropane-2-sulfinamide (620 mg) was treated with dioxane (8 mL) and $Ti(OEt)_4$ (2.0 mL). The reaction vessel was sealed and heated to 100° C. for 144 h. The reaction was cooled to 23° C. and added dropwise to a mixture of brine (20 mL) and $H_2O$ (60 mL) over 5 min. EtOAc (80 mL) was added. The resulting suspension was stirred for 1 h and then filtered. The organic phase of the filtrate was collected, while the aq phase was extracted with EtOAc (20 mL). Combined organic layers were dried ($Na_2SO_4$) and filtered. The filtrate was concentrated giving Compound E121a, which was used in the next reaction without further purification. $ESI^+$ m/z Calc'd for $C_{23}H_{26}BrN_5OS$ [M+H$^+$]: 500.1. found: 500.0 [M+H$^+$].

Compound E121b: A solution of Compound E121a (440 mg from the previous reaction) in DCM (5.0 mL) and MeOH 5.0 mL) was stirred at 23° C. $NaBH_4$ (100 mg) was added, and the reaction was stirred for 1 h. Aq NaOH (1.0 M, 1 mL) was added and the mixture was stirred for 3 h at 23° C. The reaction was concentrated under reduced pressure to remove most of the MeOH and DCM. Additional $H_2O$ (20 mL) was introduced. The system was extracted with EtOAc (2x20 mL). Combined organic extracts were concentrated. $CH_3CN$ (2 mL) and $H_2O$ (1 mL) were added, followed by AcOH (200 μL). This gave a biphasic system. The organic phase was collected and purified on a C18 column via reversed-phase HPLC (0.1% TFA in $H_2O$/$CH_3CN$ with gradient elution 95:5 to 0:100) giving Compound E121b. $ESI^+$ m/z Calc'd for $C_{23}H_{28}BrN_5OS$ [M+H$^+$]: 502.1. found: 502.1 [M+H$^+$].

Compound E121c: A vessel was charged with Compound E121b (30 mg), Xantphos (50 mg), $Pd_2dba_3$ (30 mg), and Compound Q8 (23 mg). The vessel was placed under static vacuum. Dioxane (2 mL) was added followed by Hunig's Base (100 μL). The reaction was backfilled with argon and stirred at 23° C. for 5 min. The reaction was then heated to 120° C. for 1 h. The system was then cooled to 23° C. and the reaction was diluted with EtOAc (50 mL) and washed with $H_2O$. The organic phase was dried ($Na_2SO_4$) and filtered. The filtrate was concentrated and the resulting residue was treated with PhMe and EtOAc. The solution was purified directly via chromatography on silica gel (Eluent: EtOAc gradient in hexane) giving Compound E121c. $ESI^+$ m/z Calc'd for $C_{28}H_{32}ClN_7OS$ [M+H$^+$]: 582.2. found: 582.1 [M+H$^+$].

Example 121: A solution of Compound E121c (20 mg) in DCM (1.0 mL) was treated with HCl (4.0 M in dioxane, 0.5 mL) at 23° C. for 5 min. The reaction was concentrated under reduced pressure. The residue was treated with $CH_3CN$ and $H_2O$. The solution was purified on a C18 column via reversed-phase HPLC (0.1% TFA in $H_2O$/$CH_3CN$ with gradient elution 95:5 to 0:100) giving Example 121. $^{1}$H NMR (400 MHz, Methanol-$d_4$) δ 8.26 (s, 1H), 7.99 (d, J=1.9 Hz, 1H), 7.74 (d, J=1.8 Hz, 1H), 7.54 (dd, J=7.1, 2.5 Hz, 2H), 7.44-7.32 (m, 3H), 6.35 (d, J=6.8 Hz, 1H), 4.29-3.95 (m, 2H), 3.78-3.49 (m, 3H), 3.27-3.21 (m, 2H), 2.26-2.08 (m, 1H), 2.09-1.82 (m, 2H), 1.81-1.69 (m, 1H). (LCMS): ESI$^+$ m/z Calc'd for $C_{24}H_{24}ClN_7S$ [M+H$^+$]: 478.2. Found: 478.1 [M+H$^+$].

Example 122: (3S,4S)-8-(8-((8-fluoroquinolin-4-yl)thio)imidazo[1,2-c]pyrimidin-5-yl)-3-methyl-2-oxa-8-azaspiro[4.5]decan-4-amine

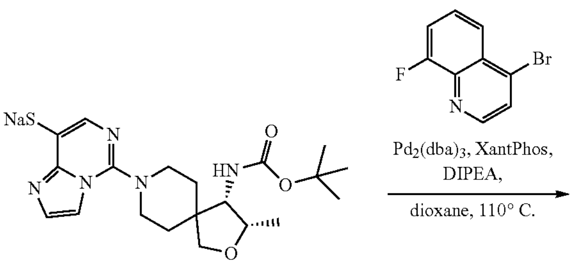

N17

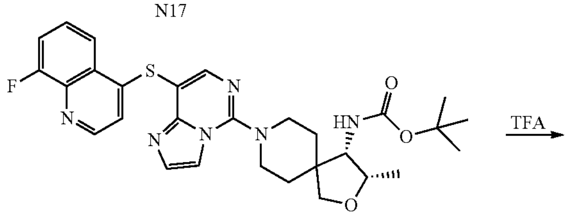

E122a

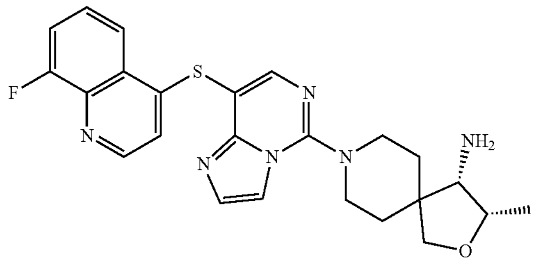

Example 122

Compound E122a: Compound N17 (42 mg, 0.075 mmol) in 1,4-dioxane (2 ml) was added $Pd_2(dba)_3$ (8 mg, 0.011 mmol), XantPhos (10 mg, 0.022 mmol), 4-bromo-8-fluoroquinoline (17 mg, 0.078 mmol), and DIPEA (17 μL, 0.145 mmol). The reaction vessel was degassed with argon, sealed, and heated to 110° C. overnight. The reaction mixture was then cooled to room temperature, filtered through Celite®, and concentrated. The resulting residue was concentrated, diluted with 1:1 acetonitrile and water each containing 0.1% TFA and purified on preparatory HPLC (0 to 100% acetonitrile in water each containing 0.1% TFA). This provided Compound E122a as a TFA salt. LCMS ESI$^+$ calc'd for $C_{29}H_{33}FN_6O_3S$: 565.2 [M+H$^+$]. found: 565.2 [M+H$^+$].

Example 122: Compound E122a was mixed with TFA (2 ml). After 4 h, the mixture was concentrated on rotovap, diluted with 1:1 acetonitrile and water each containing 0.1% TFA and purified on preparatory HPLC (0 to 100% acetonitrile in water each containing 0.1% TFA). This provided Example 122 (13 mg) as a TFA salt. $^{1}$H NMR (400 MHz, Methanol-$d_4$) δ 8.58 (d, J=5.2 Hz, 1H), 8.49 (s, 1H), 8.26 (dt, J=8.5, 1.1 Hz, 1H), 8.11 (d, J=2.2 Hz, 1H), 7.89 (d, J=2.1 Hz, 1H), 7.84 (td, J=8.2, 5.2 Hz, 1H), 7.76 (ddd, J=10.7, 7.9, 1.2 Hz, 1H), 7.18 (d, J=5.3 Hz, 1H), 4.41-4.31 (m, 1H), 4.22 (dd, J=25.0, 14.0 Hz, 2H), 4.07 (d, J=9.2 Hz, 1H), 3.97 (d, J=9.2 Hz, 1H), 3.56 (t, J=4.5 Hz, 1H), 3.54-3.43 (m, 1H), 2.22-2.09 (m, 2H), 2.08 (m, 1H), 1.89 (d, J=13.3 Hz, 1H), 1.38 (d, J=6.4 Hz, 3H). LCMS ESI$^+$ calc'd for $C_{24}H_{25}FN_6OS$: 465.2 [M+H$^+$]. found: 465.2 [M+H$^+$].

Example 123: (3S,4S)-8-(8-((7-methoxyquinolin-4-yl)thio)imidazo[1,2-c]pyrimidin-5-yl)-3-methyl-2-oxa-8-azaspiro[4.5]decan-4-amine

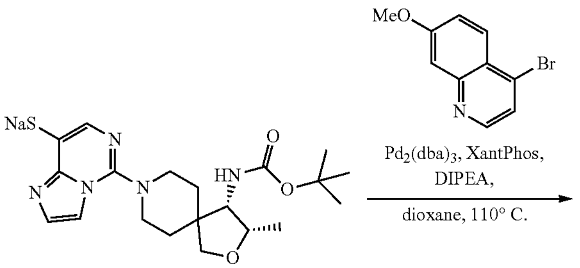

N17

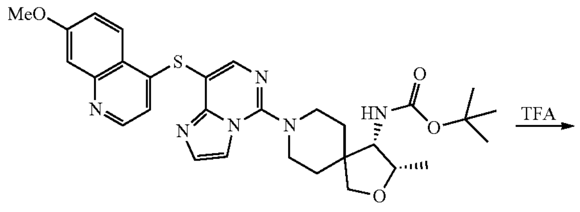

E123a

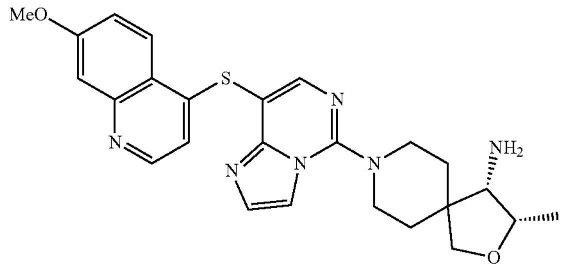

Example 123

Compound E123a: Compound N17 (33 mg, 0.075 mmol) in 1,4-dioxane (2 ml) was added $Pd_2(dba)_3$ (6.8 mg, 0.007 mmol), XantPhos (8.6 mg, 0.015 mmol), 4-bromo-7-methoxyquinoline (19 mg, 0.078 mmol), and DIPEA (17 μL, 0.098 mmol). The reaction vessel was degassed with argon, sealed, and heated to 110° C. overnight. The reaction mixture was then cooled to room temperature, filtered through Celite®, and concentrated. The resulting residue was concentrated, diluted with 1:1 acetonitrile and water each containing 0.1% TFA and purified on preparatory HPLC (0 to 100% acetonitrile in water each containing 0.1% TFA). This provided Compound E123a as a TFA salt. LCMS ESI$^+$ calc'd for $C_{30}H_{36}N_6O_4S$: 577.3 [M+H$^+$]. found: 577.2 [M+H$^+$].

Example 123: Compound E123a was mixed with TFA (2 ml). After 4 h, the mixture was concentrated on rotovap, diluted with 1:1 acetonitrile and water each containing 0.1% TFA and purified on preparatory HPLC (0 to 100% acetonitrile in water each containing 0.1% TFA). This provided Example 123 as a TFA salt. $^{1}$H NMR (400 MHz, Methanol- $d_4$) δ 8.63-8.48 (m, 2H), 8.34 (s, 1H), 7.99 (d, J=1.8 Hz, 1H), 7.76-7.59 (m, 2H), 7.50 (d, J=2.4 Hz, 1H), 7.16 (d, J=6.3 Hz, 1H), 4.45-4.33 (m, 1H), 4.25-4.15 (m, 2H), 4.11 (s, 3H), 4.06 (d, J=9.2 Hz, 1H), 3.96 (d, J=9.2 Hz, 1H), 3.56 (d, J=4.0 Hz, 1H), 3.53-3.36 (m, 2H), 2.24-2.01 (m, 3H), 1.88 (d, J=13.4 Hz, 1H), 1.37 (d, J=6.5 Hz, 3H). LCMS ESI$^+$ calc'd for $C_{25}H_{28}N_6O_2S$: 477.2 [M+H$^+$]. found: 477.2 [M+H$^+$].
Example 124: 1'-(8-((2,3-dichlorophenyl)thio)imidazo[1,2-c]pyrimidin-5-yl)-2,3-dihydrospiro[indene-1,4'-piperidin]-2-amine
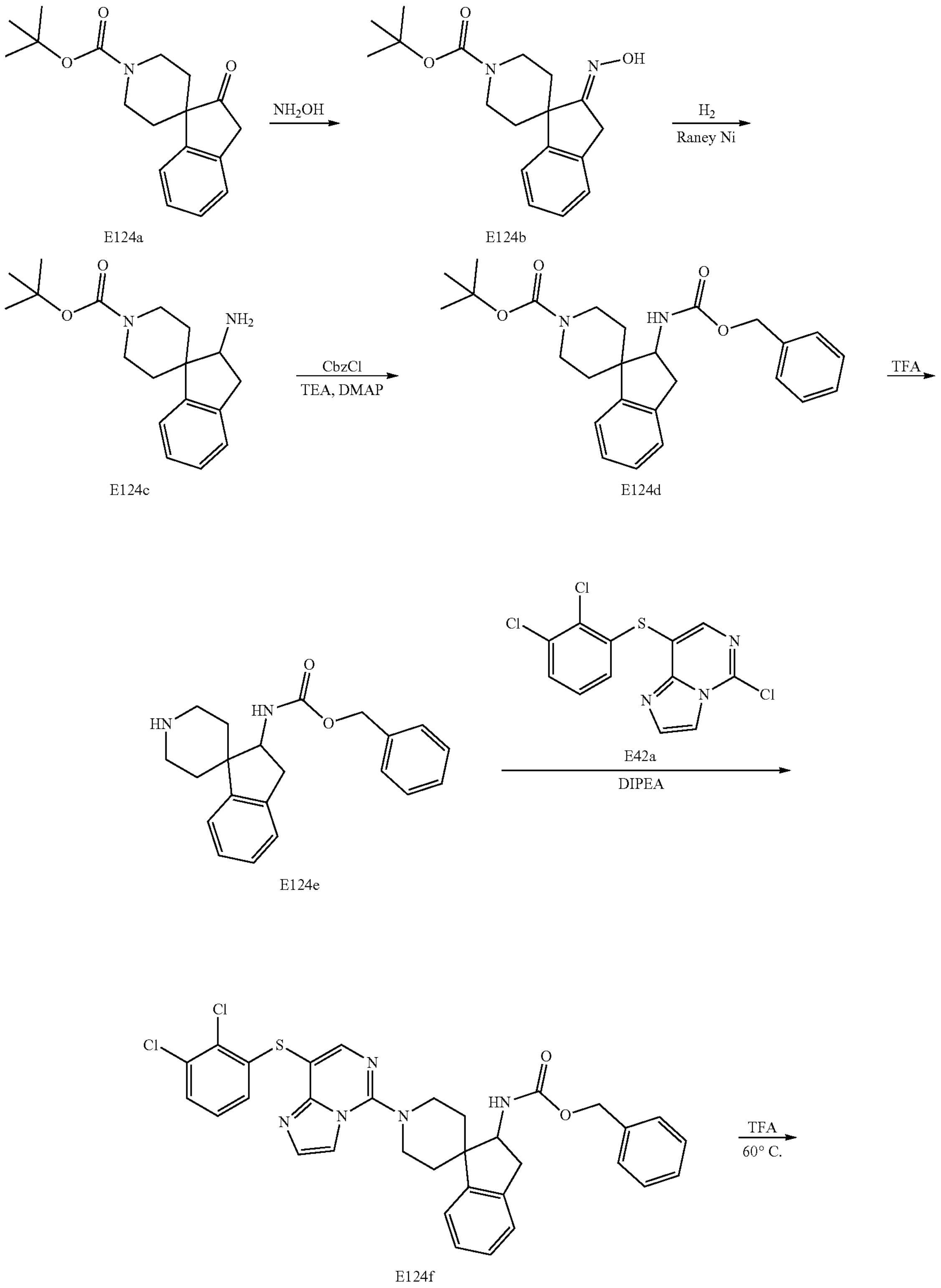

-continued

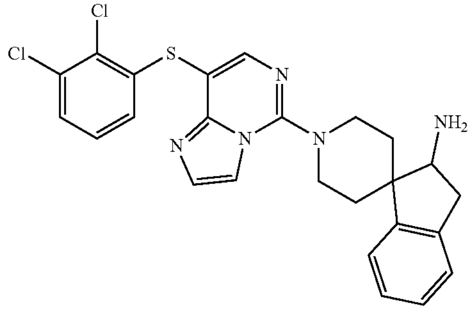

Example 124

Compound E124b: $NH_2OH$ (50% w/w/ in $H_2O$, 0.825 ml, 13.46 mmol) was added to a solution of Compound E124a (1.014 g, 3.364 mmol) in MeOH (12 ml). The reaction was heated in microwave to 120° C. for 35 min. The resulting solution was concentrated under vacuum and used directly in the next step without purifying. This provided Compound E124b. LCMS ESI$^+$ calc'd for $C_{18}H_{24}N_2O_3$: 316.2 [M+H$^+$]. found: 316.6. [M+H$^+$].

Compound E124c: Compound E124b (1.065 g, 3.364 mmol) was dissolved in MeOH (12 ml) and $NH_4OH$ (934.0 mg, 14.13 mmol) and "Raney" Ni (50% w/w slurry in water, 400 mg) were added. The vessel was secured in Parr Hydrogenator under $H_2$ (45 psi) and reacted for 16 h. The suspension was filtered through Celite and concentrated under vacuum to provide Compound E124c. The intermediate was used in the next step without purifying further. LCMS ESI$^+$ calc'd for $C_{18}H_{26}N_2O_2$: 303.2 [M+H$^+$]. found: 303.9 [M+H$^+$].

Compound E124d: Compound E124c (1.065 g, 3.522 mmol) was dissolved in DCM, DMAP (4.302 g, 0.035 mmol) was added followed by DIPEA (1.534 ml, 8.804 mmol) and CbzCl (0.595 ml, mmol) was added dropwise. The resulting solution was stirred at room temperature for 1 h. The reaction was diluted with water and EtOAc. The organic partition was dried over magnesium sulfate, concentrated in vacuo, and purified by column chromatography (0-100% EtOAc in Hexanes) giving Compound E124d. LCMS ESI$^+$ calc'd for $C_{26}H_{32}N_2O_4$: 436.2 [M+H$^+$]; 436.8 [M+H$^+$].

Compound E124e: Compound E124d (74.3 mg, 0.170 mmol) was dissolved in DCM (5 ml) and TFA (1 ml) was added. The resulting solution was stirred at room temperature for 30 min. Upon consumption of the starting material, the reaction was concentrated in vacuo, and used directly in the next step without purification. This provided Compound E124e. LCMS ESI$^+$ calc'd for $C_{21}H_{24}N_2O_2$: 337.2 [M+H$^+$]. found: 337.1 [M+H$^+$].

Compound E124f: Compound E42a (36.0 mg, 0.115 mmol) and Compound E124e (57.3 mg, 0.170 mmol) were dissolved in 1,4 Dioxane (2 mL) and DIPEA was added (0.160 ml, 0.920 mmol) the reaction stirred at 100° C. for 2 h. The mixture was diluted with EtOAc, successively washed with brine, dried over magnesium sulfate, and concentrated in vacuo, and used in the next step without purifying. This provided Compound E124f. LCMS ESI$^+$ calc'd for $C_{33}H_{29}Cl_2N_5O_2S$: 630.1 [M+H$^+$]. found: 630.3 [M+H$^+$].

Example 124: Compound E124f was dissolved in TFA (2 ml) and heated to 60° C. for 6 h. The solution was concentrated and reconstituted in water and DMF and the solution was purified on preparatory HPLC (10-100% MeCN in water with 0.1% TFA, Gemini). This provided Example 124 as TFA salt. $^1$H NMR (400 MHz, DMSO-d$_6$) δ 8.08 (s, 1H), 8.01-7.85 (m, 4H), 7.62 (d, J=1.4 Hz, 1H), 7.42 (dd, J=8.1, 1.5 Hz, 2H), 7.37-7.24 (m, 3H), 7.13 (t, J=8.0 Hz, 1H), 6.72 (dd, J=8.1, 1.4 Hz, 1H), 4.18 (s, 1H), 3.92 (dd, J=26.1, 13.7 Hz, 3H), 2.92 (d, J=17.4 Hz, 1H), 2.41 (d, J=11.5 Hz, 1H), 1.95 (d, J=14.6 Hz, 1H), 1.86-1.66 (m, 2H). LCMS ESI$^+$ calc'd for $C_{18}H_{17}Cl_2N_5S$: 496.1 [M+H$^+$]. found: 496.1 [M+H$^+$].

Example 125: 4-((5-((3S,4S)-4-amino-3-methyl-2-oxa-8-azaspiro[4.5]decan-8-yl)imidazo[1,2-c]pyrimidin-8-yl)thio)quinoline-7-carbonitrile

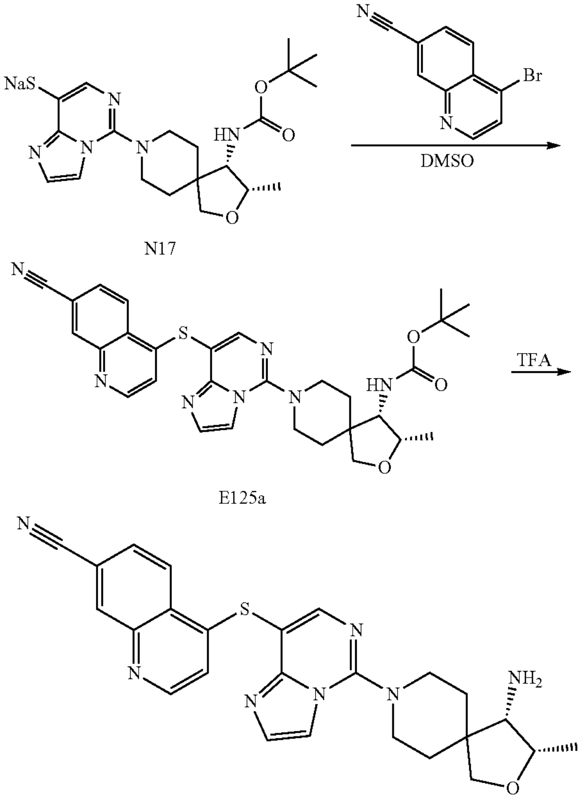

N17

E125a

Example 125

Compound E125a: The compound was prepared in a similar manner to Compound E116a using Compound N17 and 4-chloroquinoline-7-carbonitrile.

Example 125: The compound was prepared in a manner similar to Example 116 using Compound E125a as the starting material. $^1$H NMR (400 MHz, methanol-$d_4$) δ 8.70 (d, J=5.1 Hz, 1H), 8.56 (s, OH), 8.54-8.47 (m, 3H), 8.37 (s, OH), 8.13 (d, J=2.2 Hz, 1H), 8.03 (ddd, J=8.6, 6.2, 1.9 Hz, 1H), 7.92 (d, J=2.2 Hz, 1H), 7.22 (d, J=5.1 Hz, 1H), 4.52-4.32 (m, 1H), 4.32-4.18 (m, 1H), 4.18-4.02 (m, 2H), 3.95 (dd, J=11.9, 9.2 Hz, 1H), 3.70-3.43 (m, 3H), 2.34-2.08 (m, 2H), 1.92 (dd, J=17.2, 13.8 Hz, 1H), 1.58 (d, J=11.2 Hz, 0H), 1.37 (dd, J=6.5, 4.2 Hz, 4H), 1.26 (t, J=7.2 Hz, 1H). LCMS ESI$^+$ calc'd for $C_{25}H_{25}N_7OS$ [M+H$^+$]: 472.2. found: 472.2 [M+H$^+$].

Example 126: (3S,4S)-8-(8-((1,7-naphthyridin-4-yl)thio)imidazo[1,2-c]pyrimidin-5-yl)-3-methyl-2-oxa-8-azaspiro[4.5]decan-4-amine

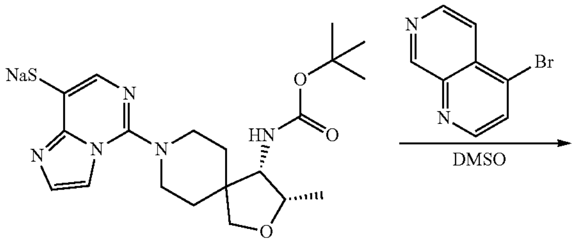

N17

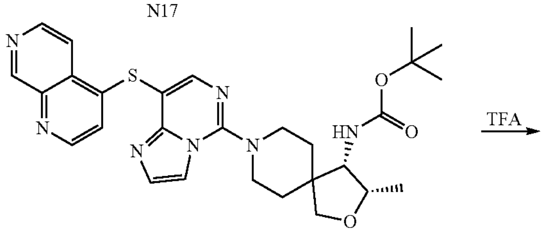

E126a

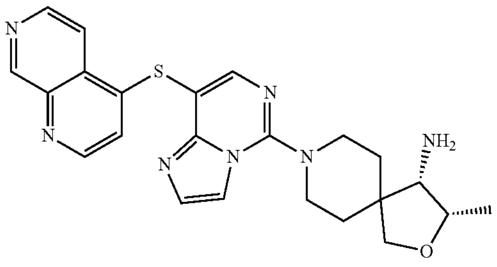

Example 126

Compound E126a: The compound was prepared in a similar manner to Compound E116a using Compound N17 and 4-chloro-1,7-naphthyridine.

Example 126: The compound was prepared in a manner similar to Example 116 using Compound E126a as the starting material. $^1$H NMR (400 MHz, Methanol-$d_4$) δ 9.57-9.41 (m, 1H), 8.75 (dd, J=7.9, 5.5 Hz, 2H), 8.47 (s, 1H), 8.36 (dd, J=6.0, 0.9 Hz, 1H), 8.09 (d, J=2.1 Hz, 1H), 7.86 (d, J=2.0 Hz, 1H), 7.26 (d, J=4.9 Hz, 1H), 4.48-4.31 (m, 1H), 4.30-4.13 (m, 2H), 4.08 (d, J=9.2 Hz, 1H), 3.96 (d, J=9.2 Hz, 1H), 3.58 (d, J=4.1 Hz, 1H), 3.54 (s, 1H), 2.29-2.11 (m, 2H), 2.04 (d, J=14.0 Hz, 1H), 1.90 (d, J=13.3 Hz, 1H), 1.38 (d, J=6.5 Hz, 3H). LCMS ESI$^+$ calc'd for $C_{23}H_{25}N_7OS$ [M+H$^+$]: 448.2; Found: 448.2 [M+H$^+$].

Example 127: 4-((5-((3S,4S)-4-amino-3-methyl-2-oxa-8-azaspiro[4.5]decan-8-yl)imidazo[1,2-c]pyrimidin-8-yl)thio)quinoline-6-carbonitrile Compound E127a: The compound was prepared in a similar manner to Compound E116a using Compound N17 and 4-chloroquinoline-6-carbonitrile.

Example 127: The compound was prepared in a manner similar to Example 116 using Compound E127a as the starting material. $^1$H NMR (400 MHz, Methanol-$d_4$) δ 8.88 (d, J=1.6 Hz, 1H), 8.68 (d, J=5.2 Hz, 1H), 8.47 (s, 1H), 8.24 (d, J=8.8 Hz, 1H), 8.15 (dd, J=8.8, 1.7 Hz, 1H), 8.08 (d, J=2.1 Hz, 1H), 7.86 (d, J=2.0 Hz, 1H), 7.19 (d, J=5.2 Hz, 1H), 4.48-4.33 (m, 1H), 4.21 (dd, J=24.6, 14.0 Hz, 2H), 4.07 (d, J=9.2 Hz, 1H), 3.96 (d, J=9.2 Hz, 1H), 3.57 (d, J=4.0 Hz, 1H), 3.56-3.41 (m, 2H), 2.24-2.10 (m, 2H), 2.04 (d, J=14.0 Hz, 1H), 1.89 (d, J=13.3 Hz, 1H), 1.38 (d, J=6.5 Hz, 3H). LCMS ESI$^+$ calc'd for $C_{25}H_{25}N_7OS$ [M+H$^+$]: 472.2; Found: 472.2 [M+H$^+$].

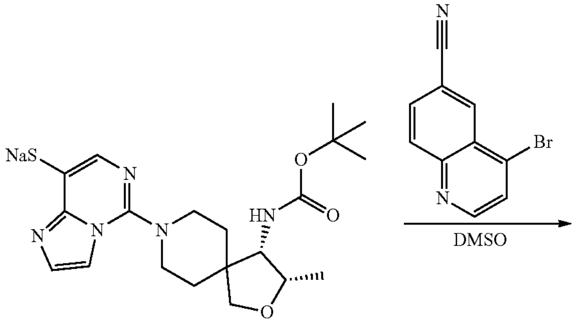

N17

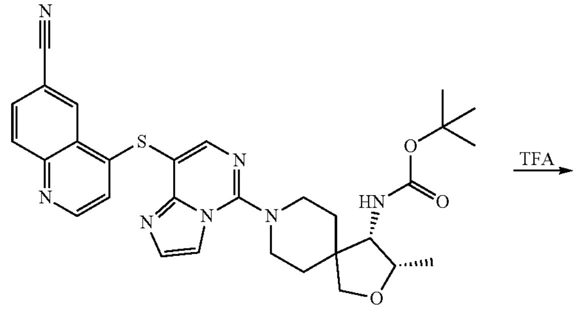

E127a

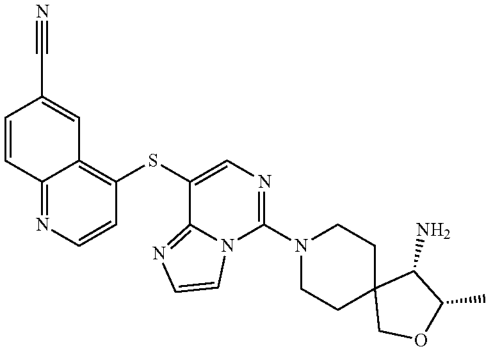

Example 127

Example 128: (3S,4S)-8-(8-((1,5-naphthyridin-4-yl) thio)imidazo[1,2-c]pyrimidin-5-yl)-3-methyl-2-oxa-8-azaspiro[4.5]decan-4-amine

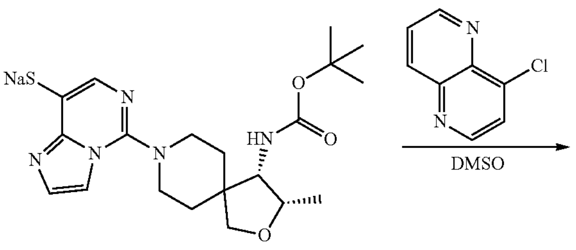

N17

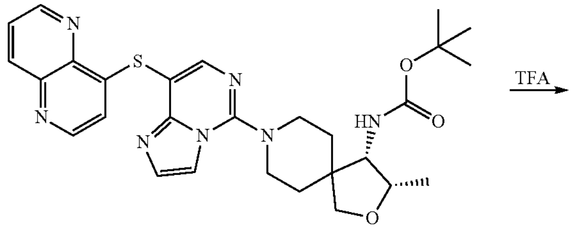

E128a

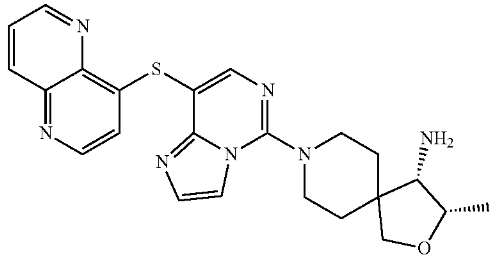

Example 128

Compound E128a: The compound was prepared in a similar manner to Compound E116a using Compound N17 and 4-chloro-1,5-naphthyridine.

Example 128: The compound was prepared in a manner similar to Example 116 using Compound E128a as the starting material. $^1$H NMR (400 MHz, Methanol-$d_4$) δ 9.11 (dd, J=4.2, 1.6 Hz, 1H), 8.62 (d, J=5.2 Hz, 1H), 8.52-8.48 (m, 1H), 8.47 (d, J=5.6 Hz, 1H), 8.09 (d, J=2.1 Hz, 1H), 7.97 (dd, J=8.6, 4.2 Hz, 1H), 7.86 (d, J=2.0 Hz, 1H), 7.19 (d, J=5.2 Hz, 1H), 4.54-4.30 (m, 1H), 4.30-4.12 (m, 2H), 4.07 (d, J=9.2 Hz, 1H), 3.97 (d, J=9.2 Hz, 1H), 3.57 (d, J=4.1 Hz, 1H), 3.55-3.38 (m, 1H), 2.27-2.12 (m, 2H), 2.05 (d, J=13.8 Hz, 1H), 1.89 (d, J=13.4 Hz, 1H), 1.38 (d, J=6.5 Hz, 3H). LCMS ESI$^+$ calc'd for $C_{23}H_{25}N_7OS$ [M+H$^+$]: 448.2; Found: 448.2 [M+H$^+$].

Example 129: (3S,4S)-3-methyl-8-(8-(quinolin-5-ylthio)imidazo[1,2-c]pyrimidin-5-yl)-2-oxa-8-azaspiro[4.5]decan-4-amine

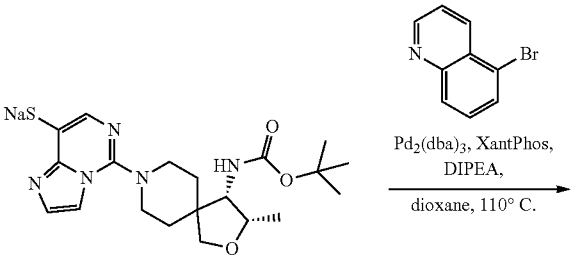

N17

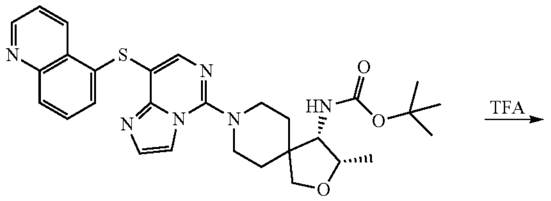

E129a

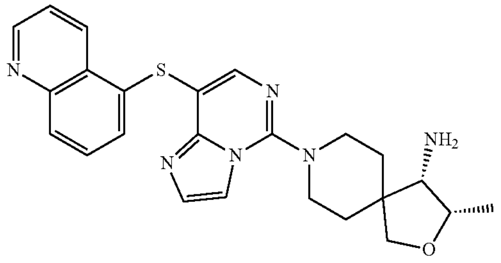

Example 129

Compound E129a: Compound N17 (49 mg, 0.111 mmol) in 1,4-dioxane (2 ml) was added $Pd_2(dba)_3$ (10 mg, 0.011 mmol), XantPhos (13 mg, 0.022 mmol), 5-bromoquinoline (24 mg, 0.117 mmol), and DIPEA (25 μL, 0.145 mmol). The reaction vessel was degassed with argon, sealed, and heated to 110° C. overnight. The reaction mixture was then cooled to room temperature, filtered through Celite®, and concentrated. The resulting residue was concentrated, diluted with 1:1 acetonitrile and water each containing 0.1% TFA and purified on preparatory HPLC (0 to 100% acetonitrile in water each containing 0.1% TFA). This provided Compound E129a as a TFA salt. LCMS ESI$^+$ calc'd for $C_{29}H_{34}N_6O_3S$: 547.2 [M+H$^+$]. found: 547.2 [M+H$^+$].

Example 129: Compound E129a was mixed with TFA (2 ml). After 4 h, the mixture was concentrated on rotovap, diluted with 1:1 acetonitrile and water each containing 0.1% TFA and purified on preparatory HPLC (0 to 100% acetonitrile in water each containing 0.1% TFA). This provided Example 129 as a TFA salt. $^1$H NMR (400 MHz, Methanol-$d_4$) δ 9.34 (dt, J=8.5, 1.2 Hz, 1H), 9.17 (dd, J=4.9, 1.5 Hz, 1H), 8.35 (s, 1H), 8.11-8.01 (m, 2H), 7.99 (dd, J=8.6, 4.9 Hz, 1H), 7.90 (d, J=2.1 Hz, 1H), 7.83 (dd, J=8.6, 7.5 Hz, 1H), 7.58 (dd, J=7.5, 1.0 Hz, 1H), 4.41-4.31 (m, 1H), 4.20-3.90 (m, 3H), 3.51-3.36 (m, 2H), 2.22-1.78 (m, 6H), 1.36 (d, J=6.5 Hz, 3H). LCMS ESI$^+$ calc'd for $C_{24}H_{26}N_6OS$: 447.2 [M+H$^+$]. found: 447.2 [M+H$^+$].

Example 130: (3S,4S)-8-(8-((1H-pyrrolo[2,3-b]pyridin-4-yl)thio)imidazo[1,2-c]pyrimidin-5-yl)-3-methyl-2-oxa-8-azaspiro[4.5]decan-4-amine

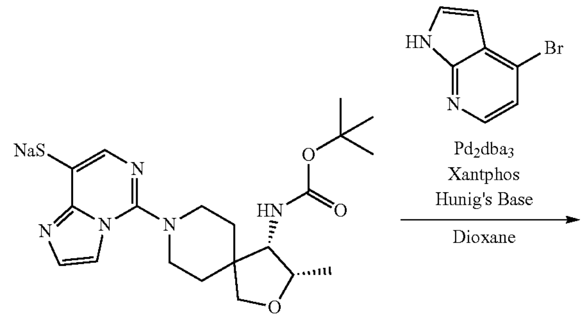

N17

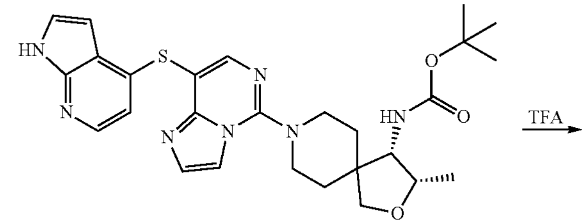

E130a

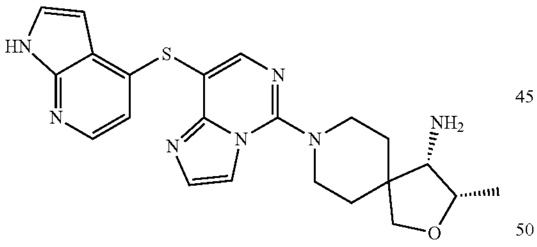

Example 130

Compound E130a: The compound was prepared in a similar manner to Compound E78a using Compound N17 and 4-bromo-1H-pyrrolo[2,3-b]pyridine.

Example 130: The compound was prepared in a manner similar to Example 84 using Compound E130a as the starting material. $^1$H NMR (400 MHz, DMSO-$d_6$) δ 11.85 (s, 1H), 8.10 (s, 1H), 7.93 (d, J=5.2 Hz, 4H), 7.86 (d, J=1.6 Hz, 1H), 7.66 (d, J=1.5 Hz, 1H), 7.50 (t, J=3.0 Hz, 1H), 6.55-6.40 (m, 2H), 4.22 (q, J=6.3, 5.9 Hz, 1H), 3.95-3.81 (m, 4H), 3.72 (d, J=9.0 Hz, 1H), 3.47 (s, 2H), 3.25 (q, J=12.0 Hz, 2H), 1.95 (t, J=10.9 Hz, 2H), 1.81 (d, J=13.8 Hz, 1H), 1.69 (d, J=13.4 Hz, 1H), 1.22 (d, J=6.5 Hz, 3H). LCMS ESI$^+$ calc'd for $C_{22}H_{25}N_7OS$ [M+H$^+$]: 436.2; Found: 436.2 [M+H$^+$].

Example 131: (3S,4S)-8-(8-((3H-imidazo[4,5-b]pyridin-7-yl)thio)imidazo[1,2-c]pyrimidin-5-yl)-3-methyl-2-oxa-8-azaspiro[4.5]decan-4-amine

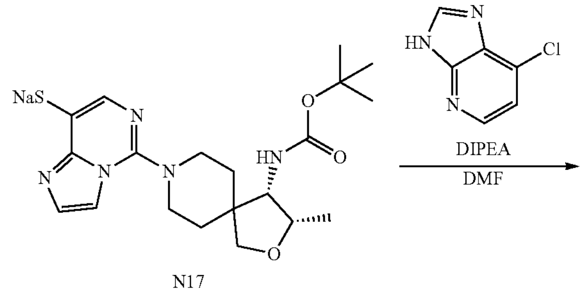

N17

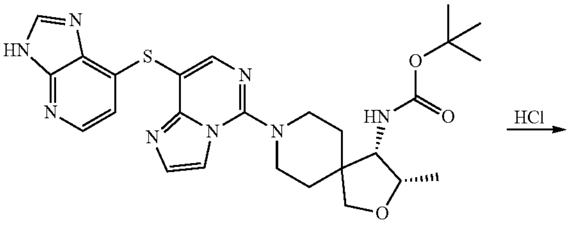

E131a

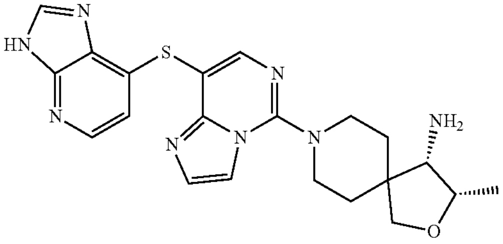

Example 131

Compound E131a: The compound was prepared in a similar manner to Compound E88a using Compound N17 and 7-chloro-3H-imidazo[4,5-b]pyridine.

Example 131: The compound was prepared in a manner similar to Example 85 using Compound E131a as the starting material. $^1$H NMR (400 MHz, Methanol-$d_4$) δ 8.67 (s, 1H), 8.42 (s, 1H), 8.17 (d, J=5.6 Hz, 1H), 8.04 (d, J=2.1 Hz, 1H), 7.83 (d, J=2.0 Hz, 1H), 6.90 (d, J=5.6 Hz, 1H), 4.41-4.29 (m, 1H), 4.24-4.09 (m, 2H), 4.06 (d, J=9.2 Hz, 1H), 3.95 (d, J=9.2 Hz, 1H), 3.56 (d, J=4.1 Hz, 1H), 3.52-3.37 (m, 2H), 2.22-1.97 (m, 3H), 1.88 (d, J=13.5 Hz, 1H), 1.37 (d, J=6.5 Hz, 3H). LCMS ESI$^+$ calc'd for $C_{21}H_{24}N_8OS$ [M+H$^+$]: 437.2. found: 437.2 [M+H$^+$].

Example 132: (3S,4S)-8-(8-((6-methoxyquinolin-4-yl)thio)imidazo[1,2-c]pyrimidin-5-yl)-3-methyl-2-oxa-8-azaspiro[4.5]decan-4-amine Compound E132a: Compound N17 (33 mg, 0.075 mmol) in 1,4-dioxane (2 ml) was added $Pd_2(dba)_3$ (6.8 mg, 0.007 mmol), XantPhos (8.6 mg, 0.015 mmol), 4-bromo-6-methoxyquinoline (19 mg, 0.078 mmol), and DIPEA (17 μL, 0.098 mmol). The reaction vessel was degassed with argon, sealed, and heated to 110° C. overnight. The reaction mixture was then cooled to room temperature, filtered through Celite®, and concentrated. The resulting residue was concentrated, diluted with 1:1 acetonitrile and water each containing 0.1% TFA and purified on preparatory HPLC (0 to 100% acetonitrile in water each containing 0.1% TFA). This provided Compound E132a as a TFA salt. LCMS ESI+ calc'd for $C_{30}H_{36}N_6O_4S$: 577.3 [M+H+]. found: 577.2 [M+H+].

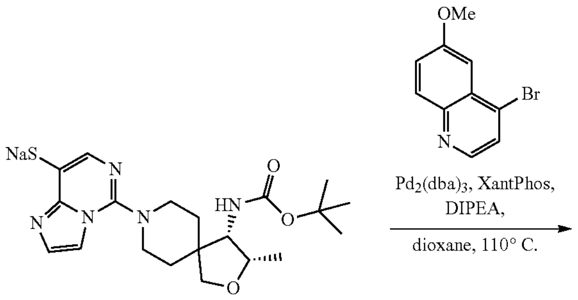

N17

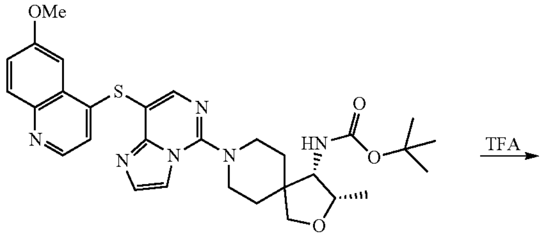

E132a

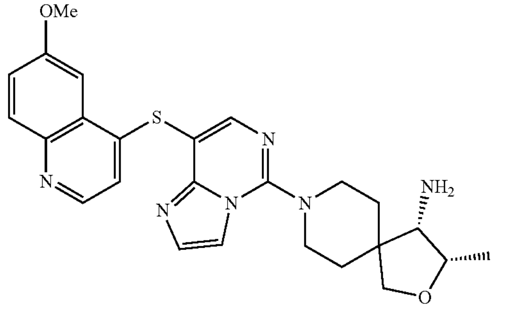

Example 132

Example 132: Compound E132a was mixed with TFA (2 ml). After 4 h, the mixture was concentrated on rotovap, diluted with 1:1 acetonitrile and water each containing 0.1% TFA and purified on preparatory HPLC (0 to 100% acetonitrile in water each containing 0.1% TFA). This provided Example 132 as a TFA salt. $^1$H NMR (400 MHz, DMSO-$d_6$) δ $^1$H NMR (400 MHz, Methanol-$d_4$) δ 8.52 (d, J=6.1 Hz, 1H), 8.39 (s, 1H), 8.15 (d, J=9.4 Hz, 1H), 8.02 (d, J=1.9 Hz, 1H), 7.87 (dd, J=9.3, 2.6 Hz, 1H), 7.77 (dd, J=8.3, 2.2 Hz, 2H), 7.32 (d, J=6.1 Hz, 1H), 4.42-4.32 (m, 1H), 4.30-4.10 (m, 1H), 4.14 (s, 3H), 4.07 (d, J=9.1 Hz, 1H), 3.96 (d, J=9.2 Hz, 1H), 3.57 (d, J=4.1 Hz, 1H), 3.54-3.37 (m, 2H), 2.14 (t, J=12.3 Hz, 2H), 2.08-2.00 (m, 1H), 1.89 (d, J=13.5 Hz, 1H), 1.37 (d, J=6.5 Hz, 3H). LCMS ESI+ calc'd for $C_{25}H_{28}N_6O_2S$: 477.2 [M+H+]. found: 477.2 [M+H+].

Example 133: (S)-1'-(8-(2,3-dichlorophenyl)-7-methylimidazo[1,2-c]pyrimidin-5-yl)-5-fluoro-1,3-dihydrospiro[indene-2,4'-piperidin]-1-amine Compound E133a: The compound was prepared in a similar manner to Compound E16a using Compound N20 and (2,3-dichlorophenyl)boronic acid.

Example 133: The compound was prepared in a manner similar to Example 85 using Compound E133a as the starting material. $^1$H NMR (400 MHz, methanol-$d_4$) δ 7.98 (d, J=2.2 Hz, 1H), 7.83 (d, J=2.1 Hz, 1H), 7.80 (dd, J=8.2, 1.6 Hz, 1H), 7.60-7.50 (m, 2H), 7.43 (dd, J=7.6, 1.5 Hz, 1H), 7.19 (dd, J=8.8, 2.4 Hz, 1H), 7.13 (td, J=8.8, 2.5 Hz, 1H), 4.50 (s, 1H), 4.19-4.07 (m, 1H), 4.02 (d, J=14.0 Hz, 1H), 3.57 (dd, J=21.8, 12.0 Hz, 2H), 3.27 (d, J=7.8 Hz, 2H), 2.33 (s, 3H), 2.25-2.10 (m, 1H), 2.07-1.86 (m, 2H), 1.76 (d, J=13.7 Hz, 1H). (LCMS): ESI+ m/z Calc'd for $C_{26}H_{24}Cl_2FN_5$ [M+H+]: 496.1. found: 496.2 [M+H+].

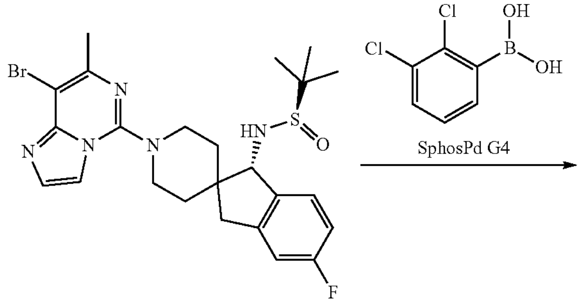

N20

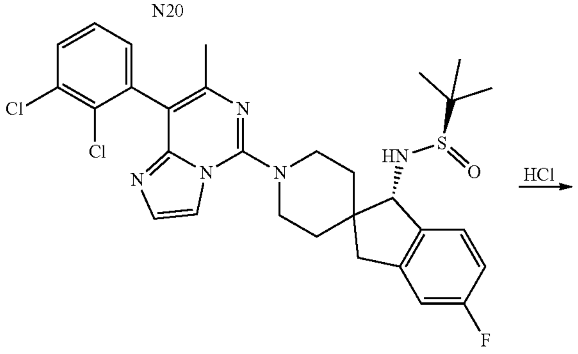

E133a

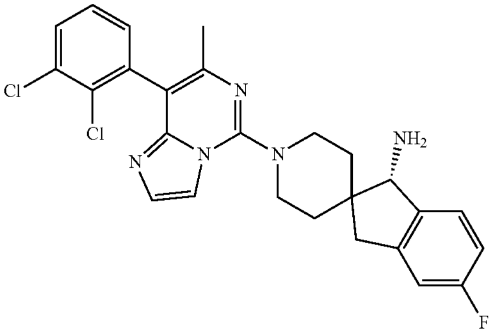

Example 133

Example 134: (3S,4S)-8-(8-((7-chloroquinolin-4-yl)thio)imidazo[1,2-c]pyrimidin-5-yl)-3-methyl-2-oxa-8-azaspiro[4.5]decan-4-amine Compound E134a: Compound N17 (33 mg, 0.075 mmol) in 1,4-dioxane (2 ml) was added $Pd_2(dba)_3$ (6.8 mg, 0.007 mmol), XantPhos (8.6 mg, 0.015 mmol), 4-bromo-7-chloroquinoline (19 mg, 0.078 mmol), and DIPEA (17 μL, 0.098 mmol). The reaction vessel was degassed with argon, sealed, and heated to 110° C. overnight. The reaction mixture was then cooled to room temperature, filtered through Celite®, and concentrated. The resulting residue was concentrated, diluted with 1:1 acetonitrile and water each containing 0.1%

TFA and purified on preparatory HPLC (0 to 100% acetonitrile in water each containing 0.1% TFA). This provided Compound E134a as a TFA salt. LCMS ESI$^+$ calc'd for $C_{29}H_{33}ClN_6O_3S$: 581.2 [M+H$^+$]. found: 581.2 [M+H$^+$].

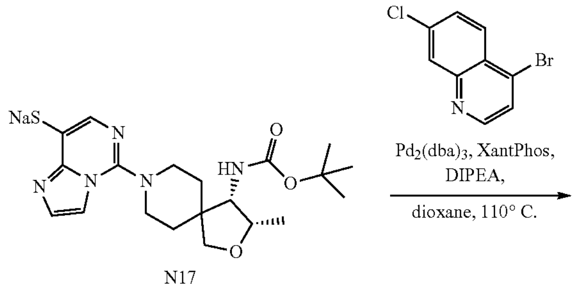

N17

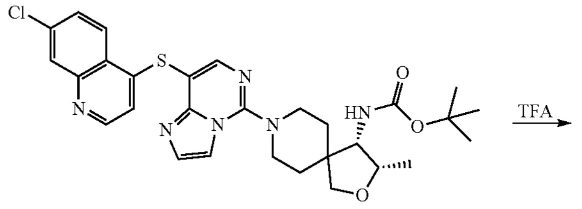

E134A

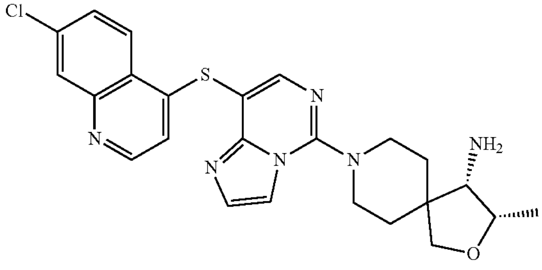

Example 134

Example 134: Compound E134a was mixed with TFA (2 ml). After 4 h, the mixture was concentrated on rotovap, diluted with 1:1 acetonitrile and water each containing 0.1% TFA and purified on preparatory HPLC (0 to 100% acetonitrile in water each containing 0.1% TFA). This provided Example 134 as a TFA salt. $^1$H NMR (400 MHz, Methanol-$d_4$) ($^1$H NMR (400 MHz, Methanol-$d_4$) δ 8.59 (d, J=5.5 Hz, 1H), 8.51 (dd, J=9.0, 0.5 Hz, 1H), 8.36 (s, 1H), 8.17-8.12 (m, 1H), 8.00 (d, J=1.9 Hz, 1H), 7.89 (dd, J=9.0, 2.1 Hz, 1H), 7.75 (d, J=1.9 Hz, 1H), 7.11 (d, J=5.6 Hz, 1H), 4.42-4.31 (m, 1H), 4.23-4.09 (m, 2H), 4.06 (d, J=9.1 Hz, 1H), 3.96 (d, J=9.2 Hz, 1H), 3.56 (d, J=4.1 Hz, 1H), 3.50-3.36 (m, 2H), 2.13 (t, J=12.1 Hz, 2H), 2.04 (d, J=13.3 Hz, 1H), 1.88 (broad d, J=13.3 Hz, 1H), 1.37 (d, J=6.5 Hz, 3H). LCMS ESI$^+$ calc'd for $C_{24}H_{25}ClN_6OS$: 481.2 [M+H$^+$]. found: 481.2 [M+H$^+$].

Example 135: (S)-1'-(8-(2,3-dichlorophenyl)-7-methylimidazo[1,2-c]pyrimidin-5-yl)-1,3-dihydrospiro[indene-2,4'-piperidin]-1-amine Compound E135a: The compound was prepared in a similar manner to Compound E16a using Compound N19 and (2,3-dichlorophenyl)boronic acid.

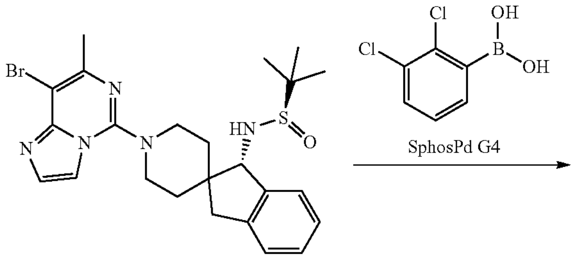

N19

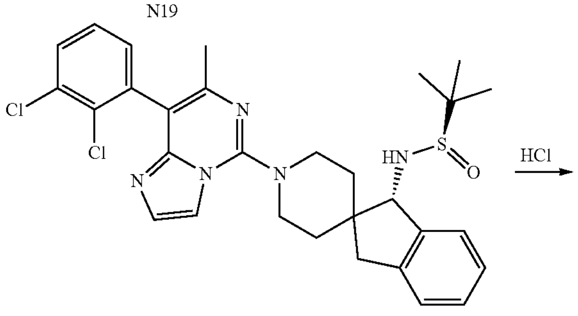

E135a

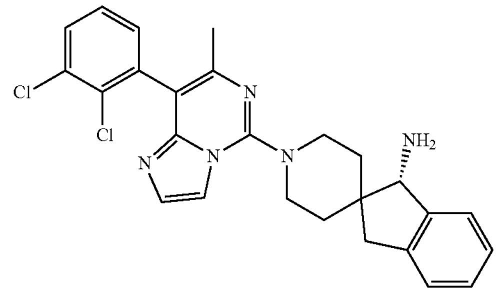

Example 135

Example 135: The compound was prepared in a manner similar to Example 85 using Compound E135a as the starting material. $^1$H NMR (400 MHz, methanol-$d_4$) δ 8.07 (d, J=2.4 Hz, 1H), 7.92 (d, J=2.3 Hz, 1H), 7.82 (dd, J=8.1, 1.6 Hz, 1H), 7.62-7.52 (m, 2H), 7.50-7.41 (m, 3H), 7.38 (ddd, J=7.5, 5.6, 3.0 Hz, 1H), 4.52 (d, J=2.0 Hz, 1H), 4.25-4.13 (m, 1H), 4.08 (ddq, J=13.9, 4.4, 2.1 Hz, 1H), 3.61 (ddddd, J=24.8, 13.7, 11.4, 5.0, 2.7 Hz, 2H), 3.27 (s, 2H), 2.36 (s, 3H), 2.28-2.15 (m, 1H), 2.12-1.99 (m, 1H), 1.93 (ddq, J=13.4, 4.7, 2.6 Hz, 1H), 1.82-1.69 (m, 1H). (LCMS): ESI$^+$ m/z Calc'd for $C_{26}H_{25}Cl_2N_5$[M+H$^+$]: 478.2; Found: 477.3 [M+H$^+$].

Example 136: (3S,4S)-3-methyl-8-(8-(naphthalen-1-ylthio)imidazo[1,2-c]pyrimidin-5-yl)-2-oxa-8-azaspiro[4.5]decan-4-amine Compound E136a: Compound N17a (35 mg, 0.075 mmol) in 1,4-dioxane (2 ml) was added $Pd_2(dba)_3$ (7, 0.008 mmol), XantPhos (9 mg, 0.015 mmol), naphthalene-1-thiol (23 mg, 0.145 mmol), and DIPEA (0.053 ml, 0.35 mmol). The reaction vessel was degassed with argon, sealed, and heated to 110° C. overnight. The reaction mixture was then cooled to room temperature, filtered through Celite®, and concentrated. The resulting residue was concentrated, diluted with 1:1 acetonitrile and water each containing 0.1% TFA and purified on preparatory HPLC (0 to 100% acetonitrile in water each containing 0.1% TFA). This provided Compound E136a. LCMS ESI$^+$ calc'd for $C_{30}H_{35}N_5O_3S$: 546.2 [M+H$^+$]. found: 546.1 [M+H$^+$].

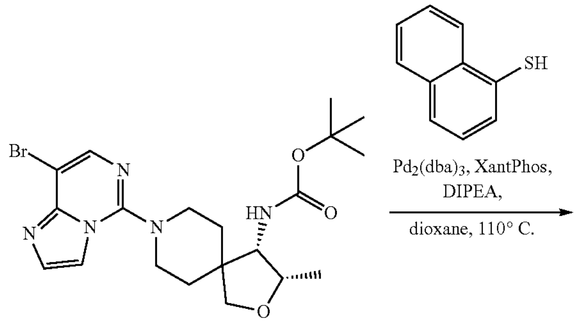

N17a

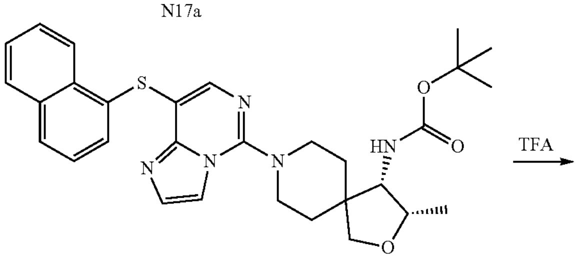

E136a

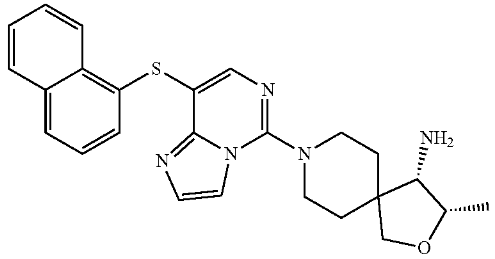

Example 136

Example 136: Compound E136a was mixed with TFA (2 ml). After 4 h, the mixture was concentrated on rotovap, diluted with 1:1 acetonitrile and water each containing 0.1% TFA and purified on preparatory HPLC (0 to 100% acetonitrile in water each containing 0.1% TFA). This provided This provided Example 136. $^1$H NMR (400 MHz, Methanol-d$_4$) δ 8.46-8.38 (m, 1H), 8.00-7.93 (m, 1H), 7.92 (d, J=1.8 Hz, 1H), 7.82 (d, J=1.9 Hz, 1H), 7.68 (s, 1H), 7.66-7.55 (m, 3H), 7.45 (dd, J=8.2, 7.2 Hz, 2H), 4.38-4.28 (m, 1H), 4.02-3.85 (m, 2H), 3.90 (d, J=9.2 Hz, 1H), 3.52-3.47 (m, 1H), 3.35-3.14 (m, 3H), 2.10-1.94 (m, 3H), 1.79 (d, J=13.7 Hz, 1H), 1.34 (d, J=6.5 Hz, 3H). LCMS ESI$^+$ calc'd for $C_{25}H_{27}N_5OS$: [M+H$^+$]; 446.2 found: 446.2.

Example 137: (S)-1'-(8-((3-amino-2-chlorophenyl) thio)imidazo[1,2-c]pyrimidin-5-yl)-1,3-dihydrospiro [indene-2,4'-piperidin]-1-amine Compound E137a: The compound was prepared in a similar manner to Compound E78a using Compound N18 and 3-bromo-2-chloroaniline.

Example 137: The compound was prepared in a manner similar to Example 85 using Compound E137a as the starting material. $^1$H NMR (400 MHz, methanol-d$_4$) δ 8.27 (s, 1H), 8.05 (d, J=2.2 Hz, 1H), 7.89 (d, J=2.1 Hz, 1H), 7.55 (d, J=7.5 Hz, 1H), 7.48-7.31 (m, 3H), 6.90 (t, J=8.0 Hz, 1H), 6.72 (dd, J=8.1, 1.4 Hz, 1H), 6.21 (dd, J=7.8, 1.4 Hz, 1H), 4.50 (s, 1H), 4.19 (d, J=14.1 Hz, 1H), 4.08 (d, J=13.4 Hz, 1H), 3.74-3.53 (m, 2H), 3.26 (s, 2H), 2.27-2.10 (m, 1H), 2.10-1.94 (m, 1H), 1.90 (d, J=13.5 Hz, 1H), 1.75 (d, J=13.6 Hz, 1H). (LCMS): ESI$^+$ m/z Calc'd for $C_{25}H_{25}N_6S$ [M+H$^+$]: 477.2. found: 477.2 [M+H$^+$].

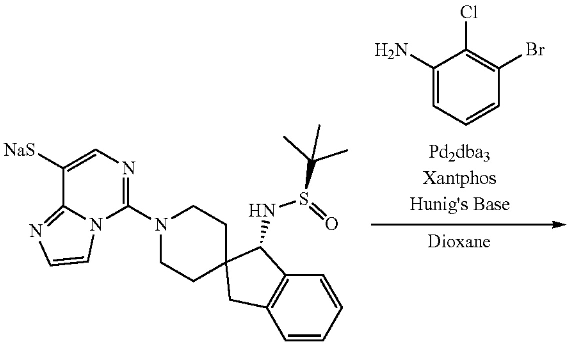

N18

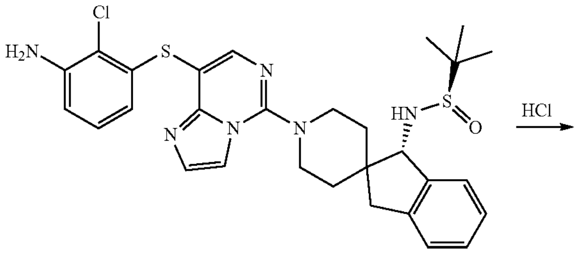

E137a

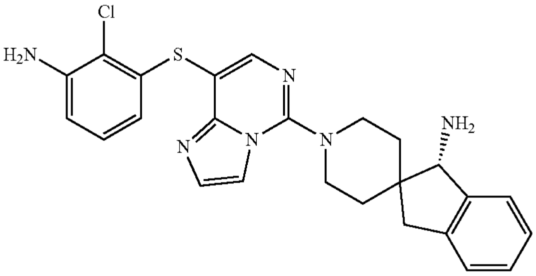

Example 137

Example 138: (S)-1'-(8-(thieno[2,3-b]pyridin-4-ylthio)imidazo[1,2-c]pyrimidin-5-yl)-1,3-dihydrospiro[indene-2,4'-piperidin]-1-amine

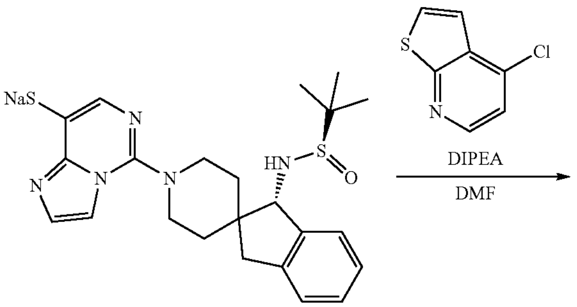

N18

-continued

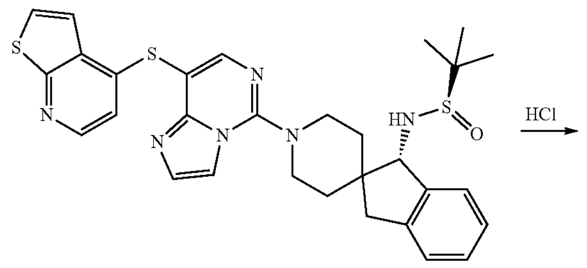

E138a

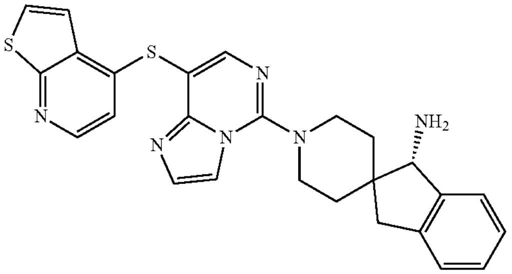

Example 138

Compound E138a: The compound was prepared in a similar manner to Compound E88a using Compound N18 and 4-chlorothieno[2,3-b]pyridine.

Example 138: The compound was prepared in a manner similar to Example 85 using Compound E138a as the starting material. $^1$H NMR (400 MHz, Methanol-$d_4$) δ 8.42 (s, 1H), 8.24 (d, J=5.2 Hz, 1H), 8.06 (d, J=2.1 Hz, 1H), 7.90 (d, J=6.1 Hz, 1H), 7.84 (d, J=2.0 Hz, 1H), 7.65 (d, J=6.1 Hz, 1H), 7.56 (d, J=7.4 Hz, 1H), 7.45 (dd, J=4.0, 1.7 Hz, 2H), 7.42-7.30 (m, 1H), 6.84 (d, J=5.2 Hz, 1H), 4.52 (s, 1H), 4.26 (d, J=13.3 Hz, 1H), 4.15 (d, J=14.0 Hz, 1H), 3.74-3.55 (m, 2H), 3.28 (s, 2H), 2.28-2.12 (m, 1H), 2.09-1.97 (m, 1H), 1.97-1.87 (m, 1H), 1.77 (d, J=13.7 Hz, 1H). (LCMS): ESI$^+$ m/z Calc'd for $C_{26}H_{24}N_6S_2$ [M+H$^+$]: 485.2; Found: 485.2 [M+H$^+$].

Example 139: (S)-1'-(8-(thieno[3,2-b]pyridin-7-ylthio)imidazo[1,2-c]pyrimidin-5-yl)-1,3-dihydrospiro[indene-2,4'-piperidin]-1-amine

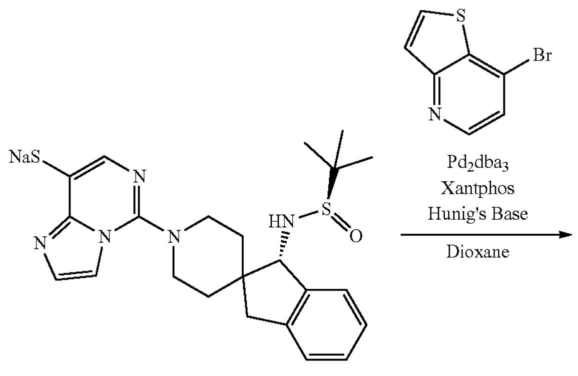

N18

-continued

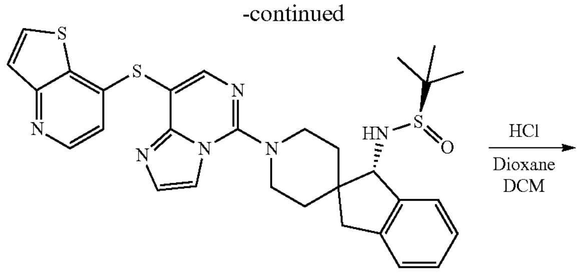

E139a

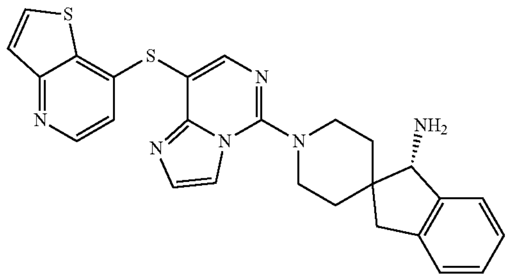

Example 139

Compound E139a: The compound was prepared in a similar manner to Compound E78a using Compound N18 and 7-bromothieno[3,2-b]pyridine. ESI$^+$ m/z Calc'd for $C_{30}H_{32}N_6OS_3$ [M+H$^+$]: 589.2; Found: 589.1 [M+H$^+$].

Example 139: The compound was prepared in a manner similar to Example 85 using Compound E139a as the starting material. $^1$H NMR (400 MHz, Methanol-$d_4$) δ 8.46 (d, J=5.8 Hz, 1H), 8.39-8.29 (m, 2H), 7.98 (d, J=1.8 Hz, 1H), 7.73-7.65 (m, 2H), 7.55 (d, J=7.5 Hz, 1H), 7.49-7.29 (m, 3H), 7.12 (d, J=5.8 Hz, 1H), 4.51 (s, 1H), 4.19 (dd, J=39.0, 14.0 Hz, 2H), 3.72-3.46 (m, 2H), 3.27 (s, 2H), 2.18 (td, J=12.3, 4.0 Hz, 1H), 2.11-1.95 (m, 1H), 1.91 (d, J=13.3 Hz, 1H), 1.77 (d, J=13.7 Hz, 1H). (LCMS): ESI$^+$ m/z Calc'd for $C_{26}H_{24}N_6S_2$ [M+H$^+$]: 485.2. found: 485.1 [M+H$^+$].

Example 140: (S)-1'-(8-(benzo[d]isothiazol-7-ylthio)imidazo[1,2-c]pyrimidin-5-yl)-1,3-dihydrospiro[indene-2,4'-piperidin]-1-amine

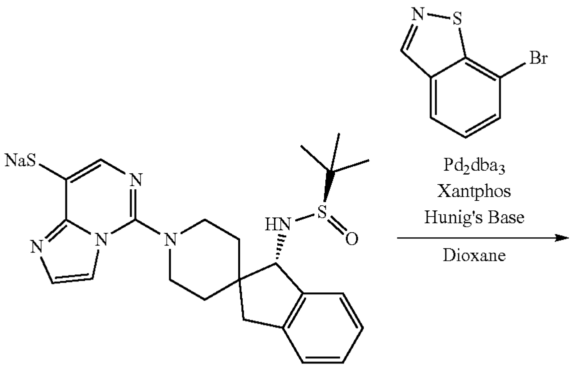

N18

-continued

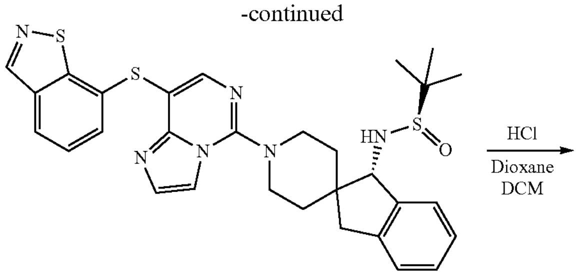

E140a

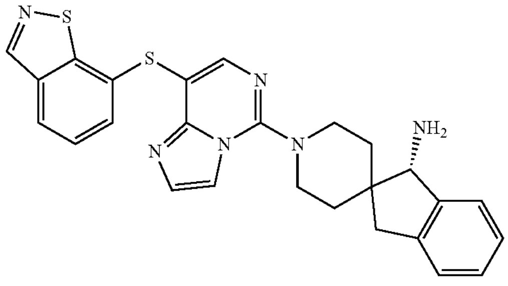

Example 140

Compound E140a: The compound was prepared in a similar manner to Compound E78a using Compound N18 and 7-bromobenzo[d]isothiazole. $ESI^+$ m/z Calc'd for $C_{30}H_{32}N_6OS_3$ $[M+H^+]$: 589.2. found: 589.1 $[M+H^+]$.

Example 140: The compound was prepared in a manner similar to Example 85 using Compound E140a as the starting material. $^1H$ NMR (400 MHz, Methanol-$d_4$) δ 9.02 (s, 1H), 8.18 (s, 1H), 8.15 (dd, J=8.0, 0.9 Hz, 1H), 7.94 (d, J=1.9 Hz, 1H), 7.79 (d, J=1.9 Hz, 1H), 7.73 (dd, J=7.4, 1.0 Hz, 1H), 7.59-7.26 (m, 5H), 4.47 (s, 1H), 4.06 (dd, J=39.6, 13.9 Hz, 2H), 3.65-3.38 (m, 2H), 3.23 (s, 2H), 2.12 (dd, J=12.3, 8.2 Hz, 1H), 2.03-1.92 (m, 1H), 1.86 (d, J=13.2 Hz, 1H), 1.71 (d, J=13.7 Hz, 1H). (LCMS): $ESI^+$ m/z Calc'd for $C_{26}H_{24}N_6S_2$ $[M+H^+]$: 485.2. found: 485.1 $[M+H^+]$.

Example 141: (S)-1'-(8-((2-(methylthio)phenyl)thio)imidazo[1,2-c]pyrimidin-5-yl)-1,3-dihydrospiro[indene-2,4'-piperidin]-1-amine Compound E141a: The compound was prepared in a similar manner to Compound E78a using Compound N18 and (2-bromophenyl)(methyl)sulfane. $ESI^+$ m/z Calc'd for $C_{30}H_{35}N_5OS_3$ $[M+H^+]$: 578.2. found: 578.1 $[M+H^+]$.

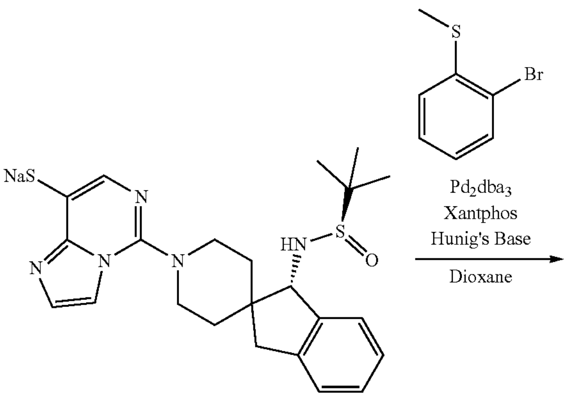

N18

-continued

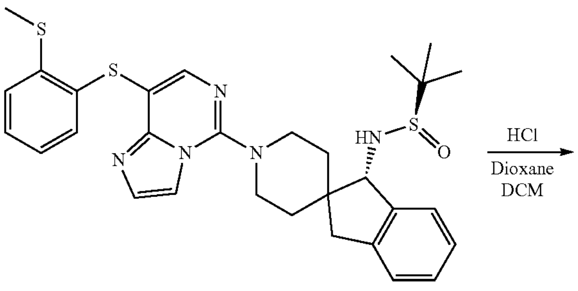

E141a

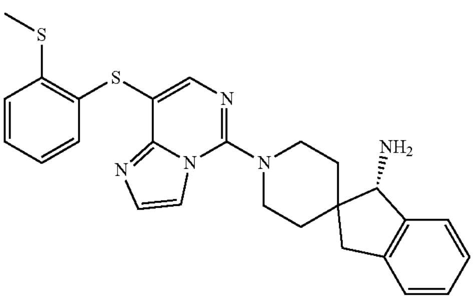

Example 141

Example 141: The compound was prepared in a manner similar to Example 85 using Compound E141a as the starting material. $^1H$ NMR (400 MHz, Methanol-$d_4$) δ 7.92 (d, J=2.0 Hz, 1H), 7.90 (s, 1H), 7.79 (d, J=2.0 Hz, 1H), 7.50 (d, J=7.4 Hz, 1H), 7.44-7.25 (m, 5H), 7.18 (dd, J=7.9, 1.5 Hz, 1H), 7.13-7.01 (m, 1H), 4.44 (s, 1H), 3.97 (dd, J=37.8, 13.7 Hz, 2H), 3.55-3.36 (m, 2H), 3.19 (s, 2H), 2.49 (s, 3H), 2.20-2.03 (m, 1H), 2.02-1.88 (m, 1H), 1.83 (d, J=13.3 Hz, 1H), 1.68 (d, J=13.7 Hz, 1H). (LCMS): $ESI^+$ m/z Calc'd for $C_{26}H_{27}N_5S_2$ $[M+H^+]$: 474.2. found: 474.2 $[M+H^+]$.

Example 142: (S)-1'-(8-((2-(ethylthio)phenyl)thio)imidazo[1,2-c]pyrimidin-5-yl)-1,3-dihydrospiro[indene-2,4'-piperidin]-1-amine

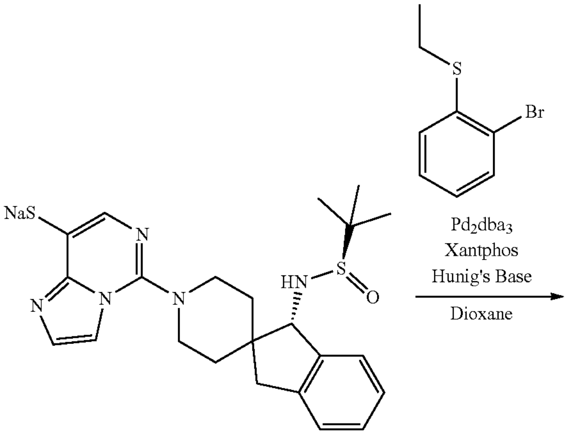

N18

-continued

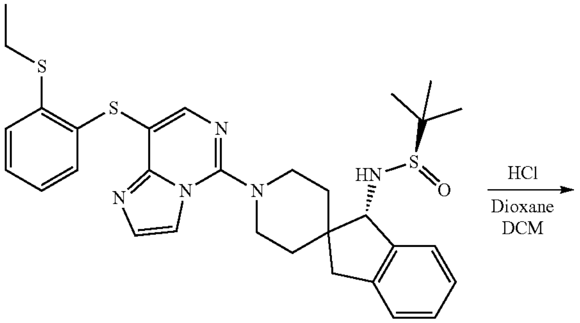

E142a

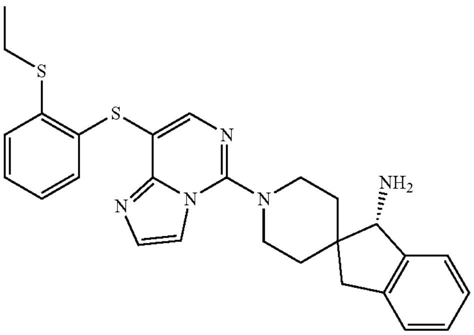

Example 142

Compound E142a: The compound was prepared in a similar manner to Compound E78a using Compound N18 and (2-bromophenyl)(ethyl)sulfane. ESI$^+$ m/z Calc'd for $C_{31}H_{37}N_5OS_3$ [M+H$^+$]: 592.2. found: 592.1 [M+H$^+$].

Example 142: The compound was prepared in a manner similar to Example 85 using Compound E142a as the starting material. $^1$H NMR (400 MHz, Methanol-d$_4$) δ 7.95 (s, 1H), 7.92 (d, J=2.0 Hz, 1H), 7.77 (d, J=1.9 Hz, 1H), 7.50 (d, J=7.5 Hz, 1H), 7.47-7.29 (m, 5H), 7.22 (td, J=7.6, 1.5 Hz, 1H), 7.08 (td, J=7.6, 1.3 Hz, 1H), 7.01 (dd, J=7.9, 1.5 Hz, 1H), 4.45 (s, 1H), 3.99 (dd, J=37.5, 13.8 Hz, 2H), 3.57-3.40 (m, 2H), 3.20 (s, 2H), 3.00 (q, J=7.4 Hz, 2H), 2.20-2.05 (m, 1H), 2.02-1.89 (m, 1H), 1.84 (d, J=13.5 Hz, 1H), 1.69 (d, J=13.9 Hz, 1H), 1.31 (t, J=7.4 Hz, 3H). (LCMS): ESI$^+$ m/z Calc'd for $C_{27}H_{29}N_5S_2$ [M+H$^+$]: 488.2; Found: 488.2 [M+H$^+$].

Example 143: (S)-1'-(8-((2-(isopropylthio)phenyl)thio)imidazo[1,2-c]pyrimidin-5-yl)-1,3-dihydrospiro[indene-2,4'-piperidin]-1-amine

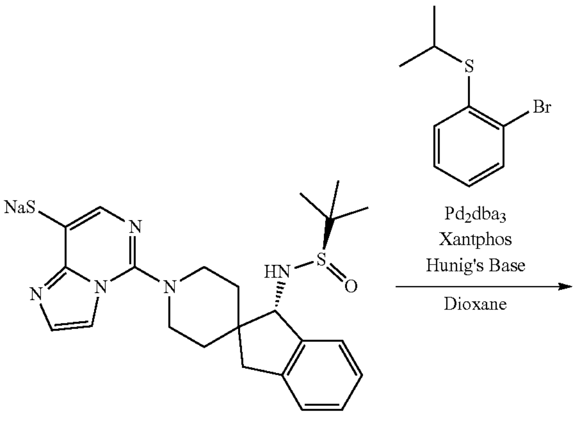

N18

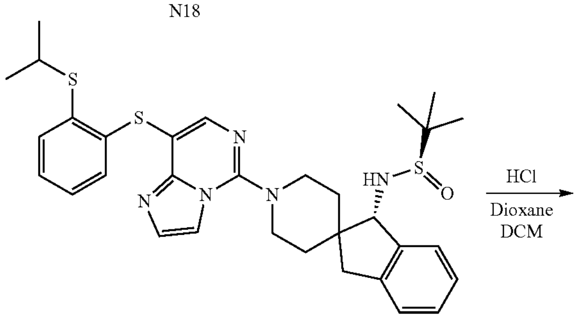

E143a

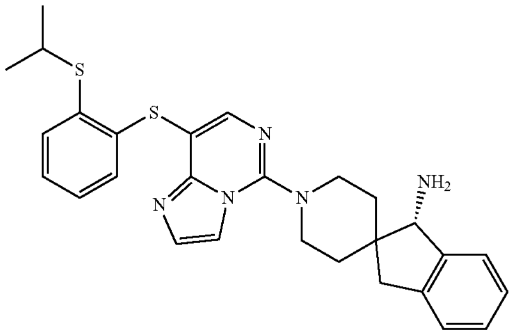

Example 143

Compound E143a: The compound was prepared in a similar manner to Compound E78a using Compound N18 and (2-bromophenyl)(isopropyl)sulfane. ESI$^+$ m/z Calc'd for $C_{32}H_{39}N_5OS_3$ [M+H$^+$]: 606.2. found: 606.1 [M+H$^+$].

Example 143: The compound was prepared in a manner similar to Example 85 using Compound E143a as the starting material. $^1$H NMR (400 MHz, Methanol-d$_4$) δ 8.13 (s, 1H), 7.98 (d, J=2.1 Hz, 1H), 7.81 (d, J=2.0 Hz, 1H), 7.54-7.45 (m, 2H), 7.45-7.26 (m, 3H), 7.18 (td, J=7.5, 1.4 Hz, 1H), 7.10 (td, J=7.7, 1.5 Hz, 1H), 6.87 (dd, J=7.9, 1.4 Hz, 1H), 4.46 (s, 1H), 4.06 (dd, J=40.8, 13.9 Hz, 2H), 3.66-3.38 (m, 3H), 3.21 (s, 2H), 2.20-2.05 (m, 1H), 2.04-1.91 (m, 1H), 1.85 (d, J=13.3 Hz, 1H), 1.70 (d, J=13.8 Hz, 1H), 1.31 (d, J=6.7 Hz, 6H). (LCMS): ESI$^+$ m/z Calc'd for $C_{28}H_{31}N_5S_2$ [M+H$^+$]: 502.2. found: 502.2 [M+H$^+$].

Example 144: (S)-1'-(8-((1,5-naphthyridin-4-yl)thio) imidazo[1,2-c]pyrimidin-5-yl)-1,3-dihydrospiro[indene-2,4'-piperidin]-1-amine

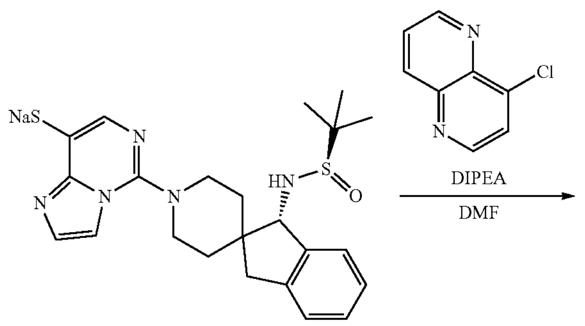

N18

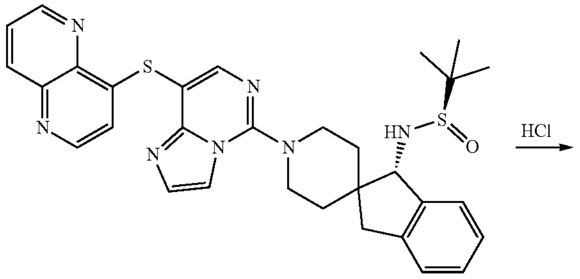

E144a

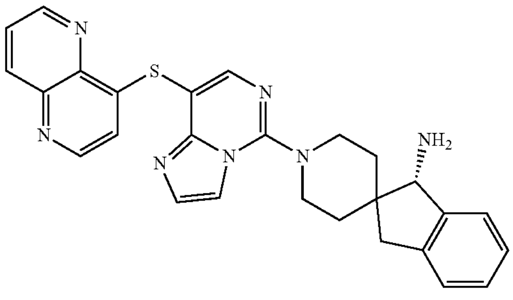

Example 144

Compound E144a: The compound was prepared in a similar manner to Compound 88a using Compound N18 and 4-chloro-1,5-naphthyridine.

Example 144: The compound was prepared in a manner similar to Example 85 using Compound E144a as the starting material. $^{1}$H NMR (400 MHz, Methanol-$d_4$) δ 9.10 (dd, J=4.2, 1.6 Hz, 1H), 8.62 (d, J=5.2 Hz, 1H), 8.52-8.38 (m, 2H), 8.10 (d, J=2.1 Hz, 1H), 7.97 (dd, J=8.6, 4.2 Hz, 1H), 7.86 (d, J=2.1 Hz, 1H), 7.57 (d, J=7.4 Hz, 1H), 7.46 (dd, J=4.0, 1.6 Hz, 2H), 7.39 (ddd, J=8.3, 5.5, 3.1 Hz, 1H), 7.18 (d, J=5.1 Hz, 1H), 4.53 (s, 1H), 4.28 (d, J=13.8 Hz, 1H), 4.18 (d, J=14.0 Hz, 1H), 3.79-3.55 (m, 2H), 3.29 (s, 2H), 2.22 (td, J=12.3, 11.4, 4.0 Hz, 1H), 2.12-1.99 (m, 1H), 1.98-1.88 (m, 1H), 1.79 (d, J=13.8 Hz, 1H). (LCMS): ESI$^{+}$ m/z Calc'd for $C_{27}H_{25}N_7S$ [M+H$^{+}$]: 480.2; Found: 480.2 [M+H$^{+}$].

Example 145: (3S,4S)-3-methyl-8-(8-(quinolin-4-ylthio)imidazo[1,2-c]pyrimidin-5-yl)-2-oxa-8-azaspiro[4.5]decan-4-amine

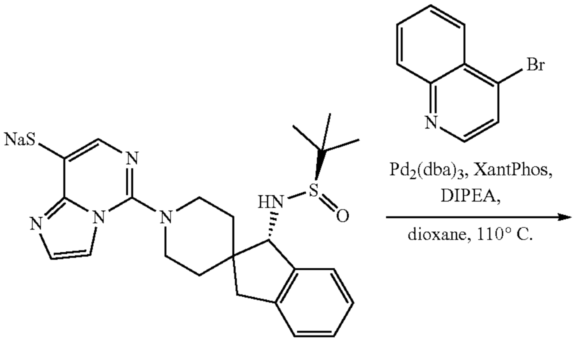

N18

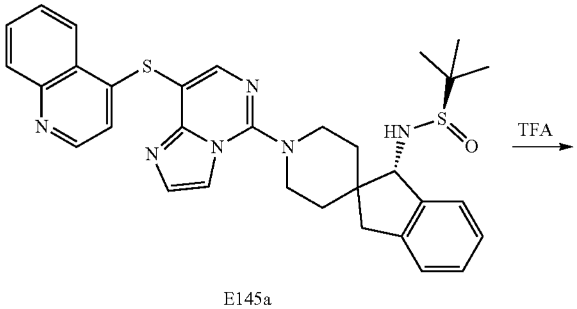

E145a

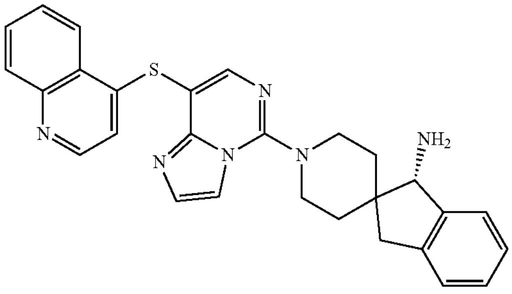

Example 145

Compound E145a: Compound N18 (25 mg, 0.052 mmol) in 1,4-dioxane (2 ml) was added $Pd_2(dba)_3$ (2 mg, 0.003 mmol), XantPhos (3 mg, 0.005 mmol), 4-bromoquinoline (16 mg, 0.079 mmol), and DIPEA (27 μL, 0.16 mmol). The reaction vessel was degassed with argon, sealed, and heated to 110° C. overnight. The reaction mixture was then cooled to room temperature, filtered through Celite®, and concentrated. The resulting residue was concentrated, diluted with 1:1 acetonitrile and water each containing 0.1% TFA and purified on preparatory HPLC (0 to 100% acetonitrile in water each containing 0.1% TFA). This provided Compound E145a as a TFA salt.

Example 145: Compound E145a was mixed with TFA (2 ml). After 4 h, the mixture was concentrated on rotovap, diluted with 1:1 acetonitrile and water each containing 0.1% TFA and purified on preparatory HPLC (0 to 100% acetonitrile in water each containing 0.1% TFA). This provided Example 145 as a TFA salt. $^{1}$H NMR (400 MHz, Methanol-$d_4$) δ 8.84 (s, 1H), 8.70 (d, J=8.5 Hz, 1H), 8.62 (s, 1H), 8.31-8.23 (m, 3H), 8.12 (ddd, J=8.4, 5.7, 2.6 Hz, 1H), 8.01 (d, J=2.0 Hz, 1H), 7.78 (s, 1H), 7.57 (d, J=7.4 Hz, 1H), 7.49-7.35 (m, 3H), 4.55 (s, 1H), 4.46 (d, J=13.9 Hz, 1H), 4.35 (d, J=13.4 Hz, 1H), 3.85-3.56 (m, 4H), 2.27 (t, J=12.1 Hz, 1H), 2.18-2.07 (m, 1H), 1.93 (d, J=13.4 Hz, 1H), 1.80 (d, J=13.5 Hz, 1H). LCMS ESI+ calc'd for $C_{28}H_{26}N_6S$: 479.2 [M+H+]. found: 479.2 [M+H+].

Example 146: (S)-1'-(8-((2,3-dichlorophenyl)thio)imidazo[1,2-c]pyrimidin-5-yl)-5,7-dihydrospiro[cyclopenta[b]pyridine-6,4'-piperidin]-5-amine

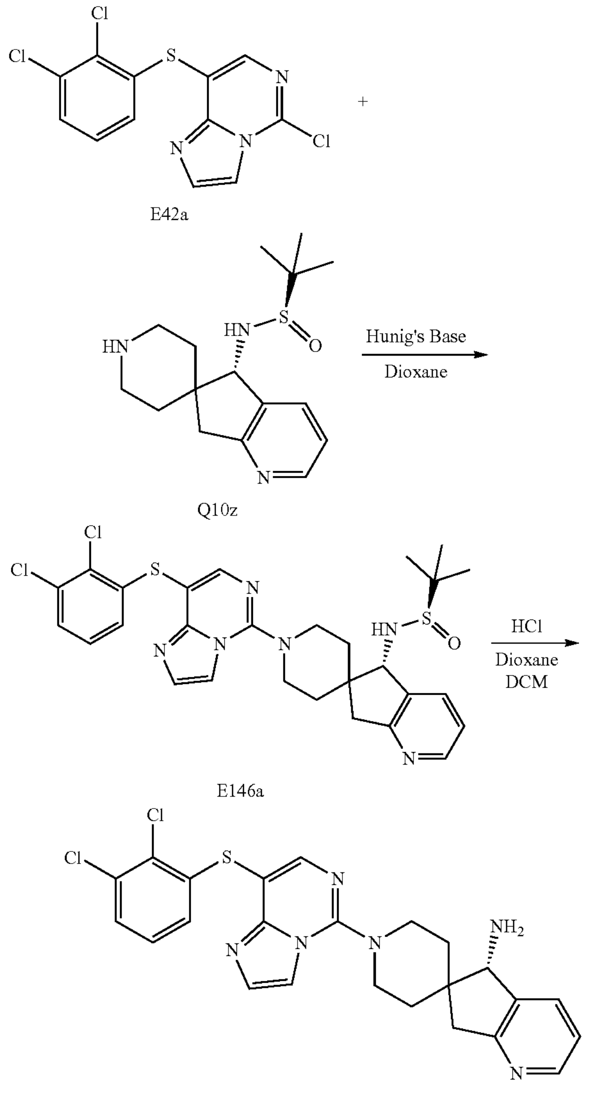

E42a
Q10z
E146a
Example 146

Example 146: A flask was charged with Hunig's Base (0.5 mL) and Compound Q10z (93 mg). Dioxane (3 mL) was added. The resulting solution was added in one portion to Compound E42a (100 mg) at 23° C. More Compound Q10z (60 mg) was added, and the reaction was heated to 80° C. The reaction was stirred for 1 h, then cooled to 23° C. The reaction was filtered giving a solution of Compound E146a. This filtrate was concentrated, then treated with DCM (5 mL) followed by HCl (4.0 M in dioxane, 3 mL). After 15 min, the reaction was concentrated under reduced pressure. The residue was treated with $CH_3CN$ and $H_2O$. The solution was purified on a C18 column via reversed-phase HPLC (0.1% TFA in $H_2O/CH_3CN$ with gradient elution 95:5 to 0:100) giving Example 146. $^1H$ NMR (400 MHz, $CD_3CN$) δ 8.59 (dd, J=5.1, 1.5 Hz, 1H), 8.20 (s, 1H), 8.09 (d, J=7.7 Hz, 1H), 7.72 (d, J=1.9 Hz, 1H), 7.61 (d, J=1.9 Hz, 1H), 7.40 (dd, J=7.8, 5.1 Hz, 1H), 7.34 (dd, J=8.0, 1.4 Hz, 1H), 7.05 (t, J=8.1 Hz, 1H), 6.77 (dd, J=8.1, 1.4 Hz, 1H), 4.64 (s, 1H), 4.09 (d, J=14.0 Hz, 1H), 3.99 (d, J=14.1 Hz, 1H), 3.54-3.21 (m, 4H), 2.22-1.60 (m, 4H). (LCMS): ESI+ m/z Calc'd for $C_{24}H_{22}Cl_2N_6S$ [M+H+]: 497.1. found: 497.2 [M+H+].

Example 147: (S)-1'-(8-((2-amino-3-chloropyridin-4-yl)thio)imidazo[1,2-c]pyrimidin-5-yl)-5,7-dihydrospiro[cyclopenta[b]pyridine-6,4'-piperidin]-5-amine

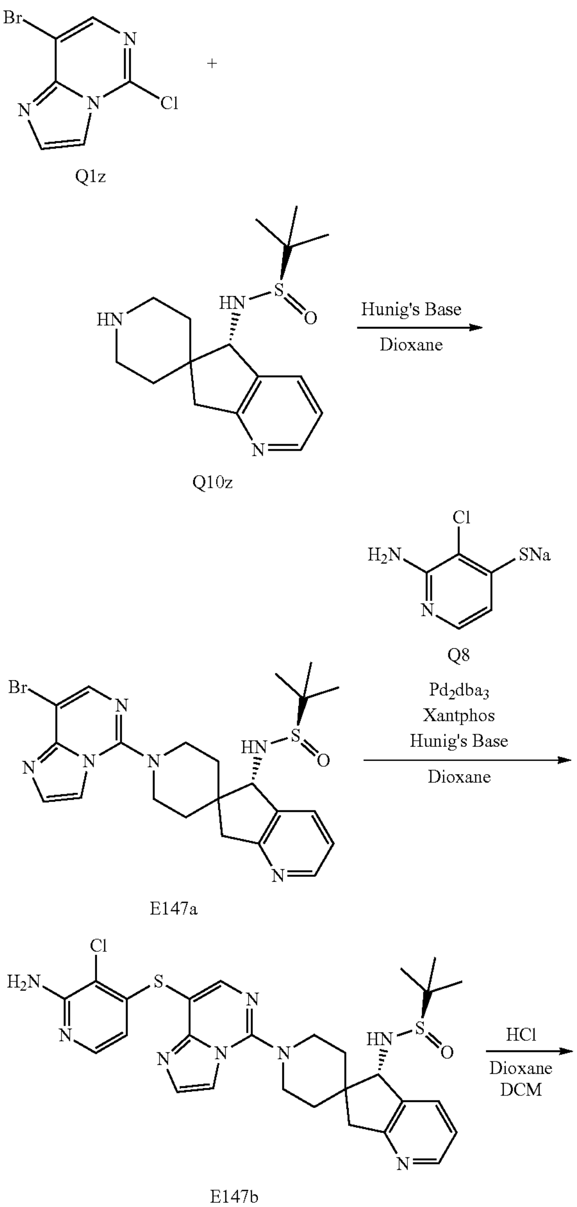

Q1z
Q10z
Q8
E147a
E147b

-continued

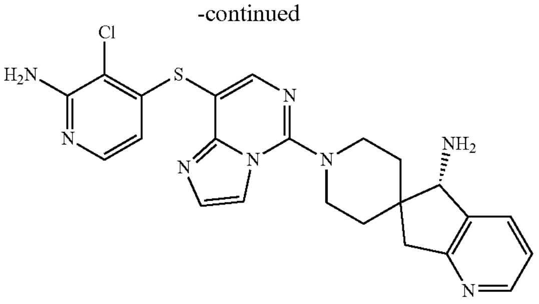

Example 147

Example 147: A flask was charged with Hunig's Base (1.0 mL) Compound Q10z (661 mg) along with dioxane (6 mL). This solution was added to Compound Q1z (500 mg) at 23° C. Completion of this reaction provided a solution of Compound E147a (LCMS): $ESI^+$ m/z Calc'd for $C_{22}H_{27}BrN_6OS$ [$M+H^+$]: 503.1, 505.1. found: 503.2, 505.1 [$M+H^+$] that was used in the next reaction below without further purification. A vessel was charged with Compound Q8 (392 mg), Xantphos (700 mg), and $Pd_2dba_3$ (490 mg). The system was placed under vacuum. The solution of Compound E147a from immediately before was treated with more Hunig's Base (1.0 mL) and dioxane (4 mL); this new solution was added to the vessel, and the reaction was placed under argon. The reaction was heated with stirring to 120° C. for 1 h then cooled to 23° C. EtOAc (50 mL) and $H_2O$ (20 mL) were added, and the resulting mixture was filtered. The filtrate was allowed to stand for several hours at 23° C., and more precipitate developed. Additional EtOAc was added to the point of solution of the precipitate. The organic phase was collected and concentrated giving a solution of Compound E147b (LCMS): $ESI^+$ m/z Calc'd for $C_{27}H_{31}ClN_8OS_2$ [$M+H^+$]: 583.2, 585.2. found: 583.1, 585.1 [$M+H^+$]. This material was treated with DCM (15 mL) followed by HCl (4.0 M in dioxane, 10 mL). $H_2O$ (200 μL) was added. After 15 min, the reaction was concentrated under reduced pressure. The residue was treated with $CH_3CN$ and $H_2O$. The solution was purified on a C18 column via reversed-phase HPLC (0.1% TFA in $H_2O/CH_3CN$ with gradient elution 95:5 to 0:100) giving Example 147. $^1H$ NMR (400 MHz, Methanol-$d_4$) δ 8.57 (dd, J=5.1, 1.6 Hz, 1H), 8.19 (s, 1H), 7.99 (dt, J=7.6, 1.3 Hz, 1H), 7.92 (d, J=1.8 Hz, 1H), 7.66 (d, J=1.7 Hz, 1H), 7.48 (d, J=6.9 Hz, 1H), 7.42 (dd, J=7.8, 5.1 Hz, 1H), 6.26 (d, J=6.8 Hz, 1H), 4.60 (s, 1H), 4.19 (d, J=13.8 Hz, 1H), 4.09 (d, J=14.2 Hz, 1H), 3.67-3.36 (m, 2H), 3.36-3.20 (m, 2H), 2.23-2.07 (m, 1H), 2.01 (d, J=6.3 Hz, 1H), 1.87 (d, J=13.2 Hz, 1H), 1.73 (d, J=13.6 Hz, 1H). (LCMS): $ESI^+$ m/z Calc'd for $C_{23}H_{23}ClN_8S$ [$M+H^+$]: 479.2, 481.2. found: 479.2, 481.1 [$M+H^+$].

Example 148: (R)-1'-(8-((2,3-dichlorophenyl)thio)imidazo[1,2-c]pyrimidin-5-yl)-5,7-dihydrospiro[cyclopenta[b]pyridine-6,4'-piperidin]-5-amine

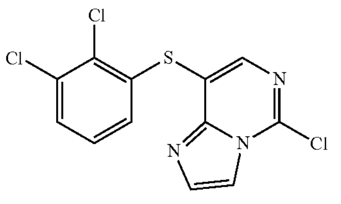

E42a

+

-continued

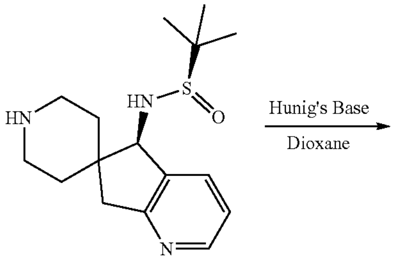

Q10y

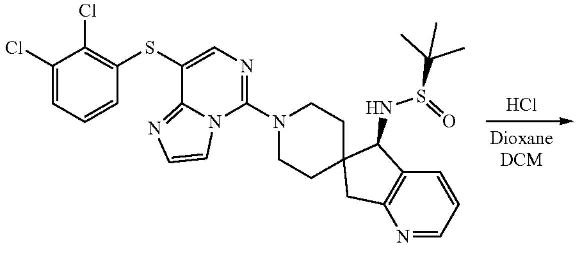

E148a

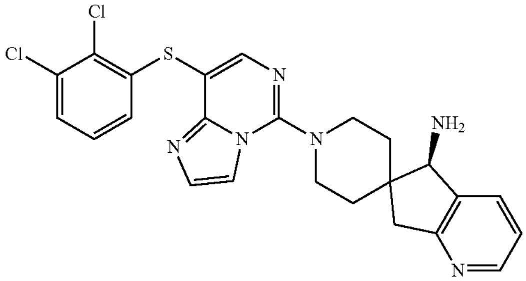

Example 148

Example 148: The compound was prepared in a manner similar to Example 146 using Compound Q10y as the starting material instead of Compound Q10z, giving Example 148. $^1H$ NMR (400 MHz, $CD_3CN$) δ 8.61 (dd, J=5.3, 1.4 Hz, 1H), 8.27 (s, 1H), 8.18 (d, J=7.9 Hz, 1H), 7.75 (d, J=2.0 Hz, 1H), 7.63 (d, J=2.0 Hz, 1H), 7.48 (dd, J=7.8, 5.3 Hz, 1H), 7.35 (dd, J=8.0, 1.3 Hz, 1H), 7.07 (t, J=8.1 Hz, 1H), 6.78 (dd, J=8.1, 1.4 Hz, 1H), 4.67 (s, 1H), 4.13 (d, J=14.1 Hz, 1H), 4.03 (d, J=14.1 Hz, 1H), 3.59-3.23 (m, 4H), 2.28-1.97 (m, 2H), 1.92-1.67 (m, 2H). LCMS $ESI^+$ calc'd for $C_{24}H_{22}Cl_2N_6S$ [$M+H^+$]: 497.1. found: 497.2 [$M+H^+$].

Example 149: (R)-1'-(8-((2-amino-3-chloropyridin-4-yl)thio)imidazo[1,2-c]pyrimidin-5-yl)-5,7-dihydrospiro[cyclopenta[b]pyridine-6,4'-piperidin]-5-amine

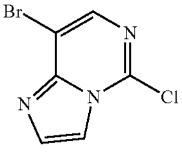

+

Q1z

-continued

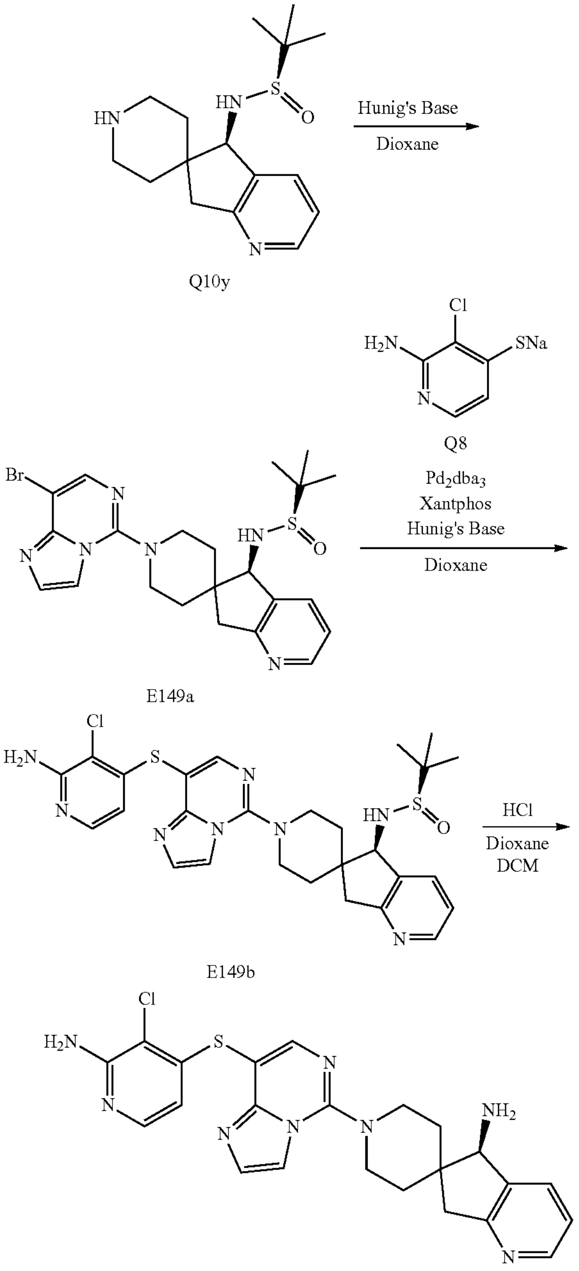

Q10y

Q8

E149a

E149b

Example 149

Example 149: The compound was prepared in a manner similar to Example 147 using Compound Q10y as the starting material instead of Compound Q10z, giving Example 149. $^1H$ NMR (400 MHz, $CD_3CN$) δ 8.61 (dd, J=5.1, 1.5 Hz, 1H), 8.27 (s, 1H), 8.07 (dd, J=7.8, 1.4 Hz, 1H), 7.99 (d, J=1.9 Hz, 1H), 7.75 (d, J=1.8 Hz, 1H), 7.53 (d, J=7.0 Hz, 1H), 7.48 (dd, J=7.8, 5.2 Hz, 1H), 6.33 (d, J=6.9 Hz, 1H), 4.65 (s, 1H), 4.38-4.02 (m, 2H), 3.70-3.48 (m, 2H), 3.44-3.31 (m, 2H), 2.24-2.12 (m, 1H), 2.13-1.99 (m, 1H), 1.91 (d, J=13.4 Hz, 1H), 1.78 (d, J=13.6 Hz, 1H). LCMS $ESI^+$ calc'd for $C_{23}H_{23}ClN_8S$ $[M+H^+]$: 479.2; Found: 479.2 $[M+H^+]$.

SHP-2 Biochemical Assay

Materials

Recombinant SHP-2 full length protein was generated in house. SHP-2 protein tyrosine phosphatase (PTP) domain protein (Catalog number SPR0217-20 ug), NaCl (Catalog number S6546-1L), and KCl (Catalog number 60142-500 mL) were purchased from Sigma-Aldrich (St. Louis, Mo.). IRS-1_pY1172(dPEG8)pY1222 peptide (H2N-LN(pY)IDLDLV-(dPEG8)LST(pY)ASINFQK-amide) was custom made by AnaSpec (Fremont, Calif.). DiFMUP substrate (Catalog number D6567), EDTA (Catalog number E177-500 mL), DTT (Catalog number P2325), and 384-well black polystyrene non-binding surface (Catalog number 3820) were purchased from Fisher Scientific (Hanover Park, Ill.). HEPES (Catalog number 15630-080) was purchased from Life Technologies (Pleasanton, Calif.), and Tween-20 (Catalog number 95059-250) was purchased from VWR (Radnor, Pa.).

Method

Inhibition of SHP-2 activity by small molecule inhibitors was monitored by a biochemical DiFMUP pseudosubstrate-fluorogenic assay. SHP-2 enzyme at final concentration of 0.2 nM was incubated with an IRS-1 activator peptide at a final concentration of 1 μM in SHP-2 assay buffer (60 mM HEPES, pH 7.2-7.5, 0.05% Tween-20, 75 mM NaCl, 75 mM KCl, 1 mM EDTA, and 5 mM DTT) for 75 min at room temperature. The reaction mix was added to the 384-well non-binding plate which had been pre-spotted with 1:3 serial diluted compounds from 10,000-0.005 nM, and incubated at room temperature for 90 min. DiFMUP substrate at final concentration of 50 μM was then added to the wells and incubated for additional 30 min at room temperature. The final reaction volume was 20 μl/well. The fluorescence intensity of the reaction product was measured by Envision at excitation and emission wavelengths of 340 nm and 450 nm, respectively. The inhibitor dose response curves were generated using normalized $IC_{50}$ regression curve fitting by in house dose response analysis tools. The wells with DMSO vehicle were used as controls (100% signal). The percent (%) control of SHP-2 compound was calculated as: (Compound well fluorescence counts/DMSO fluorescence counts)×100%.

SHP-2 Cell Based Assay: NCI-H358 3D Tumor Spheroid Growth Inhibition Protocol

Materials

NCI-H358 cell line was purchased from ATCC (Catalog number ATCC CRL-5807) (Manassas, Va.). RPMI-1640 (Catalog number 10-040-CM) was from Corning Cellgro (Manassas, Va.), Fetal Bovine Serum (FBS) (Catalog number SH30071.03) was from HyClone (Logan, Utanh), and 100× Penicillin/Streptomycin/L-Glutamine stock (Catalog no. 30-009-CI) and 384-well ULA plates (Catalog number 3830) were from Corning (Fremont, Calif.).

Method

NCI-H358 cells were culture in RPMI-1640 with 10% FBS supplemented with 1× mixture of Penicillin, Streptomycin, and L-Glutamine. At the day of assay, the cells were trypsinized and seeded at 1000 cells/70 μl/well in 384-well ULA plates and incubated at 37° C. incubator with 5% $CO_2$ to allow spheroids to form. After 18 hours incubation, 35 μl medium was gently removed from each well followed by the addition of 35 μl of medium containing a 1:3 serial diluted SHP-2 compounds at final concentration range of 1.9-12,500 nM. The plates were incubated for additional 7 days. Then 35 μl of medium from each well was removed, and replaced with 35 μl of 3D CellTiter Glo reagent from Promega. The wells were mixed by pipetting up and down with Biomek FX for 15 times to induce cell lysis and the plates were incubated at room temperature for additional 10 min to stabilize luminescent signal. The luminescence was then read by Envision. The inhibitor dose response curves were generated using normalized cellular $IC_{50}$ (designated as $EC_{50}$ in all FIGURES to distinguish from biochemical $IC_{50}$s) by in house dose response analyses tools. The wells with DMSO vehicle were used as negative controls (0% inhibition). The % inhibition of SHP-2 compounds was calculated as: 100−[(Compound well luminescence counts/DMSO luminescence counts)×100%].

TABLE 1

| Example | Structure | Name | SHP2 $IC_{50}$ (nM) | H358 $EC_{50}$ (nM) |
|---|---|---|---|---|
| 1 | 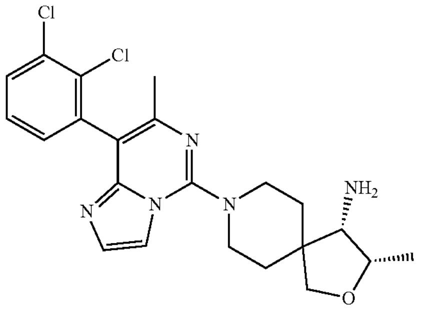 [SMILES: Cc1nc(N2CCC3(CC2)CO[C@@H](C)[C@H]3N)n2ccnc2c1-c1cccc(Cl)c1Cl] | (3S,4S)-8-(8-(2,3-dichlorophenyl)-7-methylimidazo[1,2-c]pyrimidin-5-yl)-3-methyl-2-oxa-8-azaspiro[4.5]decan-4-amine | 2.8 | 59 |
| 2 | 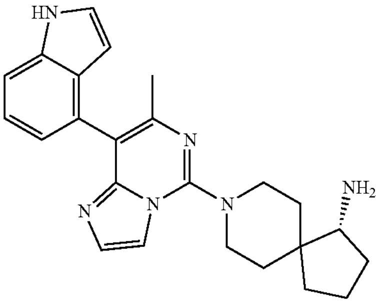 [SMILES: Cc1nc(N2CCC3(CCC[C@H]3N)CC2)n2ccnc2c1-c1cccc2[nH]ccc12] | (R)-8-(8-(1H-indol-4-yl)-7-methylimidazo[1,2-c]pyrimidin-5-yl)-8-azaspiro[4.5]decan-1-amine | 47 | 590 |
| 3 | 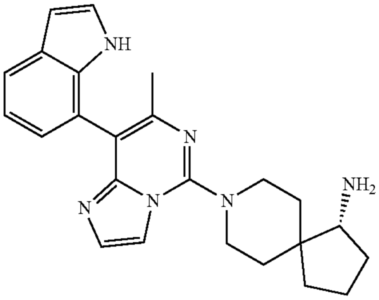 [SMILES: Cc1nc(N2CCC3(CCC[C@H]3N)CC2)n2ccnc2c1-c1cccc2cc[nH]c12] | (R)-8-(8-(1H-indol-7-yl)-7-methylimidazo[1,2-c]pyrimidin-5-yl)-8-azaspiro[4.5] decan-1-amine | 86 | |
| 4 | 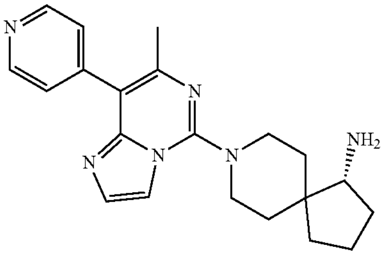 [SMILES: Cc1nc(N2CCC3(CCC[C@H]3N)CC2)n2ccnc2c1-c1ccncc1] | (R)-8-(7-methyl-8-(pyridin-4-yl)imidazo[1,2-c] pyrimidin-5-yl)-8-azaspiro[4.5] decan-1-amine | 1800 | |
| 5 | 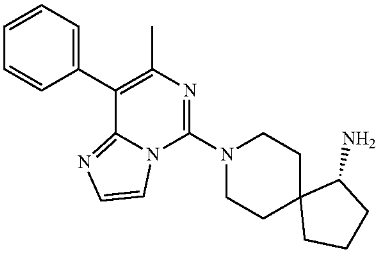 [SMILES: Cc1nc(N2CCC3(CCC[C@H]3N)CC2)n2ccnc2c1-c1ccccc1] | (R)-8-(7-methyl-8-phenylimidazo[1,2-c]pyrimidin-5-yl)-8-azaspiro[4.5] decan-1-amine | 90 | 670 |

TABLE 1-continued

| Example | Structure | Name | SHP2 $IC_{50}$ (nM) | H358 $EC_{50}$ (nM) |
|---|---|---|---|---|
| 6 | 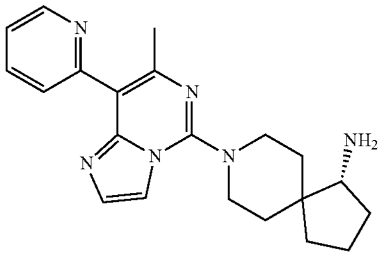 [SMILES: Cc1nc(N2CCC3(CCC[C@H]3N)CC2)n2ccnc2c1-c1ccccn1] | (R)-8-(7-methyl-8-(pyridin-2-yl)imidazo[1,2-c]pyrimidin-5-yl)-8-azaspiro[4.5] decan-1-amine | 5400 | |
| 7 | 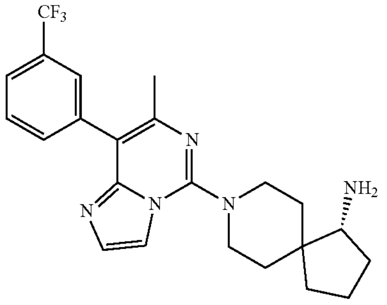 [SMILES: Cc1nc(N2CCC3(CCC[C@H]3N)CC2)n2ccnc2c1-c1cccc(C(F)(F)F)c1] | (R)-8-(7-methyl-8-(3-(trifluoromethyl) phenyl)imidazo[1,2-c]pyrimidin-5-yl)-8-azaspiro[4.5] decan-1-amine | 1300 | >12500 |
| 8 | 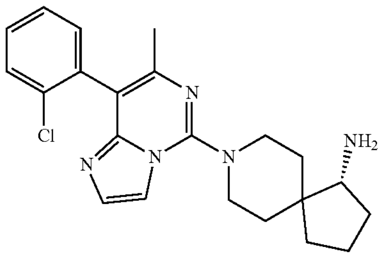 [SMILES: Cc1nc(N2CCC3(CCC[C@H]3N)CC2)n2ccnc2c1-c1ccccc1Cl] | (R)-8-(8-(2-chlorophenyl)-7-methylimidazo[1,2-c]pyrimidin-5-yl)-8-azaspiro[4.5] decan-1-amine | 26 | |
| 9 | 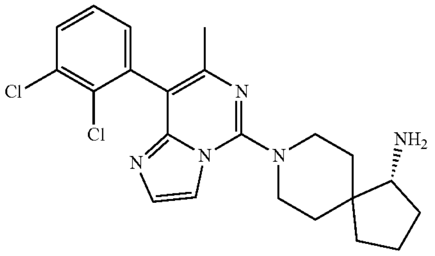 [SMILES: Cc1nc(N2CCC3(CCC[C@H]3N)CC2)n2ccnc2c1-c1cccc(Cl)c1Cl] | (R)-8-(8-(2,3-dichlorophenyl)-7-methylimidazo[1,2-c]pyrimidin-5-yl)-8-azaspiro[4.5]decan-1-amine | 4.1 | 120 |
| 10 | 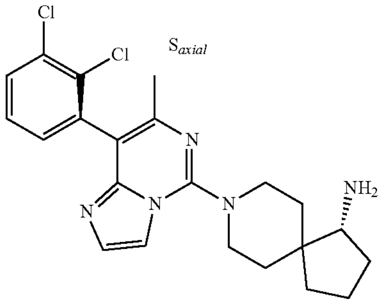 | ($S_{axial}$,R)-8-(8-(2,3-dichlorophenyl)-7-methylimidazo[1,2-c]pyrimidin-5-yl)-8-azaspiro[4.5]decan-1-amine | 52 | 970 |

TABLE 1-continued

| Example | Structure | Name | SHP2 $IC_{50}$ (nM) | H358 $EC_{50}$ (nM) |
|---|---|---|---|---|
| 11 | 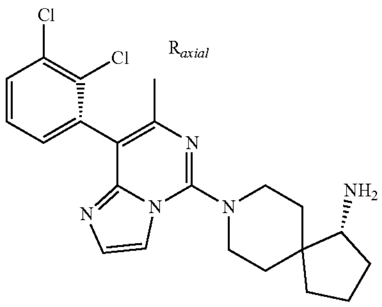 | ($R_{axial}$,R)-8-(8-(2,3-dichlorophenyl)-7-methylimidazo[1,2-c]pyrimidin-5-yl)-8-azaspiro[4.5]decan-1-amine | 3.6 | 60 |
| 12 | 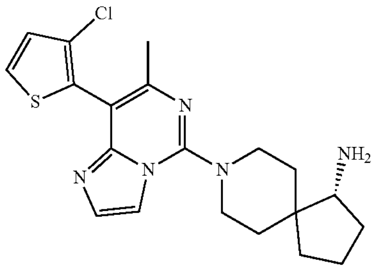 [SMILES: Cc1nc(N2CCC3(CCC[C@H]3N)CC2)n2ccnc2c1-c1sccc1Cl] | (R)-8-(8-(3-chlorothiophen-2-yl)-7-methylimidazo[1,2-c]pyrimidin-5-yl)-8-azaspiro[4.5]decan-1-amine | 90 | 420 |
| 13 | 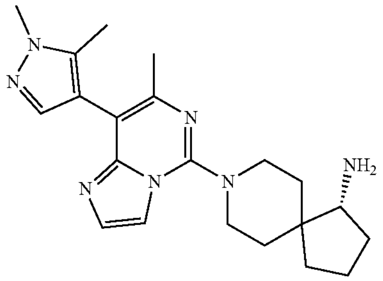 [SMILES: Cc1nc(N2CCC3(CCC[C@H]3N)CC2)n2ccnc2c1-c1cnn(C)c1C] | (R)-8-(8-(1,5-dimethyl-1H-pyrazol-4-yl)-7-methylimidazo[1,2-c]pyrimidin-5-yl)-8-azaspiro[4.5]decan-1-amine | 1000 | 3300 |
| 14 | 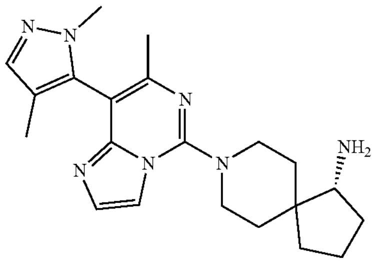 [SMILES: Cc1cnn(C)c1-c1c(C)nc(N2CCC3(CCC[C@H]3N)CC2)n2ccnc12] | (R)-8-(8-(1,4-dimethyl-1H-pyrazol-5-yl)-7-methylimidazo[1,2-c]pyrimidin-5-yl)-8-azaspiro[4.5]decan-1-amine | >10000 | |
| 15 | 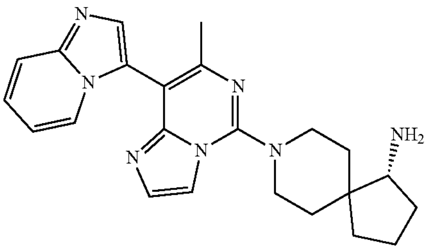 [SMILES: Cc1nc(N2CCC3(CCC[C@H]3N)CC2)n2ccnc2c1-c1cnc2ccccn12] | (R)-8-(8-(imidazo[1,2-a]pyridin-3-yl)-7-methylimidazo[1,2-c]pyrimidin-5-yl)-8-azaspiro[4.5]decan-1-amine | 350 | 3200 |

TABLE 1-continued

| Example | Structure | Name | SHP2 $IC_{50}$ (nM) | H358 $EC_{50}$ (nM) |
|---|---|---|---|---|
| 16 | 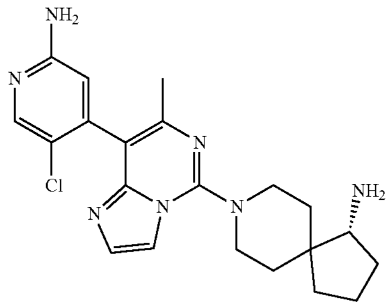 [SMILES: Cc1nc(N2CCC3(CCC[C@H]3N)CC2)n2ccnc2c1-c1cc(N)ncc1Cl] | (R)-8-(8-(2-amino-5-chloropyridin-4-yl)-7-methylimidazo[1,2-c]pyrimidin-5-yl)-8-azaspiro[4.5]decan-1-amine | 570 | |
| 17 | 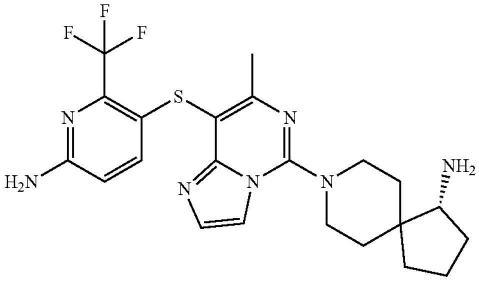 [SMILES: Cc1nc(N2CCC3(CCC[C@H]3N)CC2)n2ccnc2c1Sc1ccc(N)nc1C(F)(F)F] | (R)-8-(8-((6-amino-2-(trifluoromethyl) pyridin-3-yl)thio)-7-methylimidazo[1,2-c]pyrimidin-5-yl)-8-azaspiro[4.5]decan-1-amine | 9.9 | |
| 18 | 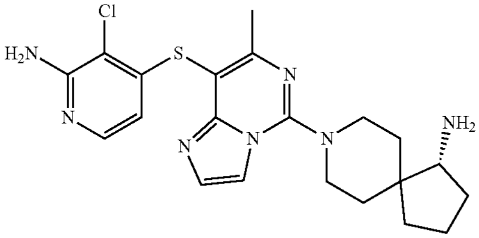 [SMILES: Cc1nc(N2CCC3(CCC[C@H]3N)CC2)n2ccnc2c1Sc1ccnc(N)c1Cl] | (R)-8-(8-((2-amino-3-chloropyridin-4-yl)thio)-7-methylimidazo[1,2-c]pyrimidin-5-yl)-8-azaspiro[4.5]decan-1-amine | 5.6 | 75 |
| 19 | 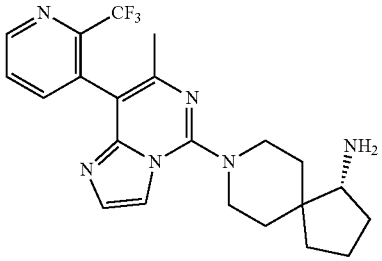 [SMILES: Cc1nc(N2CCC3(CCC[C@H]3N)CC2)n2ccnc2c1-c1cccnc1C(F)(F)F] | (R)-8-(7-methyl-8-(2-(trifluoromethyl) pyridin-3-yl)imidazo[1,2-c]pyrimidin-5-yl)-8-azaspiro[4.5]decan-1-amine | >10000 | |
| 20 | 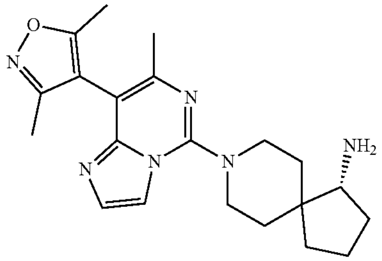 [SMILES: Cc1noc(C)c1-c1c(C)nc(N2CCC3(CCC[C@H]3N)CC2)n2ccnc12] | (R)-8-(8-(3,5-dimethylisoxazol-4-yl)-7-ethylimidazo[1,2-c]pyrimidin-5-yl)-8-azaspiro[4.5]decan-1-amine | >10000 | |

TABLE 1-continued

| Example | Structure | Name | SHP2 $IC_{50}$ (nM) | H358 $EC_{50}$ (nM) |
|---|---|---|---|---|
| 21 | 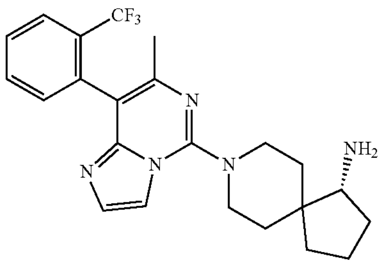 [SMILES: Cc1nc(N2CCC3(CCC[C@H]3N)CC2)n2ccnc2c1-c1ccccc1C(F)(F)F] | (R)-8-(7-methyl-8-(2-(trifluoromethyl) phenyl) imidazo[1,2-c]pyrimidin-5-yl)-8-azaspiro[4.5]decan-1-amine | >10000 | |
| 22 | 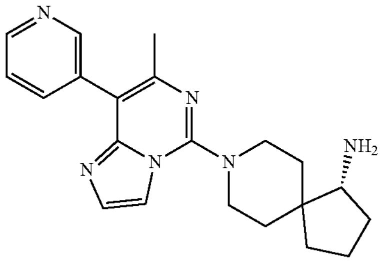 [SMILES: Cc1nc(N2CCC3(CCC[C@H]3N)CC2)n2ccnc2c1-c1cccnc1] | (R)-8-(7-methyl-8-(pyridin-3-yl)imidazo[1,2-c]pyrimidin-5-yl)-8-azaspiro[4.5]decan-1-amine | 1700 | |
| 23 | 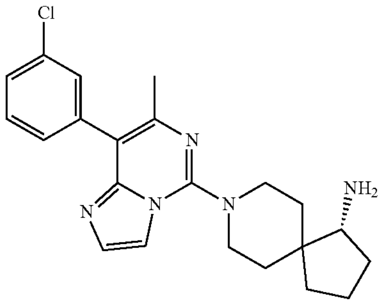 [SMILES: Cc1nc(N2CCC3(CCC[C@H]3N)CC2)n2ccnc2c1-c1cccc(Cl)c1] | (R)-8-(8-(3-chlorophenyl)-7-methylimidazo[1,2-c]pyrimidin-5-yl)-8-azaspiro[4.5]decan-1-amine | 160 | 1500 |
| 24 | 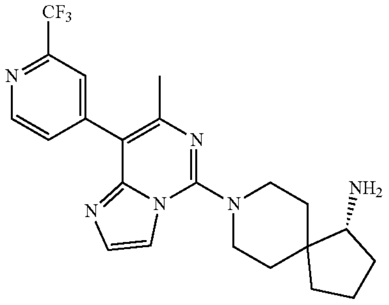 [SMILES: Cc1nc(N2CCC3(CCC[C@H]3N)CC2)n2ccnc2c1-c1ccnc(C(F)(F)F)c1] | (R)-8-(7-methyl-8-(2-(trifluoromethyl) pyridin-4-yl)imidazo[1,2-c]pyrimidin-5-yl)-8-azaspiro[4.5]decan-1-amine | >10000 | |
| 25 | 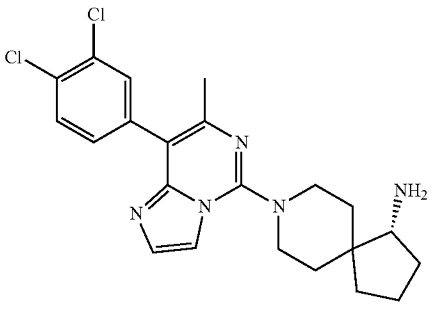 [SMILES: Cc1nc(N2CCC3(CCC[C@H]3N)CC2)n2ccnc2c1-c1ccc(Cl)c(Cl)c1] | (R)-8-(8-(3,4-dichlorophenyl)-7-methylimidazo[1,2-c]pyrimidin-5-yl)-8-azaspiro[4.5]decan-1-amine | 95 | 1500 |

TABLE 1-continued

| Example | Structure | Name | SHP2 $IC_{50}$ (nM) | H358 $EC_{50}$ (nM) |
|---|---|---|---|---|
| 26 | 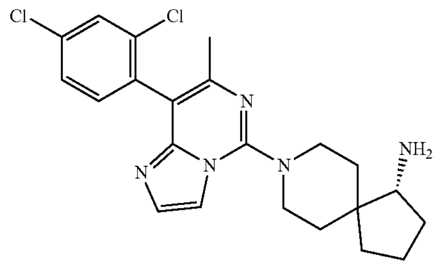 [SMILES: Cc1nc(N2CCC3(CCC[C@H]3N)CC2)n2ccnc2c1-c1ccc(Cl)cc1Cl] | (R)-8-(8-(2,4-dichlorophenyl)-7-methylimidazo[1,2-c]pyrimidin-5-yl)-8-azaspiro[4.5]decan-1-amine | 25 | 360 |
| 27 | 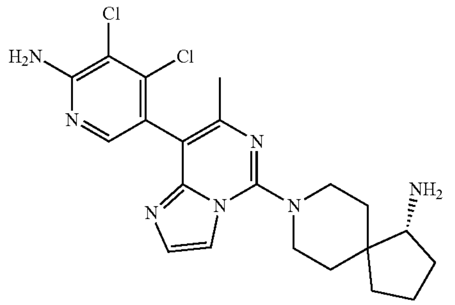 [SMILES: Cc1nc(N2CCC3(CCC[C@H]3N)CC2)n2ccnc2c1-c1cnc(N)c(Cl)c1Cl] | (R)-8-(8-(4-amino-2,3-dichlorophenyl)-7-methylimidazo[1,2-c]pyrimidin-5-yl)-8-azaspiro[4.5]decan-1-amine | 15 | 180 |
| 28 | 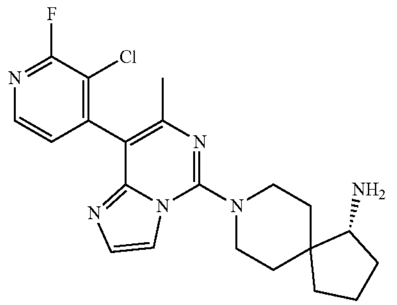 [SMILES: Cc1nc(N2CCC3(CCC[C@H]3N)CC2)n2ccnc2c1-c1ccnc(F)c1Cl] | (R)-8-(8-(3-chloro-2-fluoropyridin-4-yl)-7-methylimidazo[1,2-c]pyrimidin-5-yl)-8-azaspiro[4.5]decan-1-amine | 74 | 380 |
| 29 | 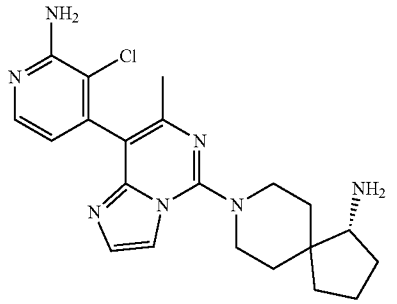 [SMILES: Cc1nc(N2CCC3(CCC[C@H]3N)CC2)n2ccnc2c1-c1ccnc(N)c1Cl] | (R)-8-(8-(2-amino-3-chloropyridin-4-yl)-7-methylimidazo[1,2-c]pyrimidin-5-yl)-8-azaspiro[4.5]decan-1-amine | 1300 | 5500 |
| 30 | 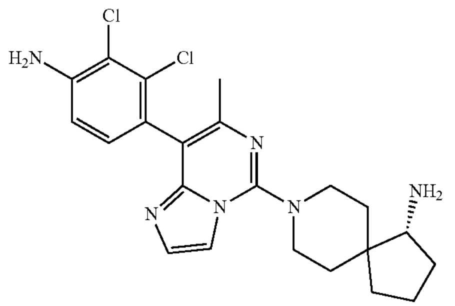 [SMILES: Cc1nc(N2CCC3(CCC[C@H]3N)CC2)n2ccnc2c1-c1ccc(N)c(Cl)c1Cl] | (R)-8-(8-(3-chloro-2-fluoropyridin-4-yl)-7-methylimidazo[1,2-c]pyrimidin-5-yl)-8-azaspiro[4.5]decan-1-amine | 430 | 2100 |

TABLE 1-continued

| Example | Structure | Name | SHP2 $IC_{50}$ (nM) | H358 $EC_{50}$ (nM) |
|---|---|---|---|---|
| 31 | 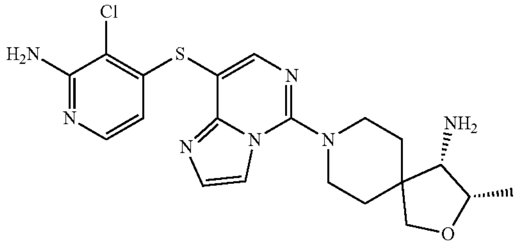 [SMILES: C[C@@H]1OCC2(CCN(c3ncc(Sc4ccnc(N)c4Cl)c4nccn34)CC2)[C@@H]1N] | (3S,4S)-8-(8-((2-amino-3-chloropyridin-4-yl)thio)imidazo[1,2-c]pyrimidin-5-yl)-3-methyl-2-oxa-8-azaspiro[4.5]decan-4-amine | 5.0 | 53 |
| 32 | 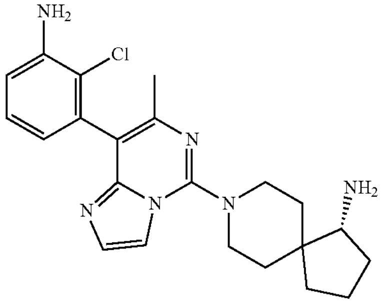 [SMILES: Cc1nc(N2CCC3(CCC[C@H]3N)CC2)n2ccnc2c1-c1cccc(N)c1Cl] | (R)-8-(8-(3-chloro-2-fluoropyridin-4-yl)-7-methylimidazo[1,2-c]pyrimidin-5-yl)-8-azaspiro[4.5]decan-1-amine | 510 | |
| 33 | 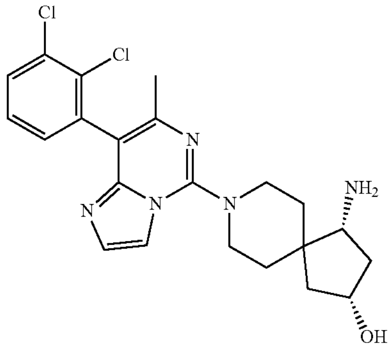 [SMILES: Cc1nc(N2CCC3(CC2)C[C@@H](O)C[C@H]3N)n2ccnc2c1-c1cccc(Cl)c1Cl] | (2R,4R)-4-amino-8-(8-(2,3-dichlorophenyl)-7-methylimidazo[1,2-c]pyrimidin-5-yl)-8-azaspiro[4.5]decan-2-ol | 3.1 | 32 |
| 34 | 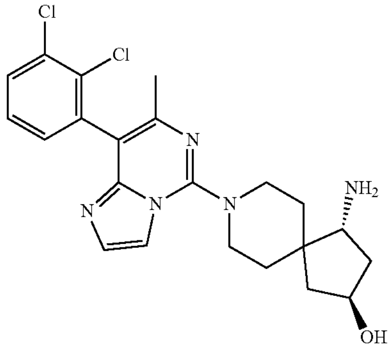 [SMILES: Cc1nc(N2CCC3(CC2)C[C@H](O)C[C@H]3N)n2ccnc2c1-c1cccc(Cl)c1Cl] | (2S,4R)-4-amino-8-(8-(2,3-dichlorophenyl)-7-methylimidazo[1,2-c]pyrimidin-5-yl)-8-azaspiro[4.5]decan-2-ol | 3.3 | |
| 35 | 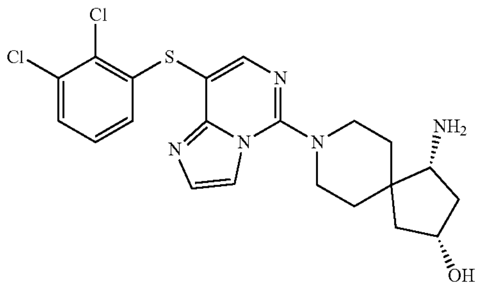 [SMILES: N[C@@H]1C[C@H](O)CC12CCN(c1ncc(Sc3cccc(Cl)c3Cl)c3nccn13)CC2] | (2R,4R)-4-amino-8-(8-((2,3-dichlorophenyl)thio) imidazo[1,2-c]pyrimidin-5-yl)-8-azaspiro[4.5]decan-2-ol | 1.2 | 32 |

TABLE 1-continued

| Example | Structure | Name | SHP2 $IC_{50}$ (nM) | H358 $EC_{50}$ (nM) |
|---|---|---|---|---|
| 36 | 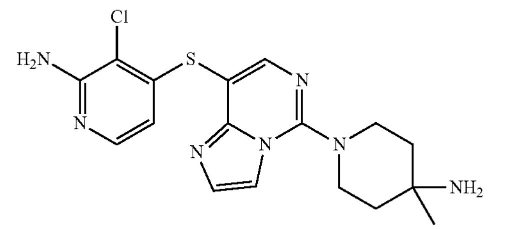 [SMILES: CC1(N)CCN(c2ncc(Sc3ccnc(N)c3Cl)c3nccn23)CC1] | 1-(8-((2,3-dichlorophenyl)thio) imidazo[1,2-c]pyrimidin-5-yl)azepan-4-amine | 280 | >12500 |
| 37 | 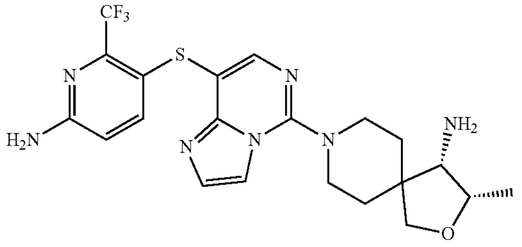 [SMILES: C[C@@H]1OCC2(CCN(c3ncc(Sc4ccc(N)nc4C(F)(F)F)c4nccn34)CC2)[C@@H]1N] | (3S,4S)-8-(8-((6-amino-2-(trifluoromethyl) pyridin-3-yl)thio)imidazo[1,2-c]pyrimidin-5-yl)-3-methyl-2-oxa-8-azaspiro[4.5]decan-4-amine | 17 | |
| 38 | 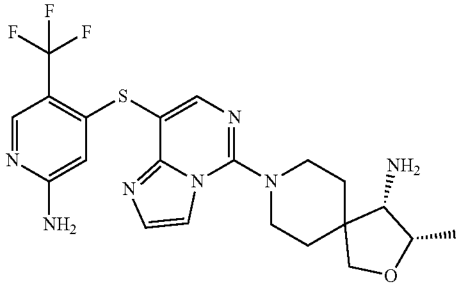 [SMILES: C[C@@H]1OCC2(CCN(c3ncc(Sc4cc(N)ncc4C(F)(F)F)c4nccn34)CC2)[C@@H]1N] | (3S,4S)-8-(8-((2-amino-5-(trifluoromethyl) pyridin-4-yl)thio)imidazo [1,2-c]pyrimidin-5-yl)-3-methyl-2-oxa-8-azaspiro[4.5]decan-4-amine | 5.9 | 59 |
| 39 | 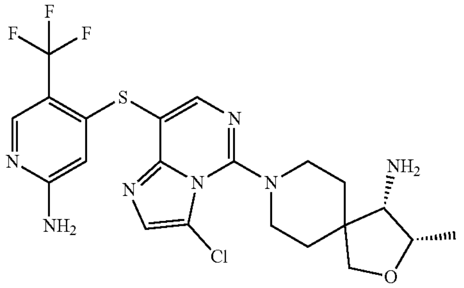 [SMILES: C[C@@H]1OCC2(CCN(c3ncc(Sc4cc(N)ncc4C(F)(F)F)c4ncc(Cl)n34)CC2)[C@@H]1N] | (3S,4S)-8-(8-((2-amino-5-(trifluoromethyl) pyridin-4-yl)thio)imidazo[1,2-c]pyrimidin-5-yl)-3-methyl-2-oxa-8-azaspiro[4.5]decan-4-amine | 76 | 570 |
| 40 | 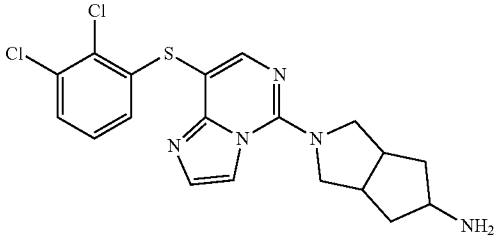 [SMILES: NC1CC2CN(c3ncc(Sc4cccc(Cl)c4Cl)c4nccn34)CC2C1] | 2-(8-((2,3-dichlorophenyl)thio) imidazo[1,2-c]pyrimidin-5-yl)octahydrocyclo penta[c]pyrrol-5-amine | 190 | 3200 |

TABLE 1-continued

| Example | Structure | Name | SHP2 $IC_{50}$ (nM) | H358 $EC_{50}$ (nM) |
|---|---|---|---|---|
| 41 | 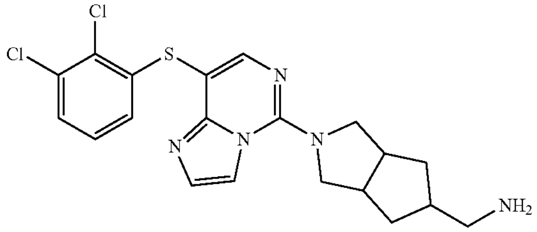 [SMILES: NCC1CC2CN(c3ncc(Sc4cccc(Cl)c4Cl)c4nccn34)CC2C1] | (2-(8-((2,3-dichlorophenyl)thio)imidazo[1,2-c]pyrimidin-5-yl)octahydrocyclopenta[c]pyrrol-5-yl)methanamine | 150 | 3200 |
| 42 | 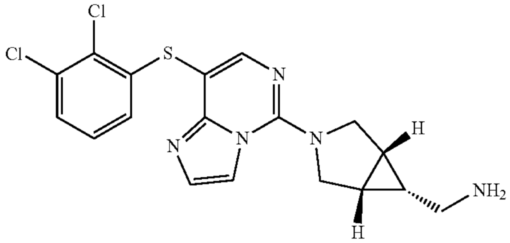 [SMILES: NC[C@H]1[C@H]2CN(c3ncc(Sc4cccc(Cl)c4Cl)c4nccn34)C[C@@H]12] | ((1R,5S,6r)-3-(8-((2,3-dichlorophenyl)thio)imidazo[1,2-c]pyrimidin-5-yl)-3-azabicyclo[3.1.0]hexan-6-yl)methanamine | 80 | 1300 |
| 43 | 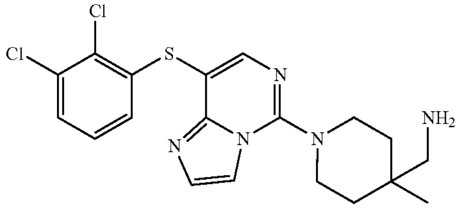 [SMILES: CC1(CN)CCN(c2ncc(Sc3cccc(Cl)c3Cl)c3nccn23)CC1] | (1-(8-((2,3-dichlorophenyl)thio)imidazo[1,2-c]pyrimidin-5-yl)-4-methylpiperidin-4-yl)methanamine | 23 | |
| 44 | 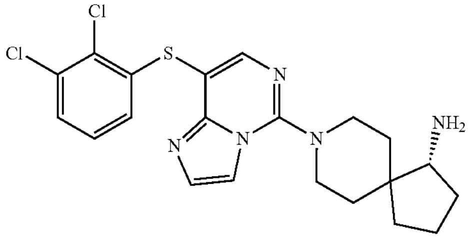 [SMILES: N[C@@H]1CCCC12CCN(c1ncc(Sc3cccc(Cl)c3Cl)c3nccn13)CC2] | (R)-8-(8-((2,3-dichlorophenyl)thio)imidazo[1,2-c]pyrimidin-5-yl)-8-azaspiro[4.5]decan-1-amine | 2.8 | 130 |
| 45 | 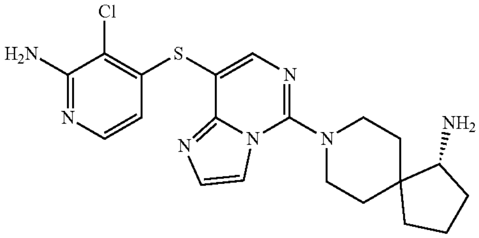 | (R)-8-(8-((2-amino-3-chloropyridin-4-yl)thio)imidazo[1,2-c]pyrimidin-5-yl)-8-azaspiro[4.5]decan-1-amine | 5.6 | 170 |
| 46 | 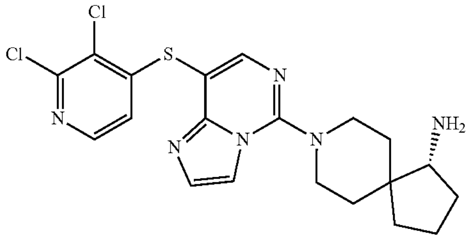 [SMILES: N[C@@H]1CCCC12CCN(c1ncc(Sc3ccnc(Cl)c3Cl)c3nccn13)CC2] | (R)-8-(8-((2,3-dichloropyridin-4-yl)thio)imidazo[1,2-c]pyrimidin-5-yl)-8-azaspiro[4.5]decan-1-amine | 3.1 | 31 |

TABLE 1-continued

| Example | Structure | Name | SHP2 $IC_{50}$ (nM) | H358 $EC_{50}$ (nM) |
|---|---|---|---|---|
| 47 | 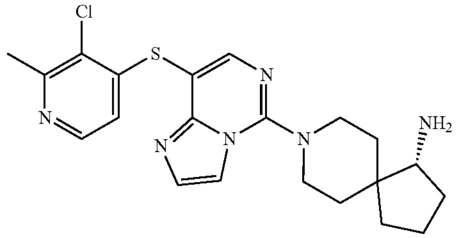 [SMILES: Cc1nccc(Sc2cnc(N3CCC4(CCC[C@H]4N)CC3)n3ccnc23)c1Cl] | (R)-8-(8-((3-chloro-2-methylpyridin-4-yl)thio)imidazo[1,2-c]pyrimidin-5-yl)-8-azaspiro[4.5]decan-1-amine | 7.6 | 150 |
| 48 | 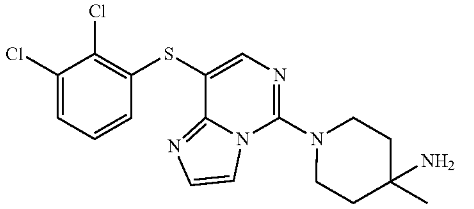 [SMILES: CC1(N)CCN(c2ncc(Sc3cccc(Cl)c3Cl)c3nccn23)CC1] | 1-(8-((2,3-dichlorophenyl)thio) imidazo[1,2-c]pyrimidin-5-yl)-4-methylpiperidin-4-amine | 120 | 1700 |
| 49 | 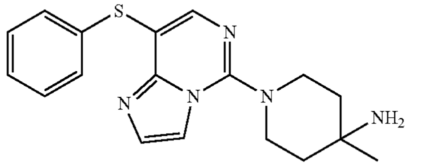 [SMILES: CC1(N)CCN(c2ncc(Sc3ccccc3)c3nccn23)CC1] | 4-methyl-1-(8-(phenylthio) imidazo[1,2-c]pyrimidin-5-yl)piperidin-4-amine | 7200 | |
| 50 | 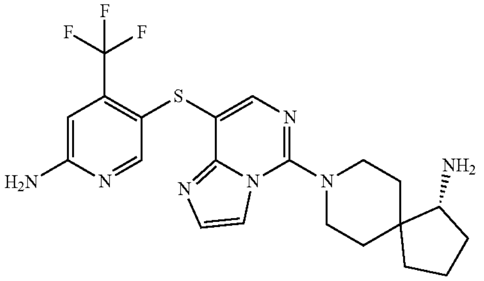 [SMILES: Nc1cc(C(F)(F)F)c(Sc2cnc(N3CCC4(CCC[C@H]4N)CC3)n3ccnc23)cn1] | (R)-8-(8-((6-amino-4-(trifluoromethyl) pyridin-3-yl)thio)imidazo[1,2-c]pyrimidin-5-yl)-8-azaspiro[4.5]decan-1-amine | 7500 | |
| 51 | 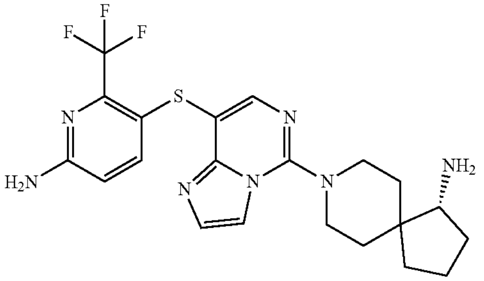 [SMILES: Nc1ccc(Sc2cnc(N3CCC4(CCC[C@H]4N)CC3)n3ccnc23)c(C(F)(F)F)n1] | (R)-8-(8-((6-amino-2-(trifluoromethyl) pyridin-3-yl)thio)imidazo[1,2-c]pyrimidin-5-yl)-8-azaspiro[4.5]decan-1-amine | 15 | |
| 52 | 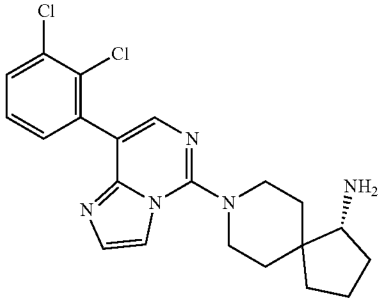 [SMILES: N[C@@H]1CCCC12CCN(c1ncc(-c3cccc(Cl)c3Cl)c3nccn13)CC2] | (R)-8-(8-(2,3-dichlorophenyl) imidazo[1,2-c]pyrimidin-5-yl)-8-azaspiro[4.5]decan-1-amine | 280 | >12500 |

TABLE 1-continued

| Example | Structure | Name | SHP2 $IC_{50}$ (nM) | H358 $EC_{50}$ (nM) |
|---|---|---|---|---|
| 53 | 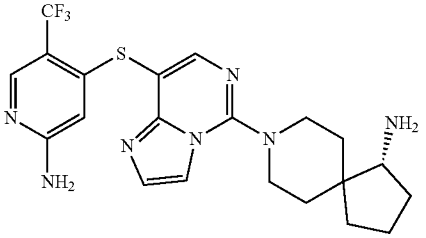 [SMILES: Nc1cc(Sc2cnc(N3CCC4(CCC[C@H]4N)CC3)n3ccnc23)c(C(F)(F)F)cn1] | (R)-8-(8-((2-amino-5-(trifluoromethyl) pyridin-4-yl)thio)imidazo[1,2-c]pyrimidin-5-yl)-8-azaspiro[4.5]decan-1-amine | 12 | |
| 54 | 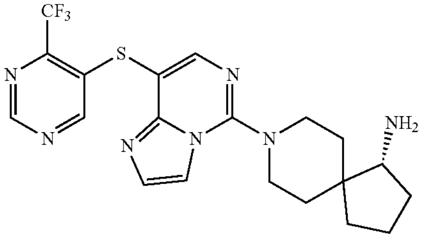 [SMILES: N[C@@H]1CCCC12CCN(c1ncc(Sc3cncnc3C(F)(F)F)c3nccn13)CC2] | (R)-8-(8-((4-(trifluoromethyl) pyrimidin-5-yl)thio)imidazo[1,2-c]pyrimidin-5-yl)-8-azaspiro[4.5] decan-1-amine | 4800 | |
| 55 | 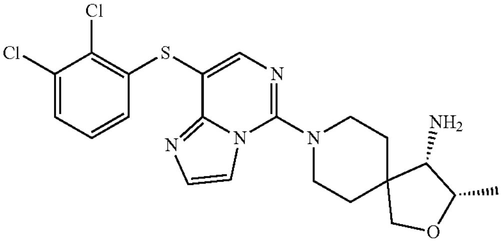 | (3S,4S)-8-(8-((2,3-dichlorophenyl) thio)imidazo[1,2-c]pyrimidin-5-yl)-3-methyl-2-oxa-8-azaspiro[4.5]decan-4-amine | 1.5 | 49 |
| 56 | 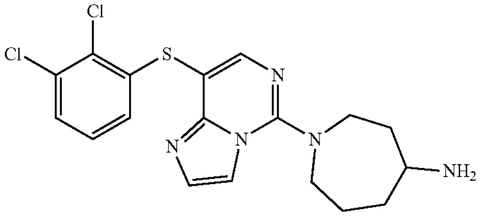 [SMILES: NC1CCCN(c2ncc(Sc3cccc(Cl)c3Cl)c3nccn23)CC1] | 1-(8-((2,3-dichlorophenyl)thio) imidazo[1,2-c]pyrimidin-5-yl)azepan-4-amine | 75 | 990 |
| 57 | 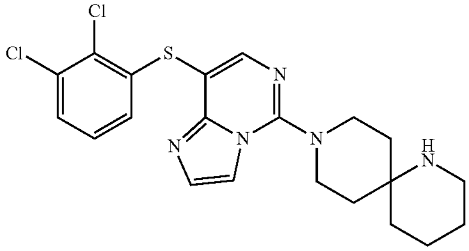 [SMILES: Clc1cccc(Sc2cnc(N3CCC4(CCCCN4)CC3)n3ccnc23)c1Cl] | 9-(8-((2,3-dichlorophenyl)thio) imidazo[1,2-c]pyrimidin-5-yl)-1,9-diazaspiro[5.5] undecane | 500 | >12500 |
| 58 | 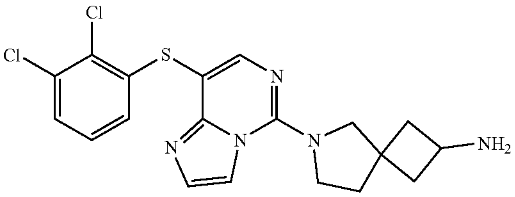 [SMILES: NC1CC2(CCN(c3ncc(Sc4cccc(Cl)c4Cl)c4nccn34)C2)C1] | 6-(8-((2,3-dichlorophenyl) thio)imidazo[1,2-c]pyrimidin-5-yl)-6-azaspiro[3.4]octan-2-amine | 340 | 4400 |

TABLE 1-continued

| Example | Structure | Name | SHP2 $IC_{50}$ (nM) | H358 $EC_{50}$ (nM) |
|---|---|---|---|---|
| 59 | 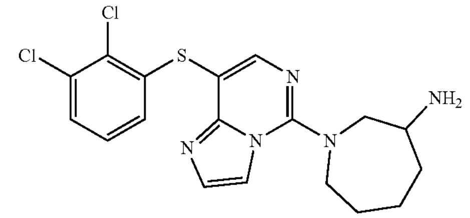 [SMILES: NC1CCCCN(c2ncc(Sc3cccc(Cl)c3Cl)c3nccn23)C1] | 1-(8-((2,3-dichlorophenyl)thio) imidazo[1,2-c]pyrimidin-5-yl)azepan-3-amine | >10000 | |
| 60 | 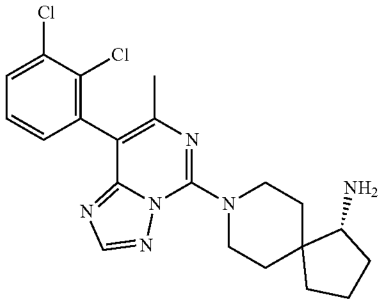 [SMILES: Cc1nc(N2CCC3(CCC[C@H]3N)CC2)n2ncnc2c1-c1cccc(Cl)c1Cl] | (R)-8-(8-(2,3-dichlorophenyl)-7-methyl-[1,2,4]triazolo[1,5-c]pyrimidin-5-yl)-8-azaspiro[4.5]decan-1-amine | 97 | |
| 61 | 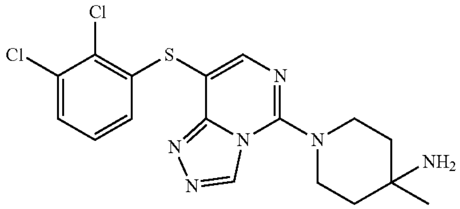 [SMILES: CC1(N)CCN(c2ncc(Sc3cccc(Cl)c3Cl)c3nncn23)CC1] | 1-(8-((2,3-dichlorophenyl)thio)-[1,2,4]triazolo[4,3-c]pyrimidin-5-yl)-4-methylpiperidin-4-amine | 130 | 2300 |
| 62 | 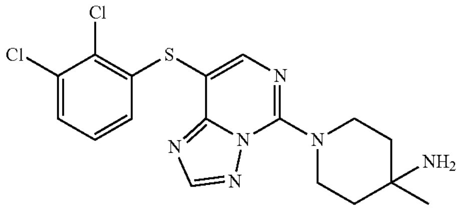 [SMILES: CC1(N)CCN(c2ncc(Sc3cccc(Cl)c3Cl)c3ncnn23)CC1] | 1-(8-((2,3-dichlorophenyl)thio)-[1,2,4]triazolo[1,5-c]pyrimidin-5-yl)-4-methylpiperidin-4-amine | 1300 | >12500 |
| 63 | 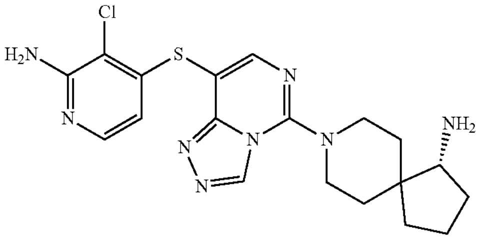 [SMILES: Nc1nccc(Sc2cnc(N3CCC4(CCC[C@H]4N)CC3)n3cnnc23)c1Cl] | (R)-8-(8-((2-amino-3-chloropyridin-4-yl)thio)-[1,2,4]triazolo[4,3-c]pyrimidin-5-yl)-8-azaspiro[4.5]decan-1-amine | 13 | 580 |
| 64 | 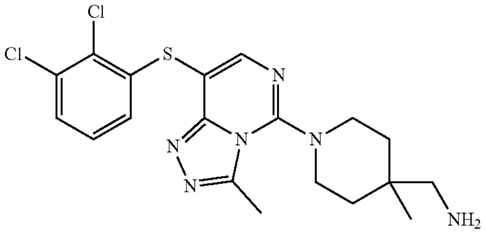 [SMILES: Cc1nnc2c(Sc3cccc(Cl)c3Cl)cnc(N3CCC(C)(CN)CC3)n12] | (1-(8-((2,3-dichlorophenyl)thio)-3-methyl-[1,2,4]triazolo[4,3-c]pyrimidin-5-yl)-4-methylpiperidin-4-yl)methanamine | 800 | |

TABLE 1-continued

| Example | Structure | Name | SHP2 $IC_{50}$ (nM) | H358 $EC_{50}$ (nM) |
|---|---|---|---|---|
| 65 | 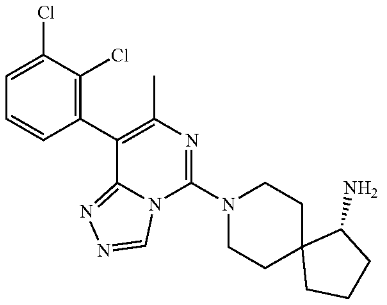 [SMILES: Cc1nc(N2CCC3(CCC[C@H]3N)CC2)n2cnnc2c1-c1cccc(Cl)c1Cl] | (R)-8-(8-(2,3-dichlorophenyl)-7-methyl[1,2,4]triazolo[4,3-c]pyrimidin-5-yl)-8-azaspiro[4.5]decan-1-amine | 20 | |
| 66 | 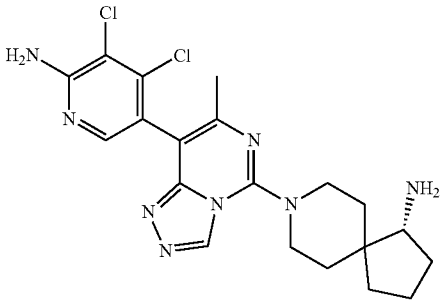 [SMILES: Cc1nc(N2CCC3(CCC[C@H]3N)CC2)n2cnnc2c1-c1cnc(N)c(Cl)c1Cl] | (R)-8-(8-(6-amino-4,5-dichloropyridin-3-yl)-7-methyl-[1,2,4]triazolo[4,3-c]pyrimidin-5-yl)-8-azaspiro[4.5]decan-1-amine | 140 | 2900 |
| 67 | 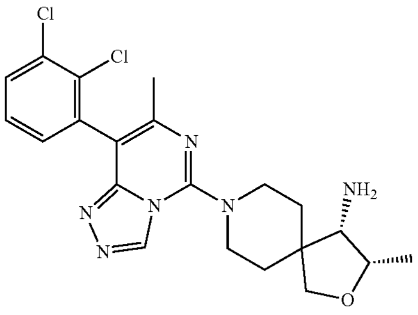 [SMILES: Cc1nc(N2CCC3(CC2)CO[C@@H](C)[C@H]3N)n2cnnc2c1-c1cccc(Cl)c1Cl] | (3S,4S)-8-(8-(2,3-dichlorophenyl)-7-methyl-[1,2,4]triazolo[4,3-c]pyrimidin-5-yl)-3-methyl-2-oxa-8-azaspiro[4.5]decan-4-amine | 6.4 | 100 |
| 68 | 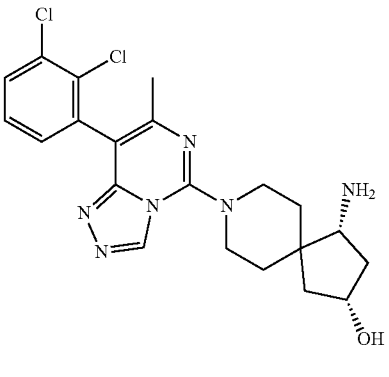 [SMILES: Cc1nc(N2CCC3(CC2)C[C@@H](O)C[C@H]3N)n2cnnc2c1-c1cccc(Cl)c1Cl] | (2R,4R)-4-amino-8-(8-(2,3-dichlorophenyl)-7-methyl-[1,2,4]triazolo[4,3-c]pyrimidin-5-yl)-8-azaspiro[4.5]decan-2-ol | 9.4 | 440 |

TABLE 1-continued

| Example | Structure | Name | SHP2 $IC_{50}$ (nM) | H358 $EC_{50}$ (nM) |
|---|---|---|---|---|
| 69 | 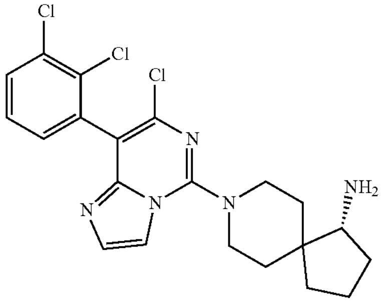 [SMILES: N[C@@H]1CCCC12CCN(c1nc(Cl)c(-c3cccc(Cl)c3Cl)c3nccn13)CC2] | (R)-8-(7-chloro-8-(2,3-dichlorophenyl)-imidazo[1,2-c]pyrimidin-5-yl)-8-azaspiro[4.5]decan-1-amine | 3.1 | 86 |
| 70 | 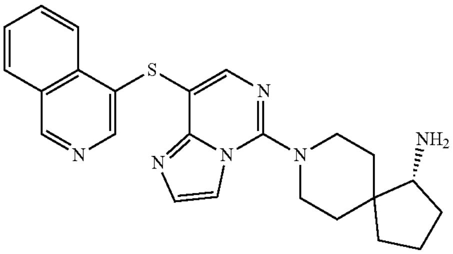 [SMILES: N[C@@H]1CCCC12CCN(c1ncc(Sc3cncc4ccccc34)c3nccn13)CC2] | (R)-8-(8-(isoquinolin-4-ylthio)imidazo[1,2-c]pyrimidin-5-yl)-8-azaspiro[4.5]decan-1-amine | 670 | 3900 |
| 71 | 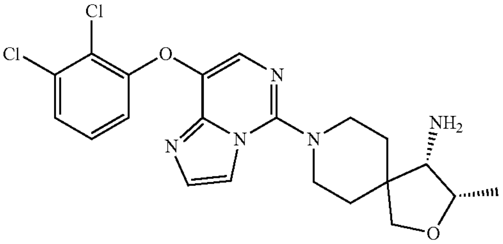 [SMILES: C[C@@H]1OCC2(CCN(c3ncc(Oc4cccc(Cl)c4Cl)c4nccn34)CC2)[C@@H]1N] | (3S,4S)-8-(8-(2,3-dichlorophenoxy) imidazo[1,2-c]pyrimidin-5-yl)-3-methyl-2-oxa-8-azaspiro[4.5]decan-4-amine | 120 | 1400 |
| 72 | 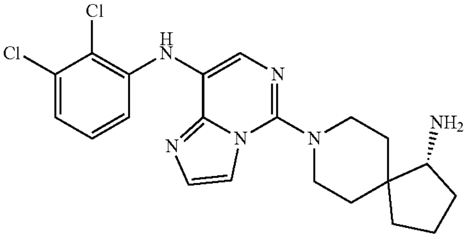 [SMILES: N[C@@H]1CCCC12CCN(c1ncc(Nc3cccc(Cl)c3Cl)c3nccn13)CC2] | (R)-8-(8-((2,3-dichlorophenyl) amino)imidazo[1,2-c]pyrimidin-5-yl)-8-azaspiro[4.5]decan-1-amine | 2000 | >12500 |
| 73 | 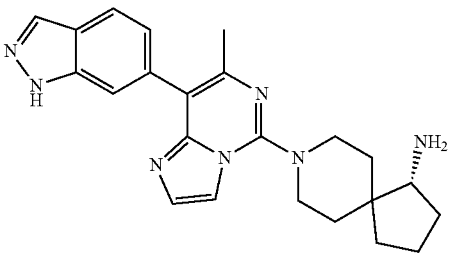 [SMILES: Cc1nc(N2CCC3(CCC[C@H]3N)CC2)n2ccnc2c1-c1ccc2cn[nH]c2c1] | (R)-8-(8-(1H-indazol-6-yl)-7-methylimidazo[1,2-c]pyrimidin-5-yl)-8-azaspiro[4.5]decan-1-amine | 30 | 550 |

TABLE 1-continued

| Example | Structure | Name | SHP2 $IC_{50}$ (nM) | H358 $EC_{50}$ (nM) |
|---|---|---|---|---|
| 74 | 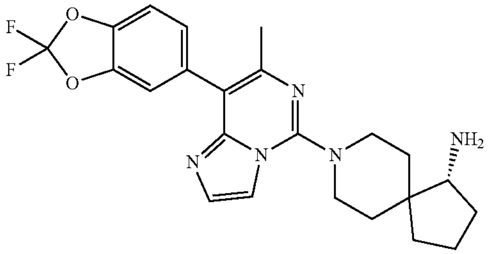 [SMILES: Cc1nc(N2CCC3(CCC[C@H]3N)CC2)n2ccnc2c1-c1ccc2c(c1)OC(F)(F)O2] | (R)-8-(8-(2,2-difluorobenzo[d][1,3]dioxol-5-yl)-7-methylimidazo[1,2-c]pyrimidin-5-yl)-8-azaspiro[4.5]decan-1-amine | 860 | >12500 |
| 75 | 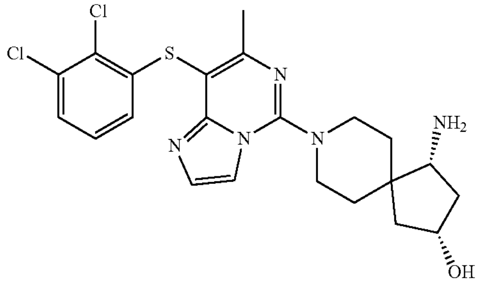 [SMILES: Cc1nc(N2CCC3(CC2)C[C@@H](O)C[C@H]3N)n2ccnc2c1Sc1cccc(Cl)c1Cl] | (2R,4R)-4-amino-8-(8-((2,3-dichlorophenyl)thio)-7-methylimidazo[1,2-c]pyrimidin-5-yl)-8-azaspiro[4.5]decan-2-ol | 3.9 | 48 |
| 76 | 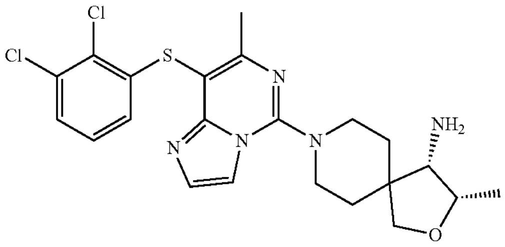 [SMILES: Cc1nc(N2CCC3(CC2)CO[C@@H](C)[C@H]3N)n2ccnc2c1Sc1cccc(Cl)c1Cl] | (3S,4S)-8-(8-((2,3-dichlorophenyl)thio)-7-methylimidazo[1,2-c]pyrimidin-5-yl)-3-methyl-2-oxa-8-azaspiro[4.5]decan-4-amine | 3.3 | 59 |
| 77 | 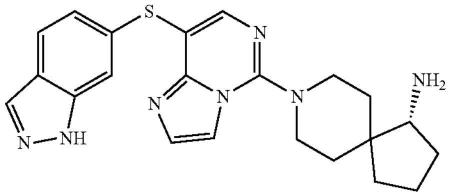 [SMILES: N[C@@H]1CCCC12CCN(c1ncc(Sc3ccc4cn[nH]c4c3)c3nccn13)CC2] | (R)-8-(8-((1H-indazol-6-yl)thio)imidazo[1,2-c]pyrimidin-5-yl)-8-azaspiro[4.5]decan-1-amine | 180 | 3100 |
| 78 | 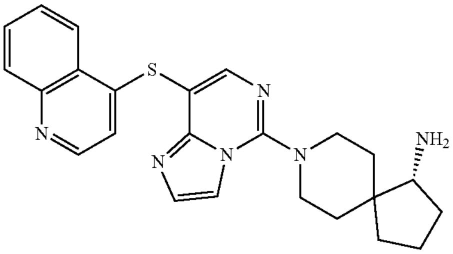 [SMILES: N[C@@H]1CCCC12CCN(c1ncc(Sc3ccnc4ccccc34)c3nccn13)CC2] | (R)-8-(8-(quinolin-4-ylthio)imidazo[1,2-c]pyrimidin-5-yl)-8-azaspiro[4.5]decan-1-amine | 5.9 | 95 |
| 79 | 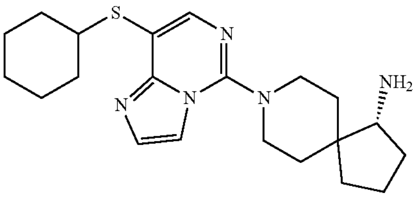 [SMILES: N[C@@H]1CCCC12CCN(c1ncc(SC3CCCCC3)c3nccn13)CC2] | (R)-8-(8-(cyclohexylthio)imidazo[1,2-c]pyrimidin-5-yl)-8-azaspiro[4.5]decan-1-amine | 5300 | >12500 |

TABLE 1-continued

| Example | Structure | Name | SHP2 $IC_{50}$ (nM) | H358 $EC_{50}$ (nM) |
|---|---|---|---|---|
| 80 | 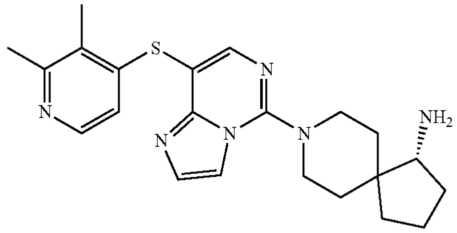 [SMILES: Cc1nccc(Sc2cnc(N3CCC4(CCC[C@H]4N)CC3)n3ccnc23)c1C] | (R)-8-(8-((2,3-dimethylpyridin-4-yl)thio)imidazo[1,2-c]pyrimidin-5-yl)-8-azaspiro[4.5]decan-1-amine | 28 | 270 |
| 81 | 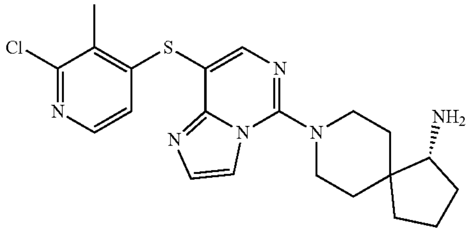 [SMILES: Cc1c(Sc2cnc(N3CCC4(CCC[C@H]4N)CC3)n3ccnc23)ccnc1Cl] | (R)-8-(8-((2-chloro-3-methylpyridin-4-yl)thio)imidazo[1,2-c]pyrimidin-5-yl)-8-azaspiro[4.5]decan-1-amine | 7.2 | 82 |
| 82 | 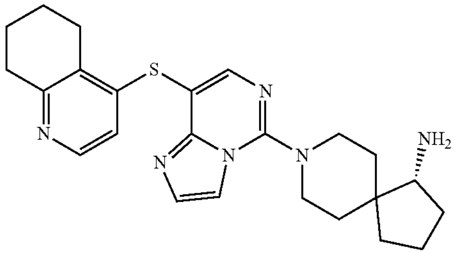 [SMILES: N[C@@H]1CCCC12CCN(c1ncc(Sc3ccnc4c3CCCC4)c3nccn13)CC2] | (R)-8-(8-((5,6,7,8-tetrahydroquinolin-4-yl)thio)imidazo[1,2-c]pyrimidin-5-yl)-8-azaspiro[4.5]decan-1-amine | 11 | 125 |
| 83 | 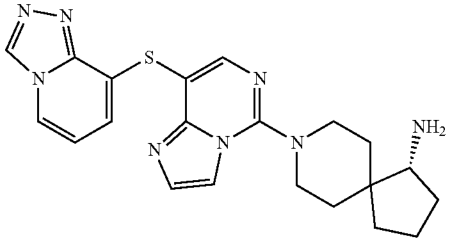 [SMILES: N[C@@H]1CCCC12CCN(c1ncc(Sc3cccn4cnnc34)c3nccn13)CC2] | (R)-8-(8-([1,2,4]triazolo[4,3-a]pyridin-8-ylthio)imidazo[1,2-c]pyrimidin-5-yl)-8-azaspiro[4.5]decan-1-amine | 150 | >12500 |
| 84 | 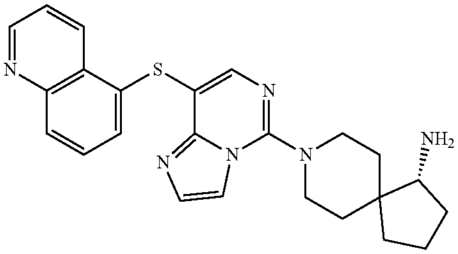 [SMILES: N[C@@H]1CCCC12CCN(c1ncc(Sc3cccc4ncccc34)c3nccn13)CC2] | (R)-8-(8-([1,2,4]triazolo[4,3-a]pyridin-8-ylthio)imidazo[1,2-c]pyrimidin-5-yl)-8-azaspiro[4.5]decan-1-amine | 11 | 240 |
| 85 | 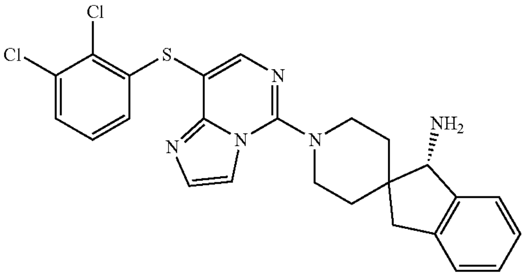 [SMILES: N[C@@H]1c2ccccc2CC12CCN(c1ncc(Sc3cccc(Cl)c3Cl)c3nccn13)CC2] | (S)-1'-(8-((2,3-dichlorophenyl)thio)imidazo[1,2-c]pyrimidin-5-yl)-1,3-dihydrospiro[indene-2,4'-piperidin]-1-amine | 2.1 | 11 |

TABLE 1-continued

| Example | Structure | Name | SHP2 $IC_{50}$ (nM) | H358 $EC_{50}$ (nM) |
|---|---|---|---|---|
| 86 | 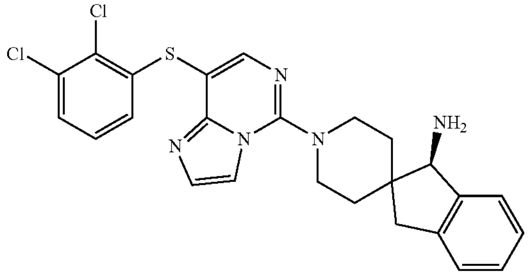 [SMILES: N[C@H]1c2ccccc2CC12CCN(c1ncc(Sc3cccc(Cl)c3Cl)c3nccn13)CC2] | (R)-1'-(8-((2,3-dichlorophenyl)thio)imidazo[1,2-c]pyrimidin-5-yl)-1,3-dihydrospiro[indene-2,4'-piperidin]-1-amine | 250 | 350 |
| 87 | 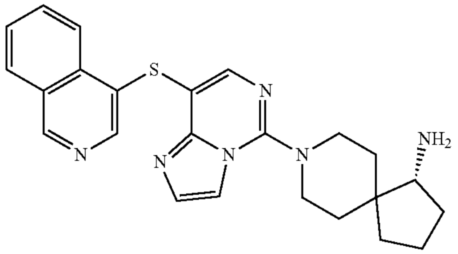 [SMILES: N[C@@H]1CCCC12CCN(c1ncc(Sc3cncc4ccccc34)c3nccn13)CC2] | (R)-8-(8-(isoquinolin-4-ylthio)imidazo[1,2-c]pyrimidin-5-yl)-8-azaspiro[4.5]decan-1-amine | 670 | 3900 |
| 88 | 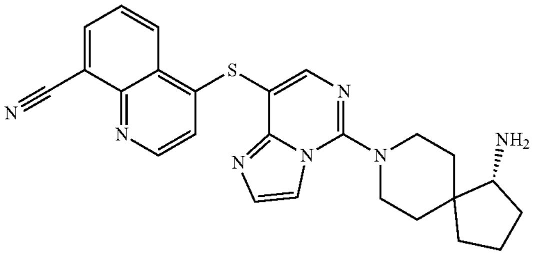 [SMILES: N#Cc1cccc2c(Sc3cnc(N4CCC5(CCC[C@H]5N)CC4)n4ccnc34)ccnc12] | (R)-4-((5-(1-amino-8-azaspiro[4.5]decan-8-yl)imidazo[1,2-c]pyrimidin-8-yl)thio)quinoline-8-carbonitrile | 18 | 160 |
| 89 | 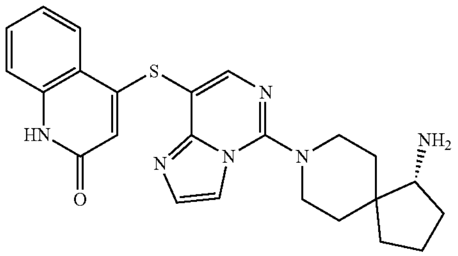 [SMILES: N[C@@H]1CCCC12CCN(c1ncc(Sc3cc(=O)[nH]c4ccccc34)c3nccn13)CC2] | (R)-4-((5-(1-amino-8-azaspiro[4.5]decan-8-yl)imidazo[1,2-c]pyrimidin-8-yl)thio)quinolin-2(1H)-one | >10000 | >12500 |
| 90 | 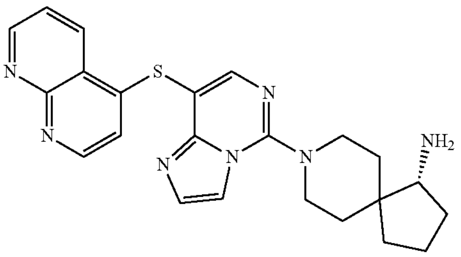 [SMILES: N[C@@H]1CCCC12CCN(c1ncc(Sc3ccnc4ncccc34)c3nccn13)CC2] | (R)-8-(8-((1,8-naphthyridin-4-yl)thio)imidazo[1,2-c]pyrimidin-5-yl)-8-azaspiro[4.5]decan-1-amine | 37 | 410 |

TABLE 1-continued

| Example | Structure | Name | SHP2 $IC_{50}$ (nM) | H358 $EC_{50}$ (nM) |
|---|---|---|---|---|
| 91 | 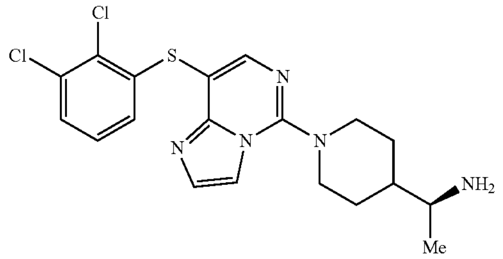 [SMILES: C[C@H](N)C1CCN(c2ncc(Sc3cccc(Cl)c3Cl)c3nccn23)CC1] | (S)-1-(1-(8-((2,3-dichlorophenyl)thio)imidazo[1,2-c]pyrimidin-5-yl)piperidin-4-yl)ethan-1-amine | 170 | 2000 |
| 92 | 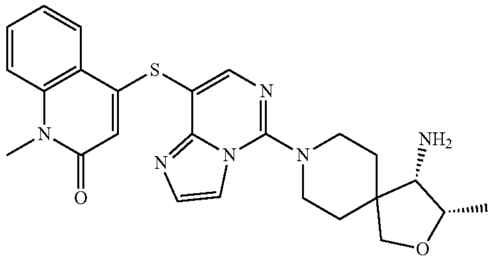 [SMILES: C[C@@H]1OCC2(CCN(c3ncc(Sc4cc(=O)n(C)c5ccccc45)c4nccn34)CC2)[C@@H]1N] | 4-((5-((3S,4S)-4-amino-3-methyl-2-oxa-8-azaspiro[4.5]decan-8-yl)imidazo[1,2-c]pyrimidin-8-yl)thio)-1-methylquinolin-2(1H)-one | >10000 | >12500 |
| 93 | 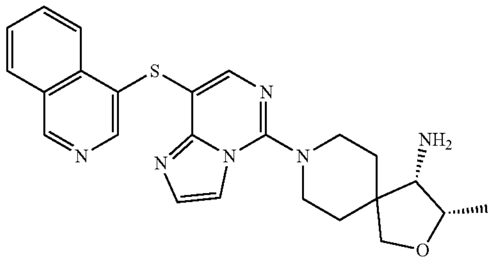 [SMILES: C[C@@H]1OCC2(CCN(c3ncc(Sc4cncc5ccccc45)c4nccn34)CC2)[C@@H]1N] | (3S,4S)-8-(8-(isoquinolin-4-ylthio)imidazo[1,2-c]pyrimidin-5-yl)-3-methyl-2-oxa-8-azaspiro[4.5]decan-4-amine | 480 | >12500 |
| 94 | 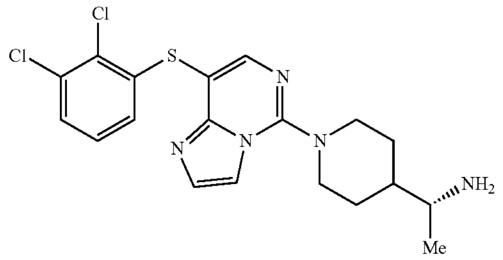 [SMILES: C[C@@H](N)C1CCN(c2ncc(Sc3cccc(Cl)c3Cl)c3nccn23)CC1] | (R)-1-(1-(8-((2,3-dichlorophenyl)thio)imidazo[1,2-c]pyrimidin-5-yl)piperidin-4-yl)ethan-1-amine | 170 | 1000 |
| 95 | 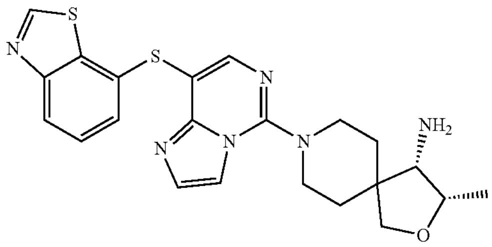 [SMILES: C[C@@H]1OCC2(CCN(c3ncc(Sc4cccc5ncsc45)c4nccn34)CC2)[C@@H]1N] | (3S,4S)-8-(8-(benzo[d]thiazol-7-ylthio)imidazo[1,2-c]pyrimidin-5-yl)-3-methyl-2-oxa-8-azaspiro[4.5]decan-4-amine | 5.2 | 95 |
| 96 | 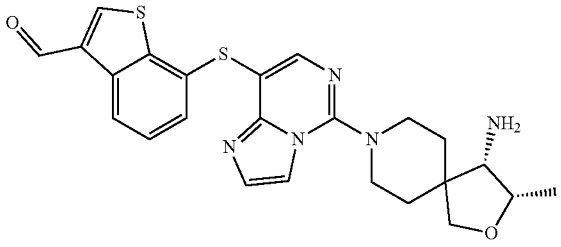 [SMILES: C[C@@H]1OCC2(CCN(c3ncc(Sc4cccc5c(C=O)csc45)c4nccn34)CC2)[C@@H]1N] | 7-((5-((3S,4S)-4-amino-3-methyl-2-oxa-8-azaspiro[4.5]decan-8-yl)imidazo[1,2-c]pyrimidin-8-yl)thio)benzo[b]thiophene-3-carbaldehyde | 4.1 | 97 |

TABLE 1-continued

| Example | Structure | Name | SHP2 $IC_{50}$ (nM) | H358 $EC_{50}$ (nM) |
|---|---|---|---|---|
| 97 | 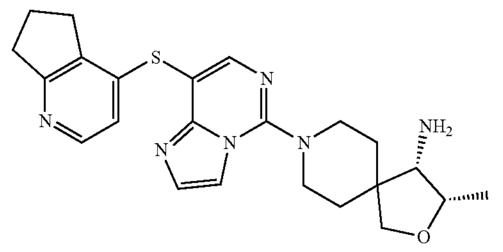 [SMILES: C[C@@H]1OCC2(CCN(c3ncc(Sc4ccnc5c4CCC5)c4nccn34)CC2)[C@@H]1N] | (3S,4S)-8-(8-((6,7-dihydro-5H-cyclopenta[b]pyridin-4-yl)thio)imidazo[1,2-c]pyrimidin-5-yl)-3-methyl-2-oxa-8-azaspiro[4.5]decan-4-amine | 11 | 110 |
| 98 | 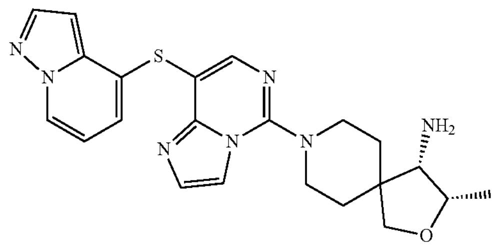 [SMILES: C[C@@H]1OCC2(CCN(c3ncc(Sc4cccn5nccc45)c4nccn34)CC2)[C@@H]1N] | (3S,4S)-3-methyl-8-(8-(pyrazolo[1,5-a]pyridin-4-ylthio)imidazo[1,2-c]pyrimidin-5-yl)-2-oxa-8-azaspiro[4.5]decan-4-amine | 16 | 250 |
| 99 | 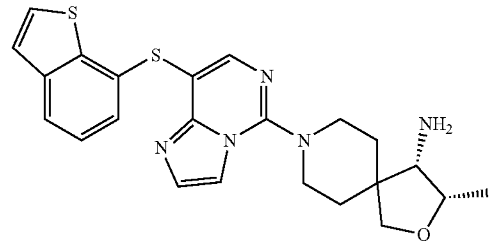 | (3S,4S)-8-(8-(benzo[b]thiophene-7-ylthio)imidazo[1,2-c]pyrimidin-5-yl)-3-methyl-2-oxa-8-azaspiro[4.5]decan-4-amine | 4.1 | 96 |
| 100 | 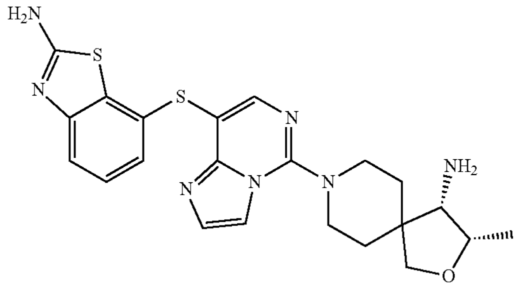 [SMILES: C[C@@H]1OCC2(CCN(c3ncc(Sc4cccc5nc(N)sc45)c4nccn34)CC2)[C@@H]1N] | (3S,4S)-8-(8-((2-aminobenzo[d]thiazol-7-yl)thio)imidazo[1,2-c]pyrimidin-5-yl)-3-methyl-2-oxa-8-azaspiro[4.5]decan-4-amine | 6.7 | 140 |
| 101 | 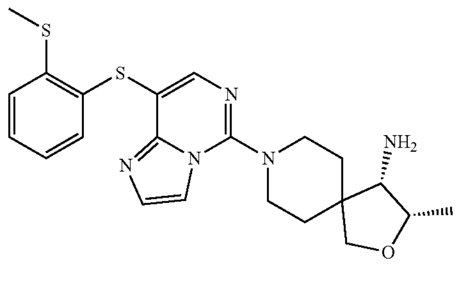 [SMILES: CSc1ccccc1Sc1cnc(N2CCC3(CC2)CO[C@@H](C)[C@H]3N)n2ccnc12] | (3S,4S)-3-methyl-8-(8-((2-(methylthio)phenyl)thio)imidazo[1,2-c]pyrimidin-5-yl)-2-oxa-8-azaspiro[4.5]decan-4-amine | 5.7 | 84 |

TABLE 1-continued

| Example | Structure | Name | SHP2 $IC_{50}$ (nM) | H358 $EC_{50}$ (nM) |
|---|---|---|---|---|
| 102 | 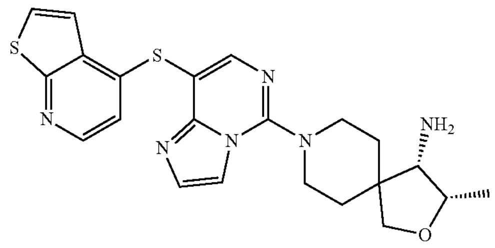 [SMILES: C[C@@H]1OCC2(CCN(c3ncc(Sc4ccnc5sccc45)c4nccn34)CC2)[C@@H]1N] | (3S,4S)-3-methyl-8-(8-(thieno[2,3-b]pyridin-4-ylthio)imidazo[1,2-c]pyrimidin-5-yl)-2-oxa-8-azaspiro[4.5]decan-4-amine | 4.0 | 66 |
| 103 | 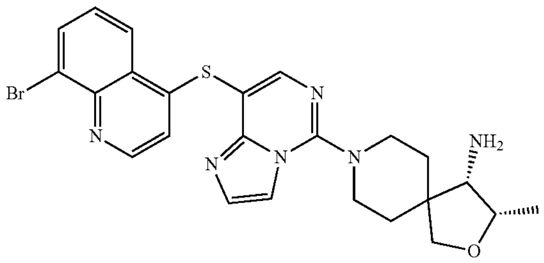 [SMILES: C[C@@H]1OCC2(CCN(c3ncc(Sc4ccnc5c(Br)cccc45)c4nccn34)CC2)[C@@H]1N] | (3S,4S)-8-(8-((8-bromoquinolin-4-yl)thio)imidazo[1,2-c]pyrimidin-5-yl)-3-methyl-2-oxa-8-azaspiro[4.5]decan-4-amine | 4.6 | 150 |
| 104 | 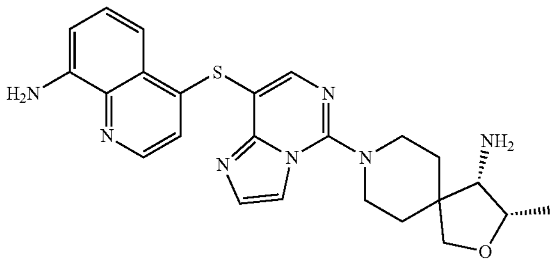 [SMILES: C[C@@H]1OCC2(CCN(c3ncc(Sc4ccnc5c(N)cccc45)c4nccn34)CC2)[C@@H]1N] | (3S,4S)-8-(8-((8-aminoquinolin-4-yl)thio)imidazo[1,2-c]pyrimidin-5-yl)-3-methyl-2-oxa-8-azaspiro[4.5]decan-4-amine | 4.2 | 74 |
| 105 | 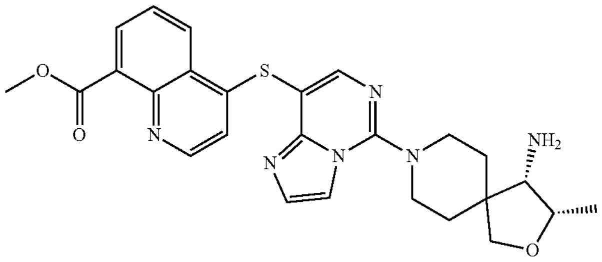 | methyl 4-((5-((3S,4S)-4-amino-3-methyl-2-oxa-8-azaspiro[4.5]decan-8-yl)imidazo[1,2-c]pyrimidin-8-yl)thio)quinoline-8-carboxylate | 82 | 760 |
| 106 | 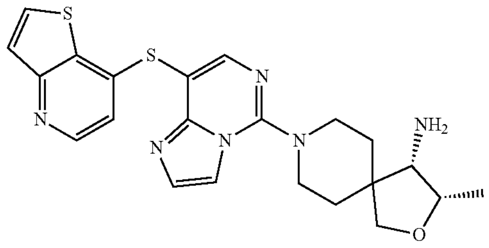 [SMILES: C[C@@H]1OCC2(CCN(c3ncc(Sc4ccnc5ccsc45)c4nccn34)CC2)[C@@H]1N] | (3S,4S)-3-methyl-8-(8-(thieno[3.2-b]pyridin-7-ylthio)imidazo[1,2-c]pyrimidin-5-yl)-2-oxa-8-azaspiro[4.5]decan-4-amine | 4.2 | 39 |
| 107 | 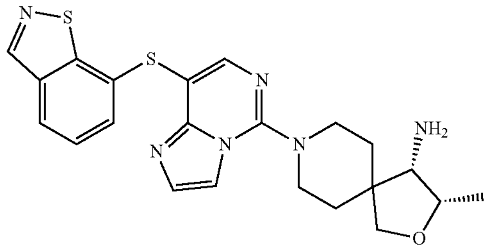 [SMILES: C[C@@H]1OCC2(CCN(c3ncc(Sc4cccc5cnsc45)c4nccn34)CC2)[C@@H]1N] | (3S,4S)-8-(8-(benzo[d]isothiazol-7-ylthio)imidazo[1,2-c]pyrimidin-5-yl)-3-methyl-2-oxa-8-azaspiro[4.5]decan-4-amine | 3.7 | 64 |

TABLE 1-continued

| Example | Structure | Name | SHP2 $IC_{50}$ (nM) | H358 $EC_{50}$ (nM) |
|---|---|---|---|---|
| 108 | 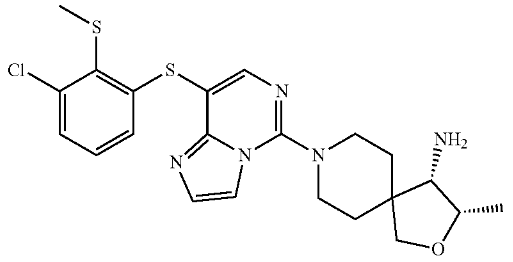 [SMILES: CSc1c(Cl)cccc1Sc1cnc(N2CCC3(CC2)CO[C@@H](C)[C@H]3N)n2ccnc12] | (3S,4S)-8-(8-((3-chloro-2-(methylthio)phenyl)thio)imidazo[1,2-c]pyrimidin-5-yl)-3-methyl-2-oxa-8-azaspiro[4.5]decan-4-amine | 3.3 | 87 |
| 109 | 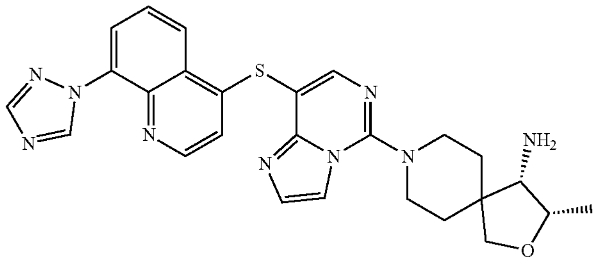 [SMILES: C[C@@H]1OCC2(CCN(c3ncc(Sc4ccnc5c(-n6cncn6)cccc45)c4nccn34)CC2)[C@@H]1N] | (3S,4S)-8-(8-((8-(1H-1,2,4-triazol-1-yl)quinolin-4-yl)thio)imidazo[1,2-c]pyrimidin-5-yl)-3-methyl-2-oxa-8-azaspiro[4.5]decan-4-amine | 18 | 260 |
| 110 | 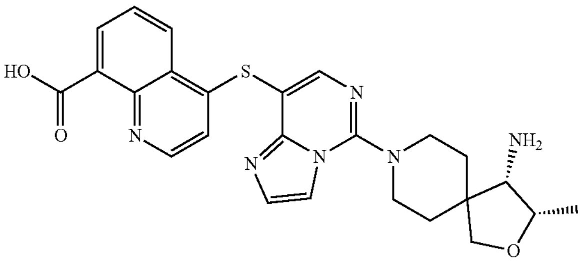 | 4-((5-((3S,4S)-4-amino-3-methyl-2-oxa-8-azaspiro[4.5]decan-8-yl)imidazo[1,2-c]pyrimidin-8-yl)thio)quinoline-8-carboxylic acid | 190 | 930 |
| 111 | 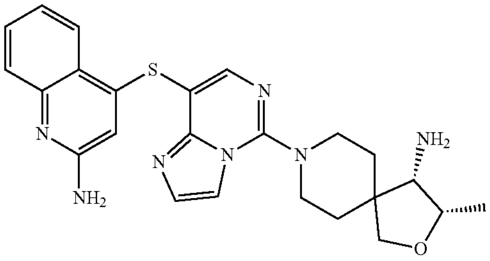 [SMILES: C[C@@H]1OCC2(CCN(c3ncc(Sc4cc(N)nc5ccccc45)c4nccn34)CC2)[C@@H]1N] | (3S,4S)-8-(8-((2-aminoquinolin-4-yl)thio)imidazo[1,2-c]pyrimidin-5-yl)-3-methyl-2-oxa-8-azaspiro[4.5]decan-4-amine | 7.1 | 170 |
| 112 | 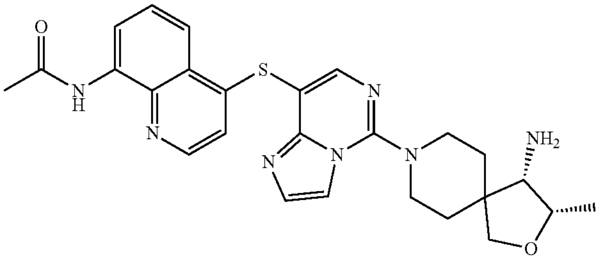 [SMILES: CC(=O)Nc1cccc2c(Sc3cnc(N4CCC5(CC4)CO[C@@H](C)[C@H]5N)n4ccnc34)ccnc12] | N-(4-((5-((3S,4S)-4-amino-3-methyl-2-oxa-8-azaspiro[4.5]decan-8-yl)imidazo[1,2-c]pyrimidin-8-yl)thio)quinolin-8-yl)acetamide | 10 | 56 |

TABLE 1-continued

| Example | Structure | Name | SHP2 $IC_{50}$ (nM) | H358 $EC_{50}$ (nM) |
|---|---|---|---|---|
| 113 | 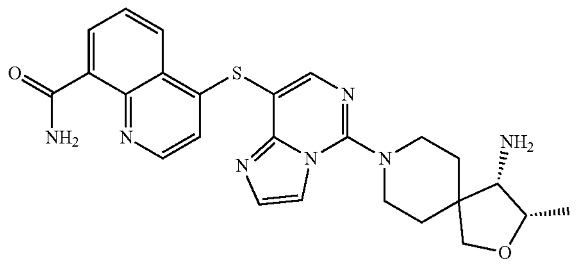 [SMILES: C[C@@H]1OCC2(CCN(c3ncc(Sc4ccnc5c(C(N)=O)cccc45)c4nccn34)CC2)[C@@H]1N] | 4-((5-((3S,4S)-4-amino-3-methyl-2-oxa-8-azaspiro[4.5]decan-8-yl)imidazo[1,2-c]pyrimidin-8-yl)thio)quinoline-8-carboxamide | 11 | 340 |
| 114 | 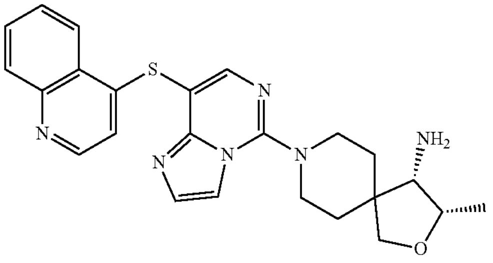 [SMILES: C[C@@H]1OCC2(CCN(c3ncc(Sc4ccnc5ccccc45)c4nccn34)CC2)[C@@H]1N] | (3S,4S)-3-methyl-8-(8-(quinolin-4-ylthio)imidazo [1,2-c]pyrimidin-5-yl)-2-oxa-8-azaspiro[4.5] decan-4-amine | 6.8 | 64 |
| 115 | 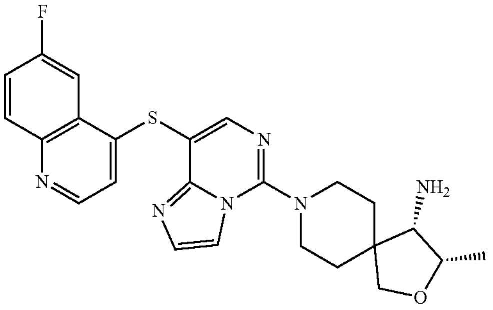 [SMILES: C[C@@H]1OCC2(CCN(c3ncc(Sc4ccnc5ccc(F)cc45)c4nccn34)CC2)[C@@H]1N] | (3S,4S)-8-(8-((6-fluoroquinolin-4-yl)thio)imidazo[1,2-c]pyrimidin-5-yl)-3-methyl-2-oxa-8-azaspiro[4.5]decan-4-amine | 8.4 | 90 |
| 116 | 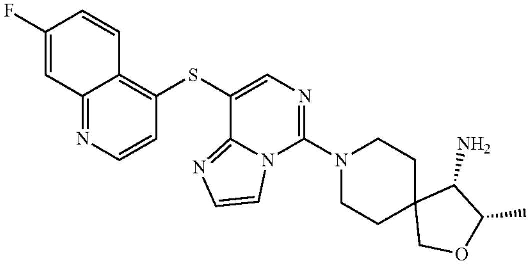 [SMILES: C[C@@H]1OCC2(CCN(c3ncc(Sc4ccnc5cc(F)ccc45)c4nccn34)CC2)[C@@H]1N] | (3S,4S)-8-(8-((7-fluoroquinolin-4-yl)thio)imidazo[1,2-c]pyrimidin-5-yl)-3-methyl-2-oxa-8-azaspiro[4.5]decan-4-amine | 8.0 | 72 |
| 117 | 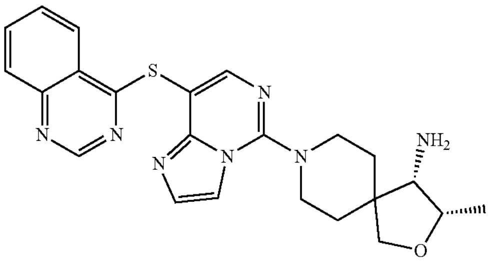 [SMILES: C[C@@H]1OCC2(CCN(c3ncc(Sc4ncnc5ccccc45)c4nccn34)CC2)[C@@H]1N] | (3S,4S)-3-methyl-8-(8-(quinazolin-4-ylthio)imidazo[1,2-c]pyrimidin-5-yl)-2-oxa-8-azaspiro[4.5] decan-4-amine | >10000 | >12500 |

TABLE 1-continued

| Example | Structure | Name | SHP2 $IC_{50}$ (nM) | H358 $EC_{50}$ (nM) |
|---|---|---|---|---|
| 118 | 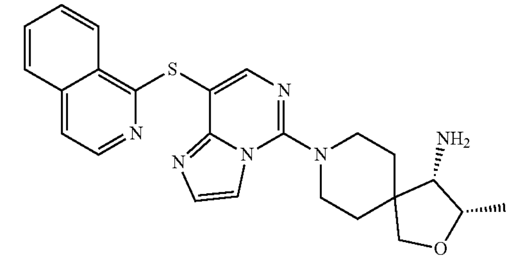 [SMILES: C[C@@H]1OCC2(CCN(c3ncc(Sc4nccc5ccccc45)c4nccn34)CC2)[C@@H]1N] | (3S,4S)-8-(8-(isoquinolin-1-ylthio)imidazo[1,2-c]pyrimidin-5-yl)-3-methyl-2-oxa-8-azaspiro[4.5]decan-4-amine | 550 | |
| 119 | 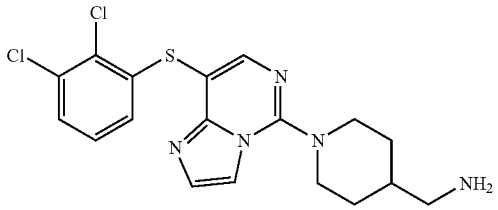 [SMILES: NCC1CCN(c2ncc(Sc3cccc(Cl)c3Cl)c3nccn23)CC1] | (1-(8-((2,3-dichlorophenyl)thio) imidazo[1,2-c]pyrimidin-5-yl)piperidin-4-yl)methanamine | 73 | 2200 |
| 120 | 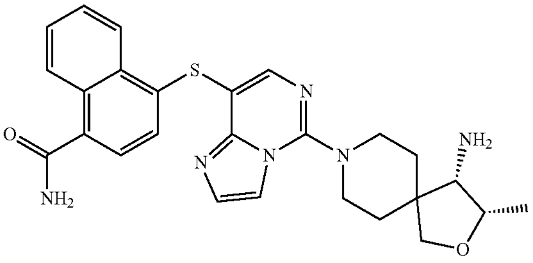 [SMILES: C[C@@H]1OCC2(CCN(c3ncc(Sc4ccc(C(N)=O)c5ccccc45)c4nccn34)CC2)[C@@H]1N] | 4-((5-((3S,4S)-4-amino-3-methyl-2-oxa-8-azaspiro[4.5]decan-8-yl) imidazo[1,2-c]pyrimidin-8-yl)thio)-1-naphthamide | 26 | 500 |
| 121 | 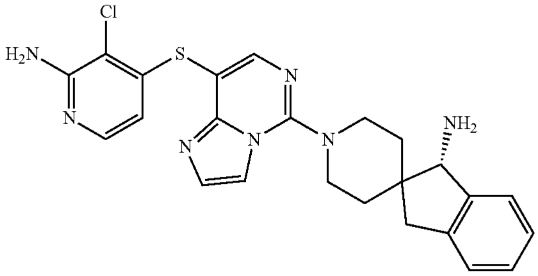 [SMILES: Nc1nccc(Sc2cnc(N3CCC4(CC3)Cc3ccccc3[C@H]4N)n3ccnc23)c1Cl] | (S)-1'-(8-((2-amino-3-chloropyridin-4-yl)thio)imidazo[1,2-c]pyrimidin-5-yl)-1,3-dihydrospiro[indene-2,4'-piperidin]-1-amine | 4.8 | 4.2 |
| 122 | 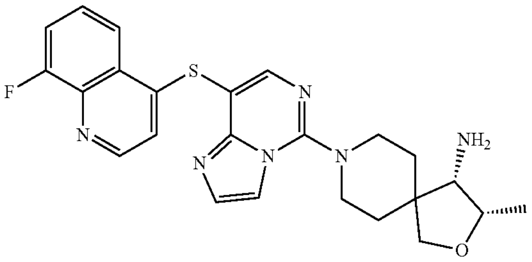 [SMILES: C[C@@H]1OCC2(CCN(c3ncc(Sc4ccnc5c(F)cccc45)c4nccn34)CC2)[C@@H]1N] | (3S,4S)-8-(8-((8-fluoroquinolin-4-yl)thio)imidazo[1,2-c]pyrimidin-5-yl)-3-methyl-2-oxa-8-azaspiro[4.5]decan-4-amine | 9.1 | 70 |

TABLE 1-continued

| Example | Structure | Name | SHP2 $IC_{50}$ (nM) | H358 $EC_{50}$ (nM) |
|---|---|---|---|---|
| 123 | 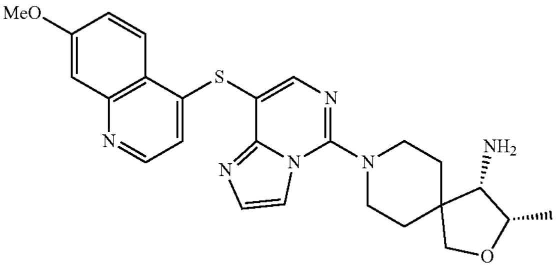 [SMILES: COc1ccc2c(Sc3cnc(N4CCC5(CC4)CO[C@@H](C)[C@H]5N)n4ccnc34)ccnc2c1] | (3S,4S)-8-(8-((7-methoxyquinolin-4-yl)thio) imidazo[1,2-c] pyrimidin-5-yl)-3-methyl-2-oxa-8-azaspiro[4.5] decan-4-amine | 6.8 | 95 |
| 124 | 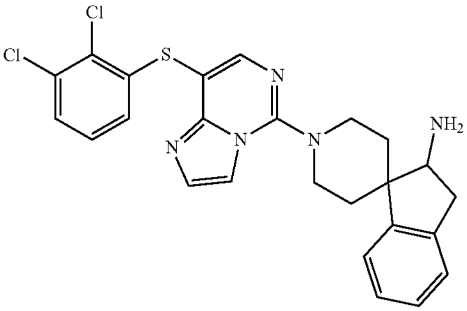 [SMILES: NC1Cc2ccccc2C12CCN(c1ncc(Sc3cccc(Cl)c3Cl)c3nccn13)CC2] | 1'-(8-((2,3-dichlorophenyl) thio)imidazo[1,2-c]pyrimidin-5-yl)-2,3-dihydrospiro [indene-1,4'-piperidin]-2-amine | 23 | 750 |
| 125 | 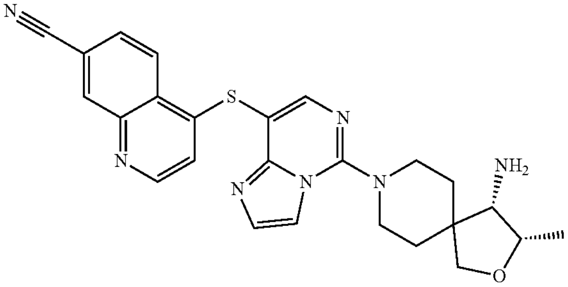 [SMILES: C[C@@H]1OCC2(CCN(c3ncc(Sc4ccnc5cc(C#N)ccc45)c4nccn34)CC2)[C@@H]1N] | 4-((5-((3S,4S)-4-amino-3-methyl-2-oxa-8-azaspiro[4.5]decan-8-yl)imidazo[1,2-c]pyrimidin-8-yl)thio)quinoline-7-carbonitrile | 51 | |
| 126 | 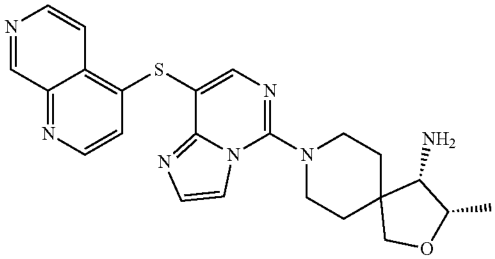 [SMILES: C[C@@H]1OCC2(CCN(c3ncc(Sc4ccnc5cnccc45)c4nccn34)CC2)[C@@H]1N] | (3S,4S)-8-(8-((1,7-naphthyridin-4-yl)thio)imidazo[1,2-c]pyrimidin-5-yl)-3-methyl-2-oxa-8-azaspiro[4.5] decan-4-amine | 15 | 120 |
| 127 | 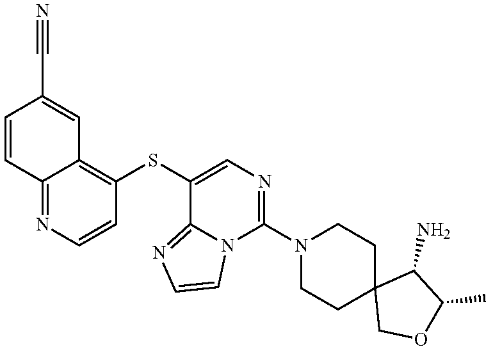 [SMILES: C[C@@H]1OCC2(CCN(c3ncc(Sc4ccnc5ccc(C#N)cc45)c4nccn34)CC2)[C@@H]1N] | 4-((5-((3S,4S)-4-amino-3-methyl-2-oxa-8-azaspiro[4.5]decan-8-yl)imidazo[1,2-c]pyrimidin-8-yl)thio)quinoline-6-carbonitrile | 30 | 270 |

TABLE 1-continued

| Example | Structure | Name | SHP2 $IC_{50}$ (nM) | H358 $EC_{50}$ (nM) |
|---|---|---|---|---|
| 128 | 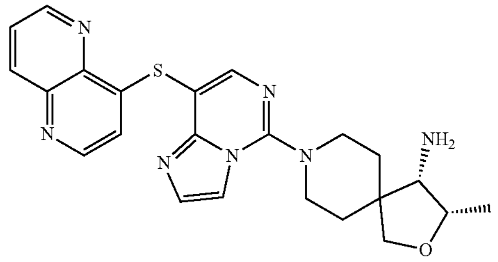 [SMILES: C[C@@H]1OCC2(CCN(c3ncc(Sc4ccnc5cccnc45)c4nccn34)CC2)[C@@H]1N] | (3S,4S)-8-(8-((1,5-naphthyridin-4-yl)thio)imidazo[1,2-c]pyrimidin-5-yl)-3-methyl-2-oxa-8-azaspiro[4.5]decan-4-amine | 14 | 59 |
| 129 | 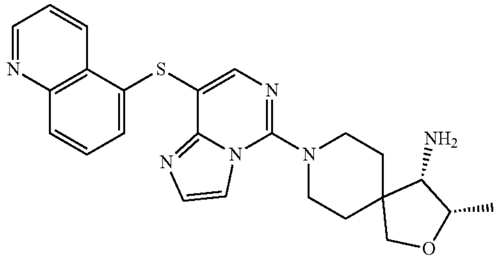 [SMILES: C[C@@H]1OCC2(CCN(c3ncc(Sc4cccc5ncccc45)c4nccn34)CC2)[C@@H]1N] | (3S,4S)-3-methyl-8-(8-(quinolin-5-ylthio)imidazo[1,2-c]pyrimidin-5-yl)-2-oxa-8-azaspiro[4.5]decan-4-amine | 10 | 150 |
| 130 | 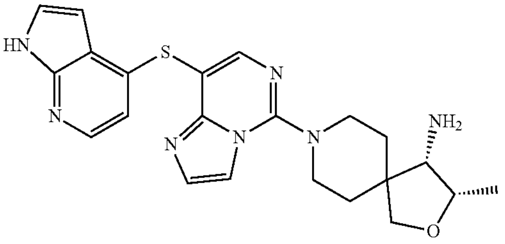 [SMILES: C[C@@H]1OCC2(CCN(c3ncc(Sc4ccnc5[nH]ccc45)c4nccn34)CC2)[C@@H]1N] | (3S,4S)-8-(8-((1H-pyrrolo[2,3-b]pyridin-4-yl)thio)imidazo[1,2-c]pyrimidin-5-yl)-3-methyl-2-oxa-8-azaspiro[4.5]decan-4-amine | 5.7 | 57 |
| 131 | 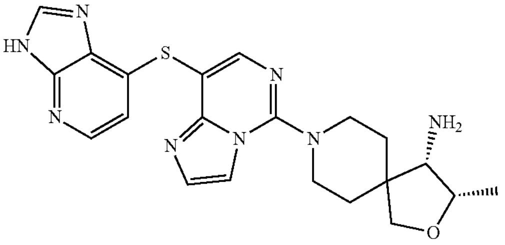 [SMILES: C[C@@H]1OCC2(CCN(c3ncc(Sc4ccnc5[nH]cnc45)c4nccn34)CC2)[C@@H]1N] | (3S,4S)-8-(8-((3H-imidazo[4,5-b]pyridin-7-yl)thio)imidazo[1,2-c]pyrimidin-5-yl)-3-methyl-2-oxa-8-azaspiro[4.5]decan-4-amine | 27 | 2100 |
| 132 | 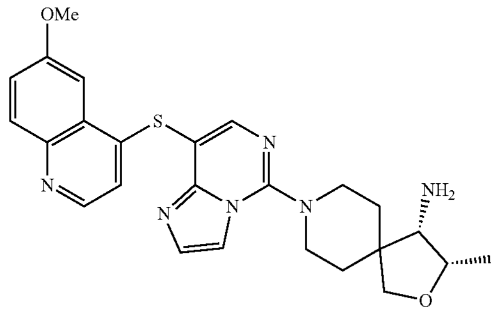 [SMILES: COc1ccc2nccc(Sc3cnc(N4CCC5(CC4)CO[C@@H](C)[C@H]5N)n4ccnc34)c2c1] | (3S,4S)-8-(8-((6-methoxyquinolin-4-yl)thio)imidazo[1,2-c]pyrimidin-5-yl)-3-methyl-2-oxa-8-azaspiro[4.5]decan-4-amine | 22 | 290 |

TABLE 1-continued

| Example | Structure | Name | SHP2 $IC_{50}$ (nM) | H358 $EC_{50}$ (nM) |
|---|---|---|---|---|
| 133 | 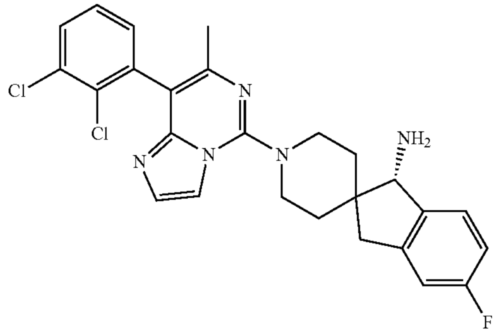 [SMILES: Cc1nc(N2CCC3(CC2)Cc2cc(F)ccc2[C@H]3N)n2ccnc2c1-c1cccc(Cl)c1Cl] | (S)-1'-(8-(2,3-dichlorophenyl)-7-methylimidazo[1,2-c]pyrimidin-5-yl)-5-fluoro-1,3-dihydrospiro[indene-2,4'-piperidin]-1-amine | | 21 |
| 134 | 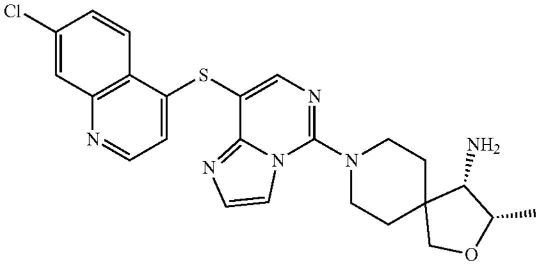 [SMILES: C[C@@H]1OCC2(CCN(c3ncc(Sc4ccnc5cc(Cl)ccc45)c4nccn34)CC2)[C@@H]1N] | (3S,4S)-8-(8-((7-chloroquinolin-4-yl)thio)imidazo[1,2-c]pyrimidin-5-yl)-3-methyl-2-oxa-8-azaspiro[4.5]decan-4-amine | 9 | |
| 135 | 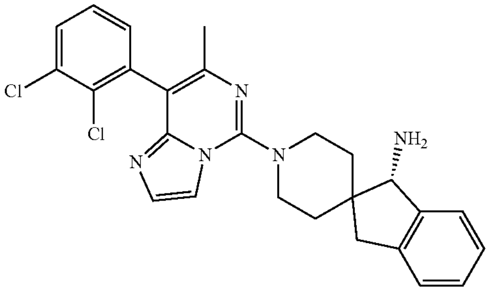 [SMILES: Cc1nc(N2CCC3(CC2)Cc2ccccc2[C@H]3N)n2ccnc2c1-c1cccc(Cl)c1Cl] | (S)-1'-(8-(2,3-dichlorophenyl)-7-methylimidazo[1,2-c]pyrimidin-5-yl)-1,3-dihydrospiro[indene-2,4'-piperidin]-1-amine | 5.4 | 14 |
| 136 | 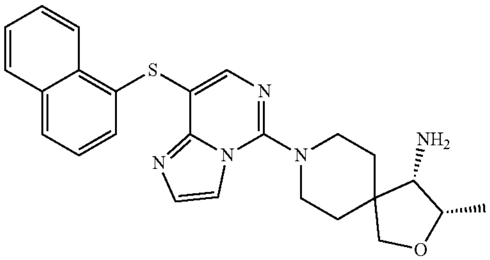 [SMILES: C[C@@H]1OCC2(CCN(c3ncc(Sc4cccc5ccccc45)c4nccn34)CC2)[C@@H]1N] | (3S,4S)-3-methyl-8-(8-(naphthalen-1-ylthio)imidazo[1,2-c]pyrimidin-5-yl)-2-oxa-8-azaspiro[4.5]decan-4-amine | 4.3 | 130 |
| 137 | 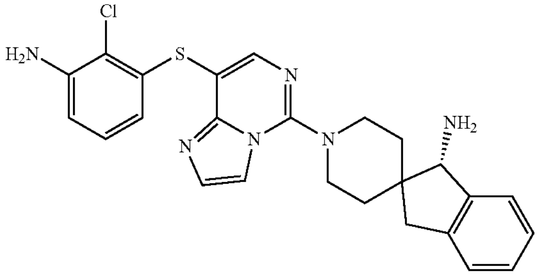 | (S)-1'-(8-((3-amino-2-chlorophenyl)thio)imidazo[1,2-c]pyrimidin-5-yl)-1,3-dihydrospiro[indene-2,4'-piperidin]-1-amine | | 12 |

TABLE 1-continued

| Example | Structure | Name | SHP2 $IC_{50}$ (nM) | H358 $EC_{50}$ (nM) |
|---|---|---|---|---|
| 138 | 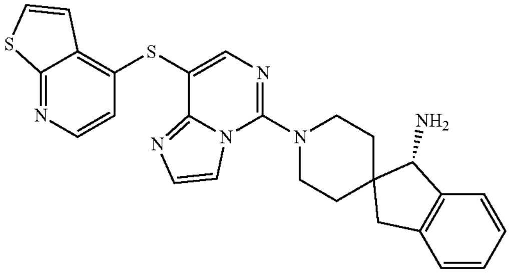 [SMILES: N[C@@H]1c2ccccc2CC12CCN(c1ncc(Sc3ccnc4sccc34)c3nccn13)CC2] | (S)-1'-(8-(thieno[2,3-b]pyridin-4-ylthio)imidazo[1,2-c]pyrimidin-5-yl)-1,3-dihydrospiro[indene-2,4'-piperidin]-1-amine | 2.2 | 11 |
| 139 | 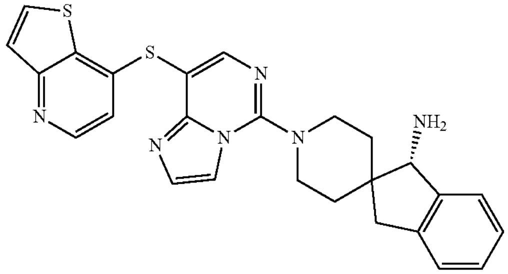 [SMILES: N[C@@H]1c2ccccc2CC12CCN(c1ncc(Sc3ccnc4ccsc34)c3nccn13)CC2] | (S)-1'-(8-(thieno[3,2-b]pyridin-7-ylthio)imidazo[1,2-c]pyrimidin-5-yl)-1,3-dihydrospiro[indene-2,4'-piperidin]-1-amine | 1.7 | 8.9 |
| 140 | 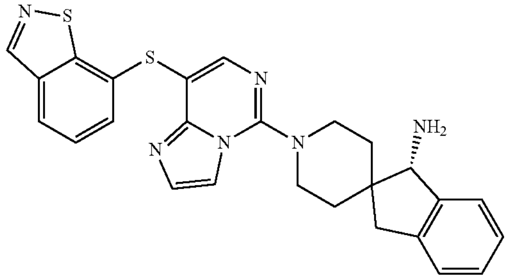 [SMILES: N[C@@H]1c2ccccc2CC12CCN(c1ncc(Sc3cccc4cnsc34)c3nccn13)CC2] | (S)-1'-(8-(benzo[d]isothiazol-7-ylthio)imidazo[1,2-c]pyrimidin-5-yl)-1,3-dihydrospiro[indene-2,4'-piperidin]-1-amine | 2.6 | 18 |
| 141 | 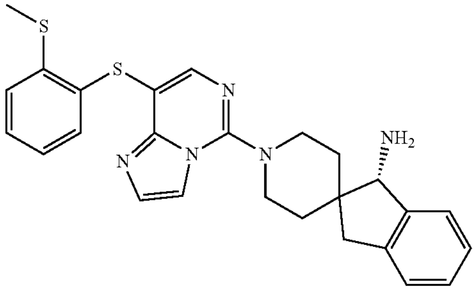 [SMILES: CSc1ccccc1Sc1cnc(N2CCC3(CC2)Cc2ccccc2[C@H]3N)n2ccnc12] | (S)-1'-(8-((2-(methylthio)phenyl)thio)imidazo[1,2-c]pyrimidin-5-yl)-1,3-dihydrospiro[indene-2,4'-piperidin]-1-amine | 1.8 | 30 |
| 142 | 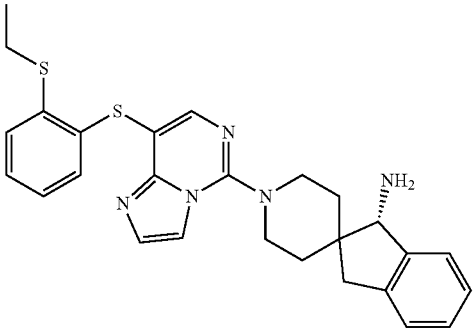 [SMILES: CCSc1ccccc1Sc1cnc(N2CCC3(CC2)Cc2ccccc2[C@H]3N)n2ccnc12] | (S)-1'-(8-((2-(ethylthio)phenyl)thio)imidazo[1,2-c]pyrimidin-5-yl)-1,3-dihydrospiro[indene-2,4'-piperidin]-1-amine | 4.0 | 60 |

TABLE 1-continued

| Example | Structure | Name | SHP2 $IC_{50}$ (nM) | H358 $EC_{50}$ (nM) |
|---|---|---|---|---|
| 143 | 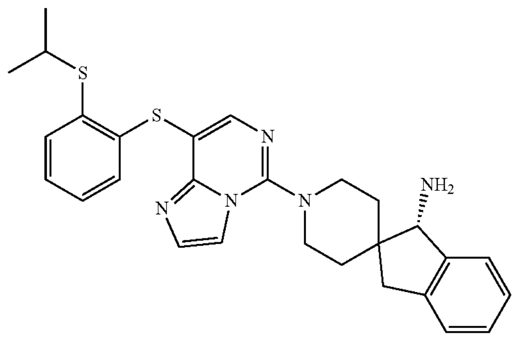 [SMILES: CC(C)Sc1ccccc1Sc1cnc(N2CCC3(CC2)Cc2ccccc2[C@H]3N)n2ccnc12] | (S)-1'-(8-((2-(isopropylthio)phenyl)thio)imidazo[1,2-c]pyrimidin-5-yl)-1,3-dihydrospiro[indene-2,4'-piperidin]-1-amine | 11 | 260 |
| 144 | 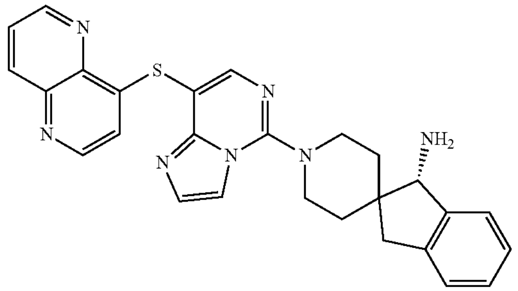 [SMILES: N[C@@H]1c2ccccc2CC12CCN(c1ncc(Sc3ccnc4cccnc34)c3nccn13)CC2] | (S)-1'-(8-((1,5-naphthyridin-4-yl)thio)imidazo[1,2-c]pyrimidin-5-yl)-1,3-dihydrospiro[indene-2,4'-piperidin]-1-amine | 3.6 | 4.4 |
| 145 | 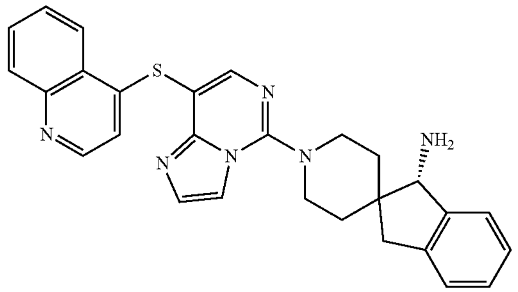 [SMILES: N[C@@H]1c2ccccc2CC12CCN(c1ncc(Sc3ccnc4ccccc34)c3nccn13)CC2] | (S)-1'-(8-(quinolin-4-ylthio)imidazo[1,2-c]pyrimidin-5-yl)-1,3-dihydrospiro[indene-2,4'-piperidin]-1-amine | 2.8 | 20 |
| 146 | 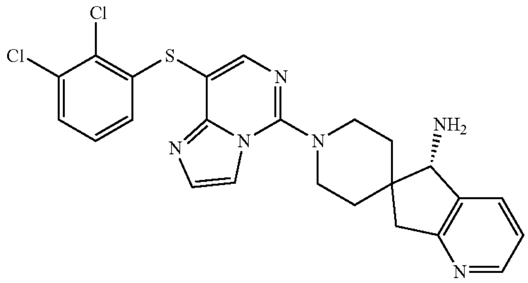 [SMILES: N[C@@H]1c2cccnc2CC12CCN(c1ncc(Sc3cccc(Cl)c3Cl)c3nccn13)CC2] | (S)-1'-(8-((2,3-dichlorophenyl)thio)imidazo[1,2-c]pyrimidin-5-yl)-5,7-dihydrospiro[cyclopenta[b]pyridine-6,4'-piperidin]-5-amine | 1.7 | 15 |
| 147 | 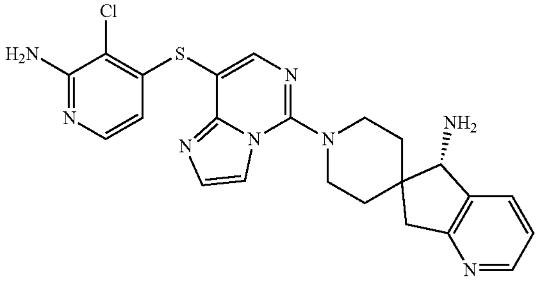 [SMILES: Nc1nccc(Sc2cnc(N3CCC4(CC3)Cc3ncccc3[C@H]4N)n3ccnc23)c1Cl] | (S)-1'-(8-((2-amino-3-chloropyridin-4-yl)thio)imidazo[1,2-c]pyrimidin-5-yl)-5,7-dihydrospiro[cyclopenta[b]pyridine-6,4'-piperidin]-5-amine | 4.8 | 5.5 |

TABLE 1-continued

| Example | Structure | Name | SHP2 $IC_{50}$ (nM) | H358 $EC_{50}$ (nM) |
|---|---|---|---|---|
| 148 | 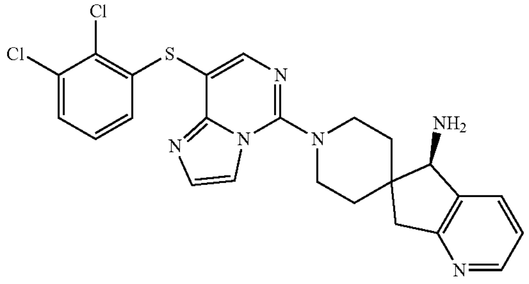 [SMILES: N[C@H]1c2cccnc2CC12CCN(c1ncc(Sc3cccc(Cl)c3Cl)c3nccn13)CC2] | (R)-1'-(8-((2,3-dichlorophenyl)thio) imidazo[1,2-c]pyrimidin-5-yl)-5,7-dihydrospiro [cyclopenta[b] pyridine-6,4'-piperidin]-5-amine | 41 | 132 |
| 149 | 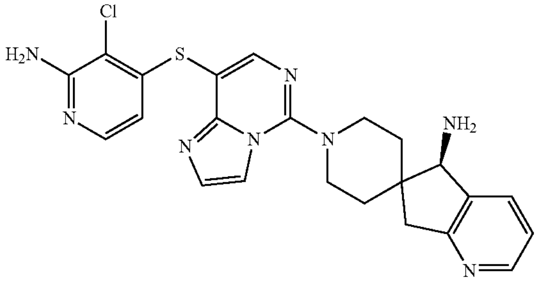 [SMILES: Nc1nccc(Sc2cnc(N3CCC4(CC3)Cc3ncccc3[C@@H]4N)n3ccnc23)c1Cl] | (R)-1'-(8-((2-amino-3-chloropyridin-4-yl)thio)imidazo[1,2-c]pyrimidin-5-yl)-5,7-dihydrospiro [cyclopenta[b] pyridine-6,4'-piperidin]-5-amine | 75 | 101 |

What is claimed is:

1. A compound having formula (VII):

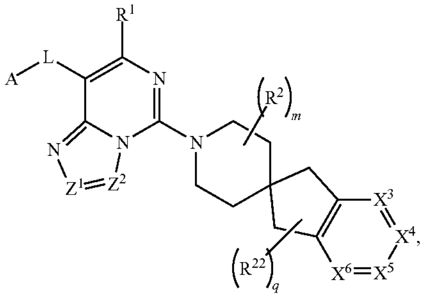

(VII)

or a pharmaceutically acceptable salt; wherein:

A is selected from $C_{6-10}$aryl, 5-10 membered heteroaryl, $C_{3-12}$cycloalkyl, and 4-12 membered heterocyclyl; each A is optionally substituted with one to six $R^A$ independently selected from halo, cyano, hydroxyl, azido, nitro, $C_{1-6}$alkyl, $C_{1-6}$haloalkyl, $C_{1-6}$alkoxyl, $C_{1-4}$alkylene-OH, oxo, $=NR^{a1}$, $-SR^{a1}$, $-OR^{a1}$, $-NR^{a1}R^{a2}$, $-COR^{a2}$, $-CONR^{a1}R^{a2}$, $-COOR^{a2}$, $-N(R^{a2})-C(O)R^{a2}$, $-N(R^{a2})-C(O)OR^{a2}$, $-N(R^{a2})-C(O)-NR^{a2}R^{a2}$, $-N(R^{a2})-SO_2R^{a2}$, $-SO_2R^{a2}$, $-SO_2OR^{a2}$, $-SO_2NR^{a1}R^{a2}$, $-O-SO_2-NR^{a1}R^{a2}$, $-O(CO)-N-R^{a1}R^{a2}$, $C_{3-8}$cycloalkyl, 3-8 membered heterocyclyl, $C_{6-10}$ aryl, 5-10 membered heteroaryl, $-C_{1-4}$alkylene-$C_{3-8}$cycloalkyl, $-C_{1-4}$alkylene-(3-8 membered heterocyclyl), $-C_{1-4}$ alkylene-$C_{6-10}$aryl, and $-C_{1-4}$alkylene-(5-10 membered heteroaryl);

wherein the $C_{3-8}$cycloalkyl, 3-8 membered heterocyclyl, $C_{6-10}$aryl, 5-10 membered heteroaryl, $-C_{1-4}$alkylene-$C_{3-8}$cycloalkyl, $-C_{1-4}$alkylene-(3-8 membered heterocyclyl), $-C_{1-4}$alkylene-$C_{6-10}$aryl, and $-C_{1-4}$alkylene-(5-10 membered heteroaryl) of $R^A$ are independently optionally substituted with one to three groups selected from halo, cyano, hydroxyl, $C_{1-4}$alkyl, $C_{1-4}$haloalkyl, $C_{1-4}$alkoxyl, and $C_{1-4}$alkylene-OH;

wherein the 5-10 membered heteroaryl of A, and $R^A$ contains one to five heteroatoms independently selected from S, N, and O, and optionally comprises one to three C(O) or one $S(O)_2$;

L is selected from a bond, —S—, and —O—;

$Z^1$ and $Z^2$ are independently selected from N and $CR^3$; wherein $R^3$ is selected from H, halo, hydroxyl, cyano, $C_{1-4}$alkyl, $C_{1-4}$haloalkyl, $C_{1-4}$alkoxyl, $C_{1-4}$alkylene-OH, $-NR^{c1}R^{c2}$, $-C(O)OR^{c1}$, $C_{6-10}$aryl, and 5-10 membered heteroaryl; wherein each $C_{6-10}$aryl, and 5-10 membered heteroaryl of $R^3$ is independently optionally substituted with one to three groups independently selected from halo, hydroxyl, cyano, $C_{1-4}$alkyl, $C_{1-4}$haloalkyl, $C_{1-4}$alkoxyl, $-N(R^{c1})-SO_2R^{c1}$, and $-SO_2R^{c1}$;

$R^1$ is selected from H, halo, $-NR^{c1}R^{c2}$, $C_{1-4}$alkyl, and $C_{1-4}$ haloalkyl;

each $R^2$ is independently selected from halo, cyano, nitro, $-O-C_{1-6}$alkyl, oxo, $-NR^{c1}R^{c2}$, $-(SO_v)-R^{c1}$, $-NR^{c1}(SO_v)-R^{c1}$, $-C(O)OR^{c1}$, $-C(O)-NR^{c1}R^{c2}$, $-S(O_2)-NR^{c1}R^{c2}$, $C_{1-6}$alkyl, $C_{2-6}$alkenyl, $C_{2-6}$alkynyl, $C_{1-4}$alklene-OH, $-C_{1-4}$alkylene-$NR^{c1}R^{c2}$, $C_{3-8}$cycloalkyl, 3-6 membered heterocyclyl, $-O-C_{3-8}$cycloalkyl, —O-(3-6 membered heterocyclyl), $C_{6-10}$aryl, and 5-10 membered heteroaryl;

each $R^{22}$ is independently selected from halo, $-NR^{c1}R^{c2}$, hydroxyl, azido, cyano, oxo, $-C(O)OR^{c1}$, $C_{1-4}$alkyl, $C_{1-4}$haloalkyl, $C_{1-4}$alkoxyl, $C_{1-4}$alkylene-$NR^{c1}R^{c2}$, $-C_{1-4}$alkylene-$O-C_{1-4}$alkyl, —$C_{1-4}$alkylene-OH, —CO—$NR^{c1}R^{c2}$, —C(O)$OR^{c1}$, —$N(R^{c1})$—C(O)$R^{c1}$, —$N(R^{c1})$—C(O)$OR^{c1}$, —$N(R^{c1})$—C(O)—$NR^{c1}R^{c2}$, —$N(R^{c1})$—$(SO_v)R^{c1}$, —$SO_2R^{c1}$, —$SO_2OR^{c1}$, —$SO_2R^{c1}R^{c2}$, $C_{3-8}$ cycloalkyl, 3-6 membered heterocyclyl, $C_{6-10}$aryl, and 5-10 membered heteroaryl;

each $X^3$, $X^4$, $X^5$, and $X^6$ is independently selected from $CR^{xx}$, and N; wherein $R^{xx}$ is selected from H, halo, cyano, hydroxyl, azido, nitro, $C_{1-6}$alkyl, $C_{1-6}$haloalkyl, $C_{1-6}$alkoxyl, $C_{1-4}$alkylene-OH, —$SR^{a1}$, —$OR^{a1}$, —$NR^{a1}R^{a2}$, —$COR^{a2}$, —$CONR^{a1}R^{a2}$, —$COOR^{a2}$, —$N(R^{a2})$—C(O)$R^{a2}$, —$N(R^{a2})$—C(O)$OR^{a2}$, —$N(R^{a2})$—C(O)—$NR^{a2}R^{a2}$, —$N(R^{a2})$—$SO_2R^{a2}$, —$SO_2R^{a2}$, —$SO_2OR^{a2}$, —$SO_2R^{a1}R^{a2}$, —O—$SO_2$—$NR^{a1}R^{a2}$, —O(CO)—$NR^{a1}R^{a2}$, $C_{3-8}$cycloalkyl, 3-8 membered heterocyclyl, $C_{6-10}$aryl, 5-10 membered heteroaryl, —$C_{1-4}$alkylene-$C_{3-8}$cycloalkyl, —$C_{1-4}$alkylene-(3-8 membered heterocyclyl), —$C_{1-4}$alkylene-$C_{6-10}$aryl, and —$C_{1-4}$alkylene-(5-10 membered heteroaryl);

$R^{a1}$ is selected from H, $C_{1-4}$alkyl, $C_{1-4}$haloalkyl, $C_{1-4}$alkylene-OH, $C_{1-4}$alkylene-$COOR^{a2}$, —$C_{1-4}$alkylene-$C_{1-4}$alkoxyl, and —C(O)—$NH_2$;

$R^{a2}$ is selected from H, $C_{1-4}$alkyl, $C_{1-4}$haloalkyl, $C_{1-4}$alkylene-OH, $C_{3-8}$cycloalkyl, 3-8 membered heterocyclyl, $C_{6-10}$aryl, and 5-10 membered heteroaryl; wherein the $C_{1-4}$alkyl, $C_{1-4}$haloalkyl, $C_{1-4}$alkylene-OH, $C_{3-8}$cycloalkyl, 3-8 membered heterocyclyl, $C_{6-10}$aryl, and 5-6 membered heteroaryl of $R^{a2}$ are independently optionally substituted with one to three groups selected from halo, cyano, hydroxyl, —$COOR^{a3}$, $C_{1-4}$alkyl, $C_{1-4}$haloalkyl, $C_{1-4}$alkylene-OH, and $C_{1-4}$alkoxyl; wherein $R^{a3}$ is selected from H, $C_{1-4}$alkyl, and $C_{1-4}$haloalkyl;

$R^{c1}$ and $R^{c2}$ are independently selected from H, $C_{1-6}$alkyl, and $C_{1-6}$haloalkyl; wherein each of the $C_{1-6}$alkyl and $C_{1-6}$haloalkyl of $R^{c1}$ and $R^{c2}$ is optionally substituted with one or two groups selected from $C_{1-4}$alkoxyl, and $C_{1-4}$alklene-OH;

v is selected from 0, 1, and 2;

m is selected from 0, 1, 2, 3, and 4; and q is selected from 0, 1, 2, 3, and 4.

2. The compound of claim 1, or a pharmaceutically acceptable salt, wherein L is —S—.

3. The compound of claim 1, or a pharmaceutically acceptable salt, wherein $R^4$ is independently selected from F, Cl, —$CH_3$, —$CF_3$, and —$NH_2$.

4. The compound of claim 1, or a pharmaceutically acceptable salt, wherein $R^1$ is selected from H, halo, and $C_{1-4}$alkyl.

5. The compound of claim 1, or a pharmaceutically acceptable salt, wherein $R^1$ is selected from Cl and —$CH_3$.

6. The compound of claim 1, or a pharmaceutically acceptable salt, wherein $Z^1$ and $Z^2$ are CH.

7. The compound of claim 1, wherein q is 1 or 2.

8. The compound of claim 1, wherein p is selected from 0, 1, and 2.

9. The compound of claim 1, wherein $X^3$, $X^4$, $X^5$, and $X^6$ are each CH.

10. The compound of claim 1, wherein each $R^{22}$ is selected from $CH_3$, $CH_2NH_2$, $NH_2$, and OH.

11. The compound of claim 1, selected from:

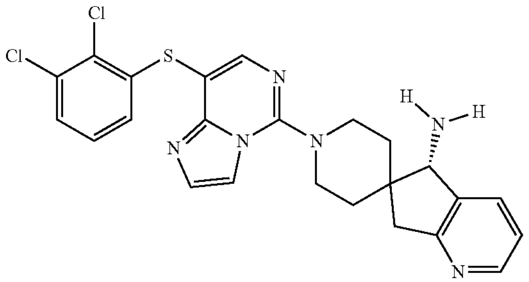

;

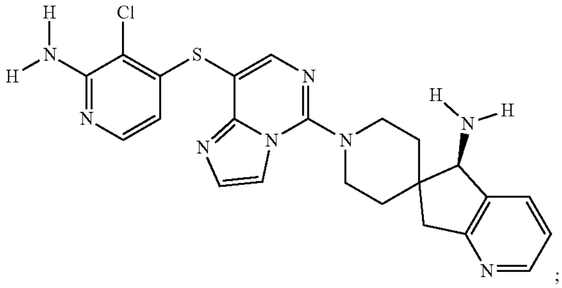

;

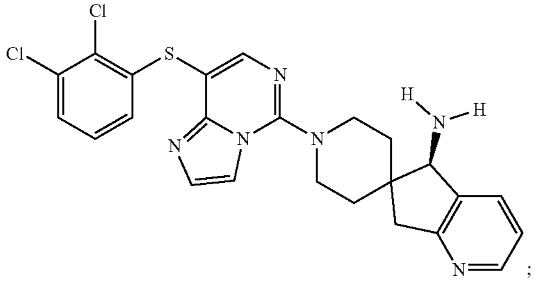

;

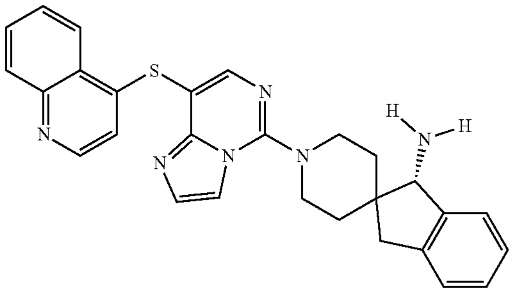

;

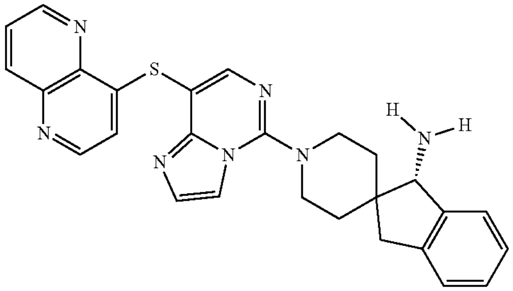

;

-continued
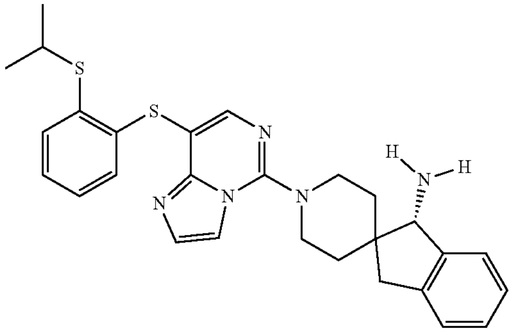
;
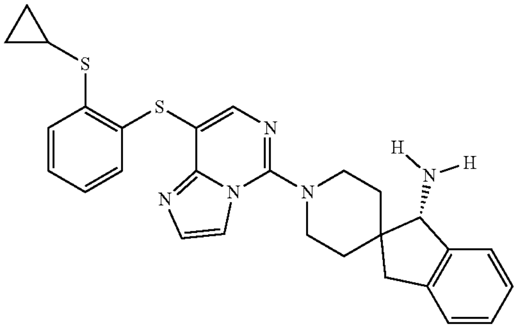
;
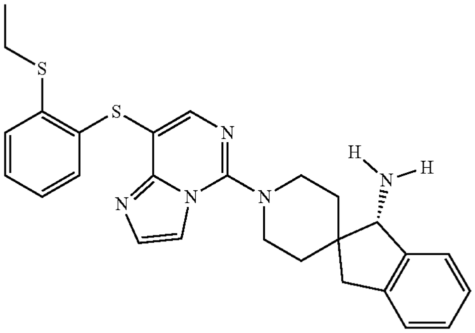
;
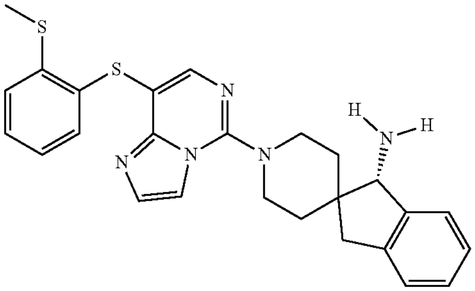
;
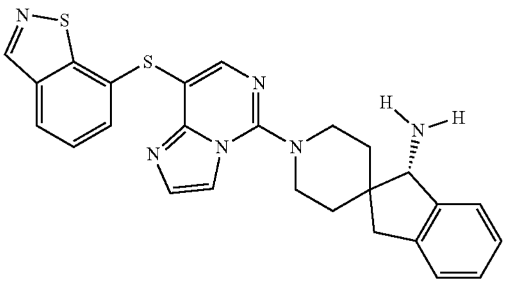
;
-continued
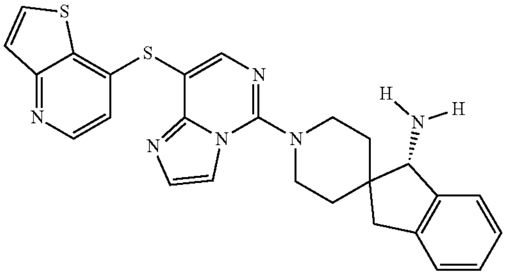
;
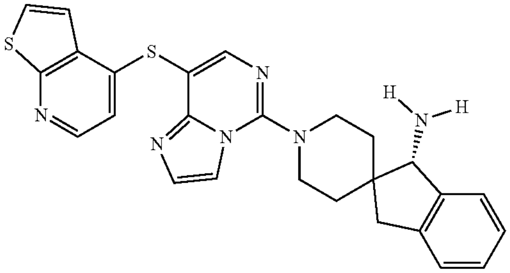
;
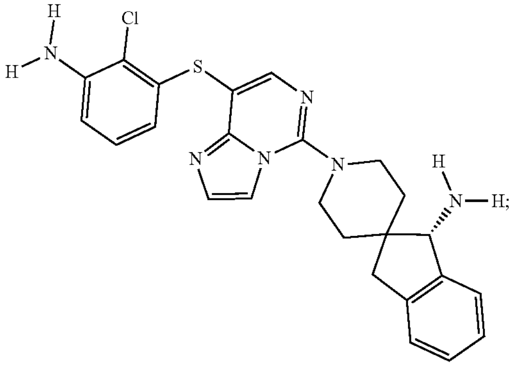
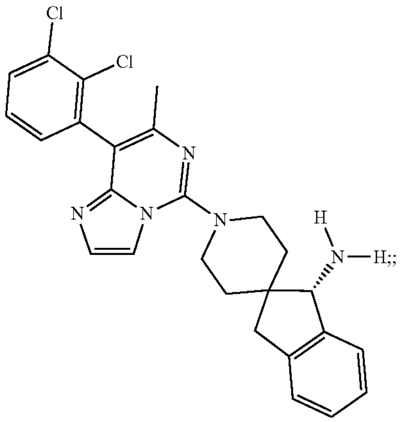

-continued
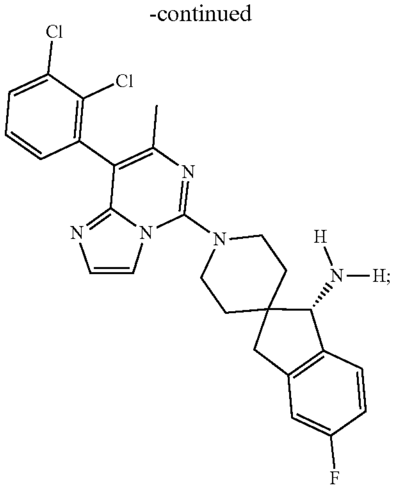
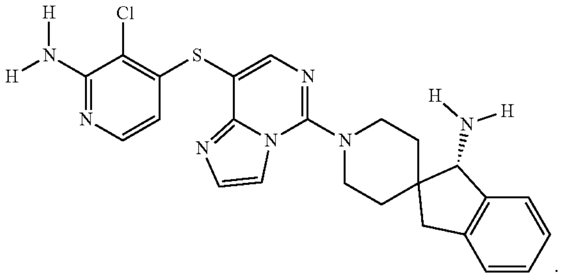 [SMILES: Nc1nccc(Sc2cnc(N3CCC4(CC3)Cc3ccccc3[C@H]4N)n3ccnc23)c1Cl]
12. A compound having the structure:
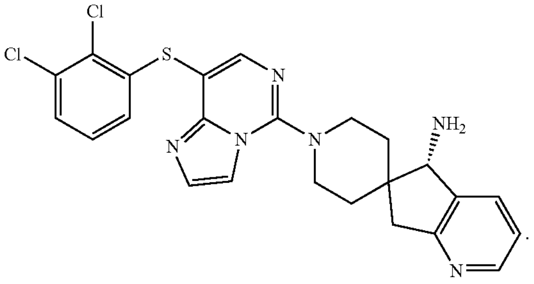 [SMILES: N[C@@H]1c2cccnc2CC12CCN(c1ncc(Sc3cccc(Cl)c3Cl)c3nccn13)CC2 ; "."]
13. A pharmaceutical composition comprising a compound of claim 1 and at least one pharmaceutically acceptable carrier.
* * * * *

UNITED STATES PATENT AND TRADEMARK OFFICE
CERTIFICATE OF CORRECTION

PATENT NO. : 11,179,397 B2
APPLICATION NO. : 16/591092
DATED : November 23, 2021
INVENTOR(S) : Chin et al.

It is certified that error appears in the above-identified patent and that said Letters Patent is hereby corrected as shown below:

In the Claims

Column 349, Line 61, Claim 1, delete "$C_{6-10}$ aryl," and insert -- $C_{6-10}$aryl, --;

Column 350, Line 59, Claim 1, delete "$C_{1-4}$alklene-OH," and insert -- $C_{1-4}$alkylene-OH, --;

Column 351, Lines 4-5, Claim 1, delete "$C_{3-8}$ cycloalkyl," and insert -- $C_{3-8}$cycloalkyl, --;

Column 351, Line 15, Claim 1, delete "—$SO_2R^{a1}R^{a2}$," and insert -- —$SO_2NR^{a1}R^{a2}$, --;

Column 351, Line 41, Claim 1, delete "$C_{1-4}$alklene-OH;" and insert -- $C_{1-4}$alkylene-OH; --;

Column 354, Lines 50-56, Claim 11, delete " 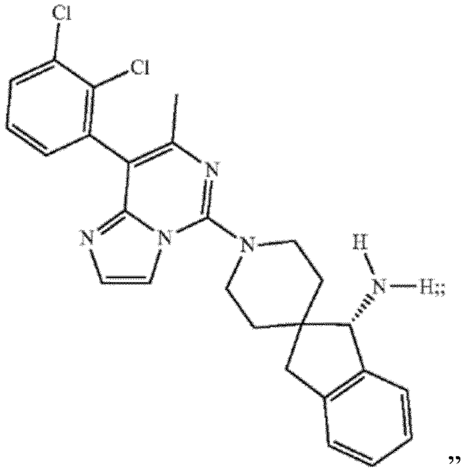 " and insert -- 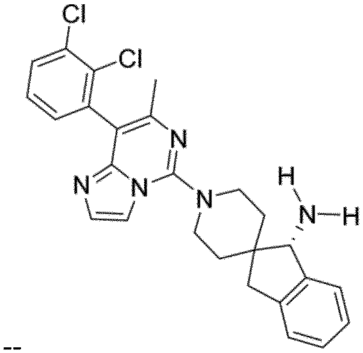 ; --.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*